US009187753B2

(12) United States Patent
Lee et al.

(10) Patent No.: US 9,187,753 B2
(45) Date of Patent: Nov. 17, 2015

(54) **TRANSCRIPTIONAL CONTROL IN *ALICYCLOBACILLUS ACIDOCALDARIUS* AND ASSOCIATED GENES, PROTEINS, AND METHODS**

(71) Applicant: Battelle Energy Alliance, LLC, Idaho Falls, ID (US)

(72) Inventors: Brady D. Lee, Idaho Falls, ID (US); David N. Thompson, Idaho Falls, ID (US); William A. Apel, Jackson, WY (US); Vicki S. Thompson, Idaho Falls, ID (US); David W. Reed, Idaho Falls, ID (US); Jeffrey A. Lacey, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 0 days.

(21) Appl. No.: 14/256,819

(22) Filed: Apr. 18, 2014

(65) Prior Publication Data
US 2014/0273238 A1 Sep. 18, 2014

Related U.S. Application Data

(62) Division of application No. 12/380,008, filed on Feb. 20, 2009, now Pat. No. 8,716,011.

(60) Provisional application No. 61/030,820, filed on Feb. 22, 2008.

(51) Int. Cl.
| | |
|---|---|
| *C12N 15/63* | (2006.01) |
| *C12N 15/67* | (2006.01) |
| *C07H 21/04* | (2006.01) |
| *C12N 15/74* | (2006.01) |
| *C07K 14/195* | (2006.01) |

(52) U.S. Cl.
CPC .............. *C12N 15/74* (2013.01); *C07K 14/195* (2013.01)

(58) Field of Classification Search
CPC ...................................................... C12N 15/74
USPC ........................................... 435/252.3, 320.1
See application file for complete search history.

(56) References Cited

U.S. PATENT DOCUMENTS

| | | | |
|---|---|---|---|
| 4,237,226 A | 12/1980 | Grethlein | |
| 4,581,333 A | 4/1986 | Kourilsky et al. | |
| 4,624,922 A | 11/1986 | Horikoshi et al. | |
| 5,098,825 A | 3/1992 | Tchen et al. | |
| 5,882,905 A | 3/1999 | Saha et al. | |
| 5,916,795 A | 6/1999 | Fukunaga et al. | |
| 5,948,667 A | 9/1999 | Cheng et al. | |
| 6,083,733 A | 7/2000 | Gronberg et al. | |
| 6,268,197 B1 | 7/2001 | Schulein et al. | |
| 6,426,211 B1 | 7/2002 | de Buyl et al. | |
| 6,506,585 B2 | 1/2003 | Danielsen et al. | |
| 6,777,212 B2 | 8/2004 | Asakura et al. | |
| 6,833,259 B2 | 12/2004 | Bhosle et al. | |
| 7,727,755 B2 | 6/2010 | Thompson et al. | |
| 7,858,353 B2 | 12/2010 | Thompson et al. | |
| 7,923,234 B2 | 4/2011 | Thompson et al. | |
| 7,960,534 B2 | 6/2011 | Thompson et al. | |
| 8,071,748 B2 | 12/2011 | Thompson et al. | |
| 8,202,716 B2 | 6/2012 | Thompson et al. | |
| 2003/0134395 A1 | 7/2003 | Shetty et al. | |
| 2003/0233674 A1 | 12/2003 | Gabor et al. | |
| 2003/0233675 A1 | 12/2003 | Cao et al. | |
| 2004/0029129 A1 | 2/2004 | Wang et al. | |
| 2005/0112742 A1 | 5/2005 | Thompson et al. | |
| 2006/0105442 A1 | 5/2006 | Wu et al. | |
| 2006/0211083 A1 | 9/2006 | Katzen et al. | |
| 2007/0082381 A1 | 4/2007 | Wilting et al. | |
| 2007/0134778 A1 | 6/2007 | Benning et al. | |
| 2007/0148728 A1 | 6/2007 | Johnson et al. | |
| 2009/0203107 A1 | 8/2009 | Thompson et al. | |
| 2009/0215168 A1 | 8/2009 | Lee et al. | |
| 2009/0221049 A1 | 9/2009 | Shaw, IV et al. | |
| 2009/0226978 A1 | 9/2009 | Thompson et al. | |
| 2009/0253205 A1 | 10/2009 | Thompson et al. | |
| 2009/0263859 A1 | 10/2009 | Thompson et al. | |
| 2009/0269827 A1 | 10/2009 | Thompson et al. | |
| 2010/0203583 A1 | 8/2010 | Thompson et al. | |
| 2010/0311110 A1 | 12/2010 | Thompson et al. | |
| 2011/0081683 A1 | 4/2011 | Thompson et al. | |

(Continued)

FOREIGN PATENT DOCUMENTS

| | | |
|---|---|---|
| DE | 19717893 A1 | 1/1999 |
| WO | 81/00577 A1 | 3/1981 |

(Continued)

OTHER PUBLICATIONS

Aden et al., "Lignocellulosic Biomass to Ethanol Process Design and Economics Utilizing Co-Current Dilute Acid Prehydrolysis and Enzymatic Hydrolysis for Corn Stover," NREL/TP-510-32438, National Renewable Energy Laboratory, Golden Colorado. Jun. 2002, pp. 1-88.
Avella et al., "A New Class of Biodegradable Materials: Poly-3-hydroxy-butyrate/Steam Exploded Straw Fiber Composites. I. Thermal and Impact Behaviour," Journal of Applied Polymer Science, vol. 49, 2091-2103 (1993).
Badger, P.C., "Ethanol from cellulose: A general review," In: J. Janick and A. Whipkey (eds.), Trands in new crops and new uses. ASHS Press, Alexandria, VA, 2002, pp. 17-21.
Bailey et al., "Interlaboratory testing of methods for assay of xylanase activity," Journal of Biotechnology, 23 (1992) 257-270.
Barany, F., 1991, PNAS. USA, 88: 189-193.
Bergquist et al., "Molecular diversity of thermophilic cellulolytic and hemicellulolytic bacteria," FEMS Microbiology Ecology 28 (1999) 99-110.
Bertoldo et al., 2004, Eng. Life Sci., 4, No. 6.
Bhatia et al., "Microbial beta-Glucosidases: Cloning, Properties, and Applications," Critical Reviews in Biotechnology, 22(4):375-407, Jan. 1, 2002.

(Continued)

*Primary Examiner* — Padma V Baskar
(74) *Attorney, Agent, or Firm* — TraskBritt

(57) ABSTRACT

Isolated and/or purified polypeptides and nucleic acid sequences encoding polypeptides from *Alicyclobacillus acidocaldarius* are provided. Further provided are methods of modulating transcription or transcription or transcriptional control using isolated and/or purified polypeptides and nucleic acid sequences from *Alicyclobacillus acidocaldarius*.

8 Claims, 196 Drawing Sheets

(56) References Cited

U.S. PATENT DOCUMENTS

2011/0275135 A1    11/2011    Lee et al.
2012/0015407 A1    1/2012    Thompson et al.

FOREIGN PATENT DOCUMENTS

| WO | 99/06584 A1 | 2/1999 |
| WO | 03/068926 A1 | 8/2003 |
| WO | 2005/066339 A1 | 7/2005 |
| WO | 2006/117247 A1 | 11/2006 |

OTHER PUBLICATIONS

Blast Search of Seq. ID. 36, accessed Apr. 22, 2009, 54 pages.
Blast Search of Seq. ID. 456, accessed Apr. 22, 2009, 48 pages.
Blast Search of Seq. ID. 458, accessed Apr. 22, 2009, 59 pages.
Blast Search of Seq. ID. 460, accessed Apr. 22, 2009, 37 pages.
Blast Search of Seq. ID. 462, accessed Apr. 22, 2009, 35 pages.
Blast Search of Seq. ID. 464, accessed Apr. 22, 2009, 45 pages.
Bork, Peer, "Powers and Pitfalls in Sequence Analysis: The 70% Hurdle," Genome Research, 2000, 10:398-400.
Borman, S., 2006, Glycosylation Engineering. Chem. Eng. News, 84(36): 13-22.
Bowie et al., "Deciphering the Message in Protein Sequences: Tolerance to Amino Acid Substitutions," Science, 1990, 247:1306-1310.
Breves et al., "Genes Encoding Two Different beta-Glucosidases of Thermoanaerobacter brockii are Clustered in a Common Operon," Applied and Environmental Microbiology, vol. 63, No. 10, Oct. 1997, pp. 3902-3910.
Broun et al. "Catalytic Plasticity of Fatty Acid Modification Enzymes Underlying Chemical Diversity of Plant Lipids" Science vol. 282 Nov. 13, 1998 pp. 1315-1317 (4 pages).
Buckholz, R. G., 1993, Yeast systems for the expression of heterologous gene products. Curr. Op. Biotechnology 4: 538-542.
Burg, J. L. et al., 1996, Mol. and Cell. Probes, 10: 257-271.
Chu, B. C. F. et al., 1986, NAR, 14: 5591-5603.
Collins et al., "Xylanaes, Xylanase Families and Extremophilic Xylanses," FEMS Microbiology Review, 2005, pp. 3-23.
Cowling, Ellis B., "Physical and Chemical Constrains in the Hydrolysis of Cellulose and Lignocellulosic Materials," Biotechnol. & Bioeng. Symposium No. 5, 163-181 (1975).
Crout et al., "Glycosidases and glycosyl transferases in glycoside and oligosaccharide synthesis," Current Opinion in Chemical Biology, Current Biology Ltd, London, GB, vol. 2, No. 1, Feb. 1, 1998, pp. 98-111.
Dale, M. Clark, "Enzymatic simultaneous saccharification and fermentation (SSF) of biomass to ethanol in a pilot 130 liter multistage continuous reactor separator," Bio-Process Innovation, Inc., W. Lafayette, IN, 2005, 10 pages.
Database EMBL [Online]. Mar. 16, 2007. XP-002627757. Database accession No. ER073884, 1 page.
Database Geneseq [Online]. May 21, 1998. XP-002627734. Database accession No. AAW35004, 1 page.
Database UniProt [Online]. May 1, 1997. XP-002630045. Database accession No. P96090, 1 page.
Database UniProt [Online]. Oct. 1, 2001. XP-002627736. Database accession No. Q97UI4, 1 page.
Database UniProt [Online]. Feb. 10, 2009. XP-000002659383. Database accession No. B7DT70, 1 page.
Database UniProt [Online]. Jun. 26, 2007. XP-002627735. Database accession No. A5IKZ4, 1 page.
Database UniProt [Online]. Nov. 3, 2009. XP-002627733. Database accession No. C8WTP2, 1 page.
Database Uniprot [Online]. Nov. 3, 2009. Database accession No. C8WVZ2, 2 pages.
Database UniProt [Online]. Feb. 10, 2009. XP-002674095. Database accession No. B7DM51, 1 page.
Devos et al. "Practical Limits of Functiona Prediction" Proteins: Structure, Function, and Genetics 41 (2000) pp. 98-107 (10 pages).
Duck, P. et al., 1990, Biotechniques, 9: 142-147.
Eckert et al., "A Thermoacidophilic Endoglucanase (CelB), etc.," Eur. J. Biochem. 270, 2003, pp. 3593-3602.
Eckert et al., "Gene cloning, sequencing, and characterization of a family 9 endoglucanase (CelA) with an unusual pattern of activity from the theremoacidophile Alicyclobacillus acidocaldarius ATCC27009," Applied Microbiology and Biotechnology, vol. 60, pp. 428-436 (2002).
Eckert, Kelvin, "Dissertation, Cloning and Characterization of two glycosidases from the acidothermophile Alicyclobacillus acidocaldarius ATCC27009," Berlin, Dec. 18, 1971, 113 pages.
Edwards, C. P., and Aruffo, A., 1993, Current applications of COS cell based transient expression systems. Curr. Op. Biotechnology 4: 558-563.
Ehrman, Tina, "Standard Method for Determination of Total Solids in Biomass," Chemical Analysis and Testing Task, Laboratory Analytical Procedure, Oct. 28, 1994, 242 total pages.
EMBL Submission CP001728, Sep. 2009. [Retrieved from the internet: URL:http://www.ebi.ac.uk/Tools/dbfetch/embifetch?style=html&id=CP001728&Submit=Go], 51 pages.
Erlich, H.A., J Clin. Immunol., Nov. 1989; 9(6):437-47.
Fan et al., "The Nature of Lignocellulosics and Their Pretreatments for Enzymatic Hydrolysis," Advances in Biochemical Engineering/Biotechnology, 1982, vol. 23/1982, 157-187.
Flanagan, et al., "Development of gas phase bioreactors for the removal of nitrogen oxides from synthetic flue gas streams," Fuel 81 (2002) 1953-1961.
Fushinobu et al., "Crystallographic and mutational analyses of an extremely acidophilic and acid-stable xylanase: biased distribution of acidic residues and importance of Asp37 for catalysis at low pH," Protein Engineering vol. 11, No. 12, pp. 1121-1128, 1998.
Garrote, G, H Dominguez, and JC Parajo, 2001, Manufacture of xylose-based fermentation media from corncobs by posthydrolysis of autohydrolysis liquors, Appl. Biochem. Biotechnol., 95:195-207.
GenBank: E17054.1 Direct Submission Alicyclobacillus acidocaldarius genomic DNA clone pOP3 containing acyl carrier protein gene. Nov. 5, 2005 [Retrieved from the Internet Jan. 23, 2010: http://www.ncbi.nlm.nih.gov/nuccore/E17054.1?ordinalpos=2&tool=Entr.
GenBank: AJ252161.1 Alicyclobacillus acidocaldarius maltose/maltodextrine transport gene region(malEFGR genese, cdaA gene and glcA gene), NCBI, Hulsmann, A. http://www.ncbi.nlm.nih.gov/nuccore/AJ252161 (Jan. 6, 2000).
Gessesse, Amare, "Purification and Properties of Two Thermostable Alkaline Xylanases from an Alkaliphilic Bacillus sp.," Applied and Environmental Microbiology, Sep. 1998, pp. 3533-3535.
Glenn et al., "Transformation of Acidiphilium by electroporation and conjugation," Can J Microbiol. May 1992;38 (5):387-93.
Goldstein et al., "The Hydrolysis of Cellulose with Superconcentrated Hydrochloric Acid," Biotechnology and Bioengineering Symp. No. 13, pp. 17-25 (1983).
Grassin et al., "Chapter 2.13, Fruit Juices," (T. Godfrey and S. West, eds.), Industrial Enzymology, 2nd Ed., pp. 227-264 (1996).
Grethlein, H. E., "Pretreatment for enhanced hydrolysis of cellulosic biomass," Biotechnol. Adv. 1984. 2:43-62.
Grethlein, Hans E., "Comparison of the Economics of Acid and Enzymatic Hydrolysis of Newsprint," Biotechnology and Bioengineering, vol. XX, pp. 503-525 (1978).
Guateli, J. C. et al., 1990, PNAS. USA, 87: 1874-1878.
Hamelinck, CN, G van Hooijdonk, and APC Faaij, 2005, Ethanol from lignocellulosic biomass: techno-economic performance in short-, middle-, and long-term, Biomass Bioenergy, 28:384-410.
Hanselmann, K.W., "Lignochemicals," Experientia 38 (1982) pp. 176-189.
Houghton et al., "Fungal Upgrading of Wheat Straw for Straw-Thermoplastics Production," Applied Biochemistry and Biotechnology, vol. 113-116, 2004, pp. 71-93.
Hulsmann et al., "Maltose and maltodextrin transport in the thermoacidophilic gram-positive bacterium Alicyclobacillus acidocaldarius is mediated by a high-affinity transport system that includes a maltose binding protein tolerant to low pH," J. Bacteriology, Nov. 2000, p. 6292-6301.
Huygen, K. et al., 1996, Nature Medicine, 2(8): 893-898.

(56) References Cited

OTHER PUBLICATIONS

Ito et al., "Purification and properties of acid stable xylanases from Aspergillus kawachii," Bioscience Biotechnology and Biochemistry 56 (4):547-550, Apr. 1992.
Jeffries, 1996, Curr. Op. in Biotech., 7:337-342.
Jones et al., "Cloning and transcriptional analysis of the Thermoanaerobacter ethanolicus strain 39E maltose ABC transport system," Extremophiles 2002, 6:291-299.
Keller et al., "Microbial Pretreatment of Biomass: Potential for Reducing the Severity of Thermochemical Biomass Pretreatment," Applied Biochemistry and Biotechnology, vol. 105-108, 2003.
Kenealy et al., "Rapid 2,2'-bicinchoninic-based xylanase assay compatible with high throughput screening," Biotechnology Letters 25: 1619-1623, 2003.
Kievitis, T. et al., 1991, J. Virol. Methods, 35: 273-286.
Knappert et al., "Partial Acid Hydrolysis of Cellulosic Materials as a Pretreatment for Enzymatic Hydrolysis," Biotechnology and Bioengineering, vol. XXII, pp. 1449-1463 (1980).
Kohler, G. et al., 1975, Nature, 256(5517): 495497.
Kulkarni et al., "Molecular and biotechnological aspects of xylanases," FEMS Microbiology Reviews 23 (1999) 411-456.
Kwoh, D. Y. et al., 1989, PNAS. USA, 86: 1173-1177.
Lau et al., "PCR ligation mutagenesis in transformable streptococci: application and efficiency," Journal of Microbiological Methods 49 (2002) 193-205.
Lauro et al., "Characterization of a β-glycosidase from the thermoacidophilic bacterium Alicyclobacillus acidocaldarius," Extremophiles (2006) 10:301-310.
Lauro et al., "Isolation and characterization of a new family 42 beta-galactosidase from the thermoacidophilic bacterium Alicyclobacillus acidocaldarius: Identification of the active site residues," Biochimica et Biophysica Acta 1784 (2008) 292-301.
Lavarack et al., "The acid hydrolysis of sugarcane begasse hemicellulose to produce xylose, arabinose, glucose and other products," Biomass and Bioenergy 23 (2002) 367-380.
Lee et al., "Oxygen Effects on Thermophilic Microbial Populations in Biofilters Treating Nitric Oxide Containing Off-Gas Streams," Environmental Progress, vol. 20, No. 3, Oct. 2001.
Lin et al., "Purification, Characterization, and Gene Cloning of Thermopsin, a Thermostable Acid Protease from Sulfolobus acidocaldarius," The Journal of Biological Chemistry, 1990, vol. 265, No. 3, pp. 1490-1495.
Liu C, and CE Wyman, 2003, The effect of flow rate of compressed hot water on xylan, lignin, and total mass removal from corn stover, Ind. Eng. Chem. Res., 42:5409-5416.
Lucas et al., C4-Dicarboxylate Transporter/Malic Acid Transport Protein [Alicyclobacillus acidocaldarius LAA1], GenBank Direct Submission, Accession No. EED06059, Dec. 17, 2008 (Retrieved from the Internet Dec. 15, 2009: <URL:http://www.ncbl.nlm.nlh.gov/.
Luckow, V. A., 1993, Baculovirus systems for the expression of human gene products. Curr. Op. Biotechnology 4: 564-572.
Lynd et al., 2002, Micro. and Mol. Biol. Rev., vol. 66, No. 3, p. 506-577.
Lynd, Lee R., "Overview and Evaluation of Fuel Ethanol from Cellulosic Biomass: Technology, Economics, the Environment, and Policy," Annu. Rev. Energy Environ. 1996, 21:403-65.
MacKenzie et al., "Multiple Chromosomes in Bacteria: The Yin and Yang of trp Gene Localization in Rhodobacter sphaeroides 2.4.1," Genetics 153: 525-538 (Oct. 1999).
Malherbe and Cloete, 2002, Re/View in Environmental Science and Bio/Technology, 1: 105-114.
Manchenko, Gennady P., "Handbook of Detection of Enzymes on Electrophoretic Gels," CRC Press, Inc. 1994, pp. 220-240.
Matthews, J. A. et al., 1988, Anal. Biochem., 169: 1-25.
McCoy, Michael, "Chemical Makers Try Biotech Paths," Chemical Engineering News, Jun. 22, 1998, pp. 13-19.
Merrifield, R. D., 1966, J. Am. Chem. Soc., 88(21): 5051-5052.
Michel et al., "Specificity of the protein secretory apparatus: secretion of the heat-labile enterotoxin B subunit pentamers by different species of Gram bacteria," Gene 152 (1995) pp. 41-45.
Miele, E. A. et al., 1983, J. Mol. Biol., 171: 281-295.
Mielenz, 2001, Curr. Op. in Micro., 4:324-329.
Mosier et al., "Industrial Scale-Up of pH-Controlled Liquid Hot Water Pretreatment of Corn Fiber for Fuel Ethanol Production," Applied Biochemistry and Biotechnology, vol. 125, 2005, pp. 77-97.
Needleman and Wunsch, J. Mol. Biol. 48: 443 (1970).
Ng et al., 1981, Applied and Environmental Microbiology, 41(6):1337-1343.
Ohta et al., "Purification and Characterization of an Acidophilic Xylanase from Aureobasidium pullulans var. melanigenum and Sequence Analysis of the Encoding Gene," Journal of Bioscience and Bioengineering, vol. 92, No. 3, 262-270, 2001.
Olins, P. O., and Lee, S. C., 1993, Recent advances in heterologous gene expression in *E. coli*. Curr. Op. Biotechnology 4: 520-525.
Ooshima et al., "Simultaneous saccharification and fermentation of cellulose: Effect of ethanol on enzymatic saccharification of cellulose," Department of Applied Chemistry, Faculty of Engineering, Osaka City University, Osaka 558, Japan, Jun. 5, 1984.
Pajunen et al., Microbiology (2005) 151, 1209-1218.
Patel et al., (2006), "Medium and long-term opportunities and risks of the biotechnological production of bulk chemicals from renewable resources: The potential of white biotechnology". The BREW Project. Final Report prepared under the European Commission's GROWTH Programme (DG Research), (publica.fraunhofer.de/eprints/N-48834.pdf).
Database UniProt [Online]. Feb. 10, 2009. XP-002695727. Database accession No. B7DUZ1, 1 page.
Database UniProt [Online]. Feb. 10, 2009. XP-002698982. Database accession No. B7DRM6, 1 page.
Extended Supplementary European Search Report for EP 09 70 3173, dated Apr. 20, 2011, 7 pages.
Extended Supplementary European Search Report for EP 09 82 3952, dated Sep. 20, 2011, 7 pages.
Extended Supplementary European Search Report for EP 09 70 9191, dated Mar. 29, 2012, 6 pages.
Extended Supplementary European Search Report for EP 09 75 5307, dated Apr. 18, 2012, 4 pages.
Extended Supplementary European Search Report for EP 10 74 6882, dated Aug. 27, 2012, 9 pages.
Extended Supplementary European Search Report for EP 09 74 3132, dated Apr. 19, 2013, 4 pages.
Extended Supplementary European Search Report for EP 09 75 5308, dated Jun. 18, 2013, 3 pages.
International Search Report and Written Opinion of the International Search Authority for PCT/US09/32333, mailed Jun. 19, 2009, 9 pages.
International Search Report of the International Searching Authority for PCT/US06/42566, dated Jul. 25, 2008.
PCT International Search Report and Written Opinion of the International Search Authority for PCT/US11/34852, dated Oct. 21, 2011, 12 pages.
PCT International Search Report and Written Opinion of the International Searching Authority for PCT/US09/00442, dated May 18, 2009, 8 pages.
PCT International Search Report and Written Opinion of the International Searching Authority for PCT/US09/34701, dated Jan. 12, 2010, 10 pages.
PCT International Search Report and Written Opinion of the International Searching Authority for PCT/US09/35275, dated Feb. 25, 2010, 13 pages.
PCT International Search Report and Written Opinion of the International Searching Authority for PCT/US09/35331, dated Feb. 23, 2010, 10 pages.
PCT International Search Report and Written Opinion of the International Search Authority for PCT/US09/35307, dated Jun. 10, 2010, 10 pages.
PCT International Search Report and Written Opinion of the International Search Authority for PCT/US10/25521, dated Jul. 14, 2010, 12 pages.

(56) References Cited

OTHER PUBLICATIONS

Supplemental European Search Report for EP 06 82 7231, dated Nov. 12, 2009, 6 pages.
Kraus et al., "Identification of a co-repressor binding site in catabolite control protein CcpA," Molecular Microbiology (1998) 30(5), 955-963.
EC-PDB Database. EC 3.2.1.23 Beta Galactosidase. Hydrolysis of terminal non-reducing beta-D-galactose residues in beta-D-galactosides, www.ebi.ac.uklthornton-srv/databases/cgi-bin/enzymes/GetPage.pl?ec_numbers=3.2.1.23, accessed Jan. 28, 2012.
EC-PDB Database, EC 3.2.1.55 Alpha-N-arabinofuranosidase, Hydrolysis of terminal non-reducing alpha-L-arabinofuranoside residues in alpha-L-arabinosides, www.ebi.ac.uklthornton-srv/databases/cgi-bin/enzymes/GetPage.pl?ec_number=3.2.1.55, accessed Jan. 28, 2012.
EC-PDB Database, EC 3.2.1.21 Beta Glucosidase, Hydrolysis of terminal, non-reducing beta-D-Giucosyl Residues with release of Beta-D-glucose, www.ebi.ac.uklthornton-srv/databases/cgi-bin/enzymes/GetPage.pl?ec_number=3.2.1.21, accessed Jan. 28, 2012.
EC-PDB Database, EC 3.2.1.91 Cellulose 1 ,4-beta-cellobiosidase (non-reducing end), Hydrolysis of (1->4)-beta-D-glucosidic linkages in cellulose and cellotetraose, releasing cellobiose from the non-reducing ends of the chains, www.ebi.ac.uklthornton-srv/databases/cgi-bin/enzymes/GetPage.pl?ec_number=3.2.1.91, accessed Jan. 28, 2012.
EC-PDB Database, EC 3.2.1.37 Xylan 1 ,4-beta-xylosidase, Hydrolysis of (1->4)-beta-D-xylans, to remove successive D-xylose residues from teh non-reducing termini, www.ebi.ac.uklthornton-srv/databases/cgi-bin/enzymes/GetPage.pl?ec_number=3.2.1.37, accessed Jan. 28, 2012.
PCT International Search Report and Written Opinion of the International Searching Authority for PCT/US10/51095, dated Dec. 2, 2010, 11 pages.
Pearson and Lipman, Proc. Natl. Acad. Sci. (U.S.A.) 85: 2444 (1988).
Perlack et al., "Biomass as Feedstock for a Bioenergy and Bioproducts Industry: The Technical Feasibility of a Billion-Ton Annual Supply," USDA and DOE, Apr. 2005, 78 pages.
Peyton et al., "Biotransformation of Toxic Organic and Inorganic Contaminants by Halophilic Bacteria," Halophilic Microorganisms, Antonio Ventosa (Ed.), Springer, 2004, pp. 315-331.
Ragauskas et al., "The Path Forward for Biofuels and Biomaterials," Science, Jan. 27, 2006, vol. 311, pp. 484-4589.
Ramos et al., "Biomechanical and Biochemical Pulping of Sugarcane Bagasse with Ceriporiopsis subvermispora Fungal and Xylanase Pretreatments," J. Agric. Food Chem. 2001, 49, 1180-1186.
Saeman et al., "Quantitative Saccharification of Wood and Cellulose," Industrial and Engineering Chemistry, Jan. 1945, vol. 17, No. 1, pp. 35-37.
Saha et al., "Dilute Acid Pretreatment, Enzymatic Saccharification, and Fermentation of Rice Hulls to Ethanol," Biotechnol. Prog. 2005, 21, 816-822.
Sanchez-Pescador, R., 1988, J. Clin. Microbiol., 26(10): 1934-1938.
Sa-Pereira et al., "Rapid production of thermostable cellulose-free xylanase by a strain of Bacillus subtilis and its properties," Enzyme and Microbial Technology, 30 (2002) 924-933.
Schafer et al., "X-ray Structures of the Maltose-Maltodextrin-binding Protein of the Thermoacidophilic Bacterium Alicyclobacillus acidocaldarius Provide Insight into Acid Stability of Proteins," J. Mol. Biol. 2004, 335:261-274.
Schäffer, C. et al., 2001, Prokaryotic glycosylation. Proteomics, 1: 248-261.
Scheffel et al., "Functional reconstitution of a maltrose ATP-binding cassette transporter from the thermoacidophilic gram-positive bacterium Alicyclobacillus acidocaldarius," Biochem Biophy Acta, 2004, 1656(1):57-65.
Schell et al., "Dilute-Sulfuric Acid Pretreatment of Corn Stover in Pilot-Scale Reactor, Applied Biochemistry and Biotechnology," vol. 105-108, 2003, pp. 69-85.
Schneider, "Import of solutes by ABC transporters—the maltose system. ABC protein: from bacteria to man," Elsevier Science, London 2003, p. 157-185. [Retrieved from the Internet on Jan. 24, 2010; <http://www2.hu-berlin.de/biologie/baktphys/paper/1_ABC/r.
Schwarz, Wolfgang H., "A list of cellulolytic bacteria," Technische Universitat Munchen, Apr. 24, 2003, 8 pages.
Schwermann, B. et al., 1994, Purification, properties and structural aspects of a thermoacidophilic a-amylase from Alicyclobacillus acidocaldarius ATCC 27009, insight into acidostability of proteins. Eur. J. Biochem. 226: 981-991.
Seffernick et al. "Melamine Deaminase and Atrazine Chlorohydrolase: 98 Percent Identical but Functionally Different" Journal of Bacteriology vol. 183, No. 8, Apr. 2001 pp. 2045-2410 (6 pages).
Shallom et al., "Microbial hemicellulases," Current Opinion in Microbiology, Current Biology Ltd, GB, vol. 6, No. 3, Jun. 1, 2003, pp. 219-228.
Simpson et al., "An extremely Thermostable xylanase from the thermophilic eubacterium Thermotoga," Biochem. J. (1991) 277, 413-417.
Smook, G.A., "Handbook for Pulp & Paper Technologists," Tappi Pr; 2nd Ed. (Jun. 1992) pp. 65-88.
Subramaniyan et al., "Cellulase-free xylanases from Bacillus and other microorganisms," FEMS Microbiology Letters 183 (2000) 1-7.
Sunna et al., "Glycosyl hydrolases from hyperthermophiles," Extremophiles (1997) 12-13.
Techapun et al., "Production of a cellulose-free xylanase from agricultural waste materials by a thermotolerant Streptomyces sp.," Biotechnology Letters 23: 1685-1689, 2001.
Thompson et al., "Comparison of Pretreatment Methods on the Basis of Available Surface Area," Bioresource Technology 39 (1992) 155-163.
Thompson et al., "In Vitro Degradation of Natural Insoluble Lignin in Aqueous Media by the Extracellular Peroxidases of Phanerochaete chrysosporium," 1998 John Wiley & Sons, Inc. pp. 704-717.
Thompson et al., "Measurement of fumonsins in corn with a fiber-optic fluoroimmunosensor," SPIE vol. 2980, (2010) pp. 532-538.
Thompson et al., "Preliminary Investigation of Fungal Bioprocessing of Wheat Straw for Production of Straw-Thermoplastic Composites," Applied Biochemistry and Biotechnology, vol. 105-108, 2003, pp. 423-436.
Thompson et al., "Purification and Characterization of a Novel Thermo-Alkali-Stable Catalase from Thermus brockianus," Biotechnol. Prog. 2003, 19, 1292-1299.
Thompson et al., "Thermoacidophilic Cellulases and Hemicellulases from Alicyclobacillus acidocaldarius," Idaho National Laboratory, 2006, 1 page.
Thompson, et al., "Chapter 31: Changes in the Rate of Enzymatic Hydrolysis and Surface Area Available to Cellulase with Pretreatment Methods," Biotechnology in Pulp and Paper Manufacture: Applications and Fundamental Investigations. Proceedings of the Fourth International Conference on Biotechnology in the Pulp and Paper Industry (ICBPPI), May 16-19, 1989,Raleigh, NC and Myrtle Beach, SC, USA. Kirk, T.K. and Chang, H.M. (eds.). Butterworth-Heinemann, Boston, 1990, pp. 329-338.
Tsao, G.T., "Bacterial Hydrolysis: A Review," Anaerobic Digestion and Carbohydrate Hydrolysis of Waste, Ferrero et al. (eds.), Elsevier Applied Science Publishers, London, 1984, pp. 83-99.
Tsao, GT, MR Ladisch, and HR Bungay, 1987. Biomass Refining, In Advanced Biochemical Engineering, Wiley Interscience, N.Y., 79-101.
Turner et al., "Potential and utilization of thermophiles and thermostable enzymes in biorefining," Microbial Cell Factories, Biomed Central, London, NL, vol. 6, No. 1, Mar. 15, 2007, p. 9.
Uhl et al., "The first description of an archaeal hemicellulase: the xylanase from Thermococcus zilligii strain AN1," Extremophiles (1999) 3:263-267.
Uniprot Direct submission Q9RHZ5_ALIAC, "Putative maltose transport membrane protein malF," Nov. 13, 2007. [Retrieved from the Internet Jan. 22, 2010: <http://www.uniprot.org/uniprot/Q9RHZ5.txt?version=30?].
UniProtKB/TrEMBL Q9JRQ1 [online]. Oct. 1, 2000. Available on the Internet at <<URL://http://www.uniprot.org/uniprot/Q9JRQ1>>.
Upreti et al., 2003, Bacterial glycoproteins: Functions, biosynthesis and applications. Proteomics, 3: 363-379.

(56) References Cited

OTHER PUBLICATIONS

Urdea, M. S., 1988, Nucleic Acids Research, II: 4937-4957.
Vieille and Zeikus, 2001, Micro. and Mol. Biol. Rev., vol. 65, No. 1, p. 1-43.
Viikari et al., "Xylanases in bleaching: From an idea to the industry," FEMS Microbiology Reviews 13 (1994) 335-350.
Walker, G. T. et al., 1992, NAR 20: 1691-1696.
Walker, G.T. et al., 1992, PNAS. USA, 89:392-396.
Walseth, Curtis S., Occurrence of Cellulases in Enzyme Preparations from Microorganisms, TAPPI vol. 35, No. 5, May 1952, pp. 228-233.
Ward et al., "Characterization of a new bacteriophage which infects bacteria of the genus Acidiphilium," Journal of General Virology (1993) 74: 2419-2425.
Ward et al., "Electrotransformation of Acidophilic, Heterotrophic, Gram-negative Bacteria," Electrotransformation of Bacteria, Natalie Eynard, Justin Teissie (eds.), Springer (2000) pp. 94-103.
Whisstock et al. "Prediction of Protein Function from Protein Sequence and Structure" Quarlty Reviews of Biophysics 36, 3 (2003) pp. 307-340 (35 pages).
Witkowski et al. "Conversion of a β-Ketoacyl Synthase to a Malonyl Decarboxylase by Replacement of the Active-Site Cysteine with Glutamine" American Chemical Society, Biochemistry, vol. 38, No. 36, 1999 pp. 11643-11650 (8 pages).
Wright et al., "Ethanol from Biomass by Enzymatic Hydrolysis," Chemical Engineering Progress, Aug. 1988, pp. 62-74.
Yuan et al., Expression of acidophilic alpha-amylase from Alicyclobacillus acidocaldarius, Sheng Wu Gong Cheng Xue Bao, Jan. 2005, 21(1):78-83. Abstract only.

FIG. 1

```
ref|YP_001210812.1|    ------------------------------------------MKEKEVILTVNGLKKL
ref|YP_001111548.1|    ------------------------------------------MKEKDVMLTVTGLKQL
ref|ZP_01666866.1|     ------------------------------------------MAEKQTILTVDGLKKI
RAAC01465              MTIPFFRTMVSSMAHSARAARDGMHASRYSGSLEAPTGSKGETAMADKEVLLTPEGLRKL
ref|YP_001039288.1|    -------------------------------------------NKEVVLTYEGLQKL
ref|ZP_01576004.1|     ------------------------------------------MSAKEVVLTYEGLKKL
                                                                  *..:**  **:::

ref|YP_001210812.1|    ESELELLKSVKRREVAERIKQAIEFGDITENSEYEDAKNEQAFIEGRILTLEKMLRNAKI
ref|YP_001111548.1|    EDELEQLKTVKRRQVAERIKQAIEFGDISENSEYEDAKNEQAFIEGRILTLEKMLRNAKI
ref|ZP_01666866.1|     EQKLEHLKSVRRREVAERIKQAIEFGDISENSEYEDAKNEQAFIEGEILTLEKMLRNAKV
RAAC01465              EEELELLKSVKRREVAERIKVAISYGDISENSEYEDAKNEQAFIEGRIMTLEKQLRNARV
ref|YP_001039288.1|    EQELENLKTVKRREVAERIKQALSFGDISENSEYDEAKNEQAYIEGRIFQLENMLKNAKV
ref|ZP_01576004.1|     EEELEFLRGTKRKEVAERIKQALSFGDISENSEYDEAKNEQAQVEGRIVQLESMLKHARI
                       *.:** *:  .:*::****** *:.:***:*****:.****** :**.*. **. *::*::

ref|YP_001210812.1|    IDDENIGTEVVSIGSTVLLKDLECGDEYKYTIVGSAEADPGANKISNESPVGRAILGQPK
ref|YP_001111548.1|    IDDENLDNEVVSLGSKVILKDLEFGDELEYSIVGSVEADPDANKISNESPVGRAILGQSK
ref|ZP_01666866.1|     IDEGEISTDTVTIGSTVVLKDLEFGDELEYTLVGSAEADPMEFKISNESPVGQAIMGQKV
RAAC01465              INEDEVDTNVVSIGSTVKVLDLDLDEEVEYTIVGSAEANPAENKISNESPVGKALLGKQI
ref|YP_001039288.1|    IDEEDIQTDVVSIGSKVKVLDMEFDEEVEYYIVGSTEADPSQYKISNESPVGKALIGGKI
ref|ZP_01576004.1|     IDEDEVNTDVVSIGSKVRIFDIEFDEEVEYLIVGSTEANPLKSKISNESPVGAALIGHTK
                       *::  ::..:.*::**.* :  *::  .:* :* :*.:*    ********* *::* ref|YP_001210812.1|    GSVVEVTVPAGQLKYQIIDILR
ref|YP_001111548.1|    GSVVEVNVPAGILKYEIVDILR
ref|ZP_01666866.1|     GSVVEVNVPAGILKYKILEIKR
RAAC01465              GSIVEVNVPAGVIKFKILEIKR
ref|YP_001039288.1|    GDIVEVTVPDGVIKFKILEIRK
ref|ZP_01576004.1|     GETVEVQVPDGVLKFKILEISK
                       *. *** ** * :*::*::* :
```

FIG. 2

```
ref|YP_145986.1|          ---------------MIEIEKPKIETVELSEDAKYGKFVVEPLERGYGTTLGNSLRRILL
ref|YP_001124263.1|       ---------------MIEIEKPKIETVELSEDAKYGKFVVEPLERGYGTTLGNSLRRILL
ref|NP_241028.1|          ---------------MIEIEKPVIETIEISEDAKYGKFVVEPLERGYGTTLGNSLRRILL
RAAC00371                 ---------------MIEIEKPRIEIVEQTGD--YGKFVCEPLERGYGTTLGNSLRRILL
ref|YP_001210899.1|       ---------------MLEIEKPKIEIVEMSDDNTYGKFVVEPLERGYGITLGNSLRRILL
ref|YP_001111617.1|       ---------------MLEIEKPKIEIVEQSEDNTYGKFVVEPLERGYGITLGNSLRRILL
                                         *:*** .:*.:*   *** **** ********* ref|YP_145986.1|          SSLPGAAVTSVQIDGVLHEFSTIDGVVEDVTAIILNIKKLALKIYSDEEKTLEIDVQGEG
ref|YP_001124263.1|       SSLPGAAVTSVQIDGVLHEFSTIEGVVEDVTAIILNVKKLALKIYSDEEKTLEIDVQGEG
ref|NP_241028.1|          SSLPGAAVTSVQIDGVLHEFSTIEGVVEDVTTIVLNLKQLALKIYSDEDKTLEIDTQGEG
RAAC00371                 SSIPGAAVRSVKIEGVLHEFSTIPGVVEDVTEIILNLKRLSLKIHSDEEKTLIIDAVGPG
ref|YP_001210899.1|       SSLPGAAVTSVKIDGVLHEFSTIPGVVEDVTDIILNLKNLCLKIYGDEEKVLRVEASTEG
ref|YP_001111617.1|       SSLPGAAVTSVKIEGVLHEFATVPGVQEDVTDIILNLKNLCLKIHSDEEKVLRVEAQTEG
                          :* :*:******.*:.  ** *:**:*.*.*:.:*.*  ::.  * ref|YP_145986.1|          VVTAADITHDSDVEILNPDLHIATLAEGGRLRMRMTAKRGRGYVPAEANKREDQPIGVIP
ref|YP_001124263.1|       VVTAADITHDSDVEILNPDLHIATLAEGGRLRMRMTARRGRGYVPAEANKREDQPIGVIP
ref|NP_241028.1|          VVTAGDLTHDSDVDVLNPDLHIATLTTGAHLRMRITAKRGRGYVPAEGNKSDELAIGVIP
RAAC00371                 VVTAGDIRADSDVDIMNPDLHIATLTEGARIYMEMRAGRGRGYVPAHRNKPEEQEIGLIP
ref|YP_001210899.1|       VVKAKDIIHDADVEIMNPDLTIATLAENARLYMEITVAKGRGYVSAERNKKGDHIIGVIP
ref|YP_001111617.1|       PVTAGDIIHDADVEILNPDLHLATLDTGGRLFMEISVNLGRGYSSAEKNKKGEHIIGVIP
                           *.* *:.  *:**::**** :***   . :: *.:   :****.*. **   **:**

ref|YP_145986.1|          IDSIYTPVSRVSYQVENTRVGQVTDYDKLTIDVWTDGSIGPKEAISLGAKILTEHLNIFV
ref|YP_001124263.1|       IDSIYTPVSRVSYQVENTRVGQVTDYDKLTIDVWTDGSIGPKEAISLGAKILTEHLNIFV
ref|NP_241028.1|          IDSIYTPVSRVNYQVENTRVGQVTNYDKLTLDVWTDGSIRPEEAVSLGAKILTEHLNIFV
RAAC00371                 IDSLYSPISRVNFSVENTRVGQITDYDKLTLEVWTDGSVAPDEAVSIGAKILTEHLMLFV
ref|YP_001210899.1|       VDSVFTPVRKVNYTVENTRVGQITDYDKLTLEVWTDGSIRPDEATSLSAKILSEHLRLFI
ref|YP_001111617.1|       IDSIYTPVRRVNYNVENTRVGQITDYDKLTLEVWTNGSIRPDEATSLSAKILSEHLRLFI
                          :**::**:. :*.: .********:*:*****:.***:**   *:.****:***.:*:

ref|YP_145986.1|          GLTDEAQNAEIMVEKEDDQKEKVLEMTIEELDLSVRSYNCLKRAGINTVQELTQKTEEDM
ref|YP_001124263.1|       GLTDEAQNAEIMVEKEDDQKEKVLEMTIEELDLSVRSYNCLKRAGINTVQELTQKTEEDM
ref|NP_241028.1|          GLTDQAQNAEIMVEKEEDQKEKVLEMTIEELDLSVRSYNCLKRAGINTVQELTQKTEEDM
RAAC00371                 GLTDRARDTDLMVEKENAHNDKILDMPIEELDLSVRSYNCLKRAGINTVAELCAKSEEEM
ref|YP_001210899.1|       GLTETVSDVEIMVEKEEEHKDRVLEMTIEELDLSVRSYNCLKRAGINTVEELIQRNEEDM
ref|YP_001111617.1|       GLTETVNDVEIMVEKEEEQKDKILEMTIEELDMSVRSYNCLKRAGINTVEELIQRNEEDM
                          *:  .  ::::***: :::::*:*.*.**.************   :.:* ref|YP_145986.1|          MKVRNLGRKSLEEVKAKLAELGLSLRKDD
ref|YP_001124263.1|       MKVRNLGRKSLEEVKAKLAELGLSLRKDD
ref|NP_241028.1|          MKVRNLGRKSLEEVQEKLGELGLGLRKEE
RAAC00371                 MKVRNLGRKSLEEVVEKLHALGLSLRKDD
ref|YP_001210899.1|       MKVRNLGKKSLEEVINKLHELGLSLRKDD
ref|YP_001111617.1|       MKVRNLGKKSLEEVINKLHELGLSLRQED
                          *******:******  **  ***.**::: 
```

FIG. 3A

```
ref|NP_240992.1|        ---MTGQLIQYGRHRQRRSYARINEVLELPNLIEIQTASYQWFLDEGLREMFQDISPIQD
ref|YP_173646.1|        ---MTGQLIQYGRHRQRRSYARINEVLELPNLIEIQTASYQWFLDEGLREMFQDISPIQD
ref|YP_001124230.1|     ---MTGRLVQYGRHRQRRSYARISEVLELPNLIEIQTSSYQWFLDEGLREMFKEISPIED
ref|YP_145951.1|        ---MTGRLVQYGRHRQRRSYARISEVLELPNLIEIQTSSYQWFLDEGLREMFREISPIED
ref|ZP_02326346.1|      ---LAGHLVQYGR-RKRRTYARINEVLEIPNLIEIQQKSYQWFLDEGLREMFQDISPIQD
RAAC00408               MTVLQGHMVKYGW-AERRSYARIREVLDLPNLIEIQQKSYEWFLREGLRETFADISPITD
                          : *:::*   :*:.:*   *.:******   :* *** * :**** * ref|NP_240992.1|        FTGNLVLEFIDYSLGEPKYPVDESKERDVTYAAPLRVKVRLINKETGEVKEQEVFMGDFP
ref|YP_173646.1|        FTGNLVLEFIDYSLGEPKYPVDESKERDVTFAAPLRVKVRLINKETGEVKEQEVFMGDFP
ref|YP_001124230.1|     FSGNLSLEFIDYSLGEPKYSVEEAKERDVTYAAPLRVKVRLINKETGEVKEQDVFMGDFP
ref|YP_145951.1|        FSGNLSLEFIDYSLGEPKYTVEEAKERDVTYAAPLRVKVRLINKETGEVKEQDVFMGDFP
ref|ZP_02326346.1|      FTGNLVLEFIDYSLGEPKYTVDDSKERDVTYAAPLRVKVRLINKETGEVKEQEVFMGDFP
RAAC00408               FTGNLVLEFVDYSLGEPKYDVEESKERDVTYAAPLRVKVRLLNKETGEVKEQEVFLGDFP
                        *:* *:********* *::.:***:*******:********:*:**** ref|NP_240992.1|        LMTDTGTFIINGAERVIVSQLVRSPSVYYSEKIDKNGKKGYTATVIPNRGAWLELETDAK
ref|YP_173646.1|        LMTETGTFIINGAERVIVSQLVRSPSVYYSQKLDKNGKKGFTATVIPNRGAWLELETDAK
ref|YP_001124230.1|     LMTETGTFIINGAERVIVSQLVRSPSVYYSDKVDKNGKRGYSATVIPNRGAWLEYETDAK
ref|YP_145951.1|        LMTETGTFIINGAERVIVSQLVRSPSVYYSDKVDKNGKRGYSATVIPNRGAWLEYETDAK
ref|ZP_02326346.1|      IMTETGTFIINGAERVIVSQLVRSPSVYYNTKVDKNGKKAFTATVIPNRGAWLELETDAK
RAAC00408               LMTETGTFIINGAERVIVSQLVRSPSVYYSSKIDKNGKRTFAATVIPNRGAWLEFETDAK
                        ::********************.  *:***:  ::********* *** ref|NP_240992.1|        DIVYVRIDRTRKIPVTVLLRALGFGSDQEIIDLLGEDEYLRNTLEKDNTDSAEKALLEIY
ref|YP_173646.1|        DIVYVRIDRTRKIPVTVLLRALGFGSDQEIVDLLGENEYLRNTLEKDNTDSTDKALLEIY
ref|YP_001124230.1|     DVVYVRIDRTRKLPVTVLLRALGFSSDQEIIDLLGDNEYLRNTLEKDNTDSTEKALIEIY
ref|YP_145951.1|        DVVYVRIDRTRKLPVTVLLRALGFSSDQEIIDLLGDNEYLRNTLEKDNTDSTEKALIEIY
ref|ZP_02326346.1|      DIIYVRIDRTRKIPVTVLLRALGFTDAEILDLLGDDEYIRNTLDKDNTDSTDKALIEIY
RAAC00408               DVVYVRIDRTRKLPITVLLRALGLSSDAEIIELLGEDEYLQNTLDKDTTDSTERALIEIY
                        *::*********:*:********::.:* ::*:::*.*::*** ref|NP_240992.1|        ERLRPGEPPTVENAKSLLDSRFFDPKRYDLANVGRYKVNKKLHIKNRLFNQRLAETLIDP
ref|YP_173646.1|        ERLRPGEPPTVENAKSLLESRFFDPKRYDLANVGRYKINKKLHIKNRLFNQRLAEKLVDP
ref|YP_001124230.1|     ERLRPGEPPTLENAKSRFFDPKRYDLASVGRYKINKKLHIKNRLFNQRLAETIADP
ref|YP_145951.1|        ERLRPGEPPTLENAKNLLASRFFDPKRYDLASVGRYKINKKLHIKNRLFNQRLAETIIDP
ref|ZP_02326346.1|      ERLRPGEPPTLDNARSLLYARFFDPKRYDLANVGRYKINKKLHIKNRLFNQRLAETLVHP
RAAC00408               ERLRPGEPPTVENARALLASRFFDPKRYDLAAVGRYKINKKLHLKNRLLNQRLAETLVDE
                        **********::**: ** :***********  *****:*****::*****:******.:  .

ref|NP_240992.1|        ETGEVIAEEGSIIDRRTLDRILPYLENNVGFRTVRMSGGVVEEDEVRLQSVKIYAPDDQD
ref|YP_173646.1|        ETGEVLAEEGTLLDRRTLDKLIPHLEKNVGFRTARTSGGVLEESDVEIQSVKIYVADDYE
ref|YP_001124230.1|     ETGEIIAEAGTMIDRRTLNRLLPYLEKGAGLQTYRPTEGVAD-GQISVQTVKIYAPNDPD
ref|YP_145951.1|        ETKEVIAEAGAMIDRRTLNRLLPYLEKGVGLQTYRPAEGVVDGD-ISVQTIKIYAPNDPD
ref|ZP_02326346.1|      ETGEIIAEAGQLVDRRLLDEILPCLEEGVGFKEYSVPNGVLESDHIPMQTIDVFSP--IE
RAAC00408               ETGEIIAEAGTVLDRRTLDRIIPRLSGKVGRFTIRGTRDLFEQDEIPLQMVKIFSP--AE
                        ** *::** *  ::*** *::::* *.    .*         ..: :..:* :.:: .   :

ref|NP_240992.1|        GEHVIRVIGNGLVEKEIKHITPADIIASINYFFNLLHSVGGTDDIDHLGNRRLRSVGELL
ref|YP_173646.1|        GERVISVISNGMVERDVKHIAPADIIASISYFFNLLHGVGDTDDIDHLGNRRLRSVGELL
ref|YP_001124230.1|     NEKVINIIGNGFIAEDVKHITPADIIASISYFFNLLHGVGDTDDIDHLGNRRLRSVGELL
ref|YP_145951.1|        GEKVINVIGNGFIAEDVKHITPADIIASISYFFNLLHGVGDTDDIDHLGNRRLRSVGELL
ref|ZP_02326346.1|      DGKVVKVISNGVIDKNVKNITPADIISSINYFINLLHGIGNTDDIDHLGNRRLRSVGELL
RAAC00408               DGKVLHVISNGELPADVKYITPSDIIAAVSYFFNLLRGVGTTDDIDHLGNRRLRSVGELL
                        . :*: :*.**   :   ::* *:*:***:::.**::*:..:* *******************
```

FIG. 3B

```
ref|NP_240992.1|         QNQFRIGLSRMERVVRERMSIQDPNSITPQALINIRPVIASIKEFFGSSQLSQFMDQTNP
ref|YP_173646.1|         QNQFRIGLSRMERVVRERMSIQDPNVITPQALINIRPVIASIKEFFGSSQLSQFMDQTNP
ref|YP_001124230.1|      QNQFRIGLSRMERVVRERMSIQDANTITPQQLINIRPVIAAIKEFFGSSQLSQFMDQTNP
ref|YP_145951.1|         QNQFRIGLSRMERVVRERMSIQDTNTITPQQLINIRPVIAAIKEFFGSSQLSQFMDQTNP
ref|ZP_02326346.1|       QNQFRIGLSRMERVVRERMSIQDANVITPQALINIRPVIASIKEFFGSSQLSQFMDQTNP
RAAC00408                QNQFRIGLSRMERVVRERMSIQDASAITPQALINIRPVIAAIKEFFGSSQLSQFMDQTNP
                         ******************..   ****.:****************** ref|NP_240992.1|         LAELTHKRRLSALGPGGLTRERAGFEVRDVHYSHYGRMCPIETPEGPNIGLINSLSTYAK
ref|YP_173646.1|         LAELTHKRRLSALGPGGLTRERAGMEVRDVHYSHYGRMCPIETPEGPNIGLINTLSSYAK
ref|YP_001124230.1|      LAELTHKRRLSALGPGGLTRERAGFEVRDVHYSHYGRMCPIETPEGPNIGLINSLSTYAK
ref|YP_145951.1|         LAELTHKRRLSALGPGGLTRERAGFEVRDVHYSHYGRMCPIETPEGPNIGLINSLSTYAK
ref|ZP_02326346.1|       LAELTHKRRLSALGPGGLTRERAGFEVRDVHHSHYGRMCPIETPEGPNIGLINSLSTFAR
RAAC00408                LAELTHKRRLSALGPGGLTRERAGFEVRDVHYSHYGRMCPIETPEGPNIGLINSLSTYAC
                         *********************:**:*******************.::* ref|NP_240992.1|         VNEFGFMETPYRRVDPETGKVTAQIDYLTADEEDNYVVAQANMKLAEDGSFIDENIIARF
ref|YP_173646.1|         VNEFGFMETPYRRVDPETGKVTSRIDYLTADEEDNYVVAQANAKLNDDGSFVDDNIIARF
ref|YP_001124230.1|      VNKFGFIETPYRRVDPETGKVTDQIDYLTADEEDNYVVAQANVPLAEDGTFLEENVIARF
ref|YP_145951.1|         VNKFGFIETPYRRVDPETGRVTDQIDYLTADEEDNYVVAQANVPLAEDGTFLEENVVARF
ref|ZP_02326346.1|       INEYGFIEAPYRRVDPKTGVVTDEIVYMTADEEDNYVVAQANAELNEDGTFAADNVYVRY
RAAC00408                VNEYGFIETPYRRVDPETGVVTDQIDYLTADEEENYLIAQANEPLTEDGHFVAEEITVRS
                         :*:.**:*.*****.  ** .*  *:.*** : .:*** * .** *    ::: .* ref|NP_240992.1|         RGENIVVSRDRVDYMDVSPKQVVSAATSCIPFLENDDSNRALMGANMQRQAVPLLVPEAP
ref|YP_173646.1|         RGENTVVPCDRVDYMDVSPKQVVSAATSCIPFLENDDSNRALMGANMQRQAVPLLVPEAP
ref|YP_001124230.1|      RGENIVVKRDRVDYMDVSPKQVVSAATACIPFLENDDSNRALMGANMQRQAVPLLQPEAP
ref|YP_145951.1|         RGENIVVKRDRVDYMDVSPKQVVSAATACIPFLENDDSNRALMGANMQRQAVPLLEPEAP
ref|ZP_02326346.1|       KDEILTLPKERVDYMDVSPKQVVSVATALIPFLENDDSNRALMGSNMQRQAVPLLMPKAP
RAAC00408                REDVITVSRDRIDYMDVSPKQVVSVATALIPFLENDDANRALMGSNMQRQAVPLLVTDSP
                         : :   .:  .:  :*:**********.:  ******:***:******** ...:* ref|NP_240992.1|         IVGTGMEHVSAKDSGAAIVSKHRGIVERVTAKEIWVRRLEEVDGKEIKGDLDKYRLQKFI
ref|YP_173646.1|         LVGTGMEHVSAKDSGAAVVSKYAGIVERVTAKEIWVRRIEEVDGKETKGDLDKYKLQKFV
ref|YP_001124230.1|      IVGTGMEYVSAKDSGAAIICKHRGIVERVEAKEIWVRRLIEVDGKEVKGDLDKYRLLKFV
ref|YP_145951.1|         IVGTGMEYVSAKDSGAAIICKHRGIVERVEAKEIWVRRLIEVDGKEVKGDLDKYRLLKFV
ref|ZP_02326346.1|       LVGTGMEYKAAKDSGVCVVAKHDGIIEKVSGNEIWLRRQEEVDGRLVSGNITKFKLHKFM
RAAC00408                LVGTGMEYQAAKDSGVCVVSKHNGVVERVTAREIWVREEAVVDGQVVKGNVHKYKLIKFA
                         :****:  :***..::..*: *:::*:*  ..***:*.    ***:  .*:: *::* ** ref|NP_240992.1|         RSNQGTSYNQRPIVKEGDVVEKREILADGPSMEKGEMALGRNVLVGFMTWEGYNYEDAII
ref|YP_173646.1|         RSNQGTSYNQRPIVREGDRIEKREILADGPSMEMGEMALGRNVLVAFMTWDGYNYEDAII
ref|YP_001124230.1|      RSNQGTCYNQRPIVKKGDIVEKGEILADGPSMDKGELALGRNVLVAFMTWDGYNYEDAII
ref|YP_145951.1|         RSNQGTCYNQRPIVKKGDIVEKGEILADGPSMDKGELALGRNVLVAFMTWDGYNYEDAII
ref|ZP_02326346.1|       RSNQGTCINQRPLVLEGQRVKAGDILADGPSTEQGELALGRNVVVAFMTWEGYNYEDAIL
RAAC00408                RSNQNTCLNQRPIVREGDRVKVGDILADGPATQNGELALGRNVLVAFMTWEGYNYEDAIL
                         ****.*. ****:*  :*:  :: :.***:****:  :  **:******.*.****:********:

ref|NP_240992.1|         LSERLVKDDVYTSIHIEEYESEARDTKLGPEEITRDIPNVGEDALRNLDERGIIRVGAEV
ref|YP_173646.1|         LSERLVKDDVYTSIHIEEYESDARDTKLGPEEITRDIPNVGEDALRNLDERGIIRIGAEV
ref|YP_001124230.1|      MSERLVKEDVYTSIHIEEYEAESRDTKLGPEEITRDIPNVGEDALKNLDERGIVRIGAEV
ref|YP_145951.1|         MSERLVKEDVYTSIHIEEYEAESRDTKLGPEEITRDIPNVGEDALKNLDERGIVRIGAEV
ref|ZP_02326346.1|       LSEKLVKEDVYTSIHIEEYESEARDTKLGPEEITRDIPNVGEDALKNLDERGIIRVGAEI
RAAC00408                ISEKMVKEDVYTSIHIEEYEIEARDTKLGPEEITRDIPNVGEDALKNLDERGIIRIGAEI
                         :**::**:***********  ::*******************:******.*:***:
```

FIG. 3C

```
ref|NP_240992.1|        KDGDILVGKVTPKGVTELTAEERLLHAIFGEKAREVRDTSLRAPHGGDGIVLDVKIFNRE
ref|YP_173646.1|        KDGDILVGKVTPKGVTELTAEERLLHAIFGEKAREVRDTSLRAPHGGDGIVLDVKIFNRE
ref|YP_001124230.1|     KDGDLLVGKVTPKGMTELTAEERLLHAIFGEKAREVRDTSLRVPHGGGGIVLDVKVFNRE
ref|YP_145951.1|        KDGDLLVGKVTPKGMTELTAEERLLHAIFGEKAREVRDTSLRVPHGGGGIVLDVKVFNRE
ref|ZP_02326346.1|      GAGDILVGKVTPKGVTELTAEERLLHAIFGEKAREVRDTSLRVPHGTDGIVVDVKVFTHE
RAAC00408               TTNDILVGKVTPKGVTELTAEERLLHAIFGEKAREVRDTSLRVPHGGAGIVVDVKVFTRE
                        .*:******:***********************.*   *:*:*..:* ref|NP_240992.1|        DGDELPPGVNQLVRVYIVQKRKIHEGDKMAGRHGNKGVISRILPEEDMPYLPDGTPIDIM
ref|YP_173646.1|        DGDELPPGVNQLVRVYIVQKRKINQGDKMAGRHGNKGVISRILPEEDMPFLPDGTPVDIM
ref|YP_001124230.1|     DGDELPPGVNQLVRVYIVQKRKISEGDKMAGRHGNKGVISRILPEEDMPFLPDGTPIDIM
ref|YP_145951.1|        DGDELPPGVNQLVRVYIVQKRKISEGDKMAGRHGNKGVISRILPEEDMPFLPDGTPIDIM
ref|ZP_02326346.1|      NGDELPPGVNQLVRVYIAQKRKISQGDKMAGRHGNKGVIARILPEEDMPFLPDGTPVEVV
RAAC00408               NGDELPAGVNQLVRVYVAQKRKISEGDKMAGRHGNKGVVARILPEEDMPFLEDGTPVEIV
                        :****.*********:.*****.:*************::.********:* ****::::

ref|NP_240992.1|        LNPLGVPSRMNIGQVLELHLGMAARRLGLHVASPVFDGASEEDVWATLEEAGMARDGKTI
ref|YP_173646.1|        LNPLGVPSRMNIGQVLELHLGMAARKLGIHVASPVFDGASEEDVWGTLEEAGMARDGKTI
ref|YP_001124230.1|     LNPLGVPSRMNIGQVFELHLGMAAKKLGLHIASPVFDGATEEDVWNILEEAGMARDAKTV
ref|YP_145951.1|        LNPLGVPSRMNIGQVFELHLGMAAKKLGLHIASPVFDGATEEDVWNILEEAGLARDAKTV
ref|ZP_02326346.1|      LNPLGVPSRMNIGQVLEVHLGMAAKQLGIHVATPVFDGAHEYDVFDTMEEAGMQRNGKTK
RAAC00408               LNPLGVPSRMNIGQVLETHLGMAAKVLGLKMATPVFDGAKPEDVFETLREAGLPEDGKQV
                        ***************:* ****: ::*:**  :  :.***: .:.* ref|NP_240992.1|        LYDGRTGEPFDNRVSVGIMYMIKLAHMVDDKLHARSTGPYSLVTQQPLGGKAQFGGQRFG
ref|YP_173646.1|        LYDGRTGEPFDNRVSVGIMYMIKLAHMVDDKLHARSTGPYSLVTQQPLGGKAQFGGQRFG
ref|YP_001124230.1|     LYDGRTGEPFDNRVSVGIMYMIKLAHMVDDKLHARSTGPYSLVTQQPLGGKAQFGGQRFG
ref|YP_145951.1|        LYDGRTGEPFDNRVSVGIMYMIKLAHMVDDKLHARSTGPYSLVTQQPLGGKAQFGGQRFG
ref|ZP_02326346.1|      LYDGRTGEEFEREVTVGVMYMIKLAHMVDDKIHARSTGPYSLVTQQPLGGKAQFGGQRFG
RAAC00408               LYDGRTGEPFENRVTVGYVYMMKLHHLVDDKIHARSTGPYSLVTQQPLGGKAQFGGQRFG
                        ********  *:..*: ::** *:**:************************* ref|NP_240992.1|        EMEVWALEAYGAAYTLQEILTVKSDDVVGRVKTYEAIVKGENVPEPGVPESFKVLIKELQ
ref|YP_173646.1|        EMEVWALEAYGAAYTLQEILTVKSDDVVGRVKTYEAIVKGENVPEPGVPESFKVLIKELQ
ref|YP_001124230.1|     EMEVWALEAYGAAYTLQEILTVKSDDVVGRVKTYEAIVKGENIPEPGVPESFKVLIKELQ
ref|YP_145951.1|        EMEVWALEAYGAAYTLQEILTVKSDDVVGRVKTYEAIVKGENIPEPGVPESFKVLIKELQ
ref|ZP_02326346.1|      EMEVWALEAYGAAYTLQEILTVKSDDVVGRVKTYESIVKGENVPEPGVPESFKVLIKELQ
RAAC00408               EMEVWALEAYGAAYTLQELLTVKSDDVVGRVKTYEAIVKGENVPEPGVPESFKVLIKELQ
                        ****************.*********** .**:*************** ref|NP_240992.1|        SLGMDVKMLSSTEEEIEMKELDDEDEQASDKLNLNIDSTE---
ref|YP_173646.1|        SLGMDVKMLSSNEEEIEMRELDDEEDQTSEKLNLNLETNE---
ref|YP_001124230.1|     SLGMDVTILT---------------------------------
ref|YP_145951.1|        SLGMDVTILT---------------------------------
ref|ZP_02326346.1|      SLGMDVKILSGDEEEIEMKELDDEDDAGSDKLNLNLEGAEMG-
RAAC00408               SLGMDVKILSGDEREIEMKEMDDDED-SPDKLNLNLEYNEVGD
                        ******.:*:
```

FIG. 4A

```
ref|YP_001124231.1|    VYPLLDVNKFEYMKIGLASPEKIRSWSYGEVKKPETINYRTLKPEKDGLFCERIFGPTKD
ref|YP_145952.1|       ---MLDVNKFEYMKIGLASPEKIRSWSYGEVKKPETINYRTLKPEKDGLFCERIFGPTKD
ref|NP_976431.1|       ---MIDVNNFEYMKIGLASPDKIRSWSYGEVKKPETINYRTLKPEKDGLFCERIFGPQKD
ref|NP_240993.1|       ---MIDVNNFEYMKIGLASPNKIRSWSRGEVKKPETINYRTLKPEKDGLFCERIFGPQKD
ref|ZP_02326345.1|     ---MMDVNNFEFMKIGLASPDKIRSWSRGEVKKPETINYRTLKPEKEGLFCEKIFGPTKD
RAAC00407              MHKLFDLNNFEFMKIGLASPEKIRSWSHGEVKKPETINYRTLRPEKEGLFCEKIFGPTRD
                          :.*:*:.***:* **************:*.***:** :* ref|YP_001124231.1|    WECHCGKYKRVRYKGVVCDRCGVEVTRSKVRRERMGHIELAAPVSHIWYFKGIPSRMGLV
ref|YP_145952.1|       WECHCGKYKRVRYKGVVCDRCGVEVTRSKVRRERMGHIELAAPVSHIWYFKGIPSRMGLV
ref|NP_976431.1|       WECHCGKYKRVRYKGVVCDRCGVEVTRAKVRRERMGHIELAAPVSHIWYFKGIPSRMGLV
ref|NP_240993.1|       WECHCGKYKRVRYKGVVCDRCGVEVTRAKVRRERMGHIELAAPVSHIWYFKGIPSRMGLV
ref|ZP_02326345.1|     WECHCGKYKRVRYKGVVCDRCGVEVTRQKVRRERMGHIELAAPVSHIWYFKGIPSRMGLA
RAAC00407              WECHCGKYKRIRYKGVVCDRCGVEVTRSKVRRERMGHIELAAPVSHIWFFKGIPSRMGLI
                       ********:************.*********************:******** ref|YP_001124231.1|    LDMSPRALEEVIYFASYVVTDPGDTPLEKKQLLSEKEYRAYREKYGQSFQASMGAEAIKK
ref|YP_145952.1|       LDMSPRALEEVIYFASYVVTDPGDTPLEKKQLLSEKEYRAYREKYGQSFQASMGAEAIKK
ref|NP_976431.1|       LDMSPRALEEVIYFASYVVTESGDTPLDKKQLLSEKEYRAYRDRYGSTFQAAMGAEAIKK
ref|NP_240993.1|       LDMSPRSLEEVIYFASYVVTDPGDTPLEKKQLLSEKEFRAYLDKYGRSFTAQMGAEAIRK
ref|ZP_02326345.1|     LDMSPRSLEEIIYFASYVVTDPGDTPLEKKQLLSEKEYRSYREKYGYAFQAGMGAEAVKK
RAAC00407              LDMSPRALEEVIYFASYVVTDPGDTPLEKKQLLSEKEYRSYREKYGYAFKAGMGAEAIRT
                       ******:***.*********:.*****.**********:*:* ::** :* * *****::.

ref|YP_001124231.1|    LLQDIDLDKEVATLKEELKTAQGQRRARIIKRLEVLESFRSSGNDPAWMVLDVLPVIPPE
ref|YP_145952.1|       LLQDIDLDKEVAALKEELKTAQGQRRARIIKRLEVLEAFRSSGNDPAWMVLDVLPVIPPE
ref|NP_976431.1|       LLQDIDLDKEVDFLKEELKTAQGQRRTRAIKRLEVLEAFRNSGNEPSWMILDVLPVIPPE
ref|NP_240993.1|       LLMDIDLDKEVDGLKEELQTAQGQRRTRAIKRLEVLEAFRNSGNEPSWMILDVLPVIPPE
ref|ZP_02326345.1|     LLQDIDIDKEVDVLKEELRTAQGQRRNAIKRLEVMEAFRNSKNKPDWMILDVLPVIPPE
RAAC00407              LLQEIDLDREVEILREELRTAQGQRRNAIKRLEVIEAFRQSGNKPSWMILEALPVIPPD
                       ** :**:*:**  *:***.*******  * ******:*:**.* *.* **:*:.******:

ref|YP_001124231.1|    LRPMVQLDGGRFATSDLNDLYRRVINRNNRLKRLLDLGAPNIIVQNEKRMLQEAVDALID
ref|YP_145952.1|       LRPMVQLDGGRFATSDLNDLYRRVINRNNRLKRLLDLGAPNIIVQNEKRMLQEAVDALID
ref|NP_976431.1|       LRPMVQLDGGRFATSDLNDLYRRVINRNNRLKRLLDLGAPSIIVQNEKRMLQEAVDALID
ref|NP_240993.1|       LRPMVQLDGGRFATSDLNDLYRRVINRNNRLKRLLDLGAPSIIVQNEKRMLQEAVDALID
ref|ZP_02326345.1|     LRPMVQLDGGRFATSDLNDLYRRVINRNNRLKRLLDLGAPDIIVQNEKRMLQEAVDALID
RAAC00407              LRPMVQLDGGRFATSDLNDLYRRVINRNNRLKRLLDLGAPDIIVQNEKRMLQEAVDALID
                       **************************************.**************** ref|YP_001124231.1|    NGRRGRPVTGPGNRPLKSLSHMLKGKQGRFQNLLGKRVDYSGRSVIVVGPNLKMYQCGL
ref|YP_145952.1|       NGRRGRPVTGPGNRPLKSLSHMLKGKQGRFQNLLGKRVDYSGRSVIVVGPNLKMYQCGL
ref|NP_976431.1|       NGRRGRPVTGPGNRPLKSLSHMLKGKQGRFQNLLGKRVDYSGRSVIVVGPNLKMYQCGL
ref|NP_240993.1|       NGRRGRPVTGPGNRPLKSLSHMLKGKQGRFQNLLGKRVDYSGRSVIVVGPNLKMYQCGL
ref|ZP_02326345.1|     NGRRGRPVTGPGNRPLKSLSHMLKGKQGRFQNLLGKRVDYSGRSVIVVGPSLKMYQCGL
RAAC00407              NGRRGRPVTGPGNRPLKSLSHMLKGKQGRFQNLLGKRVDYSGRSVIVVGPELRMYQCGL
                       **************************************************.*:****** ref|YP_001124231.1|    PKEMALELFKPFVMKELVERGLAHNIKSAKRKIERVHPEVWDVLEDVIKEHPVLLNRAPT
ref|YP_145952.1|       PKEMALELFKPFVMKELVERGLAHNIKSAKRKIERVHPEVWDVLEDVIKEHPVLLNRAPT
ref|NP_976431.1|       PKEMALELFKPFVMKELVEKGLAHNIKSAKRKIERVQPEVWDVLESVIKEHPVLLNRAPT
ref|NP_240993.1|       PKEMALELFKPFVMKELVSKGLAHNIKSAKRKVERVQPEVWDVLEEVIKEHPVLLNRAPT
ref|ZP_02326345.1|     PKEMALELFKPFVMKELVNKQLAHNIKSAKRKVERVSPEVWDVLEEVIKEHPVLLNRAPT
RAAC00407              PKEMALELFKPFVMKELVARGLAHNIKSAKRKVERVSDEVWDVVEDVIKQHPVLLNRAPT
                       ****************** : *********** *** ****** *:*** ***********
```

FIG. 4B

```
ref|YP_001124231.1|    LHRLGIQAFEPTLVEGRAIRLHPLVCTAYNADFDGDQMAVHVPLSAEAQAEARLLMLAAQ
ref|YP_145952.1|       LHRLGIQAFEPTLVEGRAIRLHPLVCTAYNADFDGDQMAVHVPLSAEAQAEARLLMLAAQ
ref|NP_976431.1|       LHRLGIQAFEPTLVEGRAIRLHPLVCTAYNADFDGDQMAVHVPLSSEAQAEARLLMLAAQ
ref|NP_240993.1|       LHRLGIQAFEPTLVEGRAIKLHPLVCTAYNADFDGDQMAVHVPLSAEAQAEARILMLAAQ
ref|ZP_02326345.1|     LHRLGIQAFEPILVEGRAIMLHPLVCTAYNADFDGDQMAVHVPLSAEAQAEARILMLAAG
RAAC00407              LHRLGIQAFEPVLVEGRAIKLHPLVCTAYNADFDGDQMAVHVPLSAEAQAEARLLMLAAH
                       ******** *** ********************:**:*** ref|YP_001124231.1|    NILNPKDGKPVVTPSQDMVLGNYYLTMEREGAIGEGMVFKDTDEALLAYHNGYVHLHSRI
ref|YP_145952.1|       NILNPKDGKPVVTPSQDMVLGNYYLTMEREGAIGEGMVFKDTDEALLAYHNGYVHLHSRI
ref|NP_976431.1|       NILNPKDGKPVVTPSQDMVLGNYYLTLEREGAIGEGMVFKDANEALLAYQNGYVHLHTRV
ref|NP_240993.1|       NILNPKDGKPVVTPSQDMVLGNYYLTMEREGAKGEGSVFKDTNEALIAYQNGYVHLHTRI
ref|ZP_02326345.1|     NILNPKDGKPVVTPSQDMVLGSFYLTTDNKHAKGSGMILRSVHEAFSVYQNGTAELHARV
RAAC00407              NILNPKDGKPVVTPTQDMVLGSYYLTIEREGAPGEGKVFASVSEVEYALHQRLITLQTRI
                       **************:******.:*** ..: * *.* :: .. *.  . ::    *::*:

ref|YP_001124231.1|    AIHAGSLKNETFTPEQNNKLLLTTVGKLIFNEILPKSFPYINEPTTENIEGRTP-DKYFL
ref|YP_145952.1|       AIHAGSLKNETFTEEQNNKLLLTTVGKLIFNEILPNSFPYINEPTTENIEGRTP-DKYFL
ref|NP_976431.1|       AVAASAVNNATFTEEQKSMLLLTTVGKLIFNEILPESFPYINEPTNSNLEKETP-AKYFV
ref|NP_240993.1|       AIPVASLGKTTFKEEQNSQLLLTTVGKLIFNEILPESFPYVNEPTAHNLEVETP-SKYMV
ref|ZP_02326345.1|     AIPAKALNKISFTDKQQDAYLITTIGKIIFNEIFPKDFPYINQSTTSNLMHGPS-DDYFA
RAAC00407              ALPAKAVGKTSFTEKQANALLITTPGKLIFNSIFPSDFPYLNSAAKSNLLGGPP-DDTFI
                       *:  :   .:: :  :*. :*. . *:** **:***.*:*..***:*..: *:    .. .:

ref|YP_001124231.1|    -DKGVDVREEIRKRELVPPFKKKVLGQIIAEVFKRFKITETSKMLDRMKDLGFQYSTKAG
ref|YP_145952.1|       -DKGVNVREEIRKRELVPPFKKKVLGQIIAEVFKRFKITETSKMLDRMKDLGFQYSTKAG
ref|NP_976431.1|       -EKGANIKEIIASREEVAPFSKKILGNIIAEVFKRFKITETSRMLDRMKNLGFPKYSTKAG
ref|NP_240993.1|       -PTSTNVKELFQERDVVAPFKKGFLGNIIAEVFKKFKITETSKMLDRMKDLGFKYSTKAG
ref|ZP_02326345.1|     FEKGSDIRAKMEELPECKAVGKDYLGSIIAECFRKYHTTETSIILDKVKQLGFTYSTKAG
RAAC00407              FEKGVDIREAILKRPIPKAVIKKDLGNIIAECFRRYGTTMTAEILDKVKRLGPHYSTLAG
                        ..  :::  :  .     .. *  **.*:** *::: * *: :**::* * * ** ref|YP_001124231.1|    ITIGVSDIVVLPEKQEILDEAQAKVDTVLKQFRRGLITDEERYERVISVWSAAKDKIQDR
ref|YP_145952.1|       ITIGVADIVVLPEKQEILDEAQAKVDTVLKQFRRGLITDEERYERVISIWSAAKDKIQDK
ref|NP_976431.1|       ITVGVSDILVLGEKDEILHEAQADVNIKQFRRGLITEEERYDRVISIWSNAKDVIQGK
ref|NP_240993.1|       ITVGVADIVVLPEKKEILAEAEKKVDRVLKQFRRGLITEEERYDRVISIWSEAKDVIQDK
ref|ZP_02326345.1|     ITVAVADVIVPKEKQEILKESEQKVQTITNQYRRGLITDDERYDRVIAIWSKAKDDITDI
RAAC00407              ITISISDIVVPEEKKRIIAEAEAKEHKLKLQYRRGLITEEEQYVTFSQIWSEAKEQISSI
                       **:..:*::* **..*: *::* * . :  *:******::*:*  . :** **:  * .

ref|YP_001124231.1|    LMKSLDKRNPIFMMSDSGARGNASNFTQLAGMRGLMANPAGRIIELPIKSSFREGLTVLE
ref|YP_145952.1|       LMKSLDKRNPIFMMSDSGARGNASNFTQLAGMRGLMANPAGRIIELPIKSSFREGLTVLE
ref|NP_976431.1|       LMKSLNKRNPIFMMSDSGARGNASNFTQLAGMRGLMANPSGRIIELPIKSSFREGLTVLE
ref|NP_240993.1|       LMGSLDKRNPIFMMSDSGARGNASNFTQLAGMRGLMANPAGRIIELPIKSSFREGLTVLE
ref|ZP_02326345.1|     LMKSLDKYNSINMMVESKARGNKSQITQLGGMRGLMANPAGKIIELPIKSNFREGLTVLE
RAAC00407              LMESMDQFNPIYMMATSGARGSNSQITQLAGMRGLMANPSGEIIQLAIKSNFREGLSVLE
                       ** *::: *.* ** . * ***. *:;*.*******:*.**:*.* *:* ref|YP_001124231.1|    YFISTHGARKGLADTALKTADSGYLTRRLVDVAQDVIVREEDCGTDRGILARALTDGTEV
ref|YP_145952.1|       YFISTHGARKGLADTALKTADSGYLTRRLVDVAQDVIVREEDCGTDRGILARALTDGTEV
ref|NP_976431.1|       YFISTHGARKGLADTALKTADSGYLTRRLVDVAQDVIVREDDCGTDRGLLIGAIKEGNEV
ref|NP_240993.1|       YFISTHGARKGLADTALKTADSGYLTRRLVDVAQDVIVREDDCGTDRGLEVEAIKEGNEI
ref|ZP_02326345.1|     YFISTHGARKGLADTALRTADSGYLTRRLVDVAQDVIVREEDCGTDKGFVVSKIQDGKEV
RAAC00407              YFISTHGARKGLADTALRTADSGYLTRRLVDVAQDTIVREHDCGTDKGLRVMEIRDGSEV
                       *****************:*****************.****.*****:*:    : :*.*:
```

FIG. 4C

```
ref|YP_001124231.1|    VVKLEERLVGRYAHKTVHHPETGEVIVRKDEMITEDIANEIIKAGITEVWIRSVFACNTR
ref|YP_145952.1|       VVKLEERLVGRYAHKTVRHPETGEVIVRKDEMITEDIANEIMKAGITEVWIRSVFACNTR
ref|NP_976431.1|       IESLYDRLVGRFARKTVKHPETGEVLVAENQLITEDIAHIVENSGVETVNIRSAFTCNTR
ref|NP_240993.1|       IEGLYDRLVGRVAFKTVRHPETGEPIVKKNELIHEDLAKQIVEAGVEQVTIRSVFTCDTR
ref|ZP_02326345.1|     IEDLFDRIEGRYAFETVRHPETGEIIVHRNELIDANLASRIVEAGVEKIQIRSVMSCRAR
RAAC00407              IEDLRDRLEGRVAFQDVYHPETGEKIVGKNEMIDEEAADKIVAAGIKEVTIRSVLTCRTR
                       :   * :*: ** *  * ******  :*  .::.*    :  *    :  *:     : ***.::* :* ref|YP_001124231.1|    HGVCKKCYGRNMATGMDVEVGEAVGIIAAQSIGEPGTQLTMRTFHTGGVAGDDITQGLPR
ref|YP_145952.1|       HGVCKKCYGRNMATGMDVEVGEAVGIIAAQSIGEPGTQLTMRTFHTGGVAGDDITQGLPR
ref|NP_976431.1|       HGVCKKCYGRNLATGTDVEVGEAVGIIAAQSIGEPGTQLTMRTPHTGGVAGDDITQGLPR
ref|NP_240993.1|       HGVCKKCYGRNLATGSDVEVGEAVGIIAAQSIGEPGTQLTMRTFHTGGVAGDDITQGLPR
ref|ZP_02326345.1|     YGVCKKCYGRNLATGQHVEIGEAVGIIAAQSIGEPGTQLTMRTFHTGGVAGDDITQGLPR
RAAC00407              HGVCQLCYGRNLATGDMVEVGEAVGIIAAQSIGEPGTQLTMRTFHTGGVAGDDITQGLPR
                       :*: *:*   :************************************* ref|YP_001124231.1|    VQELFEARNPKGQAVISEIDGTVVAINETRDNQYEIVVQSEVETRSYVAPYNARLKVEEG
ref|YP_145952.1|       VQELFEARNPKGQAVISEIDGTVISINKTRDNQYEVVVQGEVETRTYVAPYNARLKVEEG
ref|NP_976431.1|       IQEIFEARNPKGQAVISEIDGVIAAINDVKDRQ-EVVVQGEVETRTYAIPYGARLKVIPG
ref|NP_240993.1|       IQELFEARNPKGQAVITEIEGEVTNINEA-DKR-EITVKGEMETKTYSIPYGARIKVELG
ref|ZP_02326345.1|     IQELFEARNPKGQAIITEIDGMVKDIREAKDRR-EIEVEGEAESRVYSVPFGSRIRVAVN
RAAC00407              VQELFEARNPKGQAVIAEFDGVITDIREGKDKR-EIELTGESETKTYQIPYGSRIRVSVG
                       :**:**********:*:*:*  :     .  *.. *.: *:  :  .* *:: * *:.:*::*   .

ref|YP_001124231.1|    QHVERGQELTEGSVDPKQLLRVRDITSVQEYLLREVQKVYRMQGVEISDKHIEVMVRQML
ref|YP_145952.1|       QRVERGQELTEGSVDPKQLLRVRDITSVQEYLLREVQKVYRMQGVEISDKHIEVMVRQML
ref|NP_976431.1|       QQISHGKELTEGSIDPKELLKVTDITAVQEYLLREVQKVYRMQGVEIGDKHVEVMVRQML
ref|NP_240993.1|       EQVVPGQSLTEGSIDPKELLKVQGMTGVQEYLLREVQKVYRMQGVEIGDKHVEVMVRQML
ref|ZP_02326345.1|     DHIEAGDELTEGSIDPKEMLRIKGIRGVQNYILREVQKVYRNQGVEINDKHVEVMIRQML
RAAC00407              QQLEAGEELTEGSVDPKEMLRVKGLQGVQNYLLREVQRVYRLQGVDINDKHIEVMIRQML
                       :::   *..***:**::*::    .:  .**:*:*:* * ***:*.**.*:**** ref|YP_001124231.1|    RKVRVIDAGDTDVLPGTLLDVHQFTDVNAQAIREGKRPATARPVLLGITKASLETDSFLS
ref|YP_145952.1|       RKVRVIDAGDTDVLPGTLLDVHQFTDVNAKALREGKRPATARQVLLGITKASLETDSFLS
ref|NP_976431.1|       RKVRVSDAGETDVLPGTLLDIHQFTDANAKVLLQGKQPATARPVLLGITKASLETDSFLS
ref|NP_240993.1|       RKIRVIDAGDTEVLPGSLIEIQHFNDENKKVLLSGKRPATGRPVLLGITKASLETDSFLS
ref|ZP_02326345.1|     RKIRIVDAGDTNLLPGSFVDMHEYEEANKTALLEGREPAVAKPILLGITKASLETDSFLS
RAAC00407              RKVRILDAGDTDLLPGTYVDLFEYEAANREALLSGKEPAVARPALLGITKASLETDSFLS
                       **:*:  ***:*:::***  :::  .:      *   .:  .*:....:      ************** ref|YP_001124231.1|    AASFQETTRVLTDAAIKGKRDELLGLKENVIIGKLVPAGTGMARYRNVKPAV--------
ref|YP_145952.1|       AASFQETTRVLTDAAIKGKRDELLGLKENVIIGKLVPAGTGMARYRKVKPAV--------
ref|NP_976431.1|       AASFQETTRVLTDAAIKGKRDELLGLKENVIIGKLVPAGTGMNRYRKVD-----------
ref|NP_240993.1|       AASFQETTRVLTDAAIKGKRDELVGLKENVIIGKLVPAGTGMNRYRNLD-----------
ref|ZP_02326345.1|     AASFQETTRVLTDAAIKGKVDQLLGLKENVIIGKLIPAGTGMQRYRNI------------
RAAC00407              AASFQETTRVLTEAAIKGKVDRLLGLKENVIIGKLIPAGTGMVRYRNVEPEVVRPGDAEA
                       ************:******  *.*:***********:*******  ***.**::

ref|YP_001124231.1|    ------------------
ref|YP_145952.1|       ------------------
ref|NP_976431.1|       ------------------
ref|NP_240993.1|       ------------------
ref|ZP_02326345.1|     ------------------
RAAC00407              AATGEEVAETEAVSSAE
```

FIG. 5

```
ref|NP_244660.1|          --------------------SKEEIQELSMVEVAYLVMKETKEPFNYQDLLKKVAELKG
ref|NP_693930.1|          --------------------THDEIDHLSMIELGVKILKEENKAMNYKVIFNKIAELKD
RAAC00480                 MATGLSRAGREDSKMAISLARTEHEIQEMPLVELVYEILKARKEPMYFRDIMKEIQELRH
ref|ZP_01168478.1|        --------------------TKEELQEMSFIDIAYELLKGTKQQVSFTDIMNEYKTRLE
ref|ZP_01860921.1|        --------------MSLKQLSTE-ELRQKSFIELAHELLTEKKQAVTFNDLLKEIGDLLK
ref|YP_001127419.1|       --------------MSLQQQYSPEELQEMSFVELANLILLNKREALPFDQIVREAAALTG
                                            :  *:  . ..::::   ::    .: . . :  :..:

ref|NP_244660.1|          MSEEQMLDRIGYLYTDLNIDGRFVTLGDNRWGLRSWYPLEQVEEEITGPTK---------
ref|NP_693930.1|          FTDEQKQNMMAQFYTDMNVDGRFLTLGSGMWGLKRWYPVEQAEEEIT-------------
RAAC00480                 MTDEQVADVIARVFTEINVDGRFVCIGHNVWGLNRWYPTDRNAERLSGGKKFIRKTGDAF
ref|ZP_01168478.1|        VSDEEIRSRIAQFYTDLNLDGRFIAMGENRWGLRSWYPVDTMEE----------------
ref|ZP_01860921.1|        LSKEEVRSRMVQFYTDLNVDGRFIALGENRWGIRAWYPVDQIEEETVPTIKPRKKKAKKT
ref|YP_001127419.1|       ATEDDIAARLAQYYTDLNIDGRFICVGENVWGLRAWYPFDQTED----------------
                           :.::      :    :*::*:****:  :*  . **:. ***  :    :

ref|NP_244660.1|          ------------------------------------------------------------
ref|NP_693930.1|          ------------------------------------------------------------
RAAC00480                 GDEEDDEEEYEEEDVLEDDELDYDEVEAVDEEPEFDDVEVVEDEDEILPEDEYDDAPLFD
ref|ZP_01168478.1|        ------------------------------------------------------------
ref|ZP_01860921.1|        DD----------------------------------------------------------
ref|YP_001127419.1|       ------------------------------------------------------------ ref|NP_244660.1|          -----------
ref|NP_693930.1|          -----------
RAAC00480                 EEEEVEEDEED
ref|ZP_01168478.1|        -----------
ref|ZP_01860921.1|        -----------
ref|YP_001127419.1|       -----------
```

FIG. 6

```
ref|NP_465351.1|      ---MLYPSIDNLLLKIDSKYSLVTVAAKRARYMQLENDKGVLPSYQSDKFVGKALEEIHA
ref|NP_471274.1|      ---MLYPSIDNLLLKIDSKYSLVTVAAKRARYMQLENDKGVLPSYQSDKFVGKALEEIHA
ref|YP_014447.1|      ---MLYPSIDNLLLKIDSKYSLVTVAAKRARYMQLENDKGVLPSYQSDKFVGKALEEIHA
ref|YP_850042.1|      ---MLYPSIDNLLLKIDSKYSLVTVAAKRARYMQLENDKGVLPSYQSDKFVGKALEEIHA
RAAC00147             ---MIYPSIDRLLERCNSKYALVVLAAKRAR--KLQNETLNQPGASTTRNVSRALWEIHD
ref|NP_268055.1|      ---MLEPSIDKLLDQVDSKYSLVVLEAKRAH--ELRDKERPTKEFKAVKNTLRALEEIAD
                         *: ****.** : :***:**.: ****:   :*.:.      .: : . :** **

ref|NP_465351.1|      GKLVLQNDD--
ref|NP_471274.1|      GKLVLQN----
ref|YP_014447.1|      GKLVLQNDD--
ref|YP_850042.1|      GKLVLKN----
RAAC00147             GVVRCKNFDGE
ref|NP_268055.1|      GTVK-------
                      * :
```

FIG. 7

```
ref|YP_074981.1|         ------ETEARPAEAAVEAWIQQHGEAVLRLAYASLLNRAQAEDVFQEVFIRAYRHADRL
ref|YP_001275817.1|      ------------DHDAFAQLMGRYAGSVFNLAYRMLGNAQEAEDASQEIFLRAYTNLARF
RAAC01826                MRHARRNETPAEDAALLAEWMELYGGDVIRLAYSYVHNFHKAEDIAQDVFLRAWQHYGEF
ref|YP_074736.1|         MSQSDRAALPSDRTAAIDHLMREYGTKVLHLAYSYLKDRHLAEDVAQEVFIKAYRNWENF
ref|YP_001394390.1|      ----------------LERLMNCYGNDILRTAYIYLKDIHLAEDVFQDVFIKVYNNFDKF
ref|NP_244228.1|         ----------------LIAWMEEYGTAILRVVYSYVKDKQIAEDLTQEVFVRAFQSYHTY
                                            .  : :. ::. .*  : :    ***  *::*::.:

ref|YP_074981.1|         RDPDRVRPWLLQVTMNACRDLRRSWWWRRTREGSGL--EGLAEAGEGPAADPAAAAVRAD
ref|YP_001275817.1|      DQERRFSTWLLSIGSNYCIDRLR----RRRFAWLTL--DDVVLSVPTSAKGPERSAVERE
RAAC01826                QGQSSIKTWLLSITANRARDVLRSGAERREFAD-----EGEAFAREIEPCDPADLVADKL
ref|YP_074736.1|         RGESSAYTWLYRITVNLCRDKARSAWWRRLLPTDDPRAAGTPVEPDTAGDDPEEAVVLSD
ref|YP_001394390.1|      NGKSSEKTWILTITINTCRDMLRSCWIKKVLRFDDT-EYGIFNSTDDLN-DTEDTVIKNI
ref|NP_244228.1|         QTRSSAKAWLYRIAINRSKDFLKSWHAKHVYPSE------VAEEIETTEQTPEYEVLLKS
                            .*:   :  *.  *  :          ::                 .      .  .

ref|YP_074981.1|         VSQAVARAVRALPDGFRETVVLHYFEGLDAAEIARITGVRVGTVHSRLHRARQLLRRQLE
ref|YP_001275817.1|      ERDAVQRALLSLPPTYREVAVLRYWNDLSYEEITQVTGLPESTIKTRLHRARRMLAEALR
RAAC01826                ARDAVWRAIRVLPETYREVMELYYGNDLTTHEVAEILGIRDQTVRTRLHRGRQMLERALA
ref|YP_074736.1|         QRERLLDYVMQLSDAYREVIILYYYHDLTTVEIAEVTGQNENTVKTRLFRARAMLKQMLQ
ref|YP_001394390.1|      EYEDILKKVMDLPKKYKEVILLYYYQELSTSEISKILKIPEGTVRSRLYRARGILK----
ref|NP_244228.1|         DEERLAAAVFSLPLSYREVIYFYYYEELSVKEVASFTGLNENTVKTRLRKGRLLLKNLLE
                          : :     :   *.  ::*.  : *  .  *::  .        *::** :.*  :* ref|YP_074981.1|         AWG-------
ref|YP_001275817.1|      AEG-------
RAAC01826                EQGGMGVDHA
ref|YP_074736.1|         KGG-------
ref|YP_001394390.1|      ----------
ref|NP_244228.1|         KE--------
```

FIG. 8

```
ref|YP_001126509.1|      ---------------TLEQAKEQLAELGKKRGILTYEEIAERLSGFDLDSDQMDEYYEYL
ref|YP_148335.1|         ----------EAAGESLEQVKEQLAELGKKRGILTYEEIAERLSGFDLDSDQMDEYYEYL
ref|ZP_01173341.1|       MAEKSARSKEVDSELTMEQVKEQLTEVGKKTGVLAYDDIAERLSNFELDSDQMDEFYEFL
ref|YP_001376241.1|      ---------------MTLEQVKEQLTELGKKRGVLTYEEIAERMNGFEIESEQMDEYYEYL
ref|ZP_02328521.1|       ----NDQHTELETELTLEQVKDQLIELGKKRSSLTYKEIMDRLAPYDQDAEQIDDFFEHL
RAAC00896                MAKTNDEIRDEDQGITLQEAKQQLIELGKKQGSLTYEEISDRLSSFDMDADAMDDFFEQL
                                     :::..*:** *:***  .  *:*.:*   :*:    ::  :::  :*::* * ref|YP_001126509.1|      ADQGIEVISESDIETDPDIDELVK-EEEFDLN---DLSVPPGVKINDPVRMYLKEIGRVP
ref|YP_148335.1|         AEQGIEVISESDLEADPDIDDLAK-EEEFDLN---DLSVPPGVKINDPVRMYLKEIGRVP
ref|ZP_01173341.1|       GDQGVELVGD-NDDADPNVQELAKGEEEFDLN---DLSVPPGVKINDPVRMYLKEIGRVD
ref|YP_001376241.1|      GEQGIDLVGD-NDEG-PNNHQITKTEEEFDLN---DLSVPPGVKINDPVRMYLKEIGRVD
ref|ZP_02328521.1|       SEMGIDVGNE-NDDDEDNIRPGNTDNEDEDFNFEDDLTLPPGIKINDPVRMYLKEIGRVP
RAAC00896                AELGIDVVNE-RDEE------GGREDDDYDL---DDLSVPPGVKISDPVRMYLKEIGRVP
                          .: *:::  .:        :        ::: *:    ::*:.*********** ref|YP_001126509.1|      LLSAEEEIELAKRIEQGDEEAKRRLTEANLRLVVSIAKRYVGRGMLFLDLIQEGNMGLIK
ref|YP_148335.1|         LLSAEEEIELAKRIEQGDEEAKRRLTEANLRLVVSIAKRYVGRGMLFLDLIQEGNMGLIK
ref|ZP_01173341.1|       LLSAQEEISLAKRIEEGDEEAKRRLAEANLRLVVSIAKRYVGRGMLFLDLIQEGNMGLIK
ref|YP_001376241.1|      LLSAEEEIQLATRIEEGDEEAKRRLAEANLRLVVSIAKRYVGRGMLFLDLIQEGNMGLIK
ref|ZP_02328521.1|       LLSAEDEVELAKRLRTEANLRLVVSIAKRYVGRGMLFLDLIQEGNMGLIK
RAAC00896                LLSAQEEIELAKRIEQGDEEAKQRLAEANLRLVVSIAKRYVGRGMLFLDLIQEGNLGLLK
                         ****::*: . *.***:.*************************** .**:.* ref|YP_001126509.1|      AVEKFDYRKGYKFSTYATWWIRQAITRAIADQARTIRIPVHMVETINKLIRVQRQLLQDL
ref|YP_148335.1|         AVEKFDYRKGYKFSTYATWWIRQAITRAIADQARTIRIPVHMVETINKLIRVQRQLLQDL
ref|ZP_01173341.1|       AVEKFDYRKGYKFSTYATWWIRQAITRAIADQARTIRIPVHMVETINKLIRVQRQLLQDL
ref|YP_001376241.1|      AVEKFDYRKGFKFSTYATWWIRQAITRAIADQARTIRIPVHMVETINKLIRVQRQLLQDL
ref|ZP_02328521.1|       AVEKFDHTKGYKFSTYATWWIRQAITRAIADQARTIRIPVHMVETINKLIRVSRQLLQEL
RAAC00896                AVEKFDYRKGYKFSTYATWWIRQAITRAIADQARTIRIPVHMVETINKLIRVSRQLLQEL
                         ****: .*******************************************.**:* ref|YP_001126509.1|      GREPTPEEIAEEMDLTPEKVREILKIAQEPVSLETPIGEEDDSHLGDFIEDQEATSPSEH
ref|YP_148335.1|         GREPTPEEIAEEMDLTPEKVREILKIAQEPVSLETPIGEEDDSHLGDFIEDQDATSPSEH
ref|ZP_01173341.1|       GREPTPEEIAEDMDLTPDKVREILKIAQEPVSLETPIGEEDDSHLGDFIEDQDATSPSEH
ref|YP_001376241.1|      GREPTPEEIGEEMDLAPEKVREILKIAQEPVSLETPIGEEDDSHLGDFIEDQEATSPADH
ref|ZP_02328521.1|       GREPTPEEIAKEMELSTDKVREIMKIAQEPVSLETPIGEEDDSHLGDFIEDQEALAPADA
RAAC00896                GREPTPEEIAAEMDLTPEKVREIQKIAQEPVSLETPIGEEDDSHLGDFIPDDEAPAPADA
                         *********. :*:*:..:***** *******************  *::*  :*::

ref|YP_001126509.1|      AAYELLKEQLEDVLDTLTDREENVLRLRFGLDDGRTRTLEEVGKVFGVTRERIRQIEAKA
ref|YP_148335.1|         AAYELLKEQLEDVLDTLTDREENVLRLRFGLDDGRTRTLEEVGKVFGVTRERIRQIEAKA
ref|ZP_01173341.1|       AAYELLKEQLEDVLDTLTDREENVLRLRFGLDDGRTRTLEEVGKVFGVTRERIRQIEAKA
ref|YP_001376241.1|      AAYELLKEQLEDVLDTLTDREENVLRLRFGLDDGRTRTLEEVGKVFGVTRERIRQIEAKA
ref|ZP_02328521.1|       AAYELLKEQLEDVLDTLTEREENVLRLRFGLDDGRTRTLEEVGKVFGVTRERIRQIEAKA
RAAC00896                AAYELLKEQLEDVLDTLTEREENVLRLRFGLDDGRTRTLEEVGKVFGVTRERIRQIEAKA
                         ****************:*************************************** ref|YP_001126509.1|      LRKLRHPSRSKRLKDFLE
ref|YP_148335.1|         LRKLRHPSRSKRLKDFLE
ref|ZP_01173341.1|       LRKLRHPSRSKRLKDFLE
ref|YP_001376241.1|      LRKLRHPSRSKRLKDFLE
ref|ZP_02328521.1|       LRKLRHPSRSKRLKDFLE
RAAC00896                LRKLRHPSRSKRLKDFLE
                         ******************
```

FIG. 9

```
ref|YP_146980.1|         --------------------------------DEIYYIGGSEALPPPLTKEEEEQLIAR
ref|YP_001125115.1|      --------------------------------DEIYYIGGSEALPPPLTKEEEERLIER
ref|ZP_01862300.1|       --------------------------------DEIYYIGGSEALPPPLSKEEEAVLLKK
ref|ZP_01172495.1|       --------------------------------DEIFYIGGSEALPPPLSKEEEEVLLIK
ref|NP_243422.1|         --------------------------------DEIYYIGGSEALPPPLSKEEEAHLLKK
RAAC00120                MYAFQFLETKRRLALLRLRLLYIRLRIRLLGQPDEVYYVGGSEALPPPLTKEEEQYLLER
                                                         **::*:**********:****  *:  :

ref|YP_146980.1|         LAAGDDTARSLLIERNLRLVVYIARKFENTGIHIEDLISIGTIGLIKAVNTFNPEKKIKL
ref|YP_001125115.1|      LAVGDKTARSLLIERNLRLVVYIARKFENTGIHIEDLISIGTIGLIKAVNTFNPEKKIKL
ref|ZP_01862300.1|       LPNGDKTARSLLIERNLRLVVYIARKFENTGINIEDLISIGTIGLIKAVNTFNPEKKIKL
ref|ZP_01172495.1|       LPKGDKAARSMLIERNLRLVVYIARKFENTGINIEDLISIGTIGLIKAVNTFNPEKKIKL
ref|NP_243422.1|         LPSGDKAVRSMLIERNLRLVVYIARKFENTGINIEDLISIGTIGLIKAVNTFNPEKKIKL
RAAC00120                LPSGDPSVRSMLIERNLRLVVYIARKFENTGVNIEDLVSIGTIGLIKAVNTFDPSKKIKL
                         *.  :.:***************::.*************:*.***** ref|YP_146980.1|         ATYASRCIENEILMYLRRNNKVRAEVSFDEPLNIDWDGNELLLSDVLGTDDDVITKDLEA
ref|YP_001125115.1|      ATYASRCIENEILMYLRRNNKVRAEVSFDEPLNIDWDGNELLLSDVLGTEDDVITKDLEA
ref|ZP_01862300.1|       ATYASRCIENEILMYLRRNNKIRSEVSFDEPLNIDWDGNELLLSDVLGTEEDIITKDLEA
ref|ZP_01172495.1|       ATYASRCIENEILMYLRRNNKIRSEVSFDEPLNIDWDGNELLLSDVLGTEEDIITKDLEA
ref|NP_243422.1|         ATYASRCIENEILMYLRRNNKIRSEVSFDEPLNIDWDGNELLLSDVLGTDDDIITRGIEE
RAAC00120                ATYASRCIENEILMYLRRNNKLRAEVSLDEPLNVDWDGNELLLSDVLGTDSDTIYRNLED
                         *********************:*:* :*************:.* * :.:* ref|YP_146980.1|         DVDRRLLLNALRQLSDREKQIMELRFGLSGGEEKTQKDVADLLGISQSYISRLEKRIIKR
ref|YP_001125115.1|      DVDRRLLLNALRQLSDREKQIMELRFGLSGGEEKTQKDVADLLGISQSYISRLEKRIIKR
ref|ZP_01862300.1|       TVDRKLLFNALTELSDREKQIMELRFGLMGGEEKTQKDVADMLGISQSYISRLEKRIIKR
ref|ZP_01172495.1|       NVDKKLLLKALHQLTDREKQIMELRFGLSGSEEKTQKDVADMLGISQSYISRLEKRIIKR
ref|NP_243422.1|         KVDRKLLMKALHTLTDREKQIMELRFGLAGGEEKTQKDVADLLGISQSYISRLEKRIIKR
RAAC00120                EVDRELLYDALDKLSERERTIMELRFGLGTGQEMTQKDVADLLGISQSYISRLEKRILKR
                         **:.** .** *::**: ********  *:* ******:*************:**:**

ref|YP_146980.1|         LRKEFNKMM
ref|YP_001125115.1|      LRKEFNKMM
ref|ZP_01862300.1|       LKKEFNKMV
ref|ZP_01172495.1|       LKKEFNKMV
ref|NP_243422.1|         LQKEFNKMV
RAAC00120                LQREFNKMM
                         *::*****:
```

FIG. 10

```
ref|YP_001126333.1|      -----MPMDVDVKQDQSPIKDQEMKELIRRSQEGDQEARDEIIEKNMRLVWSVVQRFLNR
ref|YP_148161.1|         ------------------IKDQEMKELIRRSQEGDQEARDEIIEKNMRLVWSVVQRFLNR
pdb|1L00|C               -----------HMQGQSPIKDQEMKELIRRSQEGDQEARDEIIEKNMRLVWSVVQRFLNR
gb|AAB81194.1|           ------------------IKDQEMKELIRRSQEGDQEARDEIIEKNMRLVWSVVQRFLNR
ref|YP_001487306.1|      ----------------QLSNDEVKELIKKSQDGDQQARDLLVEKNMRLVWSVVQRFLNR
RAAC02146                MDQAKERPVPHHVDEYEKLSDEEVRELLERSHNGDAEARERLIVHNQRLVWAVVQRFLGR
                         :.::*::**:..:*:: :: :: .* **:****.* ref|YP_001126333.1|      GYEADDLFQIGCIGLLKSVDKFDLSYDVKFSTYAVPMIIGEIQRFLRDDGTVKVSRSLKE
ref|YP_148161.1|         GYEADDLFQIGCIGLLKSVDKFDLSYDVKFSTYAVPMIIGEIQRFLRDDGTVKVSRSLKE
pdb|1L00|C               GYEADDLFQIGCIGLLKSVDKFDLSYDVKFSTYAVPMIIGEIQRFLRDDGTVKVSRSLKE
gb|AAB81194.1|           GYEADDLFQIGCIGLLKSVDKFDLSYDVKFSTYAVPMIIGEIQRFLRDDGTVKVSRSLKE
ref|YP_001487306.1|      GYEPDDLFQIGCIGLLKSVDKFDLSYDVKFSTYAVPMIIGEIQRFIRDDGTVKVSRSLKE
RAAC02146                GYEAEDLFQIGCIGLMKAVDKFDLSYDVKFSTYAVPMIIGEIQRFLRDDSTVKVSRSLKE
                         *.:*******:*:****************************:*.********* ref|YP_001126333.1|      MGNKIRKAKDELSKTRGRAPTITEIADHLGVSPEEVVLAQEAVRSPASIHETVYENDGDP
ref|YP_148161.1|         MGNKIRKAKDELSKTRGRAPTVTEIADHLGISPEDVVLAQEAVRSPTSIHETVYENDGDP
pdb|1L00|C               MGNKIRKAKDELSKTRGRAPTVTEIADHLGISPEDVVLAQEAVRLPTSIHETVYENDGDP
gb|AAB81194.1|           MGNKIRKAKDELSKTRGRSPTITEIADHLGISPEDVVLAQEAVRLPTSIHETVYENDGDP
ref|YP_001487306.1|      LGNKIRRARDELSKSHGRMPTVQEIAEYLDITPEDVVLAQEAVRTPSSIHETVYENDGDP
RAAC02146                TAKQIRHVRDRLAKELGRQPHITEIAEAMGMEPSEIVFAQEALRAPASIHETVYENDGDP
                         .::**:..*.*:* ** * : ***: :.: *.::*:****:* *:************* ref|YP_001126333.1|      ITLLDQIADADEASWFEKIALKKAIEELDERERLIVYLRYYKDQTQSEVAARLGISQVQV
ref|YP_148161.1|         ITLLDQIADADEASWFDKIALKKAIEELDERERLIVYLRYYKDQTQSEVASRLGISQVQV
pdb|1L00|C               ITLLDQIADADEASWFDKIALKKAIEELDERERLIVYLRYYKDQTQSEVASRLGISQVQM
gb|AAB81194.1|           ITLLDQIADADEASWFDKIALKKAIEELDERERLIVYLRYYRDRTQSEVASRLGISQVQV
ref|YP_001487306.1|      ITLLDQIADHSEERWFDKIALKEAIKELEEREKLIVYLRYYKDQTQSEVAERLGISQVQV
RAAC02146                IYLMDQIADEETEGKFDKVELHEIIGRLPERERFIVYMRFFRDKTQSDVARVLGISQVQV
                         * *:*****  .   *:*: *:: * .* ***::***:*:::*:***:**  *******:

ref|YP_001126333.1|      SRLEKKILQHIKEKMD
ref|YP_148161.1|         SRLEKKILQHIKDKMD
pdb|1L00|C               SRLEKKILQHIK----
gb|AAB81194.1|           SRLEKKILQHIKDKMD
ref|YP_001487306.1|      SRLEKKILKQIQMQMD
RAAC02146                SRLEKRILQQIRQELE
                         *****:**::*::*:
```

FIG. 11

```
ref|YP_001212395.1|      ------------NKVEICGVNTSKLPVLTGSQMKALFEAMHK-GDASARTKLINGNLRLV
ref|ZP_01667054.1|       ------------NKVEICGVNTAKLPVLSANKMRELFEIMQQ-GNPEAREQLIYGNLRLV
RAAC00121                MTGRLGGTSLKRNKVEICGVNTSQLPVLTNAQMRELFEQLRA-GDPSAREKLVNGNLRLV
ref|YP_001125116.1|      ----MGGNNLTRNKVEICGVDTSKLPVLKNEEMRELFQRMHE-GDLEAREKLVNGNLRLV
ref|NP_243420.1|         ---------MTRNKVEICGVDTSKLPVLKNQEMRELFARLQS-GDTSARETLVNGNLRLV
ref|ZP_02330758.1|       ---------MTRNKVEICGVDTAKLPVLTNTEMRELFALLQTKNERAAREKLVNGNLRLV
                                     ********:*::****.  :*:    ::   .:    *: ****** ref|YP_001212395.1|      LSVIQRFTNRGEYVDDLFQVGCIGLMKAIDNFDLSQNVKFSTYAVPMIIGEIRRYLRDNN
ref|ZP_01667054.1|       LSVIQRFNNRGEYVDDLFQVGCIGLMKAIDNFDLSQNVKFSTYAVPMIIGEIRRYLRDNN
RAAC00121                LSVIQRFNNRGEYVDDLFQVGCIGLMKAIDNFDLSQNVRFSTYAVPMIVGEIRRYLRDNN
ref|YP_001125116.1|      LSVIQRFNNRGEFVDDLFQVGCIGLMKSIDNFDLNQNVKFSTYAVPMIIGEIRRYLRDNN
ref|NP_243420.1|         LSVIQRFNNRGEYVDDLFQVGCIGLMKSIDNFDLSQNVKFSTYAVPMIIGEIRRYLRDNN
ref|ZP_02330758.1|       LSVIQRFNNRGEFVDDLFQVGCIGLMKAIDNFDLSQNVKFSTYAVPMIIGEIRRYLRDNN
                         ****.:********:**.*:*********:********* ref|YP_001212395.1|      PIRVSRSLRDVAYKALQVRDALVNKY--SREPSINEIACELKMPREEIVFALDAIQEPIS
ref|ZP_01667054.1|       PIRVSRSMRDIAYKALQVRDALVSKF--SREPSINEIADELKIPREEIIFALDAIQEPVS
RAAC00121                PIRVSRSLRDIAYKALQVRDMLASKN--LREPSIVEIANEMNLPKEEVVFALDAIQDPVS
ref|YP_001125116.1|      PIRVSRSLRDIAYKALQVRERLMGET--AKEPSTEEIAKELGVAHEEVVLALDAIQDPVS
ref|NP_243420.1|         PIRVSRSLRDIAYKALQVRDQLMGEKQREKEPTVQEIAKELGVPKEDVVFALDAIQDPVS
ref|ZP_02330758.1|       PIRVSRSLRDIAYKALQVRDQLTNRN--SREPTIYEISEVLNVPKEDVVFALDAIQDPVS
                         *****::********: *  ..   ::  :   : :.:*:::*****:*:* ref|YP_001212395.1|      LFEPIYHDGGDPIFVMDQISDEKNQDQNWLEGIAIRDALRKLSDREKLILTLRFYEGKTQ
ref|ZP_01667054.1|       LFEPIYHDGGDPIFVMDQISDDKNQDMNWLEGVAIKEALRKLSDREKHILTLRFFEGKTQ
RAAC00121                MFEPIYHDGGDPIYVMDQIHDEREKDSAWVEGIALREAMRKLSDREKKILAKRFYEGKTQ
ref|YP_001125116.1|      LFEPIYNDGGDPIYVMDQLSDERNRDSQWIEEIALKEGLRRLNEREKMIIRKRFFQGKTQ
ref|NP_243420.1|         LFEPIYNDGGDDRNKDVQWVDEIALKEAMVRLNDREKLILNMRFYQGKTQ
ref|ZP_02330758.1|       LFEPIYHDGGDPIYVMDQISDERNKDLFWIEGIALREAMRKLGSREKMILSMRFFEGKTQ
                         :*****:******:****: *::::*   *::  :*::::..: :*..*** *:  **::****

ref|YP_001212395.1|      MEVAEEIGISQAQVSRLEKAALNHMKKHI--
ref|ZP_01667054.1|       MEVADEIGISQAQVSRLEKAALGHMRKYI--
RAAC00121                MEVADEIGISQAQVSRLEKAAIHRMYKHIQS
ref|YP_001125116.1|      MEVADEIGISQAQVSRLEKAAIRQMNKNIQ-
ref|NP_243420.1|         MEVAEEIGISQAQVSRLEKAAIQQMSKHAQS
ref|ZP_02330758.1|       MEVADEIGISQAQVSRLEKSAINQMQKHVKT
                         ****:**************.:** :* *
```

FIG. 12

```
ref|NP_842661.1|        ------------------------------------------------------------
ref|NP_829995.1|        ------------------------------------------------------------
ref|NP_976421.1|        ------------------------------------------------------------
ref|YP_001373458.1|     ------------------------------------------------------------
ref|YP_001512033.1|     ------------------------------------------------------------
RAAC02546               -------MTDQSLGRSPARLEDTAQASVPERRSRDLRRSFQLKCTISRIFVN-------- ref|NP_842661.1|        ------------------------------------------------DEAIVELVRKGNT
ref|NP_829995.1|        ------------------------------------------------DEAIVELVRKGNT
ref|NP_976421.1|        ------------------------------------------------DEAIVELVRKGNT
ref|YP_001373458.1|     ------------------------------------------------DEAIVELVRKGNI
ref|YP_001512033.1|     ------------------------------------------------VLDEVMVEIAKEGDL
RAAC02546               ----------------------------ALLPCTSLTIGGDFVMDTTLVLSAKRGDQ
                                                              *  .:*   .:.*:

ref|NP_842661.1|        DALEYLIHKYKNFVRAKSRSYFLVGADREDIVQEGMIGLFKAIRDYKEDKLSSFKAFAEL
ref|NP_829995.1|        DALEYLIHKYKNFVRAKSRSYFLVGADREDIVQEGMIGLFKAIRDYKEDKLSSFKAFAEL
ref|NP_976421.1|        DALEYLIHKYKNFVRAKSRSYFLVGADREDIVQEGMIGLFKAIRDYKEDKLSSFKAFAEL
ref|YP_001373458.1|     DALEYLIHKYKNFVRAKSRSYFLVGADREDIVQEGMIGLFKAIRDYKEDKLSSFKAFAEL
ref|YP_001512033.1|     EALEYLIKKYKNFVRAKARSYFLIGADREDIVQEGMIGLYKAIRDFKPDKLSSFRAFAEL
RAAC02546               DSFMALYREFHARIRSWIRNYWIPGADREDLMQHAWIGFWEAIRDYDVRGKVPFRAFAKM
                         ::  *  ::::  :*:   *.*:: ******::*..  **:::****:.   .*:***::

ref|NP_842661.1|        CITRQIITAIKTATRQKHIPLNSYVSLDKPI-YDEESDRTLLDVISEAKVTDPEEMIIS-
ref|NP_829995.1|        CITRQIITAIKTATRQKHIPLNSYVSLDKPI-YDEESDRTLLDVISEAKVTDPEEMIIS-
ref|NP_976421.1|        CITRQIITAIKTATRQKHIPLNSYVSLDKPI-YDEESDRTLLDVISEAKVTDPEEMIIS-
ref|YP_001373458.1|     CITRQIITAIKTATRQKHIPLNSYVSLDKPI-YDEESDRTLLDVISEAKVTDPEEMIIS-
ref|YP_001512033.1|     CITRQIITAIKTATRQKHIPLNSYVSLNKPI-YDEESDRTLLDVISGQKVTDPEELVVS-
RAAC02546               CVMREIQAALKMARRQKHVSHLTALSLDAECPWIEDAERTVLDVFVDRAAPSVDDMVFGP
                        *: *:* :*:*  *  ****:.   :  :**:     :  *:::**:***:    ... ::::..

ref|NP_842661.1|        ------QEEYTDIESKISELLSDLER----------KVLSLYLDGRSYQEISEQLNRHV
ref|NP_829995.1|        ------QEEYTDIESKISELLSDLER----------KVLSLYLDGRSYQEISEQLNRHV
ref|NP_976421.1|        ------QEEYTDIESKISELLSDLER----------KVLSLYLDGRSYQEISEQLNRHV
ref|YP_001373458.1|     ------QEEYSDIELKISELLSDLER----------KVLSLYLDGRSYQEISEQLNRHV
ref|YP_001512033.1|     ------REELGHIEDKIGEILSDLEL----------KVLMLYLEGRSYQEIAGDLERHV
RAAC02546               PPSAGPEELVAWAERHWGLRLTELER----------EVWRLRVEGHSYAEIQRMLGCGY
                              .*    *  :  .  *:**           :*  *  ::*:    * ref|NP_842661.1|        KSIDNALQRVKRK------------
ref|NP_829995.1|        KSIDNALQRVKRK------------
ref|NP_976421.1|        KSIDNALQRVKRK------------
ref|YP_001373458.1|     KSIDNALQRVKRK------------
ref|YP_001512033.1|     KSIDNALQRVKRK------------
RAAC02546               KAVDNAVQRLRRKAKMLVNNANLQT
                        *::***:**:.**
```

FIG. 13

```
ref|YP_077384.1|        ----------------------LEDEQVIEMVHVGDSDALDYLITKYRNFVRAKARSYF
ref|YP_001419777.1|     ----------------------LEDEQVIEKVHVGDSDALDYLITKYRNFVRAKARSYF
emb|CAA41793.1|         ----------------------EQQEDETVVDLVHKGDIDALEYLIHKYKNFVRAKARSYF
ref|ZP_01173595.1|      ----------------------LEDEEIIELVHRGESEALDYLIQKYRNFVRAKARSYF
ref|NP_240981.1|        ----------------------DVGLVNRVRNGDGAALEYLIHKYKNFVRAKARSYF
RAAC00418               MSTQPTPRDADAAPPYDTAPYENMTDEELVEAVHRGDTDALDYLIHKYKNFVRAKARSYF
                                              *   :::  *:   *:    :* :******** ref|YP_077384.1|        LIGADREDIVQEGMIGLYKSIRDFREDKLTSFKAFAELCITRQIITAIKTATRQKHIPLN
ref|YP_001419777.1|     LIGADREDIVQEGMIGLYKSIRDFREDKLTSFKAFAELCITRQIITAIKTATRQKHIPLN
emb|CAA41793.1|         LIGADREDIVQEGMIGLYKAIRDFREDKLTSFKAFAELCITRQIITAIKTATRQKHIPLN
ref|ZP_01173595.1|      LIGADKEDIVQEGMIGLYKAIRDFKEDKLSSFKAFAELCITRQIITAIKTATRQKHIPLN
ref|NP_240981.1|        LIGADHEDIVQEGMIGLYKAIRDFKGDKLSSFKAFAELCITRQIITAIKTATRQKHIPLN
RAAC00418               LIGADREDIVQEGMIGLYKSIRDFRGDKLSSFKAFAELCITRQIITAIKTATRQKHIPLN
                        ***:*********:: *:****************************** ref|YP_077384.1|        SYVSLDKPIYDEESDRTLLDVISGAKVMNPEELIINQEEFDDIELKMGELLSDLERKVLA
ref|YP_001419777.1|     SYVSLDKPIFDEESDRTLLDVISGAKTLNPEEMIINQEEFDDIEMKMGELLSDLERKVLV
emb|CAA41793.1|         SYVSLDKPIYDEESDRTLMDVISGTKVANPEELLINREKFDDIELKMAELLSDLERKVLV
ref|ZP_01173595.1|      SYVSLDKPIYDEESDRTLMDVISGAKVMDPEELIINQEEFDNIEVKMSELLSDLERKVLA
ref|NP_240981.1|        SYVSLDKPIYDEESDRTLLDVVCGSRVTDPEELLINQEEFDDIEVKMGELLSDLERKVLM
RAAC00418               SYVSLDKPIYDEDSDRTLLDVICTVRVADPEELIINQEEFDDIEGKMSELLSDLERQVLM
                        ********::**:*****:**:.    :. :***:**:*:**:**  **.********:**

ref|YP_077384.1|        LYLDGRSYQEISEELNRHVKSIDNALQRVKRKLEKYLELREI-
ref|YP_001419777.1|     LYLDGRSYQEISDDLNRHVKSIDNALQRVKRKLEKYLEIREI-
emb|CAA41793.1|         LYLDGQSYQEISEELNRHVKSIDNALQRVKRKLERYLEIREI-
ref|ZP_01173595.1|      LYLDGQSYQEISEELNRHVKSIDNALQRVKRKLERYLEVR---
ref|NP_240981.1|        LYLDGRSYQEISAELNRHVKSIDNALQRVKRKLERYMELKGV-
RAAC00418               LYLDGRSYQEIAVDLARHVKSIDNALQRVKRKLEKYLTVRNVI
                        *****:****:   :*  *******************:*:    ::
```

FIG. 14

```
ref|YP_181606.1|         ------------------------------------------------------------
RAAC02968                ---------------------------------------------MLDVLVDRTAPSVED
ref|YP_001409756.1|      ------------------------------------------------------------
ref|NP_976421.1|         ---------------------------------------------LLDVISEAKVTDPEE
ref|NP_842661.1|         C--------------------------------------------LLDVISEAKVTDPEE
ref|YP_001485343.1|      ---------------------------------------------LLDVISGAKALNPED ref|YP_181606.1|         ----------------WLEPAKGMN------ISHRELEVFVLMIEGHNNKEIGALLGIQY
RAAC02968                VVFGPPKGVSAEELVAWAERHWRLN------LSELEREVWRLRIEGHSYTEIQRMLGCGY
ref|YP_001409756.1|      ------------------------------LNEEETQIFELWLDGYSYKEIEEMVGVNF
ref|NP_976421.1|         MI------ISQEEYTDIESKISEL-------LSDLERKVLSLYLDGRSYQEISEQLNRHV
ref|NP_842661.1|         MI------ISQEEYTDIESKISEL-------LSDLERKVLSLYLDGRSYQEISEQLNRHV
ref|YP_001485343.1|      LI------ISKEEFDDIEMKMGEL-------LSELERKVLVLYLDGRSYQEISEDLNRHV
                                              :.. *  ::   *  ::* .  **    :.

ref|YP_181606.1|         QSVKN--------------------
RAAC02968                KAVDNAVQRLRKKARRALMRQEGAAL
ref|YP_001409756.1|      KKVDNTV------------------
ref|NP_976421.1|         KSIDNAL------------------
ref|NP_842661.1|         KSIDNAL------------------
ref|YP_001485343.1|      KSIDNAL------------------
                         : :.*
```

FIG. 15  RAAC03263

```
ref|YP_001666100.1|    ---------- ---------- ---------- ---------- ---------- ----------
ref|NP_621806.1|       ---------- ---------- ---------- ---------- ---------- ----------
ref|NP_346951.1|       ---------- ---------- ---------- ---------- ---------- ----------
ref|YP_001181188.1|    ---------- ---------- ---------- ---------- ---------- ----------
ref|YP_001317994.1|    ---------- ---------- ---------- ---------- ---------- ----------
RAAC03236              MSGCVSSLPF ILALCVSSAA PRVRALGGAW LRLGHRLAIG AAFTVCATAS HCCPTRCRMD
Clustal Consensus ref|YP_001666100.1|    ---------- -----TGIVR KVDELGRVVI PIELRRTLNI AERDALEIYV DGEQIVLKKY
ref|NP_621806.1|       ---------- -----TGIVR KVDELGRVVI PIELRRTLNI AERDALEIYV DGEQIVLKKY
ref|NP_346951.1|       ---------- --MKSTGVVR RVDELGRIVI PIELRRTLNI AEKDALEIYV DGEQIILKKY
ref|YP_001181188.1|    ---------- --MKSTGVVR KVDELGRIVL PIELRRTLDI AEKDALEIFV DGDKIILRKY
ref|YP_001317994.1|    ---------- --MKSTGIVR KVDELGRIVL PIELRRTLTI AEKDSLEIYV DGESIILKKY
RAAC03236              DHEAAKLRRR IRMLVTGYVR KVDHLGRLVI PKRLRKDLAI GQDDSIEIYV EGDAVVLSKY
Clustal Consensus                           :.*:*:  * .**: * *  .: *::**:*  :*: ::* ** ref|YP_001666100.1|    EPACIFCGNA ENVINYKGKN ICKNCLEELK ------
ref|NP_621806.1|       EPACIFCGNA ENVINYKGKN ICKNCLEELK ------
ref|NP_346951.1|       EPACIFCGDA SDVINYRGKN ICKHCLEELK ------
ref|YP_001181188.1|    EPACIFCGNA KDVIYYKGKN ICKDCMEELK ------
ref|YP_001317994.1|    EPACIFCGNA KDVTVYKTKN VCEDCLEEFR ------
RAAC03236              EPKCVFCG-E KAEKVFHERG VCGTCLEELK AKSKVS
Clustal Consensus      ** *:***   .         :: :. :*  *:**::
```

FIG. 16

```
ref|YP_001126560.1|     -----GIFSAFAFLLKELTFLVSYIKNNAFPQPLSPKEEEKYLELMAKGDEQARNRLIEH
ref|YP_148388.1|        -----GIFTAFTFLLKELTFLVSYIKNNAFPQPLSAQEEEKYLALMAKGDEQARNRLIEH
ref|ZP_01861605.1|      ------IATAIGYFLKELVFLVSYVKNNAFPQPLSSQEEKKYLRKMANGDEDARNILIEH
ref|NP_242151.1|        ------IIAALTYFFKEVLVFVSYVKNNAFPQPLSKEEERHYLKRMAEGDEEARNRLIEH
ref|YP_175113.1|        -----GILAALTYFMKEVFVFVSYVKNNAFPQPLSKEDEKKYLARMAEGDASARNMLIEH
RAAC00856               MDQVPGLLTLLALVFKDVSLFVSYVKQGAFPHPLSPEEEERAIRDYLAGDADARNRLIEH
                         :  : :    .:*::  .:***:*:.*:*  ::*.: :        .* **** ref|YP_001126560.1|     NLRLVAHIVKKFENTGEEVEDLISIGTIGLIKAIESYSPNKGTKLATYAARCIENEILMH
ref|YP_148388.1|        NLRLVAHIVKKFENTGEEVEDLISIGTIGLIKAIESYSPGKGTKLATYAARCIENEILMH
ref|ZP_01861605.1|      NLRLVAHIVKKFENTGEDPEDLISIGTIGLIKAIESYSEGKGTKLATYAARCIENEILMH
ref|NP_242151.1|        NLRLVAHIVKKFENTREHTEDLISIGTIGLIKAIESFSEGKGTKLATYAARCIENEILMH
ref|YP_175113.1|        NLRLVAHIVKKFENTREDVEDLISIGTIGLIKAIESYSEGKGTKLATYAARCIENEILMH
RAAC00856               NLRLVAHLAKKYESSGEEMDDLISIGTIGLIKAVESYRPDKGTKLATYAARCIENEILMY
                        *******:.**:*.: *. :**************:**:  .*******************:

ref|YP_001126560.1|     LRSLKKTRKDVSLHEPIGQDKEGNEISLLDILKSEGQDIVDEIQLNMELEQVKKYISVLD
ref|YP_148388.1|        LRSLKKTRKDVSLHEPIGQDKEGNEISLLDILKAEGEDIADEIHLNMELEQVKQYISVLD
ref|ZP_01861605.1|      LRALKKTKKDVSLHDPIGQDKEGNEISLIDILKSDADDVIETIQLSMELEKVRKYICVLD
ref|NP_242151.1|        LRALKKVKKDVSLHDPIGTDKEGNEITLIDVLQEDSEDIADSIQLKMEKKQIYEYIHVLD
ref|YP_175113.1|        LRALKKVKKDVSLHDPIGTDKEGNEITLIDILKDDGEDIVDVLQTEMEKKQIYEYIHVLD
RAAC00856               LRSSKKHRRDAFLSDPVGTDKDGNEMTLADLLGSDPDDVIDAVDMSWEKQKMFECLPLLA
                        :   ::*. * :*:* :*::* *:*    : :*: : :.. *  :::  : :* ref|YP_001126560.1|     EREKEVIVNRFGLGRQREKTQREIAKELGISRSYVSRIEKRALMKMFHEFYRQEK-----
ref|YP_148388.1|        EREKEVIINRFGLGRQREKTQREIAKELGISRSYVSRIEKRALMKMFHEFYRQEK-----
ref|ZP_01861605.1|      DREKEVIIGRFGLDMKEEKTQREIAKELGISRSYVSRIEKRALMKMFHEFYREEK-----
ref|NP_242151.1|        DREKEVIVGRFGLDLEEERTQREIAKELGISRSYVSRIEKRALMKLF-------------
ref|YP_175113.1|        EREKEVIIGRFGLNMEEERTQREIAKELNISRSYVSRIEKRALMKLF-------------
RAAC00856               PREREVLCKRFGLPDGEERTQREIAKELGISRSYVSRIEQKAIVKLYENMRQRKPAGSGA
                        **:**   ****    .*:*********.**********::*:  :*::

ref|YP_001126560.1|     --
ref|YP_148388.1|        --
ref|ZP_01861605.1|      --
ref|NP_242151.1|        --
ref|YP_175113.1|        --
RAAC00856               DA
```

FIG. 17

```
ref|YP_148388.1|        VKKFENTGEEVEDLISIGTIGLIKAIESYSPGKGTKLATYAARCIENEILMHLRSLKKTR
ref|YP_001126560.1|     VKKFENTGEEVEDLISIGTIGLIKAIESYSPNKGTKLATYAARCIENEILMHLRSLKKTR
ref|YP_896655.1|        VKKFENTGEDAEDLISIGTIGLIKAIESYSAGKGTKLATYAARCIENEILMHLRVLKKTK
ref|NP_980714.1|        VKKFENTGEDAEDLISIGTIGLIKAIESYSAGKGTKLATYAARCIENEILMHLRVLKKTK
gb|ABY76244.1|          VKKFENTGEDAEDLISIGTIGLIKAIESYSAGKGTKLATYAARCIENEILMHLRVLKKTK
RAAC01814               MKKFDTSGIDQDDLISIGTVGLIKAVDTYQPSKGTKFATYAARCIQNEILMQLRAQRKSR
                        :***:.:*  :  :*******:*****:::*...****:*********:*****:**   :*::

ref|YP_148388.1|        KDVSLHEPIGQDKEGNEISLLDILKAEGEDIADEIHLNMELEQVKQYISVLDEREKEVII
ref|YP_001126560.1|     KDVSLHEPIGQDKEGNEISLLDILKSEGQDIVDEIQLNMELEQVKKYISVLDEREKEVIV
ref|YP_896655.1|        KDVSLHDPIGQDKEGNEISLIDILKSESEDVIDMIQLSMELEKIKEYIDILDEREKEVIV
ref|NP_980714.1|        KDVSLHDPIGQDKEGNEISLIDILKSESEDVIDMIQLSMELEKIKEYIDILDEREKEVIV
gb|ABY76244.1|          KDVSLHDPIGQDKEGNEISLIDILKSESEDVIDMIQLSMELEKIKEYIDILDEREKEVIV
RAAC01814               KDVSLYSPIGTDKEGNEITIGDILFSESDSTEDEVSRRMELNTMRQLLDVLDERERKVIE
                        *****:.*** *******::  *** :*.:.   * :   ***: :::  :.:*****:**

ref|YP_148388.1|        NRFGLGRQREKTQREIAKELGISRSYVSRIEKRALMKMFHEFYRQEKEKR---------
ref|YP_001126560.1|     NRFGLGRQREKTQREIAKELGISRSYVSRIEKRALMKMFHEFYRQEKEKR---------
ref|YP_896655.1|        KRFGLGLDKEKTQREIAKALGISRSYVSRIEKRALMKMFHEFVRAEKEKKA--------
ref|NP_980714.1|        KRFGLGLDKEKTQREIAKALGISRSYVSRIEKRALMKMFHEFVRAEKEKKA--------
gb|ABY76244.1|          KRFGLGLDKEKTQREIAKALGISRSYVSRIEKRALMKMFHEFVRAEKEKKA--------
RAAC01814               LRFGLADGREWTQNEVADSLDISRSYVSRLEKRALLKMFHQSHVAKERKQAIRNARLQP
                        ****.  :* **.*:*. *.********:*****:****:     ::.*:
```

FIG. 18

```
ref|YP_001486125.1|      ---FHDQPILPAVRNMKQFEEFLKSPFTYGVLLDVHLGRLKGIMNEANAHHKKMFVHVDL
ref|NP_388808.1|         MMSFHNQPILPAIRNMKQFDEFLNSSFSYGVILDIHLGQLKGVIKEAQKHGKNMMVHVDL
ref|NP_830819.1|         ---FHEQKILPAVRQIKDLEKLLHSSYEYIVILDIHVGQLKSVISLAKQYCKKVFLHVDL
ref|YP_001643827.1|      ---FHEQKILPAVRQIKDLEKLLHSSYEYIVILDIHVGQLKSVVSLAKQHNKKVFLHVDL
ref|ZP_01696681.1|       ------QRILPASVNMKEFERFLKSDYEIGIFLELHISQLKYVAAMAKAEGKKMIYHVDL
RAAC02673                MNPFEGRRVLPAVRSLKDFEELMQGPHPVVVLLETNLTALPSLMRMANKAGKRLILHADL
                               :  :***    .:*::.:.::.  .    ::*:  ::    *     *:      *.:: *.**

ref|YP_001486125.1|      IHGIKHDEYGTEFICQEMKPAGIISTRSSVIVKAKQKKVYAIQRMFLLDTSAMEKSMEFV
ref|NP_388808.1|         IQGIKHDEYGAEFICQDIKPAGIISTRSNVIAKAKQKKIYAIQRLFLLDTSAMEKSMEFI
ref|NP_830819.1|         IHGLQSDGHATEYLCQEFRPYGLLSTKASVIMKAKQKGVVAIQRIFLIDSSAMEKSCNLL
ref|YP_001643827.1|      IHGLQSDGHATEFLCQEYKPYGLLSTKASVIMKAKQKGVVSIQRIFLIDSSAMEKSCNLL
ref|ZP_01696681.1|       IQGLKSDDYATEYLCQEYQPFGLISTKANVIQKAKQKGVVSIQRMFLIDSHALEKSYKLI
RAAC02673                IQGLKHDEAGTQFLCQMIRPYGIISTHASVIATAKKQGVIAIQRVFLIDSHSLRTSYRVL
                         *:*::   *    .::::**    :*  *::**::.**  .**::  :   :***:**:*:   ::..*   ..:

ref|YP_001486125.1|      GKHRPDFIEVLPGVVPNLITEVRERAGIPIFAGGFIRTKEDVERALEAGATAVTTSNTTL
ref|NP_388808.1|         GKHKPDFIEVLPGIVPSLIQEIKEKTGIPIFAGGFIRTEEDVEQALKAGAVAVTTSNTKL
ref|NP_830819.1|         DKTKPDYIEVLPGALTDVIAEVKERTGVPILAGGFIRTVEDVERALNAGATAITTSKREL
ref|YP_001643827.1|      EKTKPDYIEVLPGALTGVIAEVKERTGVPILAGGFIRTVEDVERALNAGATAITTSKKEL
ref|ZP_01696681.1|       ERTKPDYIEVLPGIAPWMITEVKERLGIPIFAGGLIRTREDVEKALKAGAEGITTSDTEL
RAAC02673                QQAKPDFLEVLPGVVPQLIAEIREQTGLPVLAGGFVRTKEDVERAVAAGATAVTTSVKAL
                           :::***    .  :*  *:::*:  *:*::*::  ****:*:  *  .:*     * ref|YP_001486125.1|      WK-
ref|NP_388808.1|         WK-
ref|NP_830819.1|         WK-
ref|YP_001643827.1|      WK-
ref|ZP_01696681.1|       WE-
RAAC02673                WQL
                         *:
```

FIG. 19

```
ref|ZP_01725195.1|         MKRHEAREKALQVLFQLD-NT------DLTVEEAMGH------IKGQPTNA-----FYEK
RAAC02112                  MTRHEARECALQALCVLDVQR------DLGSAEAIASA-----LAERGTDAGGDFTYIEE
ref|ZP_00538565.1|         MKRHMARELAVQSLFQMELS-------DLSAQEAIEFA-----VEGKEYD-----TFVTR
ref|YP_148250.1|           MKRHEAREKALQALFQIDVGR-------IPPDEALHNV-----TGGGDIDP-----FLRQ
ref|YP_001126420.1|        MKRHEAREKALQALFQIDVGH-------IPPDEAIGNV-----TGSGEVDP-----FLRQ
ref|NP_390312.1|           MKRRTAREKALQALFQIDVS-------DIAVNEAIEHA-----LDEEKTDP-----FFEQ
                           *.*: *** *:* *  ::         :    **:         :       :   .

ref|ZP_01725195.1|         IVTGTAEHLEEIDATLEQHLEKWSLARLPKIERTVLRLAVYELLYMPETPKRVVLNEAIE
RAAC02112                  LVDGTRRHLDEIDELLARHMERWSPERIGRVERNVLRLATYELLFEPELPIASAIDEAVE
ref|ZP_00538565.1|         LVEGVEANKPEIDQKLRAALVNWSFERIGNIERTILRLAVYELLFEAKIPVRVTINEAIE
ref|YP_148250.1|           LVFGVVEHQEEIDELLRANLEKWTLERVANVDRAILRMATYEMKYADDVPVSVSLDEAVE
ref|YP_001126420.1|        LVFDVIEHRAEIDELLRSNLEKWKLERVANVDRVILRMATYEMKYVDDVPVSVSLDEAVE
ref|NP_390312.1|           LVHGVLEHQDQLDEMISKHLVNWKLDRIANVDRAILRLAAYEMAYAEDIPVNVSMNEAIE
                           :*  ..   :  ::*   :   .*.  *: .::* :**:*.**: :  . *   ::**:* ref|ZP_01725195.1|         LCKTFGDDSSSKFVNGVLSK----------------------------------------
RAAC02112                  IAKTFATEQSGRFVNGVLAKLLPAVADRRRADTREAGQEKRTASAAEPAREGVDDGA
ref|ZP_00538565.1|         LTKAFADEEATKIVNGVLGKVAQEV-----------------------------
ref|YP_148250.1|           LAKKFGDWKSGSFVNGVLSKVKAAL-----------------------------
ref|YP_001126420.1|        LAKKFGDWKSGSFVNGVLSKVKAAL-----------------------------
ref|NP_390312.1|           LAKRFGDDKATKFVNGVLSNI-----------------------------
                           : * *.  .:  :*****.:
```

FIG. 20

```
ref|YP_147113.1|        ------------------------MNTQLLEALADLMREKGISKEVVMEAIEAAIVSAY
ref|YP_001125233.1|     ------------------------MNTQLLEALADLMREKGISKEVIMEAIEAALVSAY
ref|NP_243282.1|        ------------------------MNSEFMDALTTLEKEKGISKEVIIEAIEAALISGY
ref|YP_175727.1|        ------------------------MNSEFMEALSTLEADKGIKKEVIIEAIEAALISGY
ref|ZP_02330483.1|      ------------------------MNSEFIEALSEIEREKGISKDLLIDAIEAAMISSY
RAAC02902               MRTRGWLWSGDPNAPEISRRGGSLVMNVDFLEALDQLAREKGIDKEVLLEAIEAALIASY
                                                 :::.   :  :***.*:::::****:::.* ref|YP_147113.1|        KRNFGQAQNVRVDLNMDTGTIRVFARKDVVEEVADPRLEISLEDAQRINPNYQIGDVVEL
ref|YP_001125233.1|     KRNFGQAQNVRVDLNMDTGTIRVLARKDVVEEVTDPRLEISLEEAQRLNPNYQIGDVVEL
ref|NP_243282.1|        KRNFNQAQNVRVDVNRENGSIRVFARKEVVEEVFDARLEISLDEAKGINPNYEVDDVVEI
ref|YP_175727.1|        KRNFGQAQNVRVDVNRDNGSIRVFARKVVVEEVFDKRLEISEAEAQRINPHYEVDDIVEI
ref|ZP_02330483.1|      KRNFNTAQNVRVDINRQTGVIRVFARKTVVEDVLDPRLEISLTAAREINQNYQLGDIVEI
RAAC02902               RRNFHSAANVRVEVKRDTGEVHVYARKTVVEEPKDTRLEISLDAARDINPSYQIGDVVEI
                        :***  *  ****::: :.*  ::* *** ***: * ***** *:.:* *::.*:**:

ref|YP_147113.1|        EVTPRDFGRIAAQTAKQVVTQRVREAERSIIYAEFVDREEDIMTGIVQRVDPRFVYVSLG
ref|YP_001125233.1|     EVTPRDFGRIAAQTAKQVVTQRVREAERSIIYAEFVDREEDIMTGIVQRIDPRFVYVSLG
ref|NP_243282.1|        EVTPKDFGRIAAQTAKQVVTQRVREAERGIIYADFIDREEDIMTGIVQRQDNRFIYVDLG
ref|YP_175727.1|        EVTPKDFGRIAAQTAKQVVTQRVREAERGIIYSDFIDREEDIMNGIVQRQDHRFIYVDLG
ref|ZP_02330483.1|      EVTPRDFGRIAAQTAKQVVTQRIREAERGLIYNAFIDKEEDIVTGIVQRQDQRSYYVDLG
RAAC02902               EVTPRDFGRIAAQAAKQVVMQRVKEAERSVIYSKFADREEEVVSGIVSRLEPRVAYIDLG
                        ****:********:***** **::****.:**  * *:**:::.***.* : *  *:.**

ref|YP_147113.1|        KAEALLPANEQMPNETYKPHDRLKVYITKVEKTTKGPQIFVSRTHPGLLKRLFELEVPEI
ref|YP_001125233.1|     KAEALLPANEQMPNETYKPHDRLKVYITKVEKTTKGPQIFVSRTHPGLLKRLFELEVPEI
ref|NP_243282.1|        KVEALLPLSEQMPNESYRHNDRIKAYITKVEKTTKGPQIMISRTHPGLLKRLFELEVPEI
ref|YP_175727.1|        KVEALLPLSEQMPNETYKHNDRIKAYITKVEKTTKGPQILISRTHPGLLKRLFELEVPEI
ref|ZP_02330483.1|      KVEAVLPLNEVMPTEKFKHGDRVKAYITKVENTTKGPQIILSRTHPGLLKRLFELEVPEI
RAAC02902               DTEAILPQSEQMASDKLQVGKRLKVFIARVERTSKGPQIVVSRTHPGLLRRLFELEVPEI
                        ..:  .* *.:. :  .*:*.:*:.*.*:***.:****:******** ref|YP_147113.1|        YDGTVEIKSIAREAGDRSKISVHSDNPEVDPVGACVGPRGQRVQAIVDELNGEKIDIVRW
ref|YP_001125233.1|     YDGTVEIKSIAREAGDRSKISVHSDNPEVDPVGACVGPKGQRVQAIVDELHGEKIDIVRW
ref|NP_243282.1|        YDGTVELKSVAREAGDRSKISVHAENPEVDPVGACVGPKGSRVQTIVNELKGEKIDIVEW
ref|YP_175727.1|        YDGTVEIKSVSREAGDRSKIAVHSDNPEVDPVGACVGQRGQRGQVQTIVDELKGEKIDIVEW
ref|ZP_02330483.1|      FDGVVEIRSVAREAGFRSKIAVDSRNEEVDPVGSCVGPKGLRVQTIVNELRGEKIDIVRW
RAAC02902               YEGIVEIKAVAREAGSRSKIAVHSRNPEVDPIGACVGARGSRVQAIVNELNGEKVDIVEW
                        ::* ::::.: **:*.: * ***.:*:*** :* *::.*.***.* ref|YP_147113.1|        SADPVEFVANALSPAKVLRVIVNEEQKATTVIVPDYQLSLAIGKRGQNARLAAKLTGWKI
ref|YP_001125233.1|     SADPVEFVANALSPAKVLRVIVNEEQKATTVIVPDYQLSLAIGKRGQNARLAAKLTGWKI
ref|NP_243282.1|        SEDPVEYVANALSPSKVVKVNVNEEEKTTQVIVPDYQLSLAIGKRGQNARLAAKLTGWKI
ref|YP_175727.1|        SEDPVVYVANALSPAKVMKVNVLEGEKMTQVIVPDYQLSLAIGKRGQNARLAAKLTGWKI
ref|ZP_02330483.1|      MESTEEYVANALSPSKVLEVNIFEDEKMARVIVPDYQLSLAIGIKGQNARLAAKLTGWKI
RAAC02902               SEDPATFVANALSPAKVIDVHIYEDERVARTVVPDYQLSLAIGKEGQNARLAARLTGWKI
                        .. :*****:: *  *  ::  :.:********* .***:**** ref|YP_147113.1|        DIKSESE-----------------------------
ref|YP_001125233.1|     DIKSESE-----------------------------
ref|NP_243282.1|        DIKSESEAQELGLLED-EAASHE-------------
ref|YP_175727.1|        DIKSESEARELGLLDE-ENENDELEEF---------
ref|ZP_02330483.1|      DIKSETQ-----------------------------
RAAC02902               DIKSESQMASHSLLDQLEDTNEEEPEFATLSDDWLNEP
                        *****::
```

FIG. 21

```
ref|ZP_01173598.1|      --------------MEKNWYVVHTYSGYENKVKANLEKRVETMAMQDKIFRVIVPEEEETD
ref|YP_848410.1|        --------------MEKNWYVVHTYSGYENKVKANLEKRVESMGMSDKIFRVIVPEEEETE
ref|YP_089786.1|        --------------MEKKWYVVHTYSGYENKVKANLEKRVESMGMQDKIFRVVVPEEEETD
ref|NP_691027.1|        --------------MEKNWYVVHTYSGYENKVKMNLEKRVESMGMEDKIFRVIVPEDEEAE
ref|YP_173640.1|        --------------MEKNWFVVHTYSGYENKVKANLEKRVESMEMTDHIFRVLVPVEEETE
RAAC00415               MGVAGCSPCSMENLEKQWYVIHTYSGYENKVKSNLESRVQTMGMEDRIFRVVVPTEEAVE
                                      :**:*:*:********** ***.**::* * *:****:** :* .:

ref|ZP_01173598.1|      IKNGKKKVVKRKVFPGYVLVEIVMTDDSWYVVRNTPGVTGFVGSAGSGSKPTPLLPEEVN
ref|YP_848410.1|        VKNGKTKTIKRKVFPGYVLVEIVMTDDSWYVVRNTPGVTGFVGSSGSGSKPTPLLPEEAE
ref|YP_089786.1|        IKNGKKKVVKKKVFPGYVLVELVMTDDSWYVVRNTPGVTGFVGSAGSGSKPTALLPGEAE
ref|NP_691027.1|        IKNGKKKMVKKKSFPGYVLTEMVMTDDSWYVVRNTPGVTGFVGSSGHGAKPTPLMPGEID
ref|YP_173640.1|        IKNGKTKQVSRKVFPGYVLVEMVMTDDSWYVVRNTPGVTGFVGSAGAGSKPTPLMPDEVE
RAAC00415               IKNGKKRVVQRKTYPGYVLVEMIMTDDSWYVVRNTPGVTGFVGSPGAGSKPVPLMPHEVE
                        :****.: :.:*  :*****.*::********************.* *:**..*:* * :

ref|ZP_01173598.1|      VILKRMGVDEKRVDIDFEIGETVKVNEGPFANFTGSIEEIDKDKAKIKVLVNMFGRETPV
ref|YP_848410.1|        RILKSMGMVEKRAEADFEIGETVMVKEGPFADFSGKVDEMDNDKGKAKVMVNMFGRETPV
ref|YP_089786.1|        KILKRMGLEERKTEIDFELKETVKVIDGPFADFTGTIEEIDHDKNKVKVFVNMFGRETPV
ref|NP_691027.1|        VVLKRMGVSEPTVQVDFEIKENVRVTDGPFTDFTGSIEHIDTDKQKIKVHVNMFGRETPV
ref|YP_173640.1|        RILKQMGVVEAQEEVDFELKESVKVKSGPFADFVGTIEEIQVEKRKLKVHVNMFGRETPV
RAAC00415               QILSSMGVNEAKPVAQFKVGDVVRLTSGPFADMVGTVEEVHPEHQKLKVLVSMFGRETPL
                        :*. **: *      :*:: :  * : .***::: *.::.:. :: * ** *.*******:

ref|ZP_01173598.1|      ELDFTQIEKL-
ref|YP_848410.1|        EVDFNQIEKL-
ref|YP_089786.1|        ELEFTQVDKL-
ref|NP_691027.1|        ELDFSQVEKL-
ref|YP_173640.1|        ELEFGQVEKI-
RAAC00415               EADFTQVEHLP
                        * :* *::::
```

FIG. 22A

```
ref|YP_149235.1|           ----------------------------------------------------------------
ref|YP_001127411.1|        ----------------------------------------------------------------
ref|YP_001377035.1|        ----------------------------------------------------------------
ref|YP_039325.1|           ----------------------------------------------------------------
gb|AAU09403.1|             ----------------------------------------------------------------
RAAC00475                  -------------------------------MPPGHECEGRCLDIRELEEKKLTEL ref|YP_149235.1|           ---AKQYKISYYSKLTKKELIFAILKARAEQDGLFFMEGILEIIPSEGFGFLRPINYSPS
ref|YP_001127411.1|        ---ARQYKISYYSKLTKKELIFAILKARAEQDGLFFMEGVLEIIPSEGFGFLRPINYSPS
ref|YP_001377035.1|        ---AKEYKISYYSKLTKKELIFAILKARAEKEGFFFMEGVLEIIQSEGFGFLRPINYSPS
ref|YP_039325.1|           ---AKEFKISYYSKLTKKELIFAILKARAEKEGFFFMEGVLEIIQSEGFGFLRPINYSPS
gb|AAU09403.1|             ---AREYKVSYYSKLTKKELVFAILKAQAEQDGLLFMEGVLEIIQSEGFGFLRPINYSPS
RAAC00475                  YKYAREFQIPHYGSMKKKELIFAILKAQAERDGLMFAEGVLEIMP-EGYGFLRPVGYLPS
                              * :::: .:*.. :.**:**:::*::* :*:   :***:.* ** ref|YP_149235.1|           SEDIYISASQIRRFDLRNGDKVSGKVRPPKENERYFGLLHVEAVNGEDPEVAKERVHFPA
ref|YP_001127411.1|        SEDIYISASQIRRFDLRNGDKVSGKVRKPKENERYFGLLHVEAVNGEDPEIAKERVHFPA
ref|YP_001377035.1|        SEDIYISASQIRRFDLRNGDKVSGKVRPPKENERYFGLLQVEAVNGDDPESAKERVHFPA
ref|YP_039325.1|           SEDIYISASQIRRFDLRNGDKVSGKVRPPKENERYFGLLQVEAVNGDDPESAKERVHFPA
gb|AAU09403.1|             SEDIYISASQIRRFDLRNGDKVSGKVRPPKENERYYGLLHVEAVNGEDPETSKDRVHFPA
RAAC00475                  QEDIYVAASQIRRFDLRTGDLVSGKVRPPKENERYFGLLHVEAVNGYSPEVAAERLHFAA
                           .**::******. **** ***:*:**** . : :*:**.* ref|YP_149235.1|           LTPLYPNRQMKLETTPDKLSTRIIDLIAPVGFGQRGLIVAPPKAGKTMLLKEIANSITTN
ref|YP_001127411.1|        LTPLYPNRQMKLETTPDKLSTRIIDLIAPVGFGQRGLIVAPPKAGKTMLLKEIANSITAN
ref|YP_001377035.1|        LTPLYPNRQMKLETEPKKLSTRIMDLIAPVGFGQRGLIVAPPKAGKTILLKEIAHSITTN
ref|YP_039325.1|           LTPLYPDRQMKLETEPKKLPTRIMDLIAPVGFGQRGLIVAPPKAGKTSLLKEIAHSVTTN
gb|AAU09403.1|             LTPIYPNEQMLLETQPRSFSTRIIDLISPIGFGQRGLIVAPPKAGKTMLLKEIANSITTN
RAAC00475                  LTPLFPSKRIVLETTPENLATRLIDLFAPIGFGQRGMIVAPPKAGKTVLLKEIAHSIATN
                           ***::*..:: *** *  .::::::*:****.*******  ****:*:::* ref|YP_149235.1|           HPDVELIVLLIDERPEEVTDIERSVQGDVVSSTFDEVPENHIKVAELVLERAMRLVEHKR
ref|YP_001127411.1|        HPDVELIVLLIDERPEEVTDIERSVQGDVVSSTFDEVPENHIKVAELVLERAMRLVEHKR
ref|YP_001377035.1|        HPEAELIVLLIDERPEEVTDIERSVKGDVVSSTFDEVPENHIKVAELVLERAMRLVEHKK
ref|YP_039325.1|           HPEAELIVLLIDERPEEVTDIERSVKGDVVSSTFDEVPENHIKVAELVLERAMRLVEHKK
gb|AAU09403.1|             HPDAELIVLLIDERPEEVTDIERSVDGDVVSSTFDEVPENHIKVAELVLERAMRLVEHKK
RAAC00475                  YPDVHLFVLLIDERPEEVTDMQRSVKGEVIASTFDEVPENHIKVSELVLERALRLVEHKQ
                           :*:..*:.*************:***.*:*:***************.*******:******:

ref|YP_149235.1|           DVVILMDSITRLARAYNLVIPPSGRTLSGGIDPAAFHRPKRFFGAARNIEEGGSLTILAT
ref|YP_001127411.1|        DVVILMDSITRLARAYNLVIPPSGRTLSGGIDPAAFHRPKRFFGAARNIEEGGSLTILAT
ref|YP_001377035.1|        DVVILMDSITRLARAYNLVIPPSGRTLSGGIDPAAFHRPKRFFGAARNIEEGGSLTILAT
ref|YP_039325.1|           DVIILMDSITRLARAYNLVIPPSGRTLSGGIDPAAFHRPKRFFGAARNIEEGGSLTILAT
gb|AAU09403.1|             DVVILMDSITRLARAYNLVIPPSGRTLSGGIDPAAFHRPKRFFGAARNIEDGGSLTILAT
RAAC00475                  DVVILLDSLTRLTRAYNLVVPPSGRTLSGGIDPAAFHRPKRFFGAARNVEEGGSLTILAT
                           **:**:**:***:******:***********************************.*:*********
```

FIG. 22B

```
ref|YP_149235.1|        ALIDTGSRMDDVIYEEFKGTGNMELHLDRSLAERRIFPAIDIRRSGTRKEELLIPKEHLE
ref|YP_001127411.1|     ALVDTGSRMDDVIYEEFKGTGNMELHLDRSLAERRIFPAIDIRRSGTRKEELLIPKEHLD
ref|YP_001377035.1|     ALVDTGSRMDDVIYEEFKGTGNMELHLDRSLAERRIFPAIDIRRSGTRKEDLLIPKEHLD
ref|YP_039325.1|        ALVDTGSRMDDVIYEEFKGTGNMELHLDRSLAERRIFPAIDIRRSGTRKEDLLIPKEHLD
gb|AAU09403.1|          ALIDTGSRMDDVIYEEFKGTGNMELHLDRSLAEKRIFPAIDIRRSGTRKEELLIPKEHLD
RAAC00475               ALIDTGSRMDDVIYEEFKGTGNMELHLDRRLAEKRVFPSIDIRRSGTRREEALMPKEELE
                        **:*********************** ***:*:**:*********:*: *:***.*:

ref|YP_149235.1|        KLWAIRKTMADSPDFIERFLNKLRRTKSNEEF----------------------------
ref|YP_001127411.1|     KLWAIRKTMADSPDFIERFLNKLRRTKSNEEF----------------------------
ref|YP_001377035.1|     KLWGIRKTMRDTPDFVESFLRKLRQTKTNEEFLQNI------------------------
ref|YP_039325.1|        KLWGIRKTMRDTPDFVESFLRKLRQTKTNEEFLQNI------------------------
gb|AAU09403.1|          HLWAIRKSMADAPDFAEKFLKRLRQTKTNEEFFSMLT-----------------------
RAAC00475               KVWAIRKSMGDNQDFTEMFLRKFRHYKTNKEFLDSLSLNRVERKPVASAEKPAAQPVTSE
                        ::*.***:*  *   ** * **.::*: *:*:**

ref|YP_149235.1|        -
ref|YP_001127411.1|     -
ref|YP_001377035.1|     -
ref|YP_039325.1|        -
gb|AAU09403.1|          -
RAAC00475               T
```

FIG. 23A

```
ref|YP_001488275.1|    ---------------LYKQMLDLIDVGVHAIDENGHTVVYNKKMMEIESLKRSDVLHKNVL
ref|YP_173520.1|       ---------------LYQMLIDEINVGIHVIDQDGHTIIYNKKMMEIESMVDTDVLHKNLL
ref|ZP_01173129.1|     ---------------ILEQILEHVDAGIHAIDHEGRTIIYNRKMAEIEGMDPESVIGRSLL
ref|ZP_01696484.1|     ---------------LYETIMNLVDAGIHAVDEEGRTMIYNQKMRDIEGMDSREVLYKKLE
ref|ZP_02171541.1|     MQPEKLTDTAFIHPVYRKLLDYLDIGIHMINTEGRSVIYNRKMSEMEDMNPKEVLNKRIM
RAAC02984              ---MEPSVVADVWKLYQEILEFAPVGVHAVDREGRTRVYNRVMGEIDGYRPDEVLEKNVF
                                       : . ::   *:*  ::  :*::  :**: *  :::.    .*: : :

ref|YP_001488275.1|    DFFAFQDEMHSTLVQALRTGKQTVHAKQTYHNYNGKEITTINHTYPLVRDG---------
ref|YP_173520.1|       EVFTFHDDERSTLVQALKTGKVTKDVKQTYFNNKGEEITTINNTFPPFIENG---------
ref|ZP_01173129.1|     EVFPFSRREDSTLLLALQNGKGTQPAKQTYFNSKGKEITAINHAIPILAAG---------
ref|ZP_01696484.1|     DVFRFRSSEESTLLKALKTGEESHLVKQTYFNNKGREITSVNHTYPFYYKG---------
ref|ZP_02171541.1|     EIFLFDSEEESRLLQALNNNVVHKDAKQVYFNFKGQEITTVNNTFPLTVDG---------
RAAC02984              ELYELD-EETSTLWRALKTGHPVQIDEQVYVARNGRRVVTQNRTKPVVIAG---------
                       :.: :       * *  **...          :*.*   :*..:.: *.: *.   * ref|YP_001488275.1|    --LIQGAVE--ISNDVTKLERLIHHNMKKKGSTRFTFESIIGQSPAFLEVIEHAKRATRT
ref|YP_173520.1|       --KITAAVE--IAKDMTQLDHVIKKNVLRKRESHYTFDQIIGNSKAFLAVIEEAKRAART
ref|ZP_01173129.1|     --KSLGAIE--IAKDVSRIERLVKENLSRKNSDRYTFESIIGSSKAILEVVEAAKRAVRT
ref|ZP_01696484.1|     --KLAGAVE--IAEDITKIERLIRRN--HESHTGYTFHHIIGKSKAISEVIEFSRRAART
ref|ZP_02171541.1|     --EKIGAVE--IARDITKLERLSRETSRGASDARFTFDQIIGNSPAIEDVVENARRATRT
RAAC02984              --EIIGAME----IAVPREAGGAQEAADARIRRRYSFADILGESRAMQRALDLAERAARM
                         .*:*       ..:         :.           ::*   *:*.*  *:  .:: :.**.* ref|YP_001488275.1|    SSYVLIVGETGTGKELFAQSIHNGSSRSSGPFITQNCAALPDNLIESLLFGTQKGAFTGA
ref|YP_173520.1|       SSSVLIVGETGTGKELFAQSIHYASPRSHAPPLAQNCAAIPENLMESLLFGTKKGAFTGA
ref|ZP_01173129.1|     TSPILIAGETGTGKELFAQSIHGSLRSPGPFVAQNCAALPENLVESILFGTKKGAFTGA
ref|ZP_01696484.1|     SSYVLIIGETGTGKELFAQSIHYESERSRGPFIAQNCAALPDNLIESILFGTKKGAFTGA
ref|ZP_02171541.1|     TSSVLIYGETGTGKELFAQSIHNGSSRASKPFISQNCAALPDTLIEGILFGSVKGAFTGA
RAAC02984              DLPVLLVGETGTGKELFAQAIHGASARKHGPPLAQNCAAWPEGLAESVLFGTRRGGFTGA
                       :*: **********:  *  *   ::***  *:  * *.:***: :*.**** ref|YP_001488275.1|    ADQPGLFEQAQGGTLLLDEINSLNPHLQAKLLRVLQEKRVRRLGSTKEIAVDVRVIANMN
ref|YP_173520.1|       LDTPGLFEQADGGTLLLDEINSLDPALQAKLLRVIQEKTIRRIGDTKDKKVDVRIIATIN
ref|ZP_01173129.1|     VDRPGLFEQAEGGTLLLDEINSMPAPLQAKLLRVLQEKKVRRIGDTKDREIDVRVVAAIN
ref|ZP_01696484.1|     VDRAGLFEQADQGTLLLDEINALNIHLQAKLVKVKRIGGTQEKPVDVRVIATMN
ref|ZP_02171541.1|     TDHPGLFEQANGGTLMLDEINSLSASLQAKLLRAIQEKTIRRIGDTKSRSVDVRIIATMN
RAAC02984              VDRAGVFELACGGTLLLDEVHAMSPSVQAKLLRALQDGEVWPIGARRSVQTDVRVIAAMN
                        *  .*:** *  **:*::::       :******..:*:       : *    :.   ***:.* :* ref|YP_001488275.1|    EDPVDAIASGRMRKDLFYRLGIVTLFIPPLSERKEDIPTFVNHFIQKYNELFQMKVKAAD
ref|YP_173520.1|       EDPIDMIAKQRLRKDLYYRLSVVTLFIPPLRERKEDILPLIEEFIHKYNTLFQMNVKTIS
ref|ZP_01173129.1|     EDPVDAIAEGRLRKDLYYRLSAVSLFIPPLRERKEDILLLSSFFIQKYNDWFGMEVPGLD
ref|ZP_01696484.1|     ETPYEAIANHRLRKDLYYRLGVVTLFIPPLRDRLEDLPLLTGHFIQKYNPLFQMNVRGIT
ref|ZP_02171541.1|     EDPVDALSKNKLREDLYYRLSVVSIVIPPLRHRKEDLTVLIAHFIRKYNRLFQMNIQEVT
RAAC02984              VPPSAALSRGLVRPDLLYRIGAIAIHLPPLRERPEDIPLLAQAFLRRYG---EARAVRLS
                          *    ::    :* ** **:.  :::  :*** .*  **:    :   *:::*.       .

ref|YP_001488275.1|    EEVLALFKAYDWPGNVRELEHVIEAGMNMMMDEDELSMHHLPYHFRFKQMEGRPPAQLQT
ref|YP_173520.1|       EEAKAILFQHDWPGNARELEHTIEGTMNFISDETEIHIHNLPFRLRNR------------
ref|ZP_01173129.1|     EETEEQFLRYDWPGNIRELEHVIEGAMNMAEDDARITSEILPHHFRQK------------
ref|ZP_01696484.1|     PEVLTFFRSYRWPGNIRELEHMIEAAMNVMLDEDMIELRHLPMQYRQSGH----------
ref|ZP_02171541.1|     DDVFNLFSEYDWPGNVRELEHTIEGAMNLIYDDEPIGFQHLPLHLKHKFTQP--------
RAAC02984              SDAMAFLTSHDWPGNVRELEQTVRSALALWPEAREITSEMLRS-----------------
                        :.   :   :  **** ****: :..:. :   :      . *
```

FIG. 23B

```
ref|YP_001488275.1|    NSLQQTVAADTFVYTSPEQTTDFQTQMERFEKQYIVHYLEKMDDNISQTAKLLGMSRQSL
ref|YP_173520.1|       ---YQKEVKDTETGNLPAKT--LQEKMAEVEKLYILQALRENNNNVSQTAKNLGMSRQNL
ref|ZP_01173129.1|     -AETSHSFPGRNLGEPAGPQPSLSDYVASAEKAYINKVWREQDGNITRTAKILGMSRQNL
ref|ZP_01696484.1|     ------------FNSPAEKSPLLKDRLFEYEKHCILEALEANGSNISKAAEQLGLSRQSL
ref|ZP_02171541.1|     --PATSEGTERLFTQQPEPGLPLETYMDTVEKAYIQKSLTEAGGNISQAARTLGLKRQSL
RAAC02984              --------AHPLLGEGAPRELERVARAARPSDDAIRRAYEAASGNLTHAAQALGISRQRM
                               .           ..  *    ..*::::*. **:.** :

ref|YP_001488275.1|    QYRMKKL---------
ref|YP_173520.1|       QYRLKKFHL-------
ref|ZP_01173129.1|     QYRIKKHGL-------
ref|ZP_01696484.1|     QYRMKRLGI-------
ref|ZP_02171541.1|     QYRMRKFNL-------
RAAC02984              QYHVRRLGLRTSSQPK
                       **::::
```

FIG. 24A

```
ref|YP_090070.1|       ------------------------------------------------------------
ref|YP_077660.1|       ------------------------------------------------------------
ref|NP_244812.1|       ------------------------------------------------------------
ref|ZP_02171541.1|     ------------------------------------------------------------
ref|ZP_01173129.1|     ------------------------------------------------------------
RAAC02994              MIRRARIRAGSTCTIEANFVPNGQRRCRAGGAADRTGAKRALRFSDSDCKLGLHADLDRR ref|YP_090070.1|       ----------------------------------------GLHVVDENGTSVVYNKKM
ref|YP_077660.1|       ----------------------------------------GLHVVDENGTSVVYNKKM
ref|NP_244812.1|       ----------------------------------------GIHVIDTFGQTIIYNKKM
ref|ZP_02171541.1|     ----------------------------------------GIHMINTEGRSVIYNRKM
ref|ZP_01173129.1|     ----------------------------------------GIHAIDHEGRTIIYNRKM
RAAC02994              HKALCILMQARLEHAERRRGMRAQDAEARRTLLEAALDALDEGVHVVDAEGVTVFYNRKM
                                                               *:*  ::   *  ::.**:**

ref|YP_090070.1|       SQIEGMDVGDVLGKNVLDVFTFASQHDSTLLQALHHGKTNKNVKQTYFNNKGQEITTVNH
ref|YP_077660.1|       SQIEGMDVGDVLGKNVLDVFTFASQHDSTLLQALHHGKTNKNVKQTYFNNKGQEITTVNH
ref|NP_244812.1|       MEIESLTKEDVENKDFLDIFMFEEGQGSTLLEALYKKKHSKDVKQTYFNNRGKEITTINN
ref|ZP_02171541.1|     SEMEDMNPKEVLNKRIMEIFLFDSEEESRLLQALNNNVVHKDAKQVYFNFKGQEITTVNN
ref|ZP_01173129.1|     AEIEGMDPESVIGRSLLEVFPFSRREDSTLLLALQNGKGTQPAKQTYFNSKGKEITAINH
RAAC02994              ADIEAMSRQDVMGRRIDDVFSFPDAAGSTLLDAVRRGVRRDDVRQTYFNRRGQAITTVNR
                         :* :    .* .:. ::* *     * ** *:.    . .:*.***  :*: **:*.

ref|YP_090070.1|       TFPIMENGNTKGAVEIAKDVTKLERLIRENMNKTESTKYTFDSLIGVSPAFKEVIEHAKR
ref|YP_077660.1|       TFPIMENGNTKGAVEIAKDVTKLERLIRENMNKTESTKYTFDSLIGVSPAFKEVIEHAKR
ref|NP_244812.1|       TFPLYENGQVIGAIEISKDVTKLERLIRKNMESKGNTRYTFDSIGESTAIREVIENTKR
ref|ZP_02171541.1|     TFPLTVDGEKIGAVEIARDITKLERLSRETSRGASDARFTFDQIIGNSPAIEDVVENARR
ref|ZP_01173129.1|     AIPILAAGKSLGAIEIAKDVSRIERLVKENLSRKNSDRYTFESIIGSSKAILEVVEAAKR
RAAC02994              TFPVYADGRILGAVEIARDVTSVEQLRSTAFGQAG--VRYTFASIIAESLAMREVLEQARR
                       ::*:    .    :::*::  :*:*        ::**  .:*. *  *:  :*:* ::* ref|YP_090070.1|       ATRTSSSILIVGDTGTGKELFAQSIHNGSQRSTGPFISQNCAALPESLVEGLLFGTVKGA
ref|YP_077660.1|       ATRTSSSILIVGDTGTGKELFAQSIHNGSQRSTGPFISQNCAALPESLVEGLLFGTVKGA
ref|NP_244812.1|       ATRTASSVLIVGETGTGKELFAQSIHNGSDRSKGPFISQNCAAMPETLIESLLFGTKKGA
ref|ZP_02171541.1|     ATRTTSSVLIYGETGTGKELFAQSIHNGSSRASKPFISQNCAALPDTLIEGILFGSVKGA
ref|ZP_01173129.1|     AVRTTSPILIAGETGTGKELFAQSIHSGSLRSPGPFVAQNCAALPENLVESILFGTKKGA
RAAC02994              AARTDSSVLIIGETGTGKELLAQGIHAASPRRDGPFVSQNLAAIPDTLVEGILFGTARGA
                       * ** *.:**  *:******:**.:* .. * .. **: ** :**:*:.*:.:***: :**

ref|YP_090070.1|       FTGAVDRPGLFEQADGGTLLLDEINSLDFRLQAKLLRAIQEKTIRRIGASKDTPIDVRII
ref|YP_077660.1|       FTGAVDRPGLFEQADGGTLLLDEINSLDFRLQAKLLRAIQEKTIRRIGASKDTPIDVRII
ref|NP_244812.1|       YTGAIERPGLFEEAEGGTLLLDEINSLSASLQAKLLRAIQEKTIRRIGDTKSRSVDVRII
ref|ZP_02171541.1|     FTGATDHPGLFEQANGGTLMLDEINSLSASLQAKLLRAIQEKTIRRIGDTKSRSVDVRII
ref|ZP_01173129.1|     FTGAVDRPGLFEQAEGGTLLLDEINSMPAPLQAKLLRVLQEKKVRRIGDTKDREIDVRVV
RAAC02994              FTGAVDRPGLIEQANGGTLLLDELNAMPAPLQAKLLRVLQERVVRRVGDLKDRPVDVRIL
                       :*** ::***:*:*:****:***:*.:      ******:.::**:  :**:*   .:  ::**::

ref|YP_090070.1|       ATMNEDPVDAVSGQRLRKDLYYRLSVVTLFIPPLKDRKEDIMPLTQHFIDKYNALFQMEV
ref|YP_077660.1|       ATMNEDPVDAVSGQRLRKDLYYRLSVVTLFIPPLKDRKEDIMPLTQHFIDKYNALFQMEV
ref|NP_244812.1|       STINEDPIEAIASGRLRKDLYYRLGVVTLFIPPLRERKEDIVPLVDHFIAKYNERFQMEV
ref|ZP_02171541.1|     ATMNEDPVDALSKNKLREDLYYRLSVVSIVIPPLRHRKEDLTVLIAHFIRKYNRLFQMNI
ref|ZP_01173129.1|     AAINEDPVDAIAEGRLRKDLYYRLSAVSLFLPPLRERKEDILLLSSFFIQKYNDWFGMEV
RAAC02994              ATMNEDPGRAIREGRLRADLFYRLSVVTLTVPPLRSRREDIPPLVAHFIRRLNGAFGLRV
                       ::: ****  *:     :**  :**   :**:***.. .:**:  *:**:  * *  * .::
```

FIG. 24B

```
ref|YP_090070.1|      KGFEEEVRRFLLSYDWPGNVRELEHLIEGAMNLMSYEDKIELTHLP--LQYRTKPAAKEQ
ref|YP_077660.1|      KGFEEEVRRFLLSYDWPGNVRELEHLIEGAMNLMSYEDKIELTHLP--LQYRTKPAAKEQ
ref|NP_244812.1|      KGLSDEVTQLLLQYDWPGNVRELEHIIEGAMNLMIGEDLIDVRHLP--FHFRQKSLSAPL
ref|ZP_02171541.1|    QEVTDDVFNLFSEYDWPGNVRELEHTIEGAMNLIYDDEPIGFQHLP--LHLKHKFTQPPA
ref|ZP_01173129.1|    PGLDEETEEQFLRYDWPGNIRELEHVIEGAMNMAEDDARITSEILP--HHFRQKAET---
RAAC02994             EGCEPRLMDAFLAYEWPGNVRELEHVIEGAMNLMEDEAKIGFQHLPGHVRRRLEQALDEM
                          :  *:****:***** ******:    :  *    **    : : :

ref|YP_090070.1|      L---PQQGYDLFA-----PLPSASAAPL--------------KEQIENAE---KYYIQK
ref|YP_077660.1|      L---PQQGYDLFA-----PLPSASAAPL--------------KEQIENAE---KYYIQK
ref|NP_244812.1|      S----SQITSVYETGPSDAIEHSVEEQQP---------LRDLKDYLLEAE---KMYIKK
ref|ZP_02171541.1|    T----SEGTE--------RLFTQQPEP-----------GLPLETYMDTVE---KAYIQK
ref|ZP_01173129.1|    -----SHSFPGRN------LGEPAGPQ------------PSLSDYVASAE---KAYINK
RAAC02994             QGNEDQGGRDARAEVVREPTPQGASDEIP----------RGRPSFRDLVRDYARTVLQA
                          .                                         ..  :  ::

ref|YP_090070.1|      TVKKCNYNVSQAARVLGISRQSLQYRLKK----------
ref|YP_077660.1|      TVKKCNYNVSQAARVLGISRQSLQYRLKK----------
ref|NP_244812.1|      ALERNKYHVTKTAEKLGLSRQSLQYRMKRLGI-------
ref|ZP_02171541.1|    SLTEAGGNISQAARTLGLKRQSLQYRMRK----------
ref|ZP_01173129.1|    VWREQDGNITRTAKILGMSRQNLQYRIKK----------
RAAC02994             ALEETRGNVSEAARRLGMSRQNLQYWLREVAVDPARYRR
                         .  :::.:*. **:.**.***  ::.
```

FIG. 25

```
ref|YP_177603.1|        --KKGLGKGLQAFFPEQE--DKQEEQ-IVQVDLADVRPNPYQPRKTFSEEALKELSNSIR
ref|NP_244925.1|        ---KGLGKGLNAFFPEAA--DETTEQ-VEEVKLLELRPNPYQPRKTFLEEALQELADSIK
ref|ZP_02172038.1|      ---KGLGKGIGAFFPDSERYEESDSQGAQNIKIKDLRPNPYQPRKHFDDEAIDELRQSIE
ref|YP_001423363.1|     MAKGGLGKGINALFNQVD---LSEET-VEEIKISDLRPNPYQPRKQFDDESLAELKESII
RAAC00039               MAKRGLGRGLDALIPQLN---VSDEDQIVQIDIRDLRPNPYQPRRTFNEEKLQELCNSIR
ref|ZP_02327875.1|      MSKR-LGRGLDALLPSMD---IEDDDKVIEIPLSKLRANPYQPRKSFNEDGIQELAASIK
                          **:*: *::  .       :: : ..:*.******: * :: ** **

ref|YP_177603.1|        EHGILQPVTVRKA-IKGYEIVMGERRVKAAKQAGLTQIPVIVQELDENKMMEIALIENLQ
ref|NP_244925.1|        EHGILQPIVVRKSSVKGYEIVVGERRFRAAERAGLVKVPVVIRELDDQKMMEMALIENLQ
ref|ZP_02172038.1|      QHGILQPLVVRKS-IKGYEIVVGERRYRAAKAAKLDSVPAIVRELTDDEMMELALIENLQ
ref|YP_001423363.1|     QHGILQPIIVRKS-LKGYDIVAGERRYRAAKLAGKETVPAIVRDLSESLMREIALLENLQ
RAAC00039               EHGILQPLIVRRSQVKGFDIVAGERRYRAAKMAGLQVVPAVVRDLSDVLLMEIALIENLQ
ref|ZP_02327875.1|      EHGVIQPIIVR-SVLKGYEIIAGERRFRASQACGLKSIPAVVKKFSDQQVMEIALIENVQ
                        ::::   : :::*: **** :*::  .    :*.::: .: :  : *:::* ref|YP_177603.1|        REDLNPIEEAIAYEKLMEHTNSTQEQLAKRLGKSRPHIANHMRLLQLPKVVQEFISVGKL
ref|NP_244925.1|        REDLNPIEEANAYEKLMTHLQMTQEQLAVRLGKSRPHIANHLRLLQLPKVVQEFISEGKL
ref|ZP_02172038.1|      REDLNPLEEAKAYKKLMEHLSLTQDQLSVKLGKSRPHIANYLRLLQAPQIVQQYLQEEKI
ref|YP_001423363.1|     REDLSPLEEALAYDSLLKHLDLTQEQLAKRLGKSRPHIANHLRLLTLPESIQNLIAEGTL
RAAC00039               REDLNPIEIADAYAKLIEKCHLTQEQLAKRVGQSRSHITNMLRLLQLPAQIQDMVSRGTL
ref|ZP_02327875.1|      REDLNALEIAIAYQAIIDQFSLTQEELSAKVGKSRSHIANFLRLLTLPDSIKQHVSRGTL
                        ****..:* * **  ::  :  **::*: ::*:**.**:* :***  *  ::: :   ..:

ref|YP_177603.1|        TMGHGRALLGLQDKQKLSQLLEKVLQDKLSVREVEQLVQRLNEHVPRETKQVK-VKLPPI
ref|NP_244925.1|        SMGHGRALLGLANKNEISSVLNKILEEKLSVRQVEALVQQMNERVSRGTKKAK-PKLSPF
ref|ZP_02172038.1|      STGHARALLGLKEDKKLSPLLQKTIKEQWSVRHLESVIHDMNENVSRETSKGK-PALDVY
ref|YP_001423363.1|     SMGHGRTLLGLKNKDKLEPLVKKVVEEQLNVRQLEQLIQQLNNNVPRETKKKE-PVQDVV
RAAC00039               TMGHARALLSVEDAEEQLRLAEQTVKEAWSVRKLEMVIYQP-KKVSRETDK---PALPTE
ref|ZP_02327875.1|      SMGHARAIVGVKDNQKKQILADACIREQWSVRQLEEEIKKLEGNSGNAKKKSKDKKRDPY
                        : **.*::.:  :  .:      :. ..:   .**.:*   :       .  ...:

ref|YP_177603.1|        IKEQQERLRDTLGTSVLIKPGKKKGKIEIDYFSEDDLERILSLLV----
ref|NP_244925.1|        LKERQDFLRSHFGTSVAIKKGKKKGKIEIEFFSDDDLERILEML-----
ref|ZP_02172038.1|      LKDREAFLKSYFGTNVTIKPGKKKSKIEIDFFDDDDLQRILRLMSA---
ref|YP_001423363.1|     LKERESYLQNYFGTTVNIKRQKKKGKIEIEFFSNEDLERILELL-----
RAAC00039               YRRYQEQVQAYLGTSVRIQPGKKRGKIEIDYYSEDDLRRIMDLMLAHAP
ref|ZP_02327875.1|      IQQVEDQLRDVYRTTVKIKHQKNKGKIELLYYSNDDLERLLDML-----
                         :   :  ::     *.* *:  *::.***: ::.::**.*:: ::
```

FIG. 26

```
ref|NP_243941.1|            ---------------KPLLTKREREVFELLVQDKTTKEIAEQLFISEKTVRNHISNTMQK
ref|YP_176156.1|            ---------------KPLLTKREREVFELLVQDQTTKEIANHLFISEKTVRNHISNTMQK
ref|YP_080133.1|            ----------KEFQSKPLLTKREREVFELLVQDKTTKEIASELFISEKTVRNHISNAMQK
ref|YP_001376422.1|         -------------QSKPLLTKREREVFELLVQDKTTKEIASELFISEKTVRNHISNAMQK
ref|YP_001422137.1|         ----------KDFQSKPLLTKREREVFELLVQDKTTKEIASELFISEKTVRNHISNAMQK
RAAC02034                   ------MAPVKDGRGKSLLTNREREVFELLVQDKTTKEIASQLFVSEKTVRNHISNVMKK
                                  *.*:********:**..:***********.*:* ref|NP_243941.1|            LGVKGRSQAVIELIRLGELEI
ref|YP_176156.1|            LGVKGRSQAVIELIRLGELTI
ref|YP_080133.1|            LGVKGRSQAVVELLRMGELEL
ref|YP_001376422.1|         LGVKGRSQAVVELLRMGELEL
ref|YP_001422137.1|         LGVKGRSQAVVELLRMGELEL
RAAC02034                   LNVKGRSQAVVELVRLGEITI
                            *.********:**:*:**:  :
```

FIG. 27

```
ref|NP_242122.1|            ----------VRQDAWSHEDDVFLAETVLKHIEEGSTQLRAFDEVGDVLNRTSAACGFRW
RAAC00092                   MSETRQKDRAMRQDAWTTEDDEILAEIVLKHIKQGSTQLAGFNEAARRLGRTAAACGFRW
ref|ZP_01697682.1|          ----------AVRQDAWTQEEDLLLSDIVLRHIREGSTQLRAFEEAGKRMNRTAAACGFRW
ref|ZP_01860230.1|          -------------RQDAWSQDEDLLLAEVVLRHIREGGTQLQAFEEVGRKLSRTAAACGFRW
ref|YP_146960.1|            ----------VRQDAWTKEEDELLANVVLQYIREGGTQLEAFAEVGRRLSRTAAACGFRW
ref|YP_001125095.1|         ----------VRQDAWTKEEDELLANVVLEYIRTGGTQLEAFAEVGRRLSRTAAACGFRW
                                      *****: ::* :*:: **.:*. *.*** .* *..  :.:***** ref|NP_242122.1|            NAVVRQRYVKQIAEAKKERKRRKRAASYAYQLYPTA-------SQQPVVLTGEATSLTLP
RAAC00092                   NACVRKQQRYRIELAKEERKKNK-SQRVQAQLEGGD-------ADHP-----TATLMTWA
ref|ZP_01697682.1|          NSYVRKQYASEIEAAKKERKE-KKQLVRDSGRAPAE--------------EGQQTEATLF
ref|ZP_01860230.1|          NSFVRKQYKSGIELAKRQRKESKKQPVPSPAREVKQPDVKHEVASADKKVEPQSSKVTLN
ref|YP_146960.1|            NSCVRKQYKEEIEQAKQERKMRKKETPSTKESEGQE----------KVEAAVKSHLSWA
ref|YP_001125095.1|         NSYVRKQYKEEIEQAKQERKTRKKETASEKDGRGQP----------EMEAAVESKLSWA
                            *: **::     *  **.:**  *                              :  :

ref|NP_242122.1|            ---MVIEFL-QQLATHQVA---DGQTRKEQEELMK---QNEQLQERNKELEKEL---QKI
RAAC00092                   ---QVLRFLRQEKNTAQEW---ASRWRSTERQLNEWKAKYEALEADYKRVCEEL---REL
ref|ZP_01697682.1|          ---DAIRILQQLAEKSRHE---SGQLSASRRGTEEWKSK---YEALLQKY------LEE
ref|ZP_01860230.1|          ---GVIEFLEGLKDNLNQ----DKELESAYKKLEEYVGK---IEQQLEKLKEEN---SVY
ref|YP_146960.1|            ---EVLAFLQAEEQKARD----ARRTADENRAL---KNDMEQLQQMVTKLQMEK---ESL
ref|YP_001125095.1|         ---EVLAFLQAEGQKARE----IRRTADENRAL---KNDMEQLQQMVTKLQMEK---EAL
                               .: :*         . .        .       .        :   .

ref|NP_242122.1|            KQEHSIIEEDYQSMIQIMNRARRMAILQDD--EPASTQAF--KMDKNGNLEKI-------
RAAC00092                   KSTHDAITRDYKALLEIMERARKAALLDDDLIGPKFAEGFMYRIDEYGNLERITTGERME
ref|ZP_01697682.1|          KEKHEQLQKEYSALLSIMEKARQLS---EQD---------------------------
ref|ZP_01860230.1|          KEKLELLEEDHQSLLSIFEKARKMALLQESDDKVKF------QMDKNGNLQRL-------
ref|YP_146960.1|            QKQLAAIQEEYKTLLSIMERARK-------------------------------------
ref|YP_001125095.1|         QKQLAAVQEEYKTLLTIMERARK-------------------------------------
                            :.       :  .::.::: *:::**:

ref|NP_242122.1|            ---
RAAC00092                   QAE
ref|ZP_01697682.1|          ---
ref|ZP_01860230.1|          ---
ref|YP_146960.1|            ---
ref|YP_001125095.1|         ---
```

FIG. 28

```
ref|YP_001125095.1|        --------VRQDAWTKEEDELLANVVLEYIRTGGTQLEAFAEVGRRLSRTAAACGFRWNS
ref|YP_146960.1|           --------VRQDAWTKEEDELLANVVLQYIREGGTQLEAFAEVGRRLSRTAAACGFRWNS
ref|YP_896293.1|           ----EMATTRQDAWTDDEDLLLAEVVLRHIREGGTQLSAFKEVGRHLSRTPAACGFRWNS
ref|ZP_02261942.1|         ---------RQDAWTDDEDLLLAEVVLRHIREGGTQLSAFKEVGRHLSRTPAACGFRWNS
ref|NP_389392.1|           ---------RQDAWTQDEDLLLAEVVLRHIREGGTQLSAFEEVGRALTRTAAACGFRWNS
RAAC02454                  MASVEKSPVRSDAWTAEDDERLAQLVLRHIRTGSTQLKAFEEAAEQLGRTAAACGYRWNG
                                    *.****  ::*   **::**.:** *.***.** *... * **.****:***.

ref|YP_001125095.1|        YVRKQYKEEIEQAKQERKTRKKETASEKDGRGQP-----EMEAAVESKLSWAEVLAFLQA
ref|YP_146960.1|           CVRKQYKEEIEQAKQERKMRKKETPSTKESEGQE-----KVEAAVKSHLSWAEVLAFLQA
ref|YP_896293.1|           YVRKQYKERIEEAKQLRKVEHYEVKETKVLEP--------------KSITLNDVIDFLQN
ref|ZP_02261942.1|         YVRKQYKERIEEAKQLRKVEHYEVKETKVLEP--------------KLITLNDVIDFLQN
ref|NP_389392.1|           YVRKQYQSGIELAKKQRKELRKQIGVHSVNMPNSMKQTASASSEGKRDLSIQDVIQFLEQ
RAAC02454                  VIRKRYRDEIEAAKAERKALHVKTQTQKAATAP--------------TASMQEVIRFLQT
                           :**:*:.. ** ** **   : :        .              :  :*: **:

ref|YP_001125095.1|        EGQKAREIRRTADENRALKNDME-QLQQMVTKLQMEKEALQKQLA-----------AVQE
ref|YP_146960.1|           EEQKARDARRTADENRALKNDME-QLQQMVTKLQMEKESLQKQLA-----------AIQE
ref|YP_896293.1|           YKD--------------ENSLM-VLQQQIESLQTEKESLLERLS-----------VYEE
ref|ZP_02261942.1|         YKD--------------ENSLM-VLQQQIESLQTEKESLLERLS-----------VYEE
ref|NP_389392.1|           FKETP-SAQEFQLEREKLKEQIQ-SLQKELEDLRSENQTLRNQLE----------MTEE
RAAC02454                  YDEQYQRLREYVSAIEREKSELEARVRALESQLREGGPELPLSPE----------QLEE
                               :                :..:    ::    .*:    *                  :* ref|YP_001125095.1|        EYKTLLTIMERARKMM--------
ref|YP_146960.1|           EYKTLLSIMERARKMVTDS-----
ref|YP_896293.1|           EYR---------------------
ref|ZP_02261942.1|         EYR---------------------
ref|NP_389392.1|           DYKALIDIMDRARKMV--------
RAAC02454                  DSRTLFAIMERARKLLAENRSAGT
                              : :
```

FIG. 29

```
ref|ZP_01666183.1|      MKSTGIVRRVDELGRVVIPIELRRTLDIEEKDALEIYVDNDRIILRKYEPACVFCGNADE
ref|YP_077079.1|        MKSTGIVRKVDELGRVVIPIELRRTLNIEEKDSLEIYVDGDKIILRKYEPACVFCGNAAN
RAAC00212               MKSTGIVRKVDELGRVVIPIELRRTLGIGEKDALEIYVDGDRIILKKYEPACIFCGQADE
ref|YP_001666100.1|     LKSTGIVRKVDELGRVVIPIELRRTLNIAERDALEIYVDGEQIVLKKYEPACIFCGNAEN
ref|NP_621806.1|        LKSTGIVRKVDELGRVVIPIELRRTLNIAERDALEIYVDGEQIVLKKYEPACIFCGNAEN
ref|YP_752777.1|        LKSTGVVRKVDELGRIVIPIELRRTMGIEEKDALEIYVDSEKIILKKYEPACIFCGNAEE
                        :****:**:******:*********::.* *:*:******.::*:*:******:***:* :

ref|ZP_01666183.1|      VTNFKGKNVCRECLEAM---
ref|YP_077079.1|        VENFKGKNVCQSCLASM---
RAAC00212               IIHFKGKNICPSCIAEMQHA
ref|YP_001666100.1|     VINYKGKNICKNCLEELK--
ref|NP_621806.1|        VINYKGKNICKNCLEELK--
ref|YP_752777.1|        VVNYKGKNLCKSCLTEL---
                        : ::****:* .*:   :
```

FIG. 30

```
ref|YP_001666100.1|    ------------------------------------------------------------
ref|NP_621806.1|       ------------------------------------------------------------
ref|YP_001317994.1|    ------------------------------------------------------------
ref|YP_001181188.1|    ------------------------------------------------------------
ref|NP_346951.1|       ------------------------------------------------------------
RAAC03236              MSGCVSSLPFILALCVSSAAPRVRALGGAWLRLGHRLAIGAAFTVCATASHCCPTRCRMD ref|YP_001666100.1|    ----------------TGIVRKVDELGRVVIPIELRRTLNIAERDALEIYVDGEQIVLKKY
ref|NP_621806.1|       ----------------TGIVRKVDELGRVVIPIELRRTLNIAERDALEIYVDGEQIVLKKY
ref|YP_001317994.1|    ------------MKSTGIVRKVDELGRIVLPIELRRTLTIAEKDSLEIYVDGESIILKKY
ref|YP_001181188.1|    ------------MKSTGVVRKVDELGRIVLPIELRRTLDIAEKDALEIFVDGDKIILRKY
ref|NP_346951.1|       ------------MKSTGVVRRVDELGRIVIPIELRRTLNIAEKDALEIYVDGEQIILKKY
RAAC03236              DHEAAKLRRRIRMLVTGYVRKVDHLGRLVIPKRLRKDLAIGQDDSIEIYVEGDAVVLSKY
                                        :.*:*:*  .**: *  *.: *::**:*:*:  ::* ** ref|YP_001666100.1|    EPACIFCG-NAENVINYKGKNICKNCLEELK------
ref|NP_621806.1|       EPACIFCG-NAENVINYKGKNICKNCLEELK------
ref|YP_001317994.1|    EPACIFCG-NAKDVTVYKTKNVCEDCLEEFR------
ref|YP_001181188.1|    EPACIFCG-NAKDVIYYKGKNICKDCMEELK------
ref|NP_346951.1|       EPACIFCG-DASDVINYRGKNICKHCLEELK------
RAAC03236              EPKCVFCGEKAEKVFHERG--VCGTCLEELKAKSKVS
                       ** *:*** .*..*      :*  *:**::
```

FIG. 31

```
ref|YP_001666100.1|    ---------------------------------------STGIVRKVDELGRVVIPIELRR
ref|NP_621806.1|       ---------------------------------------STGIVRKVDELGRVVIPIELRR
ref|NP_346951.1|       ------------------------------------MKSTGVVRRVDELGRIVIPIELRR
ref|YP_001181188.1|    ------------------------------------MKSTGVVRKVDELGRIVLPIELRR
ref|YP_001317994.1|    ------------------------------------MKSTGIVRKVDELGRIVLPIELRR
RAAC02603              MAVSAAFAVCAIASHCCRDRCRMGDDETTVLRRKSRMIATGYVRKVDRLGRLVVPNRIRS
                                                           : :.*:*:* .:* ref|YP_001666100.1|    TLNIAERDALEIYVDGEQIVLKKYEPACIFCG-NAENVINYKGKNICKNCLEELK-----
ref|NP_621806.1|       TLNIAERDALEIYVDGEQIVLKKYEPACIFCG-NAENVINYKGKNICKNCLEELK-----
ref|NP_346951.1|       TLNIAEKDALEIYVDGEQIILKKYEPACIFCG-DASDVINYRGKNICKHCLEELK-----
ref|YP_001181188.1|    TLDIAEKDALEIFVDGDKIILRKYEPACIFCG-NAKDVIYYKGKNICKDCMEELK-----
ref|YP_001317994.1|    TLTIAEKDSLEIYVDGESIILKKYEPACIFCG-NAKDVTVYKTKNVCEDCLEEFR-----
RAAC02603              DLHLAKEDPVEIYVEADSIVLTKYEPKCVFCG--EKAEKVFHERAVCGTCLEELKTRSKR
                        * :*:.*.:**:*:.:.*:* **** *:***   .    :: : :* *:**::
```

FIG. 32

```
ref|YP_001374031.1|        ----------------------------------------MANQNSS--NQLVVPGAT
ref|NP_830661.1|           ----------------------------------------MANQNSS--NQLVVPGAT
gb|AAC62407.1|             ----------------------------------------MANNNSS--NQLVVPGVQ
RAAC00161                  ----------------------------------------MMANQNGS--NKVLVQGAN
ref|YP_037204.1|           ----------------------------------------MANKNSGSRNELLVRGAE
ref|NP_979446.1|           ----------------------------------------MANNNSGNRNELLVRGAE
                                                                   ***:*..  *:::* *.

ref|YP_001374031.1|        AAIDQMKYEIAQEFGVQLGADTTARANGSVGGEITKRLVAMAEQSLGG-
ref|NP_830661.1|           AAIDQMKYEIAQEFGVQLGADSTARANGSVGGEITKRLVAMAEQSLGG-
gb|AAC62407.1|             QALDQMKYEIASEFGVQLGPDATARANGSVGGEITKRLVQMAEQQMGGY
RAAC00161                  RALDQMKYEIATEFGVQLGPDTTARQNGSVGGEITKRLVAYAEQQLAGH
ref|YP_037204.1|           QALDQMKYEIAQEFGVQLGADTTARSNGSVGGEITKRLVAMAEQQLGG-
ref|NP_979446.1|           QALDQMKYEIAQEFGVQLGADTTARSNGSVGGEITKRLVAMAEQQLGG-
                           *:******* ******.*:*** ************* ***.:.*
```

FIG. 33

```
ref|YP_001422239.1|         ---------------------------------------QQSNSGNSNQLLVPGAAQ
ref|YP_001420593.1|         ----------------------------------------MANNNSSNQLVVPGAAQ
ref|YP_001486165.1|         ----------------------------------------MANSNSSNQLLVPGAEQ
ref|ZP_01170670.1|          ---------------------------------------MANNNSSNQLLVPGVSQ
ref|ZP_01697004.1|          ---------------------------------------QMANNSNSNQLLVSGAEQ
RAAC00923                   MYSLFEAIATPAESTFGAPRGAYGRMARSHYRCHHHIRRECKMANNSGSNRTLVPQASK
                                                                   :*...**: :*. . :

ref|YP_001422239.1|         AIDQMKYEIASEFGVNLGPETTSRANGSVGGEITKRLVSFAQQSMGG--
ref|YP_001420593.1|         AIDQMKYEIASEFGVNLGGETTSRANGSVGGEITKRLVSFAQQNMGGQ-
ref|YP_001486165.1|         AIDQMKYEIASEFGVNLGAETTARANGSVGGEITKRLVSYAQQHMGG--
ref|ZP_01170670.1|          ALDQMKYEIANEFGVNLGAETTARANGSVGGEITKRLVQMAEQQLGG--
ref|ZP_01697004.1|          ALDQMKYEIAQEFGVNLGADTTSRANGSVGGEITKRLVQMAEQQLGG--
RAAC00923                   ALDQMKYEIATEFGVNLGPDTTSRQNGSVGGEITKRLVAYAEQSLAGRA
                            *:******* ******* :**:* ************* *:* :.*
```

FIG. 34

```
ref|ZP_02330525.1|        ---SNVLVVPQANQALEQLKYEVAQELGIQIPQDGYYGYMATRDTGAIGGNITRRLVQIA
ref|ZP_02330045.1|        ---SNVLVVPQANAALDQLKYEVAQELGIVIPQDGYYGNMATRDTGAIGGHITRRLVQIA
ref|YP_001665292.1|       ----NPLVVKEAKQVMSQWKYEIANELGITPPADGYWGNLTSRDCGAVGGHMVRKMIQMA
ref|YP_001665293.1|       ----NPLVVKEAKQVMSQWKYEIARELGITPPADGYWGNLTSRDCGAVGGHMVRKMIQMA
ref|NP_623103.1|          ----NPLVVKEARQVMNQWKYEIANELGITPPADGYWGYLTSRDCGAVGGHMVRKMIQMA
RAAC00643                 MAKSNRLLLGQASRALQDMKYEIAGELGITPPADGYWGFVSSYENGSIGGSITKRLVRYA
                              * *:: :*   .:.: ***:* ****  * ***:* ::: : *::** :.::::: * ref|ZP_02330525.1|        EQSLA-------
ref|ZP_02330045.1|        EQQLS-GTQGS-
ref|YP_001665292.1|       ESQMA-------
ref|YP_001665293.1|       ESQMA-------
ref|NP_623103.1|          ESQMA-------
RAAC00643                 QERLAQGDAGSP
                          :. ::
```

FIG. 35

```
ref|NP_829946.1|            ----------------------------------------MSRRRGVMSNQFKEELAKE
ref|NP_842611.1|            ----------------------------------------MSRRRGVMSNQFKEELAKE
ref|YP_001419725.1|         ----------------------------------------MGRRRGVMSDEFKYELAKD
ref|NP_240926.1|            ----------------------------------------MSRRRGIMSDRLKEEIAKE
ref|ZP_02330558.1|          ------------------------------------------RRRSTMSDQLKNELAKD
RAAC01427                   ---------------------MPCRRIVSVSPLTREGFGMARRRSTMSDAFKVELAKE
                                                                     ***. **:  :* *:**:

ref|NP_829946.1|            LGFYDVVQKEGWGGIRAKDAGNMVKRAIEIAEQQLMKRN---
ref|NP_842611.1|            LGFYDVVQKEGWGGIRAKDAGNMVKRAIEIAEQQLMKQN---
ref|YP_001419725.1|         LGFYDTVKNEGWGGIRARDAGNMVKRAIEIAEQQMAAQN---
ref|NP_240926.1|            LGFYDTVQQEGWGGIRARDAGNMVKRAIELAEQQLAERESSR
ref|ZP_02330558.1|          LGFYDTVQKEGWGGIKAKDAGNMVKRAIQIAEQAAQKK----
RAAC01427                   LGFYDTVQREGWGGIKARDAGNMVKRAIEIAEQALAEKSGQR
                            *****.*:.******:*:**********::***    :
```

FIG. 36

```
ref|YP_173696.1|            -----------LLFAAVLLWVQYDSTL---KDSSSTWHLPMS-------------GKVIV
ref|NP_241105.1|            -----------------------------------------LS-------------GKVII
ref|ZP_01696660.1|          ------------------------------------------------------------
ref|YP_001124272.1|         ------------------------------------------------------------
ref|ZP_02329530.1|          ----------------VALLVMIYAYKLPATETWTEWTQPLA-------------GKTIA
RAAC00365                   MIMHGKHRHVPLAFAAMAMLVGATSLVVPVQDARAAWFRPLQHRVNPGVQATGIQGKVIV ref|YP_173696.1|            LDPGHGGMDGGAVSKTGTLEKEVTLAVALKLRDYLQEAGALVIMTREEDVDLADAGTAKI
ref|NP_241105.1|            LDPGHGGIDGGATSRAGALEKDITLAVSLELRDYLQEAGALVLMTREEDRDLADATTAKV
ref|ZP_01696660.1|          -------------------EKDVALSVAAKIKDYLQQQGALVIMTRETDTDLADNETKGY
ref|YP_001124272.1|         ------------------VVEKEIALNVAKKLRDYLQQQGALVLMTRETDRDLASPSTRGY
ref|ZP_02329530.1|          LDAGHGGPDGGASSKSGVIEKDINLIISLYVRDYLQQAGAIVVMTREMDKDLANPDTKGY
RAAC00365                   VDAGHGGRDSGARGVGGIEEKDITLSVALKLARYLQQGGAIVIMTRTTDTDLATERDRAM
                                              **::  *  ::    :   *: :*:***     *  *** ref|YP_173696.1|            RQRKTEDLRKRAMIINDSEADAFLSIHMNAIPSERWNGAQTFYHLKNQRNEDMAVFIQEE
ref|NP_241105.1|            RQRKVQDLKRRVEIVNGSGADMFVSIHLNAIASPRWSGAQTFYNRAIPENEPLARFVQDQ
ref|ZP_01696660.1|          SRRKVEDLRKRLSLINESEADLFISIHLNAIPQSQWHGAQTFYAPTMIENKRIATFIQAE
ref|YP_001124272.1|         SRRKTEDLRERTTFINKSDADLFISIHLNAIPSPRWRGAQTFYYGSLIENERLAKFIQAE
ref|ZP_02329530.1|          SKRKTEDLLKRAEFVIQKKADLFLSIHLNSVPSPKWRGAQAFYYPNNQDNYRLASLIQEE
RAAC00365                   RQRHLGDLRGRLNVVRRQRVDAFVSIHCNSAPSPDWRGAQVLYLKTNPHAKQLATVMQEA
                             :*:  **   *    .:    .* *:***  *:  ..   * ***.:*         :* ..:* ref|YP_173696.1|            IKRNLQNTNRYPKPIHHVYLLKEAEIPGALVEAGFLSNPQEAALLATEEYQDKMAASIYE
ref|NP_241105.1|            LKRNLENTSRYAKPINNVFLLKHAEIPGLLVEAGFLSNPSEAELLETEDYQQKVAASIYQ
ref|ZP_01696660.1|          LVRNLENTNRASKTLSNVYLLKHAKKPGCLVEIGFLSNPGEREQLKSDAYQTKVAASIYE
ref|YP_001124272.1|         LRRNLENTHRVAKMIDTVYLLKHAKKPGALVEIGFLSNPDERELLASDHYQTQLAASIYK
ref|ZP_02329530.1|          IKRNMENTDRVAKQEESVYLLKTLKMPSTLIELGFLSNPDEARMLADDKYQKKLAASIYQ
RAAC00365                   FRTELLPTHRDVQSNRTLFLLKRIEGPTVLAEIGFVSNPEEARALTTDAYQERVAFAMYE
                            :   ::   *  *    :  ::***   :  *   *  *   **:***   *      *   :  **  ::*    ::*:

ref|YP_173696.1|            GMLRFFTD-----------
ref|NP_241105.1|            GIMRYYTN---EDAPE---
ref|ZP_01696660.1|          GIMRYFT------------
ref|YP_001124272.1|         GVLRYFSN-----------
ref|ZP_02329530.1|          GILRYYAGEKV--------
RAAC00365                   ALVRYFSDPAVEQVPEDDG
                            .::*:::
```

FIG. 37A

```
ref|YP_036745.1|       ------------------------------------------------------------
ref|YP_083969.1|       ------------------------------------------------------------
ref|YP_028716.1|       ------------------------------------------------------------
ref|ZP_02259717.1|     ------------------------------------------------------------
ref|ZP_01665476.1|     ------------------------------------------------------------
RAAC01563              MFAMPSKVVVTLGSAYAPMASKDNDFCRPDEVSGATSPPRLRAPYLLVRASAREMSFFEF ref|YP_036745.1|       ------------------------------------------------------------
ref|YP_083969.1|       ------------------------------------------------------------
ref|YP_028716.1|       ------------------------------------------------------------
ref|ZP_02259717.1|     ------------------------------------------------------------
ref|ZP_01665476.1|     ------------------------------------------------------------
RAAC01563              VRDLAATHPDPDPFLCLVLDAEGGVMTSAAHGEWEKDEMAACLSAASREFPAVAAQETSM ref|YP_036745.1|       ------------------------------------------------------------
ref|YP_083969.1|       ------------------------------------------------------------
ref|YP_028716.1|       ------------------------------------------------------------
ref|ZP_02259717.1|     ------------------------------------------------------------
ref|ZP_01665476.1|     ------------------------------------------------------------
RAAC01563              SPRTEFGLSAVALLRTDGWHTAWTRLPMAVGRARHLAVIRRASDEDPRSLGRLALHLAHA ref|YP_036745.1|       ------------------RKKTEELLNKSDTLAAIGQLAAGVAHEVRNPLTVIKGFIQL
ref|YP_083969.1|       ------------------RKKTEELLNKSDTLAAIGQLAAGVAHEVRNPLTVIKGFIQL
ref|YP_028716.1|       ------------------RKKTEELLNKSDTLAAIGQLAAGVAHEVRNPLTVIKGFIQL
ref|ZP_02259717.1|     ------------------RKKTEELLNKSDTLAAIGQLAAGVAHEVRNPLTVIKGFIQL
ref|ZP_01665476.1|     ------------------IREVRHRMHHLETLAALGQLAAGTAHEIRNPLTSIRGFTQL
RAAC01563              ATQAWTSCERTLVRRSQCVIERMRKKLQEFEKVSALAQLCAGIAHEIRNPLTTARGFLQL
                                         ..  ..  ::. :.:*:.**.**.***:*****   :** **

ref|YP_036745.1|       FQIN----KEDQEK-YFDLMLSEIERIEAILQEFLSIAKTDEISTEKKNIYQIFKNVVSL
ref|YP_083969.1|       FQIN----KEDQEK-YFDLMLSEIERIEAILQEFLSIAKTDEISTEKKNIYQIFKNVVSL
ref|YP_028716.1|       FQIN----KEDQEK-YFDLMLSEIERIEAILQEFLSIAKTDEISTEKKNIYQIFKNVVSL
ref|ZP_02259717.1|     FQIN----KEDQEK-YFDLMLSEIERIEAILQEFLSIAKTDEISTEKKNIYQIFKNVVSL
ref|ZP_01665476.1|     IQTRALRRNDATTADYCRLIMQEIDHINNILTDILSLARPTTRQLSLLNIVKIVHDVIAF
RAAC01563              FAER----CDDKDRGYLELTISELDRIRELLEDFMGLCRPDREEAAEVDMVEIARSVHRF
                       :  .    :      *  * :.*:::*. :* :::.:..    .  :: :* :.* :

ref|YP_036745.1|       INTKAIMTNIQVELYTDSKDIIIECSENQLKQVFINILQNSIEAMPDGGRISIHIKEIGK
ref|YP_083969.1|       INTKAIMTNIQVELYTDSKDIIIECSENQLKQVFINILQNSIEAMPDGGRISIHIKEIGK
ref|YP_028716.1|       INTKAIMTNIQVELYTDSKDIIIECSENQLKQVFINILQNSIEAMPDGGRISIHIKEIGK
ref|ZP_02259717.1|     INTKAIMTNIQVELYADSKDIIIECSENQLKQVFINILQNSIEAMPDGGRISIHIKEIGK
ref|ZP_01665476.1|     MYGEAILSGITLRPELPPEELWVQGHIDKLKEVLINICRNAFQAMG--PGGVLTLSVAAD
RAAC01563              LVPEASLCDIAFELNVPAHPIPAAVRPAQIKQVLINLVQNALQACRGQAHAVVRLDVAEK
                       :  :*  .*  ..     ..  :       ::*:*:**: :*:::*         : :. .

ref|YP_036745.1|       -DGIIISVIDKGIGIPEERIKRLGEPFYSTKEKGTGIGLMLSYKIIESHQGNISIMSEVG
ref|YP_083969.1|       -DGIIISVIDKGIGIPEERIKRLGEPFYSTKEKGTGIGLMLSYKIIESHQGNISIMSEVG
ref|YP_028716.1|       -DGIIISVIDKGIGIPAERIKRLGEPFYSTKEKGTGIGLMLSYKIIESHQGNISIMSEVG
ref|ZP_02259717.1|     -DGIIISVIDKGIGIPEERIKRLGEPFYSTKEKGTGIGLMLSYKIIESHQGNISIMSEVG
ref|ZP_01665476.1|     TATVKIVLADTGCGMTKEVMDQIFTPFFFTKETGTGLGLAICQQIMHEHGGDIQVESTPG
RAAC01563              EDRVLVQVVDNGCGI--EHMDRIFRPFYTTKSTGTGLGLFVCKHIIESHGGSISVRSQVG
                       : :  *.* *:   *  :.::  **::**..***:**..:*::*  .:*:..* *.: *  *
```

FIG. 37B

```
ref|YP_036745.1|      VGTTVTIYLPKIQSKK-
ref|YP_083969.1|      VGTTVTIYLPKIQSKK-
ref|YP_028716.1|      VGTTVTIYLPKIQSKK-
ref|ZP_02259717.1|    VGTTVTIYLPKIQSKK-
ref|ZP_01665476.1|    QGSTFTLLLPRC-----
RAAC01563             AGTTVTVEIPKCASRRA
                      *:*.*:  :*:
```

FIG. 38

```
ref|YP_145847.1|         ------TITMGIQKGGCGKSTTTGVLAYLLSRDGYRVLAVDMDSQGN-LTELLSRKP---
RAAC02315                MERVGCTISVGLQKGGVGKSTTTALTSYILAEQGHRVLAVDFDSQGN-LTQLLTQRS---
ref|YP_536482.1|         ---MGTVIAIANQKGGVGKTTTSVNLGACLARAGQKVLLIDTDAQGNATSGIGVRKH---
ref|YP_799230.1|         ----MGKIVSISNQKGGVGKTTTSINLAANLASIGKKVLIIDMDPQGNSGSGLGIEIN---
gb|ABG00342.1|           ------TIIIGNQKGGVGKTTNTYLIAYTLAKLGIKTLVCDLDPQSNSTKALILTKS-QN
ref|YP_891181.1|         MLKMAITITVGNYKGGVGKTTNAVLNSYEFAKKGKRTLLVDLDPQSNATKSLMLTKSILN
                               : :.  *** **:*.:    . ::  * :.*  * *.*.*   . :

ref|YP_145847.1|         --SNEFTEKSVLEAMQERDPEPYIVKVND-----RLDLLPANNFLAT-----FPRWIYTG
RAAC02315                --PYDFVHRTSLEACKERDPRPYIHAISD-----NLHLLPAEDFLSQ-----FDKWIYT-
ref|YP_536482.1|         --NIENDVYDVI--VSELPIREAIMPTYI----DNLDVVPATIQLAG------AEIELTA
ref|YP_799230.1|         --TLVKTSYELL--LGESSTNECIQRTNV----SNLHIIPSNINLSG------AEADLLV
gb|ABG00342.1|           SNEIMTIDKTLMWGVQQRDLKDLPVSIIE-----NLDLLPSYIDFED-----FAKYLYKN
ref|YP_891181.1|         PDEIVTVEKTLMKGIQEGNLDGLEVEITD-----NLYLIPSYVDFQD-----FAKFLYQN
                                 :         :             .*  ::*:          .

ref|YP_145847.1|         ETYLGKYIRYKGKPTLILDDTLDKIRHRYDFIVIDTPPSLSEQTTNALCASQYVIMMFEC
RAAC02315                EVHVS-------QQMVILKNTLDVVKSDYDYILIDLPPNLGGLTLNGVCASDYCVVVCQS
ref|YP_536482.1|         QMAREKK----------LYDAVQDVKEEYDFILIDCPPSLGLLTINAFTASDSILIPVQS
ref|YP_799230.1|         EDQREYR----------LKNAVSELRSEYDYILIDCPPSLGILTINALCAADSVMITLQT
gb|ABG00342.1|           TSNEYEET-------HLLEPLFEPLKEDYDIILIDVPPLSVEVTSNAVMFSDYVLISLQT
ref|YP_891181.1|         CASEAEED-------HYFKGLLEKIKHKYDYIFIDVPPMSLEVTKNAVVASDYVLIALQT
                                       ..  ::   ** *.** **     * *..  ::  ::    :

ref|YP_145847.1|         SNWCYSAVPNFMESVEGARVHGRHNTRLLGILRTMNDVRRNDAKAFNEMIEEDY-PNEVF
RAAC02315                EPFAYDALDRYMEIIQAAQQRVNPNLRIAGILISLLDARTAIGNYITERIREEY-QDFVF
ref|YP_536482.1|         EYYALEGLSQLMNTIQLVQKHFNPDLQIEGVLMTMLDARTNLGNQVVEEVKKFF-KEKVY
ref|YP_799230.1|         EYFALEGLTQLMKIISLVQNQLNPSLELEGVLLTMFDKRTNLANQVAEDVKSYF-KDKVY
gb|ABG00342.1|           QDDSMTGAIEYIKTLVKLKMKYELGIEVLGALPMLSNSRGSVDKLIIESAKEEWGEDLVF
ref|YP_891181.1|         QERSLTGAENYVNELIKLKEQYDLDIEVVGILPVLLKNNGKVDEYIMENAREIFGEENLF
                         .  .   .  ::  ::   :   ..:  *   .   :   :.*   ..:  : ::

ref|YP_145847.1|         KTIITRKAPIGRLSLYGFEENN-ELN-QALEQYENFYKEMMERV--
RAAC02315                DTVIRRKSRIIEFSVEGIKIQT-KADREAIAMYESFVEELKARVSR
ref|YP_536482.1|         KTVIPRNVRLSEAPSHGMSIIDYDPRSRGAEEYEALAKEV------
ref|YP_799230.1|         TTIIPRNVKLSE----------------------------------
gb|ABG00342.1|           ETVIPQMERIKRFSINGITDED-RFDRKVLEMYEKVVSEMLSKL--
ref|YP_891181.1|         KNIVPQMERIKRFDVNGITEKD-RHDMNVIELYETISDELLSRI--
                          .::  :        :    .
```

FIG. 39

```
ref|YP_001423364.1|        ----KIIAITNQKGGVGKTTTSVNLGACLAYIGKRVLLVDIDPQGNATSGLGIEKADVDH
ref|NP_391977.1|           ----KIIAITNQKGGVGKTTTSVNLGACLAYIGKRVLLVDIDPQGNATSGLGIEKADVEQ
ref|YP_093870.1|           ----KIIAITNQKGGVGKTTTSVNLGACLAYIGKRVLLVDIDPQGNATSGIGVEKADVDQ
ref|YP_081433.1|           ----KIIAITNQKGGVGKTTTSVNLGACLAYIGKRVLLVDIDPQGNATSGIGVEKADVDQ
ref|YP_001488932.1|        ----KIIAITNQKGGVGKTTTSVNLSACLAYIGKRVLLVDIDPQGNATSGIGIEKADVEK
RAAC00040                  MSSARVIAIANQKGGVGKTTTAVNLGACLATLGKRVLLIDIDPQGNTTSGVGINKADVKY
                               :***:***********:***.****  :******:*******:***.*::****.

ref|YP_001423364.1|        CVYDILVDDADVTDIIKPTSVENLDVIPATIQLAGAEIELVPTISREVRLKRALESVKQN
ref|NP_391977.1|           CVYDILVDDADVIDIIKATTVENLDVIPATIQLAGAEIELVPTISREVRLKRALEAVKQN
ref|YP_093870.1|           CVYDILVDDADVKDVIKTTSVENLDVIPATIQLAGAEIELVPTISREVRLKRALESVKQN
ref|YP_081433.1|           CVYDILVDDADVKDVIKTTSVENLDVIPATIQLAGAEIELVPTISREVRLKRALESVKQN
ref|YP_001488932.1|        CVYDILVDDADVLDVIKTTEVENLDVIPATIQLAGAEIELVPTISREVRLKRALESVKQN
RAAC00040                  CVYDVIINDVNIADAIMPSGLDNLDVLPATIQLAGAEIELVPTISREVRLRRAIQGMRSR
                           ****:::*.:: * * .: ::****:********************:**::.::..

ref|YP_001423364.1|        YDYMIIDCPPSLGLLTINALTASDSVVIPVQCEYYALEGLSQLLNTVRLVQKHLNTDLMI
ref|NP_391977.1|           YDYIIIDCPPSLGLLTINALTASDSVVIPVQCEYYALEGLSQLLNTVRLVQKHLNTDLMI
ref|YP_093870.1|           YDFMIIDCPPSLGLLTINALTASDSVVIPVQCEYYALEGLSQLLNSVRLVQKHLNTDLMI
ref|YP_081433.1|           YDFMIIDCPPSLGLLTINALTASDSVVIPVQCEYYALEGLSQLLNSVRLVQKHLNTDLMI
ref|YP_001488932.1|        YDYMIIDCPPSLGLLTINALTASDSVLIPVQCEYYALEGLSQLLNTVRLVQKHLNTDLAI
RAAC00040                  YDYIVIDCPPSLGLLTVNALTAADSVMIPIQCEYYALEGLSQLLNTVRLVQKHLNTSLEV
                           **::.:**********:*****:***:**:*************:*********.* :

ref|YP_001423364.1|        EGVLLTMLDARTNLGIQVIEEVKKYFRDKVYQTIIPRNVRLSEAPSHGKPIILYDPRSRG
ref|NP_391977.1|           EGVLLTMLDARTNLGIQVIEEVKKYFRDKVYKTVIPRNVRLSEAPSHGKPIILYDPRSRG
ref|YP_093870.1|           DGVLLTMLDARTNLGIQVIEEVKKYFRDKVYKTVIPRNVRLSEAPSHGKPIILYDPRSRG
ref|YP_081433.1|           DGVLLTMLDARTNLGIQVIEEVKKYFRDKVYKTVIPRNVRLSEAPSHGKPIILYDPRSRG
ref|YP_001488932.1|        EGVLLTMLDARTNLGIQVIEEVKKYFRDKVYQTVIPRNVRLSEAPSHGKPIILYDPRSRG
RAAC00040                  EGVVLTMLDARTNLGLQVIEDVKKFFRDKVYKTIIPRNVRLSEAPSHGRPIIHYDPKSRG
                           ::*******::*:*:********:* *:* ref|YP_001423364.1|        AEVYLDLAKEVAANG
ref|NP_391977.1|           AEVYLDLAKEVAANG
ref|YP_093870.1|           AEVYLELAKEVAA--
ref|YP_081433.1|           AEVYLELAKEVAA--
ref|YP_001488932.1|        ADVYLDLAKEVDANG
RAAC00040                  AESYMELAKEVIARG
                           *: *::***** *
```

FIG. 40

```
ref|ZP_01697918.1|       ------------------------------------FFMLVMLIIYLESPLSRVHRIQIE
ref|ZP_01172488.1|       ------------------------------------LLLLFFSMIVFVIYFQSPLSRVKEISIS
emb|CAJ75583.1|          ------------------------------------FFLFILCVLYFQSPLGAVGHVEVS
ref|YP_146973.1|         ------------------------------------FFLFILCVLYFQSPLGAVGHVEVS
ref|YP_001125108.1|      ------------------------------------FFLFILCVLYFQSPLSAVRHVEVS
RAAC00113                MNRGRTGGERRESMPRQETAEERERRKARNRRIVVSFFAFIGLVAVLESPLARVRHIEVS
                                                             **  ::  :  ::***. * .:.:.

ref|ZP_01697918.1|       GNEAVSKPYILKKSGIATGENIWNI-RKDAVRKRIASIPEVDSVKVGISLPN-TLYIKVK
ref|ZP_01172488.1|       GNQTYTTKELIAVSGLSKKTNIWKVD-KGAIEGRLKELPEISGAEIKTRLPN-TVDIKVA
emb|CAJ75583.1|          GNRHLTAERIISLSGITKRTSFWKVNEQNVEKKL-TRHPEIKEATVEKQLPN-TIAIHVR
ref|YP_146973.1|         GNRHLTAERIISLSGITKRTSFWKVNEQNVEKKL-TRHPEIKEATVEKQLPN-TIAIHVR
ref|YP_001125108.1|      GNRHLPAERIISLSGITKRTSFWKVNEQNVEAKI-ARHPEIKEATVKKRLPN-TIVIDVR
RAAC00113                GNTTIPMAQIVACSGVVYGESLWEVNRKRAASEIVAKLPMVDRAAISVSWPSGTVSIHVH
                               .   ::  :       .:*::  :.       * :..:   *. *: *.* ref|ZP_01697918.1|       EHQKIGYLQQKGGFLPVLDNGSVV-KRTVKEIPAAS----LIFTGFKQDT---------H
ref|ZP_01172488.1|       EHNRIAYIAKEKSFLPVLENGMILSKQEITDIPVNA----PLLLGFKEGD---------V
emb|CAJ75583.1|          EWRRIAYVYDRQTFFPLLENGRLLKQEGTKTAPSDA----PVLVGWKDGD---------A
ref|YP_146973.1|         EWRRIAYVYDRQTFFPLLENGRLLKQEGTKTAPSDA----PVLVGWKDGD---------A
ref|YP_001125108.1|      EWRRVAYVYNRQTFFPLLENGQLLKQEAVKTAPSDA----PVLVGWKS---------GEA
RAAC00113                ERDVVAVYADPNGFYELMSNGYVYQKIPSAAGLPYP-----IVTGQDSELS---------
                         *    :.     . *   ::.**  :         :          :. *  ..

ref|ZP_01697918.1|       LHEM---------IRQMQKLPDSITNAISEVRYTPSNVDRDLVTLYMNNGFEVRASIPSF
ref|ZP_01172488.1|       LLEMIDS------LESLPKEVLNAISEIHYSPKETDEYHITLYMNDGFEVSATLRSF
emb|CAJ75583.1|          IAEMTG--------QLAELPAAVLGAMSEIHYKPTREYEDRVIVYMNDGYEVSATI---
ref|YP_146973.1|         IAEMTG--------QLAELPAAVLGAMSEIHYKPTREYEDRVIVYMNDGYEVSATI---
ref|YP_001125108.1|      IAEMTG--------QLAELPAAVLGAISEIHYKPTGEYKDRVVVYMNDGYEVSATIHN-
RAAC00113                VHQMASAAVSS-VCRQLASVPASELTGVSEIHVN----GDGTVTIYLDNDFEVLADVANL
                         : :*           :  :*     .:**::  .       : :*::::.:** * :

ref|ZP_01697918.1|       AEKMAHYPSIISQLDPK--KKGVIDL----------------------------------
ref|ZP_01172488.1|       SEKMAHYPSIISQLDPG--VSGVIDL----------------------------------
emb|CAJ75583.1|          ------------------------------------------------------------
ref|YP_146973.1|         ------------------------------------------------------------
ref|YP_001125108.1|      ------------------------------------------------------------
RAAC00113                RGSVAAIQPTIRYFEGKGYRPGVIDLTGSPPYRYTPFSSLPSSNAKTSSASGRGGPVEGT ref|ZP_01697918.1|       --------
ref|ZP_01172488.1|       --------
emb|CAJ75583.1|          --------
ref|YP_146973.1|         --------
ref|YP_001125108.1|      --------
RAAC00113                SSKTASHP
```

FIG. 41A

```
emb|CAJ75587.1|        MSSNEIVVSLDVGTSSVKVIIGEMLGSSINIIGVGNVKAEGLKKGAIVDIDKTVQSIRRA
ref|YP_146977.1|       MSSNEIVVSLDVGTSSVKVIIGEMLGSSINIIGVGNVKAEGLKKGAIVDIDKTVQSIRRA
ref|YP_001125112.1|    MSSNEIVVSLDVGTSSIKVIIGEMLGSSINIIGVGNVKSEGLKKGAIVDIDKTVHSIKRA
ref|NP_243425.1|       MNNNEIYVSLDIGTSNVRIIIGEITDGSINIIGVGNAPSEGIKKGSIVDIDETVRSIRRA
ref|ZP_02330014.1|     MSSSDIIVSLDIGTSKVRAIIGEVNNGTINIIGVGSADSEGIRKGAIVDIDQTVSSIRAA
RAAC00117              MAKEDYIVSLDIGTSKVRVIIGESTGNNLNIIGVGSASSQGLRHGAIVDIDKTVDSIREA
                       *  ..:  **:*.::  **    ....:****..  ::*:::*:***:  **:  * emb|CAJ75587.1|        VEQAERMVGLSIRRVIVGVAGSHIQLHDCHGIVAVASENREISDEDVARVIDAAQVVSIP
ref|YP_146977.1|       VEQAERMVGLSIRRVIVGVAGSHIQLHDCHGIVAVASENREISDEDVARVIDAAQVVSIP
ref|YP_001125112.1|    VEQAERMVGLSIRRVIVGVAGSHVQLQDCHGIVAVASENREISDEDVARVIDAAQVVSIP
ref|NP_243425.1|       VEQAERMVGLSIRQVIVGVNGNHVQLQPCHGVVAVSSPDREIGDEDIARVIDAAQVVSIP
ref|ZP_02330014.1|     VDHAERMVGLQISEVYVGITGNHIALQTSHGVVAVSNEDREIGEEDIERVNQAARVIALP
RAAC00117              VDHAERMVGIRIPSAYVGISGEHIQLHSSHGVVAVSSADREITDEDIERVLQQARVVALP
                       *::******:  *   . **: *.*: *:  .:*:.  :*  :: ** : *:*::* emb|CAJ75587.1|        PDREIIGVVPRQFIVDGLDGIHDPRGMLGVRLEMEGTMVTGAKTVLHNLLRCVERAGLEI
ref|YP_146977.1|       PDREIIGVVPRQFIVDGLDGIHDPRGMLGVRLEMEGTMVTGAKTVLHNLLRCVERAGLEI
ref|YP_001125112.1|    PDREIIGIVPRQFIVDGLDGIHDPRGMLGVRLEMEGTMITGAKTILHNLLRCVERAGLEI
ref|NP_243425.1|       PEREIIDVIPKQFIVDGLDEINDPRGMIGVRLEMEGTIITGSKTLLHNLLRCVERAGLEV
ref|ZP_02330014.1|     PEREIIGIVPKQYIVDGQEGIQDPRGMIGVRLEVEATIITGAKTGIHNLLRVVEKSGLKV
RAAC00117              PEREVIDVVAKEFVVDGLRGIMDPRGMLGVRLEVDAYLITGSRTAIHNIVRCVERAGLEV
                       *:**:*.::..:::***    * *****:*****::.  ::**:*  :**:*  **:**::

emb|CAJ75587.1|        SDICLQPLAAGSLVLSDDERHLGAALVDLGGGSTTVAVFEQGTLQAVSSLPVGGEHITKD
ref|YP_146977.1|       SDICLQPLAAGSLVLSDDERHLGAALVDLGGGSTTVAVFEQGTLQAVSSLPVGGEHITKD
ref|YP_001125112.1|    SDICLQPLAAGSLALSDDERHLGVALVDLGGGSTTVAVFEQGGLQAVSSLPVGGEHITKD
ref|NP_243425.1|       ADICLQALAAGSVAISKDEKSLGVCLIDIGGGSMTISCFEQGSLVDTSVIPVGGDHVTND
ref|ZP_02330014.1|     SGLILMSLAAGQLALSKDEKQIGTVLVDVGAGTTTTISVFDQGSLVATSTLPIGGDFITTD
RAAC00117              ANLVLAPMAASQIALTQDERKLGVALVDVGAGVTSVSVFANGVLMGTSIIPIGGDYVTQD
                       :.:  *  .:..:.:::.:  :*.  *:*:*.*   :::  *  :*  *  .*  :*:**:.:  * emb|CAJ75587.1|        LAIGLRTTTDDAEKIKLKHGHAFYDYASEEEVFSVPIMGTDQHQQFSQLEIADIIEARLE
ref|YP_146977.1|       LAIGLRTTTDDAEKIKLKHGHAFYDYASEEEVFSVPIMGTDQHQQFSQLEIADIIEARLE
ref|YP_001125112.1|    LAIGLRTTTEDAEKIKLKHGHAFYDYASEEEVFTVPIMGTDQHQQFSQLEIADIIEARLE
ref|NP_243425.1|       IAVGLRISTEEAIKIKHTHGHAYIDEASEEDRFEVKAIGSTEPEAFSQFELAHIIEPRME
ref|ZP_02330014.1|     ISIGLRTQMDIAEKIKLKFGCASIADSAPDQMFKVNRIGSNVDKEFSQVDLANIVEPRVQ
RAAC00117              IAIGLRTNTVAAEQVKLRHACAMVEQASEHETFRVPRMGSNKEAEFTQYDLATIIEPRMQ
                       :::***      *    ::*  ..  *    ::  .:  * *   :*:     *:*  ::*  *:*.*::

emb|CAJ75587.1|        EILQMVQQEVRRLGFRD-LPGGYVLTGGVANMPGLLELAHVVLGTSVRIAMPDYIGVRDP
ref|YP_146977.1|       EILQMVQQEVRRLGFRD-LPGGYVLTGGVANMPGLLELAHVVLGTSVRIAMPDYIGVRDP
ref|YP_001125112.1|    EILQMVQHEVRRLGFRD-LPGGYVLTGGVANMPGLLELAHVVLGTSVRVALPDYIGVRDP
ref|NP_243425.1|       EMFELINRELRRLGQHD-FPGGFVLTGGSVMMPGVLELAKETLGRNVRVAIPDYIGVREP
ref|ZP_02330014.1|     EIFQLIRGEVHRMGYSD-LAGGYVLTGGTVNLPATLVIAQEELAATVRIATPDYIGVRDP
RAAC00117              EIFGLVRKEVEKMGYADELPAGYVFHGGVMSTPSAAELAGEELQAPVRIAVPEFLGVRDP
                       *::  ::. *::.:*    * :..*:*: ** *.  :*     *  ***:*  *:::***:* emb|CAJ75587.1|        QYTIGVGLLKFAYR-----------------------------------------------
ref|YP_146977.1|       QYTIGVGLLKFAYR-----------------------------------------------
ref|YP_001125112.1|    QYTIGVGLLKFAYR-----------------------------------------------
ref|NP_243425.1|       QYTTGVGLIQFAYKNVKIQGKEVAAAVAEAGVEQEQRPKKEKERSRTNEGPGVKSKVKNW
ref|ZP_02330014.1|     AYTSGVGIIQFVIKYIR-------NRPASLNKKQPIKAAASKSGSQEKEGEGFFDRVKNF
RAAC00117              SFVNGVGMIVYAAR-------------TGLRPSSADYNAGARQVRSSNHVGVFARIKDW
                       :. ***:: :. :
```

FIG. 41B

```
emb|CAJ75587.1|           -----
ref|YP_146977.1|          -----
ref|YP_001125112.1|       -----
ref|NP_243425.1|          FKVFL
ref|ZP_02330014.1|        LKEFI
RAAC00117                 LRDFV
```

FIG. 42

```
ref|YP_001646530.1|    ------------------------MLEFDTTQDQLANIKVIGVGGGGNNAVNRMIEHG
gb|AAN04557.1|         ------------------------MLEFDTTQDQLANIKVIGVGGGGNNAVNRMIEHG
ref|YP_001375784.1|    ------------------------MLEFDTTQDQLANIKVIGVGGGGNNAVNRMIEHG
ref|YP_078922.1|       ------------------------MLEFETNIDGLASIKVIGVGGGGNNAVNRMIEND
ref|ZP_02171874.1|     ------------------------MLEFEMDTDQLATIKVIGVGGGGSNAVNRMIENG
RAAC00118              MCARTCALTPYCRRGSAEPNRLGGPTVLEFDFETDSLANIKVIGVGGGGCNAVNRMIESG
                                               :***:    * **.********* ********.

ref|YP_001646530.1|    VQGVDFIAVNTDAQALNLSKAETKMQIGGKLTRGLGAGANPEVGKKAAEESKEQIQEALR
gb|AAN04557.1|         VQGVDFIAVNTDAQALNLSKAETKMQIGGKLTRGLGAGANPEVGKKAAEESKEQIQEALR
ref|YP_001375784.1|    VQGVDFIAVNTDAQALNLSKAETKMQIGEKLTRGLGAGANPEVGKKAAEESKEQIQEALR
ref|YP_078922.1|       VQGVEFIAVNTDAQALNLSKAETKMQIGAKLTRGLGAGANPEVGKKAAEESKEQIEEALK
ref|ZP_02171874.1|     LQGVEFIAVNTDAQALQLSKAEHKLQLGGKLTRGLGAGANPDIGKKAAEESRDQLEEYLT
RAAC00118              VKGVEFIVVNTDAQALKLSKAETKLQIGEKLTRGLGAGANPEIGKKAAEESREMLANALK
                       :::.****:**: *:.:* **********.:******:: :  : * ref|YP_001646530.1|    GADMVFVTAGMGGGTGTGAAPVVAQVAKELGALTVGVVTRPFTFEGRKRATQAASGIASF
gb|AAN04557.1|         GADMVFVTAGMGGGTGTGAAPVVAQVAKELGALTVGVVTRPFTFEGRKRATQAASGIAAF
ref|YP_001375784.1|    GADMVFVTAGMGGGTGTGAAPVVAQVAKELGALTVGVVTRPFTFEGRKRATQAASGIAAF
ref|YP_078922.1|       GADMVFVTAGMGGGTGTGAAPVIAQIAKDLGALTVGVVTRPFTFEGRKRQLQAAGGISAM
ref|ZP_02171874.1|     GADMVFITAGMGGGTGTGAAPVIAEIAKEAGALTVGVVTKPFTFEGRRRMNQAQTGISDL
RAAC00118              GADMVFVTAGMGGGTGTGAAPVIAEIAKELGALTVGVVTKPFRFEQRRRMIQAEQGVNEL
                       ******:***********:.*::.**: ********:** ** *:*  **    *:  :

ref|YP_001646530.1|    KENVDTLIVIPNDRLLEIVDKNTPMLEAFREADNVLRQGVQGISDLIATPGLINLDFADV
gb|AAN04557.1|         KENVDTLIVIPNDRLLEIVDKNTPMLEAFREADNVLRQGVQGISDLIATPGLINLDFADV
ref|YP_001375784.1|    KENVDTLIVIPNDRLLEIVDKNTPMLEAFREADNVLRQGVQGISDLIATPGLINLDFADV
ref|YP_078922.1|       KEAVDTLIVIPNDRLLEIVDKNTPMLEAFREADNVLRQGVQGISDLIATPGLINLDFADV
ref|ZP_02171874.1|     KEKVDTLIVIPNDRLMEIVDKNTPMIEAFREADNVLRQGVQGISDLIAVPGLINLDFADV
RAAC00118              KQKVDTLIVIPNDRLLEIVDRNTPVLEAFREADNVLRQGVSGISDLIATPALINVDFADV
                       *:  *********::*::*********:.******..*  *:*** ref|YP_001646530.1|    KTIMSNRGSALMGIGSGNGENRAAEAAKKAISSPLLETSIDGAQGVIMNITGGANLSLYE
gb|AAN04557.1|         KTIMSNRGSALMGIGSGNGENRAAEAAKKAISSPLLETSIDGAQGVIMNITGGANLSLYE
ref|YP_001375784.1|    KTIMSNRGSALMGIGSGNGENRAAEAAKKAISSPLLETSIDGAQGVIMNITGGANLSLYE
ref|YP_078922.1|       KTIMSNKGSALMGIVATGENRAAEAAKKAVSSPLLETAIDGAQGVLMNITGGTNLSLYE
ref|ZP_02171874.1|     KTIMSEKGSALMGIGIATGESRAAEAAKKAISSPLLETSVDGAQGVLMNITGGTNLSLFE
RAAC00118              KAIMTERGSALMGIGIASGENRAAEAAKKAISSPLLETSIDGARGILMHVAGGTNLSLWE
                       *.::.****   .*******:***:**:*.:*::.**.* ref|YP_001646530.1|    VQEAADIVASASDPEVNMIFGSVINEGLKDDIVVTVIATGFDDSASTQPPKPIIRPTANH
gb|AAN04557.1|         VQEAADIVASASDPEVNMIFGSVINEGLKDDIVVTVIATGFDDSAATQPPKPIIRPTANH
ref|YP_001375784.1|    VQEAADIVASASDPEVNMIFGSVINEGLKDDIVVTVIATGFDDSIVAQQQKTLVRPKINS
ref|YP_078922.1|       VQEAADIVAAASDQDVNMIFGSVINENLKDEIVVTVIATGFIE--QDQDSSKPQRPLNQG
ref|ZP_02171874.1|     VHEAAEIVSSASDEEVNMIFGSVINDNLKDEIVVTVIATGFDEASQQKAQPKRSKPNAQK
RAAC00118              VNEAADIVSMTADPDVNMIFGAAIDPNLEDEIVVTVIATGFDGSNQQQQARQNHLHHEPH
                       *:****:**:  ::.* :******:.*  .*:*:*:*:*******   :

ref|YP_001646530.1|    TQQQQQPVAQPSKQREVKREMKREEPVVHDRHTDS---DDIDIPAFLRNRRRR-----
gb|AAN04557.1|         TQQQQQPVAQPTKQREVKREMKREEPVVHDRHTDS---DDIDIPAFLRNRRRR-----
ref|YP_001375784.1|    SHVQQQAAVQPPKHREVKREVKREEPVIHDRNTDA---DDIDIPAFLRNRRRR-----
ref|YP_078922.1|       LKQHHQP--------APKREPKREEPSMPHRSPSQPAEDTLDIPTFLRNRNKR-----
ref|ZP_02171874.1|     SGRQEQK------DQPQQKAAEVEETSQEEI-------DTLDIPTFLRNRRQR-----
RAAC00118              DNVVRGT---------VQRHPSAQDPVINVPNTGN----PWEIPAFMRRQNSRFGRDR
                                 .    ::   .  ::.           :**:*:*.:.  *
```

FIG. 43

```
ref|YP_001395809.1|    ---KDSITVSLCMIVKNEEDTIGRCLDSVKDVIDEFIIVDTGSSDNTKDVIKKYTDNIYD
ref|YP_001309701.1|    -------TISLCMIVKNEEDVIANCLESVKDIVDEMIIVDTGSDDKTKKIVKRYTDKIYD
ref|YP_001643660.1|    -------TISLCMIVKNEDEEQTISKCLESVKSVVDEIIIVDTGSTDGTKEIVKKYDAKVYD
ref|YP_520670.1|       ---------SLCMIVRNEEKTIARCLDSVCDIADEIIIVDTGSTDRTKEIVARYTDKIFD
ref|YP_147952.1|       -------TISLCMIVKNEEDVLARCLDSVQHLVDEIVIVDTGSTDRTKEIARSYTARVID
RAAC01377              MSAKTENTWSLCMIVKDEEAVLDRCLQSIADIVDEIVIVDTGSQDRTQEIARKYTDLVFD
                                 ****:: .: .**:*:  :  ::**** *  *:.:    *   : * ref|YP_001395809.1|    FEWIDDFSAARNFAFSKATKDYIFWLDADDVLLPEDVEKFKALKKNLDTSIDSVTMRYNV
ref|YP_001309701.1|    FKWIDDFSAARNFAFSKATKDYILWLDADDVVLPEDGEKFKDLKETLDPTVDSVTAKYNT
ref|YP_001643660.1|    FQWIEDFSAARNFAFSKATKEYILWLDADDIIDTEDIKKLLQLKHTLDRSTDAVSMKYYL
ref|YP_520670.1|       FAWIDDFAAARNYAFSLGTKEYLLWLDADDVILESDRLKFHNLKKNLNPSIDVVNMHYLL
ref|YP_147952.1|       FPWSDDFSAARNFSFSHATMDYIFWLDADDILPAEEQTKFLTLKRTLSSDIDSVTMIYSL
RAAC01377              FEWVDDFSEARNESFRHASMDYVLWLDADDVVSDVDRIKLAEFKKNLSSDVDAVTMWYHL
                       * *  :: * :*  .:  :*::******::    :  *:  :*..*.  * *.  * ref|YP_001395809.1|    SFDEYSNVTTSYRRNRLVKKEKNFKWIGFVHEYLEVYGNIINSEISVTHKKINYSPNRNL
ref|YP_001309701.1|    AFDEYGNVTASYRRNRLVKRSNNFQWFGFVHEYLAVGGNIINSEIAITHRKLKQTPKRNL
ref|YP_001643660.1|    TFDIEGNPTHSLRRYRLVNRSKNFQWYGFVHEYLEVYGNLINSDVGVSHKKEKAYTNRNL
ref|YP_520670.1|       AFDSSENPTFTLRRRNRLVRRGKNFRWKGAVHEYLEVSGNIMNSDIAIAHKSEEHDSERNL
ref|YP_147952.1|       AQDEYGKTISSVRRNRLVKRSSGFRWHGMVHEYLEVWGTILNSDITIIHQPNRCASDRNL
RAAC01377              AFQGDQPTVSS-RLVRLVKRSRGFVWRGRVHEYLEINGNILNSDIAIIHRPVEHDAARNL
                       :  :       :   *  ***.:  .* * *  ***** *.::**:: *:.     *** ref|YP_001395809.1|    EIFQNKLKEGVEFTPRDILYYGNELYEHRMFEDALKYYNDFLDSKRGWYEDNIHVCGKIC
ref|YP_001309701.1|    EIYQNKLKEGVVFTPRDILYYGNELYDHRMFDEALQYYNKFLDSKQGWFEDNIRVCEKIC
ref|YP_001643660.1|    KIYEKHLESGKEFSPRDVYYYANECKDHRLFDKAVKGYSRFLDEEKGWVEDNIQACLKRA
ref|YP_520670.1|       RIYEKRLEQGEEFSPRDLYYFANELYDHKQYEKAVEYYEKFLNTEKGWVEDNISACGKLA
ref|YP_147952.1|       QIYEKQLAQGKEFSPRDLFYFANELFDHQQYERAIQYYEQFLQTKKGWVEDCIAACGKVA
RAAC01377              RIYEKKLALGEDFSPRDMLYYANELLDHAQYEKAVQWYKRFLATGQCWKEDAITACFKLA
                        .*:::*  *  *:***: *:.**  :*   :: *:: *. **    :  * ** * .* * .

ref|YP_001395809.1|    DYYQSINNGEECRKYAFKSFEYDSPRAEACCRLGFSFLQENKINQAIFWYETAANLKKPI
ref|YP_001309701.1|    DYYQSIDKVEDGRRYAFRSFEYDTPRAEACCKIGFSFLHEKKYKQSAFWYEQATKLEKPK
ref|YP_001643660.1|    ECYLELGDLKKSIQSCLQSFTYDTPRGELCCHLGRVFLQQGEYSKAIYWYHAAIDGPRPK
ref|YP_520670.1|       DIYKLLGDSANAQAYLYKSFDYDTPRAEFCCRIGFNHLNAGKYQQAIFWYKLASELEKPT
ref|YP_147952.1|       DCFDALGDEEQALRYALRSFEYDTPRAECCCRLGYYFLQRKQYRLAAFWYHLATQLTMPS
RAAC01377              ECFRAMNQPEQSKQAVLHSFLYDTPRAEACCRIGYYLEEGKIDQAIFWYDLATKCRRPA
                        : :    :..  .            :  :**.*  **:: *  .*. :   : :**. *   .  * ref|YP_001395809.1|    NSLGFFSDACWTWLPHLQLCVCYDRIGKHQLAYEHNEIAGKFRPNDKKILYNRNYFQS--
ref|YP_001309701.1|    DSWGFFNDACWTWLPHLQLCVCYDRLGDHNLAYEHNEIAAKFRPNDSRILYNRNYFKS--
ref|YP_001643660.1|    D-SPFVREECHTWLPHIQLCICYDRIKEYEKAIYHNEQAALFIPNNPSIEYNR------
ref|YP_520670.1|       NSWGPKSEACWTYLPHLQLCVCYDRLGMHELAYKHNEIARDYRPDNPQILHNKKYL----
ref|YP_147952.1|       DSWGFVHHACWTWLPHLQLCVCYFYMGEYELAYQHNEKAKQYVPHHPAVLHNECLLQSIL
RAAC01377              NFVGFVNHACETWLPHIQLCVCYSRLGQYRKAYDHNERAAEYLGEDPMIVHNRSVLRAWM
                        :          . * *:***:***:**  :   :. *  *** *  :   .. : :*.

ref|YP_001395809.1|    -------
ref|YP_001309701.1|    -------
ref|YP_001643660.1|    -------
ref|YP_520670.1|       -------
ref|YP_147952.1|       AAE----
RAAC01377              DGELEKP
```

FIG. 44A

```
ref|NP_470039.1|          ------LISICMIVKNEAHILRQSLASFRKFTEEIIIVDTGSTDDTKEIAKEFTDFVYDF
ref|ZP_01929325.1|        ------LISICMIVKNEAHILRQSLASFRKFTEEIIIVDTGSTDETKEIAQEFTDFVYDF
ref|YP_848858.1|          ------LISICMIVKNEAHILRQSLASFRKFTEEIIIVDTGSTDETKEIAKEFTDFVYDF
ref|YP_001374688.1|       -------ISACLIVKNEEDMLRKCLESLQGGVDEIVVVDTGSTDTTKEIAKEFTDKVYDF
ref|NP_622177.1|          -------LSLCLITKNEEKNISRCINSVKDIVDEIVVVDTGSTDRTIEIAKSFGAKVIQI
RAAC02381                 MRRIVVLLSACLIVKNEAHVLPRCLGSLQGVADEIVVVDTGSTDDPRIAESFGARVYHF
                                 :* *:*.***  . : :.:  *.:    ..:**::******* * .**:.*    * .:

ref|NP_470039.1|          EWTGNFSDARNFAAKHATGKWILAIDADECLEEESYRKLEKQLKSPIEP--IQMAQIISF
ref|ZP_01929325.1|        EWTGNFSDARNFAAKHATGKWILAIDADECLEEESYRKLEKQLKSPTEP--IQMAQIISF
ref|YP_848858.1|          EWTGNFSDARNFAAKHATGKWILAIDADECLEEESYLQLKKQLKAPTEP--IQMAQIISF
ref|YP_001374688.1|       EWTNDFAEARNFAASKASGEWILAIDADECVDPKNLAAAIEEIQSHDNKFDVYAVEINSF
ref|NP_622177.1|          KWEDDFSKARNTAIESATGDWILFLDADEEIKKEDVSKIKSLLYDDTVEAYLFKFVNYAG
RAAC02381                 EWTGDFAVARNESLRYALGEYVLVIDADEFLPKEDGVRLRQALQERRADAYTVDLVNYLG
                           :* .:*: ***  :*    * *.::* :****  :    :.     . :

ref|NP_470039.1|          TGEKGRVTTTNQMARVYKNDGTICFRGVIHEQ-----LEAVDKHAIEAGLAEVKIYHYGY
ref|ZP_01929325.1|        TGEKGRVTTTNQMARVYKNDGTICFRGVIHEQ-----LEAIDKRPIAAGVAEVKIYHYGY
ref|YP_848858.1|          TGEKGRVTTTNQMARVYKNDGTICFRGVIHEQ-----LEGIDKHAVETGFAPVKIYHYGY
ref|YP_001374688.1|       SDKYGENLSMNHMQRIYKNNGEFHFSGAIHEQI----VEKGEGR-QELVFSALKLYHYGY
ref|NP_622177.1|          SSINSGLTEINYNYRLFRNNGKLKYIYPVHEN----LRNIEENRPPIAKKADVTILHYGY
RAAC02381                 SVARFVRSPGVRVRVFRRG--FSYMGSIHEQ----ILYDVIAKGGQIEVLDVEIHHLGY
                          :             *::..  : :   :**:          :     : : * ** ref|NP_470039.1|          MSEIVEKQDKSDRNLRLLEKEVKNNKNSGFVHFNIGQEMNRLGNKKEALKEFSEAFRL--
ref|ZP_01929325.1|        MSEIVEKQDKSDRNLRLLEKEVKNNKNSGFVHFNIGQEMNRLGNKKEALKEFSEAFRL--
ref|YP_848858.1|          MSEIVEKQGKSDRNLRLLEKEVKNNKNSGFVHFNIGQEMNRLGDKKEALKEFTKAFRL--
ref|YP_001374688.1|       LPNVVKKKNKRKRNMDILKKALKSNNNDGFTYFNYGQELRSLGKTKEALESFIKAY----
ref|NP_622177.1|          LADIRKEKNKSERYIKLISKYLESHPEDKFQHANLAVEYFNIGDYQKALKHLLIATKGMD
RAAC02381                 LAEFVALKGKSDRNLEILNQALAIDPDNFFHITNLMAEYARLGDPKKVVELGERAYDLFQ
                          :.:.     :.*  .* .*  : ::.:  .  : ..  *     *    * :*. ::.::      * ref|NP_470039.1|          --RDNNHYIWAKLSAYHISELLEQE-KRYDESLAIIEEAKVIWPNVPEFPLKKANILYVN
ref|ZP_01929325.1|        --RDHNYIWAKLSAYHIAELLEQE-KRYDESLAIIEEARVIWPNVPEFPLKKANILYVN
ref|YP_848858.1|          --RDNNQYIWAKLSAYHIAELLEQE-KRYEESLAIIEEAKVIWPNVPEFPLKKANILYLH
ref|YP_001374688.1|       QNKEDVYEEWVSRCLYFIVEMLVEL-KRYEEAIVIINDAEEVFSTAPDFPFWKGEIYFKQ
ref|NP_622177.1|          VNSVN----ATRLLRYLIGCYIGLK--DYSTALKIIKDAKDYYKDIPDFSFLEGLMYMDQ
RAAC02381                 RGRVNQPHLVLRMYRMMIAAHGDLG--NYDRVEALAREAELFFPNIPDVPFVHALYVMQR
                           .                 *           *.     :  .:*.     :   *:...:  ..

ref|NP_470039.1|          HQLEDAKEI---YKSLLENTAIDYQPI-VLYEATNFMPHKMLGTIYLEEKDYTRAMTHFS
ref|ZP_01929325.1|        HQLEDAKEI---YQSLLENAAIDYQPI-VLYEATNFMPHKMLGTIYLEEKDYTRAMTHFS
ref|YP_848858.1|          HQLEDAKEI---YHSLLDNKVIDYQPI-VLYEATNFMPHKMLGTIYLEEKDYTRAMTHFS
ref|YP_001374688.1|       KRFDDAKEV---YTHIISNNMIYQNAVFN-AGAKTFLPHVRLGEIYTQERQHQQALQHYV
ref|NP_622177.1|          KRYEKAIEA---FKESLSIGEYDGLFI-TMGGTGSYRARYMIGLCKEKLNQLNDAVKEYI
RAAC02381                 GDWRKAIRL---FERSREIGEIRSEIIDTIAGAGSYVAAAKLGELWLLEGDVELAREYFV
                             .*    .    :   .     :         :.:      :*       :  * :

ref|NP_470039.1|          KAYAENSSDYGVMFQMIMLL----------------------------------------
ref|ZP_01929325.1|        KAYAENSSDYGVMFQMIMLL----------------------------------------
ref|YP_848858.1|          KAYAENSSDYGVMFQMIMLL----------------------------------------
ref|YP_001374688.1|       EALNEN------------------------------------------------------
ref|NP_622177.1|          EVLKENPNYQEVFIKLFDLFIKNEP-----------------------------------
RAAC02381                 QSLRENLRQEGTFFFLASLLPLNDPSVFEQLRALASHDPVCLAYLALAGAVWRVDHAWRL
                          :   **
```

FIG. 44B

```
ref|NP_470039.1|         ------------------------------------------------------
ref|ZP_01929325.1|       ------------------------------------------------------
ref|YP_848858.1|         ------------------------------------------------------
ref|YP_001374688.1|      ------------------------------------------------------
ref|NP_622177.1|         ------------------------------------------------------
RAAC02381                INEIEQTPVTAPIVAKLRALGAVLGILPANDVRVDSTVEREIQWYEALFALERGDRDQAE ref|NP_470039.1|         ------------------------------------------------------
ref|ZP_01929325.1|       ------------------------------------------------------
ref|YP_848858.1|         ------------------------------------------------------
ref|YP_001374688.1|      ------------------------------------------------------
ref|NP_622177.1|         ------------------------------------------------------
RAAC02381                RCLRDQPERWERLSEWLTSKQGLCISPILDELLLARVDELLLAWLPRAEDRDLALSRVLA ref|NP_470039.1|         ------------------------------------------------------
ref|ZP_01929325.1|       ------------------------------------------------------
ref|YP_848858.1|         ------------------------------------------------------
ref|YP_001374688.1|      ------------------------------------------------------
ref|NP_622177.1|         ------------------------------------------------------
RAAC02381                SPLREEVWKAAWLGERGWECDFLALGAFRRRDIQASLNWLERGLTYEPTVRRAIVEIDLA ref|NP_470039.1|         ------------------------------------------------------
ref|ZP_01929325.1|       ------------------------------------------------------
ref|YP_848858.1|         ------------------------------------------------------
ref|YP_001374688.1|      ------------------------------------------------------
ref|NP_622177.1|         ------------------------------------------------------
RAAC02381                LCHKNIAHAQEVASQASRLFPESKLLEGIAGSLGVSPRPMRSLDDLLGGGSGLNPHRAYQ ref|NP_470039.1|         ------------------------------------------------------
ref|ZP_01929325.1|       ------------------------------------------------------
ref|YP_848858.1|         ------------------------------------------------------
ref|YP_001374688.1|      ------------------------------------------------------
ref|NP_622177.1|         ------------------------------------------------------
RAAC02381                SSVNSMPLKVKIMKLHERAVECVDQVKALVDQGDIMGARTYIQYVQDIITFLRSNLDTST ref|NP_470039.1|         ------------------------------------------------------
ref|ZP_01929325.1|       ------------------------------------------------------
ref|YP_848858.1|         ------------------------------------------------------
ref|YP_001374688.1|      ------------------------------------------------------
ref|NP_622177.1|         ------------------------------------------------------
RAAC02381                EAGKAADAAYAYFYKMLVEWFLQPSKVESEYKEMRDFWQSWADTWAKVEA
```

FIG. 45

```
ref|NP_831314.1|       ---------------------LKIGITCYPSVGGSGVVGTELGKQLAERGHEIHFITSG
ref|NP_844008.1|       ---------------------LKIGITCYPSVGGSGVVGTELGKQLAERGHEIHFITSG
ref|ZP_01172765.1|     ---------------------LKIGITCYPTVGGSGVVATELGKLLAERGHEIHFISSS
ref|YP_001487207.1|    ---------------------LKVGITCYPSVGGSGIIATELGKRLAEKGHDVHFITSS
ref|ZP_02327412.1|     ---------------------LKIGITCYPSLGGSGVVATELGKLLAEQGHEVHFIAHS
RAAC00991              ---------------------MRVGISCYPTVGGSGAVATELGKALARRGHEVHFIVTD
                                            :::.**:***:****  :.***** **.:**::***   .

ref|NP_831314.1|       LPFRLNKVYPNIYFHEVTVNQYSVFQYPPYDLALASKMAEVAQRENLDILHVHYAIPHAI
ref|NP_844008.1|       LPFRLNKVYPNIYFHEVTVNQYSVFQYPPYDLALASKMAEVAQRENLDILHVHYAIPHAI
ref|ZP_01172765.1|     LPFRLNRMYHNIFYHQVEVSQYSVFQYPPYDIALASKMAEVINREKLDLMHVHYAVPHAV
ref|YP_001487207.1|    IPFRLNKVYPNIYFHEVDVNQYAVFQYPPYDLALASKLAEVARREKLDIIHAHYAVPHAV
ref|ZP_02327412.1|     MPFRLGRFDKNVFYHEVEVSDYYVFKYPPYDLSLASKLAQVARMQELDLLHVHYAIPHAV
RAAC00991              VPFRLGAFVEHVYIHQIEPITYPVLKTPPYDFALASLMARVADEYQLDVLAHYALPFAV
                       :****.     :::  *::    *  *::  ****::***  :*.*     :**::*.***:*.*:

ref|NP_831314.1|       CAYLAKQMIGERIKIVTTLHGTDITVLGSDPSLNNLIRFGIEQSDVVTAVSHSLINETHE
ref|NP_844008.1|       CAYLAKQMIGERIKIVTTLHGTDITVLGSDPSLNNLIRFGIEQSDVVTAVSHSLINETHE
ref|ZP_01172765.1|     CAILAKQMSGRDVKIATTLHGTDITVLGYEPSLKDSIRFGIEKSDRVTAVSKSLISQTNE
ref|YP_001487207.1|    CAYLAKQMTGHSVKVVTTLHGTDITVLGYDPSLKEVIRFAIESSDRVTAVSHSLAAQTYD
ref|ZP_02327412.1|     CALLAKQMVGDHLKVVTTLHGTDITVLAQDASISNMIRFAINESDAVTAVSEDLIRETRQ
RAAC00991              CAHLAREMAKHPIRVVTTLHGTDITVLAQDPSLKSIIKLGIERSDAVTAVSQSLVRDTAR
                        ::*       ::::.**********. :.*:..  *::.*:  ***..*   :* ref|NP_831314.1|       LVKPSKEIQTVYNFIDERVYFKRNMSQLKKEYGISESEKVLIHISNFRKVKRVQDVVQAF
ref|NP_844008.1|       LVKPNKDIQTVYNFIDERVYFKRDMTQLKKEYGISESEKILIHISNFRKVKRVQDVVQAF
ref|ZP_01172765.1|     LIHPEKEIQAVYNFIDHRVYQKTGSDHLKKEYGITEDEKTVIHVSNFRAVKRVQDVVKVF
ref|YP_001487207.1|    LIKPNKKIETIHNFVDERVYLRDDHNVLKRHYGLLDHEKVVIHVSNFRKVKRVHDVIHVF
ref|ZP_02327412.1|     TLDIQKPIHKIYNFVDKRMYYPRPVEDLKREVTRP-GEKLFIHISNFRPVKRVHDVVQIF
RAAC00991              LFETDKPIRCIYNFVDPDVFRPGCGGELKRHFAPN-GERVLLHISNFRPVKRLHDVIAVF
                          ..  .*  *.  ::**:*   ::      **:.       *:  ..:*:** *::**:    * ref|NP_831314.1|       AKIVKEVDAKLLLVGDGPEFCTILQIVKNLHIEDRVLFLGKQDNVAELLAMSDLMLLLSE
ref|NP_844008.1|       AKIVTEVDAKLLLVGDGPEFCTILQLVKNLHIEDRVLFLGKQDNVAELLAMSDLMLLLSE
ref|ZP_01172765.1|     ARIESEMPAKLLLVGDGPEMSNVCKLVKELGLKEKVLFLGKQDKVEELYSISDLMLLLSE
ref|YP_001487207.1|    KKISEQVNAKLLLIGDGPEKSVVCELVKKLGLTDRVLFLGKQEKVEELYSISDLKLLLSE
ref|ZP_02327412.1|     ARVHREIPSRLLLVGEGLELSRIVSEVRELGLQDFVEFWGKQDDVAQVISLADVMLLPSE
RAAC00991              ERVARRMPAKLLLVGEGPDLGAAKRQVEEAGLGDRVHFLGRQDEVAPLFAAADLFLLPSE
                         ::   .: ::***:*:* :           *.:   :   * * *:*:.*   :  :  :*: ** **

ref|NP_831314.1|       KESFGLVLLEAMACGVPCIGTRVGGIPEVIQHGETGYLCEVGDTTGVANQAIQLLKDEEL
ref|NP_844008.1|       KESFGLVLLEAMACGVPCIGTRVGGIPEVIQHGDTGYLCEVGDTTGVADQAIQLLKDEEL
ref|ZP_01172765.1|     KESFGLVALEAMACGVPCIGTNIGGIPEVISDGETGYICKLGDIGSMAEKAAGLLADADK
ref|YP_001487207.1|    KESFGLVLLEAMACGVPCIGTDVGGIPEVITHGETGFLVPLGDIDAAAKHAVSILKDKAL
ref|ZP_02327412.1|     KESFGLVALEAMACGVPTVGSNAGGIPELITHGETGFMAEVGDVDTMSKYTIRLLEDEEL
RAAC00991              SESFGLVALEAMSCGVPVVGSTAGGIPEVVVHGETGFLAPVGRVDDMADLACKLLQDEAT
                       .**** :** :*:  ***** :  .*:**::  :*       :. :  :* * ref|NP_831314.1|       HRNMGERARESVYEQFRSEKIVSQYETIYYDVLRDDK----------
ref|NP_844008.1|       HRNMGERARESVYEQFRSEKIVSQYETIYYDVLRDDK----------
ref|ZP_01172765.1|     HTSFSHRAVQTAREKFSAEQIVSEYERLYFDML--------------
ref|YP_001487207.1|    HEQVSAAAQSSVQAHFSSEKIVSEYEELYLELIEGD-----------
ref|ZP_02327412.1|     LKRVSEACVQRARKKFCNDSLRARYEQVYYEVL--------------
RAAC00991              YRAFSARARERAVRAFHVDEKVSEYEALYREVMAAERGEHAHPRPGA
                          ..    . .   *   *: .  :.** :*  :::
```

FIG. 46

```
ref|YP_001647987.1|     ----------AGAEDGGGKTHIISLLDQFPDGEVE-------LAVFEDGIVAKEARELG
ref|NP_835081.1|        ----------AGAEDGGGKTHIISLLDQFPTGEVE-------LAVFEDGIVAKEARELG
ref|YP_001377114.1|     ----------AGAEDGGGKTHIISLLDQFPTDEVE-------LAVFEDGIVAREAREIG
ref|YP_001127183.1|     ------VLHVISGGETGGSRKHVVTLLSKFAPGTAT-------LVVFQDGPLAAEARQAG
ref|ZP_02038504.1|      ------VIHLISGGDSGGAKTHVHMLLQNLSRTPGVEVT----MVCFMEGPFSQEARELG
RAAC00650               MASERTVIVFFAGNEVGGAATHLATWAKALKGAQVDYRYR---FVSLGDGPLADELRQMG
                              :*  : **. .*:         . :         :. . :* .: * *:  * ref|YP_001647987.1|     IKVHVFSQKSRYDLSILKNISEFINKEKFDVVHTHGPRANFFVSLMKKKFAAKWVTTIHS
ref|NP_835081.1|        IKVHVFSQKSRYDLSILKNISEFINKEKFDVVHTHGPRANFYVSLMKKRIKAKWVTTIHS
ref|YP_001377114.1|     IKVHVFSQKSRYDLSILKNISRFINEEQFDIVHTHGPRANFYVSLMKKRIAAKWVTTIHS
ref|YP_001127183.1|     IDVRLLAQSSRYDLSVLSKLVALIRRERFDILHTHGPRANLYGALIKRKIAIPWMTTVHS
ref|ZP_02038504.1|      ISTVVLPGKN--IFRTFHTLKNMIREGGYEIIHCHGARGNMMGALLRKATGLPVVTTVHS
RAAC00650               MLHGAVAGTVG----AIRDLARVLRRERAWILHSHGPRMNMLASFAASSAGAIWTATIHS
                        :     ..     :     :   . : ..   ::* **.*  *:   ::        :*:**

ref|YP_001647987.1|     DPFQDFTKQGLKGWIFTKLNLKALKNIDLFPVVTNRLKKSLAALGISNEKMHVIYNGIEY
ref|NP_835081.1|        DPFQDFTKQGLKGWIFTKLNLKALKNIDLFPVVTNRLKKSLAALGISNEKMHVIYNGIEY
ref|YP_001377114.1|     DPFQDFTKQGLKGWIFTKLNLKALKDIDLFPVVTNRLKKSLEQLGISSEKMRVIYNGIEY
ref|YP_001127183.1|     DPRLDFMKSGWKGKWFTRLNVWALQKVDYFFAVSERFKESLMELGIAAERIQTIYNGIDF
ref|ZP_02038504.1|      DYRLDYMGRPISRITYGTINTLALRLLDYRIGVSDAMTDLLISRGFDPDKLFTIYNGIDF
RAAC00650               HPRYDFEGHPLKAALFPSLHLWRLSRARGLFVVQPALGDALPCR-TILEVPNAFFPRLPR
                        .  *:     .     ::         *      :  *    . *       . .:   :

ref|YP_001647987.1|     DQEKADGYN--------KKEMFNIDEDVFTAIQVARLHPVKGHEVLFDALQQTKL--EKI
ref|NP_835081.1|        DKEKAEGYN--------KKEMFNIDEDVFTAIQVARLHPVKGHEVLFDALQQTKL--EKI
ref|YP_001377114.1|     DKEKAQGYD--------KKEKFHIEEDVFTAIQVARLHPVKGHEVLFDALNNTSL--TKI
ref|YP_001127183.1|     DDAPRPHM--------LQRADLGLREDDLVIAMVARLHPIKGHALVFEALASLSD--PDM
ref|ZP_02038504.1|      TPRTPSMTR----SEYLKSVGANWPEDCVVAGIAARLNPVKDIPTLIRGFAQARQSCPKL
RAAC00650               ASRDVCAAE--------WRRRLGLNPESRLIGIAARLDPVKQIDVAIAALALLSD--LDV
                                       :        .***.*:*     :  .:           .:

ref|YP_001647987.1|     KVLLVGDGPLERELKALATEKGINDKVEFLGHRQDVKQLFASSHVNLLTSHSEGFPLVLL
ref|NP_835081.1|        KVLLVGDGPLEENLKSLATEKGINDKVEFLGHRQDVKQLFASSHVNLLTSHSEGFPLVLL
ref|YP_001377114.1|     KVLLVGDGPLEEDLKALAKEKGIDDKVQFLGHRQDVKQLFASAHINLLTSHSEGFPLVLL
ref|YP_001127183.1|     KLLVVGDGPLASELREKATQSGIGRQVQFLGFRRDVADIYALSDVALMASYSESFPLALL
ref|ZP_02038504.1|      RLLIAGDGEQMNELKALAADLGVAEDVCFAGWVSDVDSFYGALDINTLTSLSETFPYSLT
RAAC00650               HLLVAGDGRDRIRLEAAAEDCGVRHRVHFLGHLQDVRDLYCAIDVHVLPSKSEGAPTSML
                        ::*:.***    *.  *:   *       **    .:    :.*  **  *  :

ref|YP_001647987.1|     EAANQRVPSIVTRAGEIEPLIADETYGWIVPTGDGKALASAL------------------
ref|NP_835081.1|        EAANQRVPSIVTRAGEIEPLIVDETYGWIVPTGDGKALALAL------------------
ref|YP_001377114.1|     EAANQRVPSIVTRAGEIEPLIVDDTYGWVPVGDGKALANALEQ----------------
ref|YP_001127183.1|     EAANERLPVISTDVGGVSQLIASSDMGWIVPVGDRAALAQAMREARSRRHELKTMGKRLY
ref|ZP_02038504.1|      EGARAGLPTVASRVGGVPYLIDHGVNGLLFEAGDYETLAKHLTALASDETMRTHMGQRLY
RAAC00650               EAGYYGAANIGSDVPGIRRMLLDGEAGALVPSGDVQALAHAVRRLLTDTKARDAYVERFQ
                        *..      . :: .    :  ::       * :. **  :**   :

ref|YP_001647987.1|     ------------------------------------------
ref|NP_835081.1|        ------------------------------------------
ref|YP_001377114.1|     ------------------------------------------
ref|YP_001127183.1|     EHASTHFSLQRLYEETM-ATYER-------------------
ref|ZP_02038504.1|      QKGKNDYSLESTLQRQLEIYSVI-------------------
RAAC00650               RLVLPRYRPERMVVAYERGYTVIEEDAVRSGWRLPANSEQTR
```

FIG. 47

```
ref|YP_001486101.1|    --QFIVSQEDWSLHRKGYDDQQRHQKKVKEAIKNNLPDLVTEESIIMSNGKDVVKIPIRS
ref|ZP_01170532.1|     --QFVISEEDWSLHRKGHDDQQRHQEKVQDAIRNNLPDLITEESIIMSNGREVVKIPIRS
ref|NP_241897.1|       ---FVVSQENWTLHRKGYQDQRRHQEKVKEAIRKNLPDLVSEENIIMSNGREVIKIPIRS
ref|ZP_01721811.1|     ---FVISQENWSLHRKGHQDQQRHMEKVKDAIKNNLPDLVSEESIVMSNGREVIKIPIRS
ref|ZP_02327994.1|     ---FIVSRENWSLHRKGYQDQTRHQQKIKDAIKQNLPDLVTEENIILSNGKQIIKIPIRS
RAAC02421              MVEFTLQREDWSLHRKGHIDQERHREKVREAIREHLADLVSDESLIMSDGKQIIKIPIRS
                           *  ::..*:*:***:  ** :*:::**::*.**:::*.:::*:*::::****** ref|YP_001486101.1|    LDEYKIRYNYDKNKHVGQGDGDSEVGDIVARDG--SDSKQGQGKGQSAGDQAGE--DYYE
ref|ZP_01170532.1|     LDEYKIRYNYDKNKHVGQGDGDSQVGDVVARDG--SSGQKGPGKGQGAGDQPGE--DYFE
ref|NP_241897.1|       LDEYKIRYNYDKNKHVGQGDGDSQVGDVIARDP--SAGQQGPGKGQGAGDQPGE--DYFE
ref|ZP_01721811.1|     LDEFKIRYNYDNSKHVGQGQGDSNVGDVVARDG--SKANQTQGKGKEAGDKPGQ--DYYE
ref|ZP_02327994.1|     LDEYRFRFNYNKSKHVGQGDGDSQVGDVLG-----IDPYTQQGKGAGAGDQAGE--DYYE
RAAC02421              LEEYRIRYNFQKGKHVGSGSGDTAVGDLVARGKPDADGQPGPGQGEGAGSEPGV--DYAE
                       *:*:::*::*::::.****.*.: *::.       *:*  **.::.*    ** * ref|YP_001486101.1|    AEVSLMDLEEALFRELELPNLKQKELDDIIVEQIEFNDIRKTGLTGNIHKKRTMLSAFKR
ref|ZP_01170532.1|     AEVSMMELEEALFKQLELPNLRKKEQEEHLVENIEFNDIRKTGLMGNIDKKRTMMTAFKR
ref|NP_241897.1|       AEVSILELEELLFRELELPNLQQKEEDHLVVEHIEFNDIRKKGLMGNIDKRRTILSAIKR
ref|ZP_01721811.1|     AEVSLEEIQNVLFHELELPNLQQKEKAEIVTEKIEFNDIRKKGLMGNVDKKRTILNALKR
ref|ZP_02327994.1|     AEVDMEELQSLLFEELELPYLNPKERLDISTQDIIFNDIRKKGIMSNIDKKRTILENIRR
RAAC02421              AEVTLEDIQQELFRELELPDLAEKDEADMVVDTVEFRDVRKKGITANIDKKRTLLQALRH
                       ***  :  :::. **.:**** *   *:  .  .: : *.*:**.*: .*:..*:**::   :::

ref|YP_001486101.1|    NAMTGSPSFYPIYPEDIKYKTWNEVTKPESKAVVLAMMDTSGSMGLWEKYMARSFFFWMT
ref|ZP_01170532.1|     NAMTGKPAFYPIYQEDLKFKTWNEIVKPDSKAVVLAMMDTSGSMGLWEKYMARSFFFWMT
ref|NP_241897.1|       NALEGRPGLIPIYNDDLRFKTWNEVVRPESKAVVLAMMDTSGSMGRWEKYMARSFFFWMT
ref|ZP_01721811.1|     NAMHGKAEITPIHNDDLRFKIWDEVVKPESKAVVLAMMDTSGSMGAFEKYCARSFFFWMT
ref|ZP_02327994.1|     NASSGTPGIHGISPDDLRFKTWDEIEKPHSNALILAMMDTSGSMGSFEKYIARSFFFWMT
RAAC02421              AKKDDR---VVITPDDLRYKTWETIVKPDSNAVILAMMDLSGSMGLFEKYCARTFFFWMT
                       .            *  :*:::*  *: :   :*.*:*:***  * :* :**** ref|YP_001486101.1|    RFLRTKYETVDIEFIAHHTEAKVVDEEHFFSRGESGGTICSSVYRKALELIDERYPPSRY
ref|ZP_01170532.1|     RFLRTKYETVEIEFIAHHTEAKVVSEEDFFSKGESGGTICSSAYRKALELINEKYNPRRF
ref|NP_241897.1|       RFLRTKYETVDIEFIAHHTEAKVVSEEDFFSKGESGGTICSSAYRKALELINEKYDPARY
ref|ZP_01721811.1|     KFLRSKYETVEIEFIAHHTEAKVVTEEEFFTKGESGGTICSSAYKKALELIKEKYSPSRY
ref|ZP_02327994.1|     RFLRSKYEHVDIVFIAHHTEARIVSEEEFFTKGESGGTICSSAYQAALDVIDRSYPPSKY
RAAC02421              RFLRTKYANVQIRYIAHHTEAHEVDEEYFFTKGESGGTICSSAYQYALDMVNREYPPERY
                        :***:**  *:*  :*******: *  **  **::********** .*:  **::..  *  ::

ref|YP_001486101.1|    NIYPFHFSDGDNLTSDNARCVKLVSEIMKKANLFCYGEVNQYNRHSTLMSAYKHIQDEKF
ref|ZP_01170532.1|     NIYPFHFSDGDNLTSDNARCVKLVEELIAVSSMFGYGEVNQYNRHSTLMSAYKNIKNEHF
ref|NP_241897.1|       NIYPFHFSDGDNLTSDNARCLKLVHELMESSSMFGYGEVNQHNRHSTLMNAYKNLKDPRF
ref|ZP_01721811.1|     NIYPVHFSDGENISMDNEKCLKLVAELMDVSSMFGYGEVNQHNRFSTLMYTYKKIDDPKF
ref|ZP_02327994.1|     NIYPFHFSDGDNLTSDNERCVKLIQRLMERSNMFGYGEVNQYNRSSTLMQTYRHIQDPKF
RAAC02421              NIYSIHFSDGDNLTSDNEKCVQLVKELSSVSRMFGYAEVNQYSRSSTLMSAYGKLQIPRF
                       *..*: **  :*::*: .:   : :* *.****:.* **** :* ::.  :* ref|YP_001486101.1|    KHYILKQKSDVFLALKKFFQQEE-----
ref|ZP_01170532.1|     RYYILKQKADVFHAMKSFFQNEE-----
ref|NP_241897.1|       RSYVLKEKGDVYRAMKTFFKKEE-----
ref|ZP_01721811.1|     RHHILRKKGDVYDALKSFFKKNE-----
ref|ZP_02327994.1|     LYYIIREKGEVYKALKTFFAKPEG----
RAAC02421              RTYVIRDKSEIYGALRHFFSQQQGVKSA
                       :::::*.::: *:: ** : :
```

FIG. 48A

```
ref|ZP_01860158.1|      ------------------------------------------------------------
ref|YP_001421751.1|     ------------------------------------------------------------
ref|YP_148164.1|        ------------------------------------------------------------
ref|YP_001126336.1|     ------------------------------------------------------------
ref|NP_242401.1|        ------------------------------------------------------------
RAAC02142               MTLRGIGCVVPLRLAHTNADFDSVDSERGGCRMKRHSRALGLGLGALCLVATSAAPQVAR ref|ZP_01860158.1|      ----------------PFASAEEKKT-ELAAGAKSAILIERDTGTVLYDKNSHEKLPPAS
ref|YP_001421751.1|     ----------TASAPSAFAKPDGKHTSELAHEAKSAVLIERDTGSILYNKNSRERLAPAS
ref|YP_148164.1|        -----------------------AKVKLADEAKSAILIERDTGKVLYEKNAHEPLPPAS
ref|YP_001126336.1|     ---------------------------ELADEAKSAILIERDTGKVLYEKNPHEKLPPAS
ref|NP_242401.1|        ----------------PVGLAAEKQPNLAKEASSAIVIERDTGQVLFEKNSDEKLPPAS
RAAC02142               AASAPGIVQIREAADAGPTQSAPAASVDLAKQARSAVLMDFATGKVLYAKNAHERLPMAS
                                          .**   *  **:::    **  :*:  **.  *  *. **

ref|ZP_01860158.1|      MTKIMTMILIMEALDKGQIKWEDEVRTSEYAASMGGSQIFLEPGEVMTVKEMLLGISIGS
ref|YP_001421751.1|     MTKIMTMLLIMEALDKGKIKMSDKVRTSEHAASMGGSQIFLEPGEEMTVKEMLKGIAIAS
ref|YP_148164.1|        MTKIMTMLLVMEAIDEGKLSYDEKVRASEYAASMGGSQIFLEPGEEMTVDELLRGIAIGS
ref|YP_001126336.1|     MTKIMTMLLIMEAIDEGKLSYDEKVRTSEYAASMGGSQIFLEPGEEMTVDELLRAIAIGS
ref|NP_242401.1|        MTKIMTLLLIMEAIDSGKITYDDMVRTSENAASMGGSQVFLEPGEEMSVRDMIKAIAIAS
RAAC02142               ITKIMTLLLIFEAIDSGKLKWTDRVQASERAASMGGSQIFLEPGETMTVRDLVKGIAIAS
                        :*****:::*:**:*.*::.   :  *:: **** :**** *:*  :::   .*:*.* ref|ZP_01860158.1|      ANDASVAMAEHIAGSEEGFVEKMNNKVKDLGLKDTNFKNPTGLPASEHYSSAHDMAMMAK
ref|YP_001421751.1|     GNDASVAMAEYIAGSEEDFVSRMNKKAKELGLKDTSFKNPTGLPEKDHYSSAYDMAKMAK
ref|YP_148164.1|        ANDASVAMAEQIAGSEEAFVEMMNEKAKQLGLKNTHFANATGLPAEHHYSSAYDMAMMAR
ref|YP_001126336.1|     ANDASVAMAERIAGSEEAFVEMMNEKAKELGLKETKFANTTGLPAEGHYSSAYDMAIMAR
ref|NP_242401.1|        GNDASVAMAEHLAGTEEEFVGMMNEKARQLGLKNTNFVNTNGLPEKDHYTSAYDLAMISK
RAAC02142               ANDACVAMAEHLDGSEEAFVARMNQRAKELGMTDTHFANCNGLPAPNHYSSAHDIAVMSR
                         .***.*****   :   *:**  **  **::.::**::* * *  .***      **:**:*:*  :::

ref|ZP_01860158.1|      ELLKYQEITKYTGTYESYLREDTDKKFWLVNTNKLVRFYPGVDGLKTGFTNEAKYCLTAT
ref|YP_001421751.1|     ELLKYDKITQFTGTYEDYLRENTDKKFWLVNTNRLIKFYPGVDGVKTGFTGEAKYCLTAT
ref|YP_148164.1|        ELLKYEDITKYTSKYEDYLRENTDKKFWLVNTNRLVKFYPGVDGLKTGYTAEAKYCLTAT
ref|YP_001126336.1|     ELLKYEGITKYTSKYEDYLRENTDKKFWLVNTNRLVKFYPGVDGLKTGFTSEAGYCLTAT
ref|NP_242401.1|        ELLKYEDITEFTSVYEDYLRKGTDKEFWLVNTNRLVKFYPGVDGLKTGFTKEAKYCLTAT
RAAC02142               ALLMHPEITAFTSVYSDYLRKDTDHPLWLVNTNKLVRFYDGVDGLKTGYTQEAKYCLSAT
                         **  :   **  :*. *..***:.**: :******* *::** **** :***.* ** ***:**

ref|ZP_01860158.1|      AKKDNMRVIAVVFGEPTPKDRNAEISKMFDYAFSQYQTQPLFEKGASVGKAEISKGKAKE
ref|YP_001421751.1|     AKKGNMRVIAVVFGASTPKERNAQVTKMLDYAFSQFKTHPLYKRDQIVGTVKVKKGKQKL
ref|YP_148164.1|        AKKNGMRVIAVVFGAPTPKSRNAQITKMLDYAFSQYRTHPVYKRNETVARVNISKGKRSS
ref|YP_001126336.1|     AKKNGMRVIAVVFGAPTPKSRNAQITKMLDYAFHHYQAHPVYKRNETVARVDVSKGKQKS
ref|NP_242401.1|        AVKNGMRVITVVMGAPTPKERNSQITEMLDFAFSQYQTHQVYERDTYMMDLNVRKGNKKS
RAAC02142               AKRDGFRVIAVVMGEPKPTVRNAEIAAMLNYAFAHYKSVQVYPRGHVVGQVAVKRGTRDR
                        *  :..:***:**:*   ..*. **::::   *:::**    ::::    ::  :.   :       : :*.  .

ref|ZP_01860158.1|      VEAMTNEPISLLAKKGEKLDGIEKKVKLQK--LKAPVKKGDTIGKLVVEKDGKTLSETPL
ref|YP_001421751.1|     IKLTTSEPISLLAKKGENMDKVKKEVKING-NVTAPVKKGEVLGSLVLKKDGKVLVESPV
ref|YP_148164.1|        VEAVTSEPVSVLTKKGQSVEQIEKVIKVKD-NVKAPVRKGDELGVLILKQDGKEILHSPI
ref|YP_001126336.1|     VAAVTSEPVSVLTKKGQSVEQIEKVVKVKD-GVKAPVRKGDELGVLILKQDGKEILRSPL
ref|NP_242401.1|        VPIFTSESVSLVTKKGESIDNVTERVEWKE-SLLAPVHKGDVVGTLYLERDGEILSETPL
RAAC02142               VEAVTAEPVAFVTERS-SKTAYTTEIQWMT--LKAPVSRGQVVGHVLVKSGGQIVANVPV
                        :    * *.::.:::::. .                :: :   : *** :*: :*  : ::  .*: : . *:
```

FIG. 48B

```
ref|ZP_01860158.1|      IAKEDVPQASFWQ----------------
ref|YP_001421751.1|     TAKDDMEKAGFLTFLKRTM----------
ref|YP_148164.1|        VAKQTVEEASFWDLFKRVFGRFVQAG---
ref|YP_001126336.1|     VAKQTVAEASFWDLFKRVFGRFVQAG---
ref|NP_242401.1|        IAGEDVASASFWQMFKRIVGK--------
RAAC02142               VAKDDVPKATFFQSLGKTVKKVITFGQAQ
                         * : : .* *
```

FIG. 49A

```
emb|CAA04971.1|        ------------------------VQLLRPLPDPVLTLRDSASSTTLGGDRISIPWPKEG
gb|AAC32488.1|         ------------------------VQLLRPLPDPVLTLRDSASSTTLGGDRISIPWPKEG
ref|NP_824958.1|       ------------------------VAQAVRPLPTPTLGLTADETYTFEGG-KLDLPWPGQG
ref|NP_628606.1|       ------------------------VVQSMRPLPAPTLDLTAQDSFSFDGG-KPQIPWPESG
ref|ZP_02061285.1|     ------------------------------------------------------ISWPTDI
RAAC03015              MVVRSLRGFVIAIVIAIIVIGVPVLQLVRPIPQAASDVAAPLPRAIPGE-KPVIHWPSQG
                                                                              :  **  .

emb|CAA04971.1|        QGAVTVAGSGVYETFGP-EKSVPTASTAKIMTAYVLLRKHPLKRGEPGPTITV---DAQT
gb|AAC32488.1|         QGAVTVAGSGVYETFGP-EKSVPTASTAKIMTAYVLLRKHPLKRGEPGPTITV---DAQT
ref|NP_824958.1|       QSAVEVEGVGTVGTAGK-QAPKPIASVAKIMTAYVILEEHPLKGTAAGDKITV---DQQA
ref|NP_628606.1|       QAALDVQGIGSFGSSGD-QKPVPIASVAKVMTAYLVLRDHPLKSGAEGPKIKI---DQAA
ref|ZP_02061285.1|     RYGVIGTLQSGIISKNPNQGQWPLASVAKIMTAYIILKDHPLPIGQDGPTITVTQKEVNE
RAAC03015              EAALMADGVGSFGSSGP-QVPVPIASVTKVMTAYLVLQKHPLQLGQQGPSITITPDDVKV
                        . .:       .     :   :     * **.:*:****::*..***     *   .*.:   :

emb|CAA04971.1|        VAEGKAKDESRIEGLTEGQTFSQQDMLKMLMIPSGNNIGRLLARWSTKTDDQTAFVREMN
gb|AAC32488.1|         VAEGKAKDESRIEGLTEGQTFSQQDMLKMLMIPSGNNIGRLLARWSTKTDDQTAFVREMN
ref|NP_824958.1|       EDESKNEDES-TAAMTKGQKFTERQMLQMLMIPSGNNAARLLARW---DSDSETFVGKMN
ref|NP_628606.1|       EDQSQAGQES-TVDVFAGDSISQREALQAILIASANNVARLLARWD--AGSEKAFVEKMN
ref|ZP_02061285.1|     YEAFKKDGQS-VVKVALGEKLTERQLLEGLMIPSANNFAYILARWD--AGSVKAFVDKMN
RAAC03015              YERDKALGQS-VVKVAAGEQITEYQALEGLLLPSGNNMGTLLAKWC--DGSVQAFVQEMN
                         :       :*        :    *:   :::  .*.**    :**:*       :  :** :**

emb|CAA04971.1|        EAAKDLGMKNTVYTDPSGLDKGTVSTAVDQLKLAEAVMEYDVFRDVVALPNAEIPG-HGR
gb|AAC32488.1|         EAAKDLGMKNTVYTDPSGLDKGTVSTAVDQLKLAEAVMEYDVFRDVVALPNAEIPG-HGR
ref|NP_824958.1|       AAAKKLGMTNSTYTDPSGLEKTTVSTATDQLKLAKAVMQKEVFRSIVGMAKADIPGLKGT
ref|NP_628606.1|       GAAKDLGMTNTTYTDPSGLNNTTVSTAVDQVKLAKAAMKEPAFREVAAMMSYNDYK--GE
ref|ZP_02061285.1|     KTAQSLGLKDTRYEDPSGASAGTVSTPKDQFKLTQLAMQIPTFRHMVAMPQVNLPI-AGI
RAAC03015              ATAKRLGMTETHYADPTGYSPASQSDAVDQMKLFALAMQNPVFRQIVGEAQAELPV-AGL
                        :*    **:.  :  *   **:*       .   :   *   .   .      .*:   .**  :..   .   * emb|CAA04971.1|        IYNNNDRLILAGLG-IVGIKTGSNTPAGGTLSWAAYKTFDGEDRLILGTMMAQHAPGPDI
gb|AAC32488.1|         IYNNNDRLILAGLG-IVGIKTGSNTPAGGTLSWAAYKTFDGEDRLILGTMMAQHAPGPDI
ref|NP_824958.1|       IYNNND-LLVKQVG-VIGLKTGSSTPAGGNLVWAATKTVNGKVRTIYGAVLNQDAGTG--
ref|NP_628606.1|       NHGNWN-QLVGHNG-VVGIKTGTTTSALGNLVFAAKKEVGGETRTIVGAVVRQPDVGG--
ref|ZP_02061285.1|     QYNVNY---DLGKDNIVGTGSSLPAGANPVFDSKQ--GNIDIL--GVIFGASGKSS--
RAAC03015              VYNVDS---VVGHGTIIGGKTGSTLEAGGCFVFAARKVIGNREVLIIGAVLGQKGPQP--
                       :.         .  ::*   ***:.   *  . :  .     . .      *.:.

emb|CAA04971.1|        NGGDSLVLVQDNSRKVVASVREMLTSANVVKKGEVVGHVDDRFGR-RIPVVTTKSLDLVG
gb|AAC32488.1|         NGGDSLVLVQDNSRKVVASVREMLTSANVVKKGEVVGHVDDRFGR-RIPVVTTKSLDLVG
ref|NP_824958.1|       RVWDSLQLALTNSQKLIDKVQQGLISAPVVKKGQVVGYVDDQLGG-RTPVVATENMTAVG
ref|NP_628606.1|       ---GILDAALDASDELIRAAQDTLKSSTIIKKGSVVGYVDDGLGG-RTPVVASQDVKAVG
ref|ZP_02061285.1|     -----LMTALKDAIILIDTTKTQISTEKLISKNQQIGFIKVSWMKKEIPMLASQDFSTVV
RAAC03015              -----LAEALTAAVAMSQDAQKALRSVQLVSAGQTVGTLSAPWAK-PVSLVATEPVQVIG
                            *     .    :    :  :   ::.   ...  :*  :.         .:::::   :

emb|CAA04971.1|        LSGQKVTLTYGRKGDGALSRTARAGAVVGELTVGNGPDAHRIPLALKEGLTEPSLGTRLT
gb|AAC32488.1|         LSGQKVTLTYGRKGDGALSRTARAGAVVGELTVGNGPDAHRIPLALKEGLTEPSLGTRLT
ref|NP_824958.1|       WPGLKTKISIG-AGDTTVPHEAKAGKVVGELTVGDGS------------------------
ref|NP_628606.1|       WGGLTVKLTFTAD-----------------------------------------------
ref|ZP_02061285.1|     YPGMKI--TYSLYPIKDMKFPIKSNEVIGTLVINYG------------------------
RAAC03015              WGGLPVQQTYRAD-VLDPKKPIAADQVVGQLQIQVGAQTVRVPVAAASSVPAPTLSWRMK
                            *               :
```

FIG. 49B

```
emb|CAA04971.1|      RL
gb|AAC32488.1|       RL
ref|NP_824958.1|     --
ref|NP_628606.1|     --
ref|ZP_02061285.1|   --
RAAC03015            RL
```

FIG. 50A

```
ref|YP_001663198.1|    ----------------------------------------------------------------
ref|YP_001665129.1|    ----------------------------------------------------------------
ref|YP_430213.1|       ----------------------------------------------------------------
ref|YP_001212426.1|    ----------------------------------------------------------------
ref|YP_360920.1|       ----------------------------------------------------------------
RAAC02227              MHVYESRFWRWLGRMTSRLIRLGCAALAAAASLAVYQPAVRAERSTSPPVATESLIPRED ref|YP_001663198.1|    ----------------AESYPSISAKAAIVMDQETGRVLYEKNPHEKLPMASTTKIMTLL
ref|YP_001665129.1|    ----------------AESYPSISAKAAIVMDQETGRVLYEKNPHEKLPMASTTKIMTLL
ref|YP_430213.1|       --------------------PDIQAESYVLMDFRTGQVLMAKNPHERRPQAITTKITTAI
ref|YP_001212426.1|    ----------------ASSGPEIVGEAAVVIDIKNGQVLFEKNPDRRVYPASTTKIMTAV
ref|YP_360920.1|       ------------------PQIIGRAAAVINVNSGKFVYLKNADQKMYPASTTKIMTTL
RAAC02227              VLNVQSGPIPYVVGEDASSWPSIVSQAAVVMDMDTGAVVYAKHSTAPHYPASITKIMTAL
                                        *.*  ..:  :::   .* .:  *:.       *  *** * :

ref|YP_001663198.1|    VALEKGNLNDIVTVSKRAASVGGSSIWLSPGEKIDMESLLYGLMLNSGNDAATAIAEHIG
ref|YP_001665129.1|    VALEKGNLNDIVTVSKRAASVGGSSIWLSPGEKIDMESLLYGLMLNSGNDAATAIAEHIG
ref|YP_430213.1|       LALERGNLNDQVIASKNAAETPESSIYLQEGETLTLEELLYALLLRSANDAAVAIAEHIG
ref|YP_001212426.1|    IALENGRLDAAVAVPGEACNIEGSSIGLQEGEKISLEDLLYALMLNSGNDTAVAIACHVG
ref|YP_360920.1|       IALEKGNLSDRVYIDKEACYVEGSAIWLNPGEQLSLEDLLYSIMLNSANDSAIAVAKYIG
RAAC02227              LALRLGHLTDVLTASTDAVRQPPDKLYMRAGEKATLKDLLYGLLIDSANDAAVEIAERYG
                        :**. *.*   :         *       . :  :      ::.*.:::  *.**:*    :*    * ref|YP_001663198.1|    GSVENFIEIMNQKAREIGAYNTHFVTPSGLDIGIDDHYTTAYDLALITRYAFRYPKFAEI
ref|YP_001665129.1|    GSVENFIEIMNQKAREIGAYNTHFVTPSGLDIGIDDHYTTAYDLALITRYAFRYPKFAEI
ref|YP_430213.1|       GSVENFARMMNAKVQEIGARDTHYVNPHGLTA--PDHYSSAYDLALIGRYAMMNPKFREI
ref|YP_001212426.1|    GSVEAFVSMMNKKAAELGAVNTHFNNPNGLPD--PGHYSTAYDMALISRYAMQNPEFRKI
ref|YP_360920.1|       GDVATFVQEMNDKARELGAKNTHFVNPNGLPN--DDHYTTARDLALIARAAMQNPKFREI
RAAC02227              GSVAHFADMMNAEARALGATHTHFVNPSGLPD--PRHVTTAYDMAVIARAAMQIPEFRTI
                       *.*    *            :.     :  .  . .*  **            *  ::*  *:*:*   *   *:     *:*  * ref|YP_001663198.1|    VSTKEKTIPWEGKEWDRYLRNKNKLLW---IYEGADGVKTGFTNKAGRCLVSSATRDGRR
ref|YP_001665129.1|    VSTKEKTIPWEGREWDRYLRNKNKLLW---IYEGADGVKTGFTNKAGRCLVSSASREGRR
ref|YP_430213.1|       VATRQRIIPWAGKPWPRLLINENRLLWGYYAYPGADGVKNGYTTPAGQVLVASATRDNWR
ref|YP_001212426.1|    VSTRVKTIRRSVPDAQVYLENHNRLLW---LYEGATGVKTGYTVEAGQCLVSSAARQGRE
ref|YP_360920.1|       AATKTKVINR-DPKYLRFLQNHNKLLW---RYEGANGIKTGYTVKARQCLVASAARDGEE
RAAC02227              VDTRS--FDWKGTAWQATLTNLNRMLF---TYPGAIGVKTGFTSVAHETLVVAATRGGTT
                       . *:    .     .    * *  :.*:        * ** *:*.*.:*    * .  ** :*:* .

ref|YP_001663198.1|    FIAVVLNSP---PMWEDSMKILDYAFSKYKPYKVLEKG----------------------
ref|YP_001665129.1|    FIAVVLNSP---PMWEDSMKILDYAFSKYKPYKVLEKG----------------------
ref|YP_430213.1|       LIAVVMKSP---NMYRETSAILDYGFNNFHQVKLMPAGQQVALAGVRGGIAANIPAVTAD
ref|YP_001212426.1|    LLAVVMK-SEGSNIWSDSTSLMDYCFKEFRPVCLVEAGAFVADVPVKFGEPAAVAVQTGS
ref|YP_360920.1|       FIAVVLG-SEGRNVYDDATKLLDYAFNNFKTVKLVSKGQEFGKVEVAGGK----------
RAAC02227              FLAVLMDCPTDAEIRQDATNLLNYAFLHDETQRILPAGYRAGFVLARDGED---PVVTSE
                       ::**::   .  :      :    ::::*  *    . .    ::      * ref|YP_001663198.1|    ----------------------------------------------------------------
ref|YP_001665129.1|    ----------------------------------------------------------------
ref|YP_430213.1|       DVLVVEPKNETWTWQQRVELNPDLNAPV---KKGDRIGR--IIFTSHDQEV-SVDLIAAG
ref|YP_001212426.1|    SFTYNFPADKPLEIKKEVLLEKEFCAPV-RA--GEKLGEMAFYDGE--RELGRVDLV---
ref|YP_360920.1|       ------------------------EPV------KLIAAEDLYDTV---------------
RAAC02227              PVLATVPIGHPLDVIERVR----VSAPLDRAPKGAAAGELDLVDAATGRKLGSVPLVLAA
```

FIG. 50B

```
ref|YP_001663198.1|     ------------------------------------------------------------
ref|YP_001665129.1|     ------------------------------------------------------------
ref|YP_430213.1|        DVAPRP------------------------------------------------------
ref|YP_001212426.1|     ------------------------------------------------------------
ref|YP_360920.1|        ------------------------------------------------------------
RAAC02227               PFEPVPKPIPWPRLAAPAAAVILMAALVLGWRRRRRSRMAPRARVVRVQPWQESWQSARR ref|YP_001663198.1|     ---
ref|YP_001665129.1|     ---
ref|YP_430213.1|        ---
ref|YP_001212426.1|     ---
ref|YP_360920.1|        ---
RAAC02227               GRR
```

FIG. 51

```
ref|NP_622598.1|         ------------------------RTDLALEAREL---YKEREIPGVSIREEGEEGIKI
ref|YP_001665389.1|      -----------------------SIRTDLAVEAREL---YKGREIPGVRVDEKHLEGIKV
ref|YP_001320854.1|      ------------------------RTDLALEVRELYQEEKQQEIPGVKVDQEEDTDVLV
ref|YP_001512768.1|      ------------------------PNTDLAIEARELYSEKTSGEIPGVTMDNEEIEDVLI
ref|YP_001037463.1|      ------------------------------------------------------------
RAAC00872                MVISWNAARRVRLKPCHLPISRSSPRTDLAVEARELA--LREGHIRGVEEEREEHEGVVI ref|NP_622598.1|         TRVKILDERGEKAMGKPVGDYITIEAPGLLERDLDLEERVAKVLANIISELAQLKKDSHV
ref|YP_001665389.1|      TKVKILNEEGEKAMGKPVGDYITIEAPGLIERDLDLEEEVAKVLADIIKEIANLTENTQV
ref|YP_001320854.1|      TRVDVMDQQGAEIMGKKQGMYITLESPGLRKADADLKDHISQVLAKELKALLPERKNLKA
ref|YP_001512768.1|      TRVEVFNETGVSIIGKPIGKYITLESNSLRKADADFKDEMSKLLAKELRRIIPQKDDIKV
ref|YP_001037463.1|      TRVRVTSPTGEAAIGKPMGNYITLEVPRLKENDQELYEETCKALAKELTRVLNLKDDSTI
RAAC00872                TRVRVSTQVAARRLGKRKGTYVTIEAPGMRRRDFDLEDRLTRILADELKRLLPER-AETA
                         *:*  :          :**   *  *:*:*      : . * :: :.   : **. :  :

ref|NP_622598.1|         LVVGLGNWNVTPDALGPRVVSNIVVTRHLKEYAPLQFGDE-----IRSVSAFSPGVLGIT
ref|YP_001665389.1|      LVVGLGNWNVTPDALGPRVVSNIVVTRHLKEYAPQQFGDE-----IRSVSAISPGVLGIT
ref|YP_001320854.1|      LVVGLGNWNVTPDALGPKAVAKIHVTRHLFK-MYQKESDDH----MIEVSAISPGVMGTT
ref|YP_001512768.1|      LVVGLGNWDVTPDALGPKVVSKIFVTRHLFQ-MYNKEGDVD----LSEVSAISPGVMGTT
ref|YP_001037463.1|      LVIGLGNWNVTPDALGPKVVSRLMVTRHLLE--YVPDQVD--E-GVRPVCAVSPGVLGIT
RAAC00872                LVIGLGNEHVTADALGPMVVNRLFVTRHLFSYMPEVLGDGE---GYRSIAALAPGVLGLT
                         :  .*****  .*  .: ***** .              :.*.:***:* * ref|NP_622598.1|         GIETAEILKGVVDRVKPDLVITIDALASRRLERLSTTIQISNTGISPGSGVGNRRLSITS
ref|YP_001665389.1|      GIETAEILKGVVDRIKPDLIITIDALASRRLERLSTTIQISNTGISPGSGIGNRRLSITE
ref|YP_001320854.1|      GLETGEIIKGIVEHSRPDVVVVVDALASRKMERVNATIQISTTGISPGSGVGNKRMALDE
ref|YP_001512768.1|      GLETGEVIKGIVDNSKPDLVIVVDALASRKMERVNATIQISTTGITPGSGVGNKRKALNR
ref|YP_001037463.1|      GIETGEIVRGIVDRVKPDVVIAIDALASRKMERVNTTIQIADTGISPGSGVGNKRMELSR
RAAC00872                GIETSEVVLGVVERIKPDVVLAVDALAARSLERLHRTIQLSDVGIQPGAGVGNHRKAIDK
                         *:**.*:: *:*:.  :**::: .:****:* :**:    ***::  .** **:*:**:*  :

ref|NP_622598.1|         ESLGVPVIAIGVPTVVDAVTIAHDTIEYLVKELSEQTSKESVFYKVLENMNKQEKYSLIE
ref|YP_001665389.1|      QSLGIPVIAIGVPTVVDAVTIANDTIEYLTEELLKHTKEESPFYEVLKNMSQQEKYSLIQ
ref|YP_001320854.1|      ESLGVPVIAVGVPTVVDAATLTNDTIQLVIKAFSKQAQAGSEFYSMLEKLKEEEKYGLIR
ref|YP_001512768.1|      ETLGVPVIAIGVPTVVDAATLTNDTIDKVIDAFSRQAKVGSQFYNMLRELKEEEKYSLIT
ref|YP_001037463.1|      ETLGVPVIAIGVPTVVDAATMANDTIDLVIDNLIREAKEDSHFYNMLKNIDRNEKYQLIQ
RAAC00872                ETLGVPVIAIGVPTVVDAATIASDAIELVFRELGRQVP-GNAANRLLDQLTGQEKWQLVR
                         ::**:****:********.*:: *:*: :      : ...  .   :*  ::  :**: *:

ref|NP_622598.1|         EVLSPYVQNLVVTPKEIDLLIKNIALVISRGINLALQPGLTEKEMNQLLH
ref|YP_001665389.1|      EVLTPYVHNLVVTPKEIDLLVRNIASIISRGINLALQPGLTEREMNQLLH
ref|YP_001320854.1|      EVLEPYNANVMVTPKEIDDIILDLSQIIANGINIALHPGIDLKDVNRYIH
ref|YP_001512768.1|      EVLEPYSANIIVTPKEVDEVIVNLSQIIANGINIAVHPGIDLKDVN----
ref|YP_001037463.1|      EVLQPYVGNLVVTPKEIDDVVDRIAKVIANGLNIALHQGITLNDVN----
RAAC00872                EVLEPIEQNLVVAPKEVDEFMENVAYLIAKSMNVALHPAMTLEDADLVTH
                         *** *    *::*:***:*  .:  ::   :*:...:*:*::   .:   :
```

FIG. 52

```
ref|ZP_02172045.1|         ---------MKKVTVSGKTVEEAVQNGLDRLEVTAEQVDYTVLEEPEKGFLGFLGNKPAL
ref|NP_244931.1|           ---------MTKRRVSGKTVEEAVEQAIIELGTTRERITYTVVEEPKSGLFGILGSKPAV
RAAC00045                  MRRVGGLGEMRKVVATGKTIEEAVMSALVRLGVPRSQAQVRVIREPARGFLGWLSGREAE
ref|YP_001213468.1|        ---------MKAIEKSGKTVEEAVELALKDLGVTRKDVEVEVIEEPSKGIFGILGVKPAR
ref|YP_358877.1|           ---------MREIEVTGKTVEEAVSLGLEQLGVDRSLVEIEILEQPSKILGLFGQKPAK
ref|ZP_01189194.1|         ----------------GKTVEDAVEQALQKLNITRDEAEIKVIDEGSKGIFGLIGGKNAV
                                           ***:*:**  .: *   .      :: :   *::*  :. : * ref|ZP_02172045.1|         VEVRLKPDPLKEALVFLRDTIDKMGITASVEAEER----KEG-MYLTISGAE--IGVLIG
ref|NP_244931.1|           IEVVVKPDPVDRAKAFLEELLQEMDMEVEVTIEKD-----PATVLFNISGEQD-LGTLIG
RAAC00045                  VEVTVIETPLDAAKEFLRTAISKMGLGQAVIVADDVD--EEGHVKLSISADEDALPILIG
ref|YP_001213468.1|        VRVLLREGPLQKAEKFLKSVFEAMNIQVEMSLQEN-----EREVVINLRGPE--MGVLIG
ref|YP_358877.1|           VKLTIKSKVMEKARKFLDDVISAMGVNVGYEVLERDD-----HLLINLYGSD--VGILIG
ref|ZP_01189194.1|         VEVKPKVNPASIALDFLEDVLEKIPVATRVEVIEEKT--DYDQVYLNISGDN--LGIIIG
                           :.:           .  *  **       :. ::       .     :  :.: . :  :**

ref|ZP_02172045.1|         KRGQTLDSLQYLVNLVANRQSDNYMKFYLDAEGYRDRRREALETLAKRLSEKAVRTGREV
ref|NP_244931.1|           KRGQTLDSLQYLVNLVANKEEGEFIRIKLDAENYRARRKEALVQLAERLASKALRTKRPV
RAAC00045                  RRGATLDALQYLVNIVANRDASEKMRFTLDAAGYRDRRLESLRRLADEAADKAVRLGRPV
ref|YP_001213468.1|        RRGETMEALQYLVNLSANKNQEVRKKIIIDIEGYRSRREETLQKLALKLADKAKQRGRNV
ref|YP_358877.1|           YRGETLDALQYITNLAANKNEITPRRIILDAQGYRERRKKTLIRLAEKVAEKVRQKGRPF
ref|ZP_01189194.1|         YRGETLDALQYLTSLVVNRELKKYTRVLLDAEGYRERRKKTLERLANKLARKAIRVGRKV
                            ** *:::***:..:  .*::       :. :*  .**  ** ::*  **  .: *. :   * .

ref|ZP_02172045.1|         KLEPMNAHERKIIHTALQHIHTVSTYSEGREPHRRIVVVP-------
ref|NP_244931.1|           SLEPMSAHERKIIHTALQELGDVETYSEGQGIGRHVVIAPKR-----
RAAC00045                  ALDPMPRKDRKWVHAHLQSRGDVVTVSEGQEPYRRVKIIPKRHDWIE
ref|YP_001213468.1|        VLEPMNSQERRIIHTALQGRDDIYTFSEGEEPYRKIVISPKK-----
ref|YP_358877.1|           ALEPMTPQERRIIHTALQNFEGVYTYSEGEDPNRKVIIAPKR-----
ref|ZP_01189194.1|         VLEPMPPHERRIIHMLKDSEQVYTYSEGQEPYRRVLIAPR-------
                            *:**   ::*: :* *:    : * ***.   *:: : *
```

FIG. 53A

```
dbj|BAB83769.1|         ----EFKLPDIGEGIHEGEIVKWFVKPGDEVNEDDVLCEVQNDKAVVEIPSPVKGKVLEI
ref|YP_146913.1|        ----EFKLPDIGEGIHEGEIVKWFVKPGDEVNEDDVLCEVQNDKAVVEIPSPVKGKVLEI
sp|P11961|ODP2_BACST    ----EFKLPDIGEGIHEGEIVKWFVKPGDEVNEDDVLCEVQNDKAVVEIPSPVKGKVLEI
ref|YP_001125047.1|     ----EFKLPDIGEGIHEGEIVKWFVKPGDEVNEDDVLCEVQNDKAVVEIPSPVKGKVLEI
ref|ZP_01696305.1|      ----EFRLPDIGEGIHEGEIVKWFIKPGDKVSEDDVLCEVQNDKSVVEIPSPVEGTVEDI
RAAC02428               MAVVEFRLPELGEGLHEGRISKWLVQPGDTVQEDDPIAEVENDKSLVELPSPVSGKVKEI
                            ::.*:*.* :::* *.* :.:*:::****.*.*  :* dbj|BAB83769.1|         LVPEGTVATVGQTLITLDAPGYENMTF---------KGQEHEE-VKKEEKAETVS----K
ref|YP_146913.1|        LVPEGTVATVGQTLITLDAPGYENMTF---------KGQEHEE-VKKEEKAETVS----K
sp|P11961|ODP2_BACST    LVPEGTVATVGQTLITLDAPGYENMTF---------KGQEQEE-AKKEEKTETVS----K
ref|YP_001125047.1|     LVPEGTVATVGQTLITLDAPGYENMTF---------KGQEHEEAKKEEKTETVS----K
ref|ZP_01696305.1|      LVEEGSVAVVGDVLVKFDAPGYENLKFKG------DHGQDQKEEAAESAKPEPAKPEPAK
RAAC02428               KVPEGTTCVVGDVLLTFEVEGDAPAEA----------GADEKPTDKSAQKAEADAHQNAK
                         * :...:.*:.:.  *               *  :.:    *.*.       * dbj|BAB83769.1|         KEMVETAAPSAPAAE------AEADPNRRVIAMPSVRKYAREKGVDIRLVQGTKNGRIL
ref|YP_146913.1|        KEMVEIAAPSAPAAE------AEADPNRRVIAMPSVRKYAREKGVDIRLVQGTKNGRIL
sp|P11961|ODP2_BACST    EEKVDAVAPNAPAAE------AEAGPNRRVIAMPSVRKYAREKGVDIRLVQGTKNGRVL
ref|YP_001125047.1|     EESVGATAPAAAEAA-----AEADPNRRVIAMPSVRKYAREKGVDIRLVQGTKNGRIL
ref|ZP_01696305.1|      QETAETAKPAEKEAEH-----GSESADRRVIAMPSVRKYAREKGVDIQLVSGTKNGRVL
RAAC02428               ADEAPAAKPAPDAAKAD----TQESAAHEVLATPAVRKYAREQGVDIRTVKGTGNHGKVT
                        :  ..   *         ...:.*:* *:********:****:   *.***::*::

dbj|BAB83769.1|         KEDIDAFLAGGAKAAAEPTPQAAEEKAAPQAPAAKPVVPEGEFPETRE-KMSGIRRAIAK
ref|YP_146913.1|        KEDIDAFLAGGAKAAAEPTPQAAEEKAAPQAPAAKPVVPEGEFPETRE-KMSGIRRAIAK
sp|P11961|ODP2_BACST    KEDIDAFLAGGAK----PAPAAAEEKAAP--AAAKPATTEGEFPETRE-KMSGIRRAIAK
ref|YP_001125047.1|     KEDIDAFLAGGAKAAAQPAPAAEAEEKAAPQAAATPVVPEGEFPETRE-KMSGIRRAIAK
ref|ZP_01696305.1|      REDIDAYVNGPQQP------EAETGKTEAQAPASQNAIPEGEFPETRE-PMSGIRKVIAK
RAAC02428               KEDIDRAKSGTQAP-----QQAAEDKEQRPAQAQQAPAAYGEEYEERV-PMPMIRQAIAR
                        :****    *           *   :    *     .  **  * *  *.  **:.**:

dbj|BAB83769.1|         AMVHSKHTAPHVTLMDEADVTKLVAHRKKFKAIAAEKGIKLTFLPYVVKALVSALREYPV
ref|YP_146913.1|        AMVHSKHTAPHVTLMDEADVTKLVAHRKKFKAIAAEKGIKLTFLPYVVKALVSALREYPV
sp|P11961|ODP2_BACST    AMVHSKHTAPHVTLMDEADVTKLVAHRKKFKAIAAEKGIKLTFLPYVVKALVSALREYPV
ref|YP_001125047.1|     AMVHSKHTAPHVTLMDEADVTKLVAHRKKFKAIAAEKGIKLTFLPYVVKALVSALREYPT
ref|ZP_01696305.1|      AMVNSKQTAPHVTLMDDVDVTALVAHRKKFKEIAAEKGIKLTFLPYVVKALVSTLREYPV
RAAC02428               AMVKSKYTAPHVTLMDEVDVTELVKLRNEVKPLAQERGIKITYLPFIVKALIAALRTKPQ
                        *: *******:.* ** * :.* :* *:***:*:::::   * dbj|BAB83769.1|         LNTSIDDATEEIIHKHYYNIGIAADTDRGLLVPVIKHADRKPIFALAKEINELAEKAREG
ref|YP_146913.1|        LNTSIDDATEEIIHKHYYNIGIAADTDRGLLVPVIKHADRKPIFALAKEINELAEKAREG
sp|P11961|ODP2_BACST    LNTSIDDETEEIIQKHYYNIGIAADTDRGLLVPVIKHADRKPIFALAQEINELAEKARDG
ref|YP_001125047.1|     LNTSIDDQTEEIIHKHYYNIGIAADTDRGLLVPVIKHADRKPIFALAQEINELAVKARDG
ref|ZP_01696305.1|      LNSSIDDETNEIIHKHYYNIGIAADTERGLLVPVVKHADRKPVFAVSKEINELAEKARDG
RAAC02428               LNASYDEEKQELVIKHYYHIGIATDTERGLLVPVVRHADRKNIWTIAQEINDLATRGRAG
                        **:* *:  .:*:: *****:****:********:::*****.:  :  ***:** :.* *
```

FIG. 53B

```
dbj|BAB83769.1|         KLMPNEMKGASCTITNIGSAGGQWFTPVINHPEVAILGIGRIAEKPIVRDGEIVAAPMLA
ref|YP_146913.1|        KLMPNEMKGASCTITNIGSAGGQWFTPVINHPEVAILGIGRIAEKPIVRDGEIVAAPVLA
sp|P11961|ODP2_BACST    KLTPGEMKGASCTITNIGSAGGQWFTPVINHPEVAILGIGRIAEKPIVRDGEIVAAPMLA
ref|YP_001125047.1|     KLAPNEMKGASCTITNIGSAGGQWFTPVINHPEVAILGIGRIAEKPIVRDGEIVAAPVLA
ref|ZP_01696305.1|      KLAPNEMKGASITISNIGSAGGQWFTPVINRPEVAILGIGRIAEKPVVKNGEIVAAPVLA
RAAC02428               KLKPEEMKGSTISITNIGSAGGLFFTPIINYPEVAILGVGRITEKPIIKNGEFAVGQMMS
                        ** * ****:: :*:******* :***:** *******:***:***:::**:... :::

dbj|BAB83769.1|         LSLSFDHRMIDGATAQKALNHIK-------------
ref|YP_146913.1|        LSLSFDHRMIDGATAQKALNHIK-------------
sp|P11961|ODP2_BACST    LSLSFDHRMIDGATAQKALNHIK-------------
ref|YP_001125047.1|     LSLSFDHRMIDGATAQKALNHVK-------------
ref|ZP_01696305.1|      LSLSFDHRIIDGATAQNALNHIK-------------
RAAC02428               LSLSFDHRVIDGALGQQFINDIKRLLENPRLLLLEV
                        ********:**** .*: :*..:*
```

FIG. 54A

```
ref|ZP_02326222.1|      MEFKLPDVGEGIHEGEIGKWLIKEGEQVNCDQPIVEVMTDKVNAELTAPAKGVVRRLMFA
ref|NP_241081.1|        VEFRLPDVGEGMHEGEIISWFVQEGDHVKQDEPVVEVQTDKMNAELTAPVSGKIKRVYYK
RAAC01659               MEFKLADIGEGIHEGEILRWLVKEGDQVEQDAPLVEVQTDKVTAELPSPVAGVIERIMAR
ref|YP_074242.1|        -EFKLPDVGEGLHEAELLRWLVKEGDTVTEDQPIMEVQTDKATVEITSPVNGRVVKLLGQ
ref|YP_001153408.1|     IEFKFPDLGEGLVEGEIVKWHVKEGDFVKEGDPLVDVMTEKANVTLPAPATGKVVKIFAK
ref|NP_560158.1|        MEFKFPDLGEGLVEGEVIKWHVKEGDPVKEGDPLVDVMTEKATVTLPAPTTGRVVKILVR
                         **::.*:***: *.*:   *  ::**: *   . *:::* *:* .. :.:*. * : ::

ref|ZP_02326222.1|      EGDKVEVGQVLFLL----------DVEEHETLGRTGEAEQAATASPPASPPAGESSFAPV
ref|NP_241081.1|        VGEVAEVGSLLFTID-----------ENLSTFKSETHERTKRENSTEQTRPISNISLTSQ
RAAC01659               EGQVVPVGTVLAVIR----------EAGAKAAAAASGAPGAQASLQEKPAAQAHSEAQP
ref|YP_074242.1|        PGDILKVHSVVVIFDDGSPGALPTAGEVASGVAAAAPAGAQPQASLDVPAPAAQPAPAPA
ref|YP_001153408.1|     EGEIVKVGQVLCVIEEV--------------------AAQEASPKAPAAEASTSQKV-
ref|NP_560158.1|        EGEVVKVGQTLCVIEP----------------------AEGPAAGPQTEAPARP-REVA
                         *:    *   : :                                :       .

ref|ZP_02326222.1|      H-----TP-----------RRVR-------AAPYVRQLARQLKIDIEQVTVSGADGRISE
ref|NP_241081.1|        Q----KAP----------VRKGL-------ATPYVRQLAREMNINLEDVVGTGPGGRVLE
RAAC01659               GRE-AAAPQASGAAHRGGRRRAL-------ATPHVRALARKLGVDIDEIDGTGPVGRVTE
ref|YP_074242.1|        APPAPAPAPAAGAGPADRPRRA-------LATPATRRLARELGVDINQVPGTGPAGRVTS
ref|YP_001153408.1|     ------------------------------VAMPAARRLARELGIDLSKVKGTGPGGVITV
ref|NP_560158.1|        ------------------------------AMPAARRLAKELGIDLSKVKGTGPGGVITV
                                                      *  * .* **::: ::: :.: :*. * :

ref|ZP_02326222.1|      EDLRRYADS-------------------RETAEPVVPALASEAAESDHNGSAGGSKLL
ref|NP_241081.1|        QDLQNDTN-------------------LQKVKTVPSGVANVQESIERTGSS------
RAAC01659               EDVRRFAEGG-----------------REPAVEPARAHAEHAAEAQPTAALR-----
ref|YP_074242.1|        DDVRAFAARR-----------------TAPAPAQAPTQAPTEAAAPTPATPAP----
ref|YP_001153408.1|     EDVRRAAEEL-----------------ARQEKAPPAPPPAAVQPPPAIAQPQA---
ref|NP_560158.1|        EDVKRYAE-----------------ETAKATAPAPAPKAVEK------------
                        :*::  :                   :          .

ref|ZP_02326222.1|      YSPPEAKGNFVNATHMMNSEAPSCAEERIPLRGVRLKIAERMVKAVTVIPHVTQVDELEAD
ref|NP_241081.1|        ---------------------AEKRIPLKGIRKAIAEKMIKSVATIPHVTHVDEIEMD
RAAC01659               ---------------VATPAASGEPVEQVPLRGLRRRIAEHMVQAKRIIPHATHIDEVEMD
ref|YP_074242.1|        ----------------AAPAEADD--ERIPLRGIRKVIAERMVKSKYTAPHVTTVEEVDMT
ref|YP_001153408.1|     ------------PAAAQLPQPVAEEERIPVRGIRRAVAEKMAKSASAIPHAYHFEEVDVT
ref|NP_560158.1|        --------------------AEEEAEVVPVRGIRRAVAEKMSKAKRLIPHAYHLEEVDFT
                                              : :*::*:*  :**:*  ::    **.  ..:*::

ref|ZP_02326222.1|      ALQALRERLQSIAAERQLKLTYLPFFIKALIIALKEFPVFNASLDDERKEILLKRYYHIG
ref|NP_241081.1|        ALKELREQLKHYSEQKGILKTFLPFFIKAIVSALKEFPEYFNASIDEETNEIVLKKDYHIG
RAAC01659               GIEALRERLRPYAEARGVKLTSLAFFVKAVAIALKEFPYVNASVDEAQENVLLRRYYHIG
ref|YP_074242.1|        ELMAFRAQAKELAARKGIKLSFMPFIIKAVVAALREFPYLNASIDDEAQEIVLHKRYHIG
ref|YP_001153408.1|     ELVSLRERLRQEAERLGVKLTYLPFVAKAVAVALREFPMLNSSFDEERGEIVVKRRIHLG
ref|NP_560158.1|        ELIKLRERVKAEAEKRGIRLTLLPFIAKAVAMALREYPMLNSEYDEEKNAIVVKKEVNLG
                        :  :*  : :    :  ::*: :.*. : :*: .*:. *:     :::::  ::* ref|ZP_02326222.1|      IAVDTPDGLIVPVIRHADRKTVFQLAEEISQLTMQAWEGKLTLNQITGGTFTISNVGPIG
ref|NP_241081.1|        IATDTEKGLIVPVIQNADQKSLLELAGEITQLSTQARKGTLNVQQMTGSTFTISNVGPIG
RAAC01659               IAVDTEQGLIVPVVKHADEKSVFEIAREVSDLARRARENRLSLDEVTGSTFTISNAGALG
ref|YP_074242.1|        FALDTDAGLLVPVIKDADRKPVFAIAQEMNDLIARGREGKLAPDEMRGSTFTISNQGSIG
ref|YP_001153408.1|     FAVDTEQGLMVVVVRDADKKSVLEIARELNALAERARAGKASVDEVRGSTFTITNIGAIG
ref|NP_560158.1|        IGVDTEQGLVVVVVKNADKKGLLEMAKEINELAQKAREGKLELQDVRGSTFTISNIGAVG
                        :. **  **:*  *::.**.*  :: :*  *:.  *   .   ::: *.*****:* *.:*
```

FIG. 54B

```
ref|ZP_02326222.1|      SLLATPIINHPEAAILTLHKMEPRMVVRNREGVIRLMMNMALSFDHRIIDGADAIRFTNR
ref|NP_241081.1|        GLHATPIINYPEVAILALHKMEPRNVVREWESVIKLMMNMSLSFDHRLVDGATAVRFTNR
RAAC01659               GLYATPIINYPESAILGIHKMEPRPVVRNNEIVIRNIAHVSLSFDHRIIDGGMAIRFTNR
ref|YP_074242.1|        GLFFTPVINYPEVAILGIGKTQPRPVVRDGEIVIRQMAHLALSFDHRLIDGGMATRFLNR
ref|YP_001153408.1|     GVGGLPIINYPEAAIMALGKIRKIPRVVNGAVVPRDVMNVVVGFDHRVVDGAYVARFTNR
ref|NP_560158.1|        GLGGLSILNYPEAGILAVGQARKKPWAVGDRIEIRDIALLAVSFDHRVVDGAYVARFMNR
                        .:    .::*:**  .*: : : .    .   : :  : :.****::**. . ** **

ref|ZP_02326222.1|      MRQLLENPDLLWAEM-
ref|NP_241081.1|        MKELIENPNLLLMELR
RAAC01659               VRELLEEPDRLWAELR
ref|YP_074242.1|        LAELLSDPTLLMME--
ref|YP_001153408.1|     VKELLEDVGKL-----
ref|NP_560158.1|        VKELLENP--------
                        : :*:.:
```

FIG. 55

```
ref|YP_001127228.1|    ----------------QILDENGN--GDEAKIAAFSDE---WLLDAYRAMRRARVVDERL
ref|YP_149070.1|       FDPDKLP-----VEIVRILDENGN--GDEEKLAAFSDE---WLLRAYREMRRARVIDERL
RAAC01745              MDDVQVYRFTGDTKPDQVLNEAGE---MVGELPENAAD---LALEWYPFMIFCRKFDERA
ref|ZP_02326224.1|     ----------GLQEPYQVLKPDGE-LRHR-IGGEVDEA---LMIKMYENMMHVRMFDRKA
ref|NP_241079.1|       ----------------QVLTPKGE-CQYE-GSEFLDKT---FVLSMYKQMINCREFDEKA
ref|ZP_00539127.1|     ----------------RILDDAGQ-VTDTSKTDLLTKD---LSLALFTHMNRIRTFDRKA
                                       ::*    *:           :     *   * .*.:

ref|YP_001127228.1|    LRMQRQGRIGTYAPFSGQEAAQIGSVLALQKDDWIFPSYREVAVCLTHG-MPLEQFFHYV
ref|YP_149070.1|       LRMQRQGRIGTYAPFSGQEAAQIGSALALHKDDWIFPSYREVAVCLMHG-MPLEQFFHYV
RAAC01745              QLLQRQGRLGTYAPFRGQEAAQIASFAVLRPSDWVFPTYRELAGMMYHG-LEPVHALLKS
ref|ZP_02326224.1|     VNLQRQGRLGTYAPYEGQEAAQVGSAMALSPEDWLFPSYRDHAATITHG-QSLSRVLLYW
ref|NP_241079.1|       LKLQRQGRIGTYASFKGQEACQIGGALALRPTDWLFPTYRDHAAISTHG-QPWHRIFLYW
ref|ZP_00539127.1|     INLQRQGRLGTYAPFEGQEAAQVGSAYALQDKDWVFPTYRDHGATLTFG-ADMVRTFLYW
                       :****:****.:  ****.*:..  .*    **:**:**: .    .*        : :

ref|YP_001127228.1|    RGRLSGKRMPEELNIFPTQIIIAAQTLHAVGCAWATKLKGESHVSVAYFGDGATSEGDFH
ref|YP_149070.1|       QGRLSGKRMPEGVNIFPTQIIIAAQTLHAVGCAWASKLKGEPHVSVAYFGDGATSEGDFH
RAAC01745              RGHPDAGRMPEEIHMAPPQIAIAAQILHAVGAGWACKLQEKDDIAVAYFGDGATSEGDFH
ref|ZP_02326224.1|     MGHMEGSVSPEGLKIMPPCVPIATQLVHAVGTSWAAKLKGEKQASIAYFGEGATSEGDFH
ref|NP_241079.1|       MGHMDGSLSPDDRNILPPAVPIATQMLHAVGTAWADKLKGNPHVSLVFFGDGATSEGDFH
ref|ZP_00539127.1|     NGRVEGCVATDELHIFPPAVPIATQIPHAVGAAWAEKRKGSTQVAVAYFGDGATSEGDFH
                        *:  ..   .:  ::  *. : **:*  **  . *.: :   ::.::******* ref|YP_001127228.1|    EAMNFAAVYNVPVIFFCQNNQYAISVPYAKQTASRTIAQKALAYGMKGVLVDGNDVLAVY
ref|YP_149070.1|       EAMNFAAVYNVPVIFFCQNNQYAISVPYRKQTASRTIAQKALAYGMKGVLVDGNDVLAVY
RAAC01745              EGMNFASVMRLPVVFFCQNNQYAISVPVHRQMASPTIAQKAIAYGMEGLRVDGNDAFAVY
ref|ZP_02326224.1|     EALNFAGVYQTATIFFCQNNGYAISVPFHAQSASRTIAQRAAAYDIVGVRVDGNDIFAVW
ref|NP_241079.1|       EALNFAGVYQTPTIFFCQNNGYAISVPFEKQSASKTIKQRSVAYDMRGERVDGNDIFAVY
ref|ZP_00539127.1|     EGMNFASVFQAPVILFNQNNGYAISVPIQKQMHSETIAQKALAYGMPSVRIDGNDVFAVY
                       *.:***.*   ..::* *** ******   *   * ** *::  **.:  .   :**** :**:

ref|YP_001127228.1|    ETMKQAVEAARRGEGPMLIEALTYRLGPHTTADDPTKYRHPEE-VETW-RRKDPLHRLRV
ref|YP_149070.1|       ETMKQAVEAARRGEGPMLIEALTYRLGPHTTADDPTKYRRPEE-VETW-RAKDPLRRLRL
RAAC01745              QAMCYAVERARRGDGPTLIEAVTFRYGAHTTSDDPRKYRDQERLASEWREQRDPVHRLRL
ref|ZP_02326224.1|     LTVREAIKRGLAGGGPTLVEAVTFRYGAHTTSDDPRKYRDQERLASEWREQRDPVHRLRL
ref|NP_241079.1|       LTVKRAIEQARKGRGPTLIEAVTTRFGSHTTADDAKKYRDQEEIERTWKEMQDPLTRLKA
ref|ZP_00539127.1|     FTMQKALERARSGGGPTLIEAVTWRFGAHTTADDPSKYRDQ----ERSRDRVDPLERLEA
                         ::   *::  .  ***  *:**:*  * *.***:**  :**            **:.**.

ref|YP_001127228.1|    LLERRGLWTDAKEEEFVAKVNEEVTAAYEAAVASESGSIADVFDYVYSEAPKLLA-----
ref|YP_149070.1|       LLERRGLWTEAQEDALVAQVNDEVTAAYEAAIASKSGSIVDAFDCVYSEAPKLLA-----
RAAC01745              WLTRQGLWDDERQAACEEEAEARVRQAVADMEAYPHKSLEEAARHVYAEVPEALALHLAK
ref|ZP_02326224.1|     FLQKRGLWNEKDEERMLERLTGLIEDAVSEAESYPKSRPADMFKHVFADVP--------
ref|NP_241079.1|       YIQAKGWLSEEEEAQMKAKIRETIDEELSMAEQYPKPSISQMFEHVYENQP--------
ref|ZP_00539127.1|     FMKEQGFYDEQEIETIRSRHQEEVEAAVKTMESFPPPDVNDLFDHTFATLPDDL------
                        :  :*    :     :       :     :  .:    * ref|YP_001127228.1|    ------
ref|YP_149070.1|       ------
RAAC01745              RGKEAR
ref|ZP_02326224.1|     ------
ref|NP_241079.1|       ------
ref|ZP_00539127.1|     ------
```

FIG. 56

```
ref|ZP_00539126.1|         ----TLVQAVTDALRTKLTDDETTLVLGEDVGKNGGVFRATDGLQEEFGEDRIIDTPLSE
RAAC01746                  MPKWTMIEAIRDALAIALRDDPRVLVFGEDVGKNGGVFRATDGLQAEFGEARVADTPLAE
ref|YP_149069.1|           MAELTMIEAINEAMRQEMERDPRIIVLGEDVGENGGVFRATDGLLAQFGEGRVFDTPLAE
ref|YP_001127227.1|        MAELTMIEAINEAMRQEMERNSRVIVLGEDVGENGGVFRATDGLLEQFGSGRVFDTPLAE
ref|YP_001125046.1|        MAQMTMVQAITDALRIELKNDPNVLIFGEDVGVNGGVFRATEGLQAEFGEERVFDTPLAE
ref|NP_833691.1|           MAQMTMIQAITDALRVEMKNDPNVLVFGEDVGVNGGVFRATEGLQAEFGEDRVMDTPLAE
                               *:::*: :*:   :  :   :::*** ****:   :**. *: ****:* ref|ZP_00539126.1|         AGIVGTSIGLAVNGFKPIVEIQFLGFIYPAYEQIMTHVSRIRMRTMGRYGVPMVIRAPYG
RAAC01746                  KAIVGTAVGLAMAGMKPVAEIQFLGFAYEAMDQIAAQLARIRFRTQGRFTAPAVIRAPYG
ref|YP_149069.1|           SGIIGTSIGLAINGMRPIAEIQFLGFVYQAMDQLAAQAARIRFRSAGRFSCPIVVRSPYG
ref|YP_001127227.1|        SGIIGTSIGLAINGMRPIAEIQFLGFVYQAMDQLAAQAARIRFRSGGRFSCPIVVRSPYG
ref|YP_001125046.1|        SGIGGLAVGLALQGFRPVPEIQFFGFVYEVMDSISGQMARIRYRTGGRYHMPITVRSPFG
ref|NP_833691.1|           SGIGGLAVGLALEGFRPVPEIQFFGFVYEVMDSISGQLARMRYRSGGRWTAPVTVRSPFG
                            .* *  :*:***: *::*: **:  *  .::   :*:* *: **:   *  .:*:*:* ref|ZP_00539126.1|         AGIRAPEIHSDSTEALFTSMPGLKVVCPSTPYDAKGLLIAAIEDPDPVLFLESMRSYRAF
RAAC01746                  GGVRTPELHSDSLEALFAHTPGLVVVTPSRPYDAKGLLLSAIRSPDPVVFLEPIRLYRAF
ref|YP_149069.1|           GGVRTPELHSDALEALFTHSPGLKVVMPSNPYDAKGLLISAIRDEDPVLFLEPMKLYRAF
ref|YP_001127227.1|        GGVRTPELHSDALEALFTHSPGLKVVMPSNPYDAKGLLISAIRDDDPVLFFEPMKLYRAF
ref|YP_001125046.1|        GGVHTPELHSDSLEGLVAQQPGLKVVIPSTPYDAKGLLISAIRDNDPVIFLEHLKLYRSF
ref|NP_833691.1|           GGVHTPELHADSLEGLVAQQPGLKVVIPSTPYDAKGLLISAIRDNDPVIYLEHMKLYRSF
                           .*:::**:*:*: *.*.: *   ****:... ***:::* :: **:* ref|ZP_00539126.1|         KEPVPSEAYTIEIGKANCITEGQDVTLIAWGAMVQVAQKAATEAATRGISCEVIDLRTLY
RAAC01746                  REEVPEGDYQVPLGRAAVRREGSDVTLVAWGPTVPVAESAAAQVASRGISCEVLDLRTLA
ref|YP_149069.1|           RMEVPEEPYTIPLGQARVVKEGDDVTIIAWGATVPLAAKVAAEMQAKGVNAEVIDLRCLQ
ref|YP_001127227.1|        RMEVPEEPYTIPLGQARIVKEGDDVTILTWGATVPLVAKLADEMRMRGVDAEVIDLRCLQ
ref|YP_001125046.1|        RQEVPEGEYTIPIGKADIKREGKDITIIAYGAMVHESLKAAAELEKEGISAEVVDLRTVQ
ref|NP_833691.1|           RQEVPEGDYTIDLGKADIKREGTDVSVIAYGAMVHAALKAAEELEKEGISLEVVDLRTVQ
                           : **.  *  : :*:*   ** *:::::*. *   . * :  .*:. **:***  :

ref|ZP_00539126.1|         PLDRETISASVQKTGRAVIIHEAQATGGLGNDLLALINDTSFLYLRAPVARVTGFDVPVP
RAAC01746                  PLDRSALKASVEKTGRAVIVHEAVRYAGLGAEIAASIMDLAFYHLRAPIERVAGLDTPYP
ref|YP_149069.1|           PLDIDTIITSVEKTGRVMIVHEAVKTGGFGAEVAALISERALFSLSAPIVRIAGYDTPYP
ref|YP_001127227.1|        PLDIDTIIASVEKTGRVMIVHEAVKTSGFGAEVAALISERALFSLSAPIVRIAGYDTPYP
ref|YP_001125046.1|        PLDIETIIGSVEKTGRAIVVQEAQRQAGIAANVVAEINERAILSLEAPVLRVAAPDTVYP
ref|NP_833691.1|           PLDIETIIASVEKTGRVVVVQEAQKQAGIAANVVAEINDRAILNLEAPVVRVAAADTVFP
                           *  .::  :**.:::::  .*:..  :: * * : ::  * **: *::. *.  * ref|ZP_00539126.1|         LFALEDHYIPTPTRVLEAIQRTVD-
RAAC01746                  PPALEDAWLPSVTRVVEAIERVMED
ref|YP_149069.1|           VPSVEDDWLPNAERIAEGIETLL--
ref|YP_001127227.1|        VPSVEDDWLPNPARIVEGIETLM--
ref|YP_001125046.1|        FAQAESVWLPNFKDVIETAKKVM--
ref|NP_833691.1|           FSQAESVWLPNHKDIVEAVNKVM--
                                *. ::*.  : *   :   :
```

FIG. 57

```
pdb|1W85|A              --------------------------------QFPT--FQILNEEGEVVNEEAMPELSDE
sp|P21873|CDPA_BACST    --------------------------------QFPT--FQILNEEGEVVNEEAMPELSDE
ref|YP_146911.1|        --------------------------------QFPT--FQILNEEGEIVNEEAMPELSDE
ref|YP_001421036.1|     ----------------------------------------QILNAEGEVVNKDAMPDLSDD
ref|NP_243521.1|        --------------------------LEKVEGQFET--FQILNEEGEVVNEAAMPDLSDE
RAAC02426               ----------------------MTMLSQVVARFEIPYVQIVDENGNVVNPDLVPELSDD
                                                         **::  :*::**   :*:***:

pdb|1W85|A              QLKELMRRMVYTRILDQRSISLNRQGRLGFYAPTAGQEASQIASHFALEKEDFILPGYRD
sp|P21873|CDPA_BACST    QLKELMRRMVYTRILDQRSISLNRQGRLGFYAPTAGQEASQIASHFALEKEDFILPGYRD
ref|YP_146911.1|        QLKELMRRMVYTRILDQRSISLNRQGRLGFYAPTAGQEASQIASHFALEKEDFILPGYRD
ref|YP_001421036.1|     QLKELMRRMVYIRILDQRSISLSRQGRLGFYAPTAGQEASQIASHFALEQDDFILPGYRD
ref|NP_243521.1|        QLQELMKRMVYTRIWDQRAISLNRQGRLGFYAPVAGQEASMLGSQFALDKEDWILPGYRD
RAAC02426               DLRELMKRMVFTRIWDQRAIRLSRQGRLGFYAPVSGQEASMIGSEFATKKEDFLLPGYRD
                        :*:*:*:   *:*  *.*******.:***  :.*.**  .::*::****** pdb|1W85|A              VPQIIWHGLPLYQAFLFSRGHFHGNQIPEGVNVLPPQIIIGAQYIQAAGVALGLKMRGKK
sp|P21873|CDPA_BACST    VPQIIWHGLPLYQAFLFSRGHFHGNQIPEGVNVLPPQIIIGAQYIQAAGVALGLKMRGKK
ref|YP_146911.1|        VPQIIWHGLPLYQAFLFSRGHFHGNQIPEGVNVLPPQIIIGAQYIQAAGVALGLKMRGKK
ref|YP_001421036.1|     VPQLIWHGLPLHQAFLFSRGHFKGNQMPEGVNALSPQIIIGAQIIQTAGVALGLKKRGKK
ref|NP_243521.1|        IPQIVFHGLPLYQAFLYSRGHFEGGQIPDGVNVLMPQIIIGAQIVQAAGVAMGLKRKGKQ
RAAC02426               IPQLYFHGYPLHQLFLYSRGHQLGGKVPEGVNCMVPQIIIGAQIVQAAGVGLAFKLRGEK
                        :**: :** **:*  **:****    *.:*:***   ********  :*:***.:.::*  :*::

pdb|1W85|A              AVAITYTGDGGTSQGDFYEGINFAGAFKAPAIFVVQNNRFAISTPVEKQTVAKTLAQKAV
sp|P21873|CDPA_BACST    AVAITYTGDGGTSQGDFYEGINFAGAFKAPAIFVVQNNRFAISTPVEKQTVAKTLAQKAV
ref|YP_146911.1|        AVAITYTGDGGTSQGDFYEGINFAGAFKAPAIFVVQNNRFAISTPVEKQTIAKTLAQKAV
ref|YP_001421036.1|     AVAITYTGDGGASQGDFYEGMNFAGAFKAPAIFVVQNNRYAISTPVEKQSSAQTIAQKAV
ref|NP_243521.1|        NVAITYTGDGGASQGDFYEGMNFAGAYNSPAIFVVQNNRFAISVPVEKQSAAKTIAQKAV
RAAC02426               RVAVTYTGDGGTSQGDFYEGMNFAGAMNLPVVFFVQNNQYAISVPRELQTRAQTLAQKAI
                         **:*******:********:*****  :  *.:.****:.***.*  *  *: *:*:****:

pdb|1W85|A              AAGIPGIQVDGMDPLAVYAAVKAARERAINGEGPTLIETLCFRYGPHTMSGDDPTRYRSK
sp|P21873|CDPA_BACST    AAGIPGIQVDGMDPLAVYAAVKAARERAINGEGPTLIETLCFRYGPHTMSGDDPTRYRSK
ref|YP_146911.1|        AAGIPGIQVDGMDPLAVYAAVKAARERAINGEGPTLIETLCFRYGPHTMSGDDPTRYRSK
ref|YP_001421036.1|     AVGITGVQVDGMDALAVYAATAEARQRAINGEGPTLIETLTFRYGPHTMSGDDPTKYRTK
ref|NP_243521.1|        AAGIEGIQVDGMDVLAVYAATKQARERALAGDGPTLIETLCYRYGPHTMAGDDPTRYRSS
RAAC02426               AAGIPGVQVDGMDVLAVYHVMHEALERARNGEGPTMIEAVTFRYGPHTMSGDDPTRYRTK
                        *.** *:****** ****   .    *  :**  *:**  *:**::*******:*****:**::

pdb|1W85|A              ELENEWAKKDPLVRFRKFLEAKGLWSEEEENNVIEQAKEEIKEAIKKADETPKQKVTDLI
sp|P21873|CDPA_BACST    ELENEWAKKDPLVRFRKFLEAKGLWSEEEENNVIEQAKEEIKEAIKKADETPKQKVTDLI
ref|YP_146911.1|        ELENEWAKKDPLVRFRKFLEAKGLWSEEEENRVIEQAKEDIKEAIKKADETPKQKVTDLI
ref|YP_001421036.1|     EIENEWEQKDPLVRFRKFLENKGLWSEEEENKVIEQAKEEIKQAIKKADGESKPKVTELI
ref|NP_243521.1|        DLDDEWEKKDPLVRFRKFLEGKGLWSEEQENEVVEKAKEDIKAAIKKADAAPKQKVTDLI
RAAC02426               DVQEEWEKKDPLIRFRKYLEEKGLWSQEEEEAYIEEAKETVNNALKEADAAEKMTIPGLI
                        :::: **  :****:****:** *****::*    :*:***  ::  *:*:** *  .::  **

pdb|1W85|A              SIMFEELPFNLKEQYEIYKEKES-
sp|P21873|CDPA_BACST    SIMFEELPFNLKEQYEIYKEKES-
ref|YP_146911.1|        SIMFEELPANLKEQYEIYKEKES-
ref|YP_001421036.1|     ENMFEEPTFNLKEQLEIYKAKES-
ref|NP_243521.1|        GFMFEEAPQHLREQLEEYTAKES-
RAAC02426               DSMFEELTPTLKRQRAEFAGEEAN
                          ****  .  *:.*   : :*:
```

FIG. 58

```
sp|P21874|ODPB_BACST   --------------------------------------------------MAQMTMVQAI
pdb|1W85|B             --------------------------------------------------SAQMTMVQAI
ref|YP_001125046.1|    --------------------------------------------------MAQMTMVQAI
ref|YP_146912.1|       --------------------------------------------------MAQMTMVQAI
ref|ZP_01696304.1|     --------------------------------------------------MAQLTMIQAI
RAAC02427              ----------------------------------------MPARRRTDMAQMTMIQAI
                                                                         ::*** sp|P21874|ODPB_BACST   TDALRIELKNDPNVLIFGEDVGVNGGVFRATEGLQAEFGEDRVFDTPLAESGIGGLAIGL
pdb|1W85|B             TDALRIELKNDPNVLIFGEDVGVNGGVFRATEGLQAEFGEDRVFDTPLAESGIGGLAIGL
ref|YP_001125046.1|    TDALRIELKNDPNVLIFGEDVGVNGGVFRATEGLQAEFGEERVFDTPLAESGIGGLAVGL
ref|YP_146912.1|       TDALRIEMRNDPNVLVFGEDVGVNGGVFRVTEGLQAEFGEERVFDTPLAESGIGGLAIGL
ref|ZP_01696304.1|     TDALRTELKNDENVLVFGEDVGVNGGVFRATEGLQKEFGKDRVIDTPLAESGINGLAIGL
RAAC02427              THALDLELARDERVLVFGEDVGKNGGVFRATEGLQQKYGPNRVFDTPLAESGIIGLANGL
                       *.**  *:  .* .:** **.***  ::*  ::***** * ** sp|P21874|ODPB_BACST   ALQGFRPVPEIQFFGFVYEVMDSICGQMARIRYRTGGRYHMPITIRSPFGGGVHTPELHS
pdb|1W85|B             ALQGFRPVPEIQFFGFVYEVMDSICGQMARIRYRTGGRYHMPITIRSPFGGGVHTPELHS
ref|YP_001125046.1|    ALQGFRPVPEIQFFGFVYEVMDSISGQMARIRYRTGGRYHMPITVRSPFGGGVHTPELHS
ref|YP_146912.1|       ALQGFRPVPEIQFFGFVYEAMDAICGQMARIRYRTGGRYHVPITIRSPFGGGVHTPELHS
ref|ZP_01696304.1|     ALQGFRPVPEIQFFGFVFETMDSIHGQMARYRFRTGGDLKMPITIRAPFGGGVHTPEMHA
RAAC02427              AIQGFRPVPEIQFFGFVFEAFDQIAGQLARTRYRTGGRYTAPVTIRSPFGGGVHTPEMHA
                       *:**************:*.:* * **:**  *:****      *:*:*:***********:*:

sp|P21874|ODPB_BACST   DSLEGLVAQQPGLKVVIPSTPYDAKGLLISAIRDNDPVIFLEHLKLYRSFRQEVPEGEYT
pdb|1W85|B             DSLEGLVAQQPGLKVVIPSTPYDAKGLLISAIRDNDPVIFLEHLKLYRSFRQEVPEGEYT
ref|YP_001125046.1|    DSLEGLVAQQPGLKVVIPSTPYDAKGLLISAIRDNDPVIFLEHLKLYRSFRQEVPEGEYT
ref|YP_146912.1|       DSLEGLVAQQPGLKVVIPSTPYDAKGLLISAIRDNDPVIFLEHLKLYRSFRQEVPEGEYT
ref|ZP_01696304.1|     DSLEGLMAQTPGIKVVIPSTPYDAKGLLISAIRDNDPVVFLEHMKLYRSFREEVPEEEYT
RAAC02427              DSLEGLFVQTPGIKVVIPSTPYDAKGLLLSAIRDPDPVIFLEHMKLYRSFRQEVPEDDYT
                       ******..* **:**************:***** ***:****:******:****  :**

sp|P21874|ODPB_BACST   IPIGKADIKREGKDITIIAYGAMVHESLKAAAELEKE-GISAEVVDLRTVQPLDIETIIG
pdb|1W85|B             IPIGKADIKREGKDITIIAYGAMVHESLKAAAELEKE-GISAEVVDLRTVQPLDIETIIG
ref|YP_001125046.1|    IPIGKADIKREGKDITIIAYGAMVHESLKAAAELEKE-GISAEVVDLRTVQPLDIETIIG
ref|YP_146912.1|       IPIGKADIKREGKDITIIAYGAMVHESLKAAAELEKE-GISAEVVDLRTVQPLDIETIIG
ref|ZP_01696304.1|     IPLGKADVKREGKDISIIAYGAMVHESLKAADELEKE-GYSAEVVDLRTVSPLDVETIVA
RAAC02427              IPLGVANVVREGKHATVIAYGAMVHVALKAAEQWSKEKGLEAEVIDLRTVNPIDIDTIVA
                       **:*  *::  ****.  ::********  :****  :  .** *  .***:*****.*:*::**:.

sp|P21874|ODPB_BACST   SVEKTGRAIVVQEAQRQAGIAANVVAEINERAILSLEAPVLRVAAPDTVYPFAQAESVWL
pdb|1W85|B             SVEKTGRAIVVQEAQRQAGIAANVVAEINERAILSLEAPVLRVAAPDTVYPFAQAESVWL
ref|YP_001125046.1|    SVEKTGRAIVVQEAQRQAGIAANVVAEINERAILSLEAPVLRVAAPDTVYPFAQAESVWL
ref|YP_146912.1|       SVEKTGRAIVVQEAQRQAGIAANVVAEINERAILSLEAPVLRVAAPDTVYPFAQAESVWL
ref|ZP_01696304.1|     SVEKTNRAIVVQEAQRQAGVAANVVAEINERAILSLEAPVLRVTAPDTVYPFSQAEGVWI
RAAC02427              SVKKTNRAIVVQEAQRSAGAAAEIVAQINENAIYYLEAPVLRATPPDTVYPFGMIEDEWL
                       **:**.**********.** **::**:***.**   *******.::*******.  *. *:

sp|P21874|ODPB_BACST   PNFKDVIETAKKVMN-
pdb|1W85|B             PNFKDVIETAKKVMN-
ref|YP_001125046.1|    PNFKDVIETAKKVMN-
ref|YP_146912.1|       PNFKDVIETAKKVIN-
ref|ZP_01696304.1|     PTYKDILEKAKETLT-
RAAC02427              PTPEYVLKTLDKVMSL
                       *.  :  :::.  .:.:.
```

FIG. 59

```
dbj|BAB40585.1|        ------------------EHQFPKIQIVDENGNIVDSKYEDKLTPEFIKELYERLMFVRTF
ref|ZP_01171269.1|     --------------------------MIDENGNEVSG--TSGFDTELALEFYRQLVRIRVF
ref|YP_001126012.1|    ------------------------VLNEEGTVVQPEYRERITKELTMVMYRHLIRTRTF
ref|ZP_02326224.1|     -----EKEEMAMKHDKLHGLQEPYQVLKPDGE-LRHRIGGEVDEALMIKMYENMMHVRMF
ref|NP_241079.1|       --------------------------------------------VLSMYKQMINCREF
RAAC01657              MLAEHDRAERLMEIAKAEGLYEEIHLLKEDGT-LAGAVD-DIPPEVMVAMYRHMVFARAF
                                                                   :*..::    *  * dbj|BAB40585.1|        DRKAISLQRQGRLGTYAPFEGQEAAQVGSALALEKDDWLFPTYRDHAATITFGHKLSTVF
ref|ZP_01171269.1|     DRKAVSLQRQGRIGTYAPFEGQEAAQIGSAMALEESDWMFPTYRDHGAALAFGHSMRNVL
ref|YP_001126012.1|    DRKCVSLQRQGRIGTYVPYEGQEACQVGSALALNDEDWMFPTYRDHGAMMTFGRSLVNTL
ref|ZP_02326224.1|     DRKAVNLQRQGRIGTYAPYEGQEAAQVGSAMALSPEDWLFPSYRDHAATITHGQSLSRVL
ref|NP_241079.1|       DEKALKLQRQGRIGTYASFKGQEACQIGGALALRPTDWLFPTYRDHAAISTHGQPWHRIF
RAAC01657              DRKAIALQRQGRIGTYAPFEGQEAAQVASAMALAPEDFVFPSYRDHAATMVLGQSPANVL
                       *.*.: ******:***..::****.*:..*:**   *::**:****.*   .*:    :

dbj|BAB40585.1|        LYWNGRVEGCVPPEGKKIFPPAVPIATQLPHATGAAMAEKYKGTKNAAIVYFGDGATSEG
ref|ZP_01171269.1|     LFWNGRNEGCIPPEGKNIFPPGIPIATQIPHAAGAAYAEKRKGTKKAAIVYFGDGATSEG
ref|YP_001126012.1|    LYWKGRTEGCVPPEGKKIVPPSVPIATQLPHAAGAACABKWKGTKNAVIVYFGDGATSEG
ref|ZP_02326224.1|     LYWMGHMEGSVSPEGLKIMPPCVPIATQLVHAVGTSWAAKLKGEKQASIAYFGEGATSEG
ref|NP_241079.1|       LYWMGHMDGSLSPDDRNILPPAVPIATQMLHAVGTAWADKLKGNPHVSLVFFGDGATSEG
RAAC01657              LYWSGRVEGIRSPEGRHILPPSVPIATHVLHAVGAAWASRYRKESAVSIAYFGDGATSEG
                       *:* *: :* .*:. :*. ::: .*::  *  :    . :.::**** dbj|BAB40585.1|        DFHEGLNFASVFKAPVVFFNQNNSFAISVPIHKQMNSKTIAQKSVAYGIPGIRLDGNDIF
ref|ZP_01171269.1|     DFHEGLNFASIVKAPVVFFNQNNQYAISVPITRQMRSKTIAQKALAYDIPGVRVDGNDVF
ref|YP_001126012.1|    DFHEGLNFASVFNAPVVFFNQNNQYAISVPITRQMRSKTIAQKALAYDIPGVRIDGNDVF
ref|ZP_02326224.1|     DFHEALNFAGVYQTATIFFCQNNGYAISVPFHAQSASRTIAQRAAAYDIVGVRVDGNDIF
ref|NP_241079.1|       DFHEALNFAGVYQTPTIFFCQNNGYAISVPFEKQSASKTIKQRSVAYDMRGERVDGNDIF
RAAC01657              DFHEALNFAGVFHLPVLFFCQNNGYAISVPFSRQSASRTIAQRAIAYDIVGVRVDGNDAF
                       **..: :  ...: * :*** *   ::** *::  **.: *   *:**** * dbj|BAB40585.1|        AVYFYTKEALDRARNGEGPTLIEAVTWRYGAHTTADDPTKYRNQE-ESLERREKYDPILR
ref|ZP_01171269.1|     AVYRETKKALERAREGGGPTLIEAVTWRYGAHTTADDPAKYRDQQ-ESSVLRGKIDPILR
ref|YP_001126012.1|    AVYFQTAEALERARHGGGPTLIEAVTWRYGAHTTSDDPSRYRDQE-ESKKRRETTDPIKR
ref|ZP_02326224.1|     AVWLTVREAIKRGLAGGGPTLVEAVTFRYGAHTTSDDPRKYRDQERLASEWREQRDPVHR
ref|NP_241079.1|       AVYLTVKRAIEQARKGRGPTLIEAVTTRFGSHTTADDAKKYRDQEEIERTWKEMQDPLTR
RAAC01657              AVYRAVKEARSRALHGLGPTLIEAVTFRMGAHTTADDPTRYRDQKAVVEAWQK-RDPIVR
                       **:   .*  .:.  *  **:** * *:*:. :**:*:           :   **: * dbj|BAB40585.1|        VERLMKNKGIWDEKWAASVEEKASQTIEEAVKEMEAFPAPDVNDLFDHVFEKPTW-----
ref|ZP_01171269.1|     MERWLKNKDLYDENWAKRAESEAAAEIDLAIAEMEAYPPADPADIFDHVFAELIWPL---
ref|YP_001126012.1|    VVRLMQREGWWNEQWANQVQEEVNABIEQAVAEMERYPKANASDMFDYVFABPTWTIA--
ref|ZP_02326224.1|     LRLFLQKRGLWNEKDEERMLERLTGLIEDAVSEAESYPKSRPADMFKHVFADVPWSI---
ref|NP_241079.1|       LKAYIQAKGWLSEEEEAQMKAKIRETIDEELSMAEQYPKPSISQMFEHVYENQPWYV---
RAAC01657              LRLYLESQKLWSESDEAKLQDEVKARVEAAVEEALSIAPPDMEMMFDHVYAEEPWHLAAE
                       :    ::   .     .*.                 .      ::    :     ..   :*.:*: .  * dbj|BAB40585.1|        --------------
ref|ZP_01171269.1|     --------------
ref|YP_001126012.1|    --------------
ref|ZP_02326224.1|     --------------
ref|NP_241079.1|       --------------
RAAC01657              REEYRRTREGVSV
```

FIG. 60

```
dbj|BAB40586.1|         ----LTLVQAVTDGLRTMLKEKKEVIVLGEDVGKNGGVFRATDGLQEEFGEDRVIDTPLS
ref|NP_693798.1|        -TKQLTLIQAITDGMRTMLHEREEVVVLGEDVGKNGGVFRATDGLQEEFGEKRVFDTPLS
ref|YP_001126011.1|     -TKSLTLVQAVNDALRIMLKERDDVVLLGEDVGRNGGVFRATDGLLQEFGEERVIDTPLS
ref|ZP_02326223.1|      MSRSLTILQAVTEALDQKLAHDHRVVLLGEDIGVNGGVFRATDGLFVKYGEERVLDTPLA
ref|NP_241080.1|        -SQQQTMLQAINQTLDDLLATNDDVMLLGEDIGINGGVFRATDGLYEKYGKDRVVDTPLA
RAAC01658               MSRMLNLVQAINEALDLKLADDPRVVLLGEDIGKNGGVFRATDGLLEKYGEERVIDTPLA
                            .::**:.: :    *     *::****:* **********   ::*:.**.****:

dbj|BAB40586.1|         EAGIVGVSIGMAINGMLPVAEIQFLGFIYPAYEQIMTHASRIRMRTMSKFHVPLVIRAPY
ref|NP_693798.1|        EAGIIGSSIGMAINGLLPVAEIQFSGFIYPAYEQIMTHATRMRYRTKGVFTVPLVIRAPY
ref|YP_001126011.1|     EAGFTGAAIGMALNGFRPVVEIQFLGFIYPAYEQIMTHAARMRSRTRGHFTVPLVIRAPY
ref|ZP_02326223.1|      ESGIIGSAIGFALNGLLPVIEIQFLAFIYPGFEQLVSHAARMRYRTRGQFSVPIVIRTPY
ref|NP_241080.1|        ESGIIGSAIGLAMNGKRPIVEIQFLAFIYPGFEQLISHAARMRYRTRGQYNVPMVIRTPY
RAAC01658               ESAIIGTSIGMAVNGLIPVPEIQFLAFIFPALDQLFSHVARMRYRSQGQFPVPMTIRTPY
                        *:.: * :**:*:**  *: ****  .**:*.  :*::.:*.:*:*  *: . :  **:.**:**

dbj|BAB40586.1|         GAGVRAPEIHSDSVETLFTHMPGIKVVCPSTPYDAKGLLIAAIEDPDPVLFMESMKLYRS
ref|NP_693798.1|        GAGVRAPEIHSDSMEALFTHMPGIKVVCPSSPYDAKGLLISAIEDPDPVLFLEPLKLYRA
ref|YP_001126011.1|     GAGVRAPEIHSDSTEALFTHMPGVKVVCPSSPYDAKGLLIAAIEDPDPVLFLEPMRNYRA
ref|ZP_02326223.1|      GTGIRGPELHSDSIEAFFVHTPGIKVAVPSNPYDAKGLLISAIEDPDPVIFLEPAQIYRA
ref|NP_241080.1|        GAGIRGPELHSESVEAFFAHTPGLKVVAPSNPYDAKGLLTAATSDPDPVIFLEDTKLYRA
RAAC01658               GAGIHGPELHAESVESFFAHTPGLKVVVPSGPYDAKGLLISAIEDPDPVVFLEPTKLYRA
                        *:*:: .**:*:* *::*.* **:**.  ** ********  :*  .*****:*:*   : **:

dbj|BAB40586.1|         SREDVPEGKYTVEIGKARKVRDGKDVSIFAWGAMVPVATKAAEEMEK-KGVTCDVIDLRT
ref|NP_693798.1|        VRGEVPEEKYEIEIGKGKYLREGDDVTVIAWGAMVPVAMKAAEQ-AAEKGITCEVIDLRT
ref|YP_001126011.1|     FREDVPEGKYTVDIGKGKKLREGEDVTVIAWGAMVPVAMKAAEAAAK-KGIDADVIDLRT
ref|ZP_02326223.1|      FKTKVPEDMYRVPLGKASIVQEGNDVTIISWGAMMRVALTAAQQMERENGWSCEVIDLRS
ref|NP_241080.1|        FKEDVPNTLYEIPLGQAKVVQEGEDVTVIAWGGMVREALQAAKEAEKAHGWSCEIIDLRT
RAAC01658               FREEVPEGLYRVPIGKAKRVREGEDVSVFAWGSMLHTALKVAEAIERERGWTCDVIDLRT
                         . .**:.  *  : :*:.    :::*.**::::**.*:   *       .*  .::****:

dbj|BAB40586.1|         LYPLDKDAIAESVQKTGRVVIVHEAHATGGVSNDVMAVINDTAFLYLKAPIERVTGFDVP
ref|NP_693798.1|        LYPIDRAIIAESVQKTGRCVVVHEAPATGGLGNDIISIVNDTSFLYMKSPIERVTGADVH
ref|YP_001126011.1|     LYPLDKDMIAESVQKTGRTVIVQEAHATGGLANDILAVINDTSFFYQKAPAERVTGFDVP
ref|ZP_02326223.1|      LYPLDRDTIVASVQKTGRALIVHEAHKTAGVGAEIISLINEEALMYLRAPVKRITGFDVP
ref|NP_241080.1|        IAPIDRETIIESVKKTGRAIIIHEAHKTAGLGGEITALINEEALIYLKAPVKRIAGFDIP
RAAC01658               LYPLDRDAIVESVQKTGRAVVVHEAHKTAGLGAEIVSLINEEALLYLRAPIKRIAGFDVP
                        : *:*:  *  **:****  :::**  *.*:. :: :::*:  :::* ::* :*::* *:

dbj|BAB40586.1|         VPFFTLEEHYLPNTGRVVKAIEKVIHF
ref|NP_693798.1|        VPFWALEEHNIPTPARVMDAINQVINF
ref|YP_001126011.1|     VPFFAHEDDYLPTPARVLHAIEKVM--
ref|ZP_02326223.1|      VPQFSLENFYVPTVKRVKDGIADTIRF
ref|NP_241080.1|        VPQFLSENQYLPTIERMFRGIEETVSF
RAAC01658               VPFFALEDEYMPTEARIRAGIEETITF
                        **   :  *:   :*.    *:   .* ...:
```

FIG. 61A

```
ref|YP_001125466.1|    ------------------------------------------------------------
ref|YP_147353.1|       ------------------------------------------------------------
RAAC00484              MCGEGRECLAGTAGGRVLGLPRYLAPARAGARRRAGAVSNHPRRGEGRALAPDQGRPPAL
ref|ZP_01697095.1|     ------------------------------------------------------------
ref|YP_077737.1|       ------------------------------------------------------------
ref|ZP_01886631.1|     ------------------------------------------------------------ ref|YP_001125466.1|    ------------------------------------------------------------
ref|YP_147353.1|       ------------------------------------------------------------
RAAC00484              VPGRRGDVRRADGARSRPHGAPRRSLAHTGLRRGQVAGSRPSRLREGAAGPRRDAICPGV
ref|ZP_01697095.1|     ------------------------------------------------------------
ref|YP_077737.1|       ------------------------------------------------------------
ref|ZP_01886631.1|     ------------------------------------------------------------ ref|YP_001125466.1|    ------------------------------------------------------------
ref|YP_147353.1|       ------------------------------------------------------------
RAAC00484              CGRGGRPRARDLRPDLRGRRRAVGRSRLSVGPPILSAGGLARDEIGHIEPPLRVRLPHNL
ref|ZP_01697095.1|     ------------------------------------------------------------
ref|YP_077737.1|       ------------------------------------------------------------
ref|ZP_01886631.1|     ------------------------------------------------------------ ref|YP_001125466.1|    ------------------------------------------------------------
ref|YP_147353.1|       ------------------------------------------------------------
RAAC00484              VGISPLAHHPLVHRLLDGVEARPLLGPREIRRVQADVVQHAIHVQESADGGELEEDEFVL
ref|ZP_01697095.1|     ------------------------------------------------------------
ref|YP_077737.1|       ------------------------------------------------------------
ref|ZP_01886631.1|     ------------------------------------------------------------ ref|YP_001125466.1|    ------------------------------------------------------------
ref|YP_147353.1|       ------------------------------------------------------------
RAAC00484              VVAALAVRIALKTSDAQDGLRAVKARHEIRSVAKNVELVRKRTPAQDVIAHQAAAVFSPV
ref|ZP_01697095.1|     ------------------------------------------------------------
ref|YP_077737.1|       ------------------------------------------------------------
ref|ZP_01886631.1|     ------------------------------------------------------------ ref|YP_001125466.1|    ------------------------------------------------------------
ref|YP_147353.1|       ------------------------------------------------------------
RAAC00484              LGVGGGDDRVGGSLVHGGGQFGEGRWREPVVAVQGDEVRRSHVRQRRLQRVAKALVFPER
ref|ZP_01697095.1|     ------------------------------------------------------------
ref|YP_077737.1|       ------------------------------------------------------------
ref|ZP_01886631.1|     ------------------------------------------------------------ ref|YP_001125466.1|    ------------------------------------------------------------
ref|YP_147353.1|       ------------------------------------------------------------
RAAC00484              QHAHARVPQVAPRDLARSVRRSVIHDDEIPCRRGLCEHACDGHRQIARPVVHGEHHRHAR
ref|ZP_01697095.1|     ------------------------------------------------------------
ref|YP_077737.1|       ------------------------------------------------------------
ref|ZP_01886631.1|     ------------------------------------------------------------
```

FIG. 61B

```
ref|YP_001125466.1|     ----------------------------------------------------------------
ref|YP_147353.1|        ----------------------------------------------------------------
RAAC00484               LSPGAHGEPLLCAEHDAKIRYNECKSSRKAWESAVIEDKVRLEFMGVQALLLRLPEEVPI
ref|ZP_01697095.1|      ----------------------------------------------------------------
ref|YP_077737.1|        ----------------------------------------------------------------
ref|ZP_01886631.1|      ---------------------------------------------------------------- ref|YP_001125466.1|     -----------------------EGIKEIVPAFSSLTVY--YDPVVAGNYADVCAWLREN
ref|YP_147353.1|        -----------------------EGIEEIVPAFSSLTIY--YDPLVID-YIGIGAWLRKN
RAAC00484               ETGEALDRLLSLRAALLRELEGVDGIEDITIGYRSVAVYARFEDVSPD---DVLARARRA
ref|ZP_01697095.1|      ---------------------------VTVLYDPFKVYAKFG-------EYPYRYVSRY
ref|YP_077737.1|        -----------------------VPAFTSVTVFYQPFEVYRKMESGKAV--DSPYEKVKAL
ref|ZP_01886631.1|      ----------------------------------PTEV---------------------
                                                            . :

ref|YP_001125466.1|     I-GSTGQA---ARHSTR---TIVIPVCYGGEFGPDLADVARFHGMTEDEVVALHSSGRYR
ref|YP_147353.1|        I-RRSEQA---VRRSAR---TVVIPVCYGGEFGPDLPDVARFHGMTEDEVIALHSAGRYR
RAAC00484               IQGSQGSP-VPATRPEA---VVTLPVVYGGSFGPDLDAVAERAGLSPQDVIRLHQEAVYR
ref|ZP_01697095.1|      FTRLLEKAQPAFIPEPR---TVDIPVCYGGEFGPDLENVARINDLTPEEVIRIHASGDYT
ref|YP_077737.1|        LDHHLQELTMEEETDQR---TVEIPVCYGGRFGPDLEEVADINGLTAQEVIDIHTSGEYL
ref|ZP_01886631.1|      --------------------VEIPVIYGGEYGPDLDVVAQHTGLSVAEVIRRHSDVEYL
                                              : :  *  **      .::    :*:    *      * ref|YP_001125466.1|     VYMIGFSPGFAYLGGLSPRLATPRRPVPRTTVPAGSVGIAGGQTGVYPLATPGGWQLIGR
ref|YP_147353.1|        VYMIGFSPGFAYLGGLSPRLATPRRSVPRTKVPAGSVGIAGGQTGVYPLATPGGWQLIGR
RAAC00484               VAMIGFSPGFAYLIGLPEPLRVPRRETPRSRVERGSVGIAGFQTGVYSFATPGGWQIIGR
ref|ZP_01697095.1|      VYMIGFAPGFPYIGGMPEKIAAPRKKTPRLKIPERSVGIAGKQTGIYPIETPGGWQIIGR
ref|YP_077737.1|        VYMIGFAPGFPYLGGMSEKIAAPRRSSPRTSIPAGSVGIAGMQTGVYPLSTPGGWQLIGN
ref|ZP_01886631.1|      VYMIGFTPGFPYLGGMDPALAVPRKDSPRAKIASGAVGIAGGQTGIYPMESPGGWQIIGR
                        * ****:***.*: *:     : .**:  **    :   :***** ***:*.:  :*****:**.

ref|YP_001125466.1|     TPLRLFDPHREKPSLLSAGDIVEFRRITAEEF--------
ref|YP_147353.1|        TPLKLFDPHREKPSLLAAGDIVAFQPIGADEF--------
RAAC00484               TPVALFDVHRPSPSLLSPGDEVRFEAVTEEEYHGRFGAYT
ref|ZP_01697095.1|      TPVKLFRPDRDGPSLLQAGDKIRFRPVSLEEY--------
ref|YP_077737.1|        TPLELFKPYEQPPSLLRAGDIVKFVSVTEEEYH-------
ref|ZP_01886631.1|      TAADLFDRNRNPPALLKAGDRLRFVSITEDNYH-------
                        *.  **     . *:** .**  :  *   :   :::
```

FIG. 62

```
ref|YP_001420062.1|      ---------------MKVVKPGLLTTVQDTGRTGYQKYGVLGSGAMDTISLRIANLLAGNQ
ref|NP_242684.1|         ----------------IFRPGLLTTIQDLGRTGYLKYGVIVSGPMDEYAHRMANLLVGND
ref|NP_886151.1|         ----------------VIKPGMLSTFQDGGRHGYQHQGIPVAGAMDPRAHRLANLLAGNA
ref|YP_147354.1|         ----------------IDVIEAGLFTTVQDGGRFGYRHAGVPAGGAMDAWAYRLANALVGNN
ref|YP_001125467.1|      ----------------VIDGGFFTTVQDGGRIGYRNAGVPVGGVMDAWAYRLANALVGNE
RAAC00483                MAALARTHEPGIARVRVLAPGLFTTVQDGGRPHHRHLGVPLGGALDVLAFRSANRLVGNA
                                         :.  *:::*.** **    :  :  *:   .* :*   :  * ** *.**

ref|YP_001420062.1|      EKEAGLEITLMGPGPSFEFSEPAVIAVTGADFALHINGEPAPLWKPVLIKENSVVSFGPC
ref|NP_242684.1|         EKAALLEMTFIG--PTIQFTSDQLIAMTGGDLSPTIDGHSVPMYRPVFVKKGAVLSFGRC
ref|NP_886151.1|         ADTATLEITVAG--PTLRFEAPACVALGGADLGATLGGLPAPVLRPLVARAGDVLSFARP
ref|YP_147354.1|         GDEAVLEATMAG--PTLRFRVEAVVAVCGGDFPCTLNGQPISLWKPEIVKSGDVLEVGVC
ref|YP_001125467.1|      GDEAVLEATMSG--PTLRFHVETVIAVCGGDFPCTLNGEPMAMWKPVIIRPGDVLKVGVC
RAAC00483                EDCAALEVTGAG--PKLAFEAPAAVALCGADFLAYVDGEPLPVQRPVWLGGGAVLEIRNA
                           . * **  *  *.: *        :*: *.*:    :.*   . .: :*    . *:..

ref|YP_001420062.1|      KMGSRAYLAVAGGFDVPAVMESKSTYVRAGIGGFCGRALQKDDELPLG-----RMTPCSE
ref|NP_242684.1|         KTGCRSYLAIGGGIDVPKVMNSRSTYLRAKIGGFQGRALVEGDELICG-----APPEQTE
ref|NP_886151.1|         GQGARAYLAVHGGYDLPMVMGSQSTYLRSAFGGYHGRALAKGDQVGLR-----RPLADDA
ref|YP_147354.1|         RTGFRAYIAVSGGIDVPPVMGSRSTYVPAQLGGLSGRPLQRGDAL----------PVGV
ref|YP_001125467.1|      QAGWRAYIAVSGGIGVPSVMGSRSTYVPAQLGGLSGRPLQPGDVL----------PIGT
RAAC00483                RRGFRGYLAIRGGFLVEQVLDSRSALPRYGIG----KLLAAGDEMTYQ-----PGPAAPP
                           * *.*:*: **    : *: *:*:        :*       :  * .*:

ref|YP_001420062.1|      SIAYCLSDSFGQHGFSAPDWSVSSRGFLP-LKKNPVIRVLEGAQFHAFTEEAKLRFYQES
ref|NP_242684.1|         RLVKTCQKGI-VHSFATTKWSVVSSQRSR-DGAEKVVRVTVGSHYEQFSEASQHKFFSET
ref|NP_886151.1|         ARLDALAQQLWQLRFY-----LAATLSSP-PRD--VLRILPGPHWEAFDAASRQALLDQA
ref|YP_147354.1|         THGRRVIG-RMRWGLASAARRYIGG-------KTKTVRAVPGPEYDEFTPASRRQFFAAR
ref|YP_001125467.1|      AREHNIRK-PFRWGLSSDAGRYIDG-------KTKTVRAVPGPEYSEFTPESRRQFFAAR
RAAC00483                AGFRAISPRAAVAPFQVGGWLDQIED------EIVILRVVRGEQADWFEKGSRRAFFDRT
                                               :          :*    *.     *    ::   :

ref|YP_001420062.1|      YTVTPQSDRMGYRLKGAPLELREP-LEMVSEAVTFGTVQVPPDGNPIILLADRQTTGGYP
ref|NP_242684.1|         FQVTSKSDRMGYRLKGPTLERLEE-QELISEPISVGTIQVPADGNPIILMADRQTTGGYP
ref|NP_886151.1|         FRIGAQSDRMGYRLEGPRLRLSER-REMLSEATCFGTVQVPADGAPIVLMADRQTTGGYP
ref|YP_147354.1|         YEVTTQSDRIGYRLSGRALALVRE-REMVSEAVVFGTVQVPASGQPIVLMADSQTTGGYP
ref|YP_001125467.1|      YHVTPQSDRIGYRLSGPALVLGRE-REMVSEAVVFGTVQVPTSGQPIVLMADSQTTGGYP
RAAC00483                WQVAPRSDRMGLRLRGEPLRAPSR--QLASEPVVPGSVQVPQDGLPIVLMRECQTTGGYP
                          : :  .:***:*  **  *     *   :: **.   *::***  .*  **:*: : ******* ref|YP_001420062.1|      RMAHIISADLPLVAQTMPGEHITFRAVSLEEAELLLLEKEQQLKE-LKARL----KMEWL
ref|NP_242684.1|         RIAHVIAVDLPIIAQAKPGAAIRFQQASLKEAERL-------------------------
ref|NP_886151.1|         KLAQVATVDLPSLAQAMPGQALRFALIELEQAQRL-------------------------
ref|YP_147354.1|         RIAQVASVDLPILAQARPGDFIQFQPIEPEEAMWLYREQQQRLAR-WIAAI----RRQWE
ref|YP_001125467.1|      RIAQVAAADLPVLAQARPGDRIQFQPVAPEEAVQLYIEQQRRLGC-WIAAI----RRQWG
RAAC00483                KLATVISADLDKLAHLRPGSSVRFVEVSFEEAFRLRRVHDR-LARVWLRFVAERARQAWG
                          ::* : :.**  :*:   **   :  *         ::*   * ref|YP_001420062.1|      -----
ref|NP_242684.1|         -----
ref|NP_886151.1|         -----
ref|YP_147354.1|         GE---
ref|YP_001125467.1|      EK---
RAAC00483                SEGGD
```

FIG. 63

```
ref|ZP_01860800.1|         ------MAQKTVVLDQPAIRRALTRIAHEIIERNKGIQDCVLVGIKTRGIHLAKRLANRI
ref|ZP_01695960.1|         ------MAQKAVVMDEIMIRRALTRIAHEIIERNKGIEDTMLIGIKTRGIYLADRLAERI
ref|YP_147000.1|           --------QKAVVMDEQAIRRALTRIAHEIIERNKGIDGCVLVGIKTRGIYLARRLAERI
ref|YP_001125127.1|        --------QKAVVMDEQAIRRALTRIAHEIIERNKGIDGCVLVGIKTRGIYLARRLAERI
ref|YP_806677.1|           ------MAQSKQVVDEVTMKRALTRISYEIIEQNKGLNDLVLVGIKTRGIYLAHRIAKRL
RAAC00134                  ------MAQKTQIMDEAAMRRSLTRMAHEILERNKGLDDLVLVGIVTRGAILAERLGRKL
                                  *.  ::*:  ::*:***:::**:*:***::. :*:** *** ** *:..::

ref|ZP_01860800.1|         EEIEGAKMPVGEIDITLYRDDLTVKTANEEPEVKGSDLPVDVTDKKVILIDDVLFTGRTV
ref|ZP_01695960.1|         ERIEGRKVEVGELDITLYRDDLSKKTVDGEPEVKGANLPSSITGKKIVLVDDVLYTGRTV
ref|YP_147000.1|           EQIEGASVPVGELDITLYRDDLTVKTDDHEPLVKGTNVPFPVTERNVILVDDVLFTGRTV
ref|YP_001125127.1|        EQIEGTSVPVGELDITLYRDDLTMKTEDHEPLVKGTNVPFPVSEQKVILVDDVLFTGRTV
ref|YP_806677.1|           EQLEGLQVPVGELDIQFYRDDVHKIDHDHQPDVEGAQLPVNITGKHVILVDDVIFTGRTI
RAAC00134                  FEIEGQVVPCHRLDPRPYRDDRDRTVSPEAPAPN-----IDVADRKVILVDDVLYTGRTV
                            .:**   :    .:*   ****      *    :       :: ::::*:***::****:

ref|ZP_01860800.1|         RAALDALMDVGRPSNIQLAVLVDRGHRELPIRADFVGKNIPTSSSEKIVVELTEVDDEDQ
ref|ZP_01695960.1|         RAAMDALMDIGRPSRIQLAVLVDRGHRELPIRPDFIGKNIPTSQSERIVVQLTDVDGRDL
ref|YP_147000.1|           RAAMDAVMDLGRPARIQLAVLVDRGHRELPIRADFVGKNVPTSRSELIVVELSEVDGIDQ
ref|YP_001125127.1|        RAAMDAVMDLGRPARIQLAVLVDRGHRELPIRADFVGKNVPTSSAEVIVVELAEVDGVDQ
ref|YP_806677.1|           RAALDALMDEGRPRKISLAVLVDRGHRELPIRPDFVGKNIPTSLDEQIQVQVSELDGKDG
RAAC00134                  RAALDAMMRAGRARCVQLATLVDRGHRELPIRPDFVGKNVPTARDEQVIVRLAEVDGLDG
                           *::*  .   :..**********.:*::  * : *.:::::*. * ref|ZP_01860800.1|         VTI-----
ref|ZP_01695960.1|         VTI-----
ref|YP_147000.1|           VSIHE---
ref|YP_001125127.1|        VSIHE---
ref|YP_806677.1|           ISI-----
RAAC00134                  VWIAEGRA
                           : *
```

FIG. 64

```
ref|YP_145879.1|           ----------MYTVVGVRFKKAGKIYYFDPGDAVIPVGEFVIVETVRGIEYGKVVIANKQ
ref|YP_001124157.1|        ----------MYTVVGVRFKKAGKIYYFDPGDFVIPAGEFVIVETARGIEYGKVVIANKQ
ref|ZP_01174007.1|         ----------MYDVVGVRFKKAGKIYYFDPGDLSIQKDDFVIVETVRGVEYGKVVIARKQ
ref|YP_001642924.1|        ----------MYDVVGVRFKKAGKVYYFDPNQFDISENEFVIVETVRGIEYGKVVITKKQ
ref|ZP_01697513.1|         ----------MFNVVGIRFKKAGKVYYFDPGDFPVKKNDAVIVETARGIEYGFVVTNPKV
RAAC00215                  MRPFAGGYNLMVTIVGVRFKPAGKIYYFDPGDLPIEKGADVIVETTRGIECGRVVVGPKQ
                                     *  ::* *:*.:   :   .   *.:*  * **    * ref|YP_145879.1|           VDENDIVLPLKKVIRVANEKDKWVVEENKKAAREAYDICLRKVEEHGLEMKLVDVEYTFD
ref|YP_001124157.1|        VDENDIVLPLKKVIRVANEKDKWVVEENKKAAREAYDICLRKVEEHGLEMKLVDVEYTFD
ref|ZP_01174007.1|         VDENDVVLPLKKVLRIADQKDRMIVEENKEAAHEAYEVCCEKVSTHQLDMKLVDVEYTFD
ref|YP_001642924.1|        VDENDVVLPLKKVIRIANENDRTIVEENRHAAKEAYQVCQQKVGEHNLDMKLVDVEYTFD
ref|ZP_01697513.1|         VGEHDVVLPLKKIIRIADQKDHMTVDENKAAAKEAYGICMKKIAEHQLEMKLVDVEYTFD
RAAC00215                  VAEDDVVLPLKEVMRIATEADRAVVEENRRRAKQAMGVFREKVAKHGLEMKLVDAEYTFD
                           * *.*:*****:::*:*  :  *:  *:**:   *::*   :  .*:   * *:***.*** ref|YP_145879.1|           RNKVIFYFTADGRVDFRELVKDLASIFRTRIELRQIGVRDEAKMLGGIGPCGRMLCCSTF
ref|YP_001124157.1|        RNKVIFYFTADGRVDFRELVKDLASIFRTRIELRQIGVRDEAKMLGGIGPCGRMLCCSTF
ref|ZP_01174007.1|         RNKVIFYFTADGRVDFRELVKDLAAIFRTRIELRQIGVRDEAKMLGGIGPCGRMLCCSTF
ref|YP_001642924.1|        RNKIIFYFTADGRIDFRELVKDLAAIFRTRIELRQIGVRDEAKMLGGIGPCGRMLCCSTF
ref|ZP_01697513.1|         RNKIIFYFTADGRVDFRELVKDLASIFRTRIELRQIGVRDEAKMLGGIGPCGRMLCCSTF
RAAC00215                  RNKLIFYFTADGRVDFRELVKDLASVFRVRIELRQIGVRDEAKILGGIGPCGRLLCCSTW
                           ***:*********:*********** :** .*************:********:****:

ref|YP_145879.1|           LGDFEPVSIKMAKDQNLSLNPTKISGLCGRLMCCLKYENEEY-------
ref|YP_001124157.1|        LGDFEPVSIKMAKDQNLSLNPTKISGLCGRLMCCLKYESEEY-------
ref|ZP_01174007.1|         LGDFDPVSIKMAKDQNLSLNPTKISGLCGRLMCCLKYENDEY-------
ref|YP_001642924.1|        LGDFEPVSIKMAKDQNLSLNPAKISGLCGRLMCCLKYENDEY-------
ref|ZP_01697513.1|         LGDFEPVSIKMAKDQNLSLNPAKISGLCGRLMCCLKYENDEY-------
RAAC00215                  MGEFDPVSIRMAKDQSLSLNPSKISGLCGRLMCCLKFENDAYHDQDAMA
                           :*:*:****:*****.*****:**************:**:.:  *
```

FIG. 65

```
pdb|1M2N|A              ------------------------YLVALTGAGVSAESGIPTFRGKDGLWNRYRPEELAN
pdb|1M2K|A              ------------------------YLVALTGAGVSAESGIPTFRGKDGLWNRYRPEELAN
ref|ZP_02127016.1|      ------------------------VVFTGAGVSAESGIPTFRGAGGLWERYRAEDLAT
ref|YP_359129.1|        ------------------------HAIAFTGAGVSTESGIPDFRGNSGLWEQYPVEKVAS
ref|YP_001540277.1|     ------------------------HAIAFTGAGISTESGIPDFRGPQGLWRRFDP-ALAS
RAAC02164               MLYYCSGKPPAKRVHRHLWTWPKSHLVAITGAGISVESGLPTV---DDMVAGVPLRSLFQ
                                                :.:****:*.***:*  .    .:          :

pdb|1M2N|A              PQAFAKDPEKVWKWY----AWRMEKV----FNAQPNKAHQAFAELERLGVLKCLITQNVD
pdb|1M2K|A              PQAFAKDPEKVWKWY----AWRMEKV----FNAQPNKAHQAFAELERLGVLKCLITQNVD
ref|ZP_02127016.1|      PEAFARDPKLVWEWY----RWRQTLA----YNARPNPAHYAIAQLEEAGLVKAVITQNVD
ref|YP_359129.1|        RRALMENPAFFLNFY----RERFKSY----ANVKPNRAHEALARMEKAGIIKGIVTQNID
ref|YP_001540277.1|     IDYLNTDPKGFWEFY----IERFRVL----NNARPNKAHLALAELEKLGIIKYVITQNID
RAAC02164               PNIWREQPLEAFHAFR--VIAREWQ------RKRPNRAHLALAQAEIP-----IITQNID
                         :*    . :   *            .  :   *:*. *       ::***:* pdb|1M2N|A              GLHERAGSRNVIHLHGSLRVVRCTSCNNSFEVESAP----KIPPLPKCDKCGSLLRPGVV
pdb|1M2K|A              DLHERAGSRNVIHLHGSLRVVRCTSCNNSFEVESAP----KIPPLPKCDKCGSLLRPGVV
ref|ZP_02127016.1|      GLHQRAGSRRVVELHGSLWRARCVQCGAVYKLEKPV----EETP-PRCPRCRGLLRPDVV
ref|YP_359129.1|        GLHQKAGSKNVIEIHGTLKRVRCDRCG-KYYLPEKL----DEEEVPRC-NCGGVIRPDVV
ref|YP_001540277.1|     NLHQSAGSINVIELHGNYTTVYCMRCKTQYPFTLALRKYEEGENPPRCPKCGGILRPNVV
RAAC02164               GLHRAAGSTRVIELHGNLRELRCDACGGIFQSELAWR-----EQLPKCPTCGELLRPGFV
                         .. *  .*:..**.       *   *    :            *:*   *   ::**..* pdb|1M2N|A              WAGEMLPPDVLDAAMREVERADVIIVAGTSAVVQPAASLPLIVKQR---------------
pdb|1M2K|A              WAGEMLPPDVLDRAMREVERADVIIVAGTSAVVQPAASLPLIVKQR---------------
ref|ZP_02127016.1|      WFGEPLPREAWEEAVQLASSADVVLVVGTSGAVYPAAAIPQIAKRRGAAVVEV--------
ref|YP_359129.1|        LFGEALPRREWQIALELAERSDLVLVVGSSLVVTPANQI----------------------
ref|YP_001540277.1|     LFGEPVN--EINRALEIAALSDVALVVGSSLTVYP--------------------------
RAAC02164               LEGEEVR--HIARALDWVTEARGLLVVGTELQMTPVRELYEVARRRNVPIAWVRDHAEDW
                         **  :       *:     . :    :*.*:.  : * pdb|1M2N|A              --------------------
pdb|1M2K|A              --------------------
ref|ZP_02127016.1|      --------------------
ref|YP_359129.1|        --------------------
ref|YP_001540277.1|     --------------------
RAAC02164               VPYLLGQEGGSDSLFCPGEV
```

FIG. 66A

```
ref|YP_173587.1|         ---------GLQQLVGSVKEVRAVAKGIENDMNEQLLTGLTGSARTVVSAALF----RET
ref|NP_240935.1|         ---------GLQRFIQEQEDTQAIVQGLEVNMKEQLVSGLSGSARPAVMAALY----KET
ref|YP_892975.1|         ------KMIGLLEQFYKNEEIQSVINGLEDGLKEQLVSGMATSSRSLLMAALY----KKT
ref|NP_976379.1|         ---------GLLEQFYKNEEIQSVINGLEDGLKEQLVSGMATSSRSLLMAALY----KKT
ref|YP_001373418.1|      ---------GLLEQFYKNKEVQSIINGLEEGLKEQLVSGMATSSRSLLMAALY----KKT
RAAC01438                MCWEGDKVKGLVELMAADGALSSLADGMGPRRNDILITGVTGAGRQLVMAALYH--LRNR
                                       **  .  .       ::  .*:     :: *::*:: :.*   :  ***:      ::

ref|YP_173587.1|         GRSQ--LVVTHNLYQAQKIYEDLVELLDEDTVYLYPVNELISAEIAVASPEMKAQRLDLL
ref|NP_240935.1|         RRPQ--LVITYNLYQAQKIFEDLVELVGADHVLLYPVNDLISSEIAIASPEMKAQRIDVL
ref|YP_892975.1|         KKSQ--LIVTHNLYQAQKVHEDLVALLGEKDVWLYPVNELIASELGVASPELKAQRIEVL
ref|NP_976379.1|         KKSQ--LIVTHNLYQAQKVHEDLVALLGEKDVWLYPVNELIASELGVASPELKAQRIEVL
ref|YP_001373418.1|      KQSQ--LVVTHNLYQAQKIYEDLVSLLGEKDVWLYPVNELIASEVGVASPELKAQRIEVL
RAAC01438                RLPESMIVVTHTASHAQTIWEDLKEYLPDARVYLYPERDNALVDYLASSSDVLADRLHVL
                          .:   :::*:.  :.: *    :      * ***  .:    :  :*.:: *:*::.* ref|YP_173587.1|         NALVQDFKGIVVAPLAGIRRLLPPKALWQSSQLHLKTGEDIGDLEEFIKNFVTMGYRRSD
ref|NP_240935.1|         NQLVAGFSGIVVVPLAGMRRLLPSSLWKESQIRLSVGDDIGDLESLIRRLVRNGFTRVD
ref|YP_892975.1|         NRLAAGEHGIIVAPVAGLRRFLPMKELWKQRQIEISLGQEI-DLDTFLHTLHHIGYERKS
ref|NP_976379.1|         NRLAAGEHGIIVAPVAGLRRFLPMKELWKQRQIEISLGQEI-DLDTFLHTLHHIGYERKS
ref|YP_001373418.1|      NRLAAGENGIIVAPVAGLRRFLPMKELWKQKQIEINLGQEV-DLDALLHTLHHIGYERKS
RAAC01438                EALAQEGPVVVVTTLLAAWQPVTKKSHFLHSLVNLAVGESK-PIDDVVAQLVRGGYERVS
                          :  *.      ::*..:.    :  :..   :     :.:   *:.   :: .:    *:  * .

ref|YP_173587.1|         MVSAPGEFSVRGGIVDLYPLTKEHPLRIELFDTEVDSMRYFSLETQRSEGMIDEVTIGPA
ref|NP_240935.1|         MVTTPGECSVRGGIIDLYPLTEEDPIRIELFDTEIDSIRTFTIEDQRSKDSLSEVVIGPA
ref|YP_892975.1|         MVEAPGEFSLRGGILDIYPLTEELPFRIEFFDTEVDSIRLFDVDEQRSQDKKESVRFGPA
ref|NP_976379.1|         MVEAPGEFSLRGGILDIYPLTEELPFRIEFFDTEVDSIRLFDVDEQRSQDKKESVRFGPA
ref|YP_001373418.1|      MVEAPGEFSLRGGILDIYPLTEELPFRIEFFDTEVDSIRLFDVEEQRSQDKRESVKFGPA
RAAC01438                LVESRGQFSVRGGILDVFPMGHDLPYRIEWFDTDIDSIRTFDPATQRSQDKRDRVSFGPA
                         :*  :  *:  *:****:*::*:  .: *  * *::**:*  *     *** ::.     . *  :*** ref|YP_173587.1|         QEVLLHHSHYSHGAKLLEEKYEATLKKVASKQTRDKLQEHIPFEIAQLKQSATFEGMYKY
ref|NP_240935.1|         AEIIMDEEHFIQGASRLEDRLSQTLKKVKKKEVKEKLTEQISFDISELKQKHPFPSMYKY
ref|YP_892975.1|         TEFLFSQEELKSGIKHLEEGLTKTMQKLSDDKLKTTVLETVSHEIEMLKNGQSIEQMFKY
ref|NP_976379.1|         TEFLFSQEELKSGIKHLEEGLTKTMQKLSDDKLKTTVLETVSHEIEMLKNGQSIEQMFKY
ref|YP_001373418.1|      TEFVFSPEELRVGIEHLEGLMKTMQKLSDDKIKTAVLETVSHEIELLKNGQNIEQMFKY
RAAC01438                FDLMLPQPVADKVADELEARLEARLKTVTDAALRDRLEQSISADIRKLREGQPFAGVARY
                          :. ::         . **         :::.:   :      :  :*  *::   :  : :* ref|YP_173587.1|         MSLYYETPQSLLSYMPEDAFVWVDEMNRVKEMAEHLQKEEAEWHTAMLEQGSIVHGTHLS
ref|NP_240935.1|         ISLFYDDTYSLFSYVPSNGVIFVDEMSRVKEMSESLEKEEAEWHTTLIEQGEIVHDVTLA
ref|YP_892975.1|         LSIFYNEPASLIDYLPEDGVVILDEISRIQETASHLESEEAEWYISLLGEGTIIQDLSFS
ref|NP_976379.1|         LSIFYNEPASLIDYLPEDGVVILDEISRIQETASHLETEEAEWYISLLGEGTIIQDLSFS
ref|YP_001373418.1|      LSIFYKEPASLIDYLPENGVVILDEISRVQETASHLETEEAEWYTSLLSEGAIIQDLVFS
RAAC01438                QLLYPEHADTLFDHVPQPAFVCFDETARILERADVLEKEFREWLSGAMMRGEVLSGTVDA
                         ::  . .  :*::::*.  ..: ** *: * :. *:.*  **    : .* ::  .   :

ref|YP_173587.1|         LDALARLQQAPQPVLYTSLFQKQVPSTKPEQIINLSCKSMQNFHGQMDLLTSEVNRWLSN
ref|NP_240935.1|         HSVLEQMKQGVLPIVYLSLFVRHVPSTNPQNIISFQCKSMQNFHGQMPLLQSEVKRWISS
ref|YP_892975.1|         HSFEEFLHHKKRSFVYLTLFLRHIAHTHPQNIVNVTCKTMQDFHGQMQLLKTEIDRWNEG
ref|NP_976379.1|         HSFEEFLHHKKRSFVYLTLFLRHIAHTHPQNIVNVTCKTMQDFHGQMQLLKTEIDRWNEG
ref|YP_001373418.1|      HSFEEFLRHKKRSFVYLTLFLRHIAHTHPQNIVNVTCKTMQDFHGQMQLLKTEIDRWNEG
RAAC01438                IHYEAKFQELNRPKVHFATFAHTRGSQRYQQVLNISARSMQNFHGQMNVLKQELARWEKA
                         ::.     . ::  *   :     .  :::.. .::**:*****  :*   *: **  .
```

FIG. 66B

```
ref|YP_173587.1|      DYTVLFIAGTEDRANRLALNLEDEKIDAHLIEAITDLTPSKV--QIYTGHLHTGFELSEQ
ref|NP_240935.1|      QFATVFIAATRERAKRLNHVLAEEGIEALVVDGEAPLTPGQA--QIMVGALTSGFELTLH
ref|YP_892975.1|      HFTTVVLGTDDERVKKLQHILSDYDIDADIVEGTDILLPGRL--QIAVGDLHAGFEMPMQ
ref|NP_976379.1|      HFTTVVLGTDDERVKKLQHILSDYDIEADIVEGTDILLPGRL--QIAVGDLHAGFEMPMQ
ref|YP_001373418.1|   QFTTVILGTDEERAKKLQHILSDYDIEADIIESTDILLPGRL--QIAVGDLHAGFEMPMQ
RAAC01438             HTQVVFAAATKERADHLARVLDDYRIQADQVE---VFTPGSKVPQIVVANLSSGFELPMH
                       .  : .   :*..:*    *  :  *:*   : :   : *.    ** .. * :***:. :

ref|YP_173587.1|      KLVVVTEEEVFSKRAKRPKRRQKLSNAERIKSYSELAVGDLVVHTNHGVGKYLGVETLEI
ref|NP_240935.1|      KLVVITEEEIFAKKVKRPQRKQKLSNAERIKNYSELKVGDLVVHTNHGIGKYLGIETLEI
ref|YP_892975.1|      KLVVITEKELFHKKVKKSQRKQKLSNAERIKSYSELKVGDYVVHVNHGIGKFLGIETLEI
ref|NP_976379.1|      KLVVITEKELFHKKVKKSQRKQKLSNAERIKSYSELKVGDYVVHVNHGIGKFLGIETLEI
ref|YP_001373418.1|   KLVVITEKELFHKKVKSRRKQKLSNAERIKSYSELKVGDYVVHVNHGIGKFLGIETLEI
RAAC01438             RIAVIVETEVFTAKRKHRQTRAQVSDAERIKSYQELNVGDYVVHVNHGIGRYMGIKTLEV
                      ::.*:.*  *:*    : *:  :  : ::*:*****.*.**  *** ***.***:*:::*:;***:

ref|YP_173587.1|      NGVHKDYLNLRYAGNDKLYVPVEQIDQVQKYVGTEEKDPKIYALGGSDWKKVKKKVQTSV
ref|NP_240935.1|      NGVHKDYLHIRYAGNDKLYVPVEQIDQVQKYVGAEDKDPKLYSLGKSDWKKVKRRVQSSV
ref|YP_892975.1|      NGVHKDYLNIKYQGNDKLYVPIEQIDQVQKYVGSEGKDPKVYKLGGNDWKKVKTKVEKSV
ref|NP_976379.1|      NGVHKDYLNIKYQGNDKLYVPIEQIDQVQKYVGSEGKDPKVYKLGGNDWKKVKTKVEKSV
ref|YP_001373418.1|   NGVHKDYLNIKYQGNDKLYVPIEQIDQVQKYVGSEGKDPKVYKLGGNDWKKVKTKVEKSV
RAAC01438             DGRRNDYLYLSYAGGDSLYVPVDQIDQIQRYIGSGEKEPKLHSLGSSEWQKTKNRVKKSV
                      :*  :***   : * *.*.****::****:*:*:*:   *:**::  **  .:*:*.* :*:.**

ref|YP_173587.1|      EDIADDLIKLYAEREASVGHRFSSDGPEQAEFESSFPYQETEDQLRAIKEIKEDMEKQRP
ref|NP_240935.1|      EDIADDLIKLYAEREASKGFAFAPDGPEQAEFEASFPYQETEDQLRAIQEIKEDMEKERP
ref|YP_892975.1|      QDIADDLIKLYAEREASKGYAYTPDTAEQQEFESSFPYQETEDQLRSIEEIKKDMERGRP
ref|NP_976379.1|      QDIADDLIKLYAEREASKGYAYTPDTAEQQEFESSFPYQETEDQLRSIEEIKKDMERGRP
ref|YP_001373418.1|   QDIADDLIKLYAEREASKGYAFTPDTAEQREFESSFPYQETEDQLRSIEEIKKDMERSRP
RAAC01438             RDIAGDLLKLYAKREATPGHAFSPDTPWQADFENMFPYEETPDQLRAIAEIKRDMEKPRP
                       .***.**:****:***. *. ::.*  . * :** ***:** ****:* *** ***: **

ref|YP_173587.1|      MDRLLCGDVGYGKTEVAIRAAFKAIMDGKQVAILVPTTILAQQHFETISDRFSDFPITVG
ref|NP_240935.1|      MDRLLCGDVGYGKTEVAIRAAFKAIMNGKQVAILVPTTIQERFADYPINIG
ref|YP_892975.1|      MDRLLCGDVGYGKTEVAIRAAFKAIMDEKQVAILVPTTILAQQHYETIRERFQDYPINIG
ref|NP_976379.1|      MDRLLCGDVGYGKTEVAIRAAFKAIMDEKQVAILVPTTILAQQHYETIRERFQDYPINIG
ref|YP_001373418.1|   MDRLLCGDVGYGKTEVAIRAAFKAIMDEKQVAILVPTTILAQQHYETIRERFQDYPINIG
RAAC01438             MDRLLCGDVGYGKTEVAMRAAFKAVMDGKQVAVLVPTTVLAQQHYETFKERFAGFPVKIE
                      ****************.******:*: ****:*****:****:**: :**  .:*::.:

ref|YP_173587.1|      VLSRFRSRKEQTEVLKGLKAGSVDLVVGTHRLLSKDVQFRDLGLLIVDEEQRFGVTHKEK
ref|NP_240935.1|      VLSRFRSRKEQSQTLKGLKAGSVDLVVGTHRLLSKDVQFKDLGLLIVDEEQRFGVTHKEK
ref|YP_892975.1|      LLSRFRTRKQQNETIKGLKDGTVDIVIGTHRILSKDVTYKDLGLLIIDEEQRFGVTHKEK
ref|NP_976379.1|      LLSRFRTRKQQNETIKGLKDGTVDIVIGTHRILSKDVTYKDLGLLIIDEEQRFGVTHKEK
ref|YP_001373418.1|   LLSRFRTRKEQNETIKGLKDGTVDIVIGTHRILSKDVTYKDLGLLIIDEEQRFGVTHKEK
RAAC01438             MLSRFRTRKETQEVLKGLKEGTIDIVIGTHRLLQNSVQFKDLGLLIVDEEQRFGVTHKEK
                      :***::   .. :****  *::*:*:****:*:..*  ::****;********** ref|YP_173587.1|      IKRMKANIDVLTLTATPIPRTLHMSMLGVRDLSVIETPPENRFPVQTYVVEFNPAIVREA
ref|NP_240935.1|      IKQLKANIDVLTLTATPIPRTLHMSMLGVRDLSVIETPPENRFPVQTYVVEYNSPLVREA
ref|YP_892975.1|      IKQLKANVDVLTLTATPIPRTLHMSMLGVRDLSVIETPPENRFPVQTYVVEYNPALMREA
ref|NP_976379.1|      IKQLKANVDVLTLTATPIPRTLHMSMLGVRDLSVIETPPENRFPVQTYVVEYNPALMREA
ref|YP_001373418.1|   IKQLKANIDVLTLTATPIPRTLHMSMLGVRDLSVIETPPENRFPVQTYVVEYNPALIREA
RAAC01438             LKQLRANVDCLTLTATPIPRTLHMSMLGVRDLSIIETPPENRFPVQTYVVEYNEGLVKEA
                      :*::.**:* ************************.****************:*   :::**
```

FIG. 66C

```
ref|YP_173587.1|         IERELSRGGQVYVLYNRVEDIERMTEQISTLVPDARVSYAHGQMNERELESIILDFLEGE
ref|NP_240935.1|         IERELSRGGQVYFLYNRVENIERMANEISMLVPDARVSFAHGQMKESELESIMLAFLEGE
ref|YP_892975.1|         IERELARGGQVYFLYNRVEDIERKADEISMLVPDARVTYAHGKMNESELESVMLSFLEGQ
ref|NP_976379.1|         IERELARGGQVYFLYNRVEDIERKADEISMLVPDARVTYAHGKMNESELESVMLSFLEGQ
ref|YP_001373418.1|      IERELARGGQIYFLYNRVEDIERKADEISMLVPEARVTYAHGKMNESELESVMLSFLEGQ
RAAC01438                IERELARGGQVYFVYNDVQTIHRMAERVQSLVPDARVSVAHGQMAEAELERVMLDFLEGE
                         *****:****:*..:** *: *.* ::.:. ***:***: ***:* * *** ::* ****:

ref|YP_173587.1|         SDVLVTTTIIETGVDIPNVNTLIVCNADKMGLSQLYQIRGRVGRSNRVAYSYFTYQPDKV
ref|NP_240935.1|         SDVLVTTTIIETGVDIPNVNTLIIHGADKMGLSQLYQIRGRVGRSNRVAYAYFTYQRDKV
ref|YP_892975.1|         HDVLVSTTIIETGVDIPNVNTLIVFDADRMGLSQLYQLRGRVGRSNRVAYAYFAYKRDKV
ref|NP_976379.1|         HDVLVSTTIIETGVDIPNVNTLIVFDADRMGLSQLYQLRGRVGRSNRVAYAYFAYKRDKV
ref|YP_001373418.1|      YDVLVSTTIIETGVDIPNVNTLIVYDADRMGLSQLYQLRGRVGRSNRVAYAYFAYKRDKV
RAAC01438                YDVLVTTTIIETGLDIPNVNTLIVYDADKFGLSQLYQLRGRVGRSNRIAYAYFTYQPAKV
                         ****:*******:********: .**::*******:**********:**:**:*: **

ref|YP_173587.1|         LTEVAEKRLQAIKEFTELGSGFKIAMRDLTIRGAGNLLGSQQHGFIDSVGFDLYSQMLKE
ref|NP_240935.1|         LSEVAEKRLQAIKEFTELGSGFKIAMRDLAIRGAGNLLGAQQHGFIESVGFDLYSQMLKE
ref|YP_892975.1|         LSEVAEKRLQAIKEFTELGSGFKIAMRDLSIRGAGNLLGAEQHGFIDSVGFDLYSQMLKD
ref|NP_976379.1|         LSEVAEKRLQAIKEFTELGSGFKIAMRDLSIRGAGNLLGAEQHGFIDSVGFDLYSQMLKD
ref|YP_001373418.1|      LSEVAEKRLQAIKEFTELGSGFKIAMRDLSIRGAGNLLGAEQHGFIDSVGFDLYSQMLKD
RAAC01438                LSEVAEKRLAAIKEFTELGSGFKIAMRDLSIRGAGNLLGAEQHGFINSVGFDMYTELLQQ
                         *:******* *****************:**********::***** :*****.*:::*::

ref|YP_173587.1|         AIEERKGEKPKEPPFKAELNVNIDAYIPERYIPDAKQKIEMYKRFKGVETLEEIADLQDE
ref|NP_240935.1|         AIEKRKGEQPKEEPRNVEIDVQVDAYIPDSYIQDAKQKIEMYKRFRGVETIEEINDLKDE
ref|YP_892975.1|         AIEQRRGTDGVENTVNVEIDLEVDAYLPDAYISDSKQKIMMYKQFRGVSAIEDIEELQEE
ref|NP_976379.1|         AIEQRRGTDGVENTVNVEIDLEVDAYLPDAYISDSKQKIMMYKQFRGVSAIEDIEELQEE
ref|YP_001373418.1|      AIEQRKGKQGIENTIDVEIDLEVDAYLPDSYISDSKQKIMMYKQFRGVSTLEDIEELQEE
RAAC01438                AIRELRGEQ-LEKPVEPTIDVPVEAYIPDTYISDPSQKVAMYKRFRAIQAVSEADDLEDE
                         **.: :* .  *  . . :::  ::**:*: ** *.:.: *:*:..:.:.: :*::* ref|YP_173587.1|         LVDRFGEYPKQVAYLFEMTKIKLIADQEKVEKI-TEGKDAVTILLTEETTNRIHVATLVD
ref|NP_240935.1|         MFDRFGEYPQEVSDLLQLTTIKIIAYQEGVESI-VESKGQWIILLSPETTEGIDGAKLFE
ref|YP_892975.1|         MIDRFGDYPQEVGYLLQIANIKVLAMKEQIELI-KQNKFEVTILFSEQASQNIDGGKLFM
ref|NP_976379.1|         MIDRFGDYPQEVGYLLQIANIKVLAMKEQIELI-KQNKFEVTILFSEQASQNIDGGKLFM
ref|YP_001373418.1|      MIDRFGDYPQEVGYLLQIANIKVLAMKEQIELI-KQTKSEVTFLFSEQASQNIDGGKLFM
RAAC01438                LIDRYGDPPQEVRNLLDVTRLKSLAMQAHADHIATQGAD-TTVRFPNEKHAPVDYPKLLS
                         ::.**:*: *:*  *::::  :*  :*       :   *  :    . .:: :  :. .*.

ref|YP_173587.1|         AAQKIGRDVSIGSQGNQIKLVIKTKQLSDETLLAYIIELLEALIRADKSKK--------
ref|NP_240935.1|         VIHKLDQQVGLGTEGERIKLTLKTKQLGTNQLLEVTETLLASLAD--------------
ref|YP_892975.1|         LGNSFGRMIGLGMEGSQLKIVMKTNGL---------------------------
ref|NP_976379.1|         LGNSFGRMIGLGMEGSQLKIVMKTNGL---------------------------
ref|YP_001373418.1|      LGNK--------------------------------------------------
RAAC01438                MAVKHKAQVTSRPNG-MIFVAFRTKGLAGDEIVRRIIAFLTDYLEMVRQSKKQEEVAGV
```

FIG. 67

```
ref|YP_117520.1|        ----------------VIAASLRRERTRAGLSLSEVAARAGIAKSTLSQLESGSGNPSL
ref|YP_707186.1|        ----------------IGPSLRRERERSGMSLTEVARRAGVAKSTLSQLESGGGNPSV
ref|YP_046943.1|        ----------------IEIVAKGLHRERQKAGLSLAELARRAGIAKSTLSQLEAAQGNPSL
ref|YP_001337847.1|     ----------------ISVIAKSLVRERARTGLSLAEVARRAGIAKSTLSQLESGNGNPSL
ref|YP_001105447.1|     ----------------MLAANLRALRERAGLSLSEVARRSGIAKTLSQLESGAGNPTI
RAAC03184               MILFDISNILIHMNIMKIVSNNLRALRLARGWSISELERRSGVAKGTISQLESGYGNPTV
                                        :. .*    *    * *::*:  *:*:**.*:****:. ***::

ref|YP_117520.1|        ETLWALCVALDMPFSRLLD-----PPRPVVHVIRAGEGPAVAAERS-DYHATLLAAGPSN
ref|YP_707186.1|        ETLWALCVALDVQMSQLLD-----PPRPRVQVIRADEGPELTSDRS-DYRATLVASSPPS
ref|YP_046943.1|        ETLWSLCVALEIPFAKLME-----SNIPQTQVIRFGEGPSVASEIA-HYQAILLANCPTG
ref|YP_001337847.1|     ETLWSLCVALDIPFARLLE-----PQVNKTQVIRRGEGTKVVAEQA-NYQAILLAACPPG
ref|YP_001105447.1|     ETVFSLSNALSVPVSSLLT-----ERLDPEVVLVRSRGLEVLSSNAVDLRMLRRMDLTET
RAAC03184               ATLWSLASALSVPFSDLIQ-----TAKETESVHESP----VLAEPSGTTRFVDRVTM-EG
                        *:::*. **.: .: *:        *              : :. :    :

ref|YP_117520.1|        TRR----------DLFRITAE----------PGQPRESQPHIPGVIEHILLAAGRALV
ref|YP_707186.1|        ARR----------DLYRLAVE----------PGPARESEPHMPGVVEHVILSAGRALV
ref|YP_046943.1|        ARR----------DVYILNTQ----------PGEPRLSHPHPIGSIEHIIIMKGCAKV
ref|YP_001337847.1|     ARR----------DIYLLLTQ----------PGADRISHPHPPGSVEHIIVTQGRARV
ref|YP_001105447.1|     VFE----------LYDQRVR----------PGEVQRSEGHP--GREHVVVTSGVLRV
RAAC03184               MIE----------IYEMVLS----------KDDERVSEAHPLGIMEHILVVQGRMEV
                         .            ::                .  :  *. *     **::: *   * ref|YP_117520.1|        GPTGEPVELAPGDYIAYPGDAPHVFEALEPGTWATLVIEY--------------
ref|YP_707186.1|        GVAGDPVELGPGDYIAYPGDVAHVFEALEAGTRAVL------------------
ref|YP_046943.1|        GLTAEPVVLNEGDYICYPADQEHIFEALDEDTRAIL------------------
ref|YP_001337847.1|     GLTSAPEELGEGDYICYPADQEHVFQALEPDTQALL------------------
ref|YP_001105447.1|     GPPDSPFELEAGDYVCFPARQPHIYETVGGPVVSVLLLEYPA------------
RAAC03184               GPIGQEIALNPGSYTTFPGYVRHVYRSLDEEARAVLWLVYPSIRAGHEGEGATL
                        *         * *.*  :*.    *::.::    . : *
```

FIG. 68

```
ref|NP_391246.1|              ---------- -----SFGEQ LRALREERKL TVNQLATYSG VSAAGISRIE NGKRGVPKPA
ref|NP_391246.1|              ---------- ---------Q LRALREERKL TVNQLATYSG VSAAGISRIE NGKRGVPKPA
ref|YP_001488252.1|           ---------- ----MKFGAY LRALREEKKL SVNQLAMYSE VSAAGISRIE NGKRGIPKPP
ref|NP_244416.1|              ---------- -MEGKQFGSF IRALRKKKGF TVNQLALYSG VSSAQISRIE NGLRGVPKPE
ref|YP_001488252.1|           ---------- ---------- LRALREEKKL SVNQLAMYSE VSAAGISRIE NGKRGIPKPP
RAAC02740                     MYNSDVRGGE SMDTLNFGEY LRSLRLARKL SINQLAEKTG ISAAHISRLE RNVREVPRPD
Clustal Consensus                                   :*:   :  : ::**   :  :*:* ***:*  .. *  :*:* ref|NP_391246.1|              TIKKLAEALK IPYEGLMYKA GYIEEVHEA- ---------R APYETKCKLL EKAEAYDLKN
ref|NP_391246.1|              TIKKLAEALK I--------- ---------- ---------- ---------- ----------
ref|YP_001488252.1|           TIKKLASALK VPYEDMMQAA GYIEE----- ---------- ---------- ----------
ref|NP_244416.1|              TIKKLSEALG HPYEDLMQAA GYIDDNTKT- ---------D LP-----ALT ERDER-----
ref|YP_001488252.1|           TIKKLASALK V--------- ---------- ---------- ---------- ----------
RAAC02740                     TLRKLALGLG VPFDELLRAA GYSEEQYEYN TKVLSRRLQR LRESKGLSLS DVAHIAGISE
Clustal Consensus             *::**: .* ref|NP_391246.1|              LAL------- ---------- ---------- ---------- ---------- ----------
ref|NP_391246.1|              ---------- ---------- ---------- ---------- ---------- ----------
ref|YP_001488252.1|           ---------- ---------- ---------- ---------- ---------- ----------
ref|NP_244416.1|              ---------- ---------- ---------- ---------- ---------- ----------
ref|YP_001488252.1|           ---------- ---------- ---------- ---------- ---------- ----------
RAAC02740                     AYLARLESAE GRLPGVTTLH RLAQVFDVTP AYLVGDTPDP KDNGPLDAWY QPKDLIQWLE
Clustal Consensus ref|NP_391246.1|              ---------- ---------- ---------- -------
ref|NP_391246.1|              ---------- ---------- ---------- -------
ref|YP_001488252.1|           ---------- ---------- ---------- -------
ref|NP_244416.1|              ---------- ---------- ---------- -------
ref|YP_001488252.1|           ---------- ---------- ---------- -------
RAAC02740                     ESEVMFEGQP LTDEDKLKIK QILAVVFMDA KRKNQRP
Clustal Consensus
```

FIG. 69

```
ref|YP_075413.1|          --EEIGRRLK AARLAKGLTL EQVEEETRIR KKYLDALESG RTVLIPGEVY VKGFLRSYGN
ref|YP_001662816.1|       --KELGEFLK SERIKMGLTL EEIQEITKIR IRYLKAIEDG DFSVMPALVY AKGFVKSYAE
ref|YP_001662816.1|       PQQNQSEAST ISEDKTNLPQ ESNVSQLTVK TSIEKVAETS KKIEYKVVPF G----ESYKV
ref|YP_001664674.1|       --KELGEFLK SERIKMGLTL EEIQEITKIR IRYLKAIEDG DFSVMPALVY AKGFVKSYAE
ref|YP_001664674.1|       PQQNQSEAST ISEDKTNLPQ ESNVSQPIVK TSIEKVAETS KKIEYKVVPF G----ESYKV
RAAC02937                 MHEQLGQILR ARRESLGLTV EDIEERTKIR KRYIEALESG QWDVLPGRVY ARGFVRSYAE
Clustal Consensus            ::  ..       . *.  *.  .   ::    .. * .       :        .**

ref|YP_075413.1|          FLGLDGEGLV EEYKALKARP AAEDGAGNGG PAEAPAREPE AAIAASAPRA -SAEPRQPAF
ref|YP_001662816.1|       ALGLDGNELV KKY------- ---------- ---------- ---------- ----------
ref|YP_001662816.1|       EISVPGEKCW FSVKVDGN-- ---------- ---------- ---------- ----------
ref|YP_001664674.1|       ALGLDGNELV KKY------- ---------- ---------- ---------- ----------
ref|YP_001664674.1|       EISVPGEKCW FSVKVDGN-- ---------- ---------- ---------- ----------
RAAC02937                 VLGLDGSELL EKYVDGGDAG SAEP----GV RAESPALTSE NRAADRKPAA RMVEPRSLN-
Clustal Consensus         :.: *.         .

ref|YP_075413.1|          ATPPRRSSRS RPKRRRNGPG PGVYFLRRLM VALILILPLA AAGWWFWGRQ AAAPPPQEPG
ref|YP_001662816.1|       ---------- ---------- ---------- ---------- ---------- ----------
ref|YP_001662816.1|       ---------- ---------- ---------- ---------- ---------- ----------
ref|YP_001664674.1|       ---------- ---------- ---------- ---------- ---------- ----------
ref|YP_001664674.1|       ---------- ---------- ---------- ---------- ---------- ----------
RAAC02937                 ---EMERTRS RAHERHERSR RETYDRPVRS VGSWVGQGLL IVGALVVVGG LYVLLHHHHG
Clustal Consensus ref|YP_075413.1|          QVAQEPGTTA QQPEPEPEPE PEPEPEPEQP PASGQPVPAK PVITVGAPQG DEVD--ITIT
ref|YP_001662816.1|       ---------- ---------- ---------- ---------- ---------- ----------
ref|YP_001662816.1|       --VVYEGLMT KDMSKIFDVK DSITILMGYP PAVKITVDGE ELPTVQTPSP VTI-------
ref|YP_001664674.1|       ---------- ---------- ---------- ---------- ---------- ----------
ref|YP_001664674.1|       --VVYEGLMT KDMSKIFDVK DSITILMGYP PAVKITVDGE ELPTVHTPSP VTI-------
RAAC02937                 QATHRTNTTT SSPQKTQATK P-ATHQTAPP KRTTQPIQKA QTVVVALPYA NGMYTYKVLH
Clustal Consensus ref|YP_075413.1|          ASEVQLEMDF TQGFPWLEVY SGGETLY--- WSKASGPLSF TGKD-FRIRI GFVAGFQLAL
ref|YP_001662816.1|       ---------- ---------- ---------- ---------- ---------- ----------
ref|YP_001662816.1|       ---------- ---------- ---------- ---------- ---------- ----------
ref|YP_001664674.1|       ---------- ---------- ---------- ---------- ---------- ----------
ref|YP_001664674.1|       ---------- ---------- ---------- ---------- ---------- ----------
RAAC02937                 AASLQVVVTV NSGELWFSAT ADGQAVAPNV ILNQGQSKSF SAQNNVTFHL GHVQGVSITV
Clustal Consensus ref|YP_075413.1|          NGEPV----- ---------- -
ref|YP_001662816.1|       ---------- ---------- -
ref|YP_001662816.1|       ---------- ---------- -
ref|YP_001664674.1|       ---------- ---------- -
ref|YP_001664674.1|       ---------- ---------- -
RAAC02937                 DGQPVQLPNI TWAPVVVIER G
Clustal Consensus
```

FIG. 70

```
ref|YP_034761.1|         ----LSKLIKKLLKERALSMRQLGMLTNIDPATISRIMNGKQPPKQKHLQKFAECLQVPP
ref|ZP_00237972.1|       --------------------QLGMLTNIDPATISRIMNGKQPPKQKHLQKFAECLQVPP
ref|YP_893335.1|         --------------------QLGMLTNIDPATISRIMNGKQPPKQKHLQKFAECLQVPP
ref|YP_001373772.1|      --------------------QLGTLTNIDPSTISRIISGKQQAKQKHLQKFAECLKVPP
ref|ZP_02329595.1|       ----LGSTIKALLKERSLSMRKLSALTGIDTATISRIVNGKQAAKPDHLKVFALHLGVPV
RAAC00675                MMGHLEETVKSLLRRRSMSMRQLATATGISVSTISKMIAGKQRVNLDYLRRIADALGVPP
                             :*.   *.*. :*::: *   :  .:*: :*   *  * ** ref|YP_034761.1|         QLLFDE--MYPDSPHINKEKT-----DMYTSLDTIQQTLQSSNLFDFDYTTTRVKQELEN
ref|ZP_00237972.1|       QLLFDE--MYPDSPHINKEKT-----DMYTSLDTIQQTLQSSNLFDFDYTTTRVKQELEN
ref|YP_893335.1|         QLLFDE--MYPDSPHINKEKT-----DMYTSLDTIQQTLQSSNLFDFDYTTTRVKQELEN
ref|YP_001373772.1|      QLLYGA--LHSASSPIKKEKI-----DMYNSIDTIQDTLQSSNLFDYDYTTIRVKQELEN
ref|ZP_02329595.1|       ERLFQA-----AGYDVGTNKTS-TEIGIHTSINRIKEVLQSSNFFDYELTTELVQKELFK
RAAC00675                LTLAEA-----AGLPLIKEPIGPTDGDRQTSMNALLEYLGLGNLN---VLRTEIERELEK
                           *             .  :  .:      . .*::  : *  .*:           :: :** :

ref|YP_034761.1|         YERYAQTTEGEKRIHESFASKLEQIDSAGPFIEQLTDMYQQFCNETIPKEERAVLGGALL
ref|ZP_00237972.1|       YERYAQTTEGEKRIHESFASKLEQIDSAGPFIEQLTDMYQQFCNETIPKEERAVLGGALL
ref|YP_893335.1|         YERYAQTTEGEKRIHESFASKLEQIDSAGPFIEQLTDMYQQFCNETIPKEERAVLGGALL
ref|YP_001373772.1|      YERYAQTTEGQMRIHESFSTKLKQIDSTGPFIEQLTEMYQQFCKDTISETERAVIGSALL
ref|ZP_02329595.1|       YEQYALTEEGQRVIHNEFSSKVEKVNGSGPFIDELRQMHELFCSREVSQDTRAIAGSALL
RAAC00675                YEAYAQTEEGRQFIAEKYLAKRGQIQGIGDFLRDLDDIYDRFSRPDTPEDERRILASGIL
                           * **.  *  .: :*  :::. * *: :*  :::: *.    .: * : ...:* ref|YP_034761.1|         YFILSTDIIPDYLFPIGYLDDAIAVELAKEKL--------------
ref|ZP_00237972.1|       YFILSTDIIPDYLFPIGYLDDAIAVELAKEKL--------------
ref|YP_893335.1|         YFILSTDIIPDYLFPIGYLDDAIAVELAKEKL--------------
ref|YP_001373772.1|      YPVLSTDIIPDYIFPIGYLDDAIAVELVKEKLAHFRK---------
ref|ZP_02329595.1|       YFILSADIIPDYVFPIGYLDDAIAVQMVRNRLS-------------
RAAC00675                YFLLATDAIPDYLFPAGYLDDAIAMQMVRERLARRREMKDQGAEGS
                         **:*::*  ****:**  ********:::.::::*
```

FIG. 71

```
gb|AAB91591.1|           MSPFGQQLRELRRARKLTVNQLAVYSGISSATISKIENGKRGTPKPATIKKLAAVLKVPY
ref|NP_391247.1|         MSPFGQQLRELRRARKLTVNQLAVYSGISSATISKIENGKRGTPKPATIKKLAAVLKVPY
ref|YP_001422657.1|      MNTFGKQLRELRRARKLTVNQLAVYSGVSSATISRIENGHRGIPKPATIRKLADTLKIPY
ref|YP_093160.1|         MTNFGHHLRQLRERKKLTVNQLAMYSGVSSAGISRIENGKRGVPKPATIRKLADALKVPY
ref|NP_391246.1|         MESFGEQLRALREERKLTVNQLATYSGVSAAGISRIENGKRGVPKPATIKKLAEALKIPY
RAAC02292                MSQFGQYLRKLRKERNLTINQLALYSGVSSALISRIENGQRGRPKPDTLKKLASALKVPY
                         *  **. ** **.  ::**:**** ***:*:* **:****:** *** *::*** .**:**

gb|AAB91591.1|           ENLMAAAGHIRAFPEEIREASES---------------------------------------
ref|NP_391247.1|         ENLMAAAGHIQAFPEEIREASE----------------------------------------
ref|YP_001422657.1|      EELMARAGHIKAFQEEIRETSES---------------------------------------
ref|YP_093160.1|         EELMASAGYISAS--TVQEARS----------------------------------------
ref|NP_391246.1|         EGLMYKAGYIEE--------------------------------------------------
RAAC02292                EDLLLHAGVLNEQISRTSESRDLKPVDPSWYKRQVPIPVLGSIRAGTPVEMLALNSSEFV
                         * *:  **  :   ** :

gb|AAB91591.1|           ------------------------------------------------------------
ref|NP_391247.1|         ------------------------------------------------------------
ref|YP_001422657.1|      ------------------------------------------------------------
ref|YP_093160.1|         ------------------------------------------------------------
ref|NP_391246.1|         ------------------------------------------------------------
RAAC02292                LVDSDLLGNHEGFALEVVGDSMIGDYIFPGDLVIVKYTSNFSPQDICVVAINGEEATLKR gb|AAB91591.1|           --------------------------------------------
ref|NP_391247.1|         --------------------------------------------
ref|YP_001422657.1|      --------------------------------------------
ref|YP_093160.1|         --------------------------------------------
ref|NP_391246.1|         --------------------------------------------
RAAC02292                VKCQGDICILTPSNPSMEPMVYNSVDVHVIGVVVEVRRRLRNK
```

FIG. 72

```
ref|NP_845841.1|        ------------------------------MYIPKYFAIQDEKMKYEIMEQNSFATLFSQH
ref|ZP_02260616.1|      ------------------------------MYIPKYFAIQDEKMKYEIMEQNSFATLFSQH
ref|ZP_02256143.1|      ------------------------------MYIPKYFAIQDEEMKYEIMEQNSFATLFSQH
ref|ZP_00235680.1|      ------------------------------MYIPKYFAIQDEEVKYEIIEQNSFAILFSQH
ref|NP_241278.1|        ------------------------------MYIPKAFHVDDVNELITFIRNHSFGIMVSQT
RAAC01655               ------------------------------MYIPRSFELKDAQLIETVLREHSFAVLVTSV
                                                      ****: * :.* :   .::::**. :.:.

ref|NP_845841.1|        NGEPYATHLPLLLNR---ETLTLHGHFARPNEQWKDIGTQQVLAIFQGPHSYISPSWYET
ref|ZP_02260616.1|      NGEPYATHLPLLLNR---ETLTLHGHFARPNEQWKDIGTQQVLAIFQGPHSYISPSWYET
ref|ZP_02256143.1|      NGEPYATHLPLLLNR---ETLTLHGHFARPNEQWKDIGNQQVLAIFQGPHSYISPSWYET
ref|ZP_00235680.1|      NEESYATHLPLLLNR---ETLTLHGHFARPNDQWKDSGNQQVLAIFQGPHSYISPSWYET
ref|NP_241278.1|        EEEPFATHLPFLLDEQKGENGVLISHLARANPHWQGLQDQKVLVVFQGPHAYISPTWYDE
RAAC01655               GEDIMATHVPLVYDP---AEAALFGHLARANPQAKHLHEAQCLAVFQGPHAYVSPAWYGL
                         :  ***:*::  :     .*  .*:**.*  : :     : *.:*****:*:**:**

ref|NP_845841.1|        KNAVPTWNYVAVHVYGELELVEDEQELIDSLQDLVDTYEDPQSTYSLNDVDPNYMEGLSK
ref|ZP_02260616.1|      KNAVPTWNYVAVHVYGELELVEDEQELIDSLQDLVDTYEDPQSTYSLNDVDPNYMEGLSK
ref|ZP_02256143.1|      NNAVPTWNYVAVHVYGELKFVEDEQELIDSLQELVHKYEDPESAYSLNDVDPNYMGGLSK
ref|ZP_00235680.1|      NNAVPTWNYVAVHVYGELEIVEDEQELIDSLQKLVYKYEDPKSTYSLNDVDPNYMTGLSK
ref|NP_241278.1|        PRTVPTWNYVAVHVYGTFRQIQDKHKVKEWIEKTVNVYEQTMNPPWEAVFDEPFMEGLLN
RAAC01655               ADQVPTWNYIAVHVYGRARVIEDEEEAVADLLQRLLLTYDP--QSPLPADRDRPYYRNLMR
                          ******:******   .::*:. : : ::  *:   ..      *   :  .* .

ref|NP_845841.1|        GIVGFKIKISKIEGKAKLSQNHSVARRKLVVEELEKVGSEGSRGIAELMRK---------
ref|ZP_02260616.1|      GIVGFKIKISKIEGKAKLSQNHSVARRKLVVEELEKVGSEGSRGIVELMRK---------
ref|ZP_02256143.1|      GIVGFKVKINKIEGKAKLSQNHSVERRNLVVEKLEKVGSEGSKGIAELMKETK-------
ref|ZP_00235680.1|      GIVGFKIKINKIEGKAKLSQNHSVERRKLVVEKLEKVGSEGSREIAELMR----------
ref|NP_241278.1|        GIVAFEIEVERMEGNWKLNQNHPIERQERVVKKLKSINEPNAQKMAELMEK---------
RAAC01655               GIVAFRIDIARIKAAAKLSQNKPLEVRARVVEALESQDDANSRAVAAWMRRLKLTHLGDD
                        ***.*.:.:  :::   **.**::.:   : **: *:.  .. .:: :. *.

ref|NP_845841.1|        -----------
ref|ZP_02260616.1|      -----------
ref|ZP_02256143.1|      -----------
ref|ZP_00235680.1|      -----------
ref|NP_241278.1|        -----------
RAAC01655               DGNESKPKGAS
```

FIG. 73

```
ref|ZP_02329455.1|      ---NVSEIIEHYLKHILQQSPNGAIEIQRNELADQFQCVPSQINYVISTRFTLEKGYLVE
RAAC00436               MASNISDIIEAYLKRLMEESGLDVIEIQRNELAEQFHCVPSQINYVISTRFTTDHGYIVE
ref|YP_077369.1|        MGKNISDIIEQYLKQILEQNGKEILEIKRSEIADKFQCVPSQINYVINTRFTSERGYIVE
ref|YP_001419762.1|     MGHNISDIIEQYLKQVLDQNGKEILEIKRSEIADKFQCVPSQINYVINTRFTSERGYIVE
ref|YP_001485328.1|     MAQNISDIIEQYLKEVLDQNGREILEIKRNEIADKFQCVPSQINYVINTRFTSERGYIVE
ref|ZP_02171828.1|      ---NISDVIEGYLKQIIEKNDQELIEVKRSELAEQFDCVPSQINYVIRTRFTVEKGYMVQ
                           *:*::** ***.::::.    :*::*.*:*::*.********** **** ::**:*:

ref|ZP_02329455.1|      SKRGGGGYVRIQKIELNSHGSILDYILTTINQSIDQSTSEGLIYRLEEGEFLTAREAKLI
RAAC00436               SKRGGGGYIRIRRVKLDKDHLLWD-VLRSLGDEVSQSASEALIERLHRDGWLTDREAALI
ref|YP_077369.1|        SKRGGGGYIRIIKIKMNDKIDLINNIMNQIYTRLSQAASDDIILRLLENGVITESEAKLM
ref|YP_001419762.1|     SKRGGGGYIRIIKIKMNNEVVLINNIISQIHTHLSQAASDDIILRLLEDGVISEREAKMM
ref|YP_001485328.1|     SKRGGGGYIRIIKVKMNDEVDLLNNIISQIYHRLSQAASDHIIMRLVENNILSEREAKMM
ref|ZP_02171828.1|      SKRGGGGYIRITRVTPDNHLQLYDQLIDLSGDEISQTAAMHLIGRLLEEEAITKREANLM
                        ********:**  ::   :..   : : ::        :.*::: :* **  .  :: ** ::

ref|ZP_02329455.1|      RAAISRDVLQFKLP----------------------
RAAC00436               SAMLRREVLALGLPYRDRLRAKLLASALQALAAHRKP
ref|YP_077369.1|        VSVMDRSVLYIDLP----------------------
ref|YP_001419762.1|     VSVMDRSVLYIDLP----------------------
ref|YP_001485328.1|     ISVMDRSVLHIDLP----------------------
ref|ZP_02171828.1|      ESVMNREVLSIRLPY---------------------
                         : : *.** : **
```

FIG. 74

```
ref|YP_001485324.1|     -DVWGRRIRAYRKLKGYTQEGFAKRLGISVSVLGEIERGNRLPTNQLVGQIADALNITVE
ref|YP_077366.1|        -EIWGRRIRAYRKLKGYTQEGFAKALGISVSVLGEVERGNRMPTESMLRDVANTLNITVE
ref|NP_829977.1|        -EKWGRRIRAFRKLKGYTQEGFAKELGVSVSVLGEVERGNRSPSQDFVVEVAKALNVSIE
ref|YP_001124204.1|     -ERWGRRIRAFRKLKGYTQERLAKELGVSVSILGEIERGNRMPSDSLVEQIAELLNISVE
ref|YP_145925.1|        -ERWGRRIRAFRKLKGYTQERLAKELGISVSILGEIERGNRMPSDSLVGQIAERLNISVE
RAAC01464               MDAFGRRLRAFRKLKHMTQADLARALGVSLATIGGIERGTRQPTAHLVSAIASALSVDVE
                          :*::**     :*: **:*:: :* :***.* *:   ::   :*. *.: :* ref|YP_001485324.1|     EL----------------------------------------
ref|YP_077366.1|        EL----------------------------------------
ref|NP_829977.1|        EL----------------------------------------
ref|YP_001124204.1|     ELTPP-------------------------------------
ref|YP_145925.1|        ELAPP-------------------------------------
RAAC01464               ELCGPTWPGDGWDRGAAEDAADSRAGHGHATVDGPHSPLDQGAMVR
                        **
```

FIG. 75

```
ref|ZP_01440002.1|      -----DRSEEVAA-ILSLIANPARLRILCLLAEGEMQVGALAERVGLSQSALSQHLAKLR
ref|ZP_01419169.1|      --------DDACA-LLKALANPHRLMIVCALIDGEQSVGALAHLLGVRETLASQHLGLLR
RAAC00579               MTHGPDMPEDVCMRCLAVLGEPQRLRILRALAEGEQTAGALSERLGVRQNTLSHHMRQLR
ref|YP_001623237.1|     ---------------LEAIAEPTRRRILDAIRTGERSVGDLVEIVGMHQPGISRHLKVLR
ref|NP_896891.1|        ---------------LKALADPTRLDVIHALAEGERCVCDLTADLGITQSRLSFHLRVLR
ref|ZP_01084741.1|      ---------DQARALLKALGDPVRLRVIEALGGGERCVCDLVTDLGLAQSKLSFHLKVLK
                                 *  :.:* *  ::  :   **  .  *    :*: :    * *:   *:

ref|ZP_01440002.1|      AGGAVETRR---DRQTIYYRL---------------------------------
ref|ZP_01419169.1|      RDGVVAARR---DGQTIYYGLRGGQARALV----ETLS------------------
RAAC00579               EHGLVEVRRHPHDERFTFYRLNGRRLRALS----AVLTDWAARADAECETSGRWSS
ref|YP_001623237.1|     DSGLVEVRQ---DAQRRLYRLRAEPLKELD----QWLEPYRLEWAGRLDA------
ref|NP_896891.1|        DCGLLTDR---HSGRWTYYRLQPDALSALE----DWLAALRQHCSRS---------
ref|ZP_01084741.1|      QAGLLADRQ---EGRWIYYRLRPETLGALQ----AWLTDLGAHCGA----------
                           *  :   *      .  :   * *
```

FIG. 76

```
ref|YP_954024.1|         -----VPAERLAATFKALADPARVKLLSLIAA------------ARDGE--------ACI
ref|ZP_00050136.2|       ---------ELARTFKALADPTRVQLLAIVAAQ------------EGHE--------ACV
ref|YP_001156989.1|      --------ERLAGVLKALADPARLRLLSLIQS------------APEGE--------ACV
ref|YP_001360254.1|      --------------LKALADPARLRLLSLVA-------------AHEGGE--------ACV
RAAC03156                MMVIDVTNEEVLTCLHALADKSRFQILQMMAKG---SIATCCDRIEAYEN------GCCV
ref|YP_591607.1|         --------------LRAVADPTRRRILRMLGEK---------GHCSIGE-----STGLCA
                                       : :*:** :* ::* ::                *         * ref|YP_954024.1|         CDLTAPLGLSQPTVSHHMKLLVDAGLVSRQQRGKW-AYY---RIQRDALDRVAQDVAALT
ref|ZP_00050136.2|       CDLTGPVGLSQPTVSHHLKILVDAGLLTREQRGRW-AYY---SLVPGALARVAG---SLT
ref|YP_001156989.1|      CDLTAPLGLSQPTVSHHLRILTEAGLLEREKRGVW-AYY---RLVPTAIATIAD---LLT
ref|YP_001360254.1|      CDLTEPLGLSQPTVSHHLKVLVEAGLLTRDKRGVW-AYF---AVVPETLNALAA--VLVT
RAAC03156                ADVVAVTGLSQPTVSHHLKVLEKAGLVRRESRGPWTCYFPNSQALEEVVKALTSELMMPA
ref|YP_591607.1|         RDIEAKIKLSQPTVSHHMKILADAGLITGQRRGQW-TWY---RRDETAVRQMTKKFREEL
                          *:      ********:::*  .***:    : ** *   ::         .:  ::

ref|YP_954024.1|         S------------------------
ref|ZP_00050136.2|       -------------------------
ref|YP_001156989.1|      -------------------------
ref|YP_001360254.1|      PA-----------------------
RAAC03156                NVHNHEKGECCPCPDGSPMSPSTCET
ref|YP_591607.1|         -------------------------
```

FIG. 77

```
ref|YP_001309477.1|     ---------------------------MIHITNLKESLPFKALSSDVRMNILEILSQYK
ref|YP_001180339.1|     ---------------------------IDNLKEAKILFEALASDARLEIINLLSKHR
RAAC00603               MSPCRPLSESSGLFYTHVKIMAGVGDRVIHIKELRSGLPLFKALGSEVRVALLELLLEHG
ref|NP_242735.1|        -----------------------------LPVYEALASKVRLAIIQQLTRKS
ref|YP_173905.1|        -----------------------------KQSLPVYEALASRIRLNVLQLLAERS
ref|ZP_00603386.1|      -----------------------------LPVYEALASKTRIKIIQLLSKK-
                                                    :::**.*  *: ::: * .

ref|YP_001309477.1|     QLNMNELSEKLDLTNGAVTMHIKKLEECGLIKTTNLTGKHGLQKICSLHEDKFVIDI--G
ref|YP_001180339.1|     EMNMNEIAQKLGLTNGAVTQHMKKLIAAGIVTISAASGKHGNQKICRLVEDKIIINI--V
RAAC00603               RLNMDEIAKRLGITNGAVTQHVRKLEECGLVVTETAGARHGLQKFCYVNEQKILVEL--A
ref|NP_242735.1|        -MNIRELAEAVGLSSAIMTMHIKKLEKAGIIRTEMVPGKAGIQKLCILDTDHIEINFPPK
ref|YP_173905.1|        -MNIKELAESQQVSSAIMTKHVQKLEKAGLIDTTHVRGKAGVQKMCSLRVRHAQIAFPNK
ref|ZP_00603386.1|      KMNVKDLAKELGVSSAITTMHVKKLEEANIIKTEKVGQ----QKISSLRVDKIDISFPEK
                         :*: ::::   ::..  * *::**  ..::       **:. :    :  : :

ref|YP_001309477.1|     KQDVENS-YHIDLNIGHYSNYDITPTCGIATKDSIIGEVDNPNYFADPERINADILWFTK
ref|YP_001180339.1|     TK-HPQKLYECEIKVGNYSIFEVYPTCGLATKDKLIGEVDDPKYFAHPEHVNCDIIWFTK
RAAC00603               PETKDQDVYEVDIRVGHYVSFEVWPTCGLATAETIIGTFDDPRYFADPQHIDAEIVWLTK
ref|NP_242735.1|        KE-SLKLYHQTILSVGHYTDFLVEPTCGLATAEKIIGEFDEPRYFLDPERVNAKILWFSK
ref|YP_173905.1|        ENGPTRAFHESHVSVGHFTDFYVEPTCGLATPETIVGEFDEPRYFLDPMRVNARILWFYK
ref|ZP_00603386.1|      IFNAFDT-KETSIPIGHYTNYAIEPTCGLATIHDFIGKVDEPRYFMDPRRMDARILWFTS
                            :  :*::    :  :  ****:**  .  :*  .*:*.**  .*  :::.  *:*:  .

ref|YP_001309477.1|     GSIEYRIPNYLKPSEVFSELQISMEISSEAPGVCSIWPSDIHFYLNNVNVGRWTSPGDFG
ref|YP_001180339.1|     GYVEYIIPNFLRQNQKAVEIQISFEISSEAPGVSENWPSDIYFYLNGVELGYWTSPGDFG
RAAC00603               GYLEYWIPNFIRTDRPVEEIQIIAELASEAPSYNNDYPSDIHFSINGVDIGYWTSPGDFG
ref|NP_242735.1|        GYIEYKIPNFLHHSENPKELEISLELSSEAPFTNDNWPSDISFYFNNVKIGIWTSPGDFG
ref|YP_173905.1|        GFVEYKLSNFIHGGETPKELEISMELSSEAPFTNDNWPSDVSFTFNGVSLGYWRSPGDFG
ref|ZP_00603386.1|      GFVEYQAPNFLNTEDTLEMLEVSVEISSEFPFSNDNWPSDITFSLNGVELGTWTSPGDFA
                        *  :**  .*::..         :::   *::** *      .:***.* :*.*.:*  * *****.

ref|YP_001309477.1|     -DSKGILTPSWWNPHWNQYGLLKLLTINSFGTFIDGIKISDVTLEDLELTYKSDILLKLA
ref|YP_001180339.1|     GETKGIFTPDWWFPNWNQYGLLKLLSVSEDGTYIDGFKISNVTIKDIDIESKNEIRFRVA
RAAC00603               -DERGRQNPSWWPPHLNQYGHLKLVRVNHEGTFIDGCKISDVTIEDLQPFQGHAIPLRFS
ref|NP_242735.1|        -DSPGKYTPDWWPKVINQYGLLKFIRITKEGTFIEGAKISDVTIDDVH-IRSKQWSFRVA
ref|YP_173905.1|        -DQKGKYTPAWWPRGINQYGLLKVIRITEAGTFIDGKQLSDVKLADVS-IREKVWTFRVA
ref|ZP_00603386.1|      -DIRGKYTPDWYPDNLNQYGLLKTIRITKHLTNMNGEPLSNITINDI-PKEQDTWHLRIE
                         :    * .* *:        **** ** :  :.    * ::*   *::..: *:           ::.

ref|YP_001309477.1|     VPEETKHVGGLTIFGKNFGNYNQGISVRLVY------
ref|YP_001180339.1|     VPDHAKNIGGVTLFGRNFGNYDQDIKFRIFY------
RAAC00603               VPENARHVGGMTIFGRRFGHYDQDIKVRVIYGRGARD
ref|NP_242735.1|        VPDDAENVGGVTIFGEGFGNYNQDIIFRLYY------
ref|YP_173905.1|        VGEEGVHIGGVTLFGSSFGNYDQDIVFRLYY------
ref|ZP_00603386.1|      VKDDAKHVGGCTLFGKGFGNYDQDIKLKVYY------
                        *  :.    ::**  *:**   **:*:*.*  .::   *
```

FIG. 78

```
ref|YP_001664041.1|      -----KRIKELRKKKGITQKELASYLGISDRAVGYYESGQRTPPPDILQKIADFFNVSTD
ref|YP_085042.1|         ------RIKSLRKKENLTQKQLAEKIGVSQRMIGYYESEERFPPHDVLSKLADCFSVSAD
ref|NP_242309.1|         ---FPERLRYLRKKHGLTMKELGKKINVAESTISGYENGNRKPDMDTLVKMAEYFNSSTD
RAAC03180                MSSFPERLSELLSATNSTKRALARAIGISERMIQYYITGAKSPTLDVLVAMADYFNVGLD
ref|ZP_02038515.1|       ---FEERLYQLRRERGISQEELANIIGVSRQAVQKWESGASQPNIDNLVAISEYFGVTLD
ref|YP_001210714.1|      ---FAKRLSFLITKNKLSKQAVANAINVSRPAVSQFANGENLPSVEKLIALADFFDVSLD
                              *:  *          :  .:.  :.::     :   :  .    *   : *  :::  *.    * ref|YP_001664041.1|      YLLG------------------
ref|YP_085042.1|         YLLG------------------
ref|NP_242309.1|         YLLG------------------
RAAC03180                YLAGRSDDPTPPPRSPSSGWDP
ref|ZP_02038515.1|       YL--------------------
ref|YP_001210714.1|      YLVG------------------
                         **
```

FIG. 79

```
ref|ZP_02309926.1|        ----FSKRLSELRKKKGFSQYKLADELGFSRGQVANYEQGTREPDYQTLLKIAEFFNVST
ref|ZP_01941236.1|        ----FSKRLSELRKKKGFSQYKLADELGFSRGQVANYEQGTREPDYQTLLKIAEFFNVST
ref|ZP_01926077.1|        ----FSKRLSELRKKKGFSQYKLADELGFSRGQVANYEQGTREPDYQTLLKIAEFFNVST
ref|NP_469419.1|          ----FSKRLSELRKKKGFSQYKLADELGFSRGQVANYEQGTREPDYQTLLKIAEFFNVST
RAAC02417                 MMMTFGERLAQLRRSKGLSQYALAEQLKMTRGQIANYEQGTREPDIETLKKLADFFDVSI
ref|YP_001111866.1|       ----------------MTQEQLAQQLGFTRGQVSNYEQGSREPDFETLKKIADFFKVTT
                                          ::*   **::* ::***::*****:****  :** *:*:**.*:

ref|ZP_02309926.1|        DYL-LGR----DDNNLADTIAAHID--SNATEEDIKEILAYIEEKR--KEHANEKEINIT
ref|ZP_01941236.1|        DYL-LGR----DDNNLADTIAAHID--SNATEEDIKEILAYIEEKR--KEHANEREINIT
ref|ZP_01926077.1|        DYL-LGR----DDNNLAETIAAHID--SNASEEDIKEILAYIEEKR--KEHVNEEEINIT
ref|NP_469419.1|          DYL-LGR----DDNNLADTIAAHID--SNASEEDMKEILAYIEEKR--KEHANEEEIDIT
RAAC02417                 DFLVLGKPNVSDFNGLTNEVKRTLEALSQMSVEKQQEVADFAEYLRS-KEEQPVVEYDVR
ref|YP_001111866.1|       DYM-LGR---------------TD--DPTPVDKLIELSALAGQQK--FDPMK-------
                          *:: **:                 :    . .:. *:         :    :

ref|ZP_02309926.1|        EIASKEDEEINKFVDEN--EDFKVVAARVM--------------
ref|ZP_01941236.1|        EIASKEDEAVDKFVEEN--EDFKAVAARVM--------------
ref|ZP_01926077.1|        EIASKEDDAVDKFVEEN--EDFKAVAARVM--------------
ref|NP_469419.1|          DIAAKKDADVAKFVEEN--PDFKAVAARVM--------------
RAAC02417                 EIAANMEKALYAHGDEDLIQHFEEIMRRVIRRYDERASQDQQNR
ref|YP_001111866.1|       ELPPEAQRSL---------EDFIDYLMRK---------------
                          ::..: :  :           .*     *
```

FIG. 80

```
ref|NP_625321.1|           ------------EQRRALILDEVRRGGVRVNELTRKLGVSDMTVRRDLDALSRQGVLEK
ref|NP_822608.1|           -----ENQNLLAEQRRALILDEVRRGGVRVNELTRKLGVSDMTVRRDLDALARQGVLEK
ref|YP_001103030.1|        ------------RQRQEVILNEVRRTGAVQVSALVLQLGVSDMTIRRDLDALARRGLVEK
ref|ZP_00996757.1|         ------------QRRAAILSMVQDSGAVRVSDLVEHLGVSDMTVRRDIERLDTDGLLER
ref|YP_001363698.1|        ------------QRQEVILDAVRTHGGVRVADLVERLGVSEMTVRRDIGELSRRGLVAR
RAAC01912                  MIKRREVRTVYPKERQRVLLELLAQHGFASYRQLAERLGVSEITVRRDMKALEAQGLVET
                                       :*:   :*.    *  .    *. :****::*:***:   *   *::

ref|NP_625321.1|           VHGGAVPVAEASTHEPGFEAKSGLEPTAKEDIARAAAELVAPGAAIALSGGTTTYALAHR
ref|NP_822608.1|           VHGGAVPVVEASTHEPGFEAKSGLELTAKEDIARAAAELVAPGTAIALSGGTTTYALAHQ
ref|YP_001103030.1|        VYGGATSMVGRSTDEPGFEAKSVRQLAEKEAIAMLAAEQVRPGTAIGLSAGTTTWTLARH
ref|ZP_00996757.1|         VHGGALALLPRATDEPGFTAKSSLMTAAKHAIALAAARLVDPGATIGISAGTTTYEFARA
ref|YP_001363698.1|        VHGGAAS-VARSSEEPGFAAKAGLRPDAKRAIARAAADLVPDGASVALSAGTTTAEVARE
RAAC01912                  AFG--GGQVARAARELPYTDKRILQIPEKIAIAKAALRQIESGMTIAIAAGTTTWVLAQH
                           ..*      ::  *   : *          * ** *   :  * ::.::.****  .*:

ref|NP_625321.1|           LVDVPDLTVVTNSVRVADVFHVAQRTSGARQGGATVVLTGG-VRTPSDSLVGPVADQAIA
ref|NP_822608.1|           LVDVPDLTVVTNSVRVADVFHAAQRTSGQRQGAATVVLTGG-VRTPSDSLVGPVADQAIV
ref|YP_001103030.1|        LDDVADLTVVTNSIRVADALQQRGRTDR------TVVLTGG-VRTPSDALVGPVAVQSLR
ref|ZP_00996757.1|         IRNIPHLTVVTNSVPVAQLLHESG-------GNHVVVLTGG-VRTPSDALVGPVAVAALQ
ref|YP_001363698.1|        LRDVSDLTVVTNSPRVADLLHDPADHSR------TVVLSGGT-RTPSDALVGPVARAGLR
RAAC01912                  IAGFQNLTFLTNSVNVATELSKNGYR--------DIFLTGGQFRTPSDALVGPVAEHMIR
                           :  ..**.:*** **  :            :.*:** *****:******     :

ref|NP_625321.1|           TLHFDALFLGVHGISAEAGLSTPNLAEAETNRRLVQSARRVVVVADHTKWGVVGLSSFAA
ref|NP_822608.1|           ALHFDVLFLGVHGISVEAGLSTPNLAEAETNRRLVQSARRVVVVADHTKWGTVGLSSFAS
ref|YP_001103030.1|        SLHLDLVFLGVHGIAARAGFTTPNLNESETNRALAEAANRLVVVADHSKWSTVGISTIVD
ref|ZP_00996757.1|         GLHVDRLFLGAHGIDRNAGLTTPNLVEAETNRALVRASRSVCVLADHSKVGIVGLSTFMA
ref|YP_001363698.1|        GLHVDLLFLGVHGLDAAAGLSTPNLSEADTNRALMDCAARVVVVADASKWGVVGLTSFAD
RAAC01912                  QFRADILFVGASGLHVDHGLSTPNVLEAAVNRAMMERAARVVVVLADHTKWGVESLMSFAK
                           ::  * :*:*:*. *:    *::***: *: .**  :  :  :   *:** :*   .: ::

ref|NP_625321.1|           LEQVDTLVTD--SGLSADARAEVAE-HLGLVVAGEPEPEA-------
ref|NP_822608.1|           LDQVDTLVTD--AGLPAGARAEVSEHLRRLVVAGEP-----------
ref|YP_001103030.1|        LHEVDLLISD--DGLPQEARQVLSENVPELVLAEVP-----------
ref|ZP_00996757.1|         LHEVDTLITD--PGTPARVRALLEDSVDHLVLAEVASA---------
ref|YP_001363698.1|        LGSVDVLVTD--AALDPSARPVISDLVGELVVAGTPQEE--------
RAAC01912                  LSEIDALITD--RWPGEAEAAALAECDVDLIVADAPNAESSKRGDAQ
                           *  .:* *::*           : :       *::*   .
```

FIG. 81

```
ref|YP_001169444.1|         --------------------------------IRRRIVSLNYPPGLMIFENAVAAEFGVSRTP
RAAC02663                   MGLRGGGDVIAGVTYGVAKKTLGEQAYEVIREEILSLRLHPGQTVYESDFTRMLNMSRTP
ref|NP_435364.1|            ------------------ETAAAQVERDLRESIIRLELAPGMRLSEQEIATRMGVSRQP
ref|YP_001313948.1|         ------------------ETTAAQVERDLRESIIRLELAPGSRLSEQEIATRMGVSRQP
ref|ZP_01509063.1|          --------DLTASVSFD-SHEPIGKQIFRALRQAIFVGQLVPGTPLSEKEVSDMFQVSRQP
ref|YP_527240.1|            ------------------------QIFEYLRDAIVSMELRPGQMIAETSLAEQFGVSRTP
                                                    :*  *. . ** : * .: : :** * ref|YP_001169444.1|         VHQAFMRLSHEGLLDVLPQRGARVSFLSRSTIIHAQYVRECLEAAAFFDAAR--IWDAAD
RAAC02663                   VREAVRALAMERLIEVLPQRGMKVALISERQVEETRFVRESLELSVIRRVAEDVAQDASV
ref|NP_435364.1|            VREALIALGKSKLVDIRPNRGTVVVRISARQMMEARFVREAIEVAVARRASETF--DSWT
ref|YP_001313948.1|         VREALIALGKSKLVDIRPNRGTVVVRISARQMMEARFVREAIEVAVAQRASE--AFDSWT
ref|ZP_01509063.1|          VREAFIKLVEAGVLQVLPQRGTFVKRISPRQVREGRFIREAIETAVVKKAAVSIS-DEQL
ref|YP_527240.1|            VREALIKLSNIGFVEVLPQRGTYVTKFSTQKILEARFIREALEVAVAADLAS-----NVT
                            *::*. *   .::: *:** * :*    :  . :::**.:* :.    :

ref|YP_001169444.1|         AAHLQ---RERRAQDLIEAQREAVARGDYLRFTELDVAFHTEILGVLGNDLLLACVSQMR
RAAC02663                   RARLE---REMARS--LQDQREAAEAGDALQFMHADDAFHQIFLQHFDNETLTAIVAQMR
ref|NP_435364.1|            RR-----KIDTILAR----QKAANEAHDHNAFRREDEQFHIAIAEGAGCGLAWNAVSDIK
ref|YP_001313948.1|         RG-----RIDTILSR----QRAAEEINDHNAFRREDEQFHIAIAEGAGCGLAWNAIADIK
ref|ZP_01509063.1|          QA------LADNLRD----QKIAAKANDTAAFLALDEAFHYAIAQAIDCTAAWETIQDIK
ref|YP_527240.1|            EE------LVEACQAIIEAQSKAADEDDSITFQKLDDEFHQMLAQHTQYARVGSLIEAEK
                                        *   *      *    *  **   :        :    :

ref|YP_001169444.1|         NQLNRLRLLELREAHHEKRMIADHEALLAAVSAGRADEARRRLITHLKTLEDFREEIFGR
RAAC02663                   GHLNRVRMLSLFEPERMKRLVGEHERVAEAVLSGNADRSAEAMHHHLAKLMEDLPGIKAR
ref|NP_435364.1|            AHMDRVCNLQLRHPDSMKKLIAEHEAIITAIDARDADAAAAAMRSHLNGILADLPQIEAD
ref|YP_001313948.1|         AHMDRVCNFQLRHPDLMKNLIAEHEAIIIAIDARNAEAAANAMRRHLNGILSDLPQIEAD
ref|ZP_01509063.1|          AQMDRVRYLSLPDVSPLDLLIKQHAKILAGLRAHDASAAEEAMRNHLREILMSLGPIAAR
ref|YP_527240.1|            AHMDRVRNLSLQEAGQFKRVLAQHKAIVKAIKAGDANKAQEAMSTHMREVYKILTVIPAE
                             ::: *:  :.* .    . :: :*  :  .: : *. :    : *: :     *  .

ref|YP_001169444.1|         HPDLFRP
RAAC02663                   HPAFFGP
ref|NP_435364.1|            NPDLF--
ref|YP_001313948.1|         NPDLF--
ref|ZP_01509063.1|          NPAWF--
ref|YP_527240.1|            HPEYF--
                            :*  *
```

FIG. 82

```
ref|YP_643029.1|            --------LRRPEPLYRQVYEVLRRRILAGEYGAGEVLQESRAAEELRVSRTPVREALRQ
RAAC01158                   MERRSVTAIQRSEPLVKQVYKYLYHAILSGEFRPRDKVVETHIAERLQVSRSPVREAIRL
ref|YP_077724.1|            -------SIQRAVSYHDQVHHYLKDMIIKGGYQPGERIYESKIAKELQVSRSPVREAIRT
ref|YP_001308645.1|         --------IEKAPSYYDQAYNSIKAMIFNGILKPGDRIYESKLASEFQISRSPVREAIRS
ref|YP_174340.1|            --------VERPIPYYEQFYHSIKKMIFTGHFKPGDRIVETQLAKEFNVSKSPIREAIRI
ref|YP_516602.1|            -----MSAITKSLPFHLQIYEILKGKILNGEISRGERLYENKISQELGVSRSPVREALRM
                                 : :. .    * :. :    *: *       : : *.: :..: :*::*:***:* ref|YP_643029.1|            LEREGLLVARGTE-RVVADPSREEFVDLYTCRAALEGLVAERAARLAEEEELREMEEALE
RAAC01158                   LIQRDLLVEDADG-VRVFQPTQRDFAELYEMRLALEPVAAERAAENAHSTCVAALHENVK
ref|YP_077724.1|            LEQEGLLLIDDKSKITVYEPTIKDLEEIYQCRQALESLAVSLATRLASNETLELISETLS
ref|YP_001308645.1|         LEKDGLLVIGDKSKITIYKPTKEDIENIYECRQALESQAAKLTTLKASNKELDKIEKILL
ref|YP_174340.1|            LEKEGLVIVDEKSRVIVYKPTQKDVEEVYFCRMALESFAVSEATKIASDEDIHELEKLLI
ref|YP_516602.1|            LEQDELVVVTSTG-LIVNPMEFSDMEEIYQCRMALEPFAAKISADKLTNEDLAALRNLVI
                             * :   *::             :.  ::*  *  ***  ... ::    .  :  : :

ref|YP_643029.1|            EARRAVAAGDHGGV-------LSANTRFHDLMVRSARMPPLERLMDTLRGQILVARRHIL
RAAC01158                   QTEQALALGDWDSI-------VALNKEFHECIWQMSGNRRILKAMQEITDLVQFYWRALL
ref|YP_077724.1|            EAHKHQKSQGPESA----NALLRLNTQFHDAIIEASENERLQKQLLDLRSLTFFYRSKNL
ref|YP_001308645.1|         EIKKNIDNFDDTLT----KNIIELNTKFHDLILDFSQNNHLKKLSKDLSSLTYFYRSIDV
ref|YP_174340.1|            RTDQAISSKKEEDR------IISLNELFHSTIIDYTKNLRLKKQINDLKALIYYFRILNF
ref|YP_516602.1|            QARVYHNQKAYEKV-------VESNTQFHDIIIQSSGNSRLIGIIEKIRSLIILSRKTEF
                            .              :   *  **. :   :       :      :        .

ref|YP_643029.1|            SDERIEAEICEEHASILEAIRRRDVGAARERMQRHMQNDIR-------------------
RAAC01158                   DIPNLDIQIVGDHQQIVQYIERRDSAGAHTAMKQHVAKDLRVISERFRDAKNAFKEQILD
ref|YP_077724.1|            EKPERTLEIINQHEEILRHMQDRNDAKAAESMRKHIEADLCYLKE---------------
ref|YP_001308645.1|         YEPERNIDIFNHHLEIFNYIKQRDEEKAYKAMYNHIDNDLK------------------
ref|YP_174340.1|            QGDNRANVILEQHYRIFEFIKKRDPEKAAKAMISHLELDL-------------------
ref|YP_516602.1|            ECYQREEGYLDEHEGVLEALTQRNGDEAERLLRIHIMNDFEFYS---------------
                            .      .*  :..  :   *:   *    :   *:    *:

ref|YP_643029.1|            --
RAAC01158                   EA
ref|YP_077724.1|            --
ref|YP_001308645.1|         --
ref|YP_174340.1|            --
ref|YP_516602.1|            --
```

FIG. 83

```
ref|ZP_02082978.1|         ----------------SRPLYEQVAERLRELMFKGALPQDAQLPSVRSLATELSINPNTI
ref|ZP_01962813.1|         ----------------RPIYEQITEKFRTLIYQGALPAGCRLPSVRQLAMELSINPNTI
RAAC00068                  MTLDPPWQPPAWELDPSQPLYEQIAHRLRVEIAASRLPGGARLPSVRDLAAHLRVTPNTV
ref|YP_001420528.1|        ------------EFQSSKPIYLQIADRVYYRLIRSELSPGDKLPSVREMAVQMKVNPNTI
ref|YP_430032.1|           -----------EFDNSRPIYLQIIAAIKKQLARGELQPGQKLPSQREMAEELQVNPNTV
ref|ZP_02328287.1|         -----------FNLDLSKPLYEQVLSQIRSSIAKGEIALGEKIPSVREMAQALKITPNTV
                                            :*:* *:    .   :   . .:  .  ::** *.:*   :  :.***:

ref|ZP_02082978.1|         QRAYTELERQGYIYSIKGKGSFVADNS---------------------------------
ref|ZP_01962813.1|         QRAYMTLEQEGLIYPVKGKGNFVAETRQIQEKSKEDFRKEFL-ELVRR------------
RAAC00068                  MRAYAELEQDGLLETFRGQGTFVARGSGVEARARARIARQAF-EHVRRVAADLGMRVEDL
ref|YP_001420528.1|        QRTYSEMERLGIVETRRGQGTFIAERSDLKAELKDRLTKDVFKRFIQEM-AELGL-----
ref|YP_430032.1|           QRAYREMEAMGLLETLRGQGTFISNRPGL-------------------------------
ref|ZP_02328287.1|         MRAYQELERDQLTVTRRGQGTFITSNAETVEQIKYNLAEIATGEYVRKM-TDIG------
                            *:*   :*          .  :*:*.*::

ref|ZP_02082978.1|         ------------------
ref|ZP_01962813.1|         ------------------
RAAC00068                  LRLGAEAEGGAEDDASSH
ref|YP_001420528.1|        ------------------
ref|YP_430032.1|           ------------------
ref|ZP_02328287.1|         ------------------
```

FIG. 84

```
ref|YP_642998.1|         ------GSLS-----------------------------DVAYEKLYGDITGGRLQPN
RAAC01035                MGQQDGGKLSPLWHACGITVPDDKSTGGVAHVEVPSQGYTEEECYRRLRDAIIDGTLMPS
ref|NP_822795.1|         ---PSTGEQAK-----------------------------QHALTQLRQAILHGEMAPA
emb|CAJ88752.1|          ----------------------------------------QLRQAILRGDMAPA
ref|YP_001191149.1|      ----TRGKKS------------------------------DYIYERLKTDIQRGKFLPG
ref|YP_752794.1|         VDLDSYKPLR------------------------------ELVLEAIREAIKNGVLKPR
                                                                       :   *   * : * ref|YP_642998.1|         ERLIELDIARELGVSRAAVRNALIRLEQEGLVKREPNRGARVRLVSEEEAVEILEARMAL
RAAC01035                QRLVEMDLARWLGASRATIRTVLARLEQEGLVERERYRGARVRHVSHEEAVEILEVRMAL
ref|NP_822795.1|         QRLVENELAEQFGVTRASIRAALIDLAAEGLVERIRNRGSRVRVVTVEEAVAITECRMVL
emb|CAJ88752.1|          QRLVENELAEQFGVTRASIRAALIDLESQGLVERIRNRGSRVRVVTVEEAVAITECRLVL
ref|YP_001191149.1|      QRLVEDALAKEYGSSRNTIRLALTRLENDGIVKRTT-SGVIVSFIDLKEAVEILEVREVI
ref|YP_752794.1|         ERLMEIQLAEELGVSRTPIREALRKLELEGFIVMVPRKGAYVADISLKDVADVFEIRAAL
                         :**:*   :*.   * :* .:* .*   *   *:::        * *   :   ::..  :  * *  .:

ref|YP_642998.1|         ECVAVRHAALNRTQEDIAGLREILSQMESRLEAGDLLGASDLNGQFHRRLVEISNHATIS
RAAC01035                ECLIARYAALRATDEDVRRLEDIISWMRRQYEGNDLLSYSDGNARLHRTIAEISRHNTAK
ref|NP_822795.1|         EGLCAAKAAVAASDEQLTELADLGAAMTKAVADGEPVTYSELNHELHDRIREFSGQQTAV
emb|CAJ88752.1|          EGLCAAKAASAVDDGQLGELKDLGTAMRKAVADGEPLVYSDLNHELHARIREFSGQRTAV
ref|YP_001191149.1|      EGFLARKAATRISEESLQRLESTLMEMKTALENREFLRYSQLNERFHSIIYEASGNTTAQ
ref|YP_752794.1|         EALAAGLAAERITDEELEAMERLLVEKVEAISSNDMDKLVDVDTKFHEAIYRASRNQRLF
                         *  . .  **     :  .:   :                  :         : : ..:*   : .  * :

ref|YP_642998.1|         KLLKMLNSQLIRFQYRTILTPGRPASSLAEHRAIFEAVEAGDPERAEQAMRRHLSGVTEA
RAAC01035                RLLDTLNSQSVRYQYRTILAPNRSAASMQEHERIVDAIRRRDPDSAEQAMRVHLSQVCDT
ref|NP_822795.1|         ELLERLNAQLVRHRFQLALRPGRPQHSLNEHLSMIEAIRDRDPQAAEVAVRAHLTSVIEA
emb|CAJ88752.1|          ELLERLNAQLVRHRFQLALRPGRPQQSLNEHLAMIEAIEARDPQAAEAAVRAHLTSVIEA
ref|YP_001191149.1|      LLLSTLKLKMIRYQFRTVMVPGRAEVSWNEHFRIFQALKNHDENEAELWARTHVKNVREL
ref|YP_752794.1|         AIINNLREQIQRFRSTSLSYPGRMQQSMQEHRDIVEAIQSRDIQLSRQLAQEHI------
                         :: . *. :   *.:         *.*    *   **    ::.*:.   *  : :.    : *:

ref|YP_642998.1|         LR------
RAAC01035                LRSMRQGF
ref|NP_822795.1|         LR------
emb|CAJ88752.1|          LR------
ref|YP_001191149.1|      IQNNKE--
ref|YP_752794.1|         --------
```

FIG. 85

```
ref|YP_148128.1|         ------------IPIYYQLEQYMKEKIEKGEWQPGEMIPSERELAEMYDISRMTVRQAVN
ref|YP_001126297.1|      ------------VPIYYQLEQYMKEKIEKGEWQPGEMIPSERELAETYDISRMTVRQAVN
ref|ZP_01697892.1|       ------------IPIYFQIQEEIRKKIREGEWKTGEAIPSERVLSDLFEVSRMTVRQAVQ
RAAC02031                MTKGSIRSMRESVPLYKQLKSELLEKILSGEWPPGEQIPSEAELASMYDVSRTTVRQAVG
ref|ZP_01662088.1|       ------------PLYERIKGTLREGILSGHYAPASLLPSEAALGEQFNASRITVRQALA
ref|YP_900875.1|         ------------MPLYHQVESHLKENIGNGTWKAGEAIPPERMLVDQYGVSRITIRQALA
                                     *:*  ::: : : * .* :  ...:*.* * . : ** *:***:

ref|YP_148128.1|         NLVNDGYLIRRRGKGTFVAAQKIEQPLKGLT---SFSEDMRARGMEPGTIVLSFEMVPAS
ref|YP_001126297.1|      NLVNDGYLVRRRGKGTFVAAKKIEQPLKGLT---SFSEDMRARGMEPDTVVLGFETVPAS
ref|ZP_01697892.1|       GLVDEGILMRKRGSGTFISEHKVEQPLEGR--M-SFTRLMEERGMKASNKIVAFFEREAS
RAAC02031                DLVTSGFIVRRQGKGTFVAE--VDHPATSTTLY-GFAEELRAAGLPVDVRVDVIEMRTCP
ref|ZP_01662088.1|       DLQNEGLIFRRHGKGTFVSQPKAFQNVTALQ---GFAEAMSAQGHAIRNRVLKLRTLPAP
ref|YP_900875.1|         NLVAAGLLYRKHGKGTFVAGAQDRPITESLANLTGHLEELQLRGLNPQVRVLALETRTLA
                          .*   * : *::*.***::   .       .    ... .:  *     :  :   .

ref|YP_148128.1|         EKLAEGLGVTEGDDLYEVRRLRLADGLPMALETLYI--PVNLVPGLTRD-VVSGSVYEFI
ref|YP_001126297.1|      KKLAEWLAVKEGDALYEIRRLRLADGSPMALETLYI--PCALAPHLTRE-IVNGSVYEFM
ref|ZP_01697892.1|       VQEMEALTLKEPENVLHIERLRYGDEIPIVFES--IITPARIAAGLT-EEKLNRSFYQFL
RAAC02031                EDIARWLRMTRSKQVLYIERTAYVEDMAYFHERSYLVPPYQVSSRMTPDPKMYDSIYGFF
ref|ZP_01662088.1|       TDVAQALQLAPGTAVTELHRVRLLDQVPVSLEVTWLPEPLG--SSVARADLVTRDVFLVL
ref|YP_900875.1|         AEVAEALERSPAAPGWYLYRLVTVDRQPLMLSTVWL--PRDLEIELTED-ILKQHGMALL
                           .     *    .     :  :       :  *      :   : :       .  :

ref|YP_148128.1|         EKEKGMIIGSAVQTLEASVARKVEAEHLKMKEGAPVLLLERRTHLVDGRPLEVVKSVYRG
ref|YP_001126297.1|      EKEVGLAIGTAVQVIEASVARKLEVEHLQVKEGAPVLLLERRTYLTDGRPLEVVKSVYRG
ref|ZP_01697892.1|       EREKGLRLGKGYQTIEAVAASARLAKLLKVAPGSPVLSIERVTSLSDGTPFEYVKAQYAG
RAAC02031                E-QNGVRINSGSQTISAELADEEDCARFGLTPPAAVLCIERITRDESGAPVEYSLVRYPS
ref|ZP_01662088.1|       EQDAGVALGHATLAIDAALADHATATALDTGAGAALLRVERLTHDAQGTPIDFERLYFRG
ref|YP_900875.1|         LTRNGIFPLRGRQRIGASSAGPEEAQLLGIRPGDAVLCVKRVIYGAASRPLVWFRTLYRS
                          *:        .   : *   *           :   .:* ::*    . *.    : .

ref|YP_148128.1|         DRYKFMIEMKR---
ref|YP_001126297.1|      DRYKFIVEMER---
ref|ZP_01697892.1|       SRFK----------
RAAC02031                DRYQLRVHLLRHPR
ref|ZP_01662088.1|       DAFQYRLRLDR---
ref|YP_900875.1|         DRYEYEVELKR---
                         . ::
```

```
FIG. 86 ref|YP_832996.1|        ------SKSEQAYAAVKARIVDGTYSPGYRLVLAKIAEDLGVSVVPVREAIRRLEAEGLV
ref|YP_950253.1|        ----PGSKSEQAYQAVKARIVNGAYSPGYRLVLGSIAKDLGFSVVPVREAIRRLEAEGLV
ref|YP_949591.1|        ------SKSQQAYAAVKARIVEGTYTPGYRLVLAKIAEDLGFSVVPVREAIRRLEAEGLV
ref|YP_001127075.1|     ------NKTQLAYEYILSHIESGAYGPGYRVVIDQIARELGLSSIPVREAIRQLEAEGLV
ref|YP_148880.1|        ------NKTQLAYEYILSRIENGVYGPGYRVVIDQIARELGLSSIPVREAIRQLEAEGLV
RAAC03005               MTKHPPSKQQVAYQTLKQRILEGTYGPGYRIVIDRIAKELGVSAIPIREAIRRLEAEGLV
                              .* :  **    :   :* .*.* ****:*:   .:.* :*:***:***** ref|YP_832996.1|        TFERNVGATVSGIDPTEYLYTMQTLSIVEGAATALSAPLIGSADVARARAVNEEMRECLE
ref|YP_950253.1|        TFERNVGATVAGIDPTEYLYTMQTLSIVEGAATALSAPLIDSVAISRARAVNEEMRECLD
ref|YP_949591.1|        KFERNVGATVSGIDPTEYLYTMQTLSIVEGAATALSAPLIDSVAIARARAVNEEMRECLE
ref|YP_001127075.1|     EFKPYAGAVVSTINEKEYVETLSVLAVLEGYATALGSAKLTKEAIKQLEQLNEQMERALE
ref|YP_148880.1|        EFKPYTGAVVSNINEKEYIETLSVLAVLEGYATALGSAHLTKEAINELERLNEWMERALE
RAAC03005               EVERFSGAKVTRIDAKMYEDILSALAVLEGYATAQAYRNLTDEDFDALRQTNEAMRQARS
                         .:   ** *: *: .  *   :...*::** ***  .  :   . .  ** *... .

ref|YP_832996.1|        HFDPVRFTRLNQDFHSVLFEHCPNPHILDLVHRGWNRLASLRSSTFRFVPGRARDSVDEH
ref|YP_950253.1|        HFDPVRFTRLNQDFHSVLFEHCPNPHILDLVHRGWNRLASLRSSTFRFVPGRARASVDEH
ref|YP_949591.1|        HFDPVRFTALNQDFHSVLFEHCPNPHILDLVHRGWNRLASLRSSTFRFVPGRAQESVREH
ref|YP_001127075.1|     ELELERFSELNYAFHSLIYSHCGNAYLEEQIKQIWQRMKRIRVYGFTFVPQRAKASIGEH
ref|YP_148880.1|        ELELERFSELNYEFHSLIYAHCGNAYLEEQIKQIWQRMKRIRAYGFTFVPQRAKASIEEH
RAAC03005               DFDLTLYSRLNQQFHEIILRRCNNRYLVDEIHAVRERMDAMRVSVFNLIPHRASDSIAEH
                         .::    :: ** **.::  :* *  ::  :  :      :*:   :*     * ::* ** *: **

ref|YP_832996.1|        EALLRLIESGAGADEIEKAARLHRSATLDAY----------------------------
ref|YP_950253.1|        EALLKLIETGADADTIEKAARLHRSATLNAY----------------------------
ref|YP_949591.1|        EALLRLIENAADADTIEKAARQHRAATLDAY----------------------------
ref|YP_001127075.1|     REMIRLLREQAPPHEVEQYARQHKMNTIEAFLR--------------------------
ref|YP_148880.1|        REIIRLLREQAPPHEIEQYVRQHKINTAEAFKR--------------------------
RAAC03005               DKLIQLMAVDVGEDAVERFARQHRLATLEAFRRWNEQHTRLVAERREWYRAPREIHRPGA
                         :::*:    .  .:*:  .* *:   * :*:

ref|YP_832996.1|        --
ref|YP_950253.1|        --
ref|YP_949591.1|        --
ref|YP_001127075.1|     --
ref|YP_148880.1|        --
RAAC03005               DS
```

FIG. 87

```
ref|YP_073926.1|         ------------RVSSQRIYQQIVDQITRMVQEGTLRPGDRLPPERQLAEEFGVSRSAVR
ref|YP_431134.1|         ----------------TKKIYEEIVQQIKDLIGEGNLKPGDRLPSERELSERLAVSRASVR
emb|CAB08003.1|          --------------------------------GELKPGDKLDSVQALAESFQVSRSAVR
ref|YP_001422711.1|      ----------------TKKIYEEVADALLEKIKAGELKPGEKLDSVQALSESFQVSRSAVR
ref|YP_080763.1|         ----------------TKKIYEEVAEALLESIKSGELEPGDKLDSVQALADSFQVSRSAVR
RAAC02459                MNALDPEGDATMREASSKLYMEIAEEIRRQIEEGAFRPGDRLPTLRELADRFGVSRATVR
                                          * :.**::* . : *:: : ***::**

ref|YP_073926.1|         EALSALRMLGLVEARVGEGTFVTQPPDERFISPLALVLTIEQSEAVGRELLELRAALEAE
ref|YP_431134.1|         EALSALAAMGVIVIRPGEGTFVQNIRNGAIVEPLAMALLLDRQAAM--ELLEARQALEGE
emb|CAB08003.1|          EALSALKAMGLVEMKQGEGTYLKEFELNQISQPLSAALLMKKEDVK--QLLEVRKLLEIG
ref|YP_001422711.1|      EALSALKAMGLVDMKQGEGTYIREFEPSHVSQPLSSALLMKKEDVK--QLLEVRKLLELG
ref|YP_080763.1|         EALSALKAMGMVEMKQGEGTYVKRFEPEQISIPLSAALLMKKKDVA--ELLEVRKILEIG
RAAC02459                EALSALRGQGLVEFRHGMGTYVRAASVEMWMQPLDAAILLSYDNVR--DLVELQTAVLAQ
                         ******   *::   : * **::            **   .: :. .    :*:* :  :

ref|YP_073926.1|         SAALAAVRREAEDLAAMEEALGDMERDLQEGRLGAEADWRFHDAVASASGNSLLLQTMRS
ref|YP_431134.1|         AAYLAARRAGPEDLEKMEELLKEMEHDLQRGILGEEADLRFHLAIAEAARNSVLARLMHT
emb|CAB08003.1|          VASLAAEKRTEADLERIQDALKEMGSIEADGELGEKADFAFHLALADASQNELLKHLMNH
ref|YP_001422711.1|      VAAMAAEKRTEDDLQKIRQALLEMKDIDGDEELGEKADFSFHMALAEASQNGLLKHLMNH
ref|YP_080763.1|         AVSSAAQKRTEDDLGRMQEALEDMKLADGNGELGEKADLAFHLALAGASQNDLLKGLMNH
RAAC02459                IAYRAAAQRMESDYSVLSHALFELEASPRRGEHRIASELKFFSVLAELAGNRLLENALRV
                         .  **  :      *    : . * ::              ::  *. ..:*   : * :*    :.

ref|YP_073926.1|         LSDTMKEALGLYRE-QL-----------------------------------------
ref|YP_431134.1|         VSDTMRQALKTSRQ-RLYTTAGNP-------------EKLFAQHNQIYEAIKAHDPRA
emb|CAB08003.1|          VSSLLLETMRETRKIWLFSKKTSV-------------QRLYEEHERIYNAVAAGNGAQ
ref|YP_001422711.1|      VSALLLETMRETRKIWLFSKRTSV-------------QRLYEEHERIYSAVAAKDADE
ref|YP_080763.1|         VSSLLIETMR------------------------------------------------
RAAC02459                LQEALRSSLRLLNPKLDLGVQACRRVYNAVQTGRPADARDAVYAYGEAILRAVAEKKGRG
                         :.   :  .::

ref|YP_073926.1|         --------
ref|YP_431134.1|         ARKAI---
emb|CAB08003.1|          AEAAMLAH
ref|YP_001422711.1|      AEAAMTAH
ref|YP_080763.1|         --------
RAAC02459                QSAMM---
```

FIG. 88

```
ref|YP_147389.1|         ---------------MNAMERENTVKSVRRALQIIEIVSTKKDGLGVTEIAKQMDINKSS
ref|YP_001125502.1|      -----------------------VKSVSRALQIIDIVSTKKDGLGVTEIAKQMDINKSS
ref|NP_243003.1|         -----------------------VKSVDRALTIISLVSEHKQGLGVTDVAAKLSLTKSS
RAAC01353                MCRSPAEKHRRARKDEVNRLEDYTVKSVDKALLLLEVVSEHPDGIAITELAQSVGMYKST
ref|YP_001665938.1|      -----------------------VQSLERALKILEVLGKNPNGLGVTELAREVDLPKST
ref|YP_360107.1|         ---------------------DTLIQSVDRALRILDTFSLKEKELGVTEIANRLGLHKST
                                                ::*: :** ::. ..  :  . :.:*::*   ..:  **:

ref|YP_147389.1|         VYRILTTLAQYGYIEQHPETERYKLGYKFLELSSKLLDSIDLRQEAKPYLRELEKETNEV
ref|YP_001125502.1|      VYRILTTLAQHGYIEQHPETERYKLGYKFLEISSKLLDSIDLRQEARPYLRQLEKETNEV
ref|NP_243003.1|         AYKLLATLVEHGFIEQDEETKKYRLGYRYLELSATLLESIDIRRQARPFLEQLEATTNEV
RAAC01353                VHRLLGTMMRRGYIEQDPVSGRYKLGYTVLDLGMKLLSSIDLRREAMPALQELALASGEV
ref|YP_001665938.1|      VYRLLSTLAKWGYVEQEKENEKYKLGLKIIELSSNILNNLELREVARQYLEELMEFANEV
ref|YP_360107.1|         VFGLLRTLEHWGYVEQNQVTGKYRLGLKLLELGNRVKEGLDLRAVALPFLQDLVERYGET
                          .. :* *:. . *::**.  . :*:**   :::.  :  ..:::* *  *.:*   .*.

ref|YP_147389.1|         IHLVVYDQGEVIYIEKLEGTETLRMHSKVGKRAPMHCTAVGKAILAHLPPAVAAEIIDRK
ref|YP_001125502.1|      VHLVVYDQGEVIYIEKLEGTETLRMHSKVGKRAPMHCTAVGKAILAYLPPTVTAEIIDRK
ref|NP_243003.1|         VHLVLYDQGEMVYIDKLEGTKTLRTHSKIGRRAPIHCTSVGKVIMAYLPEKVQISLIERY
RAAC01353                VHLALLDRGSVVYIEKVESPNTIRMHSRVGTRVPVHATGLGKAILAFLPKREVQDIVRRY
ref|YP_001665938.1|      VHLCVLRDGEIVYIDKVESHNTIQMYSQIGKRAPVHCTAVGKAILAFLPQEEAISILKTK
ref|YP_360107.1|         VHLAVHDRGEIVYIEKVEGPNAIRMYSQIGRRAPMHCTGVGKAILAFRPEKEIEEIIRTK
                         :**  :   *.::**:*:*. :::: :*::* *.*:*.*.:.**.*:*. *    .::

ref|YP_147389.1|         GLPKHTDWTITDREAFFRELETVRQNGYALDLEENEYGIRCVAVPIFDYTGGVVAAISVS
ref|YP_001125502.1|      GLPKHTDLTITDREAFFRELDSVRQNGYALDLEENEYGIRCVAVPIFDYTGSVVAAVSVS
ref|NP_243003.1|         GLPPHTERTITDKETFMKELEKIRLEGYGYEMEENEPGITCIAAPIFDYQGAITAAVSIS
RAAC01353                GLPRLTPHTITDADAFWASLEETRSTGFAFDMEEHQEGVCCVAAPIFAHDGRVMAAVSVS
ref|YP_001665938.1|      GLPRKTPNTITSLEEMLKHLEEIRRLGYAIDNVEHEEGIRCVAAPIFDYTGQVVASVSIS
ref|YP_360107.1|         GLKYFTPNTITDPKKLHEELSLIRENGYSLDREEIEIGLRCVAAPIRDSQNTVVAAISVA
                         **   *  ***.   :  *. *  *  *:. :    *  : *: *:*.**    .  : *::*::

ref|YP_147389.1|         GPTIRMTDDRITSLTVRMRQIGKELSARLGYR------
ref|YP_001125502.1|      GPTIRMTDDRIAGLAMRMRQIGKELSARLGHR------
ref|NP_243003.1|         GPSIRLSKERLHELRPLIIAIGKKISQRLGYQ------
RAAC01353                GPALRMTRERMVELVPLVKRAGERISERLGYRRERVAP
ref|YP_001665938.1|      GPEYRVTWEKVPGLAVKVKEITKKISQRLGY-------
ref|YP_360107.1|         GPSIRMTEEKIQELIVSVKEAALEISKRLGYQ------
                         **  *::  ::: .  *    :       .:* *** :
```

FIG. 89

```
ref|ZP_02329176.1|         ---------TVRSVERALDILLCFRDSSEL-TLTEISNQAGLHKSTVHRLLASLEGKGFL
RAAC02432                  MPHTPSGQTTVRAVERALDILLLFTHSPRAWSLSEIARATGLHKSTVHRLLLALQQKGFV
ref|YP_076367.1|           -------------MERALDVLLCFAGERGGLGVTQIAEKLGLYKSTVHRILAALESRGFV
ref|NP_694155.1|           MNDSPKG---IRTLQRSIDILNCFIEKNSELTLTEISLYTGLAKSTTTRLLSTLEMNNFV
ref|YP_001126042.1|        ----------LRTVQRAIDILYCFTLEEQELSLTEIANKISLAKSTTTRLLATLEQNRLV
ref|YP_643152.1|           ------------AAVRVADVLLLFASGPDALGVSEISRRLGLSKAVVHRILRSLASRGLV
                                        *  *:*   *              :::*:   .* *:..  *:*  :*   . ::

ref|ZP_02329176.1|         LRDSSGDKYRLGFSVWELSANLSQGDDISMLLLPEMEWLRDQVGETISIYVRDGKERVRI
RAAC02432                  RRESESDRYVLGWSLYGLGANAALHDRWSDAAKPILRRLRDETNETVSLYVRNGLERIRI
ref|YP_076367.1|           RRDPATGRYHLGLRALELAQVYLSSGDLPTIALGEMLQLRDLAQETVSLYVRDGAERVRV
ref|NP_694155.1|           EKDEVNAKYRLGKQIYFLGFVAGQTFELNSLAKSTMERLREQTKETVNLYILDGKHRVCV
ref|YP_001126042.1|        IKNPETLKYRLGQGLYYLGHIAGKSIEVREIAKPVMERLRNETRETVNLYVLEQGARVCI
ref|YP_643152.1|           SHDAESRSYGLGPAAAALGARALAGLELRRVALPVLRRLQRETGETTTLSELVGTARVYL
                              ::           *  **       *.                 :   *:    . **  .:         *:  :

ref|ZP_02329176.1|         QAVQSKHAIRRVAPVGARMPLYVGASSKVLVAFGDEALQVELAHD----ARSSVGLDPTA
RAAC02432                  LAVESLQPIRNVASVGERYPLTIGASGKVLLAFSNSAVIEAACHP----DRLPNGVRQVD
ref|YP_076367.1|           QRAEGPLTVRRVVGLGERLPLYLGASGKVLLAWCPPEERARILDA-----QLPAGFDRTA
ref|NP_694155.1|           QQFESLQSVKHMISVGQKLPLTVGASGKVFLAYQSKEFIEDAM------DTQPLKKSKVD
ref|YP_001126042.1|        EQYEGLQSLRHMVKIGERLPLWAGAGGKVLLAYQSPSFQERIL------AQVPTEERRTR
ref|YP_643152.1|           DQVPSLKEIKMTVEVGRPFPLHAGASSKAILAFAPPEVREHVLEGPLEALTPLTVTDRAR
                                .  ::        :*      **   **..*.::*:                                   .

ref|ZP_02329176.1|         ---FLKQLAETREQGFATSMEEREPGAAALSAPILNRSGKLVAALAISGPISRLTPEQMQ
RAAC02432                  ---LRQQLEAIRREGYALSRQERDAGAAAIAAPVLNEDGSCLYAIAVSGPVERMTEDKMR
ref|YP_076367.1|           ---LEARLAEAREQGWALSLEEREEGVASVAAPVIDRAGRCVAALAISGPVSRFTDDRV-
ref|NP_694155.1|           ---LKNELDLIIKEKYAVSIEERESGTSAAAAPIFNFQNEVVAVLSVSGPASRL------
ref|YP_001126042.1|        ---LTAELEMIRQRGSTSSIDEREVGSAAVAAPIFNIHGEVNACLSISGPTHRFTPQAIR
ref|YP_643152.1|           ---LEVELGQIRESGTAVSCGERQSGAGSVAAPVIGVDGYAVGSISVCGPVDRFGEETVE
                              :    .*     .    : *  **:   *   .:   :**::.    .        :::.**  *:

ref|ZP_02329176.1|         ------------------
RAAC02432                  DMVTPLKRAAEELSERLAE
ref|YP_076367.1|           ------------------
ref|NP_694155.1|           ------------------
ref|YP_001126042.1|        ------------------
ref|YP_643152.1|           RM----------------
```

FIG. 90

```
ref|YP_001662226.1|      --TIKDVAKRANVAPSTVSRVIADNPRISKETKERVWKAMEELGYYPNAIARSLASKVTN
ref|YP_001664166.1|      --TIKDVAKRANVAPSTVSRVIADNPRISKETKERVWKAMEELGYYPNAIARSLASKVTN
ref|NP_624096.1|         --TIKDVAKRANVAPSTVSRVIADSPRISKETKERVWKAMEELGYYPNAIARSLASKVTN
ref|ZP_02171282.1|       --TIKDVAKLANVAPSTVSRVIANSPRISERTKETVREAMKELGYHPNFNARSLANKSTN
emb|CAB65654.1|          MATIKDVARLANVSPSTVSRVLANSPRISEETKRRVRAALEQLNYHPNAFARGLVTNSTG
RAAC00570                MATIKDVARLANVSPSTVSRVLANSPRISEETKRRVRAALEQLNYHPNAFARGLVTNSTG
                           ******: ***.*******:*:.****:.**. *  *:::*.*:**  **.*..: *.

ref|YP_001662226.1|      TLGLIMPRSTEEAFSNPFFPEVMRGISVVAHREKYDLLLSTSGNQEEEKEAVINMVKGKR
ref|YP_001664166.1|      TLGLIMPRSTEEAFSNPFFPEVMRGISVVAHREKYDLLLSTSGNQEEEKEAVINMVKGKR
ref|NP_624096.1|         TLGLIMPRSTEEAFSNPFFPEVMRGISVVAHREKYDLLLSTSGNKEEEKEAVIRMVKGKR
ref|ZP_02171282.1|       TIGIVMPNSANKTFQNPFFPEVIRGISSKAHQLEYGLYLSTGQTEAEIFEEVQHMVQGKR
emb|CAB65654.1|          AIGILIPPSAQEFFVNPFFAEWMAGVAEVARQRGVDTVLSTSARG--EIETLDHMIRGRR
RAAC00570                AIGILIPPSAQEFFVNPFFAEWMAGVAEVARQRGVDTVLSTSARG--EIETLDHMIRGRR
                         ::*:::* *:::  * ****.*  : *::  *::    ***.      *  : .*::*:* ref|YP_001662226.1|      VDGIILLSSRTTDELIPWLRDEKFPFVVIGKPLDAKG--VYWVDNDNIGASKLATNYLIK
ref|YP_001664166.1|      VDGIILLSSRTTDELIPWLRDEKFPFVVIGKPLDAKG--VYWVDNDNIGASKLATNYLIK
ref|NP_624096.1|         VDGIILLSSRTTDELIPWLRDEKFPFVVIGKPLDARG--VYWVDNDNIGASKLATNYLIK
ref|ZP_02171282.1|       VDGIILLYSRVDDKVVDYLYKENFPFSVIGRPYDEKKRDITFVNNDNFKAAKTVTEYLLL
emb|CAB65654.1|          VDGVLLIGARQGDPVLQEVAKLRCPAVLLGRPADPAP--ISWVNNDNQRAAYDATVHLLN
RAAC00570                VDGVLLIGARQGDPVLQEVAKLRCPAVLLGRPADPAP--ISWVNNDNQRAAYDATVHLLN
                         ***::*: :*     *  ::    .  *  ::*:*  *       :  *:*** *:  .* :*:

ref|YP_001662226.1|      HGHREIAFISGSLEYVVSLDRLDGYKLALEENGIPFKRELAEQDEFSEDGGYRAMMRILE
ref|YP_001664166.1|      HGHREIAFISGSLEYVVSLDRLDGYKLALEENGIPFKRELVEQDEFSEDGGYRAMMRILE
ref|NP_624096.1|         HGHREIAFISGSLEYVVSLDRLDGYKLALEENGLTFKRELVEQEEFSEDGGYRAMMKILE
ref|ZP_02171282.1|       LGHKNIAFIGGNLDFVVTVDHMEGYRKALSNAGMELLDDYVVFHEELQEGGQEAVIDLMS
emb|CAB65654.1|          LGHRRIGFLGGASDLVVTMDRVAGYRQALVDHGVEPDSRLEVSSFFLEQGGYLGMMRLLA
RAAC00570                LGHRRIGFLGGASDLVVTMDRVAGYRQALVDHGVEPDSRLEVSSFFLEQGGYLGMMRLLA
                          **:.*.*:.*    : **::*:: **: **  *:            ::**   .:: ::

ref|YP_001662226.1|      -REKPTAVVVTDDVMAFGVIRAAIDKGYRVPEDISIVGFNNIPLSAFANPPLTTIDISTF
ref|YP_001664166.1|      -REKPTAVVVTDDVMAFGVIRAAIDKGYRVPEDISIVGFNNIPLSAFANPPLTTIDISTF
ref|NP_624096.1|         -RAKPTGVVVTDDVMAFGVIRATIDKGFRVPEDISIVGFNNIPLSAFANPPLTTIDISTF
ref|ZP_02171282.1|       LNDPPTAMIVADDIMTFGVMRMLSEMEMKVPDDVSIISFNNVMISELSSPPMTTVDIHIY
emb|CAB65654.1|          IPDRPTAVLCADDVLAFGGMRAAHELGFEVPGDLAIVGFNDIRLAELAHPALTSVRVHMH
RAAC00570                IPDRPTAVLCADDVLAFGGMRAAHELGFEVPGDLAIVGFNDIRLAELAHPALTSVRVHMH
                              **.::  :**::** :*      : .** *::*:.**::  ::   :: *.:*:: :    .

ref|YP_001662226.1|      DLGIKSAELLIARLKQKEIDIDHIIVPVKLVERKSCVAR-------
ref|YP_001664166.1|      DLGIKSAELLIARLKQKDVDTDHIIVPVKLVERKSCVAR-------
ref|NP_624096.1|         ELGIKSAELLIARLKQKEIESDHIIVPVKLIERKSC----------
ref|ZP_02171282.1|       NLGFEACNLLIDQILHPETGSKQVLIPHKMIKR-------------
emb|CAB65654.1|          ELGVRSAELLLEEIDQGKPLQRHVIVKHELVIRYSCGAKPIGTLTT
RAAC00570                ELGVRSAELLLEEIDQGKPLQRHVIVKHELVIRYSCGAKPIGTLTT
                         :**..:.:**: .:  :  .      ::::  :::  *
```

FIG. 91

```
ref|ZP_01188246.1|    MATIKDIAKIAGVSTATVSRVINNYPDVSEKTKKKILKIMKENNYRPNSVARSLSTSKSN
ref|ZP_01188241.1|    MVTIKDIARIAGVSTATVSRVINNYPQVNEKTKKKVLEVMKENNYRPNSVARSLSTSRSY
ref|ZP_01188890.1|    MATIKDIAKLAGVSVTTVSKVINNYPDISDKTKEKVIKIMEQQNYRPNAIARSLSTSRSR
ref|NP_242794.1|      MATIYDIAKKTGYSITTVSKVLNNYTDVSDKARKKVMDAVTEMGYFPSSSARMLTTKKSW
RAAC00269             MTTIYDIARRAGVSATTVSKVLNGYPDVSQKTREKVQRITRELGYQPNAAARGLVTRRSM
ref|NP_244559.1|      MTTIKDIAKVAGVSVTTVSRALNGYSDVNEKTRKKIKDIANELKYSPNVMARSLVMNRSK
                      *. *: :* * :***:.:*.*.::.:*:::*:    :  * *. ** *   :* ref|ZP_01188246.1|    IIGIFFTDHFNTGIHHPFFREVIYGLEKIFDEKGYDILYFTNRKWGENF---SYVEKCHD
ref|ZP_01188241.1|    TIGIFFTDHFDTGLRHPFFREVIYGLEKIFGQKGYDILYFTKRNWDDKCS---YVDKCRD
ref|ZP_01188890.1|    SIGVFFTDHLNSGLRHPFFRDIIYGIEKTFFRKGYDLILFAH-QWGDRFS---YTEKCKS
ref|NP_242794.1|      TIGVVFVESAGIGMEHPFFSSVIENFKKNVERFGYDLLFASNQI-GNEAK--TYLEHFRY
RAAC00269             SIGVFFQDDARMGFRHPFLHDIVASFQDVVGESGYDLLFFSRTTPPNAPQG--FEARARH
ref|NP_244559.1|      TIGLLVSEISREGAKDNFTFEVLCGINDRASESDYDIILFNTNTSKQKLKS--YTQLCRE
                      **:.. :      * .. * .::.::.   ..**::         :        :    :

ref|ZP_01188246.1|    RQ--VDGVVLMGVPKTDSNIPKLLDSDIPTVFVDLDIVGKKASYVISDNYRGAEMAVNYL
ref|ZP_01188241.1|    RH--VDGVVLMGVSREDTNLPQLLDSGIPTVFIDVDIIGKRASYVTLNNTDGAKMAVNYL
ref|ZP_01188890.1|    RH--VDGAILMGMPRTDPNLDKLVNSNIPTVFIDLDIVGKNATYVISDNVQGAKQAVNYL
ref|NP_242794.1|      RG--VDGIVVVCSLLNDPEVEKLMKADIPSVVIDLDSKGSSAVY--SDNEYGSELAVDYL
RAAC00269             RG--VDGLFLLGIPRTSPGLPSLVRSRIPIVSVDLDLFGPRASWLSSDNVGGARLAVEHL
ref|NP_244559.1|      RC--VDGVILQGIKKEDPYLEEVIESDIPCVMVDIPITGESVSYVTTDNVDGAKKAVETL
                      *   *  .:        .. : .::   :  * :*:   *   .  :   *:. **: * ref|ZP_01188246.1|    HSLGHTRIGMIMGISSTKVTNDRLLGYQTAIKNLGLVYNSQWILDG-RYTEEGGYQAMSK
ref|ZP_01188241.1|    YSLGHTKIGMIMGISSTKIAHDRFLGYQMALKDLSLSYNPDWVLNG-LFSEEGGYRAMNK
ref|ZP_01188890.1|    YSLGHIKIGMIMGQRITKPAQDRLIGFQEELTNLGLEYNPEWIIEA-EFGEEGGYQAMKR
ref|NP_242794.1|      VSLGHRSIAHISGDQGLFVGVQRLKGFKDAIQKLNLSISDEYIVDGGFFTYEGGQRAMEA
RAAC00269             AAMGHTKIGFVGDRYGTKPGQDRALGYHMAMQELGLTFRSEWVAEG-DFMEESGEEAMHR
ref|NP_244559.1|      IDFGHRKIAMMNGHERAYVSGKRKLGYEQALQEAGIPLQEEWVLNG-EFSEQVAEKEAYQ
                      :** *. :  .      .* *::  :.. :   ::: :.  : ...

ref|ZP_01188246.1|    YLEMDERPTAIFCQSDSMAIGAMQAIHEAGMSVPEDFSLIGFDDIEVSRYVNPALTTIKQ
ref|ZP_01188241.1|    FLKMIDRPTAIFCQSDTMAIGAMKANMNVPGDFSIIGFDDDIEISKYVKPALTTIRQ
ref|ZP_01188890.1|    IITQEIRPSAVFCQGDEMAIGAINAIKEHGYNVPQDFSIVGFDNIEISSYVSPGLTTIHQ
ref|NP_242794.1|      LLRNRVRPTAVYAAGDLMALGAIDTIRKHGLSVPEDFSIVGFDDIQMIRYTAPALTTIRQ
RAAC00269             ILEAREWPTAVFFASDMMAIGAMKALRQRGLEPGRDISLVGFDDVAIARLVTPSLTTIRQ
ref|NP_244559.1|      FLQKHSDVTAFFCASDLMALGVMKAAKLLNLRLPEQLSVIGFDDILLAQYTSPPLTTVAQ
                      :      :*.:  .*  **:*.:.:     ::*::***:: :    . * ***: * ref|ZP_01188246.1|    DKIGLGRAAGELLINIVENENESQAPVILPVELVKRDSCGR---
ref|ZP_01188241.1|    DKVKLGRAAGKLLLNIINNDLDGYKPVILPVKLIKRKSCAKL--
ref|ZP_01188890.1|    DKLTMGKKAASILLEMINNPNKTFSPVVLPTKLIERESCRKIG-
ref|NP_242794.1|      NTDLIGKTAANLLLDQINENEKQSLSVKIPVTLIERDSCRKI--
RAAC00269             NTRAMGEEAARELLDLMQNPNRPPRVITIPVELVSRDSVARIGG
ref|NP_244559.1|      NKYQMGYAAAGLLIDRLRMKEVPP-FHMLDNELIIRESVAK---
                      :.  :*  *.  *:: :.            :  *: *.*  :
```

FIG. 92

```
ref|YP_518526.1|         ------------------------------------------------------------
ref|ZP_01369294.1|       ------------------------------------------------------------
ref|YP_430255.1|         ----------------------------------------------------ETGSTDTGG
ref|YP_001213325.1|      ------------------------------------------------------------
ref|YP_361384.1|         ------------------------------------------------------------
RAAC02012                MGGIALKRHGRRLAWVAVAAAAFGAWHAWPRPERPHAHAHGSHSVAPSSASWTATDPGTT ref|YP_518526.1|         -LKDRVTVLLIGMDNRPGE-ALSNTDTLMVASLDQKSKKMVLLSVPRDTQVIL-NQKKEK
ref|ZP_01369294.1|       -LKDRVTVLLIGMDNRPGE-ALSNTDTLMVASLDQKSKKMVLLSVPRDTQVIL-NQKKEK
ref|YP_430255.1|         SQPGTLNILLLGTDARPGE-KVGNTDTIILAHFDGE--RLALLSIPRDTRVNIPGHGVDK
ref|YP_001213325.1|      ----RLNVLLLGIDARQGE-TMARTDTMILASVDTKSKQMILLSIPRDTGVEIPGHGWDK
ref|YP_361384.1|         ---GRVNILLLGVDDRHSKNRRERTDTIIFASIDSNLKKVVLVSIPRDTRVNIPGHGWDK
RAAC02012                RLGGRETILVLGSDKRPED-PRGNADVLLVASLDDSHRRIELLSIPRDTQVAFPDGRYHK
                            .:*::*  *   *   .    ..:*.::.* .*  .  :: *:*:****  *  :    .* ref|YP_518526.1|         VNAIARLQKGPISTQQYLQELLGTPIDGYVLTNFQGFKNIVDGLGGITIDVEKDMYYDTG
ref|ZP_01369294.1|       VNAIARLQKGPISTQQYLQELLGTPIDGYVLTNFQGFKNIVDGLGGITIDVEKDMYYDTG
ref|YP_430255.1|         INAAYSIG-GPDLTTSIVADLTGVPISKYVLLRWDGFIKIIDLLGGVTVNIPRDMYYY--
ref|YP_001213325.1|      INSAAVYG-GPELSMKVVSNLLGIPVRYYVLTNFSGFKDIVDALGGVTLEVEQNM-YHEG
ref|YP_361384.1|         INAAHVVG-GIDLTKQVVSDLLGKPVDYYVLVNFEDFKKVIDTLGGVTIDVEKDM-YHAD
RAAC02012                INEALASG-GPEETCMLVERLIGLPIDHYAIIRFDALVHMVDRIGGLDIDVPRNMDYRTG
                         :*       *     :     :  * *.:  *.:  .:.  : .::* :**: ::: ::* * ref|YP_518526.1|         EAQDR---FINLKKGVQRLNGTQALQYARFRNDELADITRTSRQQEVIKAIVAEATTPRN
ref|ZP_01369294.1|       EAQDR---FINLKKGVQRLNGTQALQYARFRNDELADITRTSRQQEVIKAIVAEATTPRN
ref|YP_430255.1|         DPVDGPQYKINLKKGLQHLDGHQALAFVRFRKEALGDIDRTGQQQELIKALLEKVRQPGT
ref|YP_001213325.1|      DEEYGGAYGINLKKGVQRLDGDKALQYVRYREYPMGDIDRTRAQQKFLVALAKEVLQPST
ref|YP_361384.1|         EYPY----TINLKKGRQHLNGEKALMYVRYRSDALGDISRTQRQQKFLKALAEQALQPGT
RAAC02012                DKVYG---VIRLRKGRHHLSGEQALQFVRYRHDALGDIGRTERQQAFLVALKDQLLRPQT
                         :          *.*:**  ::*.*  :** :.*:*   :.** ** **  .: *:   :    *  .

ref|YP_518526.1|         IPKLPIIIPKVYQAIDTNLNLGQIWALAMAFKNKDTYEVINQTLPGQFS-----DEE---
ref|ZP_01369294.1|       IPKLPIIIPKVYQAIDTNLNLGQIWALAMAFKNKDTYEVINQTLPGQFS-----DEE---
ref|YP_430255.1|         LLKMPRLLPEIYKNVETNMGLDEMLTMARAGLHLKNMTVVSQTLPGYFQ-----TING--
ref|YP_001213325.1|      IPKLPKLIPEISRYVKTNLSVSEMYKLAAAAKNLENGNILTQTLPGR-----PVEIGG--
ref|YP_361384.1|         LLKLPKLIPEIIQMVETDMSTKDLMSLLAFSRELNKDSIITQTLPGYFY-----NYN---
RAAC02012                LPRLPEVAFDAWKMIDTDMSLGDISRLAARAPQYKTYRTVHTTLPGSFHDP-DPSIPG--
                         : ::*  :   .   : :.*::. ::    :  .   . ... :     :      **** ref|YP_518526.1|         --GISYWKVNPKETKVILNQLF-QGKTSP-IFETIQKVHVPAQPPASKEAKP-------
ref|ZP_01369294.1|       --GISYWKVNPKETKVILNQLF-QGKTSP-IFETIQKVHVPAQPPASKEAKP-------
ref|YP_430255.1|         ---ISYWGVDPAQARQVAQALFEYGQTTK---------QVVLDAPASQT----------
ref|YP_001213325.1|      ---ISYWGVEPAEARQMVAKLF-NGETVT---------NVV-----------------
ref|YP_361384.1|         --GVSYWQADLEVAKNLVDMLFA-GQIEQ---------NIVLGTKE-------------
RAAC02012                --DLSYWVVNPAEARYVAKRFFADGEVPPRIIQDPRETRTWLPPEARAAQRPADRSTSG
                            :***  .:     ::  :    :*  *:             .
```

FIG. 93

```
ref|NP_354021.1|        ----------CPVESALSFLDGKWKGVILYHLIN----EGTLRFNELRRHIPSVTQRMLT
ref|ZP_01074644.1|      ----------CPVERALEIIGGKWKGAILYHLLDSSNQGGSIRFNELRRIMPNITQRMLT
ref|NP_772010.1|        ----------CSVEATLDLIDGKWKGVILYHL-----QDGTQRFGELRRRMPGITQRMLT
RAAC01701               MSSGHRGDSPCSAVSTLQVLSGKWKWLILYHLFQ----HPSLRFSELMRRIPGITQRVLT
ref|NP_691275.1|        ----------CSVEDALGILVGKWKPIILLHLME----KGTVRFSDLKRSIPGITQKMLT
ref|YP_174284.1|        ----------CEVDTALEILVGKWKHKILFQLMT----HDVMRFNELKRAIPGITQKMLT
                                  *  .:* .: **** ** :*        **.:* * :*.:**::**

ref|NP_354021.1|        KQLRELEEAGLISRTVFPVVPPRVDYALTPLGETMRPVISALKSWGDAHV----------
ref|ZP_01074644.1|      KQLRELAETSLISRTVYPEVPPRVEYAMTDYGKTLAPVIDSLRAWGISHL----------
ref|NP_772010.1|        KQLRALEEDKLVIRKVYAEVPPRVEYCLSELGESLRPVIDILKAWGESHQQR--------
RAAC01701               KQLRELEEEGIVERTVYPEVPPRVEYAITPYGQSLRPILDLMHAWGLEHLRRKAERALQE
ref|NP_691275.1|        KQLRELENEEIINRVVYPEVPPRVEYSISEYGRTLEDLLHAMHEWGQAHTIRKQQK-LQE
ref|YP_174284.1|        SQLRELESHDIVERKVYPQIPPKVEYSISEYGKSLQPVLDAMHEWGKNH----------
                        .*** *  .  :: *  *:. :**:*:*.::   *.::   ::   :: **  * ref|NP_354021.1|        ---
ref|ZP_01074644.1|      ---
ref|NP_772010.1|        ---
RAAC01701               PKL
ref|NP_691275.1|        ---
ref|YP_174284.1|        ---
```

FIG. 94

```
ref|ZP_02330514.1|        --------------LCPRFEHAFEILGKRWTGLIIRVLLSGPKRFKDISDVIPGMSDRML
RAAC00927                 -----MIVMGNHEQICPRFEWAFALLGKRWTGLIIRVLLEGPKRFKDISDMIPNMSDRML
ref|YP_001376921.1|       --------MEHNSCLCPKFESAFTLLSKKWTGLIIKSLLEEPKRFREIADIIPNMSDRML
ref|YP_001253394.1|       --------------MCPKFENAFELLGKRWTGLIIRTLLNGQKRFSDIAEAIPNMSARML
ref|YP_001308605.1|       --------------MCPRFENAFELLGKRWTGLIIRTLLNGQNRFSDIEEAIPNMSARML
ref|NP_347485.1|          -------------KLCPHFEAAFELLGKRWTGLIIHSLLKGAKRFSDIQDIIPNLSARML
                                       :: ** :*.*:****: .  :** :* : **.:* *** ref|ZP_02330514.1|        SERFKELEAADIVVRKVYPETPVRIEYELTEKGKALRPVMDELQKWAEKW----------
RAAC00927                 AERFKELERAGLVVRRVYAETPVRIVYELTPKGEALRPVMEAVQKWGDEWVTDSDCDEYQ
ref|YP_001376921.1|       SERLKELESEGIVVRNVYPEVPVRIEYGLTDKGKALESVMNEVQNWAEKWV---------
ref|YP_001253394.1|       TERFKELEEEGIIIRKVYPETPVRIEYELTEKGLDLQAVMDEIQKWAEKW----------
ref|YP_001308605.1|       TERFKELEKEGIIIRKVYPETPVRIEYELTEKGRDLQSAMDEIQKWAEKW----------
ref|NP_347485.1|          TERFRELEKQGIVVRKVYAETPVRIEYELTEKGRELESVMQEIQKWAEKW----------
                          :::*   .:::*.**.*.**** *     *...*: :*:*.::* ref|ZP_02330514.1|        ------------
RAAC00927                 RRYKCSSRDRAL
ref|YP_001376921.1|       ------------
ref|YP_001253394.1|       ------------
ref|YP_001308605.1|       ------------
ref|NP_347485.1|          ------------
```

FIG. 95

```
ref|YP_001643469.1|    ----------------------------------SGLTPPQFYILKILDHYGASRATQLAE
RAAC00935              MRGDMDALTQRFAQSLGVLAQEFGPHLLNRLH-TGLTAGQFFTMQMIRREGRLKVSQLAE
gb|AAB87745.1|         ----------RLDQAFYKAMKTLGPKVYEKLE-HNLTGEQFFVLNTLEQKGRITSSQLAE
ref|NP_391166.1|       -----DQLMSDIQLSLQALFQKIQPEMLESMEKQGVTPAQLFVLASLKKHGSLKVSEIAE
pdb|1S3J|A             -----DQLXSDIQLSLQALFQKIQPEXLESXEKQGVTPAQLFVLASLKKHGSLKVSEIAE
ref|YP_001422559.1|    -----DQYVSDIQKSLQTLLQNIQPEMVESMAKHEVTPAQLFVLASLKKHGSCKVSEIAE
                                           :*    *::  :   :  :  *       :::**

ref|YP_001643469.1|    KMYVKPSAITVMTDRLIDHGLVERYHDDNDRRVVVIELTKKGKTTVEEAMAARNEHIAKY
RAAC00935              RLEVTPSAITVMIDRLEHHGYVSRVRDEEDRRVVVIELTEAGRAKLAEVERAWFEMMRQM
gb|AAB87745.1|         ELQVKPSAITAMVDRLLKNDFVIRERDEKDRRAVYVRISDEGRRALKSSVKKRNIIMEKY
ref|NP_391166.1|       RMEVKPSAVTLMADRLEQKNLIARTHNTKDRRVIDLSLTDEGDIKFEEVLAGRKAIMARY
pdb|1S3J|A             RXEVKPSAVTLXADRLEQKNLIARTHNTKDRRVIDLSLTDEGDIKFEEV-----------
ref|YP_001422559.1|    RMEVKPSAVTLMADRLEQKGLIVRKHNQQDRRVIDISLTKKGETKFEDVVEGRKAILARN
                       .  *.***:*    ***  .:.  :  *  ::  :***.:  :  ::. *    .  .

ref|YP_001643469.1|    FSHLE-------------------------------------
RAAC00935              VSRIEPGAFKQCVSALETMVAAAKQLRMESYGEETPRQEV---
gb|AAB87745.1|         MSKLTEEEMEQLTTVLEKLTS----------------------
ref|NP_391166.1|       LSFLTEEEMLQAAHITAKLAQAAE-------------------
pdb|1S3J|A             -------------------------------------------
ref|YP_001422559.1|    LSVLTDDELIQSVNIIRKVAEAAENTRLIKKKTNRKEELPKHE
```

FIG. 96

```
ref|YP_001126687.1|     ---------------PSAMNEKTVAELEKLLRYIAANLKQRGREILTNYPITPPQFVALQ
ref|YP_148522.1|        ----------------------VAELEKLLRYIAANLKQRGREILTNYPITPPQFVALQ
ref|NP_693030.1|        -----------------ELSDSVNQMEKRLRYISGMIKQNGRKILNNYPITSPQFIALQ
RAAC02041               MVRFIGLWARTGCGYPLADYSPFVEEIEKALRLVAATVRRRGRVLLKDYDLTSPQFDALI
ref|YP_001320949.1|     -------------------------EIEKELRYLCTVIKQKGREILTDFQITPPQFQALQ
ref|YP_001512727.1|     ----------------ARYDDNIIEIEREIRYLCTKIKQKGREILADFSITPPQFEALQ
                                            ::*: :* :.   :::.** :* :: :*.* ref|YP_001126687.1|     WLLEEGDLTVGELSNKMYLACSTTTDLIDRMERNGLVSRVRDEHDRRVVRIHLLEKGERI
ref|YP_148522.1|        WLLEEGDLTVGELSNKMYLACSTTTDLVDRMERNGLVARVRDEHDRRVVRIRLLEKGERI
ref|NP_693030.1|        WLLEEGDLTIGELSNRISHAFSTTTDLVDRMEKNELVERVRDTNDRRVVRIHLLEKGKHI
RAAC02041               TLYNEGELTIGELSAKLYLAYSTTTDLVDRLERAGYVSRQRDLVDRRVVRVQLRDKGAQV
ref|YP_001320949.1|     YLISEDSLTIGELSNKMFLACSTITDLVDRMEKNDLVKRARDEKDRRVVRIVVVLDNGHEI
ref|YP_001512727.1|     YLNNCQGITIGELSNKMFLACSTVTDLVDRMEKNDLVKRVRDEKDKRVVRPQVSEKGYQL
                         *  .    :*:****  ::    * ** ***:**:*:    * * **  *:****   : ::* .:

ref|YP_001126687.1|     IEEVIEKRQRDLARVLENFSDEE-------------------
ref|YP_148522.1|        IEEVIEKRQRDLASVLESFSDEE-------------------
ref|NP_693030.1|        IEEVIDKRQAYLGEVLTKFSEEEKEQLNQLLDFLYTEM---
RAAC02041               IEAVLSARRAYLDSILKHVSIEQRRAILQALDLLLTNMGNS
ref|YP_001320949.1|     INQVLHARRNYLEEVLLDVSSEQRDSVLQGISLI-------
ref|YP_001512727.1|     IEEVLHARRNYLADVMKDVSEKDRKFILDGITMI-------
                        *: *:  *:  *   ::  .*  ::
```

FIG. 97

```
ref|NP_629113.1|          ---------------------------------------------------------ET
ref|NP_824479.1|          ---------------------------------------------------------DT
ref|ZP_01169478.1|        -------------------------------------------------MSKEKQNDVEL
ref|NP_631123.1|          ---------------------------------------------------------ET
RAAC02241                 MRGHEKFLLPSDTKCQLPVPNCSGTREMKSTQLLYYTTITLKMHPKEADMDQANMDSFEA
ref|YP_001508494.1|       ------------------------------------------------------DSLRD ref|NP_629113.1|          LQHEVALFARRAEQTRLGGVGQVRNSMDRAAYLLLNRLDKEGPMGVKALAASMGIDSSTV
ref|NP_824479.1|          LQHEVAVFARRAEQTRLGGVGQVRNSMDRAAYLLLNRLDKEGPMGVKALAASMGIDSSTV
ref|ZP_01169478.1|        IEYELATFIRKAVYLEQS--EKKIGQLERSAYLLLRQLDEFGPARVKELAEAFKLDISTL
ref|NP_631123.1|          IQREMTVFARRARAS----AGRMHPELSLVSYTLLGHLEERDGRRATDLAAHYALDKSTV
RAAC02241                 LEREMAIFARRLEGARQS--WRKHREIDRSAYLILLALREEGELTAGQLAARFLLDISTI
ref|YP_001508494.1|       LERELMLLARHHIAPNAARRGRTR-HLDRSAYLLLSRLEAQGPMTIGQLAEAFSLDVSTV
                          ::  *:   : *:            :.   :*  :*   *    .     **    :* **:

ref|NP_629113.1|          TRQVAPLVDTGLVKRTSHPEDGRAVVLQLSPRGVARLEEVRSSRRQLMAELTHDWAPQER
ref|NP_824479.1|          TRQVAPLVDTGLVKRTSHPEDGRAVVLQLSPRGMSRLEEVRSSRRQLMSELTHDWAPQER
ref|ZP_01169478.1|        SRQAASLESKDLIKRCSDPKDGRVSVFSITDLGKEKLEADIANRRAHYFKVLNDWTEEEK
ref|NP_631123.1|          SRQVSALERAGLIERRVDPDDHRVQVLHLTESGRDVLDRVTERRRAAFRERLADWPEEEL
RAAC02241                 SRQITPLVEAGWIAKERDEDDKRQLRLSITEAGVEALEATRASRIELYRELVGDWTEEER
ref|YP_001508494.1|       NRQTAAVLQAGLAERIPDPDGGLARKLSITPEGARRVADDRAFVIGELSGLVSTWSEDEL
                          .**  :.:     .    :   ...     : ::    *   :             *. :* ref|NP_629113.1|          ETFCALLARFNGALSAR------
ref|NP_824479.1|          EAFTALLTRFNTALSDR------
ref|ZP_01169478.1|        EIFGKLVVRLN------------
ref|NP_631123.1|          LRFAAYLERYNAWPDAAPGAER-
RAAC02241                 RTFLGLLRRLNERIRARQQAERT
ref|YP_001508494.1|       RLFASMLERLNTSIETK------
                            *   : * *
```

FIG. 98

```
ref|NP_388620.1|            ----------------------IDQVAKRSGLTKRTIRFYEEIGLIPAPKRTDGGVRLYS
ref|YP_001420380.1|         ----------------------IDQVAKRSGLTKRTIRFYEEIGLIPAPKRTEGGVRLYS
ref|YP_090401.1|            ---------------DVEWMKIDQMAKRSGLTKRTIRFYEEIGLLSSPKRTEGGVRLYS
ref|YP_077997.1|            ----------------------IDQMAKRSGLTKRTIRFYEEIGLLSSPKRTEGGVRLYS
RAAC02671                   MAYTGVRQKMRRWKMDRDKAWTVEAVAERLGITPRTLHYYEEKGLIPEVPRTPGGHRVYD
ref|YP_714968.1|            ----GVRDKDQMKKAARELCGIGQA-AQELGVSVRALRYYQEVGLLTPSGRTSGGNRLYA
                                :   *:. *:: *:::*:* :.      ** *:* ref|NP_388620.1|            EDDMEELEKVISTKEVLGFSLQELQHFMETSRQLELNKEGYLLSLDPKERKEKLEEIQET
ref|YP_001420380.1|         EDDMEELEKVTSTKEVLGFSLQELQQFMEMSRQLELNKEGYLLSLDPKERKEKLEEIQQA
ref|YP_090401.1|            EDDLEELERVISAKEVLGFSLQELQQFMETGKHLEMNKEGYLLSLDKRERKEKLEDIQRM
ref|YP_077997.1|            EDDLEELERVISAKEVLGFSLQELQQFMETGKHLEMNKEGYLLSLDKRERKEKLEDIQRM
RAAC02671                   EDTIERIEHILRLKEALGYSLQEIRSILSTEDQLKAYRARIAEGHEPEHNVQMLSESVRL
ref|YP_714968.1|            DSDLARVRRIRELQTLLGFNLDEIGTILAYEDRLAQVREFHAASDDGDRLRLLSEGETA
                            :.  : .:.::     :  **:.*:*:  ::    :*   :   . :   ... *.:

ref|NP_388620.1|            LNHQLDLIDEKIRTFQSFKE----------------------------
ref|YP_001420380.1|         LNHQLEMIDEKISTFQHFKTRLNGMKE-----------------------
ref|YP_090401.1|            LNEQMRMIDEKIEKFQSFKK-----------------------------
ref|YP_077997.1|            LNEQMRMIDEKIEKFQSFKK-----------------------------
RAAC02671                   LEDVVRHIDEKMLRLGSMREHYMDRLARIRARLEREEAATRTVGFPDQEGE
ref|YP_714968.1|            YVKLRAEIDEKISRLAAFRD-----------------------------
                            .      ****:   :  ::
```

FIG. 99

```
ref|YP_001141973.1|      --RTYSISELAREFDVTTRSIRFYEDQGLLNPARQGQTRIYSKQDRVRLKLTLRGKRLGF
ref|YP_856665.1|         --RTYSISELAREFDVTTRSIRFYEDQGLLNPARQGQTRIYSRQDRVRLKLTLRGKRLGF
ref|YP_927240.1|         ----YSISDLSKEFDITTRSIRFYEDQGLLKPKRRGQTRIYSLKDRVRLKLILRGKRLGF
ref|YP_001141729.1|      ----YSISELAHEFDITPRTIRYYEDEGLITPTREGQTRIYSHKDKIRLKLTLRGKRLGF
ref|YP_427081.1|         -RDSFSIADLAAEFSVTPRAIRFYEDKGLITPARDGMRRIYSPRDRVRLMLILRGKRLGF
RAAC00549                MRRYYTIRDLADMFDITPRTLRHYEDMGLLKPARRGAKRLYSERDRVRLQLILRGRRLGF
                          :.*  :*:   *.:*.*::*.***  **:.* * *   *:** :*::** * ***:****

ref|YP_001141973.1|      SLADIRDLFDLYDADKSSRTQLQTMLGLVADKRETLQQQLEDIKMVLLELDAAEQRCQQA
ref|YP_856665.1|         SLADIRDLFDLYDADKSSRTQLQTMLGLVADKRETLQQQLEDIKMVLLELDAAEQRCQQA
ref|YP_927240.1|         SLAETRRLFELYDADKTSVTQLNTMLALIEEKKAALQQQMDDIKVVLMELTSAEAQCRGA
ref|YP_001141729.1|      SLAEIRELFDMYDTDRSSKTQLHSMIQLINAKRQSLHQQLEDIQMVMAELEAAEQRCANS
ref|YP_427081.1|         SLKEIQEIIDLYDAEPTGEAQLRRLITTCQTSRAALRQQMEDIRITIDEIEAVEAQCRQA
RAAC00549                SLPEIAEMLDLYDADPTEITQLREVIRRGDEKLRHVELQISELEALRDELIAMRSRLQQV
                         **  :    :::: **::  :   :**. ::        .   :. *: .:: .   *: : . :

ref|YP_001141973.1|      L--------------
ref|YP_856665.1|         L--------------
ref|YP_927240.1|         LD-------------
ref|YP_001141729.1|      LN-------------
ref|YP_427081.1|         L--------------
RAAC00549                LDDKLKQCHQKGCDD
                         *
```

FIG. 100

```
dbj|BAA00729.1|         ----------------------------------------RRSMPLFPIGIVMQLTELSA
ref|NP_389627.1|        ----------------------------------------RRSMPLFPIGIVMQLTELSA
ref|NP_833433.1|        ----------------------------------------EDRRSAPLFPIGIVMDLTQLSA
ref|YP_001375615.1|     ----------------------------------------EDRRSAPLFPIGIVMDLTQLSA
ref|ZP_02328256.1|      ----------------------------------------RRNMALFPIGIVMKLTDLTA
RAAC01080               --------------MSWRALHVTISFNRSHREGRAVDLEERRNMPLFSIGTVQKLTGLSA
                                                                  . ..** * .** *:* dbj|BAA00729.1|         RQIRYYEENGLIFPARSEGNRRLFSFHDVDKLLEIKHLIEQGVNMAGIKQILAKAEAEPE
ref|NP_389627.1|        RQIRYYEENGLIFPARSEGNRRLFSFHDVDKLLEIKHLIEQGVNMAGIKQILAKAEAEPE
ref|NP_833433.1|        RQIRYYEEHNLVSPTRTKGNRRLFSFNDVDKLLEIKDLLDQGLNMAGIKQVLLMKEN---
ref|YP_001375615.1|     RQIRYYEEHNLISPTRTKGNRRLFSFNDVDKLLEIKDLLDQGLNMAGVKQVLQMKEN---
ref|ZP_02328256.1|      RQIRYYEQHELVIPARTSGNQRLYSFNDVERLLEIKDLIEKGVNIAGIKQVLLPVSKDSE
RAAC01080               RQIRYYEEHGLIQPARTPGNQRQFSFADVERLMQIRQLLDEGHNIASVKRNLLEKDRRPR
                        ******:: *: *:*: **:* :** **::*::*:.*:::* *:*.:*: *   .

dbj|BAA00729.1|         QKQNEKTKKPVKH-DLSDDELRQLLKNEL---MQAGRFQRGNTFRQGDMSRFF---
ref|NP_389627.1|        QKQNEKTKKPMKH-DLSDDELRQLLKNEL---MQAGRFQRGNTFRQGDMSRFF---
ref|NP_833433.1|        QTEAVKVKEETK--EISKTELRKILRDEL---QHTGRFNR-TSLRQGDISRFF---
ref|YP_001375615.1|     QTEAVKTKEETK--EISKAELRRILRDEL---QHTGRFNR-TSLRQGDISRFF---
ref|ZP_02328256.1|      EATYLNEASETKRKELTDSQLRQLLKQQI---VGARRPGQ-VSLIQGELSRFY---
RAAC01080               SSRPLATR------DVPDSEVYQWLEREL---MERRQTGE----FQGDLSRFYRHR
                        .              ::.. :: : *. ::          :  .   **::***:
```

FIG. 101

```
ref|YP_146517.1|         ----------------------QIIEAAAQSFAAFGYKATTMEQIAKLANVGKGTIYTF
ref|YP_001124699.1|      ----------------------QIIEAAAQSFAAFGYKATTMEQIAKLANVGKGTIYTF
ref|ZP_00739458.1|       -----FGGEDVAIDRKRS-----IIEAATKSFSAFGYKATTMDQVAKLANVGKGTIYTF
ref|NP_830863.1|         ----------MAIDRKRS------IIEAATKSFSAFGYKATTMDQVAKLANVGKGTIYTF
ref|YP_893832.1|         -----FGGDDVAIDRKRS-----IIEAATKSFSAFGYKATTMDQVAKLANVGKGTIYTF
RAAC01126                MTKLEFWSECVAMRRKRGMTVRDRIEEAAKRAFSEFGYKGTTMDQIARLAGVSKGAIYLH
                                                * ***  ::*: ****.***:*:*:**.*.**:** .

ref|YP_146517.1|         FKSKEELLDEIVSGLIMEIKAEAELAMDSSLPFSENVHRALYRILEFRQRHQLTAKLLQE
ref|YP_001124699.1|      FKSKEELLDEIVSSLIAEIKVEAEQAMDSSLPFSENVHRALYRILEFRQRHQLTAKLLQE
ref|ZP_00739458.1|       FKNKEELFGEIISNLITEMKQVAESAIRSDVSFFENVHRALYSILEFRKEHQLMIKLIQE
ref|NP_830863.1|         FKNKEELFGEIISNLITEMKQVAESAIRSDVSFFENVHRALYSILEFRKEHQLMIKLIQE
ref|YP_893832.1|         FKNKEELFGEIISNLITEMKQVAENAIRSDVSFFENVHRALYSILEFRKEHQLMIKLIQE
RAAC01126                FPSKEALFQHMLRGVIAQVRDAFESAQVEGDDYFRNLERGLRALMRFRADHAMLSKLVQE
                         * .** *: .:: .:* :::    * *  ..  : .*:.*.*  ::.**  * :  **:**

ref|YP_146517.1|         VRNIGTAAVQEVLAKLDRAMVEFIRQKIDAAVEKGEIRPCNSEITAFLMLKTYIALIVDW
ref|YP_001124699.1|      MRSIGTIAVQEVLTKFDRAMVEFIRQKIEAAVEKGEIRPCNAEITAFLMLKMYIALIVDW
ref|ZP_00739458.1|       ERDMGTKEVQEVMQQVDVEIVSVIQSYLKIAIEKGEISKCDPEITAFIMLRLYVSLIFDW
ref|NP_830863.1|         ERDMGTKEVQEVMQQVDVEIVSVIQSYLKIAIEKGEISKCDPEITAFIMLRLYVSLIFDW
ref|YP_893832.1|         ERDMGTKEVQEVMQQVDVEIVSFIQSYLKIAIEKGEISKCDPEITAFIMLRLYVSLIFDW
RAAC01126                VRQFGTAEARAGLGELEAAILDYLARHLKRGVELGVVRPCRANLVAFVLLRAYTAVLRDF
                          *.:**   .:   : :.:   ::.  :    :. ..:* * :  * .::.**::*: * ::: *:

ref|YP_146517.1|         EKDHEPLTKEQIAELFTLYFLQGL-----------------
ref|YP_001124699.1|      EKDHQPLTKEQIAELFALYFLQGL-----------------
ref|ZP_00739458.1|       EKNHEPLEKEKIAELFELYLLKGL-----------------
ref|NP_830863.1|         EKNHEPLEKEKIAELFELYLLKGL-----------------
ref|YP_893832.1|         EKNHEPLEKEKIAELFELYLLRGL-----------------
RAAC01126                PSAEGPLSEEDLYQLFTGVFVDGLRLRPGEGEPRNTQSEQER
                          .  . ** :*.: :** ::  **
```

```
FIG. 102 ref|NP_832103.1|       -----KQRPLGRPRQNKNTKSTKENILEVATRLFLTQNYQVVSMDEVAKVCGVTKATVYY
ref|NP_978750.1|       -----KQRPLGRPRQNKNTKSTKETILEVATRLFLTQNYQVVSMDEVAKVCGVTKATVYY
ref|ZP_02215257.1|     -----KQRPLGRPRQNKNTKSTKETILEVATRLFLTQNYQVVSMDEVAKVCGVTKATVYY
ref|NP_844783.1|       -----KQRPLGRPRQNKNTKSTKETILEVATRLFLTQNYQVVSMDEVAKVCGVTKATVYY
ref|YP_894956.1|       -----KQRPLGRPRQNKNTKSTKETILEVATRLFLTQNYQGVSMDEVAKVCGVTKATVYY
RAAC01138              -MRNARSRRPGRPPQVEMEEPTAEKILRAAAECFMDQGFAAVSMDDVAERAGVTKAVVYY
                        .*   *** *  :   :.* *.**..*:.  *:  *.:  **:: .***.* ref|NP_832103.1|       YYSTKADLFTATMIEMMVRIRENMSQILSTNKTLEERLLDFAKVYLHATMDIDMKNFMKD
ref|NP_978750.1|       YYSTKADLFTATMIQMMVRIRENMFQILSTNKTLKERLLDFAKVYLHATMDIDMKNFMKD
ref|ZP_02215257.1|     YFSTKADLFTATMIQMMIRIRENMSQILSTNNTLEERLLNFAKVYLHATMDIDMKNFMKD
ref|NP_844783.1|       YFSTKADLFTATMIQMMIRIRENMSQILSTNNTLEERLLNFAKVYLHATMDIDMKNFMKD
ref|YP_894956.1|       YFSTKADLFTATMIQMMIRIRENMSQILSTNNTLEERLLNFAKVYLHATMDIDMKNFMKD
RAAC01138              YYGSKTELFQRAMMEVMRASRERTQAILRENGPLRERLQKLTRTRLAIPATLDMNHILRG
                       *:..*::**   :*:::*   **.   **   * .*.***  .:::. *   .  :**::::..

ref|NP_832103.1|       AKLSLSEEQLKQLKNAEDNMYEVLEKALDNAMHIGEIPKGNAKFAAHAFVSLLSIGNFKD
ref|NP_978750.1|       AKLSLSEEQLKQLKHAEDNMYEVLEKALDNAMQIGEIPKGNAKFVAHAFVSLLSIGNFKD
ref|ZP_02215257.1|     AKLSLSEEQLKELKKAEDSMYEVLEKALDKAMQLGEIQKGNPKFAAHAFVSLLSIGNFKD
ref|NP_844783.1|       AKLSLSEEQLKELKKAEDSMYEVLEKALDKAMQLGEIQKGNPKFAAHAFVSLLSIGNFKD
ref|YP_894956.1|       AKLSLSEEQLKELKKAEDSMYEVLEKALDKAMQLGEIQKGNPKFAAHAFVSLLSIGNFKD
RAAC01138              SQRALRPDQVDEMHRAEEQLVEVIAQELHAEMEQGRLRPVDAMFVARSYLALLGMGQAEI
                       ::  :*   :*:..:::.**:.:  **:   *.   *. *.:     :.  *.*::::**.:*: :

ref|NP_832103.1|       ENHNPILANIDELAQEIVSFYWNGL---
ref|NP_978750.1|       ENHNPILTNIDELAQEIVSFYWNGL---
ref|ZP_02215257.1|     ENDNPIIISIDELAQEIVSFYWNGL---
ref|NP_844783.1|       ENDNPIIISIDELAQEIVSFYWNGL---
ref|YP_894956.1|       ENDNPIIVSIDELAQEIVSFYWNGL---
RAAC01138              RRRGGGQAAIDEIAEEIVDLLWRGIEPR
                       .. .       ***:*:***.:  *.*:
```

FIG. 103

```
ref|YP_001309939.1|    MDRRIEKSKQAIMGAFIKLMSEKDFEKITINEIAEEANVNRGTVYLHYEDKFDLMNKCID
ref|YP_001643723.1|    VDRRIIKSKEAIKNAFIELMAEKGFDKITVKDICSGADVGNRTFYLHYLDKFDLLDKLVI
RAAC00354              MDRRVQKSRQAIRDAFVALMKEKDFDHITVQDITERANVSRKTFYLHFLDKYDLLDRVME
ref|YP_001647188.1|    -DPRVKRTRQLIQDAFVALVGEKGFENVTVQHIAERAPVNRATFYSHYHDKYDLLEKSIE
ref|NP_980994.1|       -DPRVKRTRQLIQDAFVALVGEKGFENVTVQHIAERAPVNRATFYSHYHDKYDLLDKSIE
ref|YP_079403.1|       -DRRVKRTKKMIRDALSELMKNKAFEEISVTDITKKADINRGTFYLHYEDKYDLLDQSEE
                        * *: :::: * .*:   *: :* *:.::: .* . * :.. *.* *: **:**:::

ref|YP_001309939.1|    THLNQLCD------SCISDGESSNFDSKA---SLLQTFQYLEKHAIFYSNMLTNKAMPAF
ref|YP_001643723.1|    ERIEALKT------LCAP---LHDLSFRE---ACIAWFENMEQHYFFFSTMLAGKGASAF
RAAC00354              DAIRDMDEFG----QCVS-----ELDWVP---ATEQCFQYLADRYDFFGTMLTQAGAPYF
ref|YP_001647188.1|    EMLEKLAAVIKPQNRNKEDF-QLTFDSPH--PTFLALFEHIADNTNFYNVMLGDKAAGNY
ref|NP_980994.1|       EMLEKLTKVIKQKNRNKEDF-QLTFDSPH--PSFLALFEHIAENANFYNVMLGDKAAGNY
ref|YP_079403.1|       EIIQEINKIAKRSIHSMDVLNQDVIDHPL--TFVVDIFQYIKENEVFMKAVLGPKGPGSF
                       :. :             :.          *: :..  *   :*    .  :

ref|YP_001309939.1|    RERILTMALKSMEEHL-DMTGSNE--NISKNIMAQYVASAAVGVMEWWIVNSMPYPAAYM
ref|YP_001643723.1|    RKHFFDYIIEQIKDDVDIKEGINK--GFSEDMIITFFGSAIVGVVETYFMKGLPDPPEIV
RAAC00354              RRRYVESCKASFTREIRRVVGRDP--LPEEDAILQFVVNAYVGTVEWWLQEGMPYPPRVM
ref|YP_001647188.1|    SYKMMKTIQTHLTLSLSISQPDDEDLMVPRDILISYVTGAHIGMIMSWLKRGMIYTPHFM
ref|NP_980994.1|       TYKMMKAIQTHLTLSLSISQPNDEKLMVPRDILISYVTGAHLGMIMSWLKKGMIYTPHFM
ref|YP_079403.1|       RLKF-KSVLISNLKRLKTAIRTDP--IVPEDYLISYITGAHISVQQWLENGMKETPHDM
                       :             :        .: : :..* :. :   ::  ...   .. :

ref|YP_001309939.1|    AEQLWQLLK-----------------------
ref|YP_001643723.1|    AEQLGMLLD-----------------------
RAAC00354              ADRIGRMLESVYTQLPSLAEKPASPRETSQVRPA
ref|YP_001647188.1|    AMQLTRLI------------------------
ref|NP_980994.1|       AMQLTRLI------------------------
ref|YP_079403.1|       A-------------------------------
                       *
```

FIG. 104

```
ref|YP_036650.1|       ------------------------------------------------------------
ref|NP_844911.1|       ------------------------------------------------------------
ref|NP_978853.1|       ------------------------------------------------------------
ref|ZP_02256518.1|     ------------------------------------------------------------
ref|ZP_01173627.1|     ------------------------------------------------------------
RAAC02712              ----------MTGGVPHPSVSHLRDGVAECFLDG------------NLSKGEYPMSERMD ref|YP_036650.1|       -WLEELIAATNTDKRNERQMRILEAAVDMFGEKGYASTSTSEIAKRAGVAEGTIFRYYKT
ref|NP_844911.1|       -WLEELIAATNTDKRNERQMRILEAAVDMFGEKGYASTSTSEIAKRAGVAEGTIFRYYKT
ref|NP_978853.1|       -WLEELIAATNTDKRNERQMRILEAAVDMFGEKGYASTSTSEIAKRAGVAEGTIFRYYKT
ref|ZP_02256518.1|     -WLEELIAATNTDKRNQRQMRILEAAVDMFGEKGYASTSTSEIAKRAGVAEGTIFRYYKT
ref|ZP_01173627.1|     --------------LTEKQRSILLAAIQMFSEKGYSATSTNEIAKLAGVAEGTIFRHYKT
RAAC02712              QWLTELVRLNEDDRVTDRQLNILRAAVEVFAEKGFAAASTSEIAQRAGVAEGTIFRHYKT
                                     .::*    :::*.*:::.*: ******:* ref|YP_036650.1|       KKDLLLAVVMPTLMKFAAPFFVQAFAKEIFKSEYESYEGLLRVVIHNRFDFAKKHFPMIK
ref|NP_844911.1|       KKDLLLAVVMPTLMKFAAPFFVQAFAKEIFKSEYESYEGLLRVVIHNRFDFAKKHFPMIK
ref|NP_978853.1|       KKDLLLAVVMPTLTKFAAPFFVQAFAKEIFESEYESYEGLLRVVIHNRFEFAKKHFPMIK
ref|ZP_02256518.1|     KKDLLLAVVMPTLTKFAAPFFVQAFAKEIFKSEYESYEGLLRVVIHNRFEFAKKHFPMIK
ref|ZP_01173627.1|     KKDLLLAIVEPIMSDLVAPYLIQD-IEQVLKQRPIRYEDFLRSLLDNRIAFLKKNLPIVK
RAAC02712              KKDLLLSITVPVIDEFVGPFLLRD-LETILTAQHERFEDFLRAVLFNRLQFAKKYAQVLR
                       ******::. *  : .:..*::::   : ::    .  :*.:** :: **: * **   :::

ref|YP_036650.1|       ILIQEVPFHPELKNEIQQLVETELLLHFKKLIEKFQEKGEIIE-MPPATVLRLTLSAVLG
ref|NP_844911.1|       ILIQEVPFHPELKNEIQQLVETELLLHFKKLIEKFQEKGEIIE-MPPATVLRLTLSAVFG
ref|NP_978853.1|       ILIQEVPFQPELKNEIQQLVETELLSHFKKLIEKFQEKGEIIE-MPPVTVLRLTLSAVLG
ref|ZP_02256518.1|     ILIQEVPFQPELKNEIQQLVETELLSHFKKLIAKFQEEGEIIE-MPPSSVLRLTLSAVLG
ref|ZP_01173627.1|     ILIQEIPFHPDLKKRFIEQIAEKVFQQFAKIVEYYQEQGQIISGIPPKSIVRMTFSALIG
RAAC02712              ILAQEIPFHPELKAQLKQYVTENVLKRLVGIIEHFQEKGEIAR-IPARTVIRLTVSVILS
                       ** **:**:*:**  .: : :   ::: ::   ::     :**:*:*    :*.  :::*:*.*.::.

ref|YP_036650.1|       LLLTRFLLLPEEKWDDETEIENTIQFILYGLTP-------
ref|NP_844911.1|       LLLTRFLLLPEEKWDDETEIENTIQFILYGLTP-------
ref|NP_978853.1|       LLLTRFLLLPEEKWNDEAEIENTIQFILYGLTP-------
ref|ZP_02256518.1|     LLLTRFLLLPEEKWDDEVEIEHTIQFILFGLTP-------
ref|ZP_01173627.1|     HLAIRYLFLPEAQWDDEAEVERTIRFVMNGLSP-------
RAAC02712              HVVLRHILFHDAPWRDDEEIEMTVRFIVQGLRPDASRDQK
                         :   *.::: :   * *: *:* *::*:: ** *
```

FIG. 105

```
ref|ZP_02327699.1|        MTS----KKREKYQLILDAALKVFAEHGFHRSQVSKIAKAAGVADGTIYLYFKRKEDILI
RAAC01059                 MTSGLAEKRREKYEAILKAALKMFAEHGFFNSQVSKIAREAGVADGTIYLYFKNKEDILI
ref|YP_001126706.1|       -------REKPKFKQIIDAAVVVIAEHGYHQAQVSKIAKQAGVADGTIYLYFKNKEDILI
ref|YP_148542.1|          -------REKPKFKQIIDAAVVVIAEHGYHQAQVSKIAKQAGVADGTIYLYFKNKEDILI
ref|NP_243968.1|          ----MGKKKGPKYDQIIDAAVQVIAEHGYHQAQVSKIAKAAGVADGTIYLYFNNKEDVLI
ref|YP_360433.1|          ----MAKKSIDKYEAILDAAAKIIGEVGYHKAQISKIAREANVAEGTIYLYFKNKQDLLL
                                    *:. *:.**    ::.* *:..:*:****:  *.**:*******:.*:*:*:

ref|ZP_02327699.1|        SLFREKLGELVSKFNQSIETSTDMKQALYHICRIHYTELEQDVDLAFVTQIELRQSSLEL
RAAC01059                 SLFREKLGSLVRKFHEHVHEDDRADEAIRKICELHFTELEKDVQLAKVTQLELRQSSREL
ref|YP_001126706.1|       SLFQEKMGSFIEKIEQEIEGISSPLEKLYVLVRTHFSALADDPHMAVVTQLELRQSNKEL
ref|YP_148542.1|          SLFQEKMGAFIEKIEQETEGISSPLEKLYVLVKTHFSALAADPHMAVVTQLELRQSNKEL
ref|NP_243968.1|          SLFQEKMGRFVDKIRSQMNEATDVEEKLKILVNMHFKQLAADHKLAIVTQLELRQSNTEL
ref|YP_360433.1|          SLFQKRYGEFISNLKVEIAAAKTPLDKLKKLITMHLENSEKDRNFAQVTQIELRQADRDL
                          ***::: *  ::  ::.         : :   :    *      * ..:* *:**:. .:* ref|ZP_02327699.1|        RREIGKAVKPYIVLIEQLLLKGIEEEVFRPDLDVKLTRSLIFGAMDEVVTSWLVSGRKYS
RAAC01059                 HSEISKALKPYIQLIEDVLVRGIEQGIFRRDLDVKLTRLLIFGAMDEVVSSWLISGRRYS
ref|YP_001126706.1|       RQRINEVLKGYLRLIDSIIIEGMEKGEFRNDLDVRLTRQMIFGTIDETVTTWVMNEQKYD
ref|YP_148542.1|          RHRINEVLKGYLRLIDRIIMEGMEKGEFRQDLDVRLTRQMIFGTLDETVTTWVMNEQKYD
ref|NP_243968.1|          RLKINEVLKGYLNLLDELLMEGKEKGYFFQELDTRLARQMIFGTLDEVVTNWVMKDCKYD
ref|YP_360433.1|          RQKLSELLKDYFYIIESVIEEGKEQGIFRKDISTKVIRRMIFGTLDETVSSWLLSSRRYS
                          :  .:.: :* *: ::: :: .*  *:   *  ::..:: * :***:**.*:.*::.  .:*.

ref|ZP_02327699.1|        LSDQVEGTVQFFLRGI--
RAAC01059                 LSAQVDKTVDFFLRGLRA
ref|YP_001126706.1|       LAALAEPVYELLAKGCAA
ref|YP_148542.1|          LAALADPVYELLVKGCAA
ref|NP_243968.1|          LTALVKPVHQLLLGGLR-
ref|YP_360433.1|          LAKLSDDVFQLFCYGI--
                          *:    . . :::  *
```

FIG. 106

```
ref|YP_076316.1|    -----------MGRNRRREAMLQAAIGLFSDKGYHATTVREIAQAVGILPGSLYAHMASK
RAAC01638           MLSGSAGGETRMPRPSQKDQILAAARRLFSEKGYHGTTIREIAVEAGVLSGSLYAHIESK
ref|YP_603589.1|    ---------PAKTR---REQIYDVASRLFSERGYHATSMRDLAGELGMQGGSLYAHISGK
ref|NP_296097.1|    --------ETTKPR---REQIHDVASRLFSERGYHATSMRDLAGQLGMQGGSLYAHISGK
ref|YP_004584.1|    -------------R---RSQILTIAGHLFSRKGYHATSMRELARHLNLQGGSLYAHIQSK
ref|YP_144239.1|    -------------R---RSQILTIAGHLFSQRGYHATSMRELARHLNLQGGSLYAHIQSK
                                 *   :.:   *   *  :*.*::*::*     .:   ******: .* ref|YP_076316.1|    EDLLYEAVVQASERFQEAVAPIAESPGHAGERLRQAMAAHIRVVAESPAAATVFLHEWRA
RAAC01638           EDLLFEIADEGAEAFLLAARAVESKWQHPVDRLREGLRAHIRVVADKQESAKVFFHEWRA
ref|YP_603589.1|    EDLLIEIVNRAARQFDAALFTLRDDPRPADHKLREAMYRHIRVVADNMESATVFFHEWKH
ref|NP_296097.1|    EELLVEIVRGASQQFDEALFSLRDVNLPADEKLREAMFRHIQVVADNMDSATVFFHEWKH
ref|YP_004584.1|    EELLLEVVRQAAERFQKVLEELPSG--DPVTRMKALVKGHLRVIAEELPRATVFFHEWKH
ref|YP_144239.1|    EELLLEVVRQAAERFQKVLEELPSG--DPVTRMKALVKGHLRVIAEELPRATVFFHEWKH
                    *:** *  .:. *  .  :.   .   :::   :  *::*:*:.   *.**:***:

ref|YP_076316.1|    LSPQRRAMAVAHRRAYEELLARIIREGVESGVFRPVD-EKFVRLLVLSAVNWTYQWYRAD
RAAC01638           LSDDRRKVIQSKRDRYEAHWRKWIEEGMAQGAVRKAD-PKFVRLCLLSVANWVYQWYRPG
ref|YP_603589.1|    LSPAAYARVTAWRDTIDTFYRELVRQGIDEGLFRHDLDVKMTANLILSAVNWTYTWYRPG
ref|NP_296097.1|    LSAEPYAQVVAWRDTIDIFYRDLVAQGVRDGTFRADLDVRAAANLILSAVNWTYTWYRPG
ref|YP_004584.1|    LSPPLLEEAKALRRRYEEGVQAVVEEGVRAGVFRVEN-VRLATLFVLSALNWTYQWYRPD
ref|YP_144239.1|    LSPPLLEEAKALRRRYEEGVQAVVEEGVRAGVFRVEN-VRLATLFVLSALNWTYQWYRPD
                    **          :  *   :       : :*:  * .*        :   :**. **.* ***..

ref|YP_076316.1|    GPLSPEQVADQFYAIIAGGL--------------
RAAC01638           GEFTPEDIAEHFWTLLFNGIGTGQPAACELLGEA
ref|YP_603589.1|    GTLTPRDVAEGYADMLLGGL--------------
ref|NP_296097.1|    GRLSPRDVAEQFADMLLSGLMAGE----------
ref|YP_004584.1|    GPLSLEALAEAYAELVLKALG-------------
ref|YP_144239.1|    GPLSLEALAEAYAELVLKALG-------------
                    *  ::  .  :*:  :   ::   .:
```

FIG. 107

```
ref|YP_148132.1|        ----RILVVDDEERIRRLLKMYLERENYVIDEAGDGNEALEKALTNDYDVILLDLMLPGK
ref|YP_001126301.1|     -----ILVVDDEERIRRLLKMYLERENYVIDEAGDGNVALEKALANDYDVILLDLMLPGK
ref|NP_242446.1|        --EAKILVVDDEDRIRNLLKMYLEREAYDVEEASDGKEALEKALAFDYDVILLDLMMPEM
ref|YP_175331.1|        -----LLVVDDEERIRRLLRMYLEREEYQIEEASNGEEALELALAKEYDLILLDVMMPGM
ref|ZP_02330236.1|      -----ILVVDDEERIRRLLRMYLEKEGYDIEESQDGETALKLAMDKDYDLILLDIMLPGM
RAAC02161               MAQTRILVVDDEERIRRLVRMYLERNGFEVDEAADGKEALHKALNQAYALIILDLMLPGM
                            :****:*.*::****:: :  ::*: :*: **. *:    * :*:**:*:* ref|YP_148132.1|        DGIEVCKEIRAQKTTPIMMLTAKGEESNRVQGFEVGTDDYIVKPFSPREVVLRVKALLRR
ref|YP_001126301.1|     DGIEVCKEIREHKTTPIIMLTAKGEESNRVQGFEVGTDDYIVKPFSPREVVLRVKALLRR
ref|NP_242446.1|        DGIEVCQKLRKQKATPIIMLTAKGEEANRVQGFEVGTDDYIVKPFSPREVVLRVKALLRR
ref|YP_175331.1|        DGVEMCQELRKKKATPVMMLTAKGEEANRVQGFEVGADDYIVKPFSPREVVLRVKALLRR
ref|ZP_02330236.1|      DGTEVCARLRQFKTTPVIMLTAKGEETNRVHGFEVGADDYVVKPFSPREVIYRVKAILRR
RAAC02161               DGRDVCAQIRQHSNVPIMMLTAAGDEANRVHGFELGADDYVVKPFSPRELVLRVKAMLKR
                        **  ::* .:*   . .*::**** *:*:* :* :******::   **:*:* ref|YP_148132.1|        AANAAYAPVETTAKDVLVFPHLTIDNDAHRVTVDGKEVSLTPKEYELLLFLARSPDKVFD
ref|YP_001126301.1|     AANATYAPVETTTKDVLVFPHLTIDNDAHRVTVDGKEVSLTPKEYELLLFLARSPDKVFD
ref|NP_242446.1|        SSSTKFLQTDTQAKDVLVFPHLSIDNDAHRVTVADQEINLTPKEYELLYYLAQSPDKVFS
ref|YP_175331.1|        ASATKFLQTDTQTKDVLVFGPLTIDNDAHRVTVDKTEISLTPKEYELLFYLAQSPDKVFS
ref|ZP_02330236.1|      SSATAFLSKDSNSSNNIVFPHLVIEHDAHRVTAGGQEVALTPKEYELLHYLAVSPDKVFS
RAAC02161               TGEMEYAR---NAIQTLTFPGLEIQIDARRVEVNGQEVNLTPKEFDLLVYMAQRPDKVFS
                        :.          :  : :.*  *  *: **:**  . *:  *****::**  ::*  *****.

ref|YP_148132.1|        REQLLKEVWHYEFFGDLRTVDTHIKRLREKLNKASPQAGKMIVTVWGVGYKFEAVS
ref|YP_001126301.1|     REQLLKEVWHYEFFGDLRTVDTHIKRLREKLNKASPQAGKMIVTVWGVGYKFEAVS
ref|NP_242446.1|        REQLLKDVWNYDFFGDLRTVDTHIKRLREKLNRVSPQAASMISTVWGVGYKFEV--
ref|YP_175331.1|        REQLLKDVWNYEFFGDLRTVDTHVKRLREKLNRVSPEVAAIISTVWGVGYKFE---
ref|ZP_02330236.1|      REELLKDVWNYEFFGDLRTVDTHVKRLREKLNKVSPEAAVMITTVWGVGYKLEV--
RAAC02161               REELLRDVWNYQFFGDQRTVDTHIKRLREKLGQASPEVSRYIVTVWGVGYKFEVAS
                        **:**::**:*:**** ******:*******.:.**:..  * *********:*
```

FIG. 108

```
ref|YP_001213400.1|    -------EILELLEGNARLTPGQIATMLGMEEGEVTRIIKEMEEKKVILGYYTLVNWEKA
ref|YP_001114520.1|    ------LEILELLQSNSRLTAKEIAVLTGQEEDEVKGIIERLEADKTIIKYFTLINWEKA
ref|YP_358986.1|       -------EILQLLHENAKLTPKQIATMLGVTEKEVRAKIKELEERKAIIKYHTLINWEKT
ref|YP_430046.1|       ----MRKKILDLLENNGRLTAKEIAIMLALPVDQVAKEIAAMEQEKIILRYHTLINWEKA
RAAC00349              MNDALRLKICDLLHENAKLSAETIARMLGETPDVIESTIRELEEEKVILRYSAVVNWDKL
ref|ZP_02330078.1|     --DDFKLKVLELLKEDARRGSDLIATMLGANEEQVAKAIKEMEEENIIVKYATVLNWAKV
                          :: :. :.:  .   : .     :  *  :* : *: * :::** * ref|YP_001213400.1|    GEEKVSALIEVKISPQREVGFDAVAERIYRFPEVKTVRLMSGAYDLAVMVEGQNLKEVAN
ref|YP_001114520.1|    GLEKVSALIEVKMSPQRDVGFDSVAERIYRFPEVKSVHLMSGAYDLAVFLEGATMKEVAL
ref|YP_358986.1|       EYEPVMALIEVKVTPQREVGFDGIARRIYQFAEVKDVYLMSGDYDLAVMVEGSSMKEVAL
ref|YP_430046.1|       GEEEVAALIDVKVIPQRDLGFDEIASRIYRYPEVKSVFLMSGGYDLSVLVQGKSLKEVAS
RAAC00349              PVNQVTAVIDVKVLPQREVGFDAIARKIYRFDEVKSVALMSGGYDLQVTVVGRDLREVSR
ref|ZP_02330078.1|     DSDKVTALIEVQITPERGTGFDAIAERIYLFPEVKAVYLMSGSYDLQVEIEGRTLQEVSS
                         : * *:*:*:: *:*  *** :* :** : *** * **** *** * : *   ::**:

ref|YP_001213400.1|    FVAQKLASLDNVLSTTTHFVLKTYKNQGVIVEDGEEDRRLVVTP
ref|YP_001114520.1|    FVAQKLATIDNVLSTATHFVLKTYKQDGFIFEDRENDQRLVIQP
ref|YP_358986.1|       FVALKLSTIEGVQSCATHFILKTYKHEGVILDDEEEDRRLVITP
ref|YP_430046.1|       FVSQKLATLEHVQSTMTHFILKRYKQDGVIFEDQEADRRQALQP
RAAC00349              FVSEKLATLENVTSTATHFILKTYKSDGVIYDDTDGERRLMITP
ref|ZP_02330078.1|     FVSTKLSTLDRVLSTKTHFILKKYKHDGIIFEDHEDDHRMLISP
                       **: **:::: * *   ***:** **  *:.*  :*     : *
```

FIG. 109

```
ref|YP_001634921.1|         ----------MELRHLRYFEAVARHSHVTRAAAELHIAQPALSKQISQLERELGITLFDR
ref|YP_290510.1|            ----------MQLQQLAYFLAVAETRHFTRAAELSRVAQPSLSKQIKALEEELGAPLFVR
RAAC01375                   MNTRRIGRMRMELVQLEYFLAVAEYQSFRRAADAIRVSQPALSRAIQKLEGDLGAPLFVR
ref|YP_079987.1|            ----------MELYQIDHFIAVSRHKHFTKAALEQRISQPALSRSIKKLEEELGVPLFIR
ref|YP_001422015.1|         ----------MELHQIDNFIAAAAHQHFTNAAKERMISQPALSRSIIRLEEELGAPLFFR
ref|YP_001423330.1|         ----------MDWHQINYFQTVAQVQHITQAAKQLSISQPALSRSISKLEDELGVQLFDR
                                      *:    ::   * :.:      . .     :::**:  *    :    ** * ref|YP_001634921.1|         VGRSLRLTEAGEALLPYARAILAQVEEARAAMAERIGLKAGRVTIGAPPTVGAHLLPPLL
ref|YP_290510.1|            ARGNITLTPAGEILLPLAQRILADVETARREIQELAGMRRGWVRLGATPSLCAGLLADAL
RAAC01375                   TAQGVRLTPCGEAFLPHARQALAEVAAGARKVAELAGQARGVLHVGLIYSLGTRFLPDVI
ref|YP_079987.1|            KTKSIRLTKYGEQFLIKAKQARLALDEGVQQIRESVNPNAGEISVSFLHTLGSRLMPQLI
ref|YP_001422015.1|         DTKAVRLTRHGEQFLIKAKQARRALNEGVEQVKKNMSLEHGEISVSFLHTLGLRLMPQLI
ref|YP_001423330.1|         KGRNIYLNRYGKMFLHRVEQSIRQIEIGKQEVWNEIHPNSGTILLSFLPSLGMSMVPDVI
                              : *.   *:  :*   ..        :     :   :      *  :.   ::    ::.  :

ref|YP_001634921.1|         TIFHQRYPGITLRLHEAGIQSLLDLLEAGITDLAVVALPVT--DEQLTVTPLLNEPLVLI
ref|YP_290510.1|            VRFHERYPGIELHVEEGGSRDLIRALGGGELDLALIILPLHSSDPAFVTVPILRESLVVA
RAAC01375                   RTFTRTHPGVTVRLSEAPTQKLLQQLDAGEIDIAFCT-PQH--APHLTLVEILQEELVAI
ref|YP_079987.1|            AEFKKKYPNVAFRLYQAANEHLQHMVETGEADICLSSPPLP--NEHLEWTVLDTEPLYLV
ref|YP_001422015.1|         AEFKKLYPNVTFRLYQGANETLRKMVETGDADICLSSPPLP--SELLQWTVLEKEPLYAV
ref|YP_001423330.1|         SSFQHMYPHVNFQLTQASNQQIIEQLTSREVDIALTSLRDE--NDDVICQPLLTEELYLA
                              *   . :*  :  . ::  :.    .   :       *:..      .    :    *   * ref|YP_001634921.1|         VSTTHPLARRSEVM-MTELRHERWILSPSSYELREATLKACREAGFTPQTVLEGGETETL
ref|YP_290510.1|            SPISQPPPTNGGAMRITDLRDQPLVMFRRGYDVRETTLSACRAAGFEPRLAVEGGEMDAV
RAAC01375                   VPLDHPLAAKDQCH-LSDLAGEPFVAYARESGIRHVIERYCAEAGFTPRVAMEGVEDLTV
ref|YP_079987.1|            LPADHPLADRKEVA-IRSIAHEDFVCFKPGYGLRYVFDQMCRGLSISPKLAFEGEEVSTI
ref|YP_001422015.1|         LPENHPLAGNKSIQ-MKEMQDEDFVGFKPGYGLRYMFDLMCRDLNIHPHLAFEGEEVSTI
ref|YP_001423330.1|         VSAEHPLASYDEID-LKMAEHEPFISFKDTNVLHGMIKELCEKAGFSPDVVFEGEDIVTA
                              .   :*  .      :       :        : :      ::       *   .:  *    ..**  :  :

ref|YP_001634921.1|         VRFVAAGLGVSLVPALAVAGCTDVVRLTVSDQHLTRSLGLVWRSDRTASPAARALREFL-
ref|YP_290510.1|            LRFVEAGLGLAVVPSMVLRNRPGLRGTPLAEPRLLRTIALAHRKDVALSRTARAF-----
RAAC01375                   AGLVAAGVGVAVVPLHAQLDQLPVHVLRLCEP-CKRSVYMAWHTHTTLSPVARAFIAFVK
ref|YP_079987.1|            LGLVSAGLGVAILPKTAEHVHSPVAFCRVSDYRSERTIGLAVLKDHYLSPAARNFKEFV-
ref|YP_001422015.1|         LGLTAAGLGAAVLPKTAEHSYFPVVFLPVADYQCERTIALAQLKNHALSPAAERFKQF--
ref|YP_001423330.1|         SGLVGAKLGVSLIPDLHVFDKTKVKLLSVTNPICEREIGLAWRKDGYLSPAAENFIAFIQ
                              :.  *  :*   :::*                 :       : :     * :::    ..    * .*. :

ref|YP_001634921.1|         -----
ref|YP_290510.1|            -----
RAAC01375                   RMCAP
ref|YP_079987.1|            -----
ref|YP_001422015.1|         -----
ref|YP_001423330.1|         -----
```

FIG. 110

```
ref|ZP_02255842.1|        -------LKIFVTVVEQKHFSRAAELLNLSQPGVSMHIRNLENEFGTTLIQRSPKHVQVT
ref|YP_897365.1|          -------LKIFVTVVEQKHFSRAAELLNLSQPGVSMHIRNLENEFGTTLIQRSPKHVQVT
ref|NP_981573.1|          -------LKIFVTVVEQKHFSRAAELLNLSQPGVSMHIRNLENEFGTTLIQRSPKHVQVT
ref|YP_001647744.1|       -------LKIFVTVVEQKHFSRAAELLNLSQPGVSMHIRNLENEFGTTLIQRSPKHVQVT
ref|YP_146744.1|          ---MDQLLYVFVKVVEKGNFTKAAEELHMTQPAVSQHIQTLERLFDTKLLDRTNKYVKLN
RAAC00013                 MKRVDLQLRVFVTVVEENSFTRAAEKLHISQPAISQHVQTLEQRLGVRLIDRGRRRLQVN
                                  *:**.***:  *::*** *::.**.:* *::.**. ...  *::*  : :::.

ref|ZP_02255842.1|        EAGNILYIHAKQMLSLYEDAKQEINELHNVVTGTLRIGASFTIGEYLLPKILANYANENP
ref|YP_897365.1|          EAGNILYIHAKQMLSLYEDAKQKINELHNVVTGTLRIGASFTIGEYLLPKILANYANENP
ref|NP_981573.1|          EAGNILYIHAKQMLSLYEDAKQEINELHNVVTGTLRIGASFTIGEYLLPKILANYANENP
ref|YP_001647744.1|       EAGNILYIHAKQMLSLYEDAKQEINALHNVVTGTLRIGASFTIGEYLLPKILARFANENA
ref|YP_146744.1|          KAGEIVYHYAKEILGLYTRMNQLLDDLMNRASGELSIGASYTYGEYVLPQMIAKLHQHYP
RAAC00013                 PAGRIVYEHAKEILALYRRMERLIADMQEMPAGPVHVGASLTYGEYVLPHVIARFRKAYP
                           **.*:*  :**::*.**     ::   : :   :*  :  :*** * ***:**::*.  :  .

ref|ZP_02255842.1|        RVEVHTFISNTEDVLQSLRSNQIDIGLVEGQVVYADVDVET-FMQDEMKLVVPPNHPLLR
ref|YP_897365.1|          HVEVHTFISNTEDVLQSLRSNQIDIGLVEGQVVYADVDVET-FMQDEMKLVVPPNHPLLR
ref|NP_981573.1|          RVEVHTFISNTEDVLQSLRSNQIDIGLVEGQVVYADVDVET-FMQDEMKLVVPPNHPLLD
ref|YP_001647744.1|       HVEVHTFISNTEEVLQSLRSNQIDIGLVEGQVVYADVDVET-FMQDEMKLVVPPNHPLLH
ref|YP_146744.1|          LIKPTITIGNSNEIVEMVRDHQLDVGIIE-MDIEPKNVYIEPFAKDQMVVVASAHHPYAQ
RAAC00013                 AVQPSVSIANTQTIAHAVAVRQLDIGIVEGQDVVEDEVVLTPFAEDEMLVVASPASPWYA
                            ::    *.*::  : .:  .:*:*:*:*  :      *  :*:*  :*...  * ref|ZP_02255842.1|        TNEINERTLQDQ-VWVLRESGSGTRAYSDRFIHQHHLKMKRFFTFSSIQSVKEAVAAGLG
ref|YP_897365.1|          TNEMNESTLQDQ-VWVLRESGSGTRAYSDRFIHQHHLKMKRFFTFSSIQSVKEAVSAGLG
ref|NP_981573.1|          TKEVNERTLQDQ-VWVLRESGSGTRAYSDRFIHQHHLKMKRFFTFSSIQSVKEAVAAGLG
ref|YP_001647744.1|       IKGINENTLQDQ-VWVLRESGSGTRAYSDRFIHQHHLKMKRFFTFSSIQSVKEAVAAGLG
ref|YP_146744.1|          KETVQMEDLCNA-TWIVRETGSGTRKATDEFFLKHNFFPSSIMEFGSTQLIKEAVEAGLG
RAAC00013                 -EAPDRSLLERA-TWFIREPGSGTREMTDRLFTQLGIQPRDLVEYTSSQVIKESVAAGLG
                            :    :   *   .*.:.***  :*.::  :   :    :. : * * :**:* **** ref|ZP_02255842.1|        IAILSDWTVRKELLAKELFHVEVPDEQLIRPFSIVRGKYFIPSKA---------------
ref|YP_897365.1|          IAILSDWTVRKELLAKELFHVEVPNEQLIRPFSIVRGKYFIPSKA---------------
ref|NP_981573.1|          IAILSDWTVRKELLAKELFHVEIPNEQLIRPFSIVRGKYFIPSKA---------------
ref|YP_001647744.1|       IAILSDWTVRKELLAKELFHIPVPNEELIRPFSIVRGKYFIPSKA---------------
ref|YP_146744.1|          LTFLSLWTIKKELSFGTLKIIPINDEPFFRHFSLVTPKTPFYTKAMEVFLTIVRTHQPSI
RAAC00013                 LACLSRWVVARELAWGMLRTLPIPCAPVKRTFSIVTPKSAFETKASKLLYSFLMEHGSPE
                           :: **  *.: :**       *     :   .  * **:*  *   : :**

ref|ZP_02255842.1|        --------
ref|YP_897365.1|          --------
ref|NP_981573.1|          --------
ref|YP_001647744.1|       --------
ref|YP_146744.1|          SHSPQPPS
RAAC00013                 NPSLAGE-
```

FIG. 111

```
ref|YP_075596.1|         ----------------LLQHLTTFCRVVEEGSFTRAAQVLNLTQPSVTKQVGALEDYLQVQ
ref|YP_478499.1|         ------------------------IAQQGSFRRAADSLFVSQPAVSLQVQNLERQLGVV
ref|YP_430668.1|         ------------------LITFITTVEKGTLSAAAEELHLTQPAVSKQLQALEDYFGLR
ref|YP_001668480.1|      ----------------EQLITFATVAEHGNISHAAQALHLSQPAVSGQLKLLQEAFGEP
RAAC01493                MICIIFMLNLYGVMDMFEALRALVTVVSLGSVSEAARALHVTQPTVTRQIQQLERHFGQA
ref|YP_590553.1|         ----------------FDQLLTFLEVAKLGNFSRAGEKVYRSQSAVSAQIRQLEQEYGER
                                           ..  *..   *.    :  :*.:*: *:   *:

ref|YP_075596.1|         LFTRQGKRVHLTPVGELVYDYA-RQVIHLVQRCEEAVREYRSPGSGSVTVGCVHTIGLFT
ref|YP_478499.1|         LFDRSGRKVELTDAGKVVLQYS-ERILKLCREAVEALADLQKMEGGHLVLGASQTVGTYV
ref|YP_430668.1|         LLERRGREVRLTAAGEICYRHA-RIIASHLNQTRRELAELTQLVRGRLLLGASTTPGQYI
ref|YP_001668480.1|      LYQRAGRGVRLTAAGEQLLAHA-ERLRETFRQAQALREAMRGLERGTLRIGASTTPASYL
RAAC01493                LFDRSGKRLALTPAGERVHAYALEVLRKQE-ELAESLLEMSNPEAGLVRMGAGLSPTLYR
ref|YP_590553.1|         LFDRSGKIVRLSPAGEVLLEYA-QRMVALRNESLRAVADQGETPRGVLSIGANEATCLYV
                          *    *  *:  : *:  .*:       ::  .  :       . *  : :*.  :  :

ref|YP_075596.1|         LPELLAAYVREHPRVK---INVKTGNNRETVTMLLHGEVDVGLVT--TPQVHER-IEVVP
ref|YP_478499.1|         MPSLIAQYHRRYPQIS---VQLLVQSTRRIAQKLVDGQLDVAIVGGEIPFELQRHLKVMA
ref|YP_430668.1|         LPRLIGAFRREYPRV---EVILTIADTQEVVQRLQEGEIDLGVVGAAGGRGKNLSYSRLA
ref|YP_001668480.1|      LPYLIADFHARHPEV---LVTTSHGNTAEIVAALDS--VDIALIEGPPGQELPLGTAVTA
RAAC01493                LPAMVARYASMHPRVR---FQVVTGSSKVTLERLASRVVDLAIVTTPPEDE--AGVEQVA
ref|YP_590553.1|         LPDIFTEYCQQFPQVQ---ITVYRNFSRKILQAVEDGVIDLGIAT--LPVKSPS-LKVHP
                         :*  :.     :  .*.:        .           :*:.*.     :

ref|YP_075596.1|         LFEDPLVVVAGPSFAADLPPVVSNADLAQLPFIG-YVRGARFRMTTDQVLEEMGIQPQF-
ref|YP_478499.1|         LAEDEYVLVGAPGCAI---DSPALVDLLALPFIT-LDPQSSTRQTIDRVLNRHGINPAQL
ref|YP_430668.1|         G--DELVLIVPPGHRLAGATAISPGELKEEPLVW-RESGSGTRRVVEERLAAAGFTVDPE
ref|YP_001668480.1|      WREDEIVAIVPSGHPLAGSDQQALASLGAYPLVL-RESGSGVRQIVERAFARDGVAMRV-
RAAC01493                LWRDELVAVAPSYHALAG-KRATIVELAQYPLVV-MHGESGLRRQIDDLLHRAGVERPAP
ref|YP_590553.1|         IFRDRLELMVPVRHPLAAKESVTIEEIAEYPQI--FPKTGYTRQQLDKLFRP---YNSKL
                                    *                :   . : .    *   :         :

ref|YP_075596.1|         --VMEFDNHEAIKTMVALGFGIALEPVSAVQRELISGQLVRLNVPGLPRLSRTTSLILRR
ref|YP_478499.1|         NVRLELSSIEAIKNAVQAGLGVAFLSTVAVGSDVEQGRFRKLAVEGLQI-RRTLWLAFNP
ref|YP_430668.1|         QIVMELGSTEAIVSAVEAGLGISLVTSWAVEKSVKLGRLAVVTLQGVDL-KRDLYLVRRR
ref|YP_001668480.1|      --ALEIAGVEGVKEAVRAGMGV--------------------------------------
RAAC01493                P-VMETDSLEAMNRFVQAGLGLAVVPWPAVADDVTQGRLKLVHIVGCDLGQRTVTLVWRK
ref|YP_590553.1|         RVAMEIPSVGLIKSFVVSGVGVTLLSSTFAQDEVRAGKAKMLPIAGVDM-WRELGLIYRN
                          :*   .   :        *  *.*:

ref|YP_075596.1|         GERRSEAVRAFLSLL------------
ref|YP_478499.1|         ERYQSQAATRFLQGL------------
ref|YP_430668.1|         QPLSP-AAEAFVNFAA-----------
ref|YP_001668480.1|      ---------------------------
RAAC01493                ESHIPAAARAFIEWLASVGAASSSELR
ref|YP_590553.1|         DRTLPRSATAFIDLMRHRPVAKKSK--
```

FIG. 112

```
ref|YP_896056.1|         --------------------------------------------------ELRHLQYFV
ref|NP_845992.1|         --------------------------------------------------ELRHLQYFV
ref|ZP_02254866.1|       --------------------------------------------------ELRHLQYFV
ref|ZP_00743391.1|       --------------------------------------------------ELRHLQYFV
ref|YP_001375561.1|      --------------------------------------------------ELRHLQYFI
RAAC01653                ----------------------------------------------MDTELRQLEYFV
                                                                           ***:*:**:

ref|YP_896056.1|         VVAEELHFGRAAARLQMTQPPLSQQIQQLEKEMGVMLFSRTKRKVELTEAGEMFLKEVKK
ref|NP_845992.1|         VVAEELHFGRAAARLQMTQPPLSQQIQQLEKEMGVMLFSRTKRKVELTEAGEMFLKEVKK
ref|ZP_02254866.1|       VVAEELHFGRAAARLQMTQPPLSQQIQQLEKEMGVMLFSRTKRKVELTEAGEMFLKEVKK
ref|ZP_00743391.1|       VVAEELHFGRAAARLQMTQPPLSQQIQQLEKEMGVTLFSRTKRKVELTEAGEMFLKEVKK
ref|YP_001375561.1|      VVAEELHFGRAAARLQMTQPPLSQQIQQLEQEMGVMLFERTKRKVELTEAGEMFLKEVKK
RAAC01653                AVAEELHFGRAAKRLGLTQPPLSQQIQKLEDEIGVTLFDRTNRRVQLTHAGRVLLEEARK
                         .********* .:*******:.*: .**:*:*:..::*:*.:* ref|YP_896056.1|         AFEQIEKAVEIAQSAQRGEVGSLSIGFVGAAIYDILPSIVREYRKKFPRVSVALHELSTP
ref|NP_845992.1|         AFEQIEKAVEIAQSAQRGEVGSLSIGFVGAAIYDILPSIVREYRKKFPRVSVALHELSTP
ref|ZP_02254866.1|       AFEQIEKAVEIAQSAQRGEVGSLSIGFVGAAIYDILPSIVREYRKKFPRVSVALHELSTP
ref|ZP_00743391.1|       AFEQIEKAVEVAQSAQRGEVGSLSIGFVGAAIYDILPSIVREYRKKFPRVSVALHELSTP
ref|YP_001375561.1|      AFDQIEKAVEVAQSAQRGEVGSLSIGFVGAAIYDILPSIVREYRKKFPRVSVALHELSTP
RAAC01653                VLAHVQTAVKAARDAAAGRVGRLSVAFVGSATYGWLPEVIRAYQERHPDVELVLREMSTP
                         .: :::.**: *:.*  *. :.***:* *.  **..:* *:::.*  *.:.*:*:*** ref|YP_896056.1|         DQVHALHDNRIDIGFLRPPIPTQLLELEPIQKLSCTLCLPKAHPLAEKDEIHIEDLRDEP
ref|NP_845992.1|         DQVHALHDNRIDIGFLRPPIPTQLLELEPIQKLSCTLCLPKAHPLAEKDEIHIEDLRDEP
ref|ZP_02254866.1|       DQVHALHDNRIDIGFLRPPIPTQLLELEPIQKLSCTLCLPKAHPLAEKDEIHIEDLRDEP
ref|ZP_00743391.1|       DQVHALHDNRIDIGFLRPPIPTQLLELEPIQRLSCTLCLPKAHPLAEKDEIHIEDLRDEP
ref|YP_001375561.1|      EQVHALHENRIDVGFLRPPISTQLLELEPIQKLPCTLCLPKAHPLAEKEEIHIEDLRDES
RAAC01653                AQMEALTAGELDVGVLRLPAQHPDLHVRLVERDDCVAVVPSEHPLATRSSLFLVELAEEP
                          *:.**   ..:*:*.** *    *.:.  :::   *.  :*. ****  :..:.: :* :*.

ref|YP_896056.1|         FVFITRPVWPALYDTILSLCREVGFSPRIVQEATEYQTVMGLVAAGIGITVIPVSANKLY
ref|NP_845992.1|         FVFITRPVWPALYDTILSLCREVGFSPRIVQEATEYQTVMGLVAAGIGITVIPVSANKLY
ref|ZP_02254866.1|       FVFITRPVWPALYDTILSLCREVGFSPRIVQEATEYQTVMGLVAAGIGITVIPVSANKLY
ref|ZP_00743391.1|       FVFITRPVWPALYDTILSLCREVGFSPRIVQEATEYQTVMGLVAAGIGITVIPVSANKLY
ref|YP_001375561.1|      FVFITRPVWPALYDTILSLCRGVGFSPRIVQEATEYQTVMGLVAAGIGITVIPVSANKLY
RAAC01653                FVLVSRAIWPGLYDGFITLARALGFEPRVRLEVTEVQTAVGLVAAGLGVSIVPSATERVH
                         **:::*.:**.***  :::*.* :**.**:    *.**  **.:******:*::::*  :::::

ref|YP_896056.1|         KTEVVYKELYDSNFVAEMSVAYKKMNSNPELLEFLKIA--------
ref|NP_845992.1|         KTEVVYKELYDSNFVAEMSVAYKKMNSNPELLEFLKIA--------
ref|ZP_02254866.1|       KTEVVYKELYDSNFVAEMSVAYKKMNSNPELLEFLKIA--------
ref|ZP_00743391.1|       KTEVVYKELYDSNFVAEMSVAYKKMNSNPELLEFLKIA--------
ref|YP_001375561.1|      KTEVVYKDIYDSNFIAEMSVAYRKTNSSPELLEFLKIA--------
RAAC01653                RRDVRYLHIDGQSPTVELGVAWRRDTSPLVAAFLAMAESVRPGLS
                         : :* *  .:  ... .*:.**::: ::.*  :   **  :*
```

FIG. 113

```
ref|YP_001210836.1|      ---EEKVDGNLLKVLRSLAPGTHLREGLENILRAKAGALIVIGDTPEVMEIAEGGFAINA
ref|YP_001111557.1|      MVKDEKIEDKLIKLLRLVAPGTPLREGLENILRAKTGALIVIGDIPEVMELAEGGFAINA
RAAC00430                MKDDAKREAAINKILRMVAPGTVLREGIENVLRAKTGGLIVVGATETVLSMMDGGFAIQC
ref|YP_001485333.1|      ------RELDLLDIVQFVAPGTPLRAGIENVLRANTGGLIVVGYNDKVKSVVDGGFHINS
ref|NP_387969.1|         -KKGAKHELDLSSILQFVAPGTPLRAGMENVLRANTGGLIVVGYNDKVKEVVDGGFHINT
ref|NP_240971.1|         --DSEVKERFARNILKMVAPGTALRTGIDNVLRAKTGGLIVLGYNENMKGIVDGGFYLDC
                               .::: :**** ** *::*:***::*.****:*     :  : :*** ::

ref|YP_001210836.1|      DFTPSSLYELAKMDGAIILSKDAKKILAANTQLVPNQNIPSAETGIRHRTAERVAKQTGA
ref|YP_001111557.1|      DFTPAGLYELAKMDGAIILSEDAKKIIAANTQLIPDLIIPSSETGIRHRTAERVAKQCDM
RAAC00430                DLTPSHLYELAKMDGAIIISEDAKKVHYANTTLNPDHTIPTSETGTRHRTAERVARQSGQ
ref|YP_001485333.1|      AFSPAHLYELAKMDGAIILSDSGQKILYANTQLMPDATIHSSETGMRHRTAERVAKQTGC
ref|NP_387969.1|         AFSPAHLYELAKMDGAIILSDSGQKILYANTQLMPDATISSSETGMRHRTAERVAKQTGC
ref|NP_240971.1|         PFSPASLYELAKMDGAIILNEDGTKILYANTQLNPDNAISSNETGIRHRTAERVAKQTGN
                          ::*: ************:....  *:   *** * *:   *  :  *** *********:*  .

ref|YP_001210836.1|      LVIAISQRRGVITIYKGASKYVLRDIGVILSKANQAIQTLEKYRTVLDKVLVELSVLEFE
ref|YP_001111557.1|      PVISISQRRSVITVYKGSIKYFLRDISVILAKANQAVQTLEKYRSVSDRVINELSMMELQ
RAAC00430                LVICISQRRNVITLYQGNLKYVLRDISVILAKANQALQTLEKYKTVLEQELTDLSALEFE
ref|YP_001485333.1|      LIIAISERRNVITLYQGNRRYTLKDIGFILTKANQAIQTLEKYKTILDHAISALSALEFE
ref|NP_387969.1|         LVIAISERRNVITLYQENMKYTLKDIGFILTKANQAIQTLEKYKTILDKTINALNALEFE
ref|NP_240971.1|         LVISISQRRNVITLYHGHLRYALRDIGVILTKANQAIQTLDKYKSVLDQDITDLGALEFE
                          :*.**:**.***.*:    :* *:**..**:*****:***:**::: :: : *. :*::

ref|YP_001210836.1|      EVVTLFDVAKAIQRVEMVLRVVKEIERYTSELGAEGRLITMQMEELVANVESEGLLVIQD
ref|YP_001111557.1|      EVVTLFDVTKAIQRIEMVLRVVKKEIDRYISELGTEGRLIAMQMEELVANVEEEGLLIIQD
RAAC00430                EAVTLEDVTRVLQRFETVLRVTNEIRRYIIELGNEGRLVSMQLEELVSDVDEQAYLLIKD
ref|YP_001485333.1|      ELVTFGDVLSVLHRYEMVLRIKNEINMYIKELGTEGHLIRLQVNELITDMEQEAALFIKD
ref|NP_387969.1|         ELVTFSDVLSVMHRYEMVLRIKNEINMYIKELGTEGHLIKLQVIELITDMEEEAALFIKD
ref|NP_240971.1|         ELVTFHEVSQVMQRIHMVLNIKGEILNYVNELGSEGRLITMQLNELVSNLEKEVLLLIQD
                          * **: :*  .::* . .:    *  * :*: :*: **:::::.:   *.*:* ref|YP_001210836.1|      YATTIGEKTPSSILGVIGSWPAEDILDLSLIARALGYPGSASILEQHVSPRGYRILEKIP
ref|YP_001111557.1|      YATTLGEKTPESILKVIGSWPAEDLLDLVLIARALGYPGSASVLDQSVSPRGYRALRKIP
RAAC00430                FAHPECPHTPHQIMSQIHNLSSEELLDGALLARILGYPPSVNQLEESVPSRGYRILNKIS
ref|YP_001485333.1|      YV-KEKIKDPYVLLKQLQDMSSFELLDDSILYKLLGYPASTN-IDEYVYTRGYRLLHKIP
ref|NP_387969.1|         YV-KEKIKDPFVLLKELQDMSSYDLLDDSIVYKLLGYPASTN-LDDYVLPRGYRLLNKIP
ref|NP_240971.1|         YA-KEDDVDPEDVLEQMMKCSNEELLDDSNILKLLGYHKAFNVQEQQATPRGYRILHKIP
                          :.     *    :: : . .   ::**   : : ***   .   :: . .**** *.**.

ref|YP_001210836.1|      RLPLPVIDNLVKTFGTLNRILVATIEELDDVEGIGEVRARSIKEGLNRYREQLLQER--
ref|YP_001111557.1|      RLPLPVIENLVSTFQYLRTILAASIAELDEVEGIGEVRARSIKDGLTRYGEMLLQDR--
RAAC00430                RLPQPVIENLVEHFGVLSNILKASMADLDKVEGVGPVRARMIQNGLGRIQEQVLIDRQI
ref|YP_001485333.1|      RLPMPIVENVVEAFGVLDRIMEADVQDLDEVEGIGEVRAKKIKKGLKRLQEKHYIDRQL
ref|NP_387969.1|         RLPMPIVENVVEAFGVLPRIIEASAEELDEVEGIGEVRAQKIKKGLKRLQEKHYLDRQL
ref|NP_240971.1|         RLPATIVRNLVHSFENINDMLRADLKELDEVEGIGEARAKLIKDGLSRIQEQLFMDRNI
                          ***  .::  *:*      *    : ::  *   :**.***:* .**: *:.** *   *    :*
```

FIG. 114

```
ref|NP_832076.1|        ------------------------------------MNKTELIKNVAQSADISQKDASAA
ref|YP_001645033.1|     ------------------------------------MNKTELVKNVAQSADISQKDASAA
ref|NP_844759.1|        ------------------------------------MNKTELIKNVAQSADISQKDASAA
ref|YP_001375058.1|     ------------------------------------MNKTELIKNVAQSADISQKDASVA
ref|YP_535778.1|        -------------------------------------NKAALIERVAEKTGLTKKDATVA
RAAC02359               ------------------------------------MNKRDLIRKTAEETGLSQKDCEAV
                                                             **  *:...*:.:.:::**.  ..

ref|NP_832076.1|        VQSVFDTIANALQSGDKVQLIGFGTFEVRERSARTGRNPQTGEEIQIAAGKVPAFKAGKE
ref|YP_001645033.1|     VQSVFDTIANALQSGDKVQLIGFGTFEVRERSARTGRNPQTGEEIQIAAGKVPAFKAGKE
ref|NP_844759.1|        VQSVFDTIATALQSGDKVQLIGFGTFEVRERSARTGRNPQTGEEIQIAAGKVPAFKAGKE
ref|YP_001375058.1|     VQSVFDTITNALQNGDKVQLIGFGTFEVRERAARTGRNPQTGEEIQIAAGKVPAFKAGKE
ref|YP_535778.1|        VDAVFETIQDALVDGEKVQLIGFGNFEVRERAARKGRNPQTGEEIEIPASKVPAFKPGKS
RAAC02359               INTLFDTIRKTVESGEKVQIIGFGTFELRERAARTARNPRTGEAVEVPARRVPAFKPGAE
                        ::::*:**   ::  .*:***:****.**:***:**..***:***  :::.* :*****.*  .

ref|NP_832076.1|        LKEAVK-
ref|YP_001645033.1|     LKEAVK-
ref|NP_844759.1|        LKEAVK-
ref|YP_001375058.1|     LKEAVK-
ref|YP_535778.1|        LKDAVK-
RAAC02359               LKQAVQV
                        **:**:
```

FIG. 115

```
ref|YP_375842.1|         --------------------MSKAELVEKIAAQAKLTKVDAERAVNAFINVVTSSLKGGD
ref|YP_001131112.1|      --------------------MSKAELVEKIAAQANLTKVDAEKSVNAFINVVTSSLKAGD
ref|ZP_00591928.1|       ------------------LMSKAELVEKIASQAGLTKADAERAVNSFVSVVTDSLKAGE
ref|YP_001003150.1|      --------------------MNKADLAEKVAAETGVSKRVATDAVSAVFTGIEESLASGE
ref|NP_046614.1|         --------------------MNKTELIAKVAEKQGVSKKEGAPSVEKVFDTISEALKSGE
RAAC02589                MCCLTGLERMRDLLEKERELVNKGELVAEVQARVGLPKSQVLQVLNTFCEVTTERLQAGE
                                             :.* :*  ::   .  :.*     :. .      . * .*:

ref|YP_375842.1|         DVTLVGFGTFTTGDRAARQGRNPQTGKAITIPAKKVVKFKPGKALKDEV-
ref|YP_001131112.1|      DVTLVGFGTFTTGDRAERQGRNPQTGKTITIPAKTVVKFKPGKALKDEV-
ref|ZP_00591928.1|       DVTLVGFGTFSVGERAERQGRNPQTGETITIAARKAVKFKPGKALKEEVD
ref|YP_001003150.1|      DVSIPGFGKFAVVARPERQGRNPQTGELIDIPAGMNVRFKPGAPLKRSVD
ref|NP_046614.1|         KVSIPGFGTFEVRERAARKGRNPQTGEEIDIPATKAPAFKPAKALKDAV-
RAAC02589                EVSLPPLGKFQYVMRSARRQRNPQTGEMIDVPEKATVRFRPSGALKGRVN
                         .*::   :*.*      *. *: ******: * :.     *:*. .** *
```

FIG. 116

```
ref|ZP_02170919.1|    MNKTELINAVAESADLSKKDATSAVDAVFEVITDSLKKGDKVQLIGFGNFEVRERAARKG
ref|ZP_01862118.1|    MNKTELINAVAEAAELSKKDATKAVDAVFESIQDALANGDKVQLIGFGNFEVRERAARKG
ref|NP_692713.1|      MNKTDLVNAVAEKSELSKKDATKAVDAVFESVMDSLKNGEKVQLIGFGNFEVRERSARKG
ref|YP_535778.1|      -NKAALIERVAEKTGLTKKDATVAVDAVFETIQDALVDGEKVQLIGFGNFEVRERAARKG
ref|YP_359077.1|      MNKAELVSVIAEKAEMTKKDAEKALNAVLAAIEEALKKGEKVQLVGFGTFEVRERAARKG
RAAC01442             MNKMELINRVAEKTNLKKKDAESAVNAVFEIIEEALANGEKVQIIGFGTFETRSRAARSG
                       **   *:. :  : :.**   *:.**:    : ::*  .*:*::*.**.*.*:**.* ref|ZP_02170919.1|    RNPQTGEEIEIPASNVPAFKPGKALKDAVK
ref|ZP_01862118.1|    RNPQTGEEIEISASKVPAFKPGKALKDAVK
ref|NP_692713.1|      RNPQTGEEIEIPASKVPAFKPGKALKD---
ref|YP_535778.1|      RNPQTGEEIEIPASKVPAFKPGKSLKDAVK
ref|YP_359077.1|      RNPQTGQEIEIPASKVPVFKPGKLLKE---
RAAC01442             RNPQTGEVIEIPASTVPAFKPGNKLKEVTR
                      ******: ***.**.**.****: **:
```

FIG. 117

```
ref|YP_001213441.1|        MLNKVILIGRLTQDPELRYTPGGVAVARFTLAVNRARLNKQGERETDFIDVVVWQKQAET
RAAC00027                  MLNRVILIGRLTADPELRYTNNGTAVASFTLAVDRMRSGPNGERQTDFINVVVWQKQAEI
ref|YP_077145.1|           MLNSVVLIGRLTKDPELRYTPSGKAVATLRLAVDRGTVNQQGERETDFIDIVVWEKQAET
ref|NP_244917.1|           MLNRVVLVGRLTRDPELRYTPNGVAVANFTLAVNRPFSNQQGEREADFINCVVWRKQAEN
ref|YP_149334.1|           MINRVILVGRLTRDPELRYTPSGVAVATFTLAVNRPFTNQQGERETDFIQCVVWRRQAEN
ref|YP_001377189.1|        MMNRVILVGRLTKDPDLRYTPNGVAVATFTLAVNRAFTNQQGEREADFINCVIWRKQAEN
                           *:*  *:*:**  :****  .*  *  :  *:*    .  :*::*: *:*.:*** ref|YP_001213441.1|        CANYIRKGRLVAVEGRLQVRSYDDSQGIRRKAAEVVAETVRFLDR---------------
RAAC00027                  VAQYLQKGRLAAVDGRLQIRSYDNRDGQRVRVAEVVAETVRFLDRGPDQAQGSGYSAAG-
ref|YP_077145.1|           VANYLQKGRLVAVQGRLQIRQYTTQDGQKREKAEVVATTVRFLDSARD------------
ref|NP_244917.1|           VANYLKKGSLAGVDGRIQTRSYDNNEGR--------------------------------
ref|YP_149334.1|           VANFLKKGSLAGVDGRLQTRSYENQEGRRVYVTEVVADSVQFLEPKGT-SEQRGATAGGY
ref|YP_001377189.1|        VANYLKKGSLAGVDGRLQTRNYEGQDGRRVYVTEVLAESVQFLEPRNSGGEQRGSFNQQP
                           *::::**  *..*:**:* *.*    :* ref|YP_001213441.1|        --------------------------------------------
RAAC00027                  --------AQTRQQRPTPSSAPPFEDDPFADDSQLIDISEDDLPF
ref|YP_077145.1|           --------------------------------------------
ref|NP_244917.1|           --------------------------------------------
ref|YP_149334.1|           YGDPFPFGQDQNHQYPNEKGFGRIDDDPFANDGQPIDISDDDLPF
ref|YP_001377189.1|        SGAGFGNQGSNPFGQSGNSGFTK-NDDPFSNVGQPIDISDDDLPF
```

FIG. 118

```
ref|YP_001038261.1|    ------------------------------------------------------------
ref|YP_001394883.1|    ------------------------------------------------------------
ref|NP_624000.1|       ------------------------------------------------------------
ref|YP_001662406.1|    ------------------------------------------------------------
ref|YP_001664279.1|    ------------------------------------------------------------
RAAC02508              MRLSSCASSKHNTRCQLQRLGQQPHCTGQCVACSLRHPFALHWNPADVDGRIIASVTLDC ref|YP_001038261.1|    --------------------------ILVVDDEKKIVEVVKSYLEHSGYEVYEAFTGKEA
ref|YP_001394883.1|    --------------------------ILVVDDEQKIVDVIRAYLEKAGYEVHSAYNGTEA
ref|NP_624000.1|       --------------------------ILVVDDEIKILEVVKSYLEREGFSVITETNGNNV
ref|YP_001662406.1|    --------------------------IFVVDDEIKILEVVKSYLEHEGFSVITETNGNNV
ref|YP_001664279.1|    --------------------------IFVVDDEIKILEVVKSYLEHEGFSVITETNGNNV
RAAC02508              EDGMKTADCRQIVTHAGGATMKRHHTILVADDEKKIADVLSLYLEQAGFGVVCVDNGSEV
                                                 *:*.*** ** :*: ***: *: *    .*.:.

ref|YP_001038261.1|    LYVFEKVPLSLIVLDLMLPDLSGEEICKIIRKKSRVPIIMLTAKAEEEDILKGLNIGADD
ref|YP_001394883.1|    VKLFEKISPALIVLDLMLPDISGEDICKMLRKKSRVPIIMLTAKVDEKTVLEGFNIGADD
ref|NP_624000.1|       LDTFKKEKPDLVILDLMLPGISGEELCKRLRQFSNVPILMLTAKVQESDKINGFSIGADD
ref|YP_001662406.1|    LDTFKKEKPDLVILDLMLPGISGEELCKRLRQFSNVPILMLTAKVQESDKINGFSIGADD
ref|YP_001664279.1|    LNTFKKEKPDLVILDLMLPGISGEELCKRIRQFSNVPILMLTAKVQESDKINGFSIGADD
RAAC02508              LRRLEGLHPSLIILDLMLPDIPGEEVCMAVRARSAVPILMLTAKHRDEDRLRGLQIGADD
                       :  ::     *::****.:.::*  :*  * *:***  :.  .:*::***** ref|YP_001038261.1|    YITKPFSPKQLVARVTAVLRRTSDDPVPLSNIFSFNNGDLVIDSLKYEVRKGNNVVNLTP
ref|YP_001394883.1|    YVTKPFSPKQLVARVMAHLRRTEEEAIPLSNILSFNNGDLVLNVIKHEVRKNGITVNLTS
ref|NP_624000.1|       YITKPFSPRELVMRVKAILRRTTDD-VPLAEVMSFNNDDLVVDLRAHTVRKKGVVVNLTP
ref|YP_001662406.1|    YITKPFSPRELVMRVKAILRRTTDD-VPLAEVMSFNNDDLVVDLRAHTVRKKGVVVNLTP
ref|YP_001664279.1|    YLTKPFSPRELVMRVKAILRRTSDD-VPLAEVMSFNNDDLVVDFKAHTVKKKGVVVNLTP
RAAC02508              YVTKPFNPNEVVARVQAILRRTMLD-HPLADRLEYRDGDLVIDALSQVVYKGGINAELTA
                       *:****.*.::* ** *  **** : **::  :.:.:.***::    *  *   .:**.

ref|YP_001038261.1|    NEYKILMTLVKYPGKTFTRDELINMALGDDFDGFDRTVDTHIKNLRQKIETDPKSPKYIL
ref|YP_001394883.1|    SEYNILMTLVKYPQKTFTREELVNLALEEDFNGFDRIIDAHVKNLRQKIEDNSREPKYIL
ref|NP_624000.1|       NEFKILKILIRNPNRVFTREELIEKVMGFDYEGYDRTIDAHIKNLRQKIEDDTKNPVYIK
ref|YP_001662406.1|    NEFKILKILIRNPNRVFTREELIEKVMGFDYEGYDRTIDAHIKNLRQKIEDDTKNPVYIK
ref|YP_001664279.1|    NEFKILKFLIRNPNRVFTREELIEKVMGFDYEGYDRTIDAHIKNLRQKIEDDTKNPVYIK
RAAC02508              TEYKLLVILSRHPRRVFSREELIERVFGMDFRGDVRTIDAHVKNLRAKIEDDPKSPVYIQ
                       .*::* *  * : *:.*:*:**::  .:  *: *  * :*:*:**** ***  :.:.**

ref|YP_001038261.1|    TVHGVGYRFEG---
ref|YP_001394883.1|    TVYKVGYRFGGE--
ref|NP_624000.1|       TVYGVGYKF-GDGN
ref|YP_001662406.1|    TVYGVGYKF-GDGN
ref|YP_001664279.1|    TVYGVGYKF-GDGN
RAAC02508              TVYGMGYRFGGDGN
                       **: :**:* *
```

FIG. 119

```
ref|ZP_00237866.1|        -----MRLLVVEDNASLLESIVQILRDE-FEVDTALNGEEGLFLALQNIYDAILLDVMMP
ref|YP_034830.1|          -----MRLLVVEDNASLLESIVQILRDE-FEVDTALNGEEGLFLALQNIYDAILLDVMMP
ref|ZP_00739566.1|        MEGESMRLLVVEDNTSLLESIVQILRDE-FEVDTALNGEDGLFLALQNIYDAILLDVMMP
ref|YP_001643379.1|       -----MRLLVVEDNASLLESIVQILRDE-FEVDTAMNGEDGLFLALQNIYDAILLDVMMP
ref|NP_830389.1|          MEGESMRLLVVEDNASLLESIVQILRDE-FEVDTAINGEDGLFLALQNIYDAILLDVMMP
RAAC00905                 MEG-AMRILLVEDDRGLSDALAELLREESFQVDVAHDGEEGLYLAETAVYDALVVDVMLP
                             * *:*:***: .* :::.::**:* *:**.* :::    :*:::***:* ref|ZP_00237866.1|        EMDGFEVIQKIRDEKIETPVLFLTARDSLEDRVKGLDFGGDDYIVKPFQAPELKARIRAL
ref|YP_034830.1|          EMDGFEVIQKIRDEKIETPVLFLTARDSLEDRVKGLDFGGDDYIVKPFQAPELKARIRAL
ref|ZP_00739566.1|        GMDGFEVIQKIRDEKIETPVLFLTARDSLEDRVKGLDFGGDDYIVKPFQAPELKARIRAL
ref|YP_001643379.1|       EMDGFEVIQKIRDEKIETPVLFLTARDSLEDRVKGLDFGGDDYIVKPFQAPELKARIRAL
ref|NP_830389.1|          GMDGFEVIQKIRDEKIETPVLFLTARDSLEDRVKGLDFGGDDYIVKPFQAPELKARIRAL
RAAC00905                 GLSGYDLVRTLRDKRVHVPVLFLTALGDVDHRVQGLNAGGDDYLPKPFATEEFLARLRAL
                           :.*:::::.::::..***  ..::.:: *: *  : *:  :* ref|ZP_00237866.1|        LRRSGSLTTKQTIRYKGIELFGKDKDVQVDGQSMKLTLKQYELLEYLIQNSGKILMREQI
ref|YP_034830.1|          LRRSGSLTTKQTIRYKGIELFGKDKDVQVDGQSMKLTLKQYELLEYLVQNSGKILMREQI
ref|ZP_00739566.1|        LRRSGSLTTQQTIRYKGIELFGKDKDVQVDGQGIKLTLKQYELLEYLIQNSGKILMREQI
ref|YP_001643379.1|       LRRSGSLTTQQTIRYKGIELFGKDKDIQVDGQGIKLTLKQYELLEYLIQNSGKILMREQI
ref|NP_830389.1|          LRRSGSLTTQQTIRYKGIELFGKDKDVQVDGKGMKLSLKQYELLEYLVQNSGKILMREQI
RAAC00905                 LRRNRELGTDMTLRSGLLVLDPLARRAAFGNEPIKLSDKEFDLLEYLLSHRGQILMRERI
                          ***. .* *. *:*   : *    :    ...: :**: *:::*****:.: *:*****:* ref|ZP_00237866.1|        FDRVWGFDSDTTVAIVEVYVHHLRKKLEPFGYQKDIQTVRGIGYI----
ref|YP_034830.1|          FDRVWGFDSDTTVAIVEVYVHHLRKKLEPFGYQKDIQTVRGIGYI----
ref|ZP_00739566.1|        FDRVWGFDSDTTVAIVEVYVHHLRKKLEPFGYQKDIQTVRGIGYI----
ref|YP_001643379.1|       FDRVWGFDSDTTVAIVEVYVHHLRKKLEPFGYQKDIQTVRGIGYI----
ref|NP_830389.1|          FDRVWGFDSDTTVAIVEVYVHHLRKKLEPFGYQKDIQTVRGIGYI----
RAAC00905                 FNRVWGIDSDVMDTTVDLYVHYLRKKLQPFGYDTAIRTVRNVGYMWSDP
                          *:****:***.   : *:***:*****:****:.. *:***.:**:
```

FIG. 120

```
ref|YP_001244333.1|      -IPDRILLKPGILTPEEFEIMKQHTTIGFKILSRSNSPILQLGAEIALTHHERWDGSGYP
ref|ZP_02128221.1|       -IPDRILLKPGILTPEEFEIMKQHTTIGFRILSRSNSPILQLGAEIALTHHERWNGAGYP
ref|NP_228001.1|         -IPDRILLKPGILTPEEFEIMKQHTTIGFRILSRSNSPILQLGAEIALTHHERWDGSGYP
emb|CAI44346.1|          -IPDRILLKPGILTPEEFEIMKQHTTIGFRILSRSSSPILQLGAEIALTHHERWNGSGYP
RAAC01903                QIPDEILRKPGRLTPEEFDIMKMHTIYGRDMMNSPVHPFLHIGSTVAEQHHERYDGSGYP
ref|ZP_02171167.1|       QVPEEILLKPSKLTEEEWAIMKLHTSYGAEMLRETCISHFLLAAEVVEQHHERYDGSGYP
                          :*:. .  : *     *    ::    .  . :  :.:  :.    ****::*:*** ref|YP_001244333.1|      RGLKGREIPISGLIVAVADSFDAMVSKRPYKNPKPLEEAFREIESLSGKLYSPEVVEAFL
ref|ZP_02128221.1|       RGLKGREIPISGLIVAVADSFDAMVSKRPYKNPKPLEEAFREIESLSGKLYSPEVVEAFL
ref|NP_228001.1|         RGLKEREIPISGLIVAVADSFDAMVSRRPYKNPKPLEEAFREIESLSGKLYSPEVVEAFL
emb|CAI44346.1|          KGLKGKEIPLSGLIVAVADSFDAMVSRRPYKKPKTLEEAFQEIEELSGKLYSPEVVKAFL
RAAC01903                YGLKGEEIYLPAAIVAVVDSYDAMTSQRPYQRPKSKHEAIEEIRALRGKLYDPRVVDAFL
ref|ZP_02171167.1|       RGLKKEEISLEAAIVGLVDSYDAITSERVYQHARSHESALNELRGLRGIKYQPDVVDAFT
                         ***  .**  :  .  **.: .**:**:.*.* *:..:.  ..*::*:.  *  *  *.* **.**

ref|YP_001244333.1|      KLEKEITD-
ref|ZP_02128221.1|       KLEKEITD-
ref|NP_228001.1|         KLEKEITD-
emb|CAI44346.1|          KL-------
RAAC01903                KVVDTFEDT
ref|ZP_02171167.1|       DVIE-----
                          .:
```

FIG. 121

```
ref|YP_290547.1|              ---------IKVLVVDDHEFFRRGLVSVLAEEPDIEVVGEAGDGEEAVARAKELRPDVVL
ref|NP_627230.1|              ------EEPIRVLVVDDHALFRRGLEIVLAAEEDIQVVGEAGDGAEAVEKAADLLPDIVL
ref|YP_480150.1|              ----EGSALIRVLVVDDHELFLQGLQTVLEIEEDISVVGRAGNGQEALTLASGTSPDIVL
ref|YP_001509772.1|           ----RDVMPIRVLVVDDHELFLQGLQTVLETEEDISVVGRAADGQEALTLASGTTPDIVL
RAAC00981                     MGTWQDESVIKVLVVDDHELFRRGVVTVLRSTPGIYVVGEAGNGREAIECFQTLQPDVTL
ref|YP_074752.1|              ---------MKVLIVDDHLMLRKGVLSVLSNTD-LEVIGEASNGQEALELVPKLKPDLVL
                                       :::**  ::  :*:   **       : *:*.*.:*  :      :.* ref|YP_290547.1|              LDVRMPKRSGIAACAGIKEAVPDAKIVMLTMSDEEEDLFEAIKAGATGYLLKEISVVELP
ref|NP_627230.1|              MDVRMPKRGGIEACTSIKEVAPSAKIIMLTISDEEADLYDAIKAGATGYLLKEISTDEVA
ref|YP_480150.1|              MDVRMPGRDGIAAAGAIKRAVPRTRIVMLTVSDEESDLFEAIKAGAVGYLLKSIPPHEVA
ref|YP_001509772.1|           MDVRMPGRDGIAAAGAIKRAVPRTRIVMLTVSDEESDLFEAIKAGAVGYLLKSIPPHEVA
RAAC00981                     LDIHMPVCNGLETARKMREANPNTKILMLTVSETEEMLFEAVKSGASGYVLKSVSPERLI
ref|YP_074752.1|              MDINMPVLDGVEATRKLKQMYPDLKVVILTVSEIDKDLFEAIKAGADGYLLKNLGPEELV
                              :*:.**   .*: :      ::. *   :::**:*: :  *::*:*:** **:**.:    .:

ref|YP_290547.1|              EAVRAVCKGQSFINPSMATKLINEFAALARKGKDRRSQPTKP-PRLTERETEVLRLVARG
ref|NP_627230.1|              TAIRAVADGQSQISPSMASKLLTEFKSMIQRTDERRLVPA---PRLTDRELEVLKLVATG
ref|YP_480150.1|              DAVRAVHNGQSLISPSMASKLMVEFATMARGTEDRPRAHA---PHLTARELEVLKLVAEG
ref|YP_001509772.1|           DAVRAVHNGQSLISPSMASKLMVEFATMARGGEDRPRAHA---PHLTARELEVLKLVAEG
RAAC00981                     ECVRQVYEGEPVVPSSLAMKMIAEFSRTAETRMPSSESVT----ELTEREREVLQYLSAG
ref|YP_074752.1|              SSLRAAISGEAPISSVMAAKMLKEF-RQPRANTTGKQPGQ----QLSPREIEVLRLASTG
                              .:*  . .*:.  :  .:* *::  **       .    .*:   *:   :  * ref|YP_290547.1|              LNNRDIADRLYISDNTVKNHVRNILEKLQLHSRTEAAVYAIR-------------
ref|NP_627230.1|              MNNRDIAKELFISENTVKNHVRNILEKLQLHSRMEAVVYAMREKI----------
ref|YP_480150.1|              RANREIARKLFISENTVKNHVRNILDKLQLHSRMEAVMYAVRQGL----------
ref|YP_001509772.1|           RANREIARKLFISENTVKNHVRNILDKLQLHSRMEAVMYAVRQGL----------
RAAC00981                     ASNKEIARALFISENTVRNHVRHILDKLHLSNRAQAAAYAVRNGIARGRQLTSDV
ref|YP_074752.1|              LTYKEIAAKLYVAESTVKNHMRHILEKLHLRNRSEAVGYAIRTGLA---------
                              ::**     *::::.**:** :*:**:**:*  .*  :*.  **:*
```

FIG. 122A

```
ref|NP_937072.1|       ------------------------------------------------------------
ref|NP_762428.1|       ------------------------------------------------------------
ref|YP_001489923.1|    ------------------------------------------------------------
ref|ZP_01847462.1|     ------------------------------------------------------------
RAAC00986              MIVREAVHALWVALGVISALEFLNMRSSWLRRNHVYEFFTDWLPYGLIWIWIGWVDGVGN
ref|ZP_01964315.1|     ------------------------------------------------------------ ref|NP_937072.1|       ------------------------------------------------------------
ref|NP_762428.1|       ------------------------------------------------------------
ref|YP_001489923.1|    ------------------------------------------------------------
ref|ZP_01847462.1|     ------------------------------------------------------------
RAAC00986              VVMPLYATLSCALHTPNRWNRKISLLGMMIPAALYVIHERHFDPVESEILIGIAAGYVVF
ref|ZP_01964315.1|     ------------------------------------------------------------ ref|NP_937072.1|       ------------------------------------------------------------
ref|NP_762428.1|       ------------------------------------------------------------
ref|YP_001489923.1|    ------------------------------------------------------------
ref|ZP_01847462.1|     ------------------------------------------------------------
RAAC00986              HNRVRASYWAYGCANIVATGFCVLHMTPFTFGTFEETLIVSTIFALYEHDALIRARYKEE
ref|ZP_01964315.1|     --------------------------------------------------------YNRE ref|NP_937072.1|       ------------------------------------------------------------
ref|NP_762428.1|       ------------------------------------------------------------
ref|YP_001489923.1|    ------------------------------------------------------------
ref|ZP_01847462.1|     ------------------------------------------------------------
RAAC00986              RGLDPLTGLYNRRGAEEWLNHEGNAGIAVLVDLDDFKFINDFFGHDAGDEVLRKVGGLL
ref|ZP_01964315.1|     LYTDALTGIYNRRYYEERIKNSDMTAGIA-MIDLDDFKIYNDTFGHDAGDLALTTVVGIV ref|NP_937072.1|       ------------------------------------------------------------
ref|NP_762428.1|       ------------------------------------------------------------
ref|YP_001489923.1|    ------------------------------------------------------------
ref|ZP_01847462.1|     ------------------------------------------------------------
RAAC00986              LRFVSSPGIGVRWGGDEFLILAEHETAQSAEQFVEELFSQLSSLELS-LNERRLRLRCSV
ref|ZP_01964315.1|     KANVRRTDMLIRMGGDEFLLVMPDITDQIFADKLKQIQEKIHDTKVPGYSQLRLSVSIGG ref|NP_937072.1|       ------------------------------------------------------------
ref|NP_762428.1|       ------------------------------------------------------------
ref|YP_001489923.1|    ------------------------------------------------------------
ref|ZP_01847462.1|     ------------------------------------------------------------
RAAC00986              GVAYGPLGDLLITEADRALLRVKQSGKAHVEWYHSTIENQGEQLDINQYAFQKAFHQLTE
ref|ZP_01964315.1|     VLSAPGSTVENAIHKADQFMYQAKTCKNMVVTEHDEEVQDKAEGGETSKTYKYRILIVDD ref|NP_937072.1|       ------------------------------------------------------------
ref|NP_762428.1|       ------------------------------------------------------------
ref|YP_001489923.1|    --------TDLKGVITHASSAFCKISGYEKKELIGKPHNIIRHPETSKETFKKMWEE---
ref|ZP_01847462.1|     ------------------------------------------------------------
RAAC00986              FCSAPCLATDLEFRIIDLNEAYERVSGYTRHALRGQKPSMLAFGDWNRRWYPEIHET---
ref|ZP_01964315.1|     SEMNRAILSEILSEEYDIVEADSGESCIDKLRQYEREISLVLLDIVMPGMDGFGVLN---
```

FIG. 122B

```
ref|NP_937072.1|      ----------------------------------------------------------------
ref|NP_762428.1|      ----------------------------------------------------------------
ref|YP_001489923.1|   -IQKEKKFTT---ELKNLRKDGTY-----------------YWVVAEIEPKYDKKGNHI
ref|ZP_01847462.1|    -------------------------------------------------RAYREQEE
RAAC00986             -LQRGRSWTG---ILHNQREDGTIWSGEMVISPVRIGEITAGYWCMVR----RVFSGDKV
ref|ZP_01964315.1|    YMNRHHYLED----IPVIMISSEDSTEVVRRAYEMGVSDYINRPFDAGV--VHRRVYNTI ref|NP_937072.1|      ------ENLNLLLDVRETSKELVYN-----LANAVEARSKETGAHVQRV----SLISEKL
ref|NP_762428.1|      ------ENLNLLLDVRETSKELVYN-----LANAVEARSKETGAHVQRV----SLISEKL
ref|YP_001489923.1|   GYFAVREDITANKEIEEIQKEIIFT-----MGSIAESRSKETSEHIERV----AKYTELI
ref|ZP_01847462.1|    RAAWLAREVAAAVSLVEAREREIVT----LLMRAAEHRDTDTGDHVARV----AGYVGLI
RAAC00986             RTELLNYEIQVDQDTAEYIENIFLQ----VLAEVAEWGDPELHAHVLRV----RRYTNWL
ref|ZP_01964315.1|    KLYAKQRRLITLITNQVYEKEKNNRMMVEILSQIVEFRNGESGSHVLNINILTGMILESL
                            :          :.          :  .* .:  *:  .:              :

ref|NP_937072.1|      AQLYG----LSDFEVNLIKHASPLHDVGKVAIPDNILHKPSKLDAQEWEIMKKHVEYGVN
ref|NP_762428.1|      AQLYG----LSDFEVNLIKHASPLHDVGKVAIPDNILHKPGKLDAQEWEIMKKHVEYGVN
ref|YP_001489923.1|   ALELG----LEPKEAKMLKLASPMHDIGKIAIPDYILNKPAKLTPEEFEIVKTHTIKGYE
ref|ZP_01847462.1|    AEAMG----FPPDRGRLISLASTMHDVGKIAIPDAILLKRGPLSAAERREMERHAERGER
RAAC00986             AAKLADRKLIDPRDVPILSSASIAHDIGKVAIAREILFKPNTLDDVEHLYIQRHTEIGEQ
ref|ZP_01964315.1|    VQKTDKYN-ITWSERLLITTASALHDIGKIGIDDKILNKPGKLTDEEFKIMQNHTIIGAR
                       .         :       ::. **  **:**:.*   **  *    *    ::  *.   *  .

ref|NP_937072.1|      ILSK----------SKRRLFAIAKEIAGTHHEKWDGSGYPMGLKGEAIPISGRITGLADV
ref|NP_762428.1|      ILSK----------SKRRLFAIAKEIAGTHHEKWDGSGYPMGLKGEAIPISGRITGLADV
ref|YP_001489923.1|   ML-----------NLSERPLLKTAAIIALTHHEKYDGTGYPKGLKGEEIPLYGRITAIADV
ref|ZP_01847462.1|    MLES---------SSSEVVRLAAEIAGTHHERWDGTGYPRGLKGEEIPLSGRIVAVADV
RAAC00986             ILQSVLDKLDDMHVHAKRVVEYAKVIAGSHHEWWNGKGYPRGLRGNDIPLPGRLVAITDV
ref|ZP_01964315.1|    ILKNMEGYEDE------ELMMVAYQICRWHHERYDGRGYPDGLKGDEIPISAQVVSLADV
                      :*            :.  *  *. ***  :* ***  **:*:  **:  .:: ..::**

ref|NP_937072.1|      FDALGAKRSYKEPWSDEQIRQEIEAQKGKHFDPRLVDLLLENWQAFIDI-----------
ref|NP_762428.1|      FDALGAKRSYKEPWSDEQIRQEIEAQKGKHFDPRLVDLLLENWQAFIDI-----------
ref|YP_001489923.1|   FDALAHERCYKKAWRVDKIVEYIKEERGKHFDPKLVDLFFENFDKILEIKK---------
ref|ZP_01847462.1|    FDALTSARPYKAAWSLEAARDHVRAQAGTHFDPAVVEAFLGRWPAVEAL-----------
RAAC00986             LDALLSRRPYKEPWSLEEVRNYIESHRGLQFDPKLVTILLEEWAAFEDLVKEVTLYEVRE
ref|ZP_01964315.1|    YDALVGERVYKKAYSHEKAVQMILNGECGAFNPILLECLID-------------------
                      ***   * **  .:    :    : :           *:*  ::   ::

ref|NP_937072.1|      -
ref|NP_762428.1|      -
ref|YP_001489923.1|   -
ref|ZP_01847462.1|    -
RAAC00986             S
ref|ZP_01964315.1|    -
```

FIG. 123A

```
ref|ZP_01170738.1|      ------------------------------YNRFLKKLLINYIFGSLIAVLAIGATFIFTT
ref|ZP_01856429.1|      ------------------------------------------------------------
ref|YP_001114416.1|     ------------------------------------------------------------
RAAC03031               MSAAGGIHSSEVCVRRDVGCGMSWTANYEFKRLVKRLILNYFAGSVIAVLGVGGVLIFTT
ref|ZP_00539543.1|      ---------------------------QKFERQLLKNYLIGSFVAVFGVGCLFIFET
ref|ZP_02168828.1|      ------------------------------RMLINYMVGSLIAVFGVGSVFIFHT ref|ZP_01170738.1|      IDARGYDKALIWLILAGSMVIMFFTEGFFFRQHIRPIRAVFLSDGMDAESVRKAILRLKQ
ref|ZP_01856429.1|      ------------------------------------------------------------
ref|YP_001114416.1|     ------------------------------------------------------------
RAAC03031               LHLSQEDLWVICGILGGSLVLMLTADSIAFRVQIRPIRKALLTAHPTEDVLAKGYKRALH
ref|ZP_00539543.1|      LTFDARERVTLLTIMFLSVVLMFSFEYTIYRKHMRPLYQFFQTSTPSQAQLTAAFRTTHR
ref|ZP_02168828.1|      LTLSSEETLILLGIMVLSGLIMISLELFVYSKHIRPLVHFFKKGMNPQDA----YMTAHS ref|ZP_01170738.1|      FPVLTVKRIMLPHLLGLTIPAASASLYLISAGELKLSYYMVLYAAIAAFLVASMHALVEF
ref|ZP_01856429.1|      ------------------------------------------------------------
ref|YP_001114416.1|     ------------------------------------------------------------
RAAC03031               LPALAVLRVMGPHWLSFLIPGLVSSSILVRRGLLHLPMAYVWLASLGTLIVACMHAVIEF
ref|ZP_00539543.1|      FPLLTIKRILGPHFLGLSIPSSSLTALAIHFQWLEMPYYLIGLACFGAILVAILHALIEF
ref|ZP_02168828.1|      FPPFMTVRRIMGPHLLGLSIPATVMTLFALSLGFLTLPHLYVLYAWIGAILIATLHAMIEF ref|ZP_01170738.1|      YLTLRAIKPVLAHFKAANKSGW---LVQETPSTIPIKKKFRLTVLVIGVLPVLIFMVAAQ
ref|ZP_01856429.1|      ------------------------------------------------------------
ref|YP_001114416.1|     ------------------------------------------------------------
RAAC03031               FLTSRSIEPTLVTIRRRSEHMYGASVLLRGQVVVPLAFKFAMSAVVFGALPLLLFGLANA
ref|ZP_00539543.1|      FLTYRVTESMLAELTVQSQQYGHGELILTKKDFISLRKKMLISTLIIGVFPILLFVLASA
ref|ZP_02168828.1|      FMTSRAVQPLIASICARTDE----NLKLDGVKVISMKWKLLLSMLLIAVFPAALFLLAGQ ref|ZP_01170738.1|      IKLEGMGMETAVFWQWAAVVIFITVCYAMLTAKYMAEDIEEPISRLQTLMSEAENQNFAY
ref|ZP_01856429.1|      ------------------------------------------------------------
ref|YP_001114416.1|     ------------------------------------------------------------
RAAC03031               VRLTHEGLGSSTYWTWAGGILALGSLFSAFGGYLLASDVQRPIRRLEALMRRVERGDFSL
ref|ZP_00539543.1|      VQLT-ENESLRSYWSWSTLILIVILCLATFCSLLLYENIQKPILALQEGVAQIESGQLNT
ref|ZP_02168828.1|      IRESAET--TTAYWNWAFLVIVVILFVSIAGAVVLYRNMEQPILELRKNLEQVQHGEFHref|ZP_01170738.1|      LKDNVYTDEFSEVFTGFNIMIAALKQREETNRQLLESFMTVLSAALDARDPYTSGHSMRV
ref|ZP_01856429.1|      ----------------------AQQEE----LMLSFVKSFISTLDAKDPYTRGHSERV
ref|YP_001114416.1|     -----------------------------KTMFKSPLVALASAIDARDPYTRGHSERV
RAAC03031               RADDTYMDEFSDLIQGFNLMLNGLAHRDAMNRQLIDSYFATLAAALDARDPYTAGHSQRV
ref|ZP_00539543.1|      -INNPFSDEFSQLVGGFNLMVEGIQGRDQENEQLLDSLFTLFAATLDARDPYTAGHSLRV
ref|ZP_02168828.1|      EMPNYYADEFSTLINGFNSMVSGIKSRDAENERLLESFFSVFAATLDARDSYTAGHTTRV
                                                  ::  *  .  : :::**:*.** **: **

ref|ZP_01170738.1|      ASFSRDIGKRLGLHDEELKQLYQTALLHDIGKIGVPDGVLQKEGKLSDEEFEYIKAHPVI
ref|ZP_01856429.1|      ALIAQQLAKQLGYSGEFIQDIYLSGLLHDIGKIGVDDGILRKEGKLTDEEFSQIQKHPMI
ref|YP_001114416.1|     SQYSLMMGKALGLPEQDLELLERAAFLHDIGKIGIRDHILLKESPLDNEEFIIMKTHTTI
RAAC03031               ARYAEAIGRKVNLSPQTVRELRQSALLHDIGKIGIRDEILLKEGKLTDEEFAIIKQHPVI
ref|ZP_00539543.1|      AEYSVEIARAAGLADDQVELLRKSALLHDIGKIGIRDDVLLKEGRLTGEEFDKIKQHPVI
ref|ZP_02168828.1|      ADYSTQIARRSGLSGDELDLLRKSALLHDIGKIGIPDSVLLKDGKLTDEEFDKIKEHPVI
                         :   : ..:   .   : :  : ::********:  * :*  *:.  * .***  :: *. *
```

FIG. 123B

```
ref|ZP_01170738.1|      GETILKQVQPAGEVASLLPGIRSHHERIDGKGYPDGLQGEEIPYFGRIIAVADSYDAMTS
ref|ZP_01856429.1|      GYKILTGIKK---LKNILPGIRNHHEQIDGRGYPDGLRGSDIPLMARIIAVADAYDAMGS
ref|YP_001114416.1|     GQNILQQIEPNYLVQEISQGAACHHERYDGKGYPQGLQREEIPLAARIMAIADTFDAMVT
RAAC03031               GENIIRQIQPDDAMKPLLPGIRSHHERYDGKGYPDGLAGEEIPLFGRILAVADAFDAMTS
ref|ZP_00539543.1|      GVHILSQVHLPEKLQPILPGVKYHHERYDGKYPEGLAGESIPVFGRIMAIADAYDAMTS
ref|ZP_02168828.1|      GGDILEKVNLPEHLRPLLDGVRHHERFDGKGYPDGLSGDRIPLYGRIIAVADAFDAMTS
                        *  *:  :.     :  :  *    ***: **:***:**   . **  .**:*:**::*** :

ref|ZP_01170738.1|      DRPYRKGMPPEKALHILESGKGTQWDPQVADAFIELARKM------------------
ref|ZP_01856429.1|      DRPYRNGMPLERLENIFREGKGLQWDSDVIDAYFEIRDEI------------------
ref|YP_001114416.1|     DRPYRKGLPVKLALQEIKRCAGSQFDPQLAEIFL------------------------
RAAC03031               DRPYRSGMPVERAIQVLREGRGTQWDPHFVDAFIEVYREVYIPDEAKSAAREAAASTSQ
ref|ZP_00539543.1|      DRPYRKGMPVAKALAILEEGSGTQWDASFTQLFLDLKR--------------------
ref|ZP_02168828.1|      NRPYRKAMSYEQARNILQNGRGSQWDPAFIDHFMDFYEE-------------------
                        :****..:.          :.    * *:*. . : ::
```

FIG. 124

```
pdb|1B4A|A              ------------------------------------------------N
sp|O31408|ARGR_BACST    ------------------------------------------------N
ref|YP_001126414.1|     ------------------------------------------------N
ref|NP_243643.1|        ------------------------------------------------N
ref|ZP_00538558.1|      ------------------------------------------------T
RAAC01956               ---------------------------------------MKRRLSVQS
                                                                        .

pdb|1B4A|A              KGQRHIKIREIIMSNDIETQDELVDRLREAGFNVTQATVSRDIKEMQLVKVPMANGRYKY
sp|O31408|ARGR_BACST    KGQRHIKIREIIMSNDIETQDELVDRLREAGFNVTQATVSRDIKEMQLVKVPMANGRYKY
ref|YP_001126414.1|     KGQRHIKIREIIMNSDIETQDELVDRLKEAGFNVTQATVSRDIKEMQLVKVPMANGRYKY
ref|NP_243643.1|        KGQRHIKIREIIANNDVETQDELVEQLKAAGYNVTQATVSRDIKELHLVKVPMMDGRYKY
ref|ZP_00538558.1|      KGQRLIKIREIITQSEIETQDELVEELRNAGYKVTQATVSRDIKELHLVKVPLNDGRYKY
RAAC01956               KEQRLMRIREIVSQNEIETQEDLVRALEEAGFPVTQATISRDIKELQLVKVVGSNGKYKY
                        *   :::   ..::*::**   *. . *:**.::**      :*:*** pdb|1B4A|A              SLPSDQRFNPLQKLKRALVDVFIKLDGTGNLLVLRTLPGNAHAIGVLLDNLDWDEIVGTI
sp|O31408|ARGR_BACST    SLPSDQRFNPLQKLKRALVDVFIKLDGTGNLLVLRTLPGNAHAIGVLLDNLDWDEIVGTI
ref|YP_001126414.1|     SLPSDQRFNPLQKLKRALVDVFIKLDGTGNLLVLRTLPGNAHAIGVLLDNLDWGEIVGTI
ref|NP_243643.1|        SLPADQRFNPLQKLKRGLVDSFVSIDRTDNLIVMKTLPGNAHAIGALIDNLDWTEIMGTI
ref|ZP_00538558.1|      SLPADQRFNPLGKLRRLLGDSFISIDSAQNLYKVMHVLPGNANALGVLLDHLNWPELLGTV
RAAC01956               ALPTAVNKVSVDALQRRLAEVFISHARANNLIVIKVAPGNAHAIGALMDALDPPGLLGTI
                        :**:    .  .: *:*  *  :  *:.     : **:**::. ****:*:*.*:* *:    ::**:

pdb|1B4A|A              CGDDTCLIICRTPKDAKKVSNQLLSM-
sp|O31408|ARGR_BACST    CGDDTCLIICRTPKDAKKVSNQLLSM-
ref|YP_001126414.1|     CGDDTCLIICRTPKDAKKVSNQLLSM-
ref|NP_243643.1|        CGDDTILIICKDKQDGPVVTERFLNM-
ref|ZP_00538558.1|      CGDDTILMITRNEEAATEVTERILGM-
RAAC01956               CGDDTMLLVCQDEEAAVRLLNETLNIG
                        ***** *::  :   :   : :. *.:
```

FIG. 125

```
ref|YP_001127098.1|        ---------------AQKKLLPDLLEVMQKRYQILHSISLMAPIGRRALAASLGMSERVLR
ref|YP_148912.1|           ---------------AQKKLLPDLLDVMQKRYQILHSISLMAPIGRRALAASLGMSERVLR
ref|ZP_01696601.1|         ----------------KKLYPDILAVMQKRYRILRSISFAEPVGRRTLAQMLGMSERVLR
ref|ZP_01171675.1|         ----------------KRLLPDLLTVMQKRYQILQYIGFMQPVGRRSLAVSLGSTERVLR
ref|YP_176517.1|           -----------------QIVPELMETMAKRYRLLQYIRLMQPIGRRSLATNLQTSERIVR
RAAC01498                  MTMRRSGMEWTVWAAVERVAPELVRAMEHRVRVMQRIDAHAPIGRRALAQAMGQSERTLR
                                             ::  *:::  .*  :*  ::::  *      *:*:    :  :** :* ref|YP_001127098.1|        SETEFLKGQNLLSTDVSGMRLTEEGQALLHTLNDLMREALGLKELETALKQRLNVARVVV
ref|YP_148912.1|           SETEFLKGQNLLSADVSGMRLTEEGQALLHTLNDLMREALGLKELEAALQEQLGIPRVIV
ref|ZP_01696601.1|         SETDFLKNQKLIDVKPSGMSVTNDGAALLQNMESMMREISGINETEEKLKQALGLEDVVV
ref|ZP_01171675.1|         SEVDFLKNQNLISVASSGMNLTAEGKDLLERLESIMRDITGIDILEARLKEVLGVRQVIV
ref|YP_176517.1|           GEVTLLKDQGLIELTTAGMRLTEAGEALFLELADMMAELLGHRRLEEKLKEKLGVSQAIV
RAAC01498                  TELDYLKQLGLVATSSSGVSLTPEGKALLGELEPLVAEIAGRSDLAWRVSALLRIPRVIV
                              *  **   *:    :*:.*    *   *:   :  ::  *      :.   *  :   ..* ref|YP_001127098.1|        VAGDSDRSPWVKKELGRACVACMKEQLRPGDIVAVAGGTTMAAVAEMMTPDPKLA-DVLF
ref|YP_148912.1|           VAGDSDRSPWVKKEMGRACVACMKELLEPGDIVAVAGGTTMAAVAEMMTPDSKLR-DVLF
ref|ZP_01696601.1|         VQGDSDKEPWVKNELGRACAVRMKAALTGNNIIAVTGGSTMAAVADVLTPDISAKRQLLF
ref|ZP_01171675.1|         VAGNSDESPWVKSELGRACAASMKQRLKGKNTVAVTGGSTMAAVAEMLTPNLFDD-ELLF
ref|YP_176517.1|           VAGDSDEEEWVKQELGRACVDELKRVAKKGDVFAVMGGTTLAAVANMVTPDETLA-TTTF
RAAC01498                  VEGDADEDAWVTDRIGQAGSDVLAEVLQDGDIIAVTGGTTVAAVAKAMSAKPLRQ-RITV
                           * *::*.. **...:*:*       :       : .** **:*:****. ::..        .

ref|YP_001127098.1|        VPARGGLGEDVENQANTICAKMAEKATGRYRLLHVPDQLSGEAYASLIEEPAVKEVLELI
ref|YP_148912.1|           VPARGGLGEDVENQANTICAKMAEKAMGRYRLLHVPDQLSDEAYASLVEEPAVKEVLELI
ref|ZP_01696601.1|         VPARGGIGEDVANQANTICAKMAERTGGKHRVLVYVPDQVSPEVYKSVVNEPSIKEVLTLI
ref|ZP_01171675.1|         VPARGGIGEEVKNQANTICAMMAEHTASRHKFLHVPDQVSKTMYETIMKEPVINEVLNLI
ref|YP_176517.1|           VPARGGLGEKVEIQANTISAEFARRSGASYRLLHVPDQLSEEAYHSLVLERSVREILDVI
RAAC01498                  VPARGTVGEIVAYQANTIASELAAKLGGSSVLLQISDSLSQKALEQLLDDPYIQERLPII
                           ***.:.:  ***.: :*   .   .*  :.*.:*        ::   :.* *  :* ref|YP_001127098.1|        QSCRMVVHGIGEAVTMAKRRKTPPVEMEKIIARHAVAEAFGYYFNEHGDVVHKVKTVGIQ
ref|YP_148912.1|           QSCRMVVHGIGEAVTMAKRRKTPPVEMENIIARHAVAEAFGYYFNEYGDVVHKVKTVGIQ
ref|ZP_01696601.1|         KQADIVLHGIGEAMTMAERRKTGKEEMEKIIRGHAVGEAFGYYFNEQGEIVHKVRTIGLQ
ref|ZP_01171675.1|         QSAGMVLHGIGDAITMAERRKTTPEDLLKIQERKAVGEAFGYYFDEAGEVVHKVQTIGLQ
ref|YP_176517.1|           TSSAVVMHGIGDARRMAARRDSGQPFIETLKREEAVAEAFGYYFNANGEIIHKQRTIGLQ
RAAC01498                  RQATVVVHGVGDALAMARRRHATEEEIKLLEAREAKAEAFGHYFNARGEVVYAMRTIGLR
                              .. :*:**:*:*    ** **.:          :     .* .****:**:   *::::    :*:*::

ref|YP_001127098.1|        LENLPHVEHVIAVAGGASKAKAIQAYIKRAPHS-LLVTDEGAAKALV-------------
ref|YP_148912.1|           LEHLPHVEHVIAVAGGASKAKAIRAYMKRAPHS-LLVTDEGAAK----------------
ref|ZP_01696601.1|         LEDLHRIRHVFAVAGGASKAKAIKAYMNTKPESTVLITDEGAAKQIL-------------
ref|ZP_01171675.1|         LKDLADIEHVVAGGSSKAKAIRAYMKQAPSSTILITDEGAAKQLLK--------------
ref|YP_176517.1|           LGE-LEGKYVISIAGGHTKANAILAYMKNRPSD-VLVTDEGAARRLL-------------
RAAC01498                  LDDVARARVVIAVAGGQKKAQAIASVANAYRID-VLVTDEGAARRILQLETPAGKERVEH
                           *  .        . *:::***  .**:**    :           . :*:******:

ref|YP_001127098.1|        ------
ref|YP_148912.1|           ------
ref|ZP_01696601.1|         ------
ref|ZP_01171675.1|         ------
ref|YP_176517.1|           ------
RAAC01498                  GSEGWY
```

FIG. 126

```
ref|YP_090740.1|         ---------------------------MATIKEIALQAKVSSTTVSRVLNHDQSLSVAP
ref|YP_078338.1|         ---------------------------MATIKEIALQAKVSSTTVSRVLNHDQSLSVAP
ref|YP_001422307.1|      ---------------------------MVRLKDIALQASVSSATVSRILNKDDSLAVTD
ref|NP_243093.1|         ---------------------------MATIKDIAKLANVSNATVSRVLNRDATLSVTE
ref|YP_001126180.1|      ---------------------------MATLKEIAEKVGVSVATVSRVLNYDTTLSVSD
RAAC01624                MEIFLCIFTRKIILSLSPVICVKGGGKVLATMKDVAELARVSIAVVSRVLNEDRSLSVPE
                                                    :  :*::*   . ** :.***:** * :*:*.

ref|YP_090740.1|         ETRQRILDIAARLGYKSTRRREVYASGSGESPRIGIVVCQSQEEELNDPYFYSIRQGIE
ref|YP_078338.1|         ETRQRILDIAARLGYKSTRRREVYASGSGESPRIGIVVCQSQEEELNDPYFYSIRQGIE
ref|YP_001422307.1|      ETREKVLRIADELGYQPSAKRR-KNRSRSDSAPLIGVVSCLSPEVERQDPYFSAIRKGIE
ref|NP_243093.1|         ETRERIYSIAKELGYKRIKERQ---ETKKQVAPNIGIIILQSPEEEIDDPYFNSIRNGVE
ref|YP_001126180.1|      ETRKRIFEVAQELNYKTLRERS---QQARESFR-LGLIHWYSERQEIDDPYYMAIRLGVE
RAAC01624                STRKRVIEAANQLNYKVKRRQN---RSATSKIKTIAIVDFHPEEQERDDPYFWPMVRGIE
                         .**:::   * .*.*:      .:             :.::    . . * :***: .:    *:* ref|YP_090740.1|         SECFERGAF--ITKFIQLSSIR--SNQPVGD--VDGLIVIGRINFAGLQQCMGALNN--V
ref|YP_078338.1|         SECFERGAF--ITKFIQLSSIR--SNQPVGD--VDGLIVIGRINFAGLQQCMGALNN--V
ref|YP_001422307.1|      EECFRQKVF--ITSSIHLGSFQ--EHMFHEL---DGVIVIGSLQDEALTNISAAFRH--A
ref|NP_243093.1|         QTLQAKGIY--STKVIHVQDST--TTSNIDG--LDGLIIIGGVTSDKIKQMTAPLEH--L
ref|YP_001126180.1|      KECFERG-IQLVKLFKQNGA-YPIERMKELD----GIIAVGKFGPKEVSDFARGAKQ--I
RAAC01624                LECQEKGLIHPVKFYVKTPAEF--SPSELSN--FDGVLVIGAEEWSGWDDFH--HPN--V
                          :          .      :               *::  :*              :           :

ref|YP_090740.1|         VYINHTDNEELRDSVVVDFEKATGRALNHLKSLGYTRIGYIGGREKEHFRISDQETSAIE
ref|YP_078338.1|         VYINHTDNEELRDSVVVDFEKATGRALNHLKSLGYTRIGYIGGREKEHFRISDQETSAIE
ref|YP_001422307.1|      VFVNGTPDPARYDSVSVDFYAAAQKAIEHLLSLGYQRLGYIGGRER EHTVIDG-VNSNKT
ref|NP_243093.1|         VFVNRCPSEEEFDSVVIDFEKATSKALDYLFLKGFRRIGYIGGTERQLS-----DQGKVE
ref|YP_001126180.1|      VFVDCSPDERQFDSVVIDLRQATITVLDYLLQLGHTKIGYIGGRE--------YVDGETP
RAAC01624                VFLDHCPNVARYSSVLLNFSSAVKDVFNHFWRLGYRTFAYIGGTRRFG------------
                         *:::   .    .**  ::: *.  .::::    *. :.****  .

ref|YP_090740.1|         IEDKRLTAFL---EMAGSDNAKH-IYIGEYSMQQGYELMKKALLE-KNVPEAFFIASDSM
ref|YP_078338.1|         IEDKRLTAFL---EMAGSDNAKH-IYIGEYSMQQGYELMKKALLE-KNVPEAFFIASDSM
ref|YP_001422307.1|      IEDKRLTAFL---QMAG-AEPEH-VLIGEYSMHEGFRLMNEAIKGGS-LPDAFFIASDSM
ref|NP_243093.1|         IEDFRHTVYVKKMEELGLYEPSL-VFIGEYKMTEGYKLMKRAIEAG-NLPEAFFISSDPM
ref|YP_001126180.1|      IRDERETAFYEYLYVKGMYDSRD-VWIGAFTAEDGYRLMKEAIAKG-DLPTAFFIASDSM
RAAC01624                -MDERESTFR--TCVKSTVGAEPPVYHGDWSTGGGYEAMKLMLQEGAPLPRAIFVASDPM
                          * * :.:         .   .     : *  :.     *:. *:   :      :*  *:*:**.* ref|YP_090740.1|         AIGALRALRESGLKVPEDVAIVSFNGIEASEFANPPLTTVKVHTEEMGRTGVKLLLLDRLK
ref|YP_078338.1|         AIGALRALRESGLKVPEDVAIVSFNGIEASEFANPPLTTVKVHTEEMGRTGVKLLLLDRLK
ref|YP_001422307.1|      AVGALKALQEAGLQVPRDTAVVSFNDNEMAQFVDPPLTTVKVFTEQMGEMAVQLLLLDRLN
ref|NP_243093.1|         AVGALRALKEANIAVPRDVSLVSFNDNEMAQFVDPPLTTVKVFTEQMGEMAVQLLLLDRLN
ref|YP_001126180.1|      AIGALRALHEAGIAVPQDVAIVGFNDLPTAAFLHPPLSTVKVYTEFMGETAVELLIERLT
RAAC01624                AIGVIRALTEIGKRVPEDVAVVGFDDIDMAAYVNPALTTIRVQPEVMGRIGVRMLMCPYD
                         *:*.::** *  .  **.*.::.*:.    :  . .*:*::  .* **  .*.:*:

ref|YP_090740.1|         -GRELPLKVTVPSELIIRE----------------
ref|YP_078338.1|         -GRELPLKVTVPSELIIRE----------------
ref|YP_001422307.1|      -GRTVPLAVTLPTSLIVRQ----------------
ref|NP_243093.1|         -GRTLPLKVVVPTELVVRE----------------
ref|YP_001126180.1|      TKRTICKKVIVPTELVVR-----------------
RAAC01624                --PNVPVQVVMPYQLVIRESCGACGSLAAGGRDFGL
```

FIG. 127

```
ref|ZP_01696173.1|     ----------------------------------------LGEQIANELRLLILTNEIKPGDI
ref|ZP_02327860.1|     ----------------------------------------LGESIACELRLQIINGTIKPGEV
ref|ZP_00539488.1|     ----------------------------------------GDRVAHELRMRIISGKIESGTV
ref|YP_034511.1|       ----------------------------------------GDRVASELRMRIIAGAIESGTI
ref|NP_694112.1|       ----------------------------------------GEQVVAELRMRIISQAIEPETV
RAAC00077              ------------------------MRRNAGGERRLGDVIADVLRREIVWGEWPSGHV
                                                               *: :.  **  *:      . :

ref|ZP_01696173.1|     ISENQIARKYGTSRSPVRDALKALANDGLIQLERMGARVLGMGLTDIHELYDVREMIEIF
ref|ZP_02327860.1|     ISENRVAADFGTSRSPVREALKTLSNEGLIRLERMGAVVLGLSSKDVEELYDVRFLIESF
ref|ZP_00539488.1|     LSENKLAADFSVSRSPVRDALKVLASERIIRLERMGAVVVGLSKKDIQEIYDVRLLIETF
ref|YP_034511.1|       LSENKIAADFSVSRSPVREALKLLASENIIRLERMGAVVIGLTEKEIEEIYDVRLLIETF
ref|NP_694112.1|       LSENQLAKEFQVSRSPIREALKVLSSENIVRPERMGAVVIGISEKDIEEIYDVRLMMESF
RAAC00077              FSENALARRFGTSRSPVREALRQLAHEGLISLGRNGARVVGLDLGDALELYDVRSLIEQF
                       :***  :*   : .****:*:**: *:  : :: * ** *:*:  : *:**** ::* * ref|ZP_01696173.1|     AQQRVSAAP---QE---QLIQFLNETIDKMKIAAKYENHSDFAYYDFSFHDRIIRHAGHK
ref|ZP_02327860.1|     VQERLAS---INQE---PLMTKLNQIIDKMELAVKYNDIADFAYQDFSFHETTVAAAGHN
ref|ZP_00539488.1|     VFERIV---KMDRQ---DLVRELSKVLEMMKIAIKYKDADEFSYQDVLFHETIIRSIDHG
ref|YP_034511.1|       IFERL---GKMDTN---DLVRELNKIMEMMKIAIKYHDSDEFSYQDLLFHETIIRTIEHS
ref|NP_694112.1|       TFQRLL---DMDNA---SLINDLEKVVEMMKIAIKYKDVDQFSFLDMEFHETIIRSINHH
RAAC00077              TASRVCERPRAERE---SLAHTLSTLVLAMEEAASRRDWQSFSDLDLAYHDAIVRAANHR
                         .*:              *   *.  :  *: * .. :     .*:  *. :*:    * ref|ZP_01696173.1|     RILNLWNGMKSLIMAVLLVTTEHVFAHGPDHLAWVIEKHRKIVNSLLTGNEENVEQSVSA
ref|ZP_02327860.1|     RIFYLWTSIRHIVMTVMLITTEEVFSMGERKKQSVIEKHRTIIRGLESKNGEIILKTVRT
ref|ZP_00539488.1|     YVSMMWQNLKPVMESFILLSMRQRLDEDIEDFERILENHALYIEAIETGD----------
ref|YP_034511.1|       YILMIWNNLKPVMESLILLSMRTRFKEKYEDFERIIKNHELYIKAIESKDRALMIEALHQ
ref|NP_694112.1|       YIAMLWTNLKPVMECLVLLSMRYRMQEDENDFERIIENHRLIVESIKNKDANLVNNAFYK
RAAC00077              RVLRMWDEMRSLVQLTLALVMRKRMQRGDADMRGALAQHRSLAEAILAGDAAWVRRVMQS
                            :  :*  ::    ::    ::  .         :  :*         ..:   :

ref|ZP_01696173.1|     YFKDSKRTLD------------
ref|ZP_02327860.1|     YFADSRQTLHNSL---------
ref|ZP_00539488.1|     ----------------------
ref|YP_034511.1|       NFDDVQGKVE------------
ref|NP_694112.1|       NFNDVQNRVE------------
RAAC00077              HVEETRRLLEGGLRGHPAGDER
```

FIG. 128

```
ref|NP_980690.1|         ---------MLTERQLLILQTIIDDFIGSAQPVGSRTLAKKDEITFSSATIRNEMADLEE
ref|ZP_02257686.1|       ---------MLTERQLLILQTIIDDFIGSAQPVGSRTLAKKDEITFSSATIRNEMADLEE
ref|YP_038371.1|         ---------MLTERQLLILQTIIDDFIGSAQPVGSRTLAKKDEITYSSATIRNEMADLEE
ref|YP_079889.1|         ---------MLTNRQLLILQVIVNDFIRSAQPVGSRTLSKKEDITFSSATIRNEMADLEE
ref|ZP_02170056.1|       ---------MLTERQLLILKAIIDDYVSHAEPVGSRSVSKRDDIHFSPATIRNEMSDLED
RAAC00876                ---------MLTPRQQLILSAIIEDYVRMAEPIGSRALAKHEEIQYSPATIRNEMADLEE
                                  *** ** ***..*::*:: *:*:***::*::* :*.*******:***:

ref|NP_980690.1|         LGFIEKTHSSSGRVPSEKGYRFYVDHLLAPQNLPNDEIVQIKDLFAERIFEAEKIAQQSA
ref|ZP_02257686.1|       LGFIEKTHSSSGRVPSEKGYRFYVDHLLAPQNLPNDEIVQIKDLFAERIFEAEKIAQQSA
ref|YP_038371.1|         LGFIEKTHSSSGRVPSEKGYRFYVDHLLAPQNLPNDEIVQIKDLFAERIFEAEKIAQQSA
ref|YP_079889.1|         LGFIEKTHSSSGRIPSEKGYRYYVDHLLSPGKLSKTDLNIIHSIFKEKIFELEKAVQKSA
ref|ZP_02170056.1|       MGFLEKTHSSSGRIPSHKGYRHYVDHLLSPGQLSKEDIGNIQDVLRSRFHELEEVVRHSA
RAAC00876                MGYLTQPHASAGRPPSQKGYRFYVDNLLRLGQMDRETGEFLKSVFTKRIDEVEQVAREVA
                         :*:: :.*:*:..**.*:**   ::  .     :: .: ..:  . * ref|NP_980690.1|         QILSELTNYTAIVLGPKLSTNKLKNVQIVPLDRQTAVAIIVTDTGHVQSKTITVPESVDL
ref|ZP_02257686.1|       QILSELTNYTAIVLGPKLSTNKLKNVQIVPLDRQTAVAIIVTDTGHVQSKTITVPESVDL
ref|YP_038371.1|         QILSELTNYTAIVLGPKLSTNKLKNVQIVPLDRQTAVAIIVTDTGHVQSKTITVPESVDL
ref|YP_079889.1|         QVLSDLTNYTSIVLGPRLSENHLKQIQIVPIQPKKAVAILVTNTGHVENKTINFPAEVDL
ref|ZP_02170056.1|       KLLSELTNYTSIVLGPEMFESKLRQIQLIPISDKQAVAIIVTDTGHVENQTVHFPERINP
RAAC00876                NVLSMLTKQTVIVLGPKTDTEKLRKIELIPLGGGRAIAILVTNSGHVETVHVRFSSEMEA
                         ::** **: * *****.  .:*::::::*:   *:*:**::***:.  : .. ::

ref|NP_980690.1|         SDLEKMVNILNEKLSGVPMSELHNKIFKEIVTVLRGYVHNYDSAIKILDGTFQVP-LSEK
ref|ZP_02257686.1|       SDLEKMVNILNEKLSGVPMSELHNKIFKEIVTVLRGYVHNYDSAIKILDGTFQVP-LSEK
ref|YP_038371.1|         SDLEKMVNILNEKLSGVPMSELHNKIFKEIVTVLRGYVHNYDSAIKMLDGTFQVP-LSEK
ref|YP_079889.1|         SDLEKLVNILNERLRGVPISELKDRIFKEVVIFLKSHIQNYDTILHALGATLDSSVQTDR
ref|ZP_02170056.1|       DDLEKVVNILNDRLRGVPLYKLNEALSKEIHAVMKQYVNRHEAMLNVFHEVFRQHAREK-
RAAC00876                DDVETLVRVLNDKVVGVPISELRRTLYAELAGELRRTVERFEDAIAVLNEVCQVPEREEA
                         .*:*.:*.:**::: ***   :*.  :  *:   ::  :....:  : .       .

ref|NP_980690.1|         IYFGGKANMLSQPEFHDIQKVRSLLTMIDNEAEFYDILRHKQVGIQVKIGRENSSTAMED
ref|ZP_02257686.1|       IYFGGKANMLSQPEFHDIQKVRSLLTMIDNEAEFYDILRHKQVGIQVKIGRENSATAMED
ref|YP_038371.1|         IYFGGKANMLSQPEFHDIHKVRSLLTMIDNEAEFYDILRHKQVGIQVKIGRENSATAMED
ref|YP_079889.1|         LFFGGKINMLNQPEFHDIDRVKSLLSLIEKEQEILRLFQSTESGITIKIGKENDYEEMEN
ref|ZP_02170056.1|       VYFSGKTNILAQPEFNDVERVRKILNIFEEDQLVSKLFRSDQEGMTIRIGEENHFAPFDD
RAAC00876                VYIGGASNMLAQPEFHDVGKAQPILSLLEQNESISNWFPKAEDGIEVRIGAENAVVELKD
                         :::.*  *:* ****:*: :.: :*.:::::  .    :   *: ::** **   :.:

ref|NP_980690.1|         CSLISATYSIGEEQVGTIAILGPTRMQYSRVISLLQLFTRQITDGLKK-----
ref|ZP_02257686.1|       CSLISATYSIGEEQLGTIAILGPTRMQYSRVISLLQLFTRQITDGLKK-----
ref|YP_038371.1|         CSLISATYSIGEEQLGTIAILGPTRMQYSRVISLLQLFTRQFTDGLKK-----
ref|YP_079889.1|         CSLITATYTVGSKQIGSIAVIGPTRMDYSRVVGLLQHVSSDLSKALT------
ref|ZP_02170056.1|       CTIITATYEAGGQYLGTVGILGPTRMEYPRVISIMEYLATDLSKKLS------
RAAC00876                CTVIATTYRLGGVPVGHIGVLGPTRMDYNRVMQILSFTSQALTEFLTRFASSG
                         *::*::**  *   :* :.::*****:* **: ::.  :  ::. *.
```

```
FIG 129 ref|YP_001488458.1|         ------------------------KVTINEVAAYAGVSKSTVSRYINGRTNEISIEKVK
ref|YP_080909.1|            ------------------------KVTINEVAAHAGVSKSTVSRYINGKIDAISPKKVK
ref|ZP_01665756.1|          ------------------------TIRDVAQQAGVSKSTISRYLNGRYECMSLETRE
RAAC00525                   MIAGQDGGGGAPPPFAWERRHSVPKRATIQDVARAAGVSVTTVSRYLNGRYESMSENTRE
ref|YP_841318.1|            ----------------------EKLTIQDVADYAGVSKATVSRYLNRGGEQLSADVEA
ref|NP_347033.1|            ------------------------KKVVIDDVAKLAGVSKATISRYLNGKFEYMSEKTKD
                                                    .* :** **** :*:***:*    : :* .

ref|YP_001488458.1|         KIKKAIEELHYRPSQLAQGLKVRKSKVIGFIVADITNPFSVATLRGVEEICDEYGYSIMV
ref|YP_080909.1|            SIKKAIEELNYRPSQMAQGLKVKKSKVIGFLVADITNPFSVATLRGVEEVCDQYGYSIMV
ref|ZP_01665756.1|          RIARVIAELDYRPNAVARSLKQKRTHTVGAIVANILNPFSTSIIRGVEDHCKKHGFNLIL
RAAC00525                   KIAAVIAELGYRPNALAKGLKAQRTETVGAIVVNMSYPFCVGFLRAFSRTLSAAGYHLMV
ref|YP_841318.1|            RVAAAIRALGYSPSPMAQGLKRGKSRLIGLVVADVSNSFSVAVLRGVEKACRDAGYMVML
ref|NP_347033.1|            RIKESIEELNYRPNNIARSLKSNKSKLIGVVIADLTNPFSSIIIKGIGDECKARGYNMVI
                              :    *   * *  *. :*:.**   ::. :*  ::..::   .*.   ::..    *:  :::

ref|YP_001488458.1|         CNTDNRPEKEREMLLKLNAHYIEGLIINTTGQNNDILQDFQKDGVPIVLVDRKLSELKVD
ref|YP_080909.1|            CNTDNSPEKEREMLHKLNAHYIEGLIINTTGRNNDVLLDLISQDVSIVLVDRKVPGLKID
ref|ZP_01665756.1|          CNADDDPVKEREYIEMLTAKQIDGLIINTTGGNN-PLVKEVNASVPVVLIDRKAPEMGLD
RAAC00525                   AESEGDAKRERQLIESFVANRVEAIALQTSGANN-DYLEDLAREMPVVLVDRAFALRNAY
ref|YP_841318.1|            FNLGNDEQLEREAIRSLSAYRVEGFILHTLGHDAGALADAAQLGKPVVLVDRKVGDAEVD
ref|NP_347033.1|            ANSDNDVKQEEEYIKSLLDQRVEGIIVNSTGYNEEFLLSIKERGIPVSMVDRTFCEDKVD
                              :       .   *.: :    :    :::.: *** *   :    .:  ::**

ref|YP_001488458.1|         TVTTNNRDITIQLLQQMYEKSYEHIAFFTEPVDGISPREERKEAY-EQTAMSKHK--KPI
ref|YP_080909.1|            AVTTNNREVTSQIVNLMYDKGYAQVGLFTEPIKGISPREERASAY-TEIALERNAGGTPL
ref|ZP_01665756.1|          TVTVDSDLGARLAIGHLVGLGHRRIAMFTLPCDQVSPRLERVRGYQAALAEYNIPFRPEL
RAAC00525                   AIGTNNRDASREIAWQLFDLGYDCVVYLTEDERGIPTRTDRLEGY---LDACRVALREPV
ref|YP_841318.1|            LVALDNQTAVQEAAGHLVEAGYRRLLFISEPIKAISSRNERARAFQAFVAEH-VDTVGGT
ref|NP_347033.1|            SVKSNNYDITVETINYLIDAGFNSLCFFTERLDNIKPRIERERAFIDVCSKRLKKENYNI
                                  :      :.              :     ..      :     ::     :.* :*   .:

ref|YP_001488458.1|         IKEIDLKQK---EQLREELVHF-VQTNQQKKAILAANGLLMLKLISELVELGLKIPEDIG
ref|YP_080909.1|            VYEADVKDK---ESLLQSV-KSFLEMKEGKKAILGNNGLLMLKIISCLYELGISIPEDVG
ref|ZP_01665756.1|          LVETDTQLETVIAKVRELLTRAPG---ERPTAIFGANNLMTMAIVKALKRLGVAIPRDMA
RAAC00525                   VMRVRRGDP---ASFREALARVDACARKERTAVYTANGLVLMECYRPLRALGHKVPDAMG
ref|YP_841318.1|            VPEAQRGDDDALDEALRALRRGAG---QAPVAVLAANAVISLRVAASAARLGWQLGADLG
ref|NP_347033.1|            SVVDYSKAGNLEVNIYKFLNNYSG-----KKAIFAVNGVVLLHTLSAINKLNINVPKDLG
                                     . :.          *:   * ::  :          *.  :    :.

ref|YP_001488458.1|         VAGFDDTEWYKLIGPGITTVAQPSHEMGKAAMQKIKTRLEG---DESAPQTIQLDGEIIV
ref|YP_080909.1|            IAGFDDTEWYKLIGPGITTIAQPSHEMGRVAMERIIKRIEG---DESAPQTIQLEAELVL
ref|ZP_01665756.1|          VIGFDDWEWAELIDPPITVVAQPVYDMGVKAAAVLIKRIKAGKPPKKPATVVFAPQLVV-
RAAC00525                   IATFDQPDWADLVDPPLTCVRQPVEEMGEAAGRIITARLRG---EAVAAEVLVVPSTVVM
ref|YP_841318.1|            LIGFDDPEWAALVGPGLSAISQPTDDIGRVATNCLIERLQG---TQLPPRRVLLPGTLVT
ref|NP_347033.1|            ICGYDNWGWAALIPPGITTISQPSYEMGSEAAKLVLDRIEG--KASLGAVCKTLSAKLEI
                            :  :*:   *   *: * :: :  **   ::*   *    :*:..   .         :

ref|YP_001488458.1|         RKS----
ref|YP_080909.1|            RQS----
ref|ZP_01665756.1|          RASCG--
RAAC00525                   RGSTGRG
ref|YP_841318.1|            RGSTRR-
ref|NP_347033.1|            RGST---
                            * *
```

FIG. 130

```
ref|ZP_02320157.1|    ------------------------------------------------------------
ref|YP_013918.1|      ------------------------------------------------------------
ref|NP_470676.1|      ------------------------------------------------------------
ref|YP_849514.1|      ------------------------------------------------------------
ref|ZP_02330749.1|    ------------------------------------------------------------
RAAC01072             ---------------------------------------------------MGPKGVG ref|ZP_02320157.1|    ----ISKRQQDIYEFIKSEVKEKGYPPSVREIGEAVGLASSSTVHGHLARLEGKGLIRRD
ref|YP_013918.1|      ----ISKRQQDIYEFIKSEVKEKGYPPSVREIGEAVGLASSSTVHGHLARLEGKGLIRRD
ref|NP_470676.1|      ----ISKRQQDIYEFIKSEVKEKGYPPSVREIGEAVGLASSSTVHGHLARLEGKGLIRRD
ref|YP_849514.1|      ----ISKRQQDIYEFIKSEVKEKGYPPSVREIGEAVGLASSSTVHGHLARLEGKGLIRRD
ref|ZP_02330749.1|    ----LSQRQQAILEFIKNEVKEKGYPPSVREIGEAVGLASSSTVHGHLERLEKKGLIRRD
RAAC01072             TVSGLTARQRAILEFIRKNIREKGYPPSVREIGEAVGLASSSTVHGHLERLQQKGYLRRD
                      ::  **:  * *.:::**********************  :   :* ref|ZP_02320157.1|    PTKPRAIEILSLEDEAETPN-VVNIPIIGKVTAGMPITAIENIDEYFPLPEYMATGETNV
ref|YP_013918.1|      PTKPRAIEILSLEDEAETPN-VVNIPIIGKVTAGMPITAIENIDEYFPLPEYMAAGETNV
ref|NP_470676.1|      PTKPRAIEILSLEDEAETPN-VVNIPIIGKVTAGMPITAIENIEEYFPLPEYMAAGETNV
ref|YP_849514.1|      PTKPRAIEILSLEDEAETPN-VVNIPIIGKVTAGMPITAIENIEEYFPLPEYMAAGETNV
ref|ZP_02330749.1|    PTKPRAIEILDMDSSSTFSFSVTRVPLIGKVTAGMPITATENIEDYFPLPSHYVG-DHNV
RAAC01072             PTKPRALELLVDDEE---PGDVVLAPIVGRVTAGLPISALEDIEGYLPLPRDVAKGDE-V
                      ******:*:*    :..   .  *.  *::*:**::* *:*: *:***    :  * ref|ZP_02320157.1|    FMLEIDGESMINAGILDGDKVIVRQQSSAINGEIVVAMTDENEATCKRFYKEANHFRLQP
ref|YP_013918.1|      FMLEIDGESMINAGILDGDKVIVRQQSSAINGEIVVAMTDENEATCKRFYKEANHFRLQP
ref|NP_470676.1|      FMLEIDGESMINAGILDGDKVIVRQQSSAINGEIVVAMTDENEATCKRFYKEANHFRLQP
ref|YP_849514.1|      FMLEIDGESMINAGILDGDKVIVRQQNSAINGEIVVAMTDENEATCKRFYKEANHFRLQP
ref|ZP_02330749.1|    FMLSVLGDSMIETGIHDGDLVIVRQQQTADNGDIVVAMTEDDEATVKRFYKEKDHIRLQP
RAAC01072             FALRVVGESMINAGILDGDLAIVRRQTSADNGDIVVAMTDEDEATIKRFYREDGRVRLQP
                      *   *  :  *:*:; * .*:*  :* :**:::;* ****:*  .:;.**** ref|ZP_02320157.1|    ENDALEPILLNNVTILGKVIGLYRDIR
ref|YP_013918.1|      ENDALEPILLNNVTILGKVIGLYRDIR
ref|NP_470676.1|      ENDALEPIILNNVTILGKVIGLYRDI-
ref|YP_849514.1|      ENDALEPIILNNVTILGKVIGLYRDIR
ref|ZP_02330749.1|    ENSSMAPIILSNVSILGKVIGIFRNI-
RAAC01072             ENDAMSPLYFPNVTILGKVIGIFRQIR
                      **.::  *:  :  **:*******::*:*
```

FIG. 131

```
ref|YP_001124617.1|    ----------------------------------------------------------------
ref|YP_146331.1|       ----------------------------------------------------------------
ref|YP_849898.1|       ------------------------------------------------------------DNEQ
ref|NP_471127.1|       ----------------------------------------------------------------
ref|NP_465208.1|       ----------------------------------------------------------------
RAAC01366              ----------------------------------------------------MKGGGDMQA ref|YP_001124617.1|    -KEALDMLKKTGIRITPQRHAILEYLISSMSHPTADEIYKALEGKFPNMSVATVYNNLRV
ref|YP_146331.1|       LKEALDMLKKTGIRITPQRHAILEYLISSMSHPTADEIYKALEGKFPNMSVATVYNNLRV
ref|YP_849898.1|       -KEAVDVLKKTGVRITPQRHAILEFLINSHTHPTADDIYRSLEGNFPNMSVATVYNNLRV
ref|NP_471127.1|       -KEAVDVLKKTGVRITPQRHAILEFLINSHTHPTADDIYRSLEGNFPNMSVATVYNNLRV
ref|NP_465208.1|       -KEAVDVLKKTGVRITPQRHAILEFLINSHTHPTADDIYRALEGNFPNMSVATVYNNLRV
RAAC01366              QKDAVQLLKNAGLRVTPQREAILQFLLDYDGHATVDDIYTSLQDRFPSMSVSTVYNTVKQ
                        *:*:::**::*:*:****.***::*:.    *.*.*:**  :*:..**.***:****.::

ref|YP_001124617.1|    FKEVGLVKELTYGDSSSRFDFVTSNHYHVICEQCGKIVDFHYPALDEVEQLAA--HVTGF
ref|YP_146331.1|       FKEIGLVKELTYGDSSSRFDFVTSNHYHVICEECGKIVDFHYPALDEVEQLAA--HVTGF
ref|YP_849898.1|       FRDAGLIKELSYGDASSRFDFSTSNHYHAICNVCGKIVDFHYPGLDEVEHFAA--HVTGY
ref|NP_471127.1|       FRDAGLIKELSYGDASSRFDFSTSNHYHAICNVCGKIVDFHYPGLDEVEHFAA--HVTGY
ref|NP_465208.1|       FRDAGLIKELSYGDASSRFDFSTSNHYHAICNVCGKIVDFHYPGLDEVEHFAA--HMTGY
RAAC01366              LSQVGLVKEIGVGEGASRFDINVEPHHHLVCTRCGALFDFY---LEEPIQLSVPPEARGF
                       : : **:**:   *:..****:  .. *:* :*   ** :.**:    *:*  :::.  . *:

ref|YP_001124617.1|    KVDHHRMEVYGVCPDCQNEK--
ref|YP_146331.1|       KVDHHRMEVYGVCPDCQK----
ref|YP_849898.1|       EIDNHRLEVYGTCPECKEKQIN
ref|NP_471127.1|       EIDNHRLEVYGTCPECKEKQ--
ref|NP_465208.1|       EIDNHRLEVYGICPACKEKQ--
RAAC01
```

FIG. 132

```
ref|YP_077070.1|        ----------------------QRLVAIMKLLSERPGELLPLSFFTERFGAAKSTISED
RAAC01431               MPVCGRLRPRTRAELRRRAMQRHERLIRLTRRLVERPMAPIGISALAEAWGVAKSTLSED
ref|ZP_01666690.1|      ----------------------ERVVALTKLLVDRPHHLFSLGYFSELFGAAKSTISED
ref|YP_814057.1|        ----------------------ERLVDMVKYLLARPHTLIALPFFADRYGAAKSSISED
ref|NP_964223.1|        ----------------------ERLVDMVKYLLARPHTLIALPFFADRYGAAKSSISED
ref|ZP_01173986.1|      ----------------------ERLIDMTNYLLEHPRQLVSLTFFADRYGSAKSSISED
                                              :*::  :  . *   :*    . :  ::: :* *::* ref|YP_077070.1|        LALVKEALEADGSGRLRTHAGAAGGVQYWPLPSREEEQETLLELCRLLSDPGRILPGGFV
RAAC01431               VQLVREVLAEDGAGRVETLVGAQGGVRFVPQVARDRAEAFLWDVARRLASPDRVIAGEFL
ref|ZP_01666690.1|      ILTIKQALQSFGLGTLETVSGAAGGVRYLPQQEAAAINGLLTDLAERLKSADRIIPGGFL
ref|YP_814057.1|        LAILRQTLANDQNGILETVAGAAGGVRYIPFVGKKEATNYLHDLADRIEDPDRILPGNFV
ref|NP_964223.1|        LAILRQTLANDQNGILETVAGAAGGVRYIPFVGKKEATDYLHDLADRIEDPDRILPGNFV
ref|ZP_01173986.1|      LAIIKETFEQRGIGTLQTVPGAAGGVKYSVKVSDDEARPFISGLCEVIASPERLLPGGYL
                         :  ::::.:        *  :.*  ** ***::            :    :. :  . *::.*  ::

ref|YP_077070.1|        YMTDLITHPIWSARIGAIMAARFIDAEPDVVLTVETKGIPLALMVARALGLPMVVARREG
RAAC01431               YASDVLGDPDVIDTAGAMVASRFAHAGVEVVVTVETKGIPLAASAARYLHAPLAIVRREQ
ref|ZP_01666690.1|      YMSDILFDSQLMLQIGEVFMTRFQHLAPDCVMTVETKGIPLAFATARAFHVPLVIVRRGS
ref|YP_814057.1|        YLSDILGSPQDLQQIGQLIATKYAYSNVDYVMTIETKGIAIAQAVSRFLNVPFVMVRRRP
ref|NP_964223.1|        YLSDILGSPQDLRQIGQLIATKYAYSNIDYVMTIETKGIALAQAVSRFLNVPFVMVRRRP
ref|ZP_01173986.1|      YMTDILGDPAIVQKAGRVFASAFADADIDVVMTVATKGIPLAYAVGAYLNVPVVIVRRDS
                        * :*::   .       *  :.  : :          : *:*: ****.:*   ..  :   *..:.**

ref|YP_077070.1|        RVTEGPSVTLHYISGS-RRIHTMTVGLRALWRGARVLVVDDFMKAGATARAMVDVAGEMG
RAAC01431               RVTEGASLTTHYVSGSAKRIQTMSLSTRLVPRGARALIVDDFMRAGATARAVAELIGEFG
ref|ZP_01666690.1|      KVTEGPAVSINYVTGSSRRIQTMSLAKRAVPAGARVLIIDDFMKAGGTARGLVDLAQEVG
ref|YP_814057.1|        KITEGSTISVNYVASSSERVEKMELAKRLLPEGSNVLIVDDFMKGGGTLTGMEELVKEFK
ref|NP_964223.1|        KITEGSTISVNYVASSSERVEKMELAKRLLPEGSNVLIVDDFMKGGGTLTGMEELVKEFK
ref|ZP_01173986.1|      RVTEGSTVSINYVSGSAKRIQTMVLSKRSLEEGSKVLIVDDFMKAGGTVNGMISMLEEFK
                        ::***.:::  :*::.*  .*:..*  :. * :   *::*::****:.*.*    .:  .:  *.

ref|YP_077070.1|        ASVAGVGVFVSTAEPARKQVQRYVSLLTLEQVDEV--ARTVR--------------
RAAC01431               GEVCGTAVFMATSQPAQKMVADYVALLEVGPVRES--GFEVRPNLGALERRVTHVD
ref|ZP_01666690.1|      ARVVGVGVLVATAEPQEKLVEDYVALLILHEVDEHTKKTDIRPAL-----------
ref|YP_814057.1|        GTVAGMCVLCETKYASQKVVDDYQSLIKITEVDRTKKLIKVRP-------------
ref|NP_964223.1|        GTVAGMCVLCETKYASQKVVDDYQSLIKITEV-----------------------
ref|ZP_01173986.1|      AHVAGIAVLVLVEAEKAEERLVDEYLSLVQLADV---------------------
                        .  *   *:  :   ..: *   * :*: : *
```

FIG. 133

```
ref|YP_074599.1|        -MTIRDVARRAGVGVATVSRVLNGTG-YVKAETRERVLAAAAELGYVPSQLARGLVRRLS
RAAC01505               MVTIRDVARKAGVSVSTVSRVINGSG-YVGEDTERKVLLAMKELNYQPNRIARGLVSRRT
ref|YP_149084.1|        MATIRDVAKRAGVSVATVSRVLNQNG-YVNEETERRVRQAMKELNYKPNEVARALFKKTS
ref|YP_001127265.1|     MATIRDVAKRAGVSVATVSRVLNQNG-YVNEETEKRVRRAMKELNYKPSEVARALFKKTS
ref|YP_001661816.1|     -VTIKDIAKLANVSITTVSRVINNKSEGVSEETRNRILQLVKELGYQPNAIARGLVTKKT
ref|NP_621898.1|        -VTIKDIARLANVSVTTVSRVINNKPEGVSEETRQKILKLVKELGYQPNAIARGLVTKKT
                         **:*:*: *.*.::*****:*    *  :*..::    **.* *. :**.*. : :

ref|YP_074599.1|        GTVGLVVPDITNPFFPLITRGVEDAASEAGYTVFLCNTDNDPVLEAQDVRKLREHRVDGI
RAAC01505               STIGLLIPDVANPFFSEMARGVEDAAIAEGYSVLLCNSDWKSERELMYIDLLKGRWVDGI
ref|YP_149084.1|        KTVGLIVPDITNPFFPELVRAVEDVMNIYDYTVILCNSDEKVEKEREYIEVLKQKYVDGV
ref|YP_001127265.1|     KTVGLIVPDITNPFFPELVRAVEDVMNIYDYTVILCNSDEKAEKEREYIEVLKQKYVDGV
ref|YP_001661816.1|     KTIGLIIPDISNPFFPDIARGVEDSAHIYGYNVFLCNTDDNLEKESEYINALKEKYVDGI
ref|NP_621898.1|        KTIGLIIPDISNPFFPDIARGVEDSAHIYGYNVFLCNTDDNLEKESEYIRALKEKYVDGI
                         *:**::**::****. :.*.***   .*.*:***:*  .    *    *: : ***:

ref|YP_074599.1|        IFVG-TTERRELVDQLLADDIPVVVMDRQLEHADVDTVTVDNVAGAQAACRHLIELGHRR
RAAC01505               VIVG-SRSDSRVIEAAVG-DTPLVIVDRRSSEFRWS-VWTDNRQGAALVVEHLLKMGCSK
ref|YP_149084.1|        ILTTNQFAPEE--VEE--WDVPIVVLDRPLH-ERYPSVVADNYEGARLATRHLYEVGCRR
ref|YP_001127265.1|     ILTTNQLTPDE--VDE--WDVPIVVLDRPFN-EKYPSVVVDNYRGARLATRHLYDMGCRR
ref|YP_001661816.1|     IFTSSSIPKHEHIMELVKSGIPIVIMDRRVDSEDIYGVFLDNYEGGYIATKHLIDLGHKK
ref|NP_621898.1|        IFTSSSIPKHEHIIELVESGIPVVIMDRRVDSENIYGVFLDNYEGGYIATKHLIDLGHEK
                         ::.        .  *:*:**    *  ** *.  .** .:*   :

ref|YP_074599.1|        IAHAAGHQSTRTGQDRCQGYRMALEEADIPYDPACVTWGDFTFESGFRVGQVLLGLSPRP
RAAC01505               IVHIAGPSDSPSAQERRKGYEQAISQAGL---VAIVYEGDFRFASGFEIATMILEGSQRP
ref|YP_149084.1|        IAHIQGPNHVVNAMERFRGYQDEMRALGLG-DRQLVIQGNYQLKQAKE-AVMAALAEHDM
ref|YP_001127265.1|     IAHIQGPMYVVNAVERFRGYQDEMMELGIW-EQRLVIQGNYQLKQAKE-AVMAALAQQEI
ref|YP_001661816.1|     IACITGPLYTKSAKERLEGYKKALVENGMDVDERLIFEGDYKINSGIIGTEKLLGNNENV
ref|NP_621898.1|        IGCITGPLYTKSAKERLEGYKKALLDSGIKIDEKLIFEGDYKINGGIIGAERLLKDNKDM
                         *     *    .. :*  .**.   :    .:    :   *::: :     .

ref|YP_074599.1|        TAVFAGNDLIALGVIRAAEEAGLSVPDDLSVVGFDNIQMAALVRPGLTTVRQPAREMGRL
RAAC01505               DGIFAANDLMAIGVLQAAVKLGVQVPHEVAIVGYDNIPSAGYVSPSLTTVHQPSYQMGVS
ref|YP_149084.1|        DGIFAGNDAMAVGALKAVQQCGLRVPDDIAIIGYDGIPLTEMTTPELSTVSQPIYEMGAM
ref|YP_001127265.1|     DGIFAGNDAMAVGALKAVQQCGLRVPDDIAIIGYDGIPLTEMTTPELSTVSQPIYDMGAI
ref|YP_001661816.1|     TAIFACNDLMAYGAYKTIRSYGYKIPDDISIVGFDDIQLSQILEPQLTTIKQPAYDMGLA
ref|NP_621898.1|        SAIFACNDLMAYGAYKTIRSFGYKIPDDISVVGFDDIQLSQILEPQLSTIKQPAYDMGLT
                         .:** ** :* *. ::  .  *  :*.::::::*:*.*   :      * *:*: ** :**

ref|YP_074599.1|        AMTMLLERIRG---EFSGPGRRHVYPPELIVRGTT---------
RAAC01505               AFDLLLEQFVT---NSGQSARKVKFEPKLVVRDSSLKCPSRNSV
ref|YP_149084.1|        AARILI-KQI---EGKPLEKLHYQLPVQLVVRQST---------
ref|YP_001127265.1|     AARILI-KQI---EGKPLEKLHYQLPVQLIVRQST---------
ref|YP_001661816.1|     AARMLI-KLVE---GKKLKKKIINFRPQLIIRQST---------
ref|NP_621898.1|        AARMLI-KLIE---GKKLKKKIINFRPQLVIRQST---------
                        *  :*: :                    :*::* ::
```

FIG. 134

```
ref|YP_001661816.1|      -----TIKDIAKLANVSITTVSRVINNKSEGVSEETRNRILQLVKELGYQPNAIARGLVT
ref|NP_621898.1|         -----TIKDIARLANVSVTTVSRVINNKPEGVSEETRQKILKLVKELGYQPNAIARGLVT
ref|ZP_01188648.1|       ---MITIYDVAKEAGVSPSTVSRVLNN-YNNVTETTRKKVEAACKKLKYVPNANASSLKK
ref|YP_074599.1|         -----TIRDVARRAGVGVATVSRVLNG-TGYVKAETRERVLAAAAELGYVPSQLARGLVR
ref|YP_147968.1|         ---MASIKDVAKRANVSTATVSRVLRN-AGNVTEETRQRVLEAIEALNYQPNVLGRYLRR
RAAC01078                MTRMTTMADVAKRAGVSIMTVSRVVNN-SGYVKPSTRQKVLAAMQELNYVP----KGQQS
                             :: *:*: *.*. *****:..   *. **:::    * * * ref|YP_001661816.1|      KKTKTIGLIIPDISNPFFPDIARGVEDSAHIYGYNVFLCNTDDNLEKESEYINALKEKYV
ref|NP_621898.1|         KKTKTIGLIIPDISNPFFPDIARGVEDSAHIYGYNVFLCNTDDNLEKESEYIRALKEKYV
ref|ZP_01188648.1|       DNTKTLALIIPDIENPFFISILKGFDDKANKLGYDTILCNTDERLEKEKDYIKMVLKKRI
ref|YP_074599.1|         RLSGTVGLVVPDITNPFFPLITRGVEDAASEAGYTVFLCNTDNDPVLEAQDVRKLREHRV
ref|YP_147968.1|         METETVLVVVPDITNPFFSKVLRGIEAVALEHGYQVLLGDTQNDVRLEEQYLNLLPQRQV
RAAC01078                SPHDTWMLIVPDITNPFFTFIARGMEDVARKHGFRVFIANTDEDLQKEQEYVQMCLDYQV
                              *  :::*** ****  : :*.: *    *:  .:  :*:.  * :.  . .

ref|YP_001661816.1|      DG--IIFTSSS-IPKHEHIMELVKSGIPIVIMDRRVDSEDIYGVFLDNYEGGYIATKHLI
ref|NP_621898.1|         DG--IIFTSSS-IPKHEHIIELVESGIPVVIMDRRVDSENIYGVFLDNYEGGYIATKHLI
ref|ZP_01188648.1|       DG--VAISTVG-KTS-EHISEFSDRNIPYILLDRKVEGLDADIVCGDNYQGAIDLVNHLI
ref|YP_074599.1|         DG--IIFVGTT--ERRELVDQLLADDIPVVVMDRQLEHADVDTVTVDNVAGAQAACRHLI
ref|YP_147968.1|         DG--MIFLTAR--IRKELVEEMAR-QFPIVLACEYLEGADIPTVSIDNISSARKATEHLI
RAAC01078                RG--ALVVPVG-DPSRENLVRLTEHQVPFVLIDREIEGLDADLVKGDIRETSRRLVEHLL
                          *   .       *  : .: .* ::   . ::   *    *     .**:

ref|YP_001661816.1|      DLGHKKIACITGPLYTKSAKERLEGYKKALVENGMDVDERLIFEG----DYKINSGIIGT
ref|NP_621898.1|         DLGHEKIGCITGPLYTKSAKERLEGYKKALLDSGIKIDEKLIFEG----DYKINGGIIGA
ref|ZP_01188648.1|       NNGHKDIAMITGPLHVSTSRERFEGYKTALNRAGISVEEDYIKIDYVSQDYSGEKAYEMT
ref|YP_074599.1|         ELGHRRIAHAAGHQSTRTGQDRCQGYRMALEEEADIPYDPACVTWG----DFTFESGFRVG
ref|YP_147968.1|         RLGHRRIAHLSGPMNIILSRDRLRGYQQALAQHELEADAALVQEG----DFTYESGYNLT
RAAC01078                DLGHERIAAVVGPLHSASSRERLDGYRDALLHKGLPVDESLIFTA----PMTRDMDASFV
                          **. *.  *       .::*  **: **    :  :    :         .  :

ref|YP_001661816.1|      EKLLGNNENVTAIFACNDLMAYGAYKTIRSYGYKIPDDISIVGFDDIQLSQILEPQLTTI
ref|NP_621898.1|         ERLLKDNKDMSAIFACNDLMAYGAYKTIRSFGYKIPDDISVVGFDDIQLSQILEPQLSTI
ref|ZP_01188648.1|       KELLGLNEPPTAIFVANNLMALEVYKALKEEGISVPDDIAIVCFDDLNLIYEIEPFFTVM
ref|YP_074599.1|         QVLLGLSPRPTAVFAGNDLIALGVIRAAEEAGLSVPDDLVGFDNIQMAALVRPGLTTV
ref|YP_147968.1|         LKLLALEKPPTAIFAANDEMAIGAIKAVRHRGGRVPDDVAVVGFDDIQMASIFEPSLTTI
RAAC01078                DALVGRSDAPTALFLGNMFQYAHIVRRLRGLGLSIPHDISVVSFGNTDDLASVDSLATAA
                           *:    .  :*:* *          :  . *  :*.*:::* *.: :    .. . :.

ref|YP_001661816.1|      KQPAYDMGLAAARMLIKLVEGKK--LKK--KIINFRPQLIIRQST------------
ref|NP_621898.1|         KQPAYDMGLTAARMLIKLIEGKK--LKK--KIINFRPQLVIRQST------------
ref|ZP_01188648.1|       KQPAYTMGEAAAEILIKRIEMSDNGHRK--RKIVFEPELIIRKSS------------
ref|YP_074599.1|         RQPAREMGRLAMTMLLERIRGEFSGPGR---RHVYPPELIVRGTT------------
ref|YP_147968.1|         AQPMFEIGQKAMELLLALIEGT-SARRR---QLVLPDRLVIRDS-------------
RAAC01078                VQPAYNYGSLGAQLLLERIEGVRKTSTR----IVLHSEMVVRSSTAPPPVRMTKKR
                         **   *    . :*:  :.       :          .:::* :
```

FIG. 135

```
ref|YP_001391734.1|      ------------------------------------------------------------
ref|YP_001254935.1|      ------------------------------------------------------------
ref|YP_001308325.1|      ------------------------------------------------------------
ref|YP_518781.1|         ------------------------------------------------------------
ref|ZP_01171531.1|       ------------------------------------------------------------
RAAC01972                ---------------------------------------MRGRSRRPRGLAVREG ref|YP_001391734.1|      --------------------------------EPVDFEDICDLLSDVLACNVYIISRKG
ref|YP_001254935.1|      --------------------------------EPVDFEDICDLLSDVLACNVYIISRKG
ref|YP_001308325.1|      --------------------------------EPVAFQDICTLLSEVLECNVYIISKKG
ref|YP_518781.1|         -------------------------------AGHSVDFDEMANVLSESIQSNCYIVGRRG
ref|ZP_01171531.1|       -------------------------------AGKPVNFKEMAETLSEVIEANIFVVSRRG
RAAC01972                TKRRRMPGEGQGDEIVSLLEQVQELGQLLHRSNEQVEFQEVAEFLSRLMQSNVYIVGRKG
                                                        .  * *.::.  **   : .*  :::.::* ref|YP_001391734.1|      KILGSKFYS-GFECEEVREVVLKENRFPDFYNNKLLNVNETLSNSP--NHDK----CVFD
ref|YP_001254935.1|      KILGSKFYS-GFECDEVREVVLKENRFPDFYNNKLLNVNETLSNSP--NHDK----CVFD
ref|YP_001308325.1|      KVLGYTFGK-DFECEAMKKKVIEDKKFPEDYNKTLLEVNETLSNLP--NEGR----CVFQ
ref|YP_518781.1|         KILGYSFMQ-NFGCNTMEDIVVHTERFPESYNEGLLKVTETRSNTT--QVANG---CVFN
ref|ZP_01171531.1|       KLLGFAVNQ-QIENERMKK-MLEDRQFPEEYTKSLFNIQETSSNLD--VESD---YTAFP
RAAC01972                KILGYGVAE-HELTEEWLNIMTREQRFPGDFNKHLLRIEQTIANLTDEQKKP---LYVFS
                         *:    .    .         :   . :    .:  :.: *:.: :*  :*      .* ref|YP_001391734.1|      NLKDCSINNKLSTIVPINGNRERLGTLLLARFDKEFTDEDLILAEYSATIIGLEILRSKQ
ref|YP_001254935.1|      NLKDCSINNKLSTIVPINGNRERLGTLLLARFDKEFTDEDLVLAEYSATIIGLEILRSKQ
ref|YP_001308325.1|      EIGKCKKVDKLSTIVPIIGSRERLGTLILARFGNPFTDEDLVIVEYSATIVGMEMLRAMQ
ref|YP_518781.1|         EKERCHFNNKITTILPILGGGERVGTLVLAKFDQDFSEADLILAEYGATVVGMEILRIKA
ref|ZP_01171531.1|       VENKELFKNGLTTIVPIIGGGERLGTLILARLQEQFHDDDLILGEYGATVVGMEILREKA
RAAC01972                PEENESFRSKHLMITPIIGARERQGTLLFARSQRPFNEDDQILAEYAATVVALEIVHSRQ
                             .    *  **  *   **  ***::*:    . *   : *   ::  **.**::..:*:::

ref|YP_001391734.1|      DQIEEEARKKAVVQLAIGTLSYSELEAVEHIFNEL-DGTEGLLVASKIADKVGITRSVIV
ref|YP_001254935.1|      DQIEEEARKKAVVQLAIGTLSYSELEAVEHIFNEL-DGTEGLLVASKIADKVGITRSVIV
ref|YP_001308325.1|      DEITEDTRKKAVVQLAIGTLSYSELEAVEHIFDEL-NGNEGLLVASKIADKVGITRSVIV
ref|YP_518781.1|         ERAEEEARKKAAVQIAVGTLSYSELEAVEHIF-AELGGGDGLLVASKIADRVGITRSVIV
ref|ZP_01171531.1|       EEIEEEARSKAVVQMAISSLSYSELEAIEHIFEEL-NGKEGLLVASKIADRVGITRSVIV
RAAC01972                QQKEEESRQRALAHLAVESLSFSELQAAKYLLDAVRNSPEGIVVSSQIADQHGVTRSVIV
                         :.  *::*.:* .::*:  ::*:*  ::::      ..  :*::*:*:***: *:****** ref|YP_001391734.1|      NALRKFESAGVIESRSLGMKGTHIRILNDKLLEELKK----
ref|YP_001254935.1|      NALRKFESAGVIESRSLGMKGTHIRILNDKLLEELKK----
ref|YP_001308325.1|      NALRKFESAGVIESRSLGMKGTYIRILNEKLIDELKK----
ref|YP_518781.1|         NALRKFESAGVIESKSLGMKGTYIRVLNDYLLEELDK----
ref|ZP_01171531.1|       NALRKLESAGVIESRSLGMKGTYIKVLN-------------
RAAC01972                NSIRKLESAGTIESRSLGMKGTHLRILNPYVEEEINRQFER
                         *:: **:****.***:*******::::**              
```

FIG. 136

```
ref|NP_241876.1|           ----------------LAIIYYSSTGTNYQLAQWAEEAAKEAGAEVKVLKVAETAPDAAI
ref|YP_174035.1|           -----------MANVKTAVIYYSSTGTNYQLAKWAKESAEKEGAEVRLLKFPELAPDAAI
ref|YP_079193.1|           -----------MSNVKLAVVFYSMGGTNYQLAKWAAEGAKEAGADVKVLKVQELAPQSVI
ref|ZP_01169176.1|         -----------LMTVKLAIVYYSSTGTNYQMAQWAAEGAKEAGAEATIYKVQELAPESVI
ref|YP_001488917.1|        -----------MENVKLAVIYYSSTGTNYQMAKWAEAGAKEAGAEVKVLKVAELAPEAVV
RAAC00076                  MKRETRSGGNTMSNVHLTILYYSATGTNYRMAQIAAEEAARELGAEVRVRKVAELAPREVI
                                         :::*:**  ****::*: *  .*.: **:. :  *. * **   .:

ref|NP_241876.1|           DSNPAWRAHVDATKDVPAVTLDDLVWADAIMFSIPTRFGNVPSQVKAFLDTTGGLWFEGK
ref|YP_174035.1|           DSNPAWRAHVEATKDVPEVTPDDMEWADSYIFSVPSRFGVLPAQAKQFFDTLGGLWAQGK
ref|YP_079193.1|           EGNEVWKATVDATKDIPVVTSEDIEWADAIIFSTPTRFGNMASQMKQFLDTQGGLWANGK
ref|ZP_01169176.1|         EGVPAWKAHLEETKDVPVVTPDDIAEADAIIFSTPTRFGNMAAQMKQFLDTTGGIWGAGK
ref|YP_001488917.1|        ASNPAWKAHLDETKDIPEVQLSDLEWADAIIFSMPTRFGNLPAQMKQFLDTTGGLWFQGK
RAAC00076                  ETSPAWKAHVEATAHVPVATPDDVAWADAVIFSVPSRFGNIPSQMKQFLDTLGPLWAKGL
                             .*:*  ::  * .:*  .  .*:  : : *:*** ::* * *:** * :* * ref|NP_241876.1|           LANKVVSAMASASNAHGGQEATVLSLYTTMYHWGAIVAAPGYTAPETFAAGGNPYGTSVT
ref|YP_174035.1|           LANKVVSAMSSASNPHGGQEATILSVYTTMYHWGAIVVAPGYTDQSAFTSGGNPYGTSVT
ref|YP_079193.1|           TVNKVVSAMSSAQNPHGGQEATILSLYTSMMHWGAIIASPGYTDPVLFGAGGNPYGTSVT
ref|ZP_01169176.1|         TVNKVVSGMTSAQNPHGGQEATILSLYTTMYHWGAIVVTPGYSDQSLFPAGGNPYGASVT
ref|YP_001488917.1|        LANKAVSAMTSAQNPNGGQEQTILSLYTTMFHWGAIIAAPGYTDDSLYGAGGNPYGVSVT
RAAC00076                  TANKVVSAMSSAQNPHGGQEATILSLYTSMYHWGAIIAAPGFTDASAYASGGNPYGTSVT
                            ...*:**.*.:****  *:::* *** :.:::    :  :****.* ref|NP_241876.1|           VDQEGNMKEDVKA---AVAHQAKRTIQVAEWVKG-----
ref|YP_174035.1|           IDQDGNQIEDVEQ---AVKQQAKRTVTVAKAIVTG-----
ref|YP_079193.1|           VDQDGKMIEDVEA---AVKHQAKRTVTVAEWVKKG-----
ref|ZP_01169176.1|         VDQSNEIVGDKDAYKGAIKYQAKRVIGIAESVKNG-----
ref|YP_001488917.1|        VDQNGKIQEDAEA---AAKHQAKRTVNVAEWIKKGQ----
RAAC00076                  LSENGEIDPGAQD---AIRHQARRTVTIASWVKQGQAVTV
                           :.:..:  ..   .   *   **:*.: :*. :  *
```

FIG. 137

```
ref|ZP_02327651.1|              ------------------------------------LQIEFEQRRRALI
sp|O32720|SP2AA_PAEPO           ------------------------------------LQIEMEHHRGVLI
ref|NP_833792.1|                ------------------------------------LSMQLEVKRDVLC
ref|NP_846529.1|                ------------------------------------LSMQLEVKRDVLC
ref|YP_001646701.1|             ------------------------------------LSMHLEVKRDVLC
RAAC02144                       ----------------------MNFLTRPHKERGCRVSVETKLERGIVV
                                                      :.:. :  . *   :

ref|ZP_02327651.1|              VRLQGELDHHTADMVKTRMEEAIAKGDARNLVLSLRDLSFMDSSGLGVIL
sp|O32720|SP2AA_PAEPO           VRLSGELDHHTSDMVRMQMDEAIQRRQCEHIVLSLKNLQFMDSSGLGVIL
ref|NP_833792.1|                VRLEGELDHHTAEELRTKVTDMIETHGVHHIVLSLENLSFMDSSGLGVIL
ref|NP_846529.1|                VRLAGELDHHTAEELRTKVTDMIETHGVHHIVLSLENLSFMDSSGLGVIL
ref|YP_001646701.1|             VRLEGELDHHTAEELRTKVTDMIETHGVHHIILSLENLTFMDSSGLGVIL
RAAC02144                       IELKGELDHHAVEQMRDRIEQQLAEHGYRGLVMSFRNIDFMDSSGLGLIL
                                :.* ******: : :: :: : :       . :::*:.:: ********:**

ref|ZP_02327651.1|              GRYKQITGRGGKMIVCDVNPSIYRLFELSGLFKIVAIEDNERKAISSL--
sp|O32720|SP2AA_PAEPO           GRYKLINQKGGEMAVCDVNPPVHRLLDMSGLFKIMPIYDNEVNALTEL--
ref|NP_833792.1|                GRYKHVKGLGGEMVVCAISPPVKRLFEMSGLFKIVRLEESEAHALATL--
ref|NP_846529.1|                GRYKHVKGLGGEMVVCAISPPVKRLFEMSGLFKIVRLEESEAHALATL--
ref|YP_001646701.1|             GRYKHVKGLGGEMVVCAISPPVKRLFEMSGLFKIVRLEESEAHALATL--
RAAC02144                       GRYRSVSEHGGKMALCEVNPTLRRLFEMSGLLKVIPVYDSEEAAVAAILG
                                ***: :.  **:* :* :.*.: **:::***:*:: : :.*   *:: :

ref|ZP_02327651.1|              -
sp|O32720|SP2AA_PAEPO           -
ref|NP_833792.1|                -
ref|NP_846529.1|                -
ref|YP_001646701.1|             -
RAAC02144                       A
```

FIG. 138A

```
ref|YP_001125957.1|      -HRLA---ETMKTVLDAAYEGVVVVDGNGMVREINRAYCQFLGIRREDAIGKHVTEVIEN
ref|YP_147806.1|         -HRLA---ETMKTVLDAAYEGVVVVDEDGVVREINRAYCQFLGIRREEAIGKHVTEVIEN
ref|ZP_01666100.1|       ----------LESAIESMFEGFVAVDKNGYITMMNQAYGEFLGVDAKEVIGRHVTEVIEN
RAAC02439                MHELAASGDVLRLILDSMYEGIVLVDAKGHIVEINQAYLKLLNMERDRVIGRHVTEVIEN
ref|ZP_01695872.1|       MAQTKNTAEILNAVLESAYEGIAVVDENGILIEFNEAYSRFTGIKREDAIGRHVTEVIEN
ref|NP_693661.1|         ------SAEIVEVILESAYEGVAMVDRNGIIVEFNDAYSRFTGVDKKEAIGHPVQEIIEN
                               :.   ::: :..  .* :   :*   .: .:   . .: * *:*** ref|YP_001125957.1|      TRLHICVQSGIPERGYIQKIYGQPMVVHRIPIWRDGKVIGAVGMLIFQGVSEVYAIFQRL
ref|YP_147806.1|         TRLHICVQSGIPERGYIQKIYGQPMVVHRISIWRDGKVIGAIGMLIFQGVSEVYEIFRRL
ref|ZP_01666100.1|       TRMHIVAQTGKPEIGEVQRIGKHAVVVTRKPIIQDGEVVGAVGKILFKDVKDFKMLARKL
RAAC02439                TRLHRVVETGIPERGQLQRIRQHDMVVHRIPIWQGGKVVGAIGVLIFESIRDLYEIIERL
ref|ZP_01695872.1|       TNLHVTVKTAIPERGVIQYIQGQAMVVHRIPIWKGGRVVGAIGMLIFEGVSELYQIFERL
ref|NP_693661.1|         TNLHQTVKTGIAERGVIQYIQGQPMVVHRIPVWRNEELVGAIGMLIFEGVTELYQIYDRY
                         *.:*    .::.  .* *  :* *   : :** * .:  :.  ..::**:* ::*:.:  :.   :  :

ref|YP_001125957.1|      QELSR----EASRKEKNEAEASKQEAVASAAVGVERIIGRHPTIAAVKQMIRRAARVPST
ref|YP_147806.1|         QELSR----EASRKEKQETEAKPQETAASAPKGIERIIGRHPAIAAVKQMIRRAARVPST
ref|ZP_01666100.1|       NSLQS----ELEY-YKEELRK---VHGGK--YTIESIVGQSEKMEWLKTIAAKAAKGNST
RAAC02439                QEHAP----QVPS-ARPETEQGSEAHQVRWAYRIDDFLGQSRAVLDLRRMARKAAQTPVT
ref|ZP_01695872.1|       QQDSL---SARKE-KTGSKKMPDQAGFT-------QILGTSESISRVKRLARRAARTSAT
ref|NP_693661.1|         QEKKQ-----KMITEKHSRKEDSNPGQPD--NYLEQIIGQSEELTKLKRMTRKVAQTEAT
                          :.           ..        ..       ::*     :  ::  :  :.*:    * ref|YP_001125957.1|      VLITGESGTGKEVVARAIHEAGAHADGPFVSVNCAAIPEALLEAELFGYEDGAFTGAKKG
ref|YP_147806.1|         VLITGESGTGKEVVARAIHEAGPHADGPFVSVNCAAIPESLLEAELFGYEDGAFTGAKKG
ref|ZP_01666100.1|       VLILGESGTGKELFAHAIHNASARRHGPFIKVNCAALPESLLESELFGYDEGAFTGARKG
RAAC02439                VLITGESGTGKEVLAQGIHFESNRANGPFISVNCAAIPDSLLEAELFGYDEGAFTGAKRG
ref|ZP_01695872.1|       VLITGESGTGKELFAKSIHQLSTYARGLFITVNCGAIPEPLFESELFGYEEGAFTGAKKG
ref|NP_693661.1|         VLITGDSGTGKELFAKSIHQLSDYKSGPFVCVNCGAIPEQLFESELFGYEDGSFTGAKRG
                         *** *:******:.*:.**    *  *: ***.*:*: *:*:******::*:****::* ref|YP_001125957.1|      GKPGKFQLAHGGTLFLDEIGDMPLAMQAKILRVLEEKKVEKVGGLSETEVDVRIIAATNK
ref|YP_147806.1|         GKPGKFQLAHGGTLFLDEIGDMPLAMQAKILRVLEEKKVEKVGGLSGTEVDVRIIAATNK
ref|ZP_01666100.1|       GKPGKIELANGGTFFLDEIGDMPLTAMQAKLLRVLQEREIERVGGCTKTNKVDVRIIAATNR
RAAC02439                GKPGQIELAHMGTFLFLDEIGDMPLSMQAKLLRVLEDRQVQRVGGTVKREVNLRLISATNR
ref|ZP_01695872.1|       GKPGKFELAENGTLFLDEIGELSPAMQTKLLRAIQEKEAERVGGVKKYKTNVRIVAATNR
ref|NP_693661.1|         GKKGKFKLADNGTLFLDEIGEMPLAMQTKLLRVIQEKEYEKVGGLTKQPLKARVVAATNR
                         ** *:::**. **:******::.   :**:*:**.:::::  ::***    . *:::***:

ref|YP_001125957.1|      PLEEMVRDGTFREDLFYRLNIIRIHLPPLRERKTDIPALLAHHMERLCRQFGVVSKSFAK
ref|YP_147806.1|         PLEEMVRNGTFREDLFYRLNIIRIHLPPLRERKTDIPALLAYHMERMCRQFGVALKSFTK
ref|ZP_01666100.1|       DLEKMIERGEFRQDLYYRLNIISLHIPPLRERKEDIPLLCTALLKKINVQVQHWVDGVSP
RAAC02439                DLERMVEEGRFREDLYYRLNIIRLHIPPLRERKEDIPLLLAHYLDMTCERLGKPRMHLSS
ref|ZP_01695872.1|       NLEEMVEAGTFRADLYYRLNIIRIHLPPLRERKEDIPGLVSHFLKAFCRRYDLPEKRISS
ref|NP_693661.1|         NLKVMVEEGTFREDLYYRINVIELYIPPLRNRERDIPLLISSYLLTICKKYNMKKKEITP
                          *: *:. * ** **:**:*:*  :::****:*: *** *   :          .:

ref|YP_001125957.1|      EAMEVLINYSWPGNIRELVNVVEWLISMVE--GENIEREHLPAYL-------STIHPSVT
ref|YP_147806.1|         EAMEVLVHYSWPGNVRELVNVVEWLISMVE--GEKVEREHLPSYL-------STVQPAAS
ref|ZP_01666100.1|       EAMELLLAYDWPGNVRELENVLERAVNLMEEDERQILPEHLPPALKK-IHKAKDLDDGLK
RAAC02439                EVVERLLAYDWPGNVRELVHMVEVLVSLC--DSAYVRLDDFPPHLHKLLQERSSRSPAIT
ref|ZP_01695872.1|       EAVAAMMAYGWKGNVRELANTVERLVTLAD--GPEISRGDLPEAIHEAQPAKDIYAESLI
ref|NP_693661.1|         EAMAVLMKYKWYGNIRELINTIEKLVILTE--NDMIDYHHLPNYMKR---EEFTIDNRLS
                         *.:   :: :  * ** **:***  : :*   : :         :   ..:*    :
```

FIG. 138B

```
ref|YP_001125957.1|    PMP---------------DGGAN---------IADQWKEIVYQSERERIAAALVAANGNK
ref|YP_147806.1|       SLP---------------NGGVK---------MADRWKEMVYQSERERIAAALVAAGGNK
ref|ZP_01666100.1|     DLA---------------GILCD--------------------TEKQAIYKALEATGGNK
RAAC02439              PSR---------------SPACDAVPGPAVGSPGAGARERMMQVERELIEAALRESGGNK
ref|ZP_01695872.1|     -SRA--------------------------------REAGEAQEKALIIRALKNAGGNK
ref|NP_693661.1|       PIHQ-------------------------------VKQQEHIRESELIRLTLEQTGGNK
                                                          *     *   :*   :.*** ref|YP_001125957.1|    AEAARRLGIHRSTLYEKLKKYG--
ref|YP_147806.1|       AEAARRLGIHRSTLYEKLKKYGL-
ref|ZP_01666100.1|     SKAAKLLGIHRSGFYQKLHKYNI-
RAAC02439              SLAAKRLGVHRSTLYDKIKKLGIL
ref|ZP_01695872.1|     TKAAELLGIHRTTLYQKIKKYNL-
ref|NP_693661.1|       SKAAQKLGIHRTTLYQKLKK----
                       : **. **:**:  :*:*:: *
```

FIG. 139

```
ref|YP_001488778.1|      ------------------MTFTAQLREETEPLFEAIYQHPFVRGLAEGKLEKKQIIHYVKQ
ref|YP_081277.1|         ------------------MSFSAELRREADPIFEAIFEHPFVLGLASGRLEKEQLIHYVKQ
ref|YP_174256.1|         ------------------MSFTAELRKTADPIYKAIFSHPFVQGIGKGSLPADSLIHYVKQ
ref|YP_804091.1|         ------------------FSARLKAIAQPVLADIENHPFVRGIQAGAVPAAALMVYVEQ
RAAC00944                MGPSRVPLWPPAEEALLMSFSASLIAMSNPILDAILRHPFVRGIAEGNLSKAAAIRYVSQ
ref|YP_711801.1|         ------------------FSARLWASTEPVYEAILRHPFLTGLTDGTLPRAAFAHFVIQ
                                           *:* *   ::*:    *   ***:  *:   *  :     :* * ref|YP_001488778.1|      DAEYLQAFIKIYAAALSRCTDKEDIAFFHQQIEFVLDSETHPHQNLCRVAGVSYDGLQG-
ref|YP_081277.1|         DYEYLNAFIQIYGIAISKCQNRKDMEMFHEQISFVLDSEVHPHKNLCRAAGVEYETLQG-
ref|YP_174256.1|         DFEYLNTFMQIYGIAISRCENREDMAMFAEQIGFILHSETHPHHNFCKVAGVRYEDLQY-
ref|YP_804091.1|         DTCFLDAFAKVYAGALSKCTTKDQMRFFEEQIRYTLNDEAGAHQILCDIAGQKLSDHQH-
RAAC00944                DQPYLETYLRVFAHAAALAPRHEDVADFHGRMSLLLGGETQAHDNLLRYAGATPHDVEG-
ref|YP_711801.1|         DAHYLRDYARALAVCAAKAPTEDDVRALANDAAEAVAAEQAMHVDLLDALGGPAPGDPAP
                         *  :*   :  :    . . :    ..::  :       :  *   *  :     * ref|YP_001488778.1|      --------APLAPSAHHYIHHMLQVAKEGTLGEMIAVLLPCPWTYWEIGKRMLTDVQPDP
ref|YP_081277.1|         --------YPLAPSAHHYVRHMLTAAHEGTLGEILAVLLPCPWTYWEIGKKLMKDVQPDP
ref|YP_174256.1|         --------EPLAPTAHHYTRHMLDVAHRGSLAEILAVLLPCPWTYQAIGDYLYETFQPKA
ref|YP_804091.1|         --------AKQRPITYLYNEHLFNALRTGDLIDLIAAMLPCPWTYTEISQQI--VDGAAP
RAAC00944                --------QPKLPTLHHYESHLLASAARGDFAELVAAILPCHHVYVEIGQRLEPILEEKP
ref|YP_711801.1|         GGTPPGGVATVAPTTRAYTSYLLATVYGGSFLEGLAAVLPCYWIYARVGARL--LADSSP
                                      *         * : :  :*.:***   *  :.  :           .

ref|YP_001488778.1|      SHPFYEWITFYG----GLTDSITVELCKRLDQLAEAASEKEKEKMKQHFILSCQLEYKFW
ref|YP_081277.1|         SHPFYDWICFYGN----RTDSITTKFCARLDEWAETAGKAEKEKMKELFLQSCQLEYGFW
ref|YP_174256.1|         NHPFFDWISFYRS---NGEMGVTKQFCKRLDELAAHATEQEKERMQDHFLKSCQLEYSFW
ref|YP_804091.1|         DNPFLPWIEFYQPQPGQIDGSMVKTLFGMVDELAIGLSEERQHEIEQRFLRSCELEYEFW
RAAC00944                DHPFAAWIRFYAD---PGMQDATHRLFAMIDREAAHFSTERARRVEAAFVASCHLEYRFF
ref|YP_711801.1|         DPVYARWIAAYGD---PAFQAVADRVVALTDRVGAFASEPELVRAADHFAVTARYEWMFW
                          . : ** *      .   .      *..  .  .   *  :..  *:  *:

ref|YP_001488778.1|      DMAFTVEEW-----------
ref|YP_081277.1|         EMAYTVEDW-----------
ref|YP_174256.1|         EMAYVKEKW-----------
ref|YP_804091.1|         EQAYYQKDW-----------
RAAC00944                DMAYRGESWLPKEALSDVSTP
ref|YP_711801.1|         DAAWRRETW-----------
                         : *:   : *
```

FIG. 140A

```
ref|NP_646484.1|       ------------------------------------------------------------
ref|YP_001332652.1|    ------------------------------------------------------------
ref|NP_372249.1|       ------------------------------------------------------------
ref|NP_764957.1|       ------------------------------------------------------------
ref|ZP_01695369.1|     ----------------------------------------------------------MI
RAAC02632              ----------------------------------------------------------MF ref|NP_646484.1|       KKILFDVDGVFLSEERCFDVSALTVYELLMDKCYLGLHSHIDWETLT--DNDIQDIRNRI
ref|YP_001332652.1|    KKILFDVDGVFLSEERCFDVSALTVYELLMDKCYLGLHSHIDWETLT--DNDIQDIRNRI
ref|NP_372249.1|       KKILFDVDGIFLSEERCFDVSALTVYELLMDKCYLGLHSHIDWETLT--DNDIQDIRNRI
ref|NP_764957.1|       KAILFDVDGVFLSEERCFDVSAITVAELLSSPDFLNCDIDIHFDGNLTEND-INKIRRNV
ref|ZP_01695369.1|     QTVLFDVDGVLLSEERYFDASGLTVWELIHSGHYLGLAPEQFKTTLTDEE--IRRIRADV
RAAC02632              RTILFDVDGVMLSEERYFDASALTVHELLTSQRFLGLSSVSPAFSPAPAEDAIRAIRRDV
                       :.:******::***** **.*.:** **:.  .:*.         :  *. **   :

ref|NP_646484.1|       FQKDKILNKLKSLGLNSNWDMLFIVFSIHLIDILKKLSHDEIEAFMYQ-----DEPVELK
ref|YP_001332652.1|    FQKDKILNKLKSLGLNSNWDMLFIVFSIHLIDILKKLSHDEIEAFMYQ-----DEPVELK
ref|NP_372249.1|       FQKDKILNKLKSLGLNSNWDMLFIVFSIHLIDILKKLSHDEIEAFMYQ-----DEPVELK
ref|NP_764957.1|       FNNDRILNQLKSLGLNSNWDMLFIVFSIHLIDKAKQLKPSLRDQLLDE-----LLFTKET
ref|ZP_01695369.1|     FQHDEVLRFLKSRGMNANWDMIYLTFTCQLLHLLSQIKEKEAGRIRGW---LASEIGDVT
RAAC02632              FRYDAVLEGLKNIGVNANWDMVYFVFVAEWVAALERAREASEEAVDRARSVLREGFSEAS
                       *. *  :*. **.  *:*:****:::.*   .:   .:             . .

ref|NP_646484.1|       LQN---ISTNLADCFNLNEQLPLQFLDNVKVGKNNIYAALEEFATTELHVSDATLFSLKG
ref|YP_001332652.1|    LQN---ISTNLADCFNLNEQLPLQFLDNVKVGKNNIYAALEEFATTELHVSDATLFSLKG
ref|NP_372249.1|       LQN---ISTNLADCFNLNEQLPLQFLDNVKVGKNNIYAALEEFATTELHVSDATLFSLKG
ref|NP_764957.1|       LKE---IAKDLTDKT-INYSLPYDVIASFRNGKDAIYEDLEVYAKNQLELNNTSLFKLKS
ref|ZP_01695369.1|     LHE----MREVLAHYPVE-TDYSIFLNWFAKRPETKQDLLKVLDQLAYEIFGLTDTQLGK
RAAC02632              LRAIGGLLREALPGYVIAWKGYDALYEGASSRSDLMERAREALARYAPEAD---------
                       *:       :         :         :         :       .

ref|NP_646484.1|       --------ALWTLAQEVYQEWYLGSKLYEDVEKKIARTTFKTGYIYQEIILRPVDEVKVL
ref|YP_001332652.1|    --------ALWTLAQEVYQEWYLGSKLYEDVEKKIARTTFKTGYIYQEIILRPVDEVKVL
ref|NP_372249.1|       --------ALWTLAQEVYQEWYLGSKLYEDVEKKIARTTFKTGYIYQEIILRPVDEVKVL
ref|NP_764957.1|       --------ALWTLAKDIYQEWYLGKALFNQVEYKKDIQDFKKGFIYDEVILKPIEEIQLL
ref|ZP_01695369.1|     ------KGALWSVCEHASQEWYVGDQNIVASTGKPSVQTGKKGFLDEEIPLAEPEKIGAL
RAAC02632              ------AHALWQVGQETFQEWYLGD----AYTGK---ETGKAGFLTSEYPIVDPAAFAAL
                             *  :  :. **:*.      *     *  *::.*   .  . * ref|NP_646484.1|       LNDLKGAGFELGIATGRPYTETVVPFENLGLLPYFEADFIATASDVLEAENMYPQARPLG
ref|YP_001332652.1|    LNDLKGAGFELGIATGRPYTETVVPFENLGLLPYFEADFIATASDVLEAENMYPQARPLG
ref|NP_372249.1|       LNDLKGAGFELGIATGRPYTETVVPFENLGLLPYFEADFIATASDVLEAENMYPQARPLG
ref|NP_764957.1|       LQNLIEAGYQIAIATGRPRTETIIPFQSLGLKSYFKDEHIVTASEVLLAEKQFPQYQPLG
ref|ZP_01695369.1|     FSFLAEKGLKLGVGTCRPQLETYGPFRALGWLPLFHEEHIVTADDVLKAEEELGGHTPLA
RAAC02632              LADLKAAGVTLGIATGRPEIETRVPLEHFGWLSYFDPARVTNASDVVAAEERVPHARPLS
                       :  *   *    :.:.**** **  *::.:*   .*.    :..*.:*: **      **.

ref|NP_646484.1|       KPNPFSYIAALYGN-NRDKYESYINKQDNIVN-KDDVFIVGDSLADLLSAQKIGATFIGT
ref|YP_001332652.1|    KPNPFSYIAALYGN-NRDKYESYSNKQDNIVN-KDDVFIVGDSLADLLSAQKIGATFIGT
ref|NP_372249.1|       KPNPFSYIAALYGN-NRDKYESYINKQDNIVN-KDDVFIVGDSLADLLSAQKIGATFIGT
ref|NP_764957.1|       KPNPFSYIATLNGN-YNDQYERYATKQEDIVN-KDEVYIVGDSLADLLSAKKIGATFIGT
ref|ZP_01695369.1|     KPNPFTYLLALKGK--NTPARDCT-ECSLPLENGQEILIVGDSLADLLAAQKIGAQFAGI
RAAC02632              KPHPFSYLRSLMGE--ADVEKLLTVELPIPGIRG-EVLVVGDSIADKLAADRLGASFAAV
                       **:**:*:  :* *:           :     ::  :****:**  *:*.::.** *  .
```

FIG. 140B

```
ref|NP_646484.1|       LTGLKGKDAAGELEAHHADYVINHLGELRGVL------
ref|YP_001332652.1|    LTGLKGKDAAGELEAHHADYVINHLGELRGVL------
ref|NP_372249.1|       LTGLKGKDAAGELEAHHADYVINHLGELRGVL------
ref|NP_764957.1|       LTGLKGKAAHSELVANGADHVVEDITKIRKIL------
ref|ZP_01695369.1|     LTGLSGKEAKAEFEEHGADYIFENVADLKNI-------
RAAC02632              LTGLEGQAARPKFERLGADYILNHVLELRRVLSLASVE
                       ****.*: *   ::    **::.:.:  .::  :
```

FIG. 141

```
ref|ZP_02329050.1|        ------VKVADLVRTFKLEVISGEEGLKRTITVADLYRPGLEMAGYFNYHPQERVQLLGK
gb|AAX09759.1|            ------VKVSELVNQFGLEVISGEQGLKRAITVDDLYRPGLEMAGYFEYHPPERVQILGK
ref|YP_148935.1|          ------VRTKDIIEQFQLELVSGAEGIYRPITTSDLSRPGIEMAGYFAYYPAERLQLLGR
ref|YP_001127122.1|       ------VRTKDIIEQFQLELVSGAEGIYRPITTSDLSRPGIEMAGYFAYYPAERLQLLGR
ref|YP_001376898.1|       ------VRTKDLIEQFQLELVSGEEGIHRPIDTSDLSRPGIEMAGFFTYYPADRVQLLGK
RAAC02474                 MANLRGVSVRQLVRDLDLHVFNEDADLDRMIYTRDINRPGLALAGYLRYHPAERVQILGR
                                 *  . ::: . :  *.:..    .:  *  * .  *: ***: :**:: *:*  :*:*:**:

ref|ZP_02329050.1|        TEMSFYETLTGPIRQRRARQLCTSPETPCIIITRGLDIPDEIIEEAAKHHLPVLRSKVAT
gb|AAX09759.1|            TELAFFEMLPEKERKDRMERLCSSDETPCIIVTRSWKVPEELIEISSEKQIPVLRSSMAT
ref|YP_148935.1|          TELSFYETLTPEEKKSRMERLCT-DITPGIIVSRGLEVPPELIEASERQSVPVMRSTMKT
ref|YP_001127122.1|       TELSFYETLTPEEKRARMQRLCT-DITPGIIVSRGLDVPPELIEASERQSVPVMRSTMKT
ref|YP_001376898.1|       TELTFFDTLTNDQKQERMKALCT-EETPCIIVTRNQDVPKELLQASRESGVPLLRSSQTT
RAAC02474                 TELSFLRGLNEKERALRAFAFCSYQQTPCIIITRGDTPPPVLLEEAASRRIPVLGTPMVT
                          **::*    *       :  *      :*:     :.*.   *    :::  :      :*::  :      * ref|ZP_02329050.1|        TILASRLTNYLENKLAPSTTIHGVLVDVYGVGMLITGGSGIGKSETALELVKRGHRLVAD
gb|AAX09759.1|            AILSSRITSFLERKLAPTATIHGVLVDVYGVGMLITGSSGIGKSETALELVKRGHRLIAD
ref|YP_148935.1|          TRLSSRLTNYLESKLAPTTAVHGVLVDVYGVGVLITGKSGVGKSETALELVKRGHRLVAD
ref|YP_001127122.1|       TRLSSRLTNYLESKLAPTTAVHGVLVDVYGVGVLITGKSGVGKSETALELVKRGHRLVAD
ref|YP_001376898.1|       TRLSSRLTNYLEGKLAPTTAVHGVLVDVYGVGVLIIGQSGVGKSETALELVKRGHRLVAD
RAAC02474                 TRLTARISNYLEDKLAPETLQHGVLVDVYGIGILIIGSSGIGKSETGLELIKRGHRLVAD
                          :  *::*::..:** ****  :   *********:*:**  *  **:*****.***:******:**

ref|ZP_02329050.1|        DAVEIRQTADYVLSGNAPELIRHLLEIRGVGIINVMTLFGAGAVRNEKKISVVVKLETWQ
gb|AAX09759.1|            DAVEIRQTSDNQLHGTAPELIRHLLEIRGVGIINVMTLFGAGSIRNNKRISLVVRLEAWQ
ref|YP_148935.1|          DCVEIRQEDEDTLVGSAPELIEHLLEIRGLGIINMMTLFGAGAVRTHKRISLVVDLELWD
ref|YP_001127122.1|       DCVEIRQEDEDTLIGSAPELIEHLLEIRGLGIINMMTLFGAGAVLPHKRSLVIDLELWD
ref|YP_001376898.1|       DSVEIRQEDEDTLVGSSPDLIEHLLEIRGLGIINMMTLFGAGAVRNYKRITLVINLEIWD
RAAC02474                 DAVVIRQISDDYLVGSAPPLLQNLIEIRGLGVLNAMTLFGAGAVRTHKRISMVVHLEAWR
                          *.* ***   :   * *.:* *:.:*:****:*::*  *******::     *:*::*: **  * ref|ZP_02329050.1|        QDKQYDRLGLDEETTRIIDTDLPLVTIPVRPGRNLAVIIEVAAMNYRLKRMGYNAALQFT
gb|AAX09759.1|            QEKQYDRLGLDEETTRIIDTDVPLVTIPVRPGRNLAVIIEVAAMNFRLKRMGYNAALQFT
ref|YP_148935.1|          PEKQYDRLGLEEEKVKILDTELPKLTIPVRPGRNLAVIVEVAAMNFRLKRLGVNAAEEFS
ref|YP_001127122.1|       PEKQYDRLGLEEEKMKILDIELPRLTIPVRPGRNLAVIVEVAAMNFRLKRMGVNAAEEFS
ref|YP_001376898.1|       QNKNYDRLGLDEEKMKIIDTELTKITLPVRPGRNLAVIIEVAAMNFRLKRMGVNAAQQFS
RAAC02474                 DNHAYDRLGIETETMKILDIELPKVTVPVRPGRNLAVIVEVAAMNFRLKGMGLDAAKQFA
                            ::  *****:: *. :*:*  ::.  :*:*********** ******.***  :*  :**  :*:

ref|ZP_02329050.1|        NRLTETIA-------
gb|AAX09759.1|            TKLTETIS-------
ref|YP_148935.1|          ARLSDAI--------
ref|YP_001127122.1|       ARLSDAI--------
ref|YP_001376898.1|       ERLMSAI--------
RAAC02474                 AELEQMIAAQSEGSA
                            .*  .  *
```

FIG. 142

```
ref|NP_244107.1|           MNTTIYDVAREAGVSMATVSRVVNGNPNVKPATRKKVLEAIERLGYRPNAVARGLASKRT
ref|YP_176259.1|           MNTTIYDVAREAGVSMATVSRVVNGNPNVKPTTRKKVLEAIERLNYRPNAVARGLASKRT
ref|YP_148663.1|           MTVTIYDVAREANVSMATVSRVVNGNPNVKPSTRKKVLEAIERLGYRPNAVARGLASKKT
ref|YP_001126805.1|        MTVTIYDVAREANVSMATVSRVVNGNPNVKPSTRKKVLEAIERLGYRPNAVARGLASKKT
ref|ZP_01188060.1|         MKPTIKDVARKANVSVATVSRVLNNQPGYSVETEKKVLEAIDELGYHFNALARGLVGKRT
RAAC00625                  MRATIRDVAKAAGVSAATVSRALNRPDLVDPETLERVRKAMEEMSYQPSAIARGLSARRS
                           *  ** ***: *.** *****.:*    .  * ::* :*::..:.*:*.*:**** .::

ref|NP_244107.1|           TTVGVVIPDISSIFFAELARGIEDIATMYKYNIILCNSDQNKEKEIHLINTLLEKQVDGI
ref|YP_176259.1|           TTVGVIIPDISSIFFSELARGIEDIATMYKYNIILCNSDQNKDKEIHLINTLLEKQVDGI
ref|YP_148663.1|           TTVGVIIPDISSIFFAELARGIEDIATMYKYNIILSNSDQNKEKELHLLNTMLAKQVDGL
ref|YP_001126805.1|        TTVGVIIPDISSIFFAELARGIEDIATMYKYNIILSNSDQNKDKELHLLNTMLAKQVDGI
ref|ZP_01188060.1|         KTLGVLIPRISNMVSSQIMNGIEDAAHKNDHSVIICNTDNDGQKTMVYLDVLREKRVDGI
RAAC00625                  DTLGLIVPGITDFFFNELYKGIDRASQQYGMKVLLYDSEHSRERAFEGFSILSGYQVSGI
                           *:*::::*  *:..:   ::  .**: :      .:::  ::::. :: :  :. :  :*.*:

ref|NP_244107.1|           VFMGGEITNEHAEEFKRAHVPVVLAATLDAEK-EIP-SVNIDYKQAAFDAVTYLIEKGHT
ref|YP_176259.1|           VFMGGEITEEHAEQFKRAPVPIVLAATLDDEKS-FP-SVNIDYTQAEDAIQFLIEKGHK
ref|YP_148663.1|           LFMGGTITDEHVAEFQKSSVPIVLAATMGPNEIP---SVNIDYEQAAFEAVTYLLEKGNR
ref|YP_001126805.1|        LFMGGTITEEHVAEFQKSSVPIVLAATIEPNET-IP-SVNIDYEQAAFEAVTYLLERGNR
ref|ZP_01188060.1|         IVVSEMLTEEYANKLVELKVPVILISTIDETGQFP--HIKVNDEQAAYQATEYLISKGHK
RAAC00625                  IFTSKLVTEDYDPILQRVNIPVVLTLTQSAAKTPLT-AFRIDEVRAMFDVVAYLVSRGHR
                           :..  . :*:::    : . :*::*  *        ..::  :*   :.  :*:.:*:

ref|NP_244107.1|           SIGMVSGSL-EDPVNGYQKYAGYREALEERGVAFDESMVVIGDYTYDSGIDAM-NVFTK-
ref|YP_176259.1|           RIGMLSGSL-EDPINGYQKFAGYRQALQKNNIEFDENLIVIGDYTYDSGMEAM-DAFL--
ref|YP_148663.1|           RIVYVTGPT-DDPIN-QRKLAGYRRALEEHGAPYEEELVIEGDNSYDSGLEAYEKITE--
ref|YP_001126805.1|        RVAYVTGPT-DDPIN-QRKLAGYRRALEEHGVPYDEELVVEGDNSYDSGLEAYEKIAE--
ref|ZP_01188060.1|         NIAMISGTP-EDMVAGKPRLDGYKKALRENGLPVKEENIVFGDFWFDSGKECMERLLNN-
RAAC00625                  QIAMIAGKLWDDRTG-ELRLEGYREGLRHFGIEYCEARVEFGQYRFDDGYQAMQRLLER-
                           :  ::* :*    :  **:..*.. .  * : *:  :*.* :.

ref|NP_244107.1|           -LEKRP--TAIFVATDEMALGVIHGAQDHGLNIPDDIEVIGFDNTRLATMVRPTLSTVVQ
ref|YP_176259.1|           ALDEKP--TALFASNDEMALGVIHGIQDRGYDVPGDIEVLGFDNTRLATMVRPTLTTVVQ
ref|YP_148663.1|           -LAERP--TAVFAGTDEMALGIIHSAQDHGGRVPDELEVVGFDNTRLATMVRPRLTTVVQ
ref|YP_001126805.1|        -LAERP--TAVFAGTDEMALGIIHSAQDQGVRVPDELEVVGFDNTRLATMVRPRLTTVVQ
ref|ZP_01188060.1|         --NQGI--TAIFVASDEMAAGALSTAYKSGIRVPEDISIIGFDNTQLAEMTIPPLTTVSQ
RAAC00625                  -IRDVP-FTAVCTASDEMALGAIRCLNDHGYRVPDDISVMGFDDLPIARMVTPRLTTVAQ
                            .     : ...** *  :     . *  :*   ::.::***:  :* *.  * *.:** * ref|NP_244107.1|           PIYDIGAVSMRLLTKYMNK----EEVSEHI--VELPHRIEFRQSTR---
ref|YP_176259.1|           PLYDIGAVSMRLLTKLMNK----EEVDNYT--VTLPHRIESRGSTK---
ref|YP_148663.1|           PMYDIGAVAMRLLTKYMNK----EPVDHHI--VVLPHRLEVRESTK---
ref|YP_001126805.1|        PMYDIGAVAMRLLTKYMNK----EHVDNHI--VVLPHRLEVRESTK---
ref|ZP_01188060.1|         PFYQMGYKGLKLLLKAI------KGKEVNS--AILPHVIVERETVKKV-
RAAC00625                  PFHEIGEEAVKWLIRAASQ----PPSPSEIGDYLLPHRLVERESVRSIS
                           *::::*  .:: * :         .         ***  :  * :.:
```

FIG. 143

```
ref|YP_001488326.1|        --------------MVEKTVTIQLKTGLQARPAALFVQEANRFGADIFLEKDGKKVNAKS
ref|ZP_01860336.1|         --------------MIEQKVEVKLKTGLQARPAALFVQEANRFSSEVFLERNGKKVNAKS
ref|NP_693386.1|           --------------MVEKLVTVELDTGLQARPAAQFVQEANRFSSHVFLEKDDKKINAKS
ref|NP_834817.1|           --------------MVQKRVQVSLKNGLQARPAALFVQEANRFHADIFIEKDGKTVNAKS
ref|ZP_01697803.1|         --------------MIEKQLEVKLKSGLQARPAAQFVQEATRFSSEIFLEKEGRKVNAKS
RAAC00733                  --------------MVEKVLTVNLPQGLAARPAAEFVKRASSFSSQIRIGKNGHFVDAKS
                                         *::: :  :.*   * :.*. *  :.: : ::.: ::*** ref|YP_001488326.1|        IMGLMSLAISSGVTITLIADGADEQEAIEALTDFVNQE---
ref|ZP_01860336.1|         IMGLMSLAVSSGTEITLIADGTDEEQAVKHLTEFVQKES--
ref|NP_693386.1|           IMGLMSLAITKGEQIKLIAEGPDEDTAIEHL----------
ref|NP_834817.1|           IMGIMSLAIGTGSMITITTEGSDAEEALEALA---------
ref|ZP_01697803.1|         IMGLMTLAAGHGETVTLSVDGSDEEEAFEHLANYI------
RAAC00733                  VLGVMSMAIARGESVTLQAEGSDAERAVETLAELLSRDTFE
                           ::*:*:*  *    :.: .:*.* : *.: *
```

FIG. 144

```
ref|NP_244433.1|         ----MVEKQVEVKLKTGLQARPAALFVQEANRFTSEIFIEKDGKKVNAKSIMGLMSLAIG
ref|YP_001488326.1|      ----MVEKTVTIQLKTGLQARPAALFVQEANRFGADIFLEKDGKKVNAKSIMGLMSLAIS
ref|ZP_01171669.1|       ----MVEKQVEVKLRTGLQARPAALFVQEANRFSSDIFLEKDGKKVNAKSIMGLMSLAVS
ref|ZP_01860336.1|       ----------------------FVQEANRFSSEVFLERNGKKVNAKSIMGLMSLAVS
ref|ZP_02327791.1|       ----------------------FVQEANKFSSEIFVEKDEKKVNAKSIMGIMSLAIS
RAAC02466                MVMKMFEKETIVRLRGGLFARAAAKFVQEATRFKSEVFVERDGKTVNAKSIMGVMSLAIP
                                               *****.:*  :::*:*::  *.*********:****:

ref|NP_244433.1|         SGSTITLITEGNDEQEAMEALIAFIEKE----
ref|YP_001488326.1|      SGVTITLIADGADEQEAIEALTDFVNQE----
ref|ZP_01171669.1|       TGSVVNLVADGSDEEEALEELSQYIQQE----
ref|ZP_01860336.1|       SGTEITLIADGTDEEQAVKHLTEFVQKE----
ref|ZP_02327791.1|       TGTEIYISAEGSDDEQAVNALVSLVSKEEL--
RAAC02466                SGERVIIRASGTDEQAAVHQLTKLIESEELFV
                         :*   :  : :.* *::  *:. *   :..*
```

FIG. 145

```
ref|YP_001124914.1|    ------------------------------------------------------------
ref|YP_146760.1|       ------------------------------------------------------------
ref|YP_001319371.1|    ------------------------------------------------------------
ref|ZP_00742387.1|     ------------------------------------------------------------
ref|ZP_01723416.1|     ------------------------------------------------------------
RAAC02678              MGVRLRGGRADGGRAHQAVARQVPRGRVSVSHPHRARVGLSPGGERVKERAASRGSDDDF ref|YP_001124914.1|    ------------------------------------------------------------
ref|YP_146760.1|       ------------------------------------------------------------
ref|YP_001319371.1|    ------------------------------------------------------------
ref|ZP_00742387.1|     ------------------------------------------------------------
ref|ZP_01723416.1|     ------------------------------------------------------------
RAAC02678              RARHQRWQWREALDRLLWMSCWSFVLLSASYGVVRLMGRALGWRPVPYGQLMIIGGVGVV ref|YP_001124914.1|    --------------------------AINRIAKGDF--RVNLQVDWGGR--HHPFAELVT
ref|YP_146760.1|       --------------------------AINRIAKGDF--RVNLQADWGGR--NHPFAELVT
ref|YP_001319371.1|    --------------------------ALESIAKGNF--NVRLDDKFKK---DESFSRLVK
ref|ZP_00742387.1|     --------------------------IQKIAKGDFSVKIRNEEKY-----DGEIGVLVK
ref|ZP_01723416.1|     --------------------------ALRQMAKGDFNIQ--LDVK-GNK--EDQFGQLIH
RAAC02678              MLALVALLWNALGFDRDDRLFFRILDSLSEIGRGNFSARAMLEVRRGFP--DHPMNQLVL
                                                 :  :.:*:*  .    :       . : *:

ref|YP_001124914.1|    RINDMAANLQAMEDMRQEFISNVSHEIGSPLTSIRGFARALKNENLSQEQRMHYLDIIET
ref|YP_146760.1|       RINDMAANLQAMEEMRQEFISNVSHEIGSPLTSIRGFARALKNEDLSREQRLHYLDIIET
ref|YP_001319371.1|    SVNMMASGLDQMEKMRQEFISNVSHEIQSPLASIQGFAQLLQNDELSPEERKHYLSIIET
ref|ZP_00742387.1|     SINDMTDELNTMEKMRQEFISNVSHEIQSPLTSIKGFARALQDDNLSEEKRKHYLTIIET
ref|ZP_01723416.1|     GINHMAVELGELERMRQEFISNVSHEIQSPLTSINGFAKALKNIHLPEEKRQHYLEIIEL
RAAC02678              HVREMAEGLERIEQMRQEFVANVSHEMQTPLTSILGFVKALKSDGLSEGERRHYLDIIEA
                        :. *:  *   :* ***::*: :: .: *:.  *.  :* * * ref|YP_001124914.1|    ECVRLSKLSENLLRLAMLDSERYPLHPTSYRLDTQLQTLILHCEPQWAEKDVDMCAVMEK
ref|YP_146760.1|       ECVRLSKLSENLLRLAMLDSDHYPFHPTSYRLDTQLQTLILHCEPQWAEKELNMCVLFEK
ref|YP_001319371.1|    ESKRLSKLSDSLLKLAILESDSMRFEPKAYRLDKQLRNLILACEPQWREKRINMEAFLDE
ref|ZP_00742387.1|     ETTRLSKLSQNLLKLTLLESEEYTPERVSYRLDQQLKQIVLNSEPLWAEKEIELDLDLEK
ref|ZP_01723416.1|     ESNRLSKISDNLLKLTSLESQHHPFETTTYRLDKQLRNVILALEPNWVAKQLDFDLHLDN
RAAC02678              ESERLSRLADNLLKLTSLESGHHPVTLTRFRLDRQLREVAIACEPLWTEKGLFLDMQVEP
                       *  ***::::.**:*: *:*       :*** **: : :  ** *   * :  .:   .:

ref|YP_001124914.1|    VSITADEDLLSQVWLNLIHNAIKFTPKGGTITVQVQRRGEQAIVTISDTGPGIPKHDQPR
ref|YP_146760.1|       VIITADEDLLSQVWLNLIHNAIKFTPKGGTITIQLQRRGEQAIVTVSDTGPGINEHDQLR
ref|YP_001319371.1|    VTITADEDMMSQVWINLIYNSIKFTPEGGSVRVDLNQHGKTIVCKISDTGIGIPEEDQKH
ref|ZP_00742387.1|     VHVTADQESMSQVWINLIHNSIKFTPSGGTITIQLKEHETVVEVRICDSGIGISEEQKQH
ref|ZP_01723416.1|     ITITADEDLLNQVWMNLLTNSIKFTSDRGAITLTMTQHLDTITIIVQDTGIGLSEEQQMH
RAAC02678              VELEGDEDLLGQVWMNLLSNAIKFTEPGGRIQVRLEKEETGVCVSVADTGIGIRPEDVSR
                       :  : .*:: :.***:**: *:****  *  :  :  ..         : *:* *: .: :

ref|YP_001124914.1|    IFERFYKVDKSRHRAAGGSGLGLAIAKQIVDMHHGTISVQSEPGEGATFTVELP------
ref|YP_146760.1|       IFERFYKADKSRHRAAGGSGLGLSIAKKIVDIHHGIISVQSQPGEGATFTVELP------
ref|YP_001319371.1|    IFERFYKADKSRERSKKGGGLGLSITKKIIDMHYGDISVQSKSGTGTFFTVSLP------
ref|ZP_00742387.1|     IFERFYKADSSRNRASGGSGLGLAIVKKVLDLHQGEIKVESEEGKGTEFIVRIP------
ref|ZP_01723416.1|     IFERFYKADQSRTAANGGSGLGLAIVKKIIDMHHGTIAVESKLGKFTAFLITLP------
RAAC02678              VFTRFFKADRSRGKP--GNGLGLAIAKRIVEMHRGDISVESEPGRGSTFKVHLPYTQGGR
                       :* **:*:.* **   .  ****:*.*::::::* * * *:*: *   : * : :*
```

FIG. 146

```
ref|YP_001394884.1|    --------------------------------------------------------DLMFLST
ref|ZP_01574787.1|     ---------------------------------------EIGTYGDNYLNEHDIAFIND
ref|ZP_02185068.1|     ---------------------------------------ISYMGPTAYSEHDALFIAD
ref|YP_001559227.1|    ---------------------------------------ISYYGPYFLSENDFKFLSA
RAAC02507              MSLRRKIILAFFLTLSIMLVALAFILQAEVHRHFLSVVCPEINSVSPSLTQQIEVHFEQA
ref|YP_517080.1|       --------------------------------------------------------FVSA
                                                                                  * ref|YP_001394884.1|    LNR-ILISVGIISLCLALILGVIISGSLSRPILRVIESAEEISKGDYSTRIN-ENSNIIE
ref|ZP_01574787.1|     LYK-LLWAVGLFSLILSLLFGTVMSKRLVSPIARVINTAKSISKGFYSDRIT-EKSNTRE
ref|ZP_02185068.1|     MKN-NLIIVAIVALILSIFFAALVAKKISGPIVRVKDFTREIAKGDY-TSLSPEKTDIKE
ref|YP_001559227.1|    LNT-ILVSIGSVSLLFAVYIGWMLARKISGPITKTVKMTTEIAEGNYEIRFS-EHTGTKE
RAAC02507              LTQSLLWTV-LIPVVATAGVAVLVSRAITQRIFVMQKQALEIARGKWGTTIP--VEGHDE
ref|YP_517080.1|       IYQ-SLLFAGALALIIGILLSYWTSRRLISPLQNLTKAAQRVGEGHLDEHVS--VMTKDE
                        :    *     .  :    ..    :  :       .  :  .. *     .       * ref|YP_001394884.1|    INNLTSTINNLAETLQNQENLRKRLTADVSHELRTPLTTLQSHMEAILDGIWEPTQDRIN
ref|ZP_01574787.1|     INQLTVSINDLAENMEKQETLRRRLTGDVAHELRTPLATLQSHMEAMIDGIWSADSERLK
ref|ZP_02185068.1|     LDELISSVNALSVQLENQQDIRNQLSSDIAHEIRTPLTTLKGSLEAMIDGIWEITDDRLQ
ref|YP_001559227.1|    LDALVSSINNLASSLEKQEGIRKQLTSDVSHELRTPLTTIGTHIEAMIEGVWEPTTERLK
RAAC02507              LSSLANTLNSLSKQLHKQEELRRNLIQDLAHELRTPLTTLRSHIQAFYDGLWEPNRERLY
ref|YP_517080.1|       VGQLAIAFNGMADSLKKQEHLRKQFTADIAHELRTPLTSIRSYIEAFQDGVLPADKENLT
                       :.  *   :.*  ::    :.:*:  :*...:    *::**:****:::     ::*:  :*:       :..:

ref|YP_001394884.1|    SCHGEIMRINRMVNDLEKLAE--YEGENLI----LNKSEFNISEVVKNIMLNFENEYVSK
ref|ZP_01574787.1|     SCHEEIVRISKMVGDLERLAK--YESENIT----LNMDTFDITKLAKRQVQNFETEFLCK
ref|ZP_02185068.1|     SCYDEVNRITRLIGSIDKINE--IESHQDS----LNKTSFDLYALAENISSNFEALFVKK
ref|YP_001559227.1|    SCYEEINRITNLVKDLEQL--AKVENDNLK----LNITSVNILEVIDTIKDNFETEIYNK
RAAC02507              SCLEEIQRFEALVTSVERLYEADVAVHAAR----RDLSSADVNQVAQSVIQLFEPRCAEL
ref|YP_517080.1|       IINEEIERLVGLSSDLKDLNVAEMG--ALK----LNFTQVDITELIDKTVNKLIPLIQEK
                       *: *:    :   : . .:.:        :          :   ::  :: :.  :

ref|YP_001394884.1|    EI-------DFIFNSRDI--FICADKDKISQIIINLISNALKYTRQGGKVLIQVDNKNEY
ref|ZP_01574787.1|     GL-------ELELTGPSCLVY--ADKDKISQVFVNLLSNALKYTPKGGSVELHIQDNNNF
ref|ZP_02185068.1|     NI-------YYALNGD--PLFITADKDKISQVITNLLSNAVKFTPPEGTITLKIRNEENQ
ref|YP_001559227.1|    SL-------DVSVIGTAS--TILVDKERISQVIINLLSNAIKYTPDFGKIVISLEDYETN
RAAC02507              GIR-------LELRTPDVPVWVTARAQHVSQILWNLLDNAVKFTPSGGNIVVEVGHQDGK
ref|YP_517080.1|       GIA-------FEWEKP-ASVFIEGDEYHLTRLFYNLIHNAYKFTESNGRISIQMELRQSD
                        :                     ::::::: **:  ** *:*    *  :  :     :

ref|YP_001394884.1|    LELIVQDNGQGIPKEDLPYIFERFYRADKSRNRLTGGAGIGLTITKSLVEAHKGKITVES
ref|ZP_01574787.1|     IEISVEDNGLGIPEEDLPYIFERFYRADKSRDRLTGGSGIGLTICKSIVLAHGGDIYAQS
ref|ZP_02185068.1|     ALLTIADTGEGIHPKEINRIFERFYMSDLSRNSFLGGQGIGLSIVKSIIKAHNGTITVKS
ref|YP_001559227.1|    LVIQMKDNGIGIPEEELPFIFERFYRADKSRNRRTGGAGIGLAIVKSVVHSHGGKVEVSS
RAAC02507              PFLSVKDSGVGIPAEEIDNIFERFYRVDKSRDKTGGSGLGLAIVKQLVELSRGFVQVNS
ref|YP_517080.1|       VRISVCDSGIGIPKEDLPFIFERFYRAEKSRSRETGGTGIGLALVQQITQLHRGTLDVES
                         :  :  *.*      :::   **  :  .    ** *:**::  :.:      * :  ..* ref|YP_001394884.1|    ELNKGTTFKVSIP-
ref|ZP_01574787.1|     NPGKGTKFIFTVPK
ref|ZP_02185068.1|     DYGKGSTFTVILP-
ref|YP_001559227.1|    KLETGTVFRVILP-
RAAC02507              RVGRGSTFTVVWPE
ref|YP_517080.1|       NPGQGSKFTVVLP-
                         *:  *  .  *
```

FIG. 147A

```
ref|ZP_01667455.1|      MFQRTLRRLSIINSVVFLLIFLTFGAVLYGYVAYRLFDKVDDAMRFKAENFKIVNGRAIL
ref|YP_146183.1|        ------------------------------------------------------------
RAAC00906               MFRKTALRLVLLYTVVFAGILLLFSAVVYAFTDHRVRADEIATMSTAAANLRACRDEQIL
ref|ZP_01515931.1|      ------------------------------------------------------------
ref|YP_001637100.1|     ------------------------------------------------------------
ref|YP_001430381.1|     ------------------------------------------------------------ ref|ZP_01667455.1|      PGRVRFLFDPRIIILVRDSQGRVTSSFPSEVAELERL------------AALASQVDAGK
ref|YP_146183.1|        ------------------------------------------------------------
RAAC00906               PGDR---DDGEASPLHRGHSSGPGPDGDRLLAEVDETREQHLVYVLLSGTRVVLQTPAGS
ref|ZP_01515931.1|      ------------------------------------------------------------
ref|YP_001637100.1|     ------------------------------------------------------------
ref|YP_001430381.1|     ------------------------------------------------------------ ref|ZP_01667455.1|      VHISEVDSHA----------YRLISLPYRYEENVLQTERGPIVVKDVIAVSIV-----DS
ref|YP_146183.1|        ------------------------------------------------------------
RAAC00906               LTASEASIVARDGLGARPRGVSVAGVPYLGMKVELP---RPVRIGDASANAAVILYNRAQ
ref|ZP_01515931.1|      ----------------------------------------------GPAALQLGRVLNDQEQ
ref|YP_001637100.1|     ------------------------------------------------------------
ref|YP_001430381.1|     ------------------------------------------------------------ ref|ZP_01667455.1|      EVALLRNLFMIIVSGLVIGMLIIIMAGYYLARRAMVPIQAAWEKQQQFVADASHELRTPL
ref|YP_146183.1|        ---------------------------MSKRALIPIEEAYERQRQFVADASHELRTPL
RAAC00906               DVAFLRELLTILSVSAGFFAVASAGVGFALASRALRPIRRSFEEQRRFVAHASHELRTPL
ref|ZP_01515931.1|      ---VLYQLLTGLVGFGIVGAVMIGIASWWLAGRALRPAEEEAWTRQLRFISSASHELRAPL
ref|YP_001637100.1|     ---------------------------LAGRSLRPAEEEAWVRQTRFIASASHELRAPL
ref|YP_001430381.1|     ---------------------------LAGRALRPAQEEAWERQQRFIASASHELRAPL
                                                    ::  *::  *  .   ::  .* :*::  ******:**

ref|ZP_01667455.1|      AVIKSNAELMLRHPDHTIEDESIRVTN-IVREVRRMTRLVADLLTLARADANQSELQLG-
ref|YP_146183.1|        SVVFSSVEALALEEDVMKNDFARRLLDRLREELKRITKLMNDLLTLARADAKNAALELSK
RAAC00906               AVMRLQIDRMFRHPGETILDMSEVIAS-LARETSRLQRLVNDLLTLAKADEGEAVLRLR-
ref|ZP_01515931.1|      TLIRASAEVALRNAKDE--DQRELLTD-VLSESDHMRRLVDDLLTLSRLDSGGSLTLQRQ-
ref|YP_001637100.1|     TLIRASAEVALRHADDP--DQRELLSD-VLSESDHMRRLVDDLLTLSRLDSGALVLQRQ-
ref|YP_001430381.1|     TLIRASAEVALRDTPSDTADQYELLGD-ILAESDHMRRLVDDLLTLTRLDSGQLKLVIE-
                         :::   .  :     .        * :  . *  :: :*: *****::  *     * ref|ZP_01667455.1|      -AVSLSELVDAVSEQFKPLAQLEGHTLTVAVYEQLELVGDRERLYQLLVILLDNAVKYTP
ref|YP_146183.1|        QTFDFRPHAERTFQLVSELAAKKQITMHFHAPEQALVTADPDKLTQLLYILLDNAIKYTP
RAAC00906               -PVDLATIAREAALRFAPLAEEKGVQLRVSAAETP-IVADPDRLLELLSILVDNAIAFTP
ref|ZP_01515931.1|      -PITLNDFLADLHRHVSRLGEERGITITLAQARGT-VIADPDRLRQILLILIDNALRYTP
ref|YP_001637100.1|     -PVSLPSFLADLHRQVRRLGEEKGIAIQLAPITGT-VLADPDRLRQVLLILIDNALRYTP
ref|YP_001430381.1|     -PVNLADLLSRVHRQVARLGEQRGITIELTTVGGV-VQADAERLQQVLLIALDNALRHTP
                          .  :         . *. .           :   .*  ::* * :***: .**

ref|ZP_01667455.1|      PPGHILITGVRQGSHILLTVEDSGQGIPPEDLPRVFDRFYRGDKARSREK--GGTGLGLA
ref|YP_146183.1|        EGGEVTLSIRTEPKQFILSVKDTGIGIPPEDIGRIFDRFYRVDKTRSRQQ--GGHGLGLS
RAAC00906               AGGWVEIDAHASGSAAVLAVRDTGRGIPPEHLPRVFDRFYQADPSRTTR----GAGLGLS
ref|ZP_01515931.1|      TGGTITLNAELAGKQVRISVRDTGCGITPEHLPHLFERFYRADQARNRSSNTNNAGLGLS
ref|YP_001637100.1|     SGGVITIATEPAGKQIRLSVSDNGCGIAPEHLPHLFERFYRVDVARNRSD--GHAGLGLA
ref|YP_001430381.1|     SGGTITLAAAPTGRMVQITVTDTGSGIAPEHLPHIFERFYRADPARGREN--GNAGLGLS
                         * : :           ::* *.* **.**.:  ::*:***: * :*          ****:
```

FIG. 147B

```
ref|ZP_01667455.1|      IAKWIVEKHGGKIWVES--KVGVGTKFSVLLP------------------------
ref|YP_146183.1|        IAKWIVEAHGGTIHVQS--QLGQGSEFLVRLP------------------------
RAAC00906               IAKWIAEAHGGQIRIFSPGSHGTGTEVEVRLPQSRSAEPGRGRFARLLAICYKKNSS
ref|ZP_01515931.1|      IAKGLVEAHGGTIGIES--EVNKGT-------------------------------
ref|YP_001637100.1|     IAKGLVEAHSGAIGIES--EVNRGT-------------------------------
ref|YP_001430381.1|     IAKGLVEAMHGRITVTS--ALGAGTTVSVALPQGET--------------------
                        *** :.*   * * : *    . *:
```

FIG. 148

```
ref|YP_005108.1|         --DDGEGIPEEHLPHLFERFYRVDKARDRERGGSGLGLAIVKAILEAHGGEVWVESQVGK
ref|YP_144769.1|         --DDGEGIPEEHLPHLFERFYRVDKARDRERGGSGLGLAIVKAILEAHGGEVWVESQVGK
ref|ZP_01773683.1|       --DSGIGIPEKDLPRLFERFYRVDEARSRDNGGTGLGLSIVKHIVQAHGGTLEVKSEQGK
ref|YP_001157480.1|      VADTGPGIPAQHLPHIFERFYRVDTARDRGNGGSGIGLAIVRAVVSAHGGRVRAENVPGG
RAAC02211                MADNGVGIPKVHHPHVFERFYRVDEARSRAKGGAGLGLAICKAIVEAHGGRMEWESEPGE
ref|YP_001124914.1|      ISDTGPGIPKHDQPRIFERFYKVDKSRHRAAGGSGLGLAIAKQIVDMHHGTISVQSEPGE
                           *  *  ***    .  *::***:  :*  *    **:*:**:*  :  ::.  * *   :.   * ref|YP_005108.1|         GTAFSFSLPASGP-----
ref|YP_144769.1|         GTAFSFSLPASGP-----
ref|ZP_01773683.1|       GSVFSFTLPIA-------
ref|YP_001157480.1|      GAMVKVVLPPAG------
RAAC02211                GAVFTVTLPVAGPDGDGA
ref|YP_001124914.1|      GATFTVELPIRGP-----
                         *:  ...  **
```

FIG. 149A

```
ref|ZP_00739567.1|      ------------------------------------------------------------
ref|NP_830390.1|        ------------------------------------------------------------
ref|ZP_01696335.1|      ------------------------------------------------------------
ref|YP_001037228.1|     ------------------------------------------------------------
RAAC01489               MFKRLSLRLTLLTVVLLVVLYSITSLALYGIIRGFVMRSIDFNLRQAAYRVAN-TAVLTG
ref|ZP_01667455.1|      ------------------------LYGYVAYRLFDKVDDAMRFKAENFKIVNGRAILPG ref|ZP_00739567.1|      ------TWNGKIVKIEGDN--RKFRSIFEENLEKFSPKKLGELQD------IEVQGRYFR
ref|NP_830390.1|        ------TWNGKIVKIEGDN--RKFRSIFEENLESFSPEKLEELQD------IEVQGRYFR
ref|ZP_01696335.1|      ------------------------------------------------------------
ref|YP_001037228.1|     ------------------------------------------------------------
RAAC01489               IPSFASTGSPEINFVLADN--GVYTSIADPDLASALENRLNRAVDRPTFFNFTYQGEHYR
ref|ZP_01667455.1|      RVRFLF--DPRIIILVRDSQGRVTSSFPSEVAELERLAALASQVDAGKVHISEVDSHAYR ref|ZP_00739567.1|      AFSL----------QKDGEIVQIVRDI---TAEERMLNTLFLILVIGCSIGSLCAIGIG
ref|NP_830390.1|        AFSLQ----------KDGEIVQIVRDI---TAEEGMLNTLFLILVIGCSIGSLCAIGIG
ref|ZP_01696335.1|      --------------------------------------------------------AVIAG
ref|YP_001037228.1|     -------------------YIIVFLDY---TVEEKMYKPLIIISIYIVLLSIVLVFTVS
RAAC01489               VYDLP------IAAGSGGPAYVATILDD---TQTVRAMSDLRSVIVIVGLFGICGATLVG
ref|ZP_01667455.1|      LISLPYRYEENVLQTERGPIVVKDVIAVSIVDSEVALLRNLFMIIVSGLVIGMLIIIMAG ref|ZP_00739567.1|      FFLAGRALVPIQNSWEKQQQFVSDASHELRTPLAVIQSKTDVLFQSPSATIEEKAMDIST
ref|NP_830390.1|        FFLAGRALVPIQSSWEKQQQFVSDASHELRTPLAVIQSKTDVLFQSPSATIEEKAMDIST
ref|ZP_01696335.1|      LVLAERALKPIKAAWDKQTQFVSDASHEIRTPLAVIQSRVELLLRKPNETVRDVLQDIST
ref|YP_001037228.1|     FFLANRSIKPIKTSWEKQTAFIADASHELRTPLAVINSNLEIVMENENETVGSQMKWLGN
RAAC01489               FILSDRMLQPIRRAFQRQLEFVADASHELRTPLAVIQSNLGIVMEHTDQTVEENLEWLNN
ref|ZP_01667455.1|      YYLARRAMVPIQAAWEKQQQFVADASHELRTPLAVIKSNAELMLRHPDHTIEDESIRVTN
                             *:  *   **:  ::::*  *::*****:********:*.   ::: .  *: .    : .

ref|ZP_00739567.1|      ISKECRRLSKLVSNLLLLARSDSN-QIEMDKKTFELDKLLEEIVAPYKEIASYQEKEMIL
ref|NP_830390.1|        ISKECRRLSKLVSNLLLLARSDSN-QIEMDKKIFELDKLLEEIVAPYKEIASYQEKEMML
ref|ZP_01696335.1|      VLNECRRLTKLVSNLLTLARSDSD-KIEIERKPFYLDELLREIMDHFSELAAIQGKTLIL
ref|YP_001037228.1|     IQSELERMKKLVDDLLFLARADAEDEMPKEY--FDLSRLVHKIYDEFTPLCQKKSLEFLL
RAAC01489               AHGEARRLAKLVQDLLTLARSDSE-RMPVERRPVALNDLLERIHDLYETIAEMRGIELTV
ref|ZP_01667455.1|      IVREVRRMTRLVADLLTLARADAN-QSELQLGAVSLSELVDAVSEQFKPLAQLEGHTLTV
                             *  .*:  ** :** ***:*:: .    .  *. *:  :   :.   :   : :

ref|ZP_00739567.1|      KVERGVSFMGDRERIHQMMVILLDNAMKYTNEGGHIQIDCTQMSSSIRIQVKDDGIGVKE
ref|NP_830390.1|        KVERGVSFMGDRERIHQMMVILLDNAMKYTNEGGHIQIDCTQMSSSIRIQVKDDGIGVKE
ref|ZP_01696335.1|      KSAPPVTFSGDRDRIHQLIVILLDNAMKYTGDGGKIELACFESKNHVGISVQDNIGLKE
ref|YP_001037228.1|     DAKDNIVFYGNEFRIKQLITILLDNAIKFTGEGGKIILKLKVHANSIQLSVSDTGEGIAK
RAAC01489               RAEEPLVVLGDRDRLHQLLVILIDNAMKFTDAGGKVEIAATRNRNQAILSVRDTGIGIAK
ref|ZP_01667455.1|      AVYEQLELVGDRERLYQLLVILLDNAVKYTPPPGHILITGVRQGSHILLTVEDSGQIPP
                             : . *:. *:  *::.**:***:*:*   *::: :      .   :  * * *  *:

ref|ZP_00739567.1|      EDIPKLFDRFYQGDKARS---T-SEGAGLGLSIANWIVEKHYGKISVESRW-GNGTCFEV
ref|NP_830390.1|        EDIPKLFDRFYQGDKARS---T-SEGAGLGLSIANWIVEKHYGKISVESKW-GDGTCFEV
ref|ZP_01696335.1|      EDREKIFDRFFQVSKSRTK----TESLGLGLSIAKWIVEKHSGKIRVDSK-LGEGTTFTI
ref|YP_001037228.1|     EHIDKIFDRFYRVDKSRSRNHG---GSGLGLAIAKCIVNEHKGTIDVFSE-VSRGTEFTV
RAAC01489               EHLERVFDRFYTVDTARS--RHGEAKGTGLGLSIAKWIVEAHGGRISIASEGIGKGTTVRV
ref|ZP_01667455.1|      EDLPRVFDRFYRGDKARSR---EKGGTGLGLAIAKWIVEKHGGKIWVESK-VGVGTKFSV
                         *.   ::*****:   ...:*:      ****:**: **: * * *  *.   ** . :
```

FIG. 149B

```
ref|ZP_00739567.1|      IFPKNQK----------------
ref|NP_830390.1|        IFPKNQK----------------
ref|ZP_01696335.1|      TFPKKKRKDA-------------
ref|YP_001037228.1|     SLP--------------------
RAAC01489               ELPLSPKRAAGSDEGDVTAKSEA
ref|ZP_01667455.1|      LLPV-------------------
                         :*
```

FIG. 150A

```
ref|ZP_01697157.1|      ---------------------------------IEVSNRLIEKDYDSRVRVNASGELR-Q
ref|ZP_02329946.1|      ------------------------------------------------------------
ref|YP_001212380.1|     ------------------------------------------------------------
RAAC02391               MIPFAIGLGVGLAIGALFALWQMSWFRSLRRYLLDAMDAIVQGRYDVRMYEYRSRPAEIA
ref|ZP_00539202.1|      -------------------YSSTKRFLRPIAEATEVLHELSHGNYKSRVYELTAPDESRD
ref|NP_693085.1|        -----------------------------------VDRLIEGNYSARFYNGNSP-EMEE ref|ZP_01697157.1|      LTKA-INNLAHNLKQQMNEIDENEQQLTAVLENMDSGVMLIQTSGRIMLVNRAMEEMTGL
ref|ZP_02329946.1|      --RT-INRMAENLQIQMQHIRENEYRLQGVLENMVSGVMMVDQRGTITLVNRSAEDILGY
ref|YP_001212380.1|     --RS-INYLARQLKNNIEDVIAEKNRIKAILSSMSDGVIAMDAWGRMILINPVVEELFRI
RAAC02391               IFRH-FNRMAERIQETLADLSQERDILRHILQNMTTGVIYLRSDGQVQMVNHAAERLFRR
ref|ZP_00539202.1|      LGKS-INLLARNLENASSGEAMQRARLESLIEYMGAGLMLIDEKGYVLLVNRTYREMFNI
ref|NP_693085.1|        LSVK-VNTLARNMSEIAIQEQMQSEQLTTIVDNMQSGLVLIDEKGYVHVVNRKFLEMFGE
                          .* :*...:.           :    :   ::. *  *::  :    *  : :*         :

ref|ZP_01697157.1|      SSGELIGKRH------IEAGKSFGLSQLIDRSLKTGERFRDEVHL---YYPKERILDAHI
ref|ZP_02329946.1|      SSHELLNKSY------LDAGFQLEFTALLADAIETHTRVREELML---HFPQEQILEVHV
ref|YP_001212380.1|     TMAASRGKNI------LRVIRNYDLEKLLNQALETGRCMQKQIQI---LAPEPRVFQVHV
RAAC02391               PVEQWKDRDH------WTVFRNYQLGSAIDHALLFGTPWSGEFQIRDGVTVAVRLVPISA
ref|ZP_00539202.1|      -YGQSNGQLY------YRVLPNEKMSQVIEDVYLTEKPNRKQSSVRFGLNS--RTFMVSA
ref|NP_693085.1|        EESNYRGHLY------YDVFENENVHETVQKTFLYEETVKKSFVHREGLNKIY--VEVVG
                          .:              .                                         .

ref|ZP_01697157.1|      APYVGESGELR-GVVAVLHDVTETRRLEQIRSEFVANVSHELKTPVTSVKGFAETLLDGA
ref|ZP_02329946.1|      SPIVQGDGQ-RKGVLVVLHDITAVRRLERIRSEFVANVSHELKTPVAAVKGFAETLMAGA
ref|YP_001212380.1|     IP-LQNSGAERGGVVALLRDITERKILQEMRSEFVANVSHELRTPLTSIRGFAETLLDGA
RAAC02391               APRMRNKADGRHDVLMLVNDVSEWRRLERMRSDFVANVSHELKTPIAAIRGFAETLLDGD
ref|ZP_00539202.1|      AP-IFGKNGRVQGTTVVFNDITEIKKLEQMRKDFVANVSHELKTPLTSIKGFAETLLDGA
ref|NP_693085.1|        AP-IFNERNMLKGAVLVLYDITELKKLEKMRKDFVANVSHELRTPITSIRGFAETLLDNN
                         *  :  .    ..  :. *::  :  *:.:*.:********:**.:::.:******:  .

ref|ZP_01697157.1|      MYDEATLREFLKIIYDESDRLHRLISDILDLSRIEQHRILLKMEQLNVVDVVAETVQTMR
ref|ZP_02329946.1|      LEDKEMARSFLQIIYDESDRLNRLIGDILELSKIESKRIPLQFSPVDVESIVENSIQMMK
ref|YP_001212380.1|     LEEPDTARRFLEIINSETERLSRLIDELLNLSRLESHKWVPKRQPVNMGELIKRAVAILQ
RAAC02391               VDE-EAREKFLRTIYEESLRMGNLVSDLLELSKLEASDSHVDPVAVDLYEVLVRAVDRVR
ref|ZP_00539202.1|      QDVPEIREQFLNIIHDESERMQTLVEDLLELSRLEQDNYQLETTIVDVTSLLHETATLLQ
ref|NP_693085.1|        ITDPAT-KEFMEIIYKESHRLQLLIEDLLALSRLEREDFRLLIDNYDVRQMVEEILPQLH
                         . *:. * .*: *:  *: ::* **::*         :: .:: .      ::

ref|ZP_01697157.1|      KRIEKK--QLELVLPQKRHVMMEADKDRLRQILLNLVTNAIAYTPDKGRIEI------SL
ref|ZP_02329946.1|      AEAEKK--HITLESCVENELYIEADEDRLRQILINLLSNGISYTPEGGRVSIGVEFVPSL
ref|YP_001212380.1|     PRAVEKNLAIKINLP-EDLPVVQGDPDMLSQVLLNLIENAVVYTQAGGEVSIS-------
RAAC02391               PVANEK--EITIELPREQRLHVWAEPDLLLQVFLNLLTNAIHYSPPKSRVCVT-------
ref|ZP_00539202.1|      RKATEK--QMTIHLETEEEVFIRADLNRLKQVVVNLVANALNYTPNGGNVWIS-------
ref|NP_693085.1|        QKAENK--NLTFDLEVPDQLTMRADKDRMKQVLINLIDNSIHYTPSGGDICLA-------
                         :*   :       : .: : *:.:**: *.:  *:      . ::

ref|ZP_01697157.1|      IER-ENE-LDLIVSDTGIGISEKDLPRIFERFYRVDKARSRQSGGTGLGLAIVKHLVESY
ref|ZP_02329946.1|      DDNPDNERMRIRISDTGIGIPEKDLPRIFERFYRVDKARSRSSGGTGLGLSIVKHL----
ref|YP_001212380.1|     -AAATQDEMKVDVKDNGIGIPPESLSRVFERFYRVDKARSREQGGTGLGLSIVKHIIDA-
RAAC02391               -WDVLVDRVKVHVKDNGIGIPKESLPRVFERFYRVHKDRSRASGGTGLGLAIVKHIVTAL
ref|ZP_00539202.1|      -LEDGEEAVMLRIKDDGIGIHPKEMQRIFERFYRVDKARSRNSGGTGLGLAIVKHII---
ref|NP_693085.1|        -ISEETDVIHFQVKDSGIGMDEKSQTRVFERFYRVDKARSRNTGGTGLGLAIVKHIV---
                          : :  .:.* ***:  :.  *:********.* ***  ******:****:
```

FIG. 150B

```
ref|ZP_01697157.1|      HGKIRVESEEGKGSTFIVTLPRTQTRP
ref|ZP_02329946.1|      ---------------------------
ref|YP_001212380.1|     ---------------------------
RAAC02391               GGEVGVESEEGKGSDFWFTLSRLDARP
ref|ZP_00539202.1|      ---------------------------
ref|NP_693085.1|        ---------------------------
```

FIG. 151A

```
ref|YP_147095.1|           ---QYLDLFIDESKEHLQAINERLLELEKTPEDMSVVNDIFRSAHTLKGMSATMGFEDLA
ref|YP_001125215.1|        ---QYLDIFIDESKEHLQTINERLLELEQTPGDMALVNEIFRSAHTLKGMSATMGFEDLA
ref|ZP_01171502.1|         ---QYLEVFIEESREHLQAINEHLLELEKNPADLKIINEIFRSAHTLKGMSATMGYEDLA
ref|ZP_01861001.1|         --NQYLEVFIEESKEHLQTCNEQLLELEKNPENLAIVNEIFRSAHTLKGMAATMGYEDLA
ref|YP_001486785.1|        --NQYLDIFLDESREHLQTCNEKLLDLEKNPTDLQLVNDIFRAAHTLKGMSATMGYADMA
RAAC02885                  MHDEYLEAFLAESMENVERLEAFCLTLEREGSKPDLLDEMFRAAHTLKGMSATMGFSKLA
                              :**: *: ** *:::     : * :   . :::::::****:**: ..:* ref|YP_147095.1|           NLTHQMENVLDGIRNRRLSVTPELLDVIFEAVDHLEAMISSIA-AGGDGTRDVRRTVEQL
ref|YP_001125215.1|        NLTHQLENVLDGIRNQRLIVTPELLDVVFQAVDHLEAMIISIA-SGGDGKRDVGETVEQL
ref|ZP_01171502.1|         RLTHQMENVLDAIRNQKIGVTPELLDTVFLAVDDLEAMVLSIS-EGGDGKRDVSTAVKQL
ref|ZP_01861001.1|         SLTHQMENVLDAIRNSKIQVSSLILDVVFMAVDDLEAMVMSIA-EGGDGKRDVTEIVKKL
ref|YP_001486785.1|        QLTHHLENMFDAIRNEQMIVTPESMDTMFEALDHLEAMVQSIA-EGGDGKRDVTEISKKL
RAAC02885                  ALTHRVEDLLGTLRDERVRLEPRHVDALLLAVDRMRARIQAIGVSAKEPDEPDDDAMDAL
                            ***::*:::.  :*: ::  :: :*..:: *:* :.* .. . :*.  .  .    . * ref|YP_147095.1|           KRIE--QGEMPNKQAAREEPP-----------LEHAYGEFEYHVLEQAKEQGFSVYEIRV
ref|YP_001125215.1|        KRIE--QGEMPNKPTAGEQLP-----------LEHTYGEFEYHVLQQAKDQGFSIYEIRV
ref|ZP_01171502.1|         ELIE--NGQTPLMESRQEAAAAAAAAEAEVPAELRSDYDEFERTVLSQSKEQGFDVFEISI
ref|ZP_01861001.1|         ALIE--KGESLDNLQAQSEAAAAVLEAEPSNTHTAQYDQFERTVIEQSKEQGFQCFEISV
ref|YP_001486785.1|        DVTGSHAEAAPSVETADVSAAS---------ANDLDYNEFERTVLDEAREQGFKCYELNV
RAAC02885                  AGAL--RGGADVGGTREEDSKP----------FANLSDWANRAAAEGKE----LYTVHI
                                                                .::    .   :.::       :  :  :

ref|YP_147095.1|           RLRDDCLLKAARVYMVFEQLNEVGEIVKATPPVE---MLEEEQFDR--EFLVTVVSKAPA
ref|YP_001125215.1|        RLRKDCMLKAARVYMVFEQLNEAGEIVKSTPPAD---MLEEEKFDQ--EFLVTVVSKTPA
ref|ZP_01171502.1|         SLREDCLLKAARVFMVFEVLEKSGEIIKSNPPVD---VLEEEQFDS--AFTVTLVTKEPK
ref|ZP_01861001.1|         SLREDCLLKAARVFMVFELNEGCEVIKSVPAVD---VLEEENFDQ--DFLVSIVSKDSQ
ref|YP_001486785.1|        TLSDACLLKAVRVYMIFERLNEAGEVVKTVPNAE---LLESEDFES--EFSISYLSKQPM
RAAC02885                  RLAPDCVMPGVRLAMAYQALKASAILMAAHPAEEN---VMAGQVEATEAFAAVMVAPGEI
                            *   *:: ..*: * :: *:  . :: : *   :    : ..:       *      ::

ref|YP_147095.1|           DELQKRLMGISEIDDVKVS-----------MLSSNEPSAES--EKAAAP---QQPAAME
ref|YP_001125215.1|        DELRMRLMSISEIDEVEIA-----------AVTVDEPSAKSGEQDDLEP---PVSTAIG
ref|ZP_01171502.1|         EEIQAKIMKVSEIEKAEIINIDL------------MPASPAEEEPAPAPGIIQPVEEP-
ref|ZP_01861001.1|         EDIKKKVMKVSEVHKVDVRLVDL-EKGKESDSQITEQPSASTEDATDRVTGKQANVASVP
ref|YP_001486785.1|        DEVKKIVMTISEVEQVEIS----------EVSAFEEASPAEKQEAKPEQEKEEVSVPAA
RAAC02885                  DRVRQGVLDVTDVSSCEVS----------------KVSESHSAPKEDAPRAEQGDAPIE
                            : ::    :: ::::.   ..:                                      :

ref|YP_147095.1|           QAAAVQAEAEAPEKQTAKQATKTIRVNIERLDRLMNLFEELVVDRGRLEQISRELNHAEL
ref|YP_001125215.1|        QVAATQTKAEAAEKLAAKQAGKTIRVNIERLDMLMNLFEELVVDRGRLEQISRDLNHPEL
ref|ZP_01171502.1|         ---KEESRNGAPAKQASSK---TIRVNIERLDILMNLFEELVIDRGRLEQISKELNNQEL
ref|ZP_01861001.1|         VVKKEEKKESAPSKQANTG-NKTIRVNIERLDILMNLFEELVIDRGRLEQISKELNHPEL
ref|YP_001486785.1|        KAPANDAPKANGNNVAAAGGTKTIRVNIDRLDSLMNLFEELVIDRGRLEQIAKELENNEL
RAAC02885                  PRVSRHANGSSPAG-ADLRRDATLRVPVRKVDALMNTLSDLVITKTRLATLVSSADDPAL
                                .        *:**  : ::* *  ..:: :  **   . .  :.     * ref|YP_147095.1|           TETVERMSRISSDLQTIILNMRMVPVETVFNRFPRMVRQLARELGKKVRLDIIGADTELD
ref|YP_001125215.1|        TETVERMSRISSDLQTIILNMRMVPVETVFNRFPRMVRQLARELGKKVRLDVIGAETELD
ref|ZP_01171502.1|         HETVERMSRISGDLQNIILNMRMVPVETVFNRFPRMVRQLARDLNKKINLEIVGAETELD
ref|ZP_01861001.1|         NETVERMSRISGDLQNIILNMRMVPVETVFNRFPRMIRQLARDLNKKIELEIIGAETELD
ref|YP_001486785.1|        TDTVERMTRISGDLQSIILNMRMVPVETVFNRFPRMIRQLTKELNKKIELIIEGAETELD
RAAC02885                  KEAVERLDRLTGDIQDGLMRLRMVPVETIFHRYPRMMRDLEHRLQREFDFVMTGLDTEMD
                            ::***: *:::.*:*   :::.*******:*:*:***:*:* :  *::  :  * :**:*
```

FIG. 151B

```
ref|YP_147095.1|        RTVIDEIGDPLVHLIRNALDHGIEAPDVRVARGKPEEGTVQLRAYHSGNHVFIEIEDDGA
ref|YP_001125215.1|     RTVIDEIGDPLVHLIRNALDHGIEAPDIRVACGKPEEGTVKLRAYHSGNHVFIEIEDDGA
ref|ZP_01171502.1|      RTVIDEIGDPLVHLIRNALDHGVETPEVRKANGKNEEGTVVLKAYHSGNHVFIELIDDGA
ref|ZP_01861001.1|      RTVIDEIGDPLVHLLRNAIDHGIEAPEIRRQNGKPEEGTVTLKAYHSGNHVFIEISDNGG
ref|YP_001486785.1|     RTVIDEIGDPLLHLLRNSLDHGIESPEERVKKGKPEKGTVLLKAYHSGNHVFIEVEDDCG
RAAC02885               RVVLEEMGEVIVHLLRNAVDHGLEPPEARESQGKPRRGIVRLAAYTASGHVYLEVSDDGR
                         *.*::*:*:   :::::***:*.*:  *    **  ..*  *  *    :...:.*: *:* ref|YP_147095.1|        GISREKVLQKAKSRGIVSPQAAEHLNDQQIYELIFAPGFSTAEQVSDISGRGVGLDVVKS
ref|YP_001125215.1|     GISREKVLQKAIDRGIVSABEEAAHLTDQQVYGLIFSPGFSTADRISDISGRGVGLDVVKS
ref|ZP_01171502.1|      GINRDKVLQKAVKNGIITEQAGASLTDKQVYELIFASGFSTADKISDVSGRGVGLDVVKS
ref|ZP_01861001.1|      GISREKVLKKAISQGIVTEESAAALTDRQVYELILASGFSTAETISDISGRGVGLDVVKA
ref|YP_001486785.1|     GINRKKVLEKALERGVITDREAETLEDHQIDSLIFAAGFSTADTISDISGRGVGLDVVKN
RAAC02885               GIDRGRVLETAVAKGWITPEEGAAMSDESVYALLFRPGFSTAERVSDISGRGVGLDAVRE
                        **.*  :**:.*   .*  ::  .  .  :  *..:   *::  .*****:  :**:********.*:

ref|YP_147095.1|        TIESLGGTVSVDSQPGKGSLFSIQLPLTLSIISVLLVQIAEETYAIPLSSIIETALVKKE
ref|YP_001125215.1|     TIQSLGGTVTVDSQPGKGSLFSIQLPLTLSIISVLLVQIAAETYAIPLSSIMETALVKKE
ref|ZP_01171502.1|      TIESLGGTVTIDSQEGKGSTFSIQLPLTLSIISVMLIEVQKEKYAIPLSSIIETAIIKKE
ref|ZP_01861001.1|      TIESLGGSITIDSVLGEGSTFSIQLPLTLSIISVMLVEVEKEKYAIPLSSIIETAIIKKE
ref|YP_001486785.1|     KLESLGGSVSINSTEGQGSLFSIQLPLTLSIISVLLVKLEEETFAIPISSIIETAVIKKS
RAAC02885               KVEALGGQIRLNSVLGAGTTFTIELPLTLAILSALLVSVRGQVFAIPTANVDEVRRVTRD
                        .:::***  :  ::*  *  *:  *:*:*****:*:*..:*:.:  :  :***  :.:  *.   :.:.

ref|YP_147095.1|        EIFSAHNQPVIDFRGKIVPLVRLKDVFAVP-GVADDGDAVAVVIVRKGEKLAALAVDSFI
ref|YP_001125215.1|     DIFSAHNQPVIDFRGKVVPLVRLKDVFSVP-NASDEGDAVAAVIVRKGEKLAALAVDSFI
ref|ZP_01171502.1|      DIMNAHNQKVIDFRGKVVPLLFLKDVFAVPVHLEEDGY-YSVVIVRKGDKMAGLVVDSFI
ref|ZP_01861001.1|      DILNAHNQKVIDFRGKVVPLLFLEDVFEIPKQEGDDFY--SVVIVRKGDRMAGLVVDSFI
ref|YP_001486785.1|     DILQTHDREVIDFRGFIVPVVYLKKQFHVP-NANELEEELHIIVVRKGDKLTAFVVDSFI
RAAC02885               DVRHVQERPVFQDSAGIVPIVDLAERLGLG--SRRDAYPQTAVVCRDGKRRLALVVDHVL
                        ::   .:::  *::   .:**::  * .:   :**:: * . :       :: *.*.:   .:.**  .:

ref|YP_147095.1|        GQQEVVLKSLGNYLSSVFAISGATILGDGRVALIIDCNAL----
ref|YP_001125215.1|     GQQEVVLKSLGNYLSSVFAISGATILGDGRVALIIDCNAL----
ref|ZP_01171502.1|      GQQEIVLKSLGGYLNDIFAISGATILGDGQVALIVDCNALIN--
ref|ZP_01861001.1|      GQQEVVLKSLGNYLTDVFAISGATILGDGQVALIVDCNAL----
ref|YP_001486785.1|     GQQEVVLKSLGDYLPNVFAISGATILGDGQVALIVDCNAL----
RAAC02885               DELEIVNKPLGRYLQGVREFAGATILGDGRVSLILDVRSIANPA
                        .:  *:* *.**  **   .:  :*********:*:**:*   .::
```

FIG. 152

```
ref|YP_001125206.1|    -MARILVVDDAAFMRMMIKDILTKNGHEVVAEAADGRQAIEKYKETRPDIVTMDITMPEM
ref|ZP_01696550.1|     ----ILIVDDAAFMRMMIKDILTKNGYDVVAEAGDGAQAIEKYKEHRPDLVTMDITMPEV
ref|ZP_01860990.1|     MANKILIVDDAAFMRMMIKDILTKNGFEVVGEAADGNQAVEKYKELSPDLVTMDITMPEK
ref|NP_243310.1|       --ARILIVDDASFMRMMIKDILTKNGYDVVGEAHDGEQAVEKYKELSPDLVTMDITMPEK
RAAC02876              -MANILVVDDAAFMRMMIKDILTKNGHVVVGEAADGAQAVERYQELRPDLVTMDITMPEV
ref|YP_001410204.1|    -MAKVLVVDDAAFMRMMLKDILTKAGHEVVGEAANGVEAVEKYKELKPDVVTMDITMPEM
                        :*:**:*:**** *. . :* :*:*:*:*   :******* ref|YP_001125206.1|    DGITALKEIKKIDSNAKVIMCSAMGQQAMVIDAIQAGAKDFVVKPFQADRVIEAINKTL-
ref|ZP_01696550.1|     DGISALKEIKKIDPDAKVIMCSAMGQQAMVIDAIQAGAKDFIVKPFQADRVIEAIQKTL-
ref|ZP_01860990.1|     DGIAALKEIKSLDANAKIIMCSAMGQQAMVIDAIQAGAKDFIVKPFQADRVIEAIQKAL-
ref|NP_243310.1|       DGIAALKDIRAIDPNAKVIMCSAMGQQAMVIDAIQAGAKDFIVKPFQADRVIDAIQKTL-
RAAC02876              DGIEAIKRIRQIDPNARIIVCSAMGQQAMVIEAIQAGAKDFIVKPFQADRVVEAVQKALR
ref|YP_001410204.1|    NGIDAIKEIKKFDPNATVIVCSAMGQQAMVIEAIQAGAKDFIVKPFQAARVIEAIQKVLK
                       :** *:* *: :*.:* :*:***********:*******:****** **::*::*.*
```

FIG 153

```
ref|ZP_01696550.1|        ----------------IEKYKEHRPDLVTMDITMPEVDGISALKEIKKIDPDAKVIMCSA
ref|NP_243310.1|          ----------------VEKYKELSPDLVTMDITMPEKDGIAALKDIRAIDPNAKVIMCSA
ref|ZP_01725653.1|        ----------------VEKYNELKPDLVTMDITMPEMDGIAALKAIKGSDPSATVIMCSA
ref|YP_753552.1|          ----------------IEKYKELKPDLVTMDITMPEMDGIAAVKEIKAVDPAARIIMCSA
ref|YP_001559801.1|       ----------------VERYNETKPDLVMMDITMPEMDGIQALKKIKSVDPNATVIMCSA
RAAC00987                 MKLSMKLPTVTKQWSVIRRYQECKPDLVTMDLTMPNVDGIQAIKKIRAIDPDA-------
                                          :.:*:*   ** :*: * *:* *:   ** * ref|ZP_01696550.1|        MGQQAMVIDAIQAGAKDFIVKPFQADRVIEAIQKTL-
ref|NP_243310.1|          MGQQAMVIDAIQAGAKDFIVKPFQADRVIDAIQKTL-
ref|ZP_01725653.1|        MGQQAMVIDAIQAGAKDFIVKPFQADRVIEAIQKAL-
ref|YP_753552.1|          MGQQAMVIDAIQAGAKDFIVKPFQPERVIEAVSKAL-
ref|YP_001559801.1|       MGQQAMVIESIQSGAKDFIVKPFQADRVLEAVKKAI-
RAAC00987                 --------------------KPFQIDRVISAVDKALN
                                              **** :**:.*:.*::
```

FIG. 154A

```
ref|YP_148131.1|         ----SVVGKLWFTILLLVSCVLFILSILLIKFLEDYYVQEAENDLTRLATKVAEVMHDYR
ref|YP_001126300.1|      ----SVVGKLWFTILLLVSCVLFILTILLIKFFEEYYVQEAENDLTRLATKVAEVMHDYR
ref|NP_390192.1|         ----SVVGKLWFTILSLVLIVLFILTVLLLEFIENYHVEEAENDLTQLANKVAVILENHE
ref|YP_001487274.1|      ----SVVGKLWLTILFLVLIVLSILTVLLLEFIENYHVEEAKSDLTQMANKVAVILESHD
ref|YP_079616.1|         ----SVVGKLWFTILLLVSFVLFILTFFLLEFIENYHVDEAEADLTKLASKVAVIMENHK
RAAC02162                MIPNSIVAKMWLTIVGMVFVIQALLSVLLQQVFNKYIVTREEASLTQLALTIESVLATAT
                             *:*.*:*:**:  :*   :  :*:..*  :.:: * *  . : .**::*  .:   ::

ref|YP_148131.1|         DEQLARSIAWTLVDNRTKAVIVADESHYWYSPGDAG-LDNMPLSSIRQDRDLRRVLTDGK
ref|YP_001126300.1|      DEQLARSIAWTLVDNRSKAIIVADESHYWYSPGEAD-LKDMPLSSIREDSDLRRVLTDQE
ref|NP_390192.1|         DQALARSITWELADNLTSIAIIQDEKNHWYSPNDKNRLSSITVEQIQHDKDLNKALKDHK
ref|YP_001487274.1|      DQSLARSITSELADKLTSIAIIQEDGLEWYSSEKDGKLPAITKKQIEADSDLNQALKDRK
ref|YP_079616.1|         DQETARSITWELADELTSIAVIKNENEYWYSPREHQKVASITLKDIKNDPDLNEALRKHQ
RAAC02162                DRSIKEQVASDIAKRVERATVVYGIP---YTANAALKAAYDAMTPAER-----QALSRGQ
                         *.    ..::   :...     ::     *:.          .    .     ..*  :

ref|YP_148131.1|         TMKKRLYMPERHPKEKLPRDMIIVGVPMSMPDGSRGAVFIYQSLEAIADATERTKELIFL
ref|YP_001126300.1|      TVKKRLYATEWEQNGKPQHDMIIVGVPMSMPDGSRGAVFIYQSLEAIADATEHTKELIFL
ref|NP_390192.1|         KVSKRTGLSDTDTDNE----RLIVGVPYEK-DGKKGMVFLSQSLLAVKDTTKHTTRYIFL
ref|YP_001487274.1|      KISKRAEPNAGNHKDE----RIVVGVPFEA-NGKKGMVFLSQSLLAVEQTTKHTTRYIFL
ref|YP_079616.1|         KVQKRTVIS--NQKND----QLIVGVPYGK-GEDEGMVFLSQSLLAVKDTTQHTTRYILF
RAAC02162                PVTLRGALGKVNRLTV------YVQIPSAR-SPQPGMLAVSQDTSVLDEPLREIRNMVLF
                          :  *    .         *  :*   ..  *  : :  *.    .:  :.. . .:::

ref|YP_148131.1|         AAFIAIVMTTFFAFFLSTRITAPLRKMRQAAFEMARGHFDMKVPILTNDEIGGLAMAFNQ
ref|YP_001126300.1|      AAFIAIVMTTFFAFFLSTRITAPLRKMRQAAFEVARGHFDTKVPILTNDEIGGLAMAFNQ
ref|NP_390192.1|         AAGIAIVLTTFFAFFLSSRVTYPLRKMREGAQDLAKGKFDTKIPILTQDBIGELATAFNQ
ref|YP_001487274.1|      AAGIAIVLTTIFAFFLSTRVTYPLRKMKEGAQDLAKGKFDTKIPILTQDEIGELAIAFNQ
ref|YP_079616.1|         AAAIAIVLTTIFAFFLSSRITYPLRKMRQGAQDLAKGKFDTKIPILTQDEIGELAIAFNQ
RAAC02162                DTVLGVILATGFAFVISKNLSRPLVDMTRAAEEMARGHYRQRVRVVTKDEVGRLGHTFNA
                         :  :.::::*  ***.:*..::  **  .*  ..*  ::*:*::   ::   ::*:**:*  *.  :**

ref|YP_148131.1|         MGRRLQFNINALNQEKEQLASILSSMADGVITFNRDGEILITNPPAERFLQAWYFEQGND
ref|YP_001126300.1|      MGRRLQFNINALNQEKEQLASILSSMADGVITFSREGEILITNPPAERFLQAWYFEQGND
ref|NP_390192.1|         MGRQLNFHINALNQEKEQLSNILSSMADGVITINIDGTILVTNPPAERFLQAWYYEQNMN
ref|YP_001487274.1|      MGKQLTFHITALNQEKEHLSNILSSMADGVITINIDGTILMTNPPAERFLQAWYYEQNMK
ref|YP_079616.1|         MGRQLKFHITALNQEKEHLSNILSSMADGVITLNIDGTILVTNPPAERFLQAWYYEQNMN
RAAC02162                LARQLAETIEQLSMEREGLQRILSSLQDGVVATDLDGRVVLANPPAKRHLRHLSVAERGI
                         :..:*   *   *.*:* *  ****: ***::  .  :*  :::::*****:*.*.:

ref|YP_148131.1|         AEAMAPLPPQVKELFARVVREEKEQSTEVTLQGRTWVILMTPLYGK--TMVRGAVAVLRD
ref|YP_001126300.1|      AETMAPLPPQVKELFARVVREEKEQSTEVTIQGRTWVILMTPLYGK--TMVRGAVAVLRD
ref|NP_390192.1|         IKEGDNLPPEAKELFQNAVSTEKEQMIEMTLQGRSWVLLMSPLYAE--SHVRGAVAVLRD
ref|YP_001487274.1|      IKDGDELPPEARELFHTAVSTEKEQMIEVTLQGRTWVLLMSPLYNQQD--VRGAVAVLRD
ref|YP_079616.1|         VKEGHELPPEARELFQNTVSTEKEQMIEMTLQGRTWVLLMSPLYNQ--SHVRGAVAVLRD
RAAC02162                VDE-ERLPDRLMSLWVRVREQQDAVYREDTWDGRTIGITMLPLYETDGTTLRGALCVLRD
                          .     **  .*:   .   :.     * * :**:   : * *      :*:.**** ref|YP_148131.1|         MTEERRLDKLRKDFIANVSHELRTPIAMLQGYSEAIIDDIAASEKEKKEMAKVIYDESLR
ref|YP_001126300.1|      MTEERRLDKLRKDFIANVSHELRTPIAMLQGYSEAIIDDIAASEEEKKEMAKVIYDESLR
ref|NP_390192.1|         MTEERRLDKLREDFIANVSHELRTPISMLQGYSEAIVDDIASSEEDRKEIAQIIYDESLR
ref|YP_001487274.1|      MTEERRLDKLRKDFIANVSHELRTPIAMLQGYSEAIIDDIAGSEEEKKEIAQIIYDESLR
ref|YP_079616.1|         MTEERRLDKLRKDFIANVSHELRTPISMLQGYSEAIVDDIASSEEEKKEIAQVIYDESLR
RAAC02162                ITEERRLDRLRKDFIANVSHELRTPLSMLQGYTEALLDDISDDPDMRRELTEIIHDETLR
                         :******:**:***************:.*****:**::***. . . ::*::::*:***
```

FIG. 154B

```
ref|YP_148131.1|        MGRLVNDLLDLARMEAGHIELEYEQVKLVPYIERVIRKFYGLAK-EKQIELTAEFRDRDI
ref|YP_001126300.1|     MGRLVNDLLDLARMEAGHIELQYEQVELVPYVERVIRKFYGLAK-EKQIELTAEFRDENI
ref|NP_390192.1|        MGRLVNDLLDLARMESGHTGLHYEKINVNEFLEKIIRKFSGVAKEK-NIALDHDISLTEE
ref|YP_001487274.1|     MGRLVNDLLDLARMEAGHITLNLESTDTEELTEKIYRKFLGIAKEK-QVDLTYDIQV-DE
ref|YP_079616.1|        MGRLVNDLLDLARMEAGHISLNVEPVELREFFERVFRKFYGVAGDK-NITLSHNLDLHEA
RAAC02162               MKRLVNDLLNLAQLESGQFKLHFARVDLTQVMRRVARKFQALASDE--DHLTFEVSIPDH
                        * *******:**::*:*:   *.    .      .::  ***  .:*   :    *  :.   :

ref|YP_148131.1|        EIAL--DPDRIEQVLTNLIDNAIRHTESGGTVRLIIEPSGDGVTIHVQDSGSGIPEEDLP
ref|YP_001126300.1|     EIAF--DPDRIEQVLTNLIDNAIRHTEAGGTVRLIIERSGDGVTIHVQDSGSGIPEEDLP
ref|NP_390192.1|        EFMF--DEDKMEQVFTNLIDNALRHTSAGGSVSISVHSVKDGLKIDIKDSGSGIPEEDLP
ref|YP_001487274.1|     PHFV-LDPDKMEQVFTNLIDNAIRHTPEGGEVHFSVQSVESGLKMDVKDSGSGIPEEDLP
ref|YP_079616.1|        KFVF--DPDKMEQVLTNLIDNAIRHTNAGGTVHVDVQSAESGLKIAVKDSGSGIPEEDLP
RAAC02162               PVMVDGDEDRLEQVFTNLLDNAFRHTAQG-TIRFELDIRHDYAYVRVADTGSGIPEEDVP
                            .   *  ::*:*:*:*   *    :  . :.   .    : :  *:*********:* ref|YP_148131.1|        FVFERFYKADKARTRGRSGTGLGLAIAKNIVEAHKGLITVHSKLNEGTTFSFYLPARGP-
ref|YP_001126300.1|     FVFERFYKADKARTRGRSGTGLGLAIAKNIVETHKGRITVHSKLNEGTTFSFYLPAHGPK
ref|NP_390192.1|        FIFERFYKADKARTRGRAGTGLGLAIVKNIVEAHNGSITVHSRIDKGTTFSFYIP-----
ref|YP_001487274.1|     FIFERFYKADKARTRGRSGTGLGLAIVKNIVEAHQGSIHAHSKAGTGTHFTFYIP-----
ref|YP_079616.1|        FIFERFYKADKARTRGKGGTGLGLAIVKNIVDAHNGSITVHSMLNEGTSFTFYIPRNKQD
RAAC02162               YIFERFYKADKARTRSRSGTGLGLAIARQLVIEHRGEILVESHLGEGTTFTVVLPLASPN
                        ::***********.::.******.:::*   *.* *  ..*   .  ** *:.  :* ref|YP_148131.1|        ---------
ref|YP_001126300.1|     E--------
ref|NP_390192.1|        ---------
ref|YP_001487274.1|     ---------
ref|YP_079616.1|        D--------
RAAC02162               DHGEGESVS
```

FIG. 155

```
ref|YP_955166.1|         -------ILGYLGPNWFASVMGTGIVATAGASLPVHVPGLRGFALVVWVLSALWLLVLIF
ref|YP_001133548.1|      ---DRPSILGYLGPNWFASVMGTGIVATAGASLPVHMPGLRGFATAVWVLSALWLVVLIL
ref|YP_907563.1|         -----VEVLGNIGPNWFASVMGTGIVAVAGATLPVHVVGLRAFTQVVWVIAAALLLALIV
ref|ZP_00997175.1|       ------------GPNWFAAVMGTGIVANAVATLPVQVPGLLAFARVVWALDVLLLALILA
ref|YP_829143.1|         --------------NWFASIMGTGIVATAAATLPLQFPGLRTGATVVWALASMLLILLTT
RAAC00012                MGGDGMHIIRQFGVNWFTTVMGIGIVAALTYTSPIHLPFQHAVGEILFIGVNVVFVFAFA
                                       ***::** ****    : *::.           ::        :

ref|YP_955166.1|         ATFAHWLRNPVVARSHVRNPQMAHFYGAAPMALLTVGSGALLVGRDLIGERAAVDLAWVL
ref|YP_001133548.1|      AMLAHWLRNPTVARGHVRNPTMAHFYGAAPMALLTVGSGALLVGEDLIGARLAVDLAWAL
ref|YP_907563.1|         LVGGHWLRHPTVARSHARNPQMAHFYGAAPMALMTVGADAVLAGGPLIGERLAVDLDWVL
ref|ZP_00997175.1|       ATAVHWVQHHDTARSHLDHPVMSHFYGAPAMALMTVGAGALLVGQPVVGRSVAIDMASAL
ref|YP_829143.1|         ATVVHWIRHRETAQSHHSHPVMAHFYGAPPMALLTVGAGTLLLGKDVLGEQLALGIDTVL
RAAC00012                MWILRWLLTPDAAIDDFRHPGRALFYGAFAMGINVVGNDYFLIGTHMMPKHTAIAISFAI
                          :*:     .*  .. :*   :  **** .*.: .**  .** *   ::    *:  .:

ref|YP_955166.1|         WTTGTLGALFTAMTIPYLMFTQYRVEPDAAFGGWLMPVVPPMVAAATGSLLIPHMAEGPG
ref|YP_001133548.1|      WVAGTLGGLFTAMTIPYLMFTQYRVEPDAAFGGWLMPVVPPMVAAATGSLLIPHMAEGVG
ref|YP_907563.1|         WTAGTIGGLFTAVSIPFLMFTQHRVEPDAAFGGWLMPVVPPMVSAATGALLLPHMPAGSG
ref|ZP_00997175.1|       WVSGTLLGLWTAVAVPVKAFTTHEVAPDAAFGGWLMPVVPPMVSAATGPLLLPHLPAGQW
ref|YP_829143.1|         WVAGTVLGLASAVAVPYLQFTRHQVTQDSAFGGWLMPVVPPMVSASTGALLLPYVPAGQA
RAAC00012                WLAGVAASVFSVIVVPYLLFTEHKVERDETVASWLIPLVPPIVAAATGTNLIPYAG-GPG
                         *  *.   .:  :.: :*    **  ..*   * :...**:*:***:*:*:**. *:*:   * ref|YP_955166.1|         -RATMLYGCYAMFGLSLVASLIIITMVWSRLAHYGTSGTARVPTLWIVLGPLGQSI-TVA
ref|YP_001133548.1|      -RATMLYGCYAMFGLSLVASLIIITMVWSRLAHFGTSGTARVPTLWIVLGPLGQSI-TVA
ref|YP_907563.1|         -RETMLYGCYAMFGLSFVASLNIIAMIWSRLVLYGTSGTARVPTLWIVLGPLGQSI-TAA
ref|ZP_00997175.1|       -QLAMQLACTMMFGLTLVASLIVITLIWGRLVHHKVGASAAVPTLWIVLGPLGQSV-TAA
ref|YP_829143.1|         -RLSLLMGCYAMFGLSLLASIIITTLIWNRLAGHKIGAAAAVPTLWIVLGPLGQSI-TAA
RAAC00012                AQFSMTAGIVALFGMTFFLFIMTSALVYSRLVFHRRLSGQEAPTLWIEIGPIGMAMGTFC
                         :  ::   .    :**:::.   :   ::::.**. .    .***** :**:* :: * .

ref|YP_955166.1|         GL-LGTDAAL-AVDA-----RLADGMAVFAVLYGVPVWGFAVLWI---ALAAALT---VR
ref|YP_001133548.1|      GL-LGTDAAL-AVDEN----LADGMRVFAVLYGVPVWGFAVLWI---GLATALT---VR
ref|YP_907563.1|         GL-LGAAAATGAVDHE-----LAETMQAFAIIFGVPVWGFAMLWI---ALSTALT---VR
ref|ZP_00997175.1|       HT-LGVAAPTVLPEP------FGSAFTAMGLVFGLPMWGFAMLW---LAIAATVT---LR
ref|YP_829143.1|         NL-LGGNAHLAVSGT------LAQAMEALGVLYGVPVLGFALMW---AALATAIT---IR
RAAC00012                GIPLNAPHVFGPYFG---------GLRDLGAVFSIAMWGVGVWWILLSALYTFLH---LT
                             *.        :   :.   ::.:.:  *..: *       .: :     :

ref|YP_955166.1|         TLR---RGMPFALTWWSLTFPVGTFVTGTAQLALHTGL--PAFRYAAAVAYLGLLCTWL-
ref|YP_001133548.1|      TLR---RGMPFALTWWSLTFPVGTFVTGTTQLAVHTSL--PAFRYAAAIAYIGLLCTWL-
ref|YP_907563.1|         TLR---RGMPFALTWWSLTFPVGTFVTGTSQLALHTHL--PAFRVAAAAAYAGLLATWV-
ref|ZP_00997175.1|       TAR---SGLPFTLGWWSFTFPAGTVVTGTSGLAAATGA--TFLQFTALALALYAGLVLAWA-
ref|YP_829143.1|         TAR---RGLPFSLTWWSFTFPIGTCVTGLTGLAAHTHL--AVFDAMAVAGYTLLVAAWI-
RAAC00012                PKG---DGLPFHLGWWSYVFPIGSFTNGTYALHRLLGH-----PFFAVAGLVQLGILWLC
                         .      *:**  *  *  .  *:    .. * *    *    *    * * ref|YP_955166.1|         --LVAVRTVRG--GLRGGL-----------------
ref|YP_001133548.1|      --LVAVRTLRV--GIGRG-----------------
ref|YP_907563.1|         --LVAIRTVRG--SLRGNLL--------------
ref|ZP_00997175.1|       --TVAFRTARG--AWDGRLLR--------------
ref|YP_829143.1|         --IVAARTFHGS-ILQGTLFQ--------------
RAAC00012                FAIVIVRTVHG--VAAGHLIQWRRDHAHRHELKARRA
```

FIG. 156A

```
emb|CAG29823.1|      MTGGEVIRPT GGSGRRGRLR VFIGAAPGVG KTYTMLREAR RLREEGTDVV IGWVETHGRP
ref|NP_923516.1|     ---------- -----RGRLK LYLGYTPGVG KTVRMLQEAR RLRRRGVDLV VGWVETHGRP
ref|ZP_02329377.1|   ---------- -----RGRLK IYLGAVSGSG KTYHMLREAQ SLKENGIDVV LCAVSTLNRP
ref|ZP_02329377.1|   ---------- ----RRGVFK VYIGAAPGVG KTYTMLREGN DLARMGIDVI VGLLETHGRR
ref|ZP_02329377.1|   ---------- ------GRLK IYLGAVSGSG KTYHMLREAQ SLKENGIDVV LCAVSTLNRP
RAAC02761            MTGGEVIRPT GGSGRRGRLR VFIGAAPGVG KTYTMLREAR RLREEGTDVV IGWVETHGRP
Clustal Consensus            *  ::  :::* ..*  :*..  * . ** ::  :  :.* .* emb|CAG29823.1|      ATEKLLEGLE VIPPRVLKVG QATFEEPDLD AIVARRPEVC VIDELAHTNP PGAMHEKRYE
ref|NP_923516.1|     DTEALLADLE VMAPRQVAYQ GVIIPELDLE AILQRRPATV LIDELAHTNA PGSRHRKRYE
ref|ZP_02329377.1|   ETARQASGLE TIPSIDWTKD GVIQQDLNLV ALVERNPEVV LVDGLAHRNR QGALFPTRLG
ref|ZP_02329377.1|   ETAEQLGNLG MIPRRKIDYR GTTLEEMDTD AIIERAPDVV LVDELAHTNV PGSRHNKRFE
ref|ZP_02329377.1|   ETARQASGLE TIPSIDWTKD GVIQQDLNLV ALVERNPEVV LVDGLAHRNR QGALFPTRLG
RAAC02761            ATEKLLEGLE VIPPRVLKVG QATFEEPDLD AIVARRPEVC VIDELAHTNP PGAMHEKRYE
Clustal Consensus     *      .*   :.        .   : :  *:: * * .   ::* *** *    *:. .* emb|CAG29823.1|      DVMYLLDRGI SVMTAFNIQH LESVRDEVQQ QLGIRVREVV PEWFLREADE VTVIDVTPET
ref|NP_923516.1|     DVEVLLDAGV SVMSAMNIQH LESVAEAAGR LIGAVVHETV PDRLLRSAFE VQLVDASPEA
ref|ZP_02329377.1|   DISFLLEKGI SVITTVNVYE LEGVRELARK LAGVEVKTTV PSGTLEMADE VRLIDVTPET
ref|ZP_02329377.1|   DVLDILNAGI SVITTVNVQH LESLNDAVEQ ITGVRVRETV PDSILWMADE VELIDVPPQT
ref|ZP_02329377.1|   DISFLLEKGI SVITTVNVYE LEGVRELARK LAGVEVKTTV PSGTLEMADE VRLIDVTPET
RAAC02761            DVMYLLDRGI SVMTAFNIQH LESVRDEVQQ QLGIRVREVV PEWFLREADE VTVIDVTPET
Clustal Consensus    *:  :*: *: **:::.*: . **.: :  . :    *   *: .* *.   * *:* * ::*..*::

emb|CAG29823.1|      LRQRLRDGEI YPPEKVDAAL QNFFRVDRLA WLRQMSLRAV ADDVDERLEH SYERRAIPGP
ref|NP_923516.1|     VLERLQRG-- -DAARYIPPG SPFLRRSTLV YLRELALRAV AEVVDADILS --GKNGVAGP
ref|ZP_02329377.1|   ILKRLEEGNL P-----GQKE HHLFLKGNIG VLRELALRLV AEDVNGSLEK YRKSKGLSGP
ref|ZP_02329377.1|   LRQRMKEGRI YSMEKVEQAL GHFFKIGNLI ALRELALREI ADDVDERLES WERKESLRGP
ref|ZP_02329377.1|   ILKRLEEGNL P-----GQKE HHLFLKGNIG VLRELALRLV AEDVNGSLEK YRKSKGLSGP
RAAC02761            LRQRLRDGEI YPPEKVDAAL QNFFRVDRLA WLRQMSLRAV ADDVDERLEH SYERRAIPGP
Clustal Consensus    : :*:. *              ::  . :  **::::** *: *:   :      ..: **

emb|CAG29823.1|      VGAKEVVLVC VSHPDRAATL IERGRRMAMR MKGDLHVVYA AETDEDRMTE RARAEVDELR
ref|NP_923516.1|     AGVRERVLAA VSTNPASARL IRRGARIAER LDAELFVAYV ETG--RPLAP PEAQTLQEHR
ref|ZP_02329377.1|   SGAGERILVS TQYHWNGSIY VRRGQQIANR LNGDLYVICF QHTG-KPLSK EQAAFKRSLK
ref|ZP_02329377.1|   WRREETIFVC VKLNDHAERI IRRGFRIAFR LKARWHVAYL HHG----SGM EDEARLKELK
ref|ZP_02329377.1|   SGAGERILVS TQYHWNGSIY VRRGQQIANR LNGDLYVICF QHTG-KPLSK EQAAFKRSLK
RAAC02761            VGAKEVVLVC VSHPDRAATL IERGRRMAMR MKGDLHVVYA AETDEDRMTE RARAEVDELR
Clustal Consensus       * ::.. ..   .         :.** ::* *  :..  .*                . :

emb|CAG29823.1|      RLAEFHGAEW VLEP-KRDRP VGEVILRVAR RVNATQVVLG QPRKGASPRR LMAWHHPVQY
ref|NP_923516.1|     AATEAAAGEF VQLQ-NRD-- VAGALIDFAL QKNITQVIVG ESLR--SPAE ELVRGSVINT
ref|ZP_02329377.1|   KLVDKIGAVF VELPFPGRRK LADSLLDYAM KNSVTRIVLG HSKH--TRIQ ELWQGSIIND
ref|ZP_02329377.1|   GLTERIGGSF EVITGOGKKD PADLLLAKAN EYNSTQMILG KSCS--PSWR DRWQGSLVKR
ref|ZP_02329377.1|   KLVDKIGAVF VELPFPGRRK LADSLLDYAM KNSVTRIVLG HSKH--TRIQ ELWQGSIIND
RAAC02761            RLAEFHGAEW VLEP-KRDRP VGEVILRVAR RVNATQVVLG QPRKGASPRR LMAWHHPVQY
Clustal Consensus     .:   .. :           .  ::  *     . .*:::*  ..    .        ::

emb|CAG29823.1|      LLKHLQYVDL RVVG------ -------WRPL SPAAREQRNW ASERVVRE-- RKLP--GKLT
ref|NP_923516.1|     LLRTTSNIDV LIVGE----- -AESSMVGPL TPVAAQPPFA VGCLLVGADS RRAHGCGRHK
ref|ZP_02329377.1|   ILRKMTRTDL FVVADRAERD GERILPAKRK VGTKKAELYR RHSKQEMQKE IEKIRRGVFK
ref|ZP_02329377.1|   LLRGARHMDV LVV------- ---------- ---------- ---------- ----------
ref|ZP_02329377.1|   ILRKMTRTDL FVVA------ ---------- ---------- ---------- ----------
RAAC02761            LLKHLQYVDL RVVG------ ------WRPL SPAAREQRNW ASERVVRE-- RKLP--GKLT
Clustal Consensus    :*:      *:        :*
```

FIG. 156B

```
emb|CAG29823.1|         LYIGAAPGVG  KTYRMLQDAH  DWKVRGIDVV  ICLIETHGRP  ETEAQIGDLE  RIPKRRIEYG
ref|NP_923516.1|        IYLGAAPGVG  KTFAMLQEAH  HLHASGIDVV  CGVIETHGRA  ETAALIENLE  VVPKRAIGYQ
ref|ZP_02329377.1|      VYIGAAPGVG  KTYTMLREGN  DLARMGIDVI  VGLLETHGRR  ETAEQLGNLG  MIPRRKIDYR
ref|ZP_02329377.1|      ----------  ----------  ----------  ----------  ----------  ----------
ref|ZP_02329377.1|      ----------  ----------  ----------  ----------  ----------  ----------

RAAC02761               LYIGAAPGVG  KTYRMLQDAH  DWKVRGIDVV  IGLIETHGRP  ETEAQIGDLE  RIPKRRIEYG
Clustal Consensus emb|CAG29823.1|         GKVYEEPDLA  AILARRPQVV  LMDELAHTNA  PGSMFKKRYQ  DILYLLEHGV  DVVSAVNVQH
ref|NP_923516.1|        GRTFLELDVE  AVLRRRPAVV  LVDELAHTNI  AGAGNTKRFQ  DVEVLLGAGI  DVVSTLNIQH
ref|ZP_02329377.1|      GTTLERMDTD  AIIERAPDVV  LVDELAHTNV  PGSRHNKRFE  DVLDILNAGI  SVITTVNVQH
ref|ZP_02329377.1|      ----------  ----------  ----------  ----------  ----------  ----------
ref|ZP_02329377.1|      ----------  ----------  ----------  ----------  ----------  ----------
RAAC02761               GKVYEEPDLA  AILARRPQVV  LMDELAHTNA  PGSMFKKRYQ  DILYLLEHGV  DVVSAVNVQH
Clustal Consensus emb|CAG29823.1|         LESLKDRVEH  ITGATIRERV  PDWFVKLASE  VKLIDVSPET  LVERLLEGKI  YPPEKVEQAL
ref|NP_923516.1|        LESLNTLVER  TTGVKVRETL  PDLVVEAADE  VVLVDLPTGE  LTQRLREGKI  YAQAKVEQAL
ref|ZP_02329377.1|      LESLNDAVEQ  ITGVRVRETV  PDSILWMADE  VELIDVPPQT  LRQRMKEGRI  YSMEKVEQAL
ref|ZP_02329377.1|      ----------  ----------  ----------  ----------  ----------  ----------
ref|ZP_02329377.1|      ----------  ----------  ----------  ----------  ----------  ----------
RAAC02761               LESLKDRVEH  ITGATIRERV  PDWFVKLASE  VKLIDVSPET  LVERLLEGKI  YPPEKVEQAL
Clustal Consensus emb|CAG29823.1|         SNFFQLAHLA  ALREIALREV  ADVVDGRLAP  PPPADPE---  -----RILVC  VNYRPHSEAL
ref|NP_923516.1|        ANFFRPENLS  ALRELALREV  ADDCTTRKLE  EAAIGPGG--  -----RVLVC  INLRPNAEQL
ref|ZP_02329377.1|      GHFFKIGNLI  ALRELALREI  ADDVDERLES  WERKESLRGP  WRREETIFVC  VKLNDHAERI
ref|ZP_02329377.1|      ----------  ----------  ----------  ----------  ----------  ----------
ref|ZP_02329377.1|      ----------  ----------  ----------  ----------  ----------  ----------
RAAC02761               SNFFQLAHLA  ALREIALREV  ADVVDGRLAP  PPPADPE---  -----RILVC  VNYRPHSEAL
Clustal Consensus emb|CAG29823.1|         IRRGWRIADR  LQAKLYVLVV  QTEFPLSSQS  ERDFAAVRDL  AEQFGAEFLL  RPALHKSVGQ
ref|NP_923516.1|        IRRGARIASR  LSAPLVVAHI  GAHD--DGPT  ARAVERLGEL  TRQLGGEFIE  RPAAANQVPE
ref|ZP_02329377.1|      IRRGFRIAFR  LKARWHVAYL  HHGSGMEDEA  RLKELKGLTE  RLGGSFEVIT  GQGKKDPADL
ref|ZP_02329377.1|      ----------  ----------  ----------  ----------  ----------  ----------
ref|ZP_02329377.1|      ----------  ----------  ----------  ----------  ----------  ----------
RAAC02761               IRRGWRIADR  LQAKLYVLVV  QTEFPLSSQS  ERDFAAVRDL  AEQFGAEFLL  RPALHKSVGQ
Clustal Consensus emb|CAG29823.1|         VIVETAESES  VSQIVMGQPL  NRGLGARFAH  RPITYVLNRA  EFVDLHIVAY  AGRWSQPSA
ref|NP_923516.1|        QIDALAHEQG  VTLLVMGESR  RSRWEKLLHG  CVIEQVVRRV  RNLDVLIV--  ---------
ref|ZP_02329377.1|      LLAKANEYNS  TQMILGKSCS  PSWRDRWQGS  LVKRLLRGAR  HMDVLVV---  ---------
ref|ZP_02329377.1|      ----------  ----------  ----------  ----------  ----------  ---------
ref|ZP_02329377.1|      ----------  ----------  ----------  ----------  ----------  ---------
RAAC02761               VIVETAESES  VSQIVMGQPL  NRGLGARFAH  RPITYVLNRA  EFVDLHIVAY  AGRWSQPSA
Clustal Consensus
```

FIG. 157

```
ref|YP_897521.1|        MEGKILIVDDQYGIRVLLHEVFQKEGYQTFQAANGFQALDIVKKDNPDLVVLDMKIPGMD
ref|ZP_00744427.1|      MEGKILIVDDQYGIRVLLHEVFQKEGYQTFQAANGFQALDIVKKDNPDLVVLDMKIPGMD
ref|YP_001647908.1|     MEGKILIVDDQYGIRVLLHEVFQKEGYQTFQAANGFQALDIVKKDNPDLVVLDMKIPGMD
ref|YP_001377039.1|     MEGKILIVDDQYGIRVLLHEVFQKEGYQTFQAANGFQALDIVKKDNPDLVILDMKIPGMD
ref|NP_244654.1|        ---KILVVDDQYGIRVLLNEILQKDGYQMFQAANGIQALAIVEEETPDLVLLDMKIPGMD
RAAC00477               MAYKVLVVDDQFGIRVLLHEVLQREGYEVFQASNGPSALSIVEREQPDLVLLDMKIPGMD
                           *:**:****:*::*::: *: . :.: :******* ref|YP_897521.1|        GIEILKHVKEIDESIKVILMTAYGELDMIQEAKDLGALMHFAKPFDIDEIRQAVRNELAV
ref|ZP_00744427.1|      GIEILKHVKEIDESIKVILMTAYGELDMIQEAKDLGALMHFAKPFDIDEIRQAVRNELAV
ref|YP_001647908.1|     GIEILKHVKEIDESIKVILMTAYGELDMIQEAKDLGALMHFAKPFDIDEIRQAVRDQLAV
ref|YP_001377039.1|     GIEILKHVKEINADIKVILMTAYGELDMIQEAKDLGALMHFAKPFDIDEIRQAVRNEI--
ref|NP_244654.1|        GLEILRRIKDMNPNIEVIMMTAYGELNMINEAMQLGAVTHFAKPFDIDDVRAVIAENMKS
RAAC00477               GLEILRNLRKLGVDAKVIMMTAYGELDLIHEAMEMGAVAHFTKPFDIDELRRTVREHLEA
                        *:***:..:.:.. . :**:*******:*:** ::**: **:******::*  .: :.:

ref|YP_897521.1|        EA---
ref|ZP_00744427.1|      EA---
ref|YP_001647908.1|     EA---
ref|YP_001377039.1|     -----
ref|NP_244654.1|        -----
RAAC00477               RAQAE
```

FIG. 158A

```
ref|YP_848463.1|      MRFFQSVQFKLVIMYLLLIIVAMQVIGAYFVRELEGQLEKNFQNSITNSITLLDYNAREE
ref|ZP_01695448.1|    ---FQSIHFKFVLIYILLIVVAMEIIGVYFINKLENQLETNFKKSIYDQVNVLEYSIEDL
ref|ZP_02169265.1|    ---FKSIHVKIVTIYVLLILIAMQVIGVYFTQQLEDQLVENFYETLDERANLLAYNVQQE
ref|ZP_00539458.1|    ---FKSIQWKLVVIYALLILVAMQVIGVYFVRSLEKQYITNFSKSVEDRAGLVAYNVGKE
ref|NP_694373.1|      ---FRSIQLKFIIIYILLLIIAVQVIGSFFTDRLNEELTRNFKTTVGERVEMLSHNLEQA
RAAC00019             MMRFRSLRVKLVMVYTLLILFAVELIGAYFVQALTSSLVRNQAQTARTQAQLMATLIAPE
                         *:*::*::  :*  **::.*:::**  :*   *   . *   :    ::

ref|YP_848463.1|      IIKNSDNSV----KLQNDIRELLVDFSR---ASSNLIEVRIVDEK-GKILGTSNLNNQGI
ref|ZP_01695448.1|    LTKKQNQAA----DITLKVRKVLGDFK-----STDVSEIRLIDAHSGVILGTS-SNDQSI
ref|ZP_02169265.1|    MSRDEDEEE---QSLRVRTDNVLGELFN-----MENAQARVVDQF-SNVVTVTNPEEDIY
ref|ZP_00539458.1|    FDKTGDDEAS-KRQLSESLGQLLSEFSSGSTSRNDILEVQIIDQD-SIIQATSDEDNQSA
ref|NP_694373.1|      FARDRSEESGTIESLEEEIRRIINDINR----GNASTTINVVDNQ-SRVRGTNVLDDQNQ
RAAC00019             LAPGARVSN----SAVSNLLQSVPQFLN--------GTVYVLNQS---GYVMYTTAGGAL
                      :               .       . : ::              :::

ref|YP_848463.1|      VGQKSNDPLVKRTLSLGTTSEDKIYKDESNKNNRVWVNVSSIKNKGEVIGAIYLVADIES
ref|ZP_01695448.1|    VGQKTTEDIVKSVRVTGQP-EDQIYLDKQTG-DRMWVLASPIKANGELIGIIYLVSKIET
ref|ZP_02169265.1|    IGQRTTNFRIIRALG-GSTEEAVLRNENTGHRTRVLAVPVE-TEENQVVGAIYIEASMEE
ref|ZP_00539458.1|    VGQRATNSLIKKAQATSSSRVDTVLDPTTEDKIRIFAVPVTSERTGATTGMIYVRASMES
ref|NP_694373.1|      IGQKLAHPMVRDALLFNSTDDSIFYEKDTDSRVYVYVKPILGEDN-MAVGAIFYKSSLEE
RAAC00019             VGQKRIDSVATQALLHHTFAQSVRYDP--LSKSHLLAVAVPVTLHGTYLGVLEYVLSIQS
                      :**:   .         .            : .              *   :      .::

ref|YP_848463.1|      VYKQVDDITNIFITGTLIAMVITAILGILLSRTITKPIVEMKRQAYAMARGNYSRKVKVY
ref|ZP_01695448.1|    VYRQVQAINQIFMTGTVIAVLVTALLGIITARTISKPLSEIRKQAMAMARGNFARKVKVI
ref|ZP_02169265.1|    IYEQMAQTNQILLTGTMISLVLTAALGIFLSRTITRPIVEMRRQADFLGKGDFSQNVEVY
ref|ZP_00539458.1|    IYSQMQQVTRILATGTVIALVITSILGVLLSRTITRPISDMRRQAIEMRRGNFSRKVKVY
ref|NP_694373.1|      VYGQIEDINNIFLQGSILAITISAIIGILVARTITKPIMEMREQALIMANGDFTQKVNVY
RAAC00019             TYETIHQATTIFYTGSIAVLAIVMILGAIVARALTRPVMEVTRQAEVMARGDFSQRLEAM
                       *    .  *:  *::   : :     :*  :  :*::::*:  ::  .**    : .*::::.:.

ref|YP_848463.1|      GVDEIGELADSFNTLTKRVQEAQAMTEGERRKLSSVLAYMTDGVIATDRRGKVILINTPA
ref|ZP_01695448.1|    GNDEIGQLAYSFNHMTKKLQEAQASTEGERRKLDSILTHMTDGVIATDRRGRIILINEPA
ref|ZP_02169265.1|    GDDEIGQLSATFNELTNKLEEAHATTEGERRKLSSVLTHMTDGVIATDREGQIILMNRRA
ref|ZP_00539458.1|    SDDEIGQLARSFNELTDELLEANATTEAERRKLTSVLENMTDGVIATDRTLRVILMNDQA
ref|NP_694373.1|      GRDEIGQLAETFNDLNSRLKHSYATIEEERRKLSSILANMSDGVIATDNDGSVTLMNDAA
RAAC00019             SNDEIGDLVASINHLADELEEAIAANRLEQERLRAVITSMGEGVIVLDSSGQVLMMNRAA
                      . ****:*   ::*   ..:  .:  *    . *::.*  :::   * :***. *     : ::*   * ref|YP_848463.1|      EKML----RVK---HESANGRSIIDVLDIGDSYQFEDLMEVDGSLTMDRSTLDKPYILRA
ref|ZP_01695448.1|    AEML----DVS---RETVLSQPLISVLKIENEHKFDDLLTEQDSVILDFSTEEEPYILRA
ref|ZP_02169265.1|    EELT----GYS---QEEAIGYDLVGMLNLAHFMKLSDLYNMDDPILLDFEHHDEELILEA
ref|ZP_00539458.1|    KDIV----GVD---ESGIVGTNLKDLLALGDDFMIPEDGTMP-PRLLDFSSEDELFLVRA
ref|NP_694373.1|      AKLIGE-------NPEDLIGDSVIDVLHLEGKEIDLSELHSNGSMIIDFSNEDTPFLIRA
RAAC00019             RQMLS----------QAAGGEEEAIRQLELDRLMQG--------DVATGVREVRVIGNT
                       .:          .     :    :                :      :      : .:

ref|YP_848463.1|      NFSVI---QRET---GFNNGVIAVLHDITDQEKVDQERRDFVSNVSHELRTPLTSMHSYL
ref|ZP_01695448.1|    NFSVI---QNEA---GFVSGLITVLHDVTEQEKIDMERREFVANVSHELRTPLTTMRSYL
ref|ZP_02169265.1|    NFSVI---EKEN---GRKNGLIAVLHDVTEQERIEQERREFVANVSHELRTPLTSMKSYL
ref|ZP_00539458.1|    FFSPV---KKHS---GPITGMIIVLHDVTEQEQVEQDRREFVANVSHELRTPLTTMRSYL
ref|NP_694373.1|      NFSTVVD-EEEE-----VTGFITVISDVTEQQKMEQERRFVSNVSHELRTPLTTMKSYL
RAAC00019             IFHVILTSVQRR---GQVDGYVAVVRDVTEQEKLDQARRDFVSNVSHELRTPLTTVKSYL
                       *   :      ..         *   *:   *:*:*:::::    **:**:***********:::***
```

FIG. 158B

```
ref|YP_848463.1|        EALSDGAWEDKEIAPRFLEVTQNET--------ERMIRLVNDLLKLSRMDGGREHLE-KS
ref|ZP_01695448.1|      EALTDGAWKDEKIAPQFLGVTQNET--------ERMIRLVNDLLKLSKMDSKDEHLN-KE
ref|ZP_02169265.1|      EALLDGAVNDSDVAPQFLQVTSNET--------DRMIRLVNDLLQLSKMDARDDHML-MA
ref|ZP_00539458.1|      EALAEGAYQDEELAPRFLETTQNET--------ERMIRLVTDLLQLSKMDSKEYKMN-KV
ref|NP_694373.1|        EALSDGAWENKEIAPRFLDVTQKET--------NRMIRMVNDLLQLSKMDSDELPMH-KQ
RAAC00019               EVMRDLGDDEAETKREFLEVIARET--------DRMVRLTRDLLLLSGLDRGGPRSVEMR
                        *.:  :  . ..:  .    .  .     .         :**:*:. *  :* ref|YP_848463.1|        FVNFTD-FFNHIIDRFEMM-KKETIMFKRHIP-KEPVIIEIDEDKVMQVLDNIISNANKY
ref|ZP_01695448.1|      WVNFVE-FFHHVIDRFEM-AKQQNVTFKRKLP-NTEIFVEIDEDKMTQVLYNIISNALKY
ref|ZP_02169265.1|      EVNIVN-MIHHVIDRFEMSNKQENIQFRRRLPD-VPLSVMGDRDKLVQLLDNMVSNAVKY
ref|ZP_00539458.1|      RFDYIQ-FLNDILDRHDM-TKPERIRFRRKI-MKRKVYIRGDQDKLIQVADNILTNAIKY
ref|NP_694373.1|        REEFTS-YLYQVLDRYEMN-KPESIHMEKNIPNTK-AYVWMDRDKITQVLDNVITNAIKY
RAAC00019               AIPVHG-LLEGVVERFQLQAAKQELSLRVHLPQRRDVCVYGDEDMVNRVLDNVLSNALKY
                                 :  :::*.::      : : :. .:     :   *.*  : ::   *:::** **

ref|YP_848463.1|        SPDGGRISFYLKKFEDEIEISIADEGLGVPEEDLANVFDRFFRVDKARSREMGGTGLGLA
ref|ZP_01695448.1|      SPEGGQITFKLRELNEKIEVSISDQGVGIPKENVKKIFERFYRVDKARSRKLGGTGLGLA
ref|ZP_02169265.1|      SPEGGVITITLKQEKERLIVSVKDEGVGIPKENLPHVFDRFYRVDKARSRSLGGTGLGLA
ref|ZP_00539458.1|      SPEGGTITVRTMLRAKRIVISIKDEGVGIPKANLQKIFERFYRVDKARARKIGGTGLGLS
ref|NP_694373.1|        SPDGGKIRVKLDIRRHYLLVSIQDQGMGIAYDKLDKIFERFYRVDKARNRKLGGTGLGLA
RAAC00019               TPPGGRIEVRADVTAQHVTFIISDTGIGIPPEDLPHVFERFYRVEKGRSRRGGGTGLGLA
                        :* ** *      .     . : .:   * *:*:.   .: ::*:**:**:*.* *  *******:

ref|YP_848463.1|        IAREVIEAHGGRIWAERNKSKGTVIKFTL--------
ref|ZP_01695448.1|      IAKEMVEMHGGSIWASSKEGKGTTIYFTLPYEPAQED
ref|ZP_02169265.1|      IAKEIVEVHGGHIWVSSDWGKGTTFFFSL--------
ref|ZP_00539458.1|      IAKDVVSAHGGDIWAESEWGRGTTIYFTL--------
ref|NP_694373.1|        ITKELVEAHHGQIWAQSSEGKGTTILFTL--------
RAAC00019               LAREMVERMGGEIRMESEPQRGTTVYVTLRRAEEDAV
                        :::::.     * *    .  .  :**..  ..:*
```

FIG. 159

```
ref|ZP_01169692.1|      MDKKILVVDDEKPIADILQFNLKKEGYEVHCAYDGNEALEKVEEVKPDLILLDIMLPQRD
ref|ZP_01695449.1|      MDKKILVVDDEKPIADILQFNLTKEGYTVYCAYDGEEALEKVEEVQPDLIVLDIMLPKRD
ref|YP_001127497.1|     MEKRILVVDDEKPIADILQFNLQKEGYEVICAYDGEEALQKVEETMPDLILLDIMLPLKD
ref|YP_149327.1|        MEKRILVVDDEKPIADILQFNLQKEGYEVICAYDGEEALQKVEETMPDLILLDIMLPLKD
ref|YP_534941.1|        ----ILVVDDEKPISDIVKFNLTKEGYDVYTAYDGEEALQQVKEVEPDLILLDLMLPKID
RAAC00020               MPAHILVVEDEEPIANILRFALEREGYRVSCAYDGAEALERWRALQPDLILLDVMLPEVD
                            **::**::*::* * :*** * ** *::  .   **::*** * ref|ZP_01169692.1|      GMEVCREVRKKYEMPIIMLTAKDSEIDKVLGLELGADDYVTKPFSNRELIARVKANLRRH
ref|ZP_01695449.1|      GMEVCREVRKKYNMPIIMVTAKDSEIDKVLGLELGADDYVTKPFSTRELIARVKANLRRH
ref|YP_001127497.1|     GMEVCREVRKKYDMPIIMLTAKDSEIDKVLGLELGADDYVTKPFSTRELLARVKANLRRH
ref|YP_149327.1|        GMEVCREVRKKYDMPIIMLTAKDSEIDKVLGLELGADDYVTKPFSTRELLARVKANLRRH
ref|YP_534941.1|        GLEVAREVRKTHDMPIIMVTAKDSEIDKVLGLELGADDYVTKPFSNRELVARVKANLRRQ
RAAC00020               GFDVLRAIRQASGVPVIILTAKDDEVDKVLGLELGADDYVTKPFSTRELVARVKANLRRA
                        *::* * :*:    :*:*:****.*:*****************.*:********* ref|ZP_01169692.1|      QQIAAKAGEEEETN-EIAIGSLVIHPDAYVVSKRGETIELTHREFELLHYLAKHIGQVMT
ref|ZP_01695449.1|      QQTPAAPGEEEESN-EIAIGSLVIHPDAYVVSKRGETIELTHREFELLHYLAKHIGQVMT
ref|YP_001127497.1|     AQTATQEEEESETN-EIVVGPLVIRPDAYVVQKRGETIELTHREFELLHYLAKHIGQVMT
ref|YP_149327.1|        AQTANQEEGENETN-EIVIGPLVIRPDAYVVQKRGETIELTHREFELLHYLAKHIGQVMT
ref|YP_534941.1|        SAVAAKSSAEDDKNSEITVGDLTIHPEAYTVSKNGQRIELTHREFELLHYLAQHLGQVMT
RAAC00020               SDVLR----EHKENERYVVQDLVIDLAEYTVTKAGQPIPLTHREFQVLAVLAAHPGRVFT
                          *  . *  . .: *.*    *.* *  *:  * *****::*   ** * *:*:* ref|ZP_01169692.1|      REHLLQTVWGYDYYGDVRTVDVTVRRLREKIEDNPSHPTWIVTRRGVGYYLRN-
ref|ZP_01695449.1|      REHLLETVWGYDYYGDVRTVDVTVRRLREKVEDNPSHPEWIVTRRGVGYYLRN-
ref|YP_001127497.1|     REHLLQTVWGYDYYGDVRTVDVTVRRLREKIEDNPSHPSWIVTRRGVGYYLRN-
ref|YP_149327.1|        REHLLQTVWGYDYYGDVRTVDVTVRRLREKIEDNPSHPNWIVTRRGVGYYLRN-
ref|YP_534941.1|        REHLLQTVWGYDYFGDVRTVDVTVRRLREKIEDNPSRPTWLVTRRGVGYYLRN-
RAAC00020               RDQLVDQVWGSDYVGDTRAVDVTIRRLREKLEPDPSQPRYVLTRRGVGYYVRNE
                        *::*:: *** ** **.*:****:******:* :**:*  :::********:**
```

FIG. 160A

```
gb|EDQ48509.1|      ------------------------------------------------------------
gb|EDQ48476.1|      ------------------------------------------------------------
ref|ZP_01575425.1|  ------------------------------------------------------------
RAAC01715           MSFGAETGGFGAFLSRTSAKKDKNDGIYDSPARRDSFIMFREKPFSFLVGREGRANVSVR
ref|ZP_02025790.1|  ------------------------------------------------------------
ref|YP_001662047.1| ------------------------------------------------------------ gb|EDQ48509.1|      ------------------------------------------------------------
gb|EDQ48476.1|      ------------------------------------------------------------
ref|ZP_01575425.1|  ------------------------------------------------------------
RAAC01715           MPKKTNVSSSLHAIREVRTSWPSVTWDVLQQHPVELDFREVERALDGVRDRQAWLVVVVR
ref|ZP_02025790.1|  ------------------------------------------------------------
ref|YP_001662047.1| ------------------------------------------------------------ gb|EDQ48509.1|      ------------------------------------------------------------
gb|EDQ48476.1|      ------------------------------------------------------------
ref|ZP_01575425.1|  ------------------------------------------------------------
RAAC01715           SSRVVPIYPFLAQIQSAGFDCVHLLSCDAAAYVMTLAAHHPERAMEGFESALARLAADRT
ref|ZP_02025790.1|  ------------------------------------------------------------
ref|YP_001662047.1| ------------------------------------------------------------ gb|EDQ48509.1|      ------------------------------------------------------------
gb|EDQ48476.1|      ------------------------------------------------------------
ref|ZP_01575425.1|  ------------------------------------------------------------
RAAC01715           LVGVSSACDEREVVRWWQALMEATAASHWNVFESSAYSQGRRELVPLHEEDRTRLITRAV
ref|ZP_02025790.1|  ----------KAASEAITALSLNFYSASHIIAFSRDYIANRNIFPVDISVRLHEYETAI
ref|YP_001662047.1| ------------------------------------------------------------ gb|EDQ48509.1|      ----------VLECVRQCFERLKEQRAGTGTIVRVCSQLEDMACREVQEYREIRGKEAR-
gb|EDQ48476.1|      ------------------------------------------------------------
ref|ZP_01575425.1|  ------------------------------------------------------------
RAAC01715           TQLGDRGYEGIASVVEDLFAQLAERPTKLEDVAELCAQFIMAAVGQRQADGRDRMLQVP-
ref|ZP_02025790.1|  LQLN---FKAAKDVVSTLFSNLQSNFTDEASVKNICTQIYLISYRLVMSTYNLPMDEKYV
ref|YP_001662047.1| ------------------------------------------------------------ gb|EDQ48509.1|      --ARLETQLR----ACMSFSDMEDCFVEAFRSAL---EKVYGLRSEMGGKAVEIVKRWIA
gb|EDQ48476.1|      ---ALR------------------LIEARDDEK----------KEHTNQVVSRLNRYVE
ref|ZP_01575425.1|  --------------------------------------------------INQVRKTIE
RAAC01715           --ISTRQWLRFVAEECPKWWDWRDKLKQALMVVL----GREEAVRTAHSAQIGQVIEIIE
ref|ZP_02025790.1|  KMLTESSDIFQLKSIVSDMIN---DLQIQLTQSVK-----------KYSSFIEESLNYIK
ref|YP_001662047.1| ---------------------------------------------------IDEAIKLIQ
                                                                      :   . :

gb|EDQ48509.1|      EHY--SEHAELNTLAAMVYLTPSYLSKLFKQETGLTLTEYITDVRLKNAKRLLRTEPNMK
gb|EDQ48476.1|      EHL--DSDLSLTTLSDLVHLNPYYMSRLYKQMTGVNLPDYITDERIKKAKELVV-ESHLK
ref|ZP_01575425.1|  ERF--KEQISISTLARDVYLTPTYLCVLFKQVTGTTINDYLTLTRLEKAKK-LLSDPYIK
RAAC01715           RHY--DSDLDVATLASQVFLSPSYLSKRFKSETGMTIREFIVQTRLNKAKDLLLRDFHLK
ref|ZP_02025790.1|  EHL--EDDLSLEQIAQHIHINESYFSRTFKKECGNSVISYINNLRINKAKELLATS-NLK
ref|YP_001662047.1| ENY--SDLNISLNSIAEKLYITPNYLSTLFKSEMGVTFSDYLTACRIEKAKELL-KDVKVK
                    ..   . .  .: ::  :.:.  :*:.  :*.  *  .. .:    *:::** :  . :*
```

FIG. 160B

```
gb|EDQ48509.1|         VHQIGAEVGYADPAYFNKLFKKVVGVTPNEYK-----------------
gb|EDQ48476.1|         MHEICKKVGFESPAYFTRIFKKKTGSTPQEFREK----------------
ref|ZP_01575425.1|     LYDVCYEVGYLSPSYFSRLFKKYTGISPSEYRNVAI--------------
RAAC01715              AYEVGAHVGYPDPTYFNKLFKRQVGLTPKAFRDAMRQARGFKQEDSRSS
ref|ZP_02025790.1|     TFEISEAVGIHDPAYFSVLFKKNTGMSPKAYRDQ----------------
ref|YP_001662047.1|    IYEVAEAVGYTDQHYFSKVFKNITGFTPKEYREKIL--------------
                        .::    **  . **. :**. .* :*. ::
```

FIG. 161A

```
ref|NP_844784.1|      ----------------------------------------------------------------
ref|ZP_02259481.1|    ----------------------------------------------------------------
ref|YP_894957.1|      ----------------------------------------------------------------
ref|NP_978751.1|      ----------------------------------------------------------------
ref|ZP_00741477.1|    ----------------------------------------------------------------
RAAC01137             -------------------------------------------------------MHRFEPKVR ref|NP_844784.1|      ------------------------------------------------------------LPETA
ref|ZP_02259481.1|    ------------------------------------------------------------LPETA
ref|YP_894957.1|      ------------------------------------------------------------LPETA
ref|NP_978751.1|      ------------------------------------------------------------LPETA
ref|ZP_00741477.1|    ------------------------------------------------------------LPETA
RAAC01137             TWSRTWRAAAILGWLLAAALLAAVFPAASKEEINRS----------------TLLPASA
                                                                                  **  :* ref|NP_844784.1|      MSQQAEALMKKEFPNNAGNPLLVVWYRDGGLQSQDYKLIQDVYKELKASPLKEQSTLPPF
ref|ZP_02259481.1|    MSQQAEALMKKEFPNNAGNPLLVVWYRDGGLQSQDYKLIQDVYKELKASPLKEQSTLPPF
ref|YP_894957.1|      MSQQAEALMKKEFPNNAGNPLLVVWYRDGGLQSQDYKLIQDVYKELKASPLKEQSTLPPF
ref|NP_978751.1|      MSQQAEALMKKEFPNNAGNPLLVVWYRDGGLQSQDYKLIQDVYKELKASPLKEQSTLPPF
ref|ZP_00741477.1|    MSQQAEALMKKEFPNNTGNPLLVVWYRDGGLQSQDYKLIQDVYKELKANPLKEQSTLPPF
RAAC01137             PSQMATARVRDAFPASSGTPAILVFYDPTGISSADWAAIRRTVRELRTHPVTAQTQVPPL
                       **  *  *  ::.  **   .:*.*   ::*:*       *:.*  *:    *:   .  :**:    *:  *:  :**:

ref|NP_844784.1|      DTIPEQVLSKSASKDGTSFVTPVFFNKSAGTDILKENLDDLRNIVNSKVDEDPFKRKIND
ref|ZP_02259481.1|    DTIPEQVLSKSASKDGTSFVTPVFFNKSAGTDILKGNLDDLRKIVNSKVDVDPFKQKISD
ref|YP_894957.1|      DTIPEQVLSKSASKDGTSFVTPVFFNKSAGTDILKGNLDDLRKIVNSKVDVDPFKQKISD
ref|NP_978751.1|      DTIPEQALSKSASKDGTSFVTPVFFNKSAGTDILKGNLDDLRKIVNSKVDVDPFKQKISD
ref|ZP_00741477.1|    DTIPEQVLSKSASKDGTSFVTPVFFNKSAGTDILKLEKLEKKVNSKVDEDPFKQKISE
RAAC01137             DALPSGAAARFASDDGKVVSFPVLLRADASQDQLNQAVDEIDQDLRRAVGAGALNLALDR
                      *::*.   . ::  **.**.    **::. .*. * *:  ::.:  :  :.   *.  ..::   :.

ref|NP_844784.1|      AGLHVRLSGPVGIQTDAVSLFSQADVKLLVATVLLVLLILLYRSPILAILPLLVVGFA
ref|ZP_02259481.1|    SGLHVRLSGPVGIQTDAVSLFSQADVKLLIATVLLVLLILLYRSPILAILPLLVVGFA
ref|YP_894957.1|      SGLHVRLSGPVGIQTDAVSLFSQADVKLLIATVLLVLLILLYRSPILAILPLLVVGFA
ref|NP_978751.1|      SGLHVRLSGPVGIQTDAVSLFSQADVKLLVATVLLVLVLLILLYRSPILAILPLLVVGFA
ref|ZP_00741477.1|    SGLHVRLSGPVGIQTDAVSLFSQADVKLVATVLLVLVLILLILLYRSPILAILPILVVGFA
RAAC01137             PGLHAYVTGPAGIAVDATHLFQHADLALLIATTLLVLALMIVLYRSPILALVPLVSVGIA
                      .***. ::**.**  .**. **.:**: **:**.**** *:*:********:::*:: **:*
```

FIG. 161B

```
ref|NP_844784.1|      YGIISPTLGFLADHGWIKVDAQAISIMTVLLFGAGTDYCLFLISRYREYLLEEESKYKAL
ref|ZP_02259481.1|    YGIISPTLGFLADYGWIKVDAQAISIMTVLLFGAGTDYCLFLISRYREYLLEEESKYKAL
ref|YP_894957.1|      YGIISPTLGFLADHGWIKVDAQAISIMTVLLFGAGTDYCLFLISRYREYLLEEESKYKAL
ref|NP_978751.1|      YGIISPTLGFLADHGWIKVDAQAISIMTVLLFGAGTDYCLFLISRYREYLLEEESKYKAL
ref|ZP_00741477.1|    YGIISPTLGFLADHGWIKVDAQAISIMTVLLFGAGTDYCLFLISRYREYLLEEESKYKAL
RAAC01137             YAVVSSLLGAWARYGGLTFDAQTLSILTVLLFGAGTDYCLFLIARYRQELRRHERPIDAL
                      *.::*. **    * :*  :..***::**:****************:***. *  ..*   .**

ref|NP_844784.1|      QLAIKASGGAIIMSALTVVLGLGTLLLAHYGAFHRFAVPFSVAVFIMGIAALTILPAFLL
ref|ZP_02259481.1|    QLAIKASGGAIIMSALTVVLGLGTLLLAHYGAFHRFAVPFSAAVFIMGIAALTILPAFLL
ref|YP_894957.1|      QLAIKASGGAIIMSALTVVLGLGTLLLAHYGAFHRFAVPFSVAVFIMGIAALTILPALLL
ref|NP_978751.1|      QLAIKASGGAIIMSALTVVLGLGTLLLAHYGAFHRFAVPFSVAVFIMGIAALTILPALLL
ref|ZP_00741477.1|    QLAIKASGGAIIMSALTVVLGLGTLLLAHYGAFHRFAVPFSVAVFIMGIAALTILPALLL
RAAC01137             RAGYKSAAGAILMSGLTVSASLLSLLAARSPSFHEFAIPFSVAVFVMALVAITFVPALIG
                      :   . *::.***:**.***   .* :** *:    :**.**:***.***:*.::*:*::**::

ref|NP_844784.1|      IFGRTAFFPFIPRTTSMNEELARRKKKVVKVKKSKGAFSKKLGDVVVRRPWTIIMLTVFV
ref|ZP_02259481.1|    IFGRTAFFPFIPRTTSMNEELARRKKKVVKVKKSKGAFSKKLGDVVVRRPWTIIMLTVFV
ref|YP_894957.1|      IFGRAAFFPFVPRTTSMNEELARRKKKVVKVKKSKGAFSKKLGDVVVRRPWTIIMLTVFV
ref|NP_978751.1|      IFGRAAFFPFVPRTTSMNEELARRKKKVVKVKKSKGAFSKKLGDVVVRRPWTIIMLTVFV
ref|ZP_00741477.1|    IFGRIAFFPFIPRTTSMNEEFARKKKRAVKVEKSKGSFSKKLGDVVVRRPWTIIMLTVFV
RAAC01137             SLGRAAFWPRIPRYEPDAPDAGR----------PGRVSRWLGRTAVRRRKPVAVLGSLA
                      :** **:*  :**       . :  .*        *  .*: **  ..***  .:  :*  ..

ref|NP_844784.1|      LGGLASFVPRIQYTYDLLESFPKDMPSREGFTLISDHFSAGELAPVKVIVDTKGKELPIK
ref|ZP_02259481.1|    LGGLASFVPRIQYTYDLLESFPKDMPSREGFTLISDHFSAGELAPVKVIVDTKGKELPIK
ref|YP_894957.1|      LGGLASFVPRIQYTYDLLESFPKDMPSREGFTLISDHFSAGELAPVKVVVDTKGKELPIK
ref|NP_978751.1|      LGGLASFVPRIQYTYDLLESFPKDMPSREGFTLISDHFSAGELAPVKVVVDTKGKELPMK
ref|ZP_00741477.1|    LGGLASFVPRIQYTYDLLESFPKDMPSREGFTLISDHFSAGELAPVKVVVDTKGKELPIK
RAAC01137             LAACCLALPHVRTSYDLLSSFPADMPSREGYAVLSAHESPGALAPIDVLVEGGSPEGAVR
                      *... .   .:*::: :****.*** *******::::* * *.* ***.:*:*:  . * .::

ref|NP_844784.1|      --EELEKFSFVNTVKDPKEGKENKQIQMYEVSLAENPYSIEALDQIPKLKNSVEKVFKDA
ref|ZP_02259481.1|    --EELEKFSFVNTVKDPKEGKENKQIQMYEVSLAENPYSIEALDQIPKLKNSVEKVFKDA
ref|YP_894957.1|      --EELEKFSFVNTVKDPKEGKENKQIQMYEVSLAENPYSIEALDQIPKLKNSVEKVFKDA
ref|NP_978751.1|      --QELEKFSFVKTVKEPKDGKENKQIKMYEVSLAENPYSIEALDQIPKLKIHVEKVLKDA
ref|ZP_00741477.1|    --QELEKFSFVNTVKEPKEGKENKQIQMYEVSLAENPYSIEALDQIPKLKSNVEKVLKDA
RAAC01137             ---AVQSLAAVEQVH-LVAVRDHAHVALMQVELRTNPYSETAMAALS----SIERAAAKG
                        ::.:: *: *:    ::: ::  : :*.*  ****  *:   :.      :*:.   ..

ref|NP_844784.1|      GISNAED-QLWIGGETASLYDTKQITERDEAVIIPVMISIIALLLLVYLRSIVAMIYLIV
ref|ZP_02259481.1|    GISNAED-QLWIGGETASLYDTKQITERDEAIIIPVMISIIALLLLVYLRSIVAMIYLIV
ref|YP_894957.1|      GISNAED-QLWIGGETASLYDTKQITERDEAVIIPVMISIIALLLLVYLRSIVAMIYLIV
ref|NP_978751.1|      GVTKAED-QLWIGGETASLYDTKQITERDEAVIIPVMISIIALLLLVYLRSIVAMIYLIV
ref|ZP_00741477.1|    GIRNTED-QLWIGGETASLYDTKQITERDESVIIPVMISIIALLLLVYLRSVVAMIYLIV
RAAC01137             ASAGGQAAHVFLAGETAAQEDTRAITARDTRVVIPIVLVAIGLLLLVYLRSVVAPLYLLA
                      .  :   ::::.****:   **: ** **  ::**:::  *.*********:** :**:..

ref|NP_844784.1|      TVVLSFFSALGAGWLLLHYGMGAPAIQGAIPLYAFVFLVALGEDYNIFMVSEIWKNRKTQ
ref|ZP_02259481.1|    TVVLSFFSALGAGWLLLHYGMGAPAIQGAIPLYAFVFLVALGEDYNIFMVSEIWKNRKTQ
ref|YP_894957.1|      TVVLSFFSALGAGWLLLHYGMGVPAIQGAIPLYAFVFLVALGEDYNIFMVSEIWKNRKTQ
ref|NP_978751.1|      TVVLSFFSALGAGWILLHFGMGAPAIQGAIPLYAFVFLVALGEDYNIFMVSEIWKNRKTQ
ref|ZP_00741477.1|    TVVLSFFSALGAGWILLHYGMGAPAIQGAIPLYAFVFLVALGEDYNIFMVSEIWKNRKTQ
RAAC01137             TIVLSYGAAMGLGWLVIREVLHQPAMQGAIPLYAFVFLVALGEDYNIFMSRIWEVWRRG
                      *:***: :*:* **::::   :   **:*******************::*.**:    :
```

FIG. 161C

```
ref|NP_844784.1|        NHLDAVKNGVIQTGSVITSAGLILAGTFAVLGTLPIQVLVQFGIVTAIGVLLDTFIVRPL
ref|ZP_02259481.1|      NHLDAVKNGVIQTGSVITSAGLILAGTFAVLGTLPIQVLVQFGIVTAIGVLLDTFIVRPL
ref|YP_894957.1|        NHLDAVKNGVIQTGSVITSAGLILAGTFAVLGTLPIQVLVQFGIVTAIGVLLDTFIVRPL
ref|NP_978751.1|        NHLAAVKNGVIQTGSVITSAGLILAGTFAVLGTLPIQVLVQFGIVTAIGVLLDTFIVRPL
ref|ZP_00741477.1|      NHMDAVKNGVIQTGSVITSAGLILAGTFAVLGTLPIQVLVQFGIVTAIGVLLDTFIVRPL
RAAC01137               QADAAVERGVADTASVITSAGLILAGTFAMLASLPIQVLLQFGVVTAIGVLLDTFVVRPW
                        :  :. :*.**************:*.:****:*:*********:* ref|NP_844784.1|        LVPAITVVLGRFAFWP---
ref|ZP_02259481.1|      LVPAITVVLGRFAFWP---
ref|YP_894957.1|        LVPAITVVLGRFAFWP---
ref|NP_978751.1|        LVPAITVVLGRFAFWP---
ref|ZP_00741477.1|      LVPAITVVLGRFAFWP---
RAAC01137               MVPAITALLGDAARWPRRT
                        :*****.:**  * **
```

FIG. 162A

```
ref|ZP_02168855.1|      ---------- ---------- ---------- ---------- ---------- ----------
ref|ZP_02168855.1|      ---------- ---------- ---------- ---------- ---------- ----------
ref|ZP_02168855.1|      ---------- ---------- ---------- ---------- ---------- ----------
ref|ZP_02168855.1|      ---------- ---------- ---------- ---------- ---------- ----------
ref|NP_470526.1|        ---------- ---------- ---------- ---------- ---------- ----------
RAAC03013               MAERYAHFVA RFKYGIIAVW ILAVALAHVL LPQLNAIVAH KNTEFLPNSS SVVIASNWLK ref|ZP_02168855.1|      ---------- ---------- ---------- ---------- ---------- ----------
ref|ZP_02168855.1|      ---------- ---------- ---------- ---------- ---------- ----------
ref|ZP_02168855.1|      ---------- ---------- ---------- ---------- ---------- ----------
ref|ZP_02168855.1|      ---------- ---------- ---------- ---------- ---------- ----------
ref|NP_470526.1|        ---------- ---------- ---------- ---------- ---------- ----------
RAAC03013               RVDPARQAGS SAVVAMYNPH GLTAADKAWF TQKLKQVADH KPAYGVKTVT AAYNQSKSVQ ref|ZP_02168855.1|      ---------- ---------- ---------- ---------- ---------- ----------
ref|ZP_02168855.1|      ---------- ---------- ---------- ---------- ---------- ----------
ref|ZP_02168855.1|      ---------- ---------- ---------- ---------- ---------- ----------
ref|ZP_02168855.1|      ---------- ---------- ---------- ---------- ---------- ----------
ref|NP_470526.1|        ---------- ---------- ---------- ---------- ---------- ----------
RAAC03013               NQFFSADRTV EIATIGFPGN DVSKATDASL NQLHQVFQQP PKDAQILFTG DTPIENDNIN ref|ZP_02168855.1|      ---------- ---------- ---------- ---------- ---------- ----------
ref|ZP_02168855.1|      ---------- ---------- ---------- ---------- ---------- ----------
ref|ZP_02168855.1|      ---------- ---------- ---------- ---------- ---------- ----------
ref|ZP_02168855.1|      ---------- ---------- ---------- ---------- ---------- ----------
ref|NP_470526.1|        ---------- ---------- ---------- ---------- ---------- ----------
RAAC03013               ISMDGASKTA GVTIALVLVI LLVVFRSVVA PFLTLLSIGL SYLLTTNLVA VLANVGLPVS ref|ZP_02168855.1|      ---------- ---------- ---------- ---------- ---------- ----------
ref|ZP_02168855.1|      ---------- ---------- ---------- ---------- ---------- ----------
ref|ZP_02168855.1|      ---------- ---------- ---------- ---------- ---------- ----------
ref|ZP_02168855.1|      ---------- ---------- ---------- ---------- ---------- ----------
ref|NP_470526.1|        ---------- ---------- ---------- ---------- ---------- ----------
RAAC03013               TFTDTFLIAI IFGAGTDYSI IVLNRFREEA SRGLAPVDAL ARAMSGVAKT VVYSALTVFL ref|ZP_02168855.1|      ---------- ---------- ---------- ---------- ---------- ----------
ref|ZP_02168855.1|      ---------- ---------- ---------- ---------- ---------- ----------
ref|ZP_02168855.1|      ---------- ---------- ---------- ---------- ---------- ----------
ref|ZP_02168855.1|      ---------- ---------- ---------- ---------- ---------- ----------
ref|NP_470526.1|        ---------- ---------- ---------- ---------- ---------- ----------
RAAC03013               SFATLYFARF GLFRSGVGVA VGLAVTLFAC LTFLPALMMV LGRYVFWPRR NLDGASHKPS ref|ZP_02168855.1|      ---------- ---------- ---------- ---------- ---------- ----------
ref|ZP_02168855.1|      ---------- ---------- ---------- ---------- ---------- ----------
ref|ZP_02168855.1|      ---------- ---------- ---------- ---------- ---------- ----------
ref|ZP_02168855.1|      ---------- ---------- ---------- ---------- ---------- ----------
ref|NP_470526.1|        ---------- ---------- ---------- ---------- ---------- ----------
RAAC03013               RIWDLTGRTA LRHPWWTLAG VLVVLTPIAL SFTDKRTFDP TSDIPTAPSV EGFHVVSKAF ref|ZP_02168855.1|      ---------- ---------- ---------- ---------- ---------- ----------
ref|ZP_02168855.1|      ---------- ---------- ---------- ---------- ---------- ----------
ref|ZP_02168855.1|      ---------- ---------- ---------- ---------- ---------- ----------
ref|ZP_02168855.1|      ---------- ---------- ---------- ---------- ---------- ----------
ref|NP_470526.1|        ---------- ---------- ---------- ---------- ---------- ----------
RAAC03013               GPGKVLPMDV VIDTPDNLRT PEGLATIEQV SEAIAKLPFV QQVQSATRPT GSVIAEFELA ref|ZP_02168855.1|      ---------- ---------- ---------- ---------- ---------- ----------
ref|ZP_02168855.1|      ---------- ---------- ---------- ---------- ---------- ----------
```

FIG. 162B

```
ref|ZP_02168855.1|     ---------- ---------- ---------- ---------- ---------- ----------
ref|ZP_02168855.1|     ---------- ---------- ---------- ---------- ---------- ----------
ref|NP_470526.1|       ---------- ---------- ---------- ---------- ---------- ----------
RAAC03013              KQNQLAANGL GKVQTGLNQV ASHVGTKSAQ QAANAANTLS SGASALAQAG GKLSQGAAQA ref|ZP_02168855.1|     ---------- ---------- ---------- ---------- ---------- ----------
ref|ZP_02168855.1|     ---------- ---------- ---------- ---------- ---------- ----------
ref|ZP_02168855.1|     ---------- ---------- ---------- ---------- ---------- ----------
ref|ZP_02168855.1|     ---------- ---------- ---------- ---------- ---------- ----------
ref|NP_470526.1|       ---------- ---------- ---------- ---------- ---------- ----------
RAAC03013              QEGASKLAAG AQALSSGASR LTQANTQLAS GAAQVAAGSQ QVAQGADKLA TSARSIASGQ ref|ZP_02168855.1|     ---------- ---------- ---------- ---------- ---------- ----------
ref|ZP_02168855.1|     ---------- -------PDIDQFV REEGQAEAPE GFPSQIAEEL IEEDD-GFGG EEILLVYEQE
ref|ZP_02168855.1|     ---------- ---------- ---------- ---------- ---------- ----------
ref|ZP_02168855.1|     ---------- ---------- ---------- ---------- ---------- ----------
ref|NP_470526.1|       ---------- -------PPMADLV REKGELKLPD GYPSSLATEM QKKHNPDDKG SAYIAVYTAD
RAAC03013              TALANGAARE AQAAQQLANA IAAWTKAHPA EASDPNWQQI VALAQGNAAG AQQTAKAASQ ref|ZP_02168855.1|     ---------- ---------- ---------- ---------- ----DGMAEA RQGASDLSGG
ref|ZP_02168855.1|     DGFSSEQKEE IKEVLAGLSE EDHNLPIHAV TGPFDGDMEE ERLISEDGDV LIALVEMDIE
ref|ZP_02168855.1|     ---------- ---------- ---------- ---------- ---------- ----------
ref|ZP_02168855.1|     ---------- ---------- ---------- ---------- ---------- ----------
ref|NP_470526.1|       HKLTGTELNN IKKSLDSIDK NKDELHVTNV VSSFNQPELK DKFLSKDGKT MVASLTVDDT
RAAC03013              LANGTSQWAN GATSLAEGAG KVAAGASQLA AGSRGAASGA KGLSDGAAQV GQGASSLAQG ref|ZP_02168855.1|     LDELQSGHYA LLDGVGEGRN GLENFRKGLR DMLEGTEELN -------EGI GEAEDALRQV
ref|ZP_02168855.1|     AHEYADIRNE LQEASQAEGV DHDQTGEAVI NEDVVVSTEE GLVTSTYITV SLVFLVLALV
ref|ZP_02168855.1|     ---------- ---------- ---------- ---------- ---------- ----------
ref|ZP_02168855.1|     ---------- ---------- ---------- -------TEE GLVTSTYITV SLVFLVLALV
ref|NP_470526.1|       DASVKSIRNA LDKKMDVKGV DTYLTGNKLI QEDVVQGSED GLHKTEGITV VFILVVLFLV
RAAC03013              LNQLSGGARQ LQAGLGKWAA GAAQFSSGLS NAGAGENQLH SALVKLSNGV GTVKTALDET ref|ZP_02168855.1|     SKQEENPLEG LFIPNEAF-E EEAFEEAFDQ YV--TPGGQV AGMELLFEED PYSQEAMMIL
ref|ZP_02168855.1|     FKSLVSPLVP LLLLGTVYLF SISIVSRLID WVGFPVSNFT QMFVLAVVFG VGTDYCILIM
ref|ZP_02168855.1|     ---------- ---------- ---------- ---------- ---------- ----------
ref|ZP_02168855.1|     FKSLVSPLVP LLLLGTVYLF SISIVSRLID WVGFPVSNFT QMFVLAVVFG VGTDYCILIM
ref|NP_470526.1|       FRSAVAPFIP LLTVGISYLV AQSTVAFLID IFNFPVSTYT QIFMVCIMFG IGTDYCILLM
RAAC03013              AKAQTSGDPG FYVPASAISS NKSLRQALDS YI--SPDGHV ADIRVTLKSD PYSMTAIQEM ref|ZP_02168855.1|     DEVEEVAAFT LRDTPFEDKE MAFSGITSSN RDLRDVSDQD FFVTAAVMLA GIFIALTFLF
ref|ZP_02168855.1|     KRFQEEVLKD QTAFQAMLTT MRASKSTVLY SALTGFIGFA TIYLADFDLY QSAVGVAVAV
ref|ZP_02168855.1|     ---------- ---------- ---------- ---------- ---------- ----------
ref|ZP_02168855.1|     KRFQEEVLKD QTAFQAMLTT MRASKSTVLY SALTGFIGFA TIYLADFDLY QSAVGVAVAV
ref|NP_470526.1|       SRFKEEMGAG LDPRESVHAT YRTAGKTVIY SGVAVLVAFT SLYFVQFDLY RSAVAVGVGI
RAAC03013              PRLETVAQAA FTAAPIHTGQ VGFAGTTPTQ YALNQLSNQD FVRMMALILG SIFLLLVVML ref|ZP_02168855.1|     KSLIMPLYVL VSLVLTYIGS MAVAELIFVT ILGYDGIM-- ---WAVPFFS FVLLMALGVD
ref|ZP_02168855.1|     LVMMAGIWMV MPAVLALGGV RLFWPGKPGS SNPSNPLWGF IGGLTLRSPK LALVAVALLV
ref|ZP_02168855.1|     ---------- ---------- ---------- ---------- --------FS FVLLMALGVD
ref|ZP_02168855.1|     LVMMAGIWMV MPAVLALGGV RLFWP----- ---------- ---------- ----------
ref|NP_470526.1|       VVLLAALYTL VPFFMSTLGT HLFWPLNKNI SHKENKVWGA AGKFTFARPW IALLIVAAIT
RAAC03013              RSLIAPLYVI ASLTGTYFVT MACLQFVAVD VMHKAGIS-- ---WTVPFFA LLLLVALGVD
```

FIG. 162C

```
ref|ZP_02168855.1|        YSIFLMGRFR EILEEGEEIT IHDAIHIAMK RIGGTVISAA LILGGTFAAM MASGVLTLMQ
ref|ZP_02168855.1|        IPFYLFYDDL RSFDNVQEIR GDYDSVKAYE LTEEAFGQGD LFFSTLYLKT DEASWDDHGK
ref|ZP_02168855.1|        YSIFLMGRFR EILEEGEEIT IHDAIHIAMK RIGGTVISAA LILGGTFAAM MASGVLTLMQ
ref|ZP_02168855.1|        ---------- ---------- ---------- ---------- ---------- ----------
ref|NP_470526.1|          LPPILLHTGT ESFNSLDEIS DKYPSKKGFE IVSDSFGAGQ VAPTQVFIEN DDN-MRTTEY
RAAC03013                 YSIFLMSRFD EELRRHPELN LRSAMLYAMR QMGNVIFSAA AIMAGTFGSM SVSGVTTLVE ref|ZP_02168855.1|        VSTVIMTGLL LYTLVMLPVF VPACMLLLGS WNWWPLGR-- ---------- ----------
ref|ZP_02168855.1|        IAHLEQLAMN IEKVEGIRGV RGLNRPDEDV PDEFRIPEQA GILSEGMVEA LDGLDELSDG
ref|ZP_02168855.1|        VSTVIMTGLL LYTLVMLPVF VPACMLLLGS WNWWP----- ---------- ----------
ref|ZP_02168855.1|        ---------- ---------- ---------- ---------- ---------- ----------
ref|NP_470526.1|          IAQIEKISDD LSHLKGIDMV MSASRPAGKR VDDIYIKNQA GQVNDGVGQA TDGVGEVKKG
RAAC03013                 IGLSVIIGLA LYALIVLALF VPACTAIVGE AHFWPFRRVP REEQELRLPE ELAAE----- ref|ZP_02168855.1|        -------
ref|ZP_02168855.1|        I------
ref|ZP_02168855.1|        -------
ref|ZP_02168855.1|        -------
ref|NP_470526.1|          LDSASSE
RAAC03013                 -------
```

US 9,187,753 B2

TRANSCRIPTIONAL CONTROL IN *ALICYCLOBACILLUS ACIDOCALDARIUS* AND ASSOCIATED GENES, PROTEINS, AND METHODS

CROSS-REFERENCE TO RELATED APPLICATIONS

This application is a divisional of U.S. patent application Ser. No. 12/380,008, filed Feb. 20, 2009, which issued on May 16, 2014 as U.S. Pat. No. 8,716,011, which claims the benefit of the filing date of U.S. Provisional Patent Application Ser. No. 61/030,820, filed Feb. 22, 2008, for "TRANSCRIPTIONAL CONTROL IN ALICYCLOBACILLUS ACIDOCALDARIUS AND ASSOCIATED GENES, PROTEINS, AND METHODS," the disclosure of each of which is hereby incorporated herein in its entirety by this reference.

GOVERNMENT RIGHTS

This invention was made with government support under Contract Number DE-AC07-99ID13727 and Contract Number DE-AC07-05ID14517 awarded by the United States Department of Energy. The government has certain rights in the invention.

(long sequence listing—with parent (Filed with Request to Transfer CRF))

STATEMENT ACCORDING TO 37 C.F.R. §1.821(c) OR (e)

Sequence Listing Submitted as PDF File with a Request to Transfer CRF from Parent Application Pursuant to 37 C.F.R. §1.821(c) or (e), a file containing a PDF version of the Sequence Listing has been submitted concomitant with this application, the contents of which are hereby incorporated by reference. The transmittal documents of this application include a Request to Transfer CRF from the parent application.

TECHNICAL FIELD

The present invention relates generally to biotechnology. More specifically, the present invention relates to isolated and/or purified polypeptides and nucleic acid sequences encoding polypeptides from *Alicyclobacillus acidocaldarius* and methods for their use.

BACKGROUND

Bacterial DNA codes for information that regulates transcription of genes into mRNA which codes for proteins or enzymes used for control of growth and processing of energy, carbon and other compounds by the cell. Most of these transcriptional regulators/repressors function to turn on and off genes to minimize expenditure of cellular energy in response to their growth environment (i.e., presence of growth substrate, metals, temperature, etc.).

BRIEF SUMMARY OF THE INVENTION

Embodiments of the invention relate to purified and/or isolated nucleotide sequences of the genome of *Alicyclobacillus acidocaldarius*, or a homologue or fragment thereof. In one embodiment of the invention, the nucleotide sequence is selected from at least one of SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2857, 2858, 2860, 2877, 2894, 2911, and 2928 or a homologue or fragment thereof. In another embodiment of the invention, the homologue is selected from the group consisting of a nucleotide sequence having at least 80% sequence identity to at least one of SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2857, 2858, 2860, 2877, 2894, 2911, and 2928.

Embodiments of the invention may further relate to an isolated and/or purified nucleic acid sequence comprising a nucleic acid sequence encoding a polypeptide selected from the group consisting of a polypeptide having at least 90% sequence identity to at least one of SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927.

Embodiments of the invention also relate to isolated and/or purified polypeptides coded for by a nucleotide sequence comprising a nucleotide sequence of the genome of *Alicyclobacillus acidocaldarius*, or a homologue or fragment thereof. In one embodiment, the nucleotide sequence comprises a nucleotide sequence selected from the group consisting of a nucleotide sequence having at least 80% sequence identity to at least one of SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2860, 2877, 2894, 2911, and 2928.

In another embodiment of the invention, the nucleotide sequence comprises a nucleotide sequence selected from at least one of SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2860, 2877, 2894, 2911, and 2928 or a homologue or fragment thereof. In still another embodiment, the polypeptide comprises an amino acid sequence of SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927. In yet another embodiment, the polypeptide comprises an amino acid sequence selected from the group consisting of a polypeptide having at least 90% sequence identity to at least one of SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927.

In embodiments of the invention, the polypeptides may be acidophilic and/or thermophilic. In further embodiments, the polypeptides may be glycosylated, pegylated, and/or otherwise post-translationally modified.

Embodiments of methods include placing a recombinant, purified, and/or isolated polypeptide selected from the group consisting of a polypeptide having at least 90% sequence identity to SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927 in, or replacing a component, of an in-vitro transcription system such as, by way of non-limiting example, a polymerase chain reaction or a reticulocyte lysate transcription/translation system.

Further embodiments of methods include placing a cell producing or encoding a recombinant, purified, and/or isolated nucleotide sequence comprising a nucleotide sequence selected from the group consisting of a nucleotide sequences having at least 90% sequence identity to at least one of the sequences of SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2860, 2877, 2894, 2911, and 2928 and/or a recombinant, purified, and/or isolated polypeptide selected from the group consisting of a polypeptide having at least 90% sequence identity to at least one of the sequences of SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927 in an environment comprising temperatures at or above about 25, 30, 35, 40, 45, 50, 55, 60, 65, 70, 75, 80, 85, 90, and/or 95 degrees Celsius and/or a pH at, below, and/or above 8, 7, 6, 5, 4, 3, 2, 1, and/or 0.

These and other aspects of the invention will become apparent to the skilled artisan in view of the teachings contained herein.

BRIEF DESCRIPTION OF THE SEVERAL VIEWS OF THE DRAWINGS

FIG. 1 depicts a sequence alignment (ClustalW) between SEQ ID NO: 1446 (RAAC01465) and ref|ZP_01666866.1|, ref|YP_001039288.1|, ref|YP_001210812.1|, ref|YP_001111548.1|, and ref|ZP_01576004.1| (SEQ ID NOS: 1448-1452), respectively, which all have the function assigned to SEQ ID NO: 1446 in Table 1. Amino acids conserved among all sequences are indicted by a "*" and generally conserved amino acids are indicated by a ":".

FIG. 2 depicts a sequence alignment (ClustalW) between SEQ ID NO: 443 (RAAC00371) and ref|YP_145986.1|, ref|YP_001124263.1|, ref|NP_241028.1|, ref|YP_001210899.1|, and ref|YP_001111617.1| (SEQ ID NOS: 445-449), respectively, which all have the function assigned to SEQ ID NO: 443 in Table 1. Amino acids conserved among all sequences are indicted by a "*" and generally conserved amino acids are indicated by a ":".

FIGS. 3A-3C depict a sequence alignment (ClustalW) (ClustalW) between SEQ ID NO: 477 (RAAC00408) and ref|ZP_02326346.1|, ref|NP_240992.1|, ref|YP_001124230.1|, ref|YP_145951.1|, and ref|YP_73646.1| (SEQ ID NOS: 479-483), respectively, which all have the function assigned to SEQ ID NO: 477 in Table 1. Amino acids conserved among all sequences are indicted by a "*" and generally conserved amino acids are indicated by a ":".

FIGS. 4A-4C depict a sequence alignment (ClustalW) (ClustalW) between SEQ ID NO: 460 (RAAC00407) and ref|ZP_02326345.1|, ref|YP_001124231.1|, ref|NP_240993.1|, ref|YP_145952.1|, and ref|NP_976431.1| (SEQ ID NOS: 462-466), respectively, which all have the function assigned to SEQ ID NO: 460 in Table 1. Amino acids conserved among all sequences are indicted by a "*" and generally conserved amino acids are indicated by a ":".

FIG. 5 depicts a sequence alignment (ClustalW) between SEQ ID NO: 596 (RAAC00480) and ref|NP_244660.1|, ref|ZP_01168478.1|, ref|YP_001127419.1|, ref|ZP_01860921.1|, and ref|NP_693930.1| (SEQ ID NOS: 598-602), respectively, which all have the function assigned to SEQ ID NO: 596 in Table 1. Amino acids conserved among all sequences are indicted by a "*" and generally conserved amino acids are indicated by a ":".

FIG. 6 depicts a sequence alignment (ClustalW) between SEQ ID NO: 307 (RAAC00147) and ref|YP_850042.1|, ref|NP_465351.1|, ref|YP_014447.1|, ref|NP_268055.1|, and ref|NP_471274.1| (SEQ ID NOS: 309-313), respectively, which all have the function assigned to SEQ ID NO: 307 in Table 1. Amino acids conserved among all sequences are indicted by a "*" and generally conserved amino acids are indicated by a ":".

FIG. 7 depicts a sequence alignment (ClustalW) between SEQ ID NO: 1752 (RAAC01826) and ref|YP_074736.1|, ref|YP_074981.1|, ref|YP_001394390.1|, ref|NP_244228.1|, and ref|YP_001275817.1| (SEQ ID NOS: 1754-1758), respectively, which all have the function assigned to SEQ ID NO: 1752 in Table 1. Amino acids conserved among all sequences are indicted by a "*" and generally conserved amino acids are indicated by a ":".

FIG. 8 depicts a sequence alignment (ClustalW) between SEQ ID NO: 868 (RAAC00896) and ref|YP_001126509.1|, ref|YP_148335.1|, ref|ZP_02328521.1|, ref|ZP_01173341.1|, and ref|YP_001376241.1| (SEQ ID NOS: 870-874), respectively, which all have the function assigned to SEQ ID NO: 868 in Table 1. Amino acids conserved among all sequences are indicted by a "*" and generally conserved amino acids are indicated by a ":".

FIG. 9 depicts a sequence alignment (ClustalW) between SEQ ID NO: 256 (RAAC00120) and ref|NP_243422.1|, ref|YP_146980.1|, ref|YP_001125115.1|, ref|ZP_01862300.1|, and ref|ZP_01172495.1| (SEQ ID NOS: 258-262), respectively, which all have the function assigned to SEQ ID NO: 256 in Table 1. Amino acids conserved among all sequences are indicted by a "*" and generally conserved amino acids are indicated by a ":".

FIG. 10 depicts a sequence alignment (ClustalW) between SEQ ID NO: 1956 (RAAC02146) and ref|YP_001126333.1|, gb|AAB81194.1|, ref|YP_148161.1|, pdb|1L0O|C, and ref|YP_001487306.1| (SEQ ID NOS: 1958-1962), respectively, which all have the function assigned to SEQ ID NO: 1956 in Table 1. Amino acids conserved among all sequences are indicted by a "*" and generally conserved amino acids are indicated by a ":".

FIG. 11 depicts a sequence alignment (ClustalW) between SEQ ID NO: 273 (RAAC00121) and ref|ZP_02330758.1|, ref|YP_001212395.1|, ref|YP_001125116.1|, ref|NP_243420.1|, and ref|ZP_01667054.1| (SEQ ID NOS: 275-279), respectively, which all have the function assigned to SEQ ID NO: 273 in Table 1. Amino acids conserved among all sequences are indicted by a "*" and generally conserved amino acids are indicated by a ":".

FIG. 12 depicts a sequence alignment (ClustalW) between SEQ ID NO: 2262 (RAAC02546) and ref|YP_001512033.1|, ref|NP_976421.1|, ref|NP_842661.1|, ref|NP_829995.1|, and ref|YP_001373458.1| (SEQ ID NOS: 2264-2268), respectively, which all have the function assigned to SEQ ID NO: 2262 in Table 1. Amino acids conserved among all sequences are indicted by a "*" and generally conserved amino acids are indicated by a ":".

FIG. 13 depicts a sequence alignment (ClustalW) between SEQ ID NO: 511 (RAAC00418) and ref|YP_077384.1|, ref|YP_001419777.1|, emb|CAA41793.1|, ref|ZP_01173595.1|, and ref|NP_240981.1| (SEQ ID NOS: 513-517), respectively, which all have the function assigned to SEQ ID NO: 511 in Table 1. Amino acids conserved among all sequences are indicted by a "*" and generally conserved amino acids are indicated by a ":".

FIG. 14 depicts a sequence alignment (ClustalW) between SEQ ID NO: 2602 (RAAC02968) and ref|YP_001409756.1|, ref|YP_001485343.1|, ref|YP_181606.1|, ref|NP_976421.1|, and ref|NP_842661.1| (SEQ ID NOS: 2604-2608), respectively, which all have the function assigned to SEQ ID NO: 2602 in Table 1 Amino acids conserved among all sequences are indicted by a "*" and generally conserved amino acids are indicated by a ":".

FIG. 15 depicts a sequence alignment between SEQ ID NO: 2927 (RAAC03263) and RTHT02135, RTHT02135, RBLH00099, RBSB05130, and RCTH01302 (SEQ ID NOS: 2929-2933), respectively, which all have the function assigned to SEQ ID NO: 2927 in Table 1. Amino acids conserved among all sequences are indicted by a "*" and generally conserved amino acids are indicated by a ":".

FIG. 16 depicts a sequence alignment (ClustalW) between SEQ ID NO: 817 (RAAC00856) and ref|YP_001126560.1|, ref|NP_242151.1|, ref|YP_175113.1|, ref|YP_148388.1|, and ref|ZP_01861605.1| (SEQ ID NOS: 819-823), respectively, which all have the function assigned to SEQ ID NO: 817 in Table 1. Amino acids conserved among all sequences are indicted by a "*" and generally conserved amino acids are indicated by a ":".

FIG. 17 depicts a sequence alignment (ClustalW) between SEQ ID NO: 1735 (RAAC01814) and ref|YP_148388.1|, ref|YP_001126560.1|, gb|ABY76244.1|, ref|YP_896655.1|, and ref|NP_980714.1| (SEQ ID NOS: 1737-1741), respectively, which all have the function assigned to SEQ ID NO: 1735 in Table 1. Amino acids conserved among all sequences are indicted by a "*" and generally conserved amino acids are indicated by a ":".

FIG. 18 depicts a sequence alignment (ClustalW) between SEQ ID NO: 2381 (RAAC02673) and ref|YP_001486125.1|, ref|ZP_01696681.1|, ref|NP_388808.1|, ref|NP_830819.1|, and ref|YP_001643827.1| (SEQ ID NOS: 2383-2387), respectively, which all have the function assigned to SEQ ID NO: 2381 in Table 1. Amino acids conserved among all sequences are indicted by a "*" and generally conserved amino acids are indicated by a ":".

FIG. 19 depicts a sequence alignment (ClustalW) between SEQ ID NO: 1905 (RAAC02112) and ref|YP_148250.1|, ref|ZP_01725195.1|, ref|NP_390312.1|, ref|ZP_00538565.1|, and ref|YP_001126420.1| (SEQ ID NOS: 1907-1911), respectively, which all have the function assigned to SEQ ID NO: 1905 in Table 1. Amino acids conserved among all sequences are indicted by a "*" and generally conserved amino acids are indicated by a ":".

FIG. 20 depicts a sequence alignment (ClustalW) between SEQ ID NO: 2568 (RAAC02902) and ref|YP_147113.1|, ref|NP_243282.1|, ref|YP_001125233.1|, ref|YP_75727.1|, and ref|ZP_02330483.1| (SEQ ID NOS: 2570-2574), respectively, which all have the function assigned to SEQ ID NO: 2568 in Table 1 Amino acids conserved among all sequences are indicted by a "*" and generally conserved amino acids are indicated by a ":".

FIG. 21 depicts a sequence alignment (ClustalW) between SEQ ID NO: 494 (RAAC00415) and ref|ZP_01173598.1|, ref|YP_173640.1|, ref|YP_089786.1|, ref|YP_848410.1|, and ref|NP_691027.1| (SEQ ID NOS: 496-500), respectively, which all have the function assigned to SEQ ID NO: 494 in Table 1. Amino acids conserved among all sequences are indicted by a "*" and generally conserved amino acids are indicated by a ":".

FIGS. 22A and 22B depict a sequence alignment (ClustalW) between SEQ ID NO: 562 (RAAC00475) and ref|YP_149235.1|, ref|YP_001127411.1|, ref|YP_001377035.1|, gb|AAU09403.1|, and ref|YP_039325.1| (SEQ ID NOS: 564-568), respectively, which all have the function assigned to SEQ ID NO: 562 in Table 1. Amino acids conserved among all sequences are indicted by a "*" and generally conserved amino acids are indicated by a ":".

FIGS. 23A and 23B depict a sequence alignment (ClustalW) between SEQ ID NO: 2619 (RAAC02984) and ref|ZP_01173129.1|, ref|ZP_01696484.1|, ref|YP_001488275.1|, ref|ZP_02171541.1|, and ref|YP_173520.1| (SEQ ID NOS: 2621-2625), respectively, which all have the function assigned to SEQ ID NO: 2619 in Table 1. Amino acids conserved among all sequences are indicted by a "*" and generally conserved amino acids are indicated by a ":".

FIGS. 24A and 24B depict a sequence alignment (ClustalW) between SEQ ID NO: 2636 (RAAC02994) and ref|NP_244812.1|, ref|ZP_02171541.1|, ref|ZP_01173129.1|, ref|YP_090070.1|, and ref|YP_077660.1| (SEQ ID NOS: 2638-2642), respectively, which all have the function assigned to SEQ ID NO: 2636 in Table 1. Amino acids conserved among all sequences are indicted by a "*" and generally conserved amino acids are indicated by a ":".

FIG. 25 depicts a sequence alignment (ClustalW) between SEQ ID NO: 86 (RAAC00039) and ref|YP_177603.1|, ref|NP_244925.1|, ref|YP_001423363.1|, ref|ZP_02327875.1|, and ref|ZP_02172038.1| (SEQ ID NOS: 88-92), respectively, which all have the function assigned to SEQ ID NO: 86 in Table 1. Amino acids conserved among all sequences are indicted by a "*" and generally conserved amino acids are indicated by a ":".

FIG. 26 depicts a sequence alignment (ClustalW) between SEQ ID NO: 1871 (RAAC02034) and ref|YP_001422137.1|, ref|YP_080133.1|, ref|NP_243941.1|, ref|YP_176156.1|, and ref|YP_001376422.1| (SEQ ID NOS: 1873-1877), respectively, which all have the function assigned to SEQ ID NO: 1871 in Table 1. Amino acids conserved among all sequences are indicted by a "*" and generally conserved amino acids are indicated by a ":".

FIG. 27 depicts a sequence alignment (ClustalW) between SEQ ID NO: 188 (RAAC00092) and ref|ZP_01697682.1|, ref|YP_146960.1|, ref|NP_242122.1|, ref|YP_001125095.1|, and ref|ZP_01860230.1| (SEQ ID NOS: 190-194), respectively, which all have the function assigned to SEQ ID NO: 188 in Table 1. Amino acids conserved among all sequences are indicted by a "*" and generally conserved amino acids are indicated by a ":".

FIG. 28 depicts a sequence alignment (ClustalW) between SEQ ID NO: 2143 (RAAC02454) and ref|YP_001125095.1|, ref|YP_896293.1|, ref|YP_146960.1|, ref|NP_389392.1|, and ref|ZP_02261942.1| (SEQ ID NOS: 2145-2149), respectively, which all have the function assigned to SEQ ID NO: 2143 in Table 1 Amino acids conserved among all sequences are indicted by a "*" and generally conserved amino acids are indicated by a ":".

FIG. 29 depicts a sequence alignment (ClustalW) between SEQ ID NO: 341 (RAAC00212) and ref|YP_752777.1|, ref|YP_001666100.1|, ref|NP_621806.1|, ref|ZP_01666183.1|, and ref|YP_077079.1| (SEQ ID NOS: 343-347), respectively, which all have the function assigned to SEQ ID NO: 341 in Table 1. Amino acids conserved among all sequences are indicted by a "*" and generally conserved amino acids are indicated by a ":".

FIG. 30 depicts a sequence alignment (ClustalW) between SEQ ID NO: 2772 (RAAC03236) and ref|YP_001666100.1|, ref|YP_001317994.1|, ref|NP_621806.1|, ref|YP_001181188.1|, and ref|NP_346951.1| (SEQ ID NOS: 2774-2778), respectively, which all have the function assigned to SEQ ID NO: 2772 in Table 1. Amino acids conserved among all sequences are indicted by a "*" and generally conserved amino acids are indicated by a ":".

FIG. 31 depicts a sequence alignment (ClustalW) between SEQ ID NO: 2296 (RAAC02603) and ref|NP_346951.1|, ref|YP_001181188.1|, ref|YP_001666100.1|, ref|NP_621806.1|, and ref|YP_001317994.1| (SEQ ID NOS: 2298-2302), respectively, which all have the function assigned to SEQ ID NO: 2296 in Table 1. Amino acids conserved among all sequences are indicted by a "*" and generally conserved amino acids are indicated by a ":".

FIG. 32 depicts a sequence alignment (ClustalW) between SEQ ID NO: 324 (RAAC00161) and gb|AAC62407.1|, ref|YP_001374031.1|, ref|NP_830661.1|, ref|YP_037204.1|, and ref|NP_979446.1| (SEQ ID NOS: 326-330), respectively, which all have the function assigned to SEQ ID NO: 324 in Table 1. Amino acids conserved among all sequences are indicted by a "*" and generally conserved amino acids are indicated by a ":".

FIG. 33 depicts a sequence alignment (ClustalW) between SEQ ID NO: 919 (RAAC00923) and ref|YP_001422239.1|, ref|YP_001420593.1|, ref|ZP_01697004.1|, ref|ZP_01170670.1|, and ref|YP_001486165.1| (SEQ ID NOS: 921-925), respectively, which all have the function assigned to SEQ ID NO: 919 in Table 1. Amino acids conserved among all sequences are indicted by a "*" and generally conserved amino acids are indicated by a ":".

FIG. 34 depicts a sequence alignment (ClustalW) between SEQ ID NO: 749 (RAAC00643) and ref|ZP_02330525.1|, ref|NP_623103.1|, ref|ZP_02330045.1|, ref|YP_001665292.1|, and ref|YP_001665293.1| (SEQ ID NOS: 751-755), respectively, which all have the function assigned to SEQ ID NO: 749 in Table 1. Amino acids conserved among all sequences are indicted by a "*" and generally conserved amino acids are indicated by a ":".

FIG. 35 depicts a sequence alignment (ClustalW) between SEQ ID NO: 1361 (RAAC01427) and ref|NP_240926.1|, ref|ZP_02330558.1|, ref|YP_001419725.1|, ref|NP_829946.1|, and ref|NP_842611.1| (SEQ ID NOS: 1363-1367), respectively, which all have the function assigned to SEQ ID NO: 1361 in Table 1. Amino acids conserved among all sequences are indicted by a "*" and generally conserved amino acids are indicated by a ":".

FIG. 36 depicts a sequence alignment (ClustalW) between SEQ ID NO: 426 (RAAC00365) and ref|YP_173696.1|, ref|ZP_02329530.1|, ref|ZP_01696660.1|, ref|NP_241105.1|, and ref|YP_001124272.1| (SEQ ID NOS: 428-432), respectively, which all have the function assigned to SEQ ID NO: 426 in Table 1. Amino acids conserved among all sequences are indicted by a "*" and generally conserved amino acids are indicated by a ":".

FIGS. 37A and 37B depict a sequence alignment (ClustalW) between SEQ ID NO: 1531 (RAAC01563) and ref|ZP_01665476.1|, ref|ZP_02259717.1|, ref|YP_036745.1|, ref|YP_028716.1|, and ref|YP_083969.1| (SEQ ID NOS: 1533-1537), respectively, which all have the function assigned to SEQ ID NO: 1531 in Table 1. Amino acids conserved among all sequences are indicted by a "*" and generally conserved amino acids are indicated by a ":".

FIG. 38 depicts a sequence alignment (ClustalW) between SEQ ID NO: 2806 (RAAC02315) and ref|YP_145847.1|, gb|ABG00342.1|, ref|YP_536482.1|, ref|YP_891181.1|, and ref|YP_799230.1| (SEQ ID NOS: 2808-2812), respectively, which all have the function assigned to SEQ ID NO: 2806 in Table 1. Amino acids conserved among all sequences are indicted by a "*" and generally conserved amino acids are indicated by a ":".

FIG. 39 depicts a sequence alignment (ClustalW) between SEQ ID NO: 103 (RAAC00040) and ref|YP_001423364.1|, ref|NP_391977.1|, ref|YP_001488932.1|, ref|YP_093870.1|, and ref|YP_081433.1| (SEQ ID NOS: 105-109), respectively, which all have the function assigned to SEQ ID NO: 103 in Table 1 Amino acids conserved among all sequences are indicted by a "*" and generally conserved amino acids are indicated by a ":".

FIG. 40 depicts a sequence alignment (ClustalW) between SEQ ID NO: 205 (RAAC00113) and ref|ZP_01697918.1|, ref|YP_001125108.1|, emb|CAJ75583.1|, ref|YP_146973.1|, and ref|ZP_01172488.1| (SEQ ID NOS: 207-211), respectively, which all have the function assigned to SEQ ID NO: 205 in Table 1. Amino acids conserved among all sequences are indicted by a "*" and generally conserved amino acids are indicated by a ":".

FIGS. 41A and 41B depict a sequence alignment (ClustalW) between SEQ ID NO: 222 (RAAC00117) and ref|ZP_02330014.1|, emb|CAJ75587.1|, ref|YP_146977.1|, ref|YP_001125112.1|, and ref|NP_243425.1| (SEQ ID NOS: 224-228), respectively, which all have the function assigned to SEQ ID NO: 222 in Table 1. Amino acids conserved among all sequences are indicted by a "*" and generally conserved amino acids are indicated by a ":".

FIG. 42 depicts a sequence alignment (ClustalW) between SEQ ID NO: 239 (RAAC00118) and ref|YP_078922.1|, ref|YP_001375784.1|, ref|YP_02171874.1|, ref|YP_001646530.1|, and gb|AAN04557.1| (SEQ ID NOS: 241-245), respectively, which all have the function assigned to SEQ ID NO: 239 in Table 1. Amino acids conserved among all sequences are indicted by a "*" and generally conserved amino acids are indicated by a ":".

FIG. 43 depicts a sequence alignment (ClustalW) between SEQ ID NO: 1344 (RAAC01377) and ref|YP_47952.1|, ref|YP_520670.1|, ref|YP_001395809.1|, ref|YP_001309701.1|, and ref|YP_001643660.1| (SEQ ID NOS: 1346-1350), respectively, which all have the function assigned to SEQ ID NO: 1344 in Table 1. Amino acids conserved among all sequences are indicted by a "*" and generally conserved amino acids are indicated by a ":".

FIGS. 44A and 44B depict a sequence alignment (ClustalW) between SEQ ID NO: 2840 (RAAC02381) and ref|NP_622177.1|, ref|YP_848858.1|, ref|YP_001374688.1|, ref|NP_470039.1|, and ref|ZP_01929325.1| (SEQ ID NOS: 2842-2846), respectively, which all have the function assigned to SEQ ID NO: 2840 in Table 1. Amino acids conserved among all sequences are indicted by a "*" and generally conserved amino acids are indicated by a ":".

FIG. 45 depicts a sequence alignment (ClustalW) between SEQ ID NO: 1038 (RAAC00991) and ref|ZP_02327412.1|, ref|YP_001487207.1|, ref|ZP_01172765.1|, ref|NP_831314.1|, and ref|NP_844008.11 (SEQ ID NOS: 1040-1044), respectively, which all have the function assigned to SEQ ID NO: 1038 in Table 1. Amino acids conserved among all sequences are indicted by a "*" and generally conserved amino acids are indicated by a ":".

FIG. 46 depicts a sequence alignment (ClustalW) between SEQ ID NO: 766 (RAAC00650) and ref|YP_001127183.1|, ref|ZP_02038504.1|, ref|YP_001647987.1|, ref|YP_001377114.1|, and ref|NP_835081.1| (SEQ ID NOS: 768-772), respectively, which all have the function assigned to SEQ ID NO: 766 in Table 1. Amino acids conserved among all sequences are indicted by a "*" and generally conserved amino acids are indicated by a ":".

FIG. 47 depicts a sequence alignment (ClustalW) between SEQ ID NO: 2041 (RAAC02421) and ref|ZP_01721811.1|, ref|NP_241897.1|, ref|YP_001486101.1|, ref|ZP_01170532.1|, and ref|ZP_02327994.1| (SEQ ID NOS: 2043-2047), respectively, which all have the function assigned to SEQ ID NO: 2041 in Table 1. Amino acids conserved among all sequences are indicted by a "*" and generally conserved amino acids are indicated by a ":".

FIGS. 48A and 48B depict a sequence alignment (ClustalW) between SEQ ID NO: 1922 (RAAC02142) and ref|ZP_01860158.1|, ref|YP_148164.1|, ref|NP_242401.1|, ref|YP_001126336.1|, and ref|YP_001421751.1| (SEQ ID NOS: 1924-1928), respectively, which all have the function assigned to SEQ ID NO: 1922 in Table 1. Amino acids conserved among all sequences are indicted by a "*" and generally conserved amino acids are indicated by a ":".

FIGS. 49A and 49B depict a sequence alignment (ClustalW) between SEQ ID NO: 2687 (RAAC03015) and ref|NP_628606.1|, ref|ZP_02061285.1|, ref|NP_824958.1|, emb|CAA04971.1|, and gb|AAC32488.1| (SEQ ID NOS: 2689-2693), respectively, which all have the function assigned to SEQ ID NO: 2687 in Table 1. Amino acids conserved among all sequences are indicted by a "*" and generally conserved amino acids are indicated by a ":".

FIGS. 50A and 50B depict a sequence alignment (ClustalW) between SEQ ID NO: 2517 (RAAC02227) and ref|YP_430213.1|, ref|YP_001212426.1|, ref|YP_001663198.1|, ref|YP_360920.1|, and ref|YP_001665129.1| (SEQ ID NOS: 2519-2523), respectively, which all have the function assigned to SEQ ID NO: 2517 in Table 1. Amino acids conserved among all sequences are indicted by a "*" and generally conserved amino acids are indicated by a ":".

FIG. 51 depicts a sequence alignment (ClustalW) between SEQ ID NO: 834 (RAAC00872) and ref|NP_622598.1|, ref|YP_001320854.1|, ref|YP_001665389.1|, ref|YP_001037463.1|, and ref|YP_001512768.1| (SEQ ID NOS: 836-840), respectively, which all have the function assigned to SEQ ID NO: 834 in Table 1. Amino acids conserved among all sequences are indicted by a "*" and generally conserved amino acids are indicated by a ":".

FIG. 52 depicts a sequence alignment (ClustalW) between SEQ ID NO: 120 (RAAC00045) and ref|ZP_02172045.1|, ref|ZP_11089194.1|, ref|NP_244931.1|, ref|YP_001213468.1|, and ref|YP_358877.1| (SEQ ID NOS: 122-126), respectively, which all have the function assigned to SEQ ID NO: 120 in Table 1. Amino acids conserved among all sequences are indicted by a "*" and generally conserved amino acids are indicated by a ":".

FIGS. 53A and 53B depict a sequence alignment (ClustalW) between SEQ ID NO: 2092 (RAAC02428) and dbj|BAB83769.1|, ref|YP_146913.1|, sp|P11961|ODP2_BACST, ref|ZP_01696305.1|, and ref|YP_001125047.1| (SEQ ID NOS: 2094-2098), respectively, which all have the function assigned to SEQ ID NO: 2092 in Table 1. Amino acids conserved among all sequences are indicted by a "*" and generally conserved amino acids are indicated by a ":".

FIGS. 54A and 54B depict a sequence alignment (ClustalW) between SEQ ID NO: 1650 (RAAC01659) and ref|ZP_02326222.1|, ref|NP_241081.1|, ref|YP_074242.1|, ref|YP_001153408.1|, and ref|NP_560158.1| (SEQ ID NOS: 1652-1656), respectively, which all have the function assigned to SEQ ID NO: 1650 in Table 1. Amino acids conserved among all sequences are indicted by a "*" and generally conserved amino acids are indicated by a ":".

FIG. 55 depicts a sequence alignment (ClustalW) between SEQ ID NO: 1701 (RAAC01745) and ref|YP_001127228.1|, ref|YP_149070.1|, ref|ZP_00539127.1|, ref|ZP_02326224.1|, and ref|NP_241079.1| (SEQ ID NOS: 1703-1707), respectively, which all have the function assigned to SEQ ID NO: 1701 in Table 1. Amino acids conserved among all sequences are indicted by a "*" and generally conserved amino acids are indicated by a ":".

FIG. 56 depicts a sequence alignment (ClustalW) between SEQ ID NO: 1718 (RAAC01746) and ref|YP_149069.1|, ref|YP_001127227.1|, ref|ZP_00539126.1|, ref|YP_001125046.1|, and ref|NP_833691.1| (SEQ ID NOS: 1720-1724), respectively, which all have the function assigned to SEQ ID NO: 1718 in Table 1. Amino acids conserved among all sequences are indicted by a "*" and generally conserved amino acids are indicated by a ":".

FIG. 57 depicts a sequence alignment (ClustalW) between SEQ ID NO: 2058 (RAAC02426) and ref|NP_243521.1|, pdb|1W85|A, sp|P21873|ODPA_BACST, ref|YP_001421036.1|, and ref|YP_46911.1| (SEQ ID NOS: 2060-2064), respectively, which all have the function assigned to SEQ ID NO: 2058 in Table 1. Amino acids conserved among all sequences are indicted by a "*" and generally conserved amino acids are indicated by a ":".

FIG. 58 depicts a sequence alignment (ClustalW) between SEQ ID NO: 2075 (RAAC02427) and ref|ZP_01696304.1|, sp|P21874|ODPB_BACST, ref|YP_001125046.1|, pdb|1W85|B, and ref|YP_146912.1| (SEQ ID NOS: 2077-2081), respectively, which all have the function assigned to SEQ ID NO: 2075 in Table 1. Amino acids conserved among all sequences are indicted by a "*" and generally conserved amino acids are indicated by a ":".

FIG. 59 depicts a sequence alignment (ClustalW) between SEQ ID NO: 1616 (RAAC01657) and ref|ZP_02326224.1|, dbj|BAB40585.1|, ref|NP_241079.1|, ref|YP_001126012.1|, and ref|ZP_01171269.1| (SEQ ID NOS: 1618-1622), respectively, which all have the function assigned to SEQ ID NO: 1616 in Table 1. Amino acids conserved among all sequences are indicted by a "*" and generally conserved amino acids are indicated by a ":".

FIG. 60 depicts a sequence alignment (ClustalW) between SEQ ID NO: 1633 (RAAC01658) and ref|ZP_02326223.1|, ref|NP_241080.1|, dbj|BAB40586.1|, ref|YP_001126011.1|, and ref|NP_693798.1| (SEQ ID NOS: 1635-1639), respectively, which all have the function assigned to SEQ ID NO: 1633 in Table 1. Amino acids conserved among all sequences are indicted by a "*" and generally conserved amino acids are indicated by a ":".

FIGS. 61A and 61B depict a sequence alignment (ClustalW) between SEQ ID NO: 630 (RAAC00484) and ref|YP_001125466.1|, ref|ZP_01697095.1|, ref|YP_147353.1|, ref|ZP_01886631.1|, and ref|YP_077737.1| (SEQ ID NOS: 632-636), respectively, which all have the function assigned to SEQ ID NO: 630 Table 1. Amino acids conserved among all sequences are indicted by a "*" and generally conserved amino acids are indicated by a ":".

FIG. 62 depicts a sequence alignment (ClustalW) between SEQ ID NO: 613 (RAAC00483) and ref|NP_886151.1|, ref|YP_147354.1|, ref|YP_001125467.1|, ref|YP_001420062.1|, and ref|NP_242684.1| (SEQ ID NOS: 615-619), respectively, which all have the function assigned to SEQ ID NO: 613 in Table 1. Amino acids conserved among all sequences are indicted by a "*" and generally conserved amino acids are indicated by a ":".

FIG. 63 depicts a sequence alignment (ClustalW) between SEQ ID NO: 290 (RAAC00134) and ref|ZP_01860800.1|, ref|YP_47000.1|, ref|ZP_01695960.1|, ref|YP_001125127.1|, and ref|YP_806677.1| (SEQ ID NOS: 292-296), respectively, which all have the function assigned to SEQ ID NO: 290 in Table 1. Amino acids conserved among all sequences are indicted by a "*" and generally conserved amino acids are indicated by a ":".

FIG. 64 depicts a sequence alignment (ClustalW) between SEQ ID NO: 358 (RAAC00215) and ref|YP_145879.1|, ref|ZP_01697513.1|, ref|YP_001124157.1|, ref|ZP_01174007.1|, and ref|YP_001642924.1| (SEQ ID NOS: 360-364), respectively, which all have the function assigned to SEQ ID NO: 358 in Table 1. Amino acids conserved among all sequences are indicted by a "*" and generally conserved amino acids are indicated by a ":".

FIG. 65 depicts a sequence alignment (ClustalW) between SEQ ID NO: 2177 (RAAC02164) and ref|YP_359129.1|, ref|ZP_02127016.1|, ref|YP_001540277.1|, pdb|1M2N|A, and pdb|1M2K|A (SEQ ID NOS: 2179-2183), respectively, which all have the function assigned to SEQ ID NO: 2177 in Table 1. Amino acids conserved among all sequences are indicted by a "*" and generally conserved amino acids are indicated by a ":".

FIGS. 66A-66C depict a sequence alignment (ClustalW) between SEQ ID NO: 1395 (RAAC01438) and ref|YP_173587.1|, ref|NP_240935.1|, ref|YP_001373418.1|, ref|YP_892975.1|, and ref|NP_976379.1| (SEQ ID NOS: 1397-1401), respectively, which all have the function assigned to SEQ ID NO: 1395 in Table 1. Amino acids conserved among all sequences are indicted by a "*" and generally conserved amino acids are indicated by a ":".

FIG. 67 depicts a sequence alignment (ClustalW) between SEQ ID NO: 2755 (RAAC03184) and ref|YP_001105447.1|, ref|YP_117520.1|, ref|YP_046943.1|, ref|YP_707186.1|, and ref|YP_001337847.1| (SEQ ID NOS: 2757-2761), respectively, which all have the function assigned to SEQ ID NO: 2755 in Table 1. Amino acids conserved among all sequences are indicted by a "*" and generally conserved amino acids are indicated by a ":".

FIG. 68 depicts a sequence alignment between SEQ ID NO: 2859 (RAAC02740) and ref|NP_391246.1|, ref|YP_001488252.1|, ref|YP_244416.1|, ref|YP_001112264.1|, and ref|YP_430670.1| (SEQ ID NOS: 2861-2865), respectively, which all have the function assigned to SEQ ID NO: 2859 in Table 1. Amino acids conserved among all sequences are indicted by a "*" and generally conserved amino acids are indicated by a ":".

FIG. 69 depicts a sequence alignment between SEQ ID NO: 2893 (RAAC02937) and ref|YP_075413.1|, ref|YP_001662816.1|, ref|YP_001664674.1|, ref|YP_827514.1|, and ref|YP_827514.1| (SEQ ID NOS: 2895-2899), respectively, which all have the function assigned to SEQ ID NO: 2893 in Table 1. Amino acids conserved among all sequences are indicted by a "*" and generally conserved amino acids are indicated by a ":".

FIG. 70 depicts a sequence alignment (ClustalW) between SEQ ID NO: 783 (RAAC00675) and ref|YP_001373772.1|, ref|YP_034761.1|, ref|YP_893335.1|, ref|ZP_00237972.1|, and ref|ZP_02329595.1| (SEQ ID NOS: 785-789), respectively, which all have the function assigned to SEQ ID NO: 783 in Table 1. Amino acids conserved among all sequences are indicted by a "*" and generally conserved amino acids are indicated by a ":".

FIG. 71 depicts a sequence alignment (ClustalW) between SEQ ID NO: 2789 (RAAC02292) and gb|AAB91591.1|, ref|YP_001422657.1|, ref|NP_391247.1|, ref|YP_093160.1|, and ref|NP_391246.1| (SEQ ID NOS: 2791-2795), respectively, which all have the function assigned to SEQ ID NO: 2789 in Table 1. Amino acids conserved among all sequences are indicted by a "*" and generally conserved amino acids are indicated by a ":".

FIG. 72 depicts a sequence alignment (ClustalW) between SEQ ID NO: 1599 (RAAC01655) and ref|ZP_00235680.1|, ref|NP_241278.1|, ref|NP_845841.1|, ref|ZP_02260616.1|, and ref|ZP_02256143.1| (SEQ ID NOS: 1601-1605), respectively, which all have the function assigned to SEQ ID NO: 1599 Table 1. Amino acids conserved among all sequences are indicted by a "*" and generally conserved amino acids are indicated by a ":".

FIG. 73 depicts a sequence alignment (ClustalW) between SEQ ID NO: 545 (RAAC00436) and ref|ZP_02171828.1|, ref|YP_077369.1|, ref|YP_001485328.1|, ref|ZP_02329455.1|, and ref|YP_001419762.1| (SEQ ID NOS: 547-551), respectively, which all have the function assigned to SEQ ID NO: 545 in Table 1. Amino acids conserved among all sequences are indicted by a "*" and generally conserved amino acids are indicated by a ":".

FIG. 74 depicts a sequence alignment (ClustalW) between SEQ ID NO: 1429 (RAAC01464) and ref|YP_001485324.1|, ref|YP_001124204.1|, ref|YP_145925.1|, ref|YP_077366.1|, and ref|NP_829977.1| (SEQ ID NOS: 1431-1435), respectively, which all have the function assigned to SEQ ID NO: 1429 in Table 1. Amino acids conserved among all sequences are indicted by a "*" and generally conserved amino acids are indicated by a ":".

FIG. 75 depicts a sequence alignment (ClustalW) between SEQ ID NO: 698 (RAAC00579) and ref|ZP_01440002.1|, ref|NP_896891.1|, ref|YP_001623237.1|, ref|ZP_01419169.1|, and ref|ZP_01084741.1| (SEQ ID NOS: 700-704), respectively, which all have the function assigned to SEQ ID NO: 698 in Table 1. Amino acids conserved among all sequences are indicted by a "*" and generally conserved amino acids are indicated by a ":".

FIG. 76 depicts a sequence alignment (ClustalW) between SEQ ID NO: 2721 (RAAC03156) and ref|YP_954024.1|, ref|YP_001360254.1|, ref|YP_001156989.1|, ref|ZP_00050136.2|, and ref|YP_591607.1| (SEQ ID NOS: 2723-2727), respectively, which all have the function assigned to SEQ ID NO: 2721 in Table 1. Amino acids conserved among all sequences are indicted by a "*" and generally conserved amino acids are indicated by a ":".

FIG. 77 depicts a sequence alignment (ClustalW) between SEQ ID NO: 715 (RAAC00603) and ref|YP_001309477.1|, ref|YP_001180339.1|, ref|NP_242735.1|, ref|YP_173905.1|, and ref|ZP_00603386.1| (SEQ ID NOS: 717-721), respectively, which all have the function assigned to SEQ ID NO: 715 in Table 1. Amino acids conserved among all sequences are indicted by a "*" and generally conserved amino acids are indicated by a ":".

FIG. 78 depicts a sequence alignment (ClustalW) between SEQ ID NO: 2738 (RAAC03180) and ref|YP_001664041.1|, ref|YP_001210714.1|, ref|NP_242309.1|, ref|ZP_02038515.1|, and ref|YP_085042.1| (SEQ ID NOS: 2740-2744), respectively, which all have the function assigned to SEQ ID NO: 2738 in Table 1. Amino acids conserved among all sequences are indicted by a "*" and generally conserved amino acids are indicated by a ":".

FIG. 79 depicts a sequence alignment (ClustalW) between SEQ ID NO: 2024 (RAAC02417) and ref|NP_469419.1|, ref|ZP_02309926.1|, ref|ZP_01926077.1|, ref|ZP_01941236.1|, and ref|YP_001111866.1| (SEQ ID NOS: 2026-2030), respectively, which all have the function assigned to SEQ ID NO: 2024 in Table 1. Amino acids conserved among all sequences are indicted by a "*" and generally conserved amino acids are indicated by a ":".

FIG. 80 depicts a sequence alignment (ClustalW) between SEQ ID NO: 1786 (RAAC01912) and ref|YP_001103030.1|, ref|YP_001363698.1|, ref|NP_625321.1|, ref|YP_822608.1|, and ref|ZP_00996757.1| (SEQ ID NOS: 1788-1792), respectively, which all have the function assigned to SEQ ID NO: 1786 in Table 1. Amino acids conserved among all sequences are indicted by a "*" and generally conserved amino acids are indicated by a ":".

FIG. 81 depicts a sequence alignment (ClustalW) between SEQ ID NO: 2330 (RAAC02663) and ref|YP_527240.1|, ref|NP_435364.1|, ref|YP_001313948.1|, ref|YP_001169444.1|, and ref|ZP_01509063.1| (SEQ ID NOS: 2332-2336), respectively, which all have the function assigned to SEQ ID NO: 2330 in Table 1. Amino acids conserved among all sequences are indicted by a "*" and generally conserved amino acids are indicated by a ":".

FIG. 82 depicts a sequence alignment (ClustalW) between SEQ ID NO: 1191 (RAAC01158) and ref|YP_077724.1|, ref|YP_643029.1|, ref|YP_174340.1|, ref|YP_001308645.1|, and ref|YP_516602.1| (SEQ ID NOS: 1193-1197), respectively, which all have the function assigned to SEQ ID NO: 1191 in Table 1. Amino acids conserved among all sequences are indicted by a "*" and generally conserved amino acids are indicated by a ":".

FIG. 83 depicts a sequence alignment (ClustalW) between SEQ ID NO: 137 (RAAC00068) and ref|ZP_02328287.1|, ref|YP_001420528.1|, ref|YP_430032.1|, ref|ZP_02082978.1|, and ref|ZP_01962813.1| (SEQ ID NOS: 139-143), respectively, which all have the function assigned to SEQ ID NO: 137 in Table 1. Amino acids conserved among all sequences are indicted by a "*" and generally conserved amino acids are indicated by a ":".

FIG. 84 depicts a sequence alignment (ClustalW) between SEQ ID NO: 1055 (RAAC01035) and ref|YP_1642998.1|, ref|NP_822795.1|, emb|CAJ88752.1|, ref|YP_001191149.1|, and ref|YP_752794.1| (SEQ ID NOS: 1057-1061), respectively, which all have the function assigned to SEQ ID NO: 1055 in Table 1. Amino acids conserved among all sequences are indicted by a "*" and generally conserved amino acids are indicated by a ":".

FIG. 85 depicts a sequence alignment (ClustalW) between SEQ ID NO: 1854 (RAAC02031) and ref|YP_148128.1|, ref|YP_001126297.1|, ref|YP_900875.1|, ref|ZP_01662088.1|, and ref|ZP_01697892.1| (SEQ ID NOS: 1856-1860), respectively, which all have the function assigned to SEQ ID NO: 1854 in Table 1. Amino acids conserved among all sequences are indicted by a "*" and generally conserved amino acids are indicated by a ":".

FIG. 86 depicts a sequence alignment (ClustalW) between SEQ ID NO: 2653 (RAAC03005) and ref|YP_001127075.1|, ref|YP_48880.1|, ref|YP_832996.1|, ref|YP_949591.1|, and ref|YP_950253.1| (SEQ ID NOS: 2655-2659), respectively, which all have the function assigned to SEQ ID NO: 2653 in Table 1. Amino acids conserved among all sequences are indicted by a "*" and generally conserved amino acids are indicated by a ":".

FIG. 87 depicts a sequence alignment (ClustalW) between SEQ ID NO: 2160 (RAAC02459) and ref|YP_073926.1|, emb|CAB08003.1|, ref|YP_431134.1|, ref|YP_001422711.1|, and ref|YP_080763.1| (SEQ ID NOS: 2162-2166), respectively, which all have the function assigned to SEQ ID NO: 2160 in Table 1. Amino acids conserved among all sequences are indicted by a "*" and generally conserved amino acids are indicated by a ":".

FIG. 88 depicts a sequence alignment (ClustalW) between SEQ ID NO: 1293 (RAAC01353) and RAAC01353_nuc, ref|YP_147389.1|, ref|NP_243003.1|, ref|YP_001125502.1|, and ref|YP_001665938.1| (SEQ ID NOS: 1294-1298), respectively, which all have the function assigned to SEQ ID NO: 1293 in Table 1. Amino acids conserved among all sequences are indicted by a "*" and generally conserved amino acids are indicated by a ":".

FIG. 89 depicts a sequence alignment (ClustalW) between SEQ ID NO: 2109 (RAAC02432) and ref|ZP_02329176.1|, ref|YP_076367.1|, ref|NP_694155.1|, ref|YP_001126042.1|, and ref|YP_643152.1| (SEQ ID NOS: 2111-2115), respectively, which all have the function assigned to SEQ ID NO: 2109 in Table 1. Amino acids conserved among all sequences are indicted by a "*" and generally conserved amino acids are indicated by a ":".

FIG. 90 depicts a sequence alignment (ClustalW) between SEQ ID NO: 681 (RAAC00570) and emb|CAB65654.1|, ref|YP_001662226.1|, ref|YP_001664166.1|, ref|NP_624096.1|, and ref|ZP_02171282.1| (SEQ ID NOS: 683-687), respectively, which all have the function assigned to SEQ ID NO: 681 in Table 1. Amino acids conserved among all sequences are indicted by a "*" and generally conserved amino acids are indicated by a ":".

FIG. 91 depicts a sequence alignment (ClustalW) between SEQ ID NO: 375 (RAAC00269) and ref|ZP_01188890.1|, ref|ZP_11088246.1|, ref|ZP_11088241.1|, ref|NP_242794.1|, and ref|NP_244559.1| (SEQ ID NOS: 377-381), respectively, which all have the function assigned to SEQ ID NO: 375 in Table 1. Amino acids conserved among all sequences are indicted by a "*" and generally conserved amino acids are indicated by a ":".

FIG. 92 depicts a sequence alignment (ClustalW) between SEQ ID NO: 1837 (RAAC02012) and ref|YP_430255.1|, ref|YP_518526.1|, ref|ZP_01369294.1|, ref|YP_361384.1|, and ref|YP_001213325.1| (SEQ ID NOS: 1839-1843), respectively, which all have the function assigned to SEQ ID NO: 1837 in Table 1. Amino acids conserved among all sequences are indicted by a "*" and generally conserved amino acids are indicated by a ":".

FIG. 93 depicts a sequence alignment (ClustalW) between SEQ ID NO: 1667 (RAAC01701) and ref|NP_691275.1|, ref|NP_354021.1|, ref|YP_174284.1|, ref|ZP_01074644.1|, and ref|NP_772010.1| (SEQ ID NOS: 1669-1673), respectively, which all have the function assigned to SEQ ID NO: 1667 in Table 1 Amino acids conserved among all sequences are indicted by a "*" and generally conserved amino acids are indicated by a ":".

FIG. 94 depicts a sequence alignment (ClustalW) between SEQ ID NO: 936 (RAAC00927) and ref|ZP_02330514.1|, ref|NP_347485.1|, ref|YP_001253394.1|, ref|YP_001308605.1|, and ref|YP_001376921.1| (SEQ ID NOS: 938-942), respectively, which all have the function assigned to SEQ ID NO: 936 in Table 1. Amino acids conserved among all sequences are indicted by a "*" and generally conserved amino acids are indicated by a ":".

FIG. 95 depicts a sequence alignment (ClustalW) between SEQ ID NO: 953 (RAAC00935) and ref|YP_001422559.1|, ref|NP_391166.1|, gb|AAB87745.4 pdb|S3J|A, and ref|YP_001643469.1| (SEQ ID NOS: 955-959), respectively, which all have the function assigned to SEQ ID NO: 953 in Table 1 Amino acids conserved among all sequences are indicted by a "*" and generally conserved amino acids are indicated by a ":".

FIG. 96 depicts a sequence alignment (ClustalW) between SEQ ID NO: 1888 (RAAC02041) and ref|NP_693030.1|, ref|YP_001320949.1|, ref|YP_001512727.1|, ref|YP_001126687.1|, and ref|YP_148522.1| (SEQ ID NOS: 1890-1894), respectively, which all have the function assigned to SEQ ID NO: 1888 in Table 1. Amino acids conserved among all sequences are indicted by a "*" and generally conserved amino acids are indicated by a ":".

FIG. 97 depicts a sequence alignment (ClustalW) between SEQ ID NO: 2670 (RAAC02241) and ref|NP_629113.1|, ref|NP_824479.1|, ref YP_001508494.1|, ref|ZP_01169478.1|, and ref|NP_631123.1| (SEQ ID NOS: 2672-2676), respectively, which all have the function assigned to SEQ ID NO: 2670 in Table 1. Amino acids conserved among all sequences are indicted by a "*" and generally conserved amino acids are indicated by a ":".

FIG. 98 depicts a sequence alignment (ClustalW) between SEQ ID NO: 2347 (RAAC02671) and ref|NP_388620.1|, ref|YP_001420380.1|, ref|YP_090401.1|, ref|YP_077997.1|, and ref|YP_714968.1| (SEQ ID NOS: 2349-2353), respectively, which all have the function assigned to SEQ ID NO: 2347 in Table 1. Amino acids conserved among all sequences are indicted by a "*" and generally conserved amino acids are indicated by a ":".

FIG. 99 depicts a sequence alignment (ClustalW) between SEQ ID NO: 664 (RAAC00549) and ref|YP_427081.1|, ref|YP_001141973.1|, ref|YP_927240.1|, ref|YP_001141729.1|, and ref|YP_856665.1| (SEQ ID NOS: 666-670), respectively, which all have the function assigned to SEQ ID NO: 664 in Table 1. Amino acids conserved among all sequences are indicted by a "*" and generally conserved amino acids are indicated by a ":".

FIG. 100 depicts a sequence alignment (ClustalW) between SEQ ID NO: 1123 (RAAC01080) and dbj|BAA00729.1|, ref|NP_389627.1|, ref|ZP_

02328256.1|, ref|NP_833433.1|, and ref|YP_001375615.1| (SEQ ID NOS: 1125-1129), respectively, which all have the function assigned to SEQ ID NO: 1123 in Table 1. Amino acids conserved among all sequences are indicted by a "*" and generally conserved amino acids are indicated by a ":".

FIG. 101 depicts a sequence alignment (ClustalW) between SEQ ID NO: 1140 (RAAC01126) and ref|YP_146517.1|, ref|ZP_00739458.1|, ref|YP_001124699.1|, ref|YP_893832.1|, and ref|NP_830863.1| (SEQ ID NOS: 1142-1146), respectively, which all have the function assigned to SEQ ID NO: 664 in Table 1. Amino acids conserved among all sequences are indicted by a "*" and generally conserved amino acids are indicated by a ":".

FIG. 102 depicts a sequence alignment (ClustalW) between SEQ ID NO: 1174 (RAAC01138) and ref|NP_832103.1|, ref|YP_894956.1|, ref|ZP_02215257.1|, ref|NP_978750.1|, and ref|NP_844783.1| (SEQ ID NOS: 1176-1180), respectively, which all have the function assigned to SEQ ID NO: 1174 in Table 1. Amino acids conserved among all sequences are indicted by a "*" and generally conserved amino acids are indicated by a ":".

FIG. 103 depicts a sequence alignment (ClustalW) between SEQ ID NO: 409 (RAAC00354) and ref|YP_001309939.1|, ref|YP_001643723.1|, ref|YP_079403.1|, ref|YP_001647188.1|, and ref|NP_980994.1| (SEQ ID NOS: 411-415), respectively, which all have the function assigned to SEQ ID NO: 409 in Table 1. Amino acids conserved among all sequences are indicted by a "*" and generally conserved amino acids are indicated by a ":".

FIG. 104 depicts a sequence alignment (ClustalW) between SEQ ID NO: 2415 (RAAC02712) and ref|YP_036650.1|, ref|NP_978853.1|, ref|ZP_01173627.1|, ref|NP_844911.1|, and ref|ZP_02256518.1| (SEQ ID NOS: 2417-2421), respectively, which all have the function assigned to SEQ ID NO: 2415 in Table 1. Amino acids conserved among all sequences are indicted by a "*" and generally conserved amino acids are indicated by a ":".

FIG. 105 depicts a sequence alignment (ClustalW) between SEQ ID NO: 1072 (RAAC01059) and ref|ZP_02327699.1|, ref|YP_001126706.1|, ref|YP_48542.1|, ref|NP_243968.1|, and ref|YP_360433.1| (SEQ ID NOS: 1074-1078), respectively, which all have the function assigned to SEQ ID NO: 1072 in Table 1. Amino acids conserved among all sequences are indicted by a "*" and generally conserved amino acids are indicated by a ":".

FIG. 106 depicts a sequence alignment (ClustalW) between SEQ ID NO: 1565 (RAAC01638) and ref|YP_076316.1|, ref|YP_603589.1|, ref|NP_296097.1|, ref|YP_004584.1|, and ref|YP_144239.1| (SEQ ID NOS: 1567-1571), respectively, which all have the function assigned to SEQ ID NO: 1565 in Table 1. Amino acids conserved among all sequences are indicted by a "*" and generally conserved amino acids are indicated by a ":".

FIG. 107 depicts a sequence alignment (ClustalW) between SEQ ID NO: 1973 (RAAC02161) and ref|YP_148132.1|, ref|YP_001126301.1|, ref|ZP_02330236.1|, ref|NP_242446.1|, and ref|YP_175331.1| (SEQ ID NOS: 1975-1979), respectively, which all have the function assigned to SEQ ID NO: 1973 in Table 1 Amino acids conserved among all sequences are indicted by a "*" and generally conserved amino acids are indicated by a ":".

FIG. 108 depicts a sequence alignment (ClustalW) between SEQ ID NO: 392 (RAAC00349) and ref|YP_430046.1|, ref|YP_358986.1|, ref|YP_001213400.1|, ref|ZP_02330078.1|, and ref|YP_001114520.1| (SEQ ID NOS: 394-398), respectively, which all have the function assigned to SEQ ID NO: 392 in Table 1. Amino acids conserved among all sequences are indicted by a "*" and generally conserved amino acids are indicated by a ":".

FIG. 109 depicts a sequence alignment (ClustalW) between SEQ ID NO: 1327 (RAAC01375) and ref|YP_079987.1|, ref|YP_001634921.1|, ref|YP_290510.1|, ref|YP_001423330.1|, and ref|YP_001422015.1| (SEQ ID NOS: 1329-1333), respectively, which all have the function assigned to SEQ ID NO: 1327 in Table 1. Amino acids conserved among all sequences are indicted by a "*" and generally conserved amino acids are indicated by a ":".

FIG. 110 depicts a sequence alignment (ClustalW) between SEQ ID NO: 18 (RAAC00013) and ref|YP_146744.1|, ref|YP_001647744.1|, ref|NP_981573.1|, ref|ZP_02255842.1|, and ref|YP_897365.1| (SEQ ID NOS: 20-24), respectively, which all have the function assigned to SEQ ID NO: 18 in Table 1. Amino acids conserved among all sequences are indicted by a "*" and generally conserved amino acids are indicated by a ":".

FIG. 111 depicts a sequence alignment (ClustalW) between SEQ ID NO: 1480 (RAAC01493) and ref|YP_075596.1|, ref|YP_430668.1|, ref|YP_590553.1|, ref|YP_478499.1|, and ref|YP_001668480.1| (SEQ ID NOS: 1482-1486), respectively, which all have the function assigned to SEQ ID NO: 1480 in Table 1. Amino acids conserved among all sequences are indicted by a "*" and generally conserved amino acids are indicated by a ":".

FIG. 112 depicts a sequence alignment (ClustalW) between SEQ ID NO: 1582 (RAAC01653) and ref|ZP_00743391.1|, ref|YP_001375561.1|, ref|YP_896056.1|, ref|NP_845992.1|, and ref|ZP_02254866.1| (SEQ ID NOS: 1584-1588), respectively, which all have the function assigned to SEQ ID NO: 1582 in Table 1. Amino acids conserved among all sequences are indicted by a "*" and generally conserved amino acids are indicated by a ":".

FIG. 113 depicts a sequence alignment (ClustalW) between SEQ ID NO: 528 (RAAC00430) and ref|YP_001210836.1|, ref|YP_001111557.1|, ref|YP_001485333.1|, ref|NP_240971.1|, and ref|NP_387969.1| (SEQ ID NOS: 530-534), respectively, which all have the function assigned to SEQ ID NO: 528 in Table 1. Amino acids conserved among all sequences are indicted by a "*" and generally conserved amino acids are indicated by a ":".

FIG. 114 depicts a sequence alignment (ClustalW) between SEQ ID NO: 2823 (RAAC02359) and ref|NP_832076.1|, ref|YP_001645033.1|, ref|NP_844759.1|, ref|YP_001375058.1|, and ref|YP_535778.1| (SEQ ID NOS: 2825-2829), respectively, which all have the function assigned to SEQ ID NO: 2823 in Table 1. Amino acids conserved among all sequences are indicted by a "*" and generally conserved amino acids are indicated by a ":".

FIG. 115 depicts a sequence alignment (ClustalW) between SEQ ID NO: 2279 (RAAC02589) and ref|ZP_00591928.1|, ref|YP_001003150.1|, ref|NP_046614.1|, ref|YP_375842.1|, and ref|YP_001131112.1| (SEQ ID NOS: 2281-2285), respectively, which all have the function assigned to SEQ ID NO: 2279 in Table 1. Amino acids conserved among all sequences are indicted by a "*" and generally conserved amino acids are indicated by a ":".

FIG. 116 depicts a sequence alignment (ClustalW) between SEQ ID NO: 1412 (RAAC01442) and ref|ZP_02170919.1|, ref|YP_535778.1|, ref|ZP_01862118.1|, ref|NP_692713.1|, and ref|YP_359077.1| (SEQ ID NOS: 1414-1418), respectively, which all have the function assigned to SEQ ID NO: 1412 in Table 1. Amino acids conserved among all sequences are indicted by a "*" and generally conserved amino acids are indicated by a ":".

FIG. 117 depicts a sequence alignment (ClustalW) between SEQ ID NO: 69 (RAAC00027) and ref|YP_001213441.1|, ref|NP_244917.1|, ref|YP_001377189.1|, ref|YP_149334.1|, and ref|YP_077145.1| (SEQ ID NOS: 71-75), respectively, which all have the function assigned to SEQ ID NO: 69 in Table 1. Amino acids conserved among all sequences are indicted by a "*" and generally conserved amino acids are indicated by a ":".

FIG. 118 depicts a sequence alignment (ClustalW) between SEQ ID NO: 2245 (RAAC02508) and ref|NP_624000.1|, ref|YP_001662406.1|, ref|YP_001664279.1|, ref|YP_001038261.1|, and ref|YP_001394883.1| (SEQ ID NOS: 2247-2251), respectively, which all have the function assigned to SEQ ID NO: 2245 in Table 1. Amino acids conserved among all sequences are indicted by a "*" and generally conserved amino acids are indicated by a ":".

FIG. 119 depicts a sequence alignment (ClustalW) between SEQ ID NO: 885 (RAAC00905) and ref|ZP_00739566.1|, ref|NP_830389.1|, ref|YP_001643379.1|, ref|ZP_00237866.1|, and ref|YP_034830.1| (SEQ ID NOS: 887-891), respectively, which all have the function assigned to SEQ ID NO: 885 in Table 1. Amino acids conserved among all sequences are indicted by a "*" and generally conserved amino acids are indicated by a ":".

FIG. 120 depicts a sequence alignment (ClustalW) between SEQ ID NO: 1769 (RAAC01903) and ref|YP_001244333.1|, emb|CAI44346.1|, ref|ZP_02128221.1|, ref|NP_228001.1|, and ref|ZP_02171167.1| (SEQ ID NOS: 1771-1775), respectively, which all have the function assigned to SEQ ID NO: 1769 in Table 1 Amino acids conserved among all sequences are indicted by a "*" and generally conserved amino acids are indicated by a ":".

FIG. 121 depicts a sequence alignment (ClustalW) between SEQ ID NO: 987 (RAAC00981) and ref|YP_290547.1|, ref|YP_074752.1|, ref|YP_480150.1|, ref|YP_001509772.1|, and ref|NP_627230.1| (SEQ ID NOS: 989-993), respectively, which all have the function assigned to SEQ ID NO: 987 in Table 1. Amino acids conserved among all sequences are indicted by a "*" and generally conserved amino acids are indicated by a ":".

FIGS. 122A and 122B depict a sequence alignment (ClustalW) between SEQ ID NO: 1004 (RAAC00986) and ref|YP_001489923.1|, ref|ZP_01964315.1|, ref|NP_937072.1|, ref|NP_762428.1|, and ref|ZP_01847462.1| (SEQ ID NOS: 1006-1010), respectively, which all have the function assigned to SEQ ID NO: 1004 Table 1. Amino acids conserved among all sequences are indicted by a "*" and generally conserved amino acids are indicated by a ":".

FIGS. 123A and 123B depict a sequence alignment (ClustalW) between SEQ ID NO: 2704 (RAAC03031) and ref|ZP_01170738.1|, ref|ZP_00539543.1|, ref|ZP_02168828.1|, ref|ZP_01856429.1|, and ref|YP_001114416.1| (SEQ ID NOS: 2706-2710), respectively, which all have the function assigned to SEQ ID NO: 2704 Table 1. Amino acids conserved among all sequences are indicted by a "*" and generally conserved amino acids are indicated by a ":".

FIG. 124 depicts a sequence alignment (ClustalW) between SEQ ID NO: 1803 (RAAC01956) and pdb|1B4A|A, sp|O31408|ARGR_BACST, ref|ZP_00538558.1|, ref|NP_243643.1|, and ref|YP_001126414.1| (SEQ ID NOS: 1805-1809), respectively, which all have the function assigned to SEQ ID NO: 1803 in Table 1. Amino acids conserved among all sequences are indicted by a "*" and generally conserved amino acids are indicated by a ":".

FIG. 125 depicts a sequence alignment (ClustalW) between SEQ ID NO: 1497 (RAAC01498) and ref|YP_001127098.1|, ref|YP_148912.1|, ref|ZP_01696601.1|, ref|YP_176517.1|, and ref|ZP_01171675.1| (SEQ ID NOS: 1499-1503), respectively, which all have the function assigned to SEQ ID NO: 1497 in Table 1. Amino acids conserved among all sequences are indicted by a "*" and generally conserved amino acids are indicated by a ":".

FIG. 126 depicts a sequence alignment (ClustalW) between SEQ ID NO: 1548 (RAAC01624) and ref|YP_090740.1|, ref|YP_078338.1|, ref|NP_243093.1|, ref|YP_001126180.1|, and ref|YP_001422307.1| (SEQ ID NOS: 1550-1554), respectively, which all have the function assigned to SEQ ID NO: 1548 in Table 1. Amino acids conserved among all sequences are indicted by a "*" and generally conserved amino acids are indicated by a ":".

FIG. 127 depicts a sequence alignment (ClustalW) between SEQ ID NO: 171 (RAAC00077) and ref|ZP_01696173.1|, ref|ZP_02327860.1|, ref|ZP_00539488.1|, ref|NP_694112.1|, and ref|YP_034511.1| (SEQ ID NOS: 173-177), respectively, which all have the function assigned to SEQ ID NO: 171 in Table 1. Amino acids conserved among all sequences are indicted by a "*" and generally conserved amino acids are indicated by a ":".

FIG. 128 depicts a sequence alignment (ClustalW) between SEQ ID NO: 851 (RAAC00876) and ref|ZP_02170056.1|, ref|YP_079889.1|, ref|NP_980690.1|, ref|ZP_02257686.1|, and ref|YP_038371.1| (SEQ ID NOS: 853-857), respectively, which all have the function assigned to SEQ ID NO: 851 in Table 1. Amino acids conserved among all sequences are indicted by a "*" and generally conserved amino acids are indicated by a ":".

FIG. 129 depicts a sequence alignment (ClustalW) between SEQ ID NO: 647 (RAAC00525) and ref|YP_001488458.1|, ref|ZP_01665756.1|, ref|NP_347033.1|, ref|YP_080909.1|, and ref|YP_841318.1| (SEQ ID NOS: 649-653), respectively, which all have the function assigned to SEQ ID NO: 647 in Table 1. Amino acids conserved among all sequences are indicted by a "*" and generally conserved amino acids are indicated by a ":".

FIG. 130 depicts a sequence alignment (ClustalW) between SEQ ID NO: 1089 (RAAC01072) and ref|YP_849514.1|, ref|ZP_02320157.1|, ref|YP_013918.1|, ref|ZP_02330749.1|, and ref|NP_470676.1| (SEQ ID NOS: 1091-1095), respectively, which all have the function assigned to SEQ ID NO: 1089 in Table 1. Amino acids conserved among all sequences are indicted by a "*" and generally conserved amino acids are indicated by a ":".

FIG. 131 depicts a sequence alignment (ClustalW) between SEQ ID NO: 1310 (RAAC01366) and ref|YP_849898.1|, ref|NP_471127.1|, ref|NP_465208.1|, ref|YP_001124617.1|, and ref|YP_146331.1| (SEQ ID NOS: 1312-1316), respectively, which all have the function assigned to SEQ ID NO: 1310 Table 1. Amino acids conserved among all sequences are indicted by a "*" and generally conserved amino acids are indicated by a ":".

FIG. 132 depicts a sequence alignment (ClustalW) between SEQ ID NO: 1378 (RAAC01431) and ref|ZP_01666690.1|, ref|YP_077070.1|, ref|ZP_01173986.1|, ref|YP_814057.1|, and ref|NP_964223.1| (SEQ ID NOS: 1380-1384), respectively, which all have the function assigned to SEQ ID NO: 1378 in Table 1. Amino acids conserved among all sequences are indicted by a "*" and generally conserved amino acids are indicated by a ":".

FIG. 133 depicts a sequence alignment (ClustalW) between SEQ ID NO: 1514 (RAAC01505) and ref|YP_149084.1|, ref|YP_001127265.1|, ref|YP_074599.1|, ref|YP_001661816.1|, and ref|NP_621898.1| (SEQ ID NOS: 1516-1520), respectively, which all have the function assigned to SEQ ID NO: 1514 in Table 1. Amino acids conserved among all sequences are indicted by a "*" and generally conserved amino acids are indicated by a ":".

FIG. 134 depicts a sequence alignment (ClustalW) between SEQ ID NO: 1514 (RAAC01505) and ref|YP_149084.1|, ref|YP_001127265.1|, ref|YP_074599.1|, ref|YP_001661816.1|, and ref|NP_621898.1| (SEQ ID NOS: 1516-1520), respectively, which all have the function assigned to SEQ ID NO: 1514 in Table 1. Amino acids conserved among all sequences are indicted by a "*" and generally conserved amino acids are indicated by a ":".

FIG. 135 depicts a sequence alignment between SEQ ID NO: 1820 (RAAC01972) and ref|ZP_01171531.1|, ref|YP_001391734.1|, ref|YP_001308325.1|, ref|YP_518781.1|, and ref|YP_001254935.1| (SEQ ID NOS: 1822-1826), respectively, which all have the function assigned to SEQ ID NO: 1820 Table 1. Amino acids conserved among all sequences are indicted by a "*" and generally conserved amino acids are indicated by a ":".

FIG. 136 depicts a sequence alignment between SEQ ID NO: 154 (RAAC00076) and ref|YP_001488917.1|, ref|YP_079193.1|, ref|NP_241876.1|, ref|YP_174035.1|, and ref|ZP_01169176.1| (SEQ ID NOS: 156-160), respectively, which all have the function assigned to SEQ ID NO: 154 in Table 1. Amino acids conserved among all sequences are indicted by a "*" and generally conserved amino acids are indicated by a ":".

FIG. 137 depicts a sequence alignment between SEQ ID NO: 1939 (RAAC02144) and ref|ZP_02327651.1|, sp|O32720|SP2AA_PAEPO, ref|NP_833792.1|, ref|NP_846529.1|, and ref|YP_001646701.1| (SEQ ID NOS: 1941-1945), respectively, which all have the function assigned to SEQ ID NO: 1939 in Table 1. Amino acids conserved among all sequences are indicted by a "*" and generally conserved amino acids are indicated by a ":".

FIGS. 138A and 138B depict a sequence alignment between SEQ ID NO: 2126 (RAAC02439) and ref|YP_001125957.1|, ref|YP_147806.1|, ref|ZP_01695872.1|, ref|NP_693661.1|, and ref|ZP_01666100.1| (SEQ ID NOS: 2128-2132), respectively, which all have the function assigned to SEQ ID NO: 2126 Table 1. Amino acids conserved among all sequences are indicted by a "*" and generally conserved amino acids are indicated by a ":".

FIG. 139 depicts a sequence alignment between SEQ ID NO: 970 (RAAC00944) and ref|YP_001488778.1|, ref|YP_174256.1|, ref|YP_081277.1|, ref|YP_711801.1|, and ref|YP_804091.1| (SEQ ID NOS: 972-976), respectively, which all have the function assigned to SEQ ID NO: 970 in Table 1. Amino acids conserved among all sequences are indicted by a "*" and generally conserved amino acids are indicated by a ":".

FIGS. 140A and 140B depict a sequence alignment between SEQ ID NO: 2313 (RAAC02632) and ref|ZP_01695369.1|, ref|NP_764957.1|, ref|NP_646484.1|, ref|YP_001332652.1|, and ref|NP_372249.1| (SEQ ID NOS: 2315-2319), respectively, which all have the function assigned to SEQ ID NO: 2313 in Table 1. Amino acids conserved among all sequences are indicted by a "*" and generally conserved amino acids are indicated by a ":".

FIG. 141 depicts a sequence alignment between SEQ ID NO: 2211 (RAAC02474) and ref|ZP_02329050.1|, ref|YP_148935.1|, gb|AAX09759.1|, ref|YP_001127122.1|, and ref|YP_001376898.1| (SEQ ID NOS: 2213-2217), respectively, which all have the function assigned to SEQ ID NO: 2211 in Table 1. Amino acids conserved among all sequences are indicted by a "*" and generally conserved amino acids are indicated by a ":".

FIG. 142 depicts a sequence alignment between SEQ ID NO: 732 (RAAC00625) and ref|NP_244107.1|, ref|ZP_01188060.1|, ref|YP_76259.1|, ref|YP_148663.1|, and ref|YP_001126805.1| (SEQ ID NOS: 734-738), respectively, which all have the function assigned to SEQ ID NO: 732 in Table 1. Amino acids conserved among all sequences are indicted by a "*" and generally conserved amino acids are indicated by a ":".

FIG. 143 depicts a sequence alignment between SEQ ID NO: 800 (RAAC00733) and ref|ZP_01697803.1|, ref|YP_001488326.1|, ref|ZP_01860336.1|, ref|NP_834817.1|, and ref|NP_693386.1| (SEQ ID NOS: 802-806), respectively, which all have the function assigned to SEQ ID NO: 800 in Table 1. Amino acids conserved among all sequences are indicted by a "*" and generally conserved amino acids are indicated by a ":".

FIG. 144 depicts a sequence alignment between SEQ ID NO: 2194 (RAAC02466) and ref|ZP_01860336.1|, ref|ZP_02327791.1|, ref|NP_244433.1|, ref|ZP_01171669.1|, and ref|YP_001488326.1| (SEQ ID NOS: 2196-2200), respectively, which all have the function assigned to SEQ ID NO: 2194 in Table 1. Amino acids conserved among all sequences are indicted by a "*" and generally conserved amino acids are indicated by a ":".

FIG. 145 depicts a sequence alignment between SEQ ID NO: 2398 (RAAC02678) and ref|YP_001124914.1|, ref|YP_146760.1|, ref|YP_001319371.1|, ref|ZP_01723416.1|, and ref|ZP_00742387.1| (SEQ ID NOS: 2400-2404), respectively, which all have the function assigned to SEQ ID NO: 2398 in Table 1. Amino acids conserved among all sequences are indicted by a "*" and generally conserved amino acids are indicated by a ":".

FIG. 146 depicts a sequence alignment between SEQ ID NO: 2228 (RAAC02507) and ref|YP_517080.1|, ref|ZP_02185068.1|, ref|YP_001394884.1|, ref|ZP_01574787.1|, and ref|YP_001559227.1| (SEQ ID NOS: 2230-2234), respectively, which all have the function assigned to SEQ ID NO: 2228 in Table 1. Amino acids conserved among all sequences are indicted by a "*" and generally conserved amino acids are indicated by a ":".

FIGS. 147A and 147B depict a sequence alignment between SEQ ID NO: 902 (RAAC00906) and ref|ZP_01667455.1|, ref|ZP_01515931.1|, ref|YP_001430381.1|, ref|YP_001637100.1|, and ref|YP_146183.1| (SEQ ID NOS: 904-908), respectively, which all have the function assigned to SEQ ID NO: 902 Table 1. Amino acids conserved among all sequences are indicted by a "*" and generally conserved amino acids are indicated by a ":".

FIG. 148 depicts a sequence alignment between SEQ ID NO: 2364 (RAAC02211) and ref|YP_005108.1|, ref|YP_144769.1|, ref|YP_001124914.1|, ref|YP_001157480.1|, and ref|ZP_01773683.1| (SEQ ID NOS: 2366-2370), respectively, which all have the function assigned to SEQ ID NO: 2364 in Table 1. Amino acids conserved among all sequences are indicted by a "*" and generally conserved amino acids are indicated by a ":".

FIGS. 149A and 149B depict a sequence alignment between SEQ ID NO: 1463 (RAAC01489) and ref|ZP_01696335.1|, ref|ZP_01667455.1|, ref|ZP_00739567.1|, ref|YP_001037228.1|, and ref|NP_830390.1| (SEQ ID NOS: 1465-1469), respectively, which all have the function assigned to SEQ ID NO: 1463 Table 1. Amino acids conserved among all sequences are indicted by a "*" and generally conserved amino acids are indicated by a ":".

FIGS. 150A and 150B depict a sequence alignment between SEQ ID NO: 2007 (RAAC02391) and ref|ZP_01697157.1|, ref|YP_001212380.1|, ref|ZP_00539202.1|, reflNP_693085.1|, and reflZP_02329946.1| (SEQ ID NOS: 2009-2013), respectively, which all have the function assigned to SEQ ID NO: 2007 Table 1. Amino acids conserved among all sequences are indicted by a "*" and generally conserved amino acids are indicated by a ":".

FIGS. 151A and 151B depict a sequence alignment between SEQ ID NO: 2551 (RAAC02885) and reflYP_147095.1|, reflZP_01171502.1|, reflYP_001125215.1|, reflYP_001486785.1|, and reflZP_01861001.1| (SEQ ID NOS: 2553-2557), respectively, which all have the function assigned to SEQ ID NO: 2551 Table 1. Amino acids conserved among all sequences are indicted by a "*" and generally conserved amino acids are indicated by a ":".

FIG. 152 depicts a sequence alignment between SEQ ID NO: 2534 (RAAC02876) and reflYP_001125206.1|, reflZP_01696550.1|, reflYP_001410204.1|, reflZP_01860990.1|, and reflNP_243310.1| (SEQ ID NOS: 2536-2540), respectively, which all have the function assigned to SEQ ID NO: 2534 in Table 1. Amino acids conserved among all sequences are indicted by a "*" and generally conserved amino acids are indicated by a ":".

FIG. 153 depicts a sequence alignment between SEQ ID NO: 1021 (RAAC00987) and reflYP_001559801.1|, reflZP_01696550.1|, reflYP_753552.1|, reflNP_243310.1|, and reflZP_01725653.1| (SEQ ID NOS: 1023-1027), respectively, which all have the function assigned to SEQ ID NO: 1021 in Table 1. Amino acids conserved among all sequences are indicted by a "*" and generally conserved amino acids are indicated by a ":".

FIGS. 154A and 154B depict a sequence alignment between SEQ ID NO: 1990 (RAAC02162) and reflYP_148131.1|, reflYP_001126300.1|, reflYP_079616.1|, reflNP_390192.1|, and reflYP_001487274.1| (SEQ ID NOS: 1992-1996), respectively, which all have the function assigned to SEQ ID NO: 1990 Table 1. Amino acids conserved among all sequences are indicted by a "*" and generally conserved amino acids are indicated by a ":".

FIG. 155 depicts a sequence alignment between SEQ ID NO: 1 (RAAC00012) and reflYP_907563.1|, reflYP_955166.1|, reflZP_00997175.1|, reflYP_001133548.1|, and reflYP_829143.1| (SEQ ID NOS: 3-7), respectively, which all have the function assigned to SEQ ID NO: 1 in Table 1. Amino acids conserved among all sequences are indicted by a "*" and generally conserved amino acids are indicated by a ":".

FIGS. 156A and 156B depict a sequence alignment between SEQ ID NO: 2876 (RAAC02761) and emb|CAG29823.1|, reflNP_923516.1|, reflZP_02329377.1|, gb|EAY57526.1|, and reflYP_149098.1| (SEQ ID NOS: 2878-2882), respectively, which all have the function assigned to SEQ ID NO: 2876 in Table 1. Amino acids conserved among all sequences are indicted by a "*" and generally conserved amino acids are indicated by a ":".

FIG. 157 depicts a sequence alignment between SEQ ID NO: 579 (RAAC00477) and reflYP_001377039.1|, reflNP_244654.1|, reflYP_001647908.1|, reflYP_897521.1|, and reflZP_00744427.1| (SEQ ID NOS: 581-585), respectively, which all have the function assigned to SEQ ID NO: 579 in Table 1. Amino acids conserved among all sequences are indicted by a "*" and generally conserved amino acids are indicated by a ":".

FIGS. 158A and 158B depict a sequence alignment between SEQ ID NO: 35 (RAAC00019) and reflZP_02169265.1|, reflYP_848463.1|, reflNP_694373.1|, reflZP_01695448.1|, and reflZP_00539458.1| (SEQ ID NOS: 37-41), respectively, which all have the function assigned to SEQ ID NO: 35 in Table 1. Amino acids conserved among all sequences are indicted by a "*" and generally conserved amino acids are indicated by a ":".

FIG. 159 depicts a sequence alignment between SEQ ID NO: 52 (RAAC00020) and reflZP_01169692.1|, reflZP_01695449.1|, reflYP_001127497.1|, reflYP_149327.1|, and reflYP_534941.1| (SEQ ID NOS: 54-58), respectively, which all have the function assigned to SEQ ID NO: 52 in Table 1. Amino acids conserved among all sequences are indicted by a "*" and generally conserved amino acids are indicated by a ":".

FIGS. 160A and 160B depict a sequence alignment between SEQ ID NO: 1684 (RAAC01715) and gb|EDQ48509.1|, gb|EDQ48476.1|, reflZP_01575425.1|, reflZP_02025790.1|, and reflYP_001662047.1| (SEQ ID NOS: 1686-1690), respectively, which all have the function assigned to SEQ ID NO: 1684 in Table 1. Amino acids conserved among all sequences are indicted by a "*" and generally conserved amino acids are indicated by a ":".

FIGS. 161A-161C depict a sequence alignment between SEQ ID NO: 1157 (RAAC01137) and reflNP_978751.1|, reflZP_00741477.1|, reflYP_894957.1|, reflNP_844784.1|, and reflZP_02259481.1| (SEQ ID NOS: 1159-1163), respectively, which all have the function assigned to SEQ ID NO: 1157 in Table 1. Amino acids conserved among all sequences are indicted by a "*" and generally conserved amino acids are indicated by a ":".

FIGS. 162A-162C depict a sequence alignment between SEQ ID NO: 2910 (RAAC03013) and reflZP_02168855.1|, reflNP_470526.1|, reflZP_02320069.1|, reflZP_01927122.1|, and reflYP_013834.1| (SEQ ID NOS: 2912-2916), respectively, which all have the function assigned to SEQ ID NO: 2910 in Table 1. Amino acids conserved among all sequences are indicted by a "*" and generally conserved amino acids are indicated by a ":".

DETAILED DESCRIPTION OF THE INVENTION

Bacterial DNA codes for information that regulates transcription of genes into mRNA, which codes for proteins or enzymes used for; control of growth, and processing of energy, carbon and other compounds by the cell. Most of these transcriptional regulators/repressors function to turn on and off genes to minimize expenditure of cellular energy in response to their growth environment (i.e., presence of growth substrate, metals, temperature, etc.). This can become a problem related to process development because regulation and control of enzymes for a specific reaction may lead to suboptimal growth or suboptimal production of a desired metabolite (enzyme or compound). The genome of *Alicyclobacillus acidocaldarius* strain ATCC 27009 contains numerous coding sequences for transcriptional regulators and repressors of proteins related to growth, and processing of carbon by the cell. These regulators and repressors may directly affect expression of glycosyl hydrolase and/or esterase enzymes for processing of biomass outside the cell, as well as controlling production of valuable secondary metabolites.

Metabolic engineering through modification (genetic engineering) of these regulatory responses for transcription is one approach for optimization of cellular processes, by way of non-limiting example, *Alicyclobacillus acidocaldarius*. Control of these genes will allow for over-expression of desired pathways (e.g., production of glycosyl hydrolases, organic acids or alcohols), or likewise elimination or causing reduced expression of genes leading to undesired pathways or products (e.g., proteins that control transcription of glycosyl hydrolase genes). Control of these genes, or using them as loci for controlling/optimizing carbon processing in organisms, such as, by way of non-limiting example, the theanoacidophile *Alicyclobacillus acidocaldarius* has not been previously attempted using genes and proteins from *Alicyclobacillus acidocaldarius*; thereby, making use of transcriptional regulators from this source novel.

Embodiments of the invention include genes and associated proteins related to regulation of growth and metabolism of the thermoacidophile *Alicyclobacillus acidocaldarius*. Coding sequences for genes related to these processes were determined from sequence information generated from sequencing the genome of *Alicyclobacillus acidocaldarius*. These genes and proteins may represent targets for metabolic engineering of *Alicyclobacillus acidocaldarius* or other organisms. Non-limiting examples of nucleotide sequences found within the genome of *Alicyclobacillus acidocaldarius*, and amino acids coded thereby, associated with regulation of growth and carbon metabolism are listed in Table 1. Regulators and repressors may be, without limitation, of the following classes: regulators that control growth, including cell division and growth under aerobic and anaerobic conditions; regulators that respond to environmental conditions such as temperature, metal concentration and metabolite concentration; regulators of secondary metabolite pathways such as amino acids, organic acids, alcohols, antibiotics, antibiotic resistance, enzymes related to DNA processing and others; repressors related to carbon processing operons that respond to the presence or absence of organic compounds in the growth environment; signal transduction regulators that control phases of growth and carbon processing; regulators that control the response of *Alicyclobacillus acidocaldarius* to its growth environment allowing movement toward carbon sources or biofilm formation on a carbon source; and others.

Embodiments of the invention relate in part to the gene sequences and/or protein sequences comprising genes and/or proteins of *Alicyclobacillus acidocaldarius*. Genes and proteins included are those which play a role in transcription and transcriptional control. Intracellular enzyme activities may be thermophilic and/or acidophilic in nature and general examples of similar genes are described in the literature. Classes of genes, sequences, enzymes and factors include, but are not limited to, those listed in Table 1.

TABLE 1

*Alicyclobacillus* acidocaldarius genes related to transcription and transcriptional regulation

| Reference | Gene Sequence | Protein Sequence | Function |
|---|---|---|---|
| RAAC00012 | SEQ ID NO: 2 | SEQ ID NO: 1 | C4-dicarboxylate transport protein |
| RAAC00013 | SEQ ID NO: 19 | SEQ ID NO: 18 | Transcriptional regulators, LysR family |
| RAAC00019 | SEQ ID NO: 36 | SEQ ID NO: 35 | Two-component sensor kinase yycG |
| RAAC00020 | SEQ ID NO: 53 | SEQ ID NO: 52 | Two-component response regulator yycF |
| RAAC00027 | SEQ ID NO: 70 | SEQ ID NO: 69 | Single-strand DNA binding protein |
| RAAC00039 | SEQ ID NO: 87 | SEQ ID NO: 86 | Stage 0 sporulation protein J |
| RAAC00040 | SEQ ID NO: 104 | SEQ ID NO: 103 | Chromosome partitioning protein parA |
| RAAC00045 | SEQ ID NO: 121 | SEQ ID NO: 120 | Jag protein |
| RAAC00068 | SEQ ID NO: 138 | SEQ ID NO: 137 | Transcriptional regulator, GntR family |
| RAAC00076 | SEQ ID NO: 155 | SEQ ID NO: 154 | Trp repressor binding protein |
| RAAC00077 | SEQ ID NO: 172 | SEQ ID NO: 171 | Gluconate operon transcriptional repressor |
| RAAC00092 | SEQ ID NO: 189 | SEQ ID NO: 188 | Prespore specific transcriptional activator rsfA |
| RAAC00113 | SEQ ID NO: 206 | SEQ ID NO: 205 | Cell-division initiation protein DivIB |
| RAAC00117 | SEQ ID NO: 223 | SEQ ID NO: 222 | Cell division protein ftsA |
| RAAC00118 | SEQ ID NO: 240 | SEQ ID NO: 239 | Cell division protein ftsZ |
| RAAC00120 | SEQ ID NO: 257 | SEQ ID NO: 256 | RNA polymerase sigma-E factor |
| RAAC00121 | SEQ ID NO: 274 | SEQ ID NO: 273 | RNA polymerase sigma-G factor |
| RAAC00134 | SEQ ID NO: 291 | SEQ ID NO: 290 | Pyrimidine operon regulatory protein pyrR |
| RAAC00147 | SEQ ID NO: 308 | SEQ ID NO: 307 | DNA-directed RNA polymerase omega chain |
| RAAC00161 | SEQ ID NO: 325 | SEQ ID NO: 324 | Small acid-soluble spore protein |
| RAAC00212 | SEQ ID NO: 342 | SEQ ID NO: 341 | Transcription state regulatory protein abrB |
| RAAC00215 | SEQ ID NO: 359 | SEQ ID NO: 358 | Phosphorelay inhibitor |
| RAAC00269 | SEQ ID NO: 376 | SEQ ID NO: 375 | Transcriptional regulator, LacI family |
| RAAC00349 | SEQ ID NO: 393 | SEQ ID NO: 392 | Transcriptional regulator, AsnC family |
| RAAC00354 | SEQ ID NO: 410 | SEQ ID NO: 409 | Transcriptional regulator, TetR family |
| RAAC00365 | SEQ ID NO: 427 | SEQ ID NO: 426 | N-acetylmuramoyl-L-alanine amidase |
| RAAC00371 | SEQ ID NO: 444 | SEQ ID NO: 443 | DNA-directed RNA polymerase alpha chain |
| RAAC00407 | SEQ ID NO: 461 | SEQ ID NO: 460 | DNA-directed RNA polymerase beta' chain |
| RAAC00408 | SEQ ID NO: 478 | SEQ ID NO: 477 | DNA-directed RNA polymerase beta chain |
| RAAC00415 | SEQ ID NO: 495 | SEQ ID NO: 494 | Transcription antitermination protein nusG |
| RAAC00418 | SEQ ID NO: 512 | SEQ ID NO: 511 | RNA polymerase sigma-H factor |
| RAAC00430 | SEQ ID NO: 529 | SEQ ID NO: 528 | DNA-binding protein |
| RAAC00436 | SEQ ID NO: 546 | SEQ ID NO: 545 | Transcriptional regulator ctsR |
| RAAC00475 | SEQ ID NO: 563 | SEQ ID NO: 562 | Transcription termination factor rho |
| RAAC00477 | SEQ ID NO: 580 | SEQ ID NO: 579 | Sporulation initiation phosphotransferase F |
| RAAC00480 | SEQ ID NO: 597 | SEQ ID NO: 596 | DNA-directed RNA polymerase delta chain |
| RAAC00483 | SEQ ID NO: 614 | SEQ ID NO: 613 | Regulator of kinase autophosphorylation inhibitor |
| RAAC00484 | SEQ ID NO: 631 | SEQ ID NO: 630 | Kinase autophosphorylation inhibitor kipI |
| RAAC00525 | SEQ ID NO: 648 | SEQ ID NO: 647 | Kdg operon repressor |
| RAAC00549 | SEQ ID NO: 665 | SEQ ID NO: 664 | Transcriptional regulator, MerR family |
| RAAC00570 | SEQ ID NO: 682 | SEQ ID NO: 681 | Transcriptional regulator, LacI family |
| RAAC00579 | SEQ ID NO: 699 | SEQ ID NO: 698 | Transcriptional regulator, ArsR family |
| RAAC00603 | SEQ ID NO: 716 | SEQ ID NO: 715 | Transcriptional regulator, ArsR family |
| RAAC00625 | SEQ ID NO: 733 | SEQ ID NO: 732 | Catabolite control protein A |
| RAAC00643 | SEQ ID NO: 750 | SEQ ID NO: 749 | Small acid-soluble spore protein |

TABLE 1-continued

Alicyclobacillus acidocaldarius genes related to transcription and transcriptional regulation

| Reference | Gene Sequence | Protein Sequence | Function |
|---|---|---|---|
| RAAC00650 | SEQ ID NO: 767 | SEQ ID NO: 766 | Glycosyltransferase |
| RAAC00675 | SEQ ID NO: 784 | SEQ ID NO: 783 | Transcriptional regulator |
| RAAC00733 | SEQ ID NO: 801 | SEQ ID NO: 800 | Catabolite repression protein crh |
| RAAC00856 | SEQ ID NO: 818 | SEQ ID NO: 817 | RNA polymerase sigma-K factor |
| RAAC00872 | SEQ ID NO: 835 | SEQ ID NO: 834 | Spore protease |
| RAAC00876 | SEQ ID NO: 852 | SEQ ID NO: 851 | Heat-inducible transcription repressor hrcA |
| RAAC00896 | SEQ ID NO: 869 | SEQ ID NO: 868 | RNA polymerase sigma factor rpoD |
| RAAC00905 | SEQ ID NO: 886 | SEQ ID NO: 885 | Two-component response regulator |
| RAAC00906 | SEQ ID NO: 903 | SEQ ID NO: 902 | Two component system histidine kinase |
| RAAC00923 | SEQ ID NO: 920 | SEQ ID NO: 919 | Small acid-soluble spore protein |
| RAAC00927 | SEQ ID NO: 937 | SEQ ID NO: 936 | Transcriptional regulator, MarR family |
| RAAC00935 | SEQ ID NO: 954 | SEQ ID NO: 953 | Transcriptional regulator, MarR family |
| RAAC00944 | SEQ ID NO: 971 | SEQ ID NO: 970 | Transcriptional activator tenA |
| RAAC00981 | SEQ ID NO: 988 | SEQ ID NO: 987 | Two-component response regulator |
| RAAC00986 | SEQ ID NO: 1005 | SEQ ID NO: 1004 | Two-component response regulator |
| RAAC00987 | SEQ ID NO: 1022 | SEQ ID NO: 1021 | Chemotaxis protein cheY |
| RAAC00991 | SEQ ID NO: 1039 | SEQ ID NO: 1038 | Glycosyltransferase |
| RAAC01035 | SEQ ID NO: 1056 | SEQ ID NO: 1055 | Transcriptional regulator, GntR family |
| RAAC01059 | SEQ ID NO: 1073 | SEQ ID NO: 1072 | Transcriptional regulator, TetR family |
| RAAC01072 | SEQ ID NO: 1090 | SEQ ID NO: 1089 | Repressor LexA |
| RAAC01078 | SEQ ID NO: 1107 | SEQ ID NO: 1106 | Ribose operon repressor |
| RAAC01080 | SEQ ID NO: 1124 | SEQ ID NO: 1123 | Transcriptional regulator, MerR family |
| RAAC01126 | SEQ ID NO: 1141 | SEQ ID NO: 1140 | Transcriptional regulator, TetR family |
| RAAC01137 | SEQ ID NO: 1158 | SEQ ID NO: 1157 | Transporter, MMPL family |
| RAAC01138 | SEQ ID NO: 1175 | SEQ ID NO: 1174 | Transcriptional regulator, TetR family |
| RAAC01158 | SEQ ID NO: 1192 | SEQ ID NO: 1191 | Transcriptional regulator, GntR family |
| RAAC01353 | SEQ ID NO: 1294 | SEQ ID NO: 1293 | Transcriptional regulator, IclR family |
| RAAC01366 | SEQ ID NO: 1311 | SEQ ID NO: 1310 | Peroxide operon regulator |
| RAAC01375 | SEQ ID NO: 1328 | SEQ ID NO: 1327 | Transcriptional regulators, LysR family |
| RAAC01377 | SEQ ID NO: 1345 | SEQ ID NO: 1344 | Glycosyltransferase |
| RAAC01427 | SEQ ID NO: 1362 | SEQ ID NO: 1361 | SspF protein |
| RAAC01431 | SEQ ID NO: 1379 | SEQ ID NO: 1378 | Pur operon repressor |
| RAAC01438 | SEQ ID NO: 1396 | SEQ ID NO: 1395 | Transcription-repair coupling factor |
| RAAC01442 | SEQ ID NO: 1413 | SEQ ID NO: 1412 | DNA-binding protein HU |
| RAAC01464 | SEQ ID NO: 1430 | SEQ ID NO: 1429 | Transcriptional regulator, Xre family |
| RAAC01465 | SEQ ID NO: 1447 | SEQ ID NO: 1446 | Transcription elongation factor greA |
| RAAC01489 | SEQ ID NO: 1464 | SEQ ID NO: 1463 | Two component system histidine kinase |
| RAAC01493 | SEQ ID NO: 1481 | SEQ ID NO: 1480 | Transcriptional regulators, LysR family |
| RAAC01498 | SEQ ID NO: 1498 | SEQ ID NO: 1497 | Central glycolytic genes regulator |
| RAAC01505 | SEQ ID NO: 1515 | SEQ ID NO: 1514 | Ribose operon repressor |
| RAAC01563 | SEQ ID NO: 1532 | SEQ ID NO: 1531 | Sporulation kinase D |
| RAAC01624 | SEQ ID NO: 1549 | SEQ ID NO: 1548 | Ebg operon repressor |
| RAAC01638 | SEQ ID NO: 1566 | SEQ ID NO: 1565 | Transcriptional regulator, TetR family |
| RAAC01653 | SEQ ID NO: 1583 | SEQ ID NO: 1582 | Transcriptional regulators, LysR family |
| RAAC01655 | SEQ ID NO: 1600 | SEQ ID NO: 1599 | Transcriptional regulator |
| RAAC01657 | SEQ ID NO: 1617 | SEQ ID NO: 1616 | Pyruvate dehydrogenase (acetyl-transferring) |
| RAAC01658 | SEQ ID NO: 1634 | SEQ ID NO: 1633 | Pyruvate dehydrogenase (acetyl-transferring) |
| RAAC01659 | SEQ ID NO: 1651 | SEQ ID NO: 1650 | Dihydrolipoyllysine-residue acetyltransferase |
| RAAC01701 | SEQ ID NO: 1668 | SEQ ID NO: 1667 | Transcriptional regulator, MarR family |
| RAAC01715 | SEQ ID NO: 1685 | SEQ ID NO: 1684 | Two-component response regulator yesN |
| RAAC01745 | SEQ ID NO: 1702 | SEQ ID NO: 1701 | Pyruvate dehydrogenase (acetyl-transferring) |
| RAAC01746 | SEQ ID NO: 1719 | SEQ ID NO: 1718 | Pyruvate dehydrogenase (acetyl-transferring) |
| RAAC01814 | SEQ ID NO: 1736 | SEQ ID NO: 1735 | RNA polymerase sigma-K factor |
| RAAC01826 | SEQ ID NO: 1753 | SEQ ID NO: 1752 | RNA polymerase ECF-type sigma factor |
| RAAC01903 | SEQ ID NO: 1770 | SEQ ID NO:1769 | Two-component response regulator |
| RAAC01912 | SEQ ID NO: 1787 | SEQ ID NO: 1786 | Transcriptional regulator, DeoR family |
| RAAC01956 | SEQ ID NO: 1804 | SEQ ID NO: 1803 | Arginine repressor, argR |
| RAAC01972 | SEQ ID NO: 1821 | SEQ ID NO: 1820 | Transcription pleiotropic repressor codY |
| RAAC02012 | SEQ ID NO: 1838 | SEQ ID NO: 1837 | Transcriptional regulator, LytR family |
| RAAC02031 | SEQ ID NO: 1855 | SEQ ID NO: 1854 | Transcriptional regulator, GntR family |
| RAAC02034 | SEQ ID NO: 1872 | SEQ ID NO: 1871 | Germination protein gerE |
| RAAC02041 | SEQ ID NO: 1889 | SEQ ID NO: 1888 | Transcriptional regulator, MarR family |
| RAAC02112 | SEQ ID NO: 1906 | SEQ ID NO: 1905 | N utilization substance protein B |
| RAAC02142 | SEQ ID NO: 1923 | SEQ ID NO: 1922 | Serine-type D-Ala-D-Ala carboxypeptidase |
| RAAC02144 | SEQ ID NO: 1940 | SEQ ID NO: 1939 | Anti-sigma F factor antagonist |
| RAAC02146 | SEQ ID NO: 1957 | SEQ ID NO: 1956 | RNA polymerase sigma-F factor |
| RAAC02161 | SEQ ID NO: 1974 | SEQ ID NO: 1973 | Transcriptional regulatory protein resD |
| RAAC02162 | SEQ ID NO: 1991 | SEQ ID NO: 1990 | Sensor protein resE |
| RAAC02391 | SEQ ID NO: 2008 | SEQ ID NO: 2007 | Phosphate regulon sensor protein phoR |
| RAAC02417 | SEQ ID NO: 2025 | SEQ ID NO: 2024 | Transcriptional regulator, Cro/CI family |
| RAAC02421 | SEQ ID NO: 2042 | SEQ ID NO: 2041 | Glycosyltransferase |

TABLE 1-continued

*Alicyclobacillus* acidocaldarius genes related to transcription and transcriptional regulation

| Reference | Gene Sequence | Protein Sequence | Function |
|---|---|---|---|
| RAAC02426 | SEQ ID NO: 2059 | SEQ ID NO: 2058 | Pyruvate dehydrogenase (acetyl-transferring) |
| RAAC02427 | SEQ ID NO: 2076 | SEQ ID NO: 2075 | Pyruvate dehydrogenase (acetyl-transferring) |
| RAAC02428 | SEQ ID NO: 2093 | SEQ ID NO: 2092 | Dihydrolipoyllysine-residue acetyltransferase |
| RAAC02432 | SEQ ID NO: 2110 | SEQ ID NO: 2109 | Transcriptional regulator, IclR family |
| RAAC02439 | SEQ ID NO: 2127 | SEQ ID NO: 2126 | Sigma-54-dependent transcriptional activator |
| RAAC02454 | SEQ ID NO: 2144 | SEQ ID NO: 2143 | Prespore specific transcriptional activator rsfA |
| RAAC02459 | SEQ ID NO: 2161 | SEQ ID NO: 2160 | Transcriptional regulator, GntR family |
| RAAC02164 | SEQ ID NO: 2178 | SEQ ID NO: 2177 | SIR2 family protein |
| RAAC02466 | SEQ ID NO: 2195 | SEQ ID NO: 2194 | Catabolite repression protein crh |
| RAAC02474 | SEQ ID NO: 2212 | SEQ ID NO: 2211 | Hpr (ser) Kinase/Phosphatase |
| RAAC02507 | SEQ ID NO: 2229 | SEQ ID NO: 2228 | Two component system histidine kinase |
| RAAC02508 | SEQ ID NO: 2246 | SEQ ID NO: 2245 | Two-component response regulator |
| RAAC02546 | SEQ ID NO: 2263 | SEQ ID NO: 2262 | RNA polymerase sigma-H factor |
| RAAC02589 | SEQ ID NO: 2280 | SEQ ID NO: 2279 | DNA-binding protein HU |
| RAAC02603 | SEQ ID NO: 2297 | SEQ ID NO: 2296 | Transcription state regulatory protein abrB |
| RAAC02632 | SEQ ID NO: 2314 | SEQ ID NO: 2313 | Hpr (ser) Kinase/Phosphatase |
| RAAC02663 | SEQ ID NO: 2331 | SEQ ID NO: 2330 | Transcriptional regulator, GntR family |
| RAAC02671 | SEQ ID NO: 2348 | SEQ ID NO: 2347 | Transcriptional regulator, MerR family |
| RAAC02211 | SEQ ID NO: 2365 | SEQ ID NO: 2364 | Two component system histidine kinase |
| RAAC02673 | SEQ ID NO: 2382 | SEQ ID NO: 2381 | Glycerol uptake operon antiterminator regulatory protein |
| RAAC02678 | SEQ ID NO: 2399 | SEQ ID NO: 2398 | Two component system histidine kinase |
| RAAC02712 | SEQ ID NO: 2416 | SEQ ID NO: 2415 | Transcriptional regulator, TetR family |
| RAAC02227 | SEQ ID NO: 2518 | SEQ ID NO: 2517 | Serine-type D-Ala-D-Ala carboxypeptidase |
| RAAC02876 | SEQ ID NO: 2535 | SEQ ID NO: 2534 | Chemotaxis protein cheY |
| RAAC02885 | SEQ ID NO: 2552 | SEQ ID NO: 2551 | Chemotaxis protein cheA |
| RAAC02902 | SEQ ID NO: 2569 | SEQ ID NO: 2568 | N utilization substance protein A |
| RAAC02968 | SEQ ID NO: 2603 | SEQ ID NO: 2602 | RNA polymerase sigma-H factor |
| RAAC02984 | SEQ ID NO: 2620 | SEQ ID NO: 2619 | Arginine utilization regulatory protein rocR |
| RAAC02994 | SEQ ID NO: 2637 | SEQ ID NO: 2636 | Arginine utilization regulatory protein rocR |
| RAAC03005 | SEQ ID NO: 2654 | SEQ ID NO: 2653 | Transcriptional regulator, GntR family |
| RAAC02241 | SEQ ID NO: 2671 | SEQ ID NO: 2670 | Transcriptional regulator, MarR family |
| RAAC03015 | SEQ ID NO: 2688 | SEQ ID NO: 2687 | Serine-type D-Ala-D-Ala carboxypeptidase |
| RAAC03031 | SEQ ID NO: 2705 | SEQ ID NO: 2704 | Two-component response regulator |
| RAAC03156 | SEQ ID NO: 2722 | SEQ ID NO: 2721 | Transcriptional regulator, ArsR family |
| RAAC03180 | SEQ ID NO: 2739 | SEQ ID NO: 2738 | Transcriptional regulator, Cro/CI family |
| RAAC03184 | SEQ ID NO: 2756 | SEQ ID NO: 2755 | Transcriptional regulator |
| RAAC03236 | SEQ ID NO: 2773 | SEQ ID NO: 2772 | Transcription state regulatory protein abrB |
| RAAC02292 | SEQ ID NO: 2790 | SEQ ID NO: 2789 | Transcriptional regulator |
| RAAC02315 | SEQ ID NO: 2807 | SEQ ID NO: 2806 | Chromosome partitioning protein parA |
| RAAC02359 | SEQ ID NO: 2824 | SEQ ID NO: 2823 | DNA-binding protein HU |
| RAAC02381 | SEQ ID NO: 2841 | SEQ ID NO: 2840 | Glycosyltransferase |
| | SEQ ID NO: 2857 | | Catabolite-responsive element |
| | SEQ ID NO: 2858 | | Catabolite responsive element |
| RAAC02740 | SEQ ID NO: 2860 | SEQ ID NO: 2859 | Transcriptional regulator |
| RAAC02761 | SEQ ID NO: 2877 | SEQ ID NO: 2876 | Sensor protein kdpD |
| RAAC02937 | SEQ ID NO: 2894 | SEQ ID NO: 2893 | Transcriptional regulator |
| RAAC03013 | SEQ ID NO: 2911 | SEQ ID NO: 2910 | Transporter, MMPL family |
| RAAC03263 | SEQ ID NO: 2928 | SEQ ID NO: 2927 | RNA polymerase sigma-H factor |

The present invention relates to nucleotides sequences comprising isolated and/or purified nucleotide sequences of the genome of *Alicyclobacillus acidocaldarius* selected from the sequences of SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2857, 2858, 2860, 2877, 2894, 2911, and 2928 or one of their fragments.

The present invention likewise relates to isolated and/or purified nucleotide sequences, characterized in that they comprise at least one of: a) a nucleotide sequence of at least one of the sequences of SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2857, 2858, 2860, 2877, 2894, 2911, and 2928 or one of their fragments; b) a nucleotide sequence homologous to a nucleotide sequence such as defined in a); c) a nucleotide sequence complementary to a nucleotide sequence such as defined in a) or b), and a nucleotide sequence of their corresponding RNA; d) a nucleotide sequence capable of hybridizing under stringent conditions with a sequence such as defined in a), b) or c); e) a nucleotide sequence comprising a sequence such as defined in a), b), c) or d); and f) a nucleotide sequence modified by a nucleotide sequence such as defined in a), b), c), d) or e).

Nucleotide, polynucleotide, or nucleic acid sequence will be understood according to the present invention as meaning both a double-stranded or single-stranded DNA in the monomeric and dimeric (so-called in tandem) forms and the transcription products of the DNAs.

Aspects of the invention relate to nucleotide sequences in which it has been possible to isolate, purify or partially purify, starting from separation methods such as, for example, ion-exchange chromatography, by exclusion based on molecular size, or by affinity, or, alternatively, fractionation techniques based on solubility in different solvents, or starting from methods of genetic engineering such as amplification, cloning, and subcloning, it being possible for the sequences of the invention to be carried by vectors.

Isolated and/or purified nucleotide sequence fragment according to the invention will be understood as designating any nucleotide fragment of the genome of *Alicyclobacillus acidocaldarius*, and may include, by way of non-limiting example, a length of at least 8, 12, 20, 25, 50, 75, 100, 200, 300, 400, 500, 1000, or more, consecutive nucleotides of the sequence from which it originates.

Specific fragment of an isolated and/or purified nucleotide sequence according to the invention will be understood as designating any nucleotide fragment of the genome of *Alicyclobacillus acidocaldarius*, having, after alignment and comparison with the corresponding fragments of genomic sequences of *Alicyclobacillus acidocaldarius*, at least one nucleotide or base of different nature.

Homologous isolated and/or purified nucleotide sequence in the sense of the present invention is understood as meaning an isolated and/or purified nucleotide sequence having at least a percentage identity with the bases of a nucleotide sequence according to the invention of at least about 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7%, this percentage being purely statistical and it being possible to distribute the differences between the two nucleotide sequences at random and over the whole of their length.

Specific homologous nucleotide sequence in the sense of the present invention is understood as meaning a homologous nucleotide sequence having at least one nucleotide sequence of a specific fragment, such as defined above. The "specific" homologous sequences can comprise, for example, the sequences corresponding to the genomic sequence or to the sequences of its fragments representative of variants of the genome of *Alicyclobacillus acidocaldarius*. These specific homologous sequences can thus correspond to variations linked to mutations within strains of *Alicyclobacillus acidocaldarius*, and especially correspond to truncations, substitutions, deletions and/or additions of at least one nucleotide. The homologous sequences can likewise correspond to variations linked to the degeneracy of the genetic code.

The term "degree or percentage of sequence homology" refers to "degree or percentage of sequence identity between two sequences after optimal alignment" as defined in the present application.

Two amino-acids or nucleotidic sequences are said to be "identical" if the sequence of amino-acids or nucleotidic residues, in the two sequences is the same when aligned for maximum correspondence as described below. Sequence comparisons between two (or more) peptides or polynucleotides are typically performed by comparing sequences of two optimally aligned sequences over a segment or "comparison window" to identify and compare local regions of sequence similarity. Optimal alignment of sequences for comparison may be conducted by the local homology algorithm of Smith and Waterman, *Ad. App. Math* 2:482 (1981), by the homology alignment algorithm of Neddleman and Wunsch, *J. Mol. Biol.* 48:443 (1970), by the search for similarity method of Pearson and Lipman, *Proc. Natl. Acad. Sci.* (U.S.A.) 85:2444 (1988), by computerized implementation of these algorithms (GAP, BESTFIT, FASTA, and TFASTA in the Wisconsin Genetics Software Package, Genetics Computer Group (GCG), 575 Science Dr., Madison, Wis.), or by visual inspection.

"Percentage of sequence identity" (or degree of identity) is determined by comparing two optimally aligned sequences over a comparison window, where the portion of the peptide or polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity.

The definition of sequence identity given above is the definition that would be used by one of skill in the art. The definition by itself does not need the help of any algorithm, the algorithms being helpful only to achieve the optimal alignments of sequences, rather than the calculation of sequence identity.

From the definition given above, it follows that there is a well-defined and only one value for the sequence identity between two compared sequences, which value corresponds to the value obtained for the best or optimal alignment.

In the BLAST N or BLAST P "BLAST 2 sequence" software, which is available at the web site ncbi.nlm.nih.gov/gorf/bl2.html, and habitually used by the inventors and in general by the skilled person for comparing and determining the identity between two sequences, gap cost which depends on the sequence length to be compared is directly selected by the software (i.e., 11.2 for substitution matrix BLOSUM-62 for length>85).

Complementary nucleotide sequence of a sequence of the invention is understood as meaning any DNA whose nucleotides are complementary to those of the sequence of the invention, and whose orientation is reversed (antisense sequence).

Hybridization under conditions of stringency with a nucleotide sequence according to the invention is understood as meaning hybridization under conditions of temperature and ionic strength chosen in such a way that they allow the maintenance of the hybridization between two fragments of complementary DNA.

By way of illustration, conditions of great stringency of the hybridization step with the aim of defining the nucleotide fragments described above are advantageously the following.

The hybridization is carried out at a preferential temperature of 65° C. in the presence of SSC buffer, 1×SSC corresponding to 0.15 M NaCl and 0.05 M Na citrate. The washing steps, for example, can be the following: 2×SSC, at ambient temperature followed by two washes with 2×SSC, 0.5% SDS at 65° C.; 2×0.5×SSC, 0.5% SDS; at 65° C. for 10 minutes each.

The conditions of intermediate stringency, using, for example, a temperature of 42° C. in the presence of a 2×SSC buffer, or of less stringency, for example, a temperature of 37° C. in the presence of a 2×SSC buffer, respectively require a globally less significant complementarity for the hybridization between the two sequences.

The stringent hybridization conditions described above for a polynucleotide with a size of approximately 350 bases will be adapted by a person skilled in the art for oligonucleotides of greater or smaller size, according to the teachings of Sambrook et al., 1989.

Among the isolated and/or purified nucleotide sequences according to the invention, are those that can be used as a primer or probe in methods allowing the homologous sequences according to the invention to be obtained, these methods, such as the polymerase chain reaction (PCR), nucleic acid cloning, and sequencing, being well known to a person skilled in the art.

Among the isolated and/or purified nucleotide sequences according to the invention, those are again preferred that can be used as a primer or probe in methods allowing the presence of SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2857, 2858, 2860, 2877, 2894, 2911, and 2928, one of their fragments, or one of their variants such as defined below to be diagnosed.

The nucleotide sequence fragments according to the invention can be obtained, for example, by specific amplification, such as PCR, or after digestion with appropriate restriction enzymes of nucleotide sequences according to the invention, these methods in particular being described in the work of Sambrook et al., 1989. Such representative fragments can likewise be obtained by chemical synthesis according to methods well known to persons of ordinary skill in the art.

Modified nucleotide sequence will be understood as meaning any nucleotide sequence obtained by mutagenesis according to techniques well known to a person skilled in the art, and containing modifications with respect to the normal sequences according to the invention, for example, mutations in the regulatory and/or promoter sequences of polypeptide expression, especially leading to a modification of the rate of expression of the polypeptide or to a modulation of the replicative cycle.

Modified nucleotide sequence will likewise be understood as meaning any nucleotide sequence coding for a modified polypeptide, such as defined below.

The present invention relates to nucleotide sequence comprising isolated and/or purified nucleotide sequences of *Alicyclobacillus acidocaldarius*, characterized in that they are selected from the sequences SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2857, 2858, 2860, 2877, 2894, 2911, and 2928 or one of their fragments.

Embodiments of the invention likewise relate to isolated and/or purified nucleotide sequences characterized in that they comprise a nucleotide sequence selected from: a) at least one of a nucleotide sequence of SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2857, 2858, 2860, 2877, 2894, 2911, and 2928 or one of their fragments; b) a nucleotide sequence of a specific fragment of a sequence such as defined in a); c) a homologous nucleotide sequence having at least 80% identity with a sequence such as defined in a) or b); d) a complementary nucleotide sequence or sequence of RNA corresponding to a sequence such as defined in a), b) or c); and e) a nucleotide sequence modified by a sequence such as defined in a), b), c) or d).

Among the isolated and/or purified nucleotide sequences according to the invention are the nucleotide sequences of SEQ ID NOS: 13-17, 30-34, 47-51, 64-68, 81-85, 98-102, 115-119, 132-136, 149-153, 166-170, 183-187, 200-204, 217-221, 234-238, 251-255, 268-272, 285-289, 302-306, 319-323, 336-340, 353-357, 370-374, 387-391, 404-408, 421-425, 438-442, 455-459, 472-476, 489-493, 506-510, 523-527, 540-544, 557-561, 574-578, 591-595, 608-612, 625-629, 642-646, 659-663, 676-680, 693-697, 710-714, 727-731, 744-748, 761-765, 778-782, 795-799, 812-816, 829-833, 846-850, 863-867, 880-884, 897-901, 914-918, 931-935, 948-952, 965-969, 982-986, 999-1003, 1016-1020, 1033-1037, 1050-1054, 1067-1071, 1084-1088, 1101-1105, 1118-1122, 1135-1139, 1152-1156, 1169-1173, 1186-1190, 1203-1207, 1305-1309, 1322-1326, 1339-1343, 1356-1360, 1373-1377, 1390-1394, 1407-1411, 1424-1428, 1441-1445, 1458-1462, 1475-1479, 1492-1496, 1509-1513, 1526-1530, 1543-1547, 1560-1564, 1577-1581, 1594-1598, 1611-1615, 1628-1632, 1645-1649, 1662-1666, 1679-1683, 1696-1700, 1713-1717, 1730-1734, 1747-1751, 1764-1768, 1781-1785, 1798-1802, 1815-1819, 1832-1836, 1849-1853, 1866-1870, 1883-1887, 1900-1904, 1917-1921, 1934-1938, 1951-1955, 1968-1972, 1985-1989, 2002-2006, 2019-2023, 2036-2040, 2053-2057, 2070-2074, 2087-2091, 2104-2108, 2121-2125, 2138-2142, 2155-2159, 2172-2176, 2189-2193, 2206-2210, 2223-2227, 2240-2244, 2257-2261, 2274-2278, 2291-2295, 2308-2312, 2325-2329, 2342-2346, 2359-2363, 2376-2380, 2393-2397, 2410-2414, 2427-2431, 2529-2533, 2546-2550, 2563-2567, 2580-2584, 2614-2618, 2631-2635, 2648-2652, 2665-2669, 2682-2686, 2699-2703, 2716-2720, 2733-2737, 2750-2754, 2767-2771, 2784-2788, 2801-2805, 2818-2822, 2835-2839, 2852-2856, 2878-2882, 2888-2892, 2905-2909, 2922-2926, and 2939-2943, or fragments thereof and any isolated and/or purified nucleotide sequences which have a homology of at least 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7% identity with the at least one of the sequences of SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2857, 2858, 2860, 2877, 2894, 2911, and 2928 or fragments thereof. The homologous sequences can comprise, for example, the sequences corresponding to the genomic sequences *Alicyclobacillus acidocaldarius*. In the same manner, these specific homologous sequences can correspond to variations linked to mutations within strains of *Alicyclobacillus acidocaldarius* and especially correspond to truncations, substitutions, deletions and/or additions of at least one nucleotide. As will be apparent to one of ordinary skill in the art, such homologues are easily created and identified using standard techniques and publicly available computer programs such as BLAST. As such, each homologue referenced above should be considered as set forth herein and fully described.

Embodiments of the invention comprise the isolated and/or purified polypeptides coded for by a nucleotide sequence according to the invention, or fragments thereof, whose sequence is represented by a fragment. Amino acid sequences corresponding to the isolated and/or purified polypeptides which can be coded for according to one of the three possible reading frames of at least one of the sequences of SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2857, 2858, 2860, 2877, 2894, 2911, and 2928.

Embodiments of the invention likewise relate to the isolated and/or purified polypeptides, characterized in that they comprise a polypeptide selected from at least one of the amino acid sequences of SEQ ID NOS: 1, 18, 35, 52, 69, 86, 103, 120, 137, 154, 171, 188, 205, 222, 239, 256, 273, 290, 307, 324, 341, 358, 375, 392; 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927 or one of their fragments.

Among the isolated and/or purified polypeptides, according to embodiments of the invention, are the isolated and/or purified polypeptides of amino acid sequence SEQ ID NOS: 8-12, 25-29, 42-46, 59-63, 76-80, 93-97, 110-114, 127-131, 144-148, 161-165, 178-182, 195-199, 212-216, 229-233, 246-250, 263-267, 280-284, 297-301, 314-318, 331-335, 348-352, 365-369, 382-386, 399-403, 416-420, 433-437, 450-454, 467-471, 484-488, 501-505, 518-522, 535-539, 552-556, 569-573, 586-590, 603-607, 620-624, 637-641, 654-658, 671-675, 688-692, 705-709, 722-726, 739-743, 756-760, 773-777, 790-794, 807-811, 824-828, 841-845, 858-862, 875-879, 892-896, 909-913, 926-930, 943-947, 960-964, 977-981, 994-998, 1011-1015, 1028-1032, 1045-1049, 1062-1066, 1079-1083, 1096-1100, 1113-1117, 1130-1134, 1147-1151, 1164-1168, 1181-1185, 1198-1202, 1300-1304, 1317-1321, 1334-1338, 1351-1355, 1368-1372, 1385-1389, 1402-1406, 1419-1423, 1436-1440, 1453-1457, 1470-1474, 1487-1491, 1504-1508, 1521-1525, 1538-1542, 1555-1559, 1572-1576, 1589-1593, 1606-1610, 1623-1627, 1640-1644, 1657-1661, 1674-1678, 1691-1695, 1708-1712, 1725-1729, 1742-1746, 1759-1763, 1776-1780, 1793-1797, 1810-1814, 1827-1831, 1844-1848, 1861-1865, 1878-1882, 1895-1899, 1912-1916, 1929-1933, 1946-1950, 1963-1967, 1980-1984, 1997-2001, 2014-2018, 2031-2035, 2048-2052, 2065-2069, 2082-2086, 2099-2103, 2116-2120, 2133-2137, 2150-2154, 2167-2171, 2184-2188, 2201-2205, 2218-2222, 2235-2239, 2252-2256, 2269-2273, 2286-2290, 2303-2307, 2320-2324, 2337-2341, 2354-2358, 2371-2375, 2388-2392, 2405-2409, 2422-2426, 2524-2528, 2541-2545, 2558-2562, 2575-2579, 2609-2613, 2626-2630, 2643-2647, 2660-2664, 2677-2681, 2694-2698, 2711-2715, 2728-2732, 2745-2749, 2762-2766, 2779-2783, 2796-2800, 2813-2817, 2830-2834, 2847-2851, 2866-2870, 2883-2887, 2900-2914, 2917-2921, and 2934-2938, or fragments thereof or any other isolated and/or purified polypeptides which have a homology of at least 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7% identity with at least one of the sequences of SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927 or fragments thereof. As will be apparent to one of ordinary skill in the art, such homologues are easily created and identified using standard techniques and publicly available computer programs such as BLAST. As such, each homologue referenced above should be considered as set forth herein and fully described.

Embodiments of the invention also relate to the polypeptides, characterized in that they comprise a polypeptide selected from: a) a specific fragment of at least 5 amino acids of a polypeptide of an amino acid sequence according to the invention; b) a polypeptide homologous to a polypeptide such as defined in a); c) a specific biologically active fragment of a polypeptide such as defined in a) or b); and d) a polypeptide modified by a polypeptide such as defined in a), b) or c).

In the present description, the terms polypeptide, peptide and protein are interchangeable.

In embodiments of the invention, the isolated and/or purified polypeptides according to the invention may be glycosylated, pegylated, and/or otherwise post-translationally modified. In further embodiments, glycosylation, pegylation, and/or other post-translational modifications may occur in vivo or in vitro and/or may be performed using chemical techniques. In additional embodiments, any glycosylation, pegylation and/or other post-translational modifications may be N-linked or O-linked.

In embodiments of the invention any one of the isolated and/or purified polypeptides according to the invention may be enzymatically or functionally active at temperatures at or above about 25, 30, 35, 40, 45, 50, 55, 60, 65, 70, 75, 80, 85, 90, and/or 95 degrees Celsius and/or may be enzymatically or functionally active at a pH at, below, and/or above 8, 7, 6, 5, 4, 3, 2, 1, and/or 0. In further embodiments of the invention, glycosylation, pegylation, and/or other post-translational modification may be required for the isolated and/or purified polypeptides according to the invention to be enzymatically or functionally active at a pH at or below 8, 7, 6, 5, 4, 3, 2, 1, and/or 0 or at temperatures at or above about 25, 30, 35, 40, 45, 50, 55, 60, 65, 70, 75, 80, 85, 90, and/or 95 degrees Celsius.

Aspects of the invention relate to polypeptides that are isolated or obtained by purification from natural sources, or else obtained by genetic recombination, or alternatively by chemical synthesis and that they may thus contain unnatural amino acids, as will be described below.

A "polypeptide fragment" according to the embodiments of the invention is understood as designating a polypeptide containing at least 5 consecutive amino acids, preferably 10 consecutive amino acids or 15 consecutive amino acids.

In the present invention, a specific polypeptide fragment is understood as designating the consecutive polypeptide fragment coded for by a specific fragment nucleotide sequence according to the invention.

"Homologous polypeptide" will be understood as designating the polypeptides having, with respect to the natural polypeptide, certain modifications such as, in particular, a deletion, addition, or substitution of at least one amino acid, a truncation, a prolongation, a chimeric fusion, and/or a mutation. Among the homologous polypeptides, those are preferred whose amino acid sequence has at least 80% or 90%, homology with the sequences of amino acids of polypeptides according to the invention.

"Specific homologous polypeptide" will be understood as designating the homologous polypeptides such as defined above and having a specific fragment of polypeptide according to the invention.

In the case of a substitution, one or more consecutive or nonconsecutive amino acids are replaced by "equivalent" amino acids. The expression "equivalent" amino acid is directed here at designating any amino acid capable of being substituted by one of the amino acids of the base structure without, however, essentially modifying the biological activities of the corresponding peptides and such that they will be defined by the following. As will be apparent to one of ordinary skill in the art, such substitutions are easily created and identified using standard molecular biology techniques and publicly available computer programs such as BLAST. As such, each substitution referenced above should be considered as set forth herein and fully described. Examples of such substitutions in the amino acid sequences SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927 may include those isolated and/or purified polypeptides of amino acid sequence SEQ ID NOS: 8-12, 25-29, 42-46, 59-63, 76-80, 93-97, 110-114, 127-131, 144-148, 161-165, 178-182, 195-199, 212-216, 229-233, 246-250, 263-267, 280-284, 297-301, 314-318, 331-335, 348-352, 365-369, 382-386, 399-403, 416-420, 433-437, 450-454, 467-471, 484-488, 501-505, 518-522, 535-539, 552-556, 569-573, 586-590, 603-607, 620-624, 637-641, 654-658, 671-675, 688-692, 705-709, 722-726, 739-743, 756-760, 773-777, 790-794, 807-811, 824-828, 841-845, 858-862, 875-879, 892-896, 909-913, 926-930, 943-947, 960-964, 977-981, 994-998, 1011-1015, 1028-1032, 1045-1049, 1062-1066, 1079-1083, 1096-1100, 1113-1117, 1130-1134, 1147-1151, 1164-1168, 1181-1185, 1198-1202, 1300-1304, 1317-1321, 1334-1338, 1351-1355, 1368-1372, 1385-1389, 1402-1406, 1419-1423, 1436-1440, 1453-1457, 1470-1474, 1487-1491, 1504-1508, 1521-1525, 1538-1542, 1555-1559, 1572-1576, 1589-1593, 1606-1610, 1623-1627, 1640-1644, 1657-1661, 1674-1678, 1691-1695, 1708-1712, 1725-1729, 1742-1746, 1759-1763, 1776-1780, 1793-1797, 1810-1814, 1827-1831, 1844-1848, 1861-1865, 1878-1882, 1895-1899, 1912-1916, 1929-1933, 1946-1950, 1963-1967, 1980-1984, 1997-2001, 2014-2018, 2031-2035, 2048-2052, 2065-2069, 2082-2086, 2099-2103, 2116-2120, 2133-2137, 2150-2154, 2167-2171, 2184-2188, 2201-2205, 2218-2222, 2235-2239, 2252-2256, 2269-2273, 2286-2290, 2303-2307, 2320-2324, 2337-2341, 2354-2358, 2371-2375, 2388-2392, 2405-2409, 2422-2426, 2524-2528, 2541-2545, 2558-2562, 2575-2579, 2609-2613, 2626-2630, 2643-2647, 2660-2664, 2677-2681, 2694-2698, 2711-2715, 2728-2732, 2745-2749, 2762-2766, 2779-2783, 2796-2800, 2813-2817, 2830-2834, 2847-2851, 2866-2870, 2883-2887, 2900-2914, 2917-2921, and 2934-2938.

These equivalent amino acids can be determined either by depending on their structural homology with the amino acids, which they substitute, or on results of comparative tests of biological activity between the different polypeptides, which are capable of being carried out.

By way of non-limiting example, the possibilities of substitutions capable of being carried out without resulting in an extensive modification of the biological activity of the corresponding modified polypeptides will be mentioned, the replacement, for example, of leucine by valine or isoleucine, of aspartic acid by glutamic acid, of glutamine by asparagine, of arginine by lysine, etc., the reverse substitutions naturally being envisageable under the same conditions.

In a further embodiment, substitutions are limited to substitutions in amino acids not conserved among other proteins which have similar identified activity. For example, one of ordinary skill in the art may align proteins of the same function in similar organisms and determine which amino acids are generally conserved among proteins of that function. One example of a program that may be used to generate such alignments is available at the website charite.de/bioinf/strap in conjunction with the databases provided by the NCBI. Examples of such polypeptides may include, but are not limited to, those found in amino acid sequence SEQ ID NOS: 8-12, 25-29, 42-46, 59-63, 76-80, 93-97, 110-114, 127-131, 144-148, 161-165, 178-182, 195-199, 212-216, 229-233, 246-250, 263-267, 280-284, 297-301, 314-318, 331-335, 348-352, 365-369, 382-386, 399-403, 416-420, 433-437, 450-454, 467-471, 484-488, 501-505, 518-522, 535-539, 552-556, 569-573, 586-590, 603-607, 620-624, 637-641, 654-658, 671-675, 688-692, 705-709, 722-726, 739-743, 756-760, 773-777, 790-794, 807-811, 824-828, 841-845, 858-862, 875-879, 892-896, 909-913, 926-930, 943-947, 960-964, 977-981, 994-998, 1011-1015, 1028-1032, 1045-1049, 1062-1066, 1079-1083, 1096-1100, 1113-1117, 1130-1134, 1147-1151, 1164-1168, 1181-1185, 1198-1202, 1300-1304, 1317-1321, 1334-1338, 1351-1355, 1368-1372, 1385-1389, 1402-1406, 1419-1423, 1436-1440, 1453-1457, 1470-1474, 1487-1491, 1504-1508, 1521-1525, 1538-1542, 1555-1559, 1572-1576, 1589-1593, 1606-1610, 1623-1627, 1640-1644, 1657-1661, 1674-1678, 1691-1695, 1708-1712, 1725-1729, 1742-1746, 1759-1763, 1776-1780, 1793-1797, 1810-1814, 1827-1831, 1844-1848, 1861-1865, 1878-1882, 1895-1899, 1912-1916, 1929-1933, 1946-1950, 1963-1967, 1980-1984, 1997-2001, 2014-2018, 2031-2035, 2048-2052, 2065-2069, 2082-2086, 2099-2103, 2116-2120, 2133-2137, 2150-2154, 2167-2171, 2184-2188, 2201-2205, 2218-2222, 2235-2239, 2252-2256, 2269-2273, 2286-2290, 2303-2307, 2320-2324, 2337-2341, 2354-2358, 2371-2375, 2388-2392, 2405-2409, 2422-2426, 2524-2528, 2541-2545, 2558-2562, 2575-2579, 2609-2613, 2626-2630, 2643-2647, 2660-2664, 2677-2681, 2694-2698, 2711-2715, 2728-2732, 2745-2749, 2762-2766, 2779-2783, 2796-2800, 2813-2817, 2830-2834, 2847-2851, 2866-2870, 2883-2887, 2900-2914, 2917-2921, and 2934-2938.

Thus, according to one embodiment of the invention, substitutions or mutations may be made at positions that are generally conserved among proteins of that function. In a further embodiment, nucleic acid sequences may be mutated or substituted such that the amino acid they code for is unchanged (degenerate substitutions and/or mutations) and/or mutated or substituted such that any resulting amino acid substitutions or mutations are made at positions that are generally conserved among proteins of that function. Examples of such nucleic acid sequences may include, but are not limited to, those found in are the nucleotide sequences of SEQ ID NOS: 13-17, 30-34, 47-51, 64-68, 81-85, 98-102, 115-119, 132-136, 149-153, 166-170, 183-187, 200-204, 217-221, 234-238, 251-255, 268-272, 285-289, 302-306, 319-323, 336-340, 353-357, 370-374, 387-391, 404-408, 421-425, 438-442, 455-459, 472-476, 489-493, 506-510, 523-527, 540-544, 557-561, 574-578, 591-595, 608-612, 625-629, 642-646, 659-663, 676-680, 693-697, 710-714, 727-731, 744-748, 761-765, 778-782, 795-799, 812-816, 829-833, 846-850, 863-867, 880-884, 897-901, 914-918, 931-935, 948-952, 965-969, 982-986, 999-1003, 1016-1020, 1033-1037, 1050-1054, 1067-1071, 1084-1088, 1101-1105, 1118-1122, 1135-1139, 1152-1156, 1169-1173, 1186-1190, 1203-1207, 1305-1309, 1322-1326, 1339-1343, 1356-1360, 1373-1377, 1390-1394, 1407-1411, 1424-1428, 1441-1445, 1458-1462, 1475-1479, 1492-1496, 1509-1513, 1526-1530, 1543-1547, 1560-1564, 1577-1581, 1594-1598, 1611-1615, 1628-1632, 1645-1649, 1662-1666, 1679-1683, 1696-1700, 1713-1717, 1730-1734, 1747-1751, 1764-1768, 1781-1785, 1798-1802, 1815-1819, 1832-1836, 1849-1853, 1866-1870, 1883-1887, 1900-1904, 1917-1921, 1934-1938, 1951-1955, 1968-1972, 1985-1989, 2002-2006, 2019-2023, 2036-2040, 2053-2057, 2070-2074, 2087-2091, 2104-2108, 2121-2125, 2138-2142, 2155-2159, 2172-2176, 2189-2193, 2206-2210, 2223-2227, 2240-2244, 2257-2261, 2274-2278, 2291-2295, 2308-2312, 2325-2329, 2342-2346, 2359-2363, 2376-2380, 2393-2397, 2410-2414, 2427-2431, 2529-2533, 2546-2550, 2563-2567, 2580-2584, 2614-2618, 2631-2635, 2648-2652, 2665-2669, 2682-2686, 2699-2703, 2716-2720, 2733-2737, 2750-2754, 2767-2771, 2784-2788, 2801-2805, 2818-2822, 2835-2839, 2852-2856, 2878-2882, 2888-2892, 2905-2909, 2922-2926, and 2939-2943 or fragments thereof.

The specific homologous polypeptides likewise correspond to polypeptides coded for by the specific homologous nucleotide sequences such as defined above and thus comprise in the present definition the polypeptides, which are mutated or correspond to variants that can exist in *Alicyclobacillus acidocaldarius*, and which especially correspond to truncations, substitutions, deletions, and/or additions of at least one amino acid residue.

"Specific biologically active fragment of a polypeptide" according to an embodiment of the invention will be understood in particular as designating a specific polypeptide fragment, such as defined above, having at least one of the characteristics of polypeptides according to the invention. In certain embodiments the peptide is capable of behaving as at least one of the types of proteins outlined in Table 1.

The polypeptide fragments according to embodiments of the invention can correspond to isolated or purified fragments naturally present in *Alicyclobacillus acidocaldarius* or correspond to fragments that can be obtained by cleavage of the polypeptide by a proteolytic enzyme, such as trypsin or chymotrypsin or collagenase, or by a chemical reagent, such as cyanogen bromide (CNBr). Such polypeptide fragments can likewise just as easily be prepared by chemical synthesis, from hosts transformed by an expression vector according to the invention containing a nucleic acid allowing the expression of the fragments, placed under the control of appropriate regulation and/or expression elements.

"Modified polypeptide" of a polypeptide according to an embodiment of the invention is understood as designating a polypeptide obtained by genetic recombination or by chemical synthesis as will be described below, having at least one modification with respect to the normal sequence. These modifications may or may not be able to bear on amino acids at the origin of specificity, and/or of activity, or at the origin of the structural conformation, localization, and of the capacity of membrane insertion of the polypeptide according to the invention. It will thus be possible to create polypeptides of equivalent, increased, or decreased activity, and of equivalent, narrower, or wider specificity. Among the modified polypeptides, it is necessary to mention the polypeptides in which up to 5 or more amino acids can be modified, truncated at the N- or C-terminal end, or even deleted or added.

The methods allowing the modulations on eukaryotic or prokaryotic cells to be demonstrated are well known to a person of ordinary skill in the art. It is likewise well understood that it will be possible to use the nucleotide sequences coding for the modified polypeptides for the modulations, for example, through vectors according to the invention and described below.

The preceding modified polypeptides can be obtained by using combinatorial chemistry, in which it is possible to systematically vary parts of the polypeptide before testing them on models, cell cultures or microorganisms, for example, to select the compounds that are most active or have the properties sought.

Chemical synthesis likewise has the advantage of being able to use unnatural amino acids, or nonpeptide bonds.

Thus, in order to improve the duration of life of the polypeptides, according to the invention, it may be of interest to use unnatural amino acids, for example, in D form, or else amino acid analogs, especially sulfur-containing forms, for example.

Finally, it will be possible to integrate the structure of the polypeptides according to the invention, its specific or modified homologous forms, into chemical structures of polypeptide type or others. Thus, it may be of interest to provide at the N- and C-terminal ends compounds not recognized by proteases.

The nucleotide sequences coding for a polypeptide according to the invention are likewise part of the invention.

The invention likewise relates to nucleotide sequences utilizable as a primer or probe, characterized in that the sequences are selected from the nucleotide sequences according to the invention.

It is well understood that the present invention, in various embodiments, likewise relates to specific polypeptides of *Alicyclobacillus acidocaldarius*, coded for by nucleotide sequences, capable of being obtained by purification from natural polypeptides, by genetic recombination or by chemical synthesis by procedures well known to a person skilled in the art and such as described in particular below. In the same manner, the labeled or unlabeled mono- or polyclonal antibodies directed against the specific polypeptides coded for by the nucleotide sequences are also encompassed by the invention.

Embodiments of the invention additionally relate to the use of a nucleotide sequence according to the invention as a primer or probe for the detection and/or the amplification of nucleic acid sequences.

The nucleotide sequences according to embodiments of the invention can thus be used to amplify nucleotide sequences, especially by the PCR technique (polymerase chain reaction) (Erlich, 1989; Innis et al., 1990; Rolfs et al., 1991; and White et al., 1997).

These oligodeoxyribonucleotide or oligoribonucleotide primers advantageously have a length of at least 8 nucleotides, preferably of at least 12 nucleotides, and even more preferentially of at least 20 nucleotides.

Other amplification techniques of the target nucleic acid can be advantageously employed as alternatives to PCR.

The nucleotide sequences of the invention, in particular the primers according to the invention, can likewise be employed in other procedures of amplification of a target nucleic acid, such as: the TAS technique (Transcription-based Amplification System), described by Kwoh et al. in 1989; the 3SR technique (Self-Sustained Sequence Replication), described by Guatelli et al. in 1990; the NASBA technique (Nucleic Acid Sequence Based Amplification), described by Kievitis et al. in 1991; the SDA technique (Strand Displacement Amplification) (Walker et al., 1992); and the TMA technique (Transcription Mediated Amplification).

The polynucleotides of the invention can also be employed in techniques of amplification or of modification of the nucleic acid serving as a probe, such as: the LCR technique (Ligase Chain Reaction), described by Landegren et al. in 1988 and improved by Barany et al. in 1991, which employs a thermostable ligase; the RCR technique (Repair Chain Reaction), described by Segev in 1992; the CPR technique (Cycling Probe Reaction), described by Duck et al. in 1990; the amplification technique with Q-beta replicase, described by Miele et al. in 1983 and especially improved by Chu et al. in 1986, Lizardi et al. in 1988, then by Burg et al., as well as by Stone et al. in 1996.

In the case where the target polynucleotide to be detected is possibly an RNA, for example, an mRNA, it will be possible to use, prior to the employment of an amplification reaction with the aid of at least one primer according to the invention or to the employment of a detection procedure with the aid of at least one probe of the invention, an enzyme of reverse transcriptase type in order to obtain a cDNA from the RNA contained in the biological sample. The cDNA obtained will thus serve as a target for the primer(s) or the probe(s) employed in the amplification or detection procedure according to the invention.

The detection probe will be chosen in such a manner that it hybridizes with the target sequence or the amplicon generated from the target sequence. By way of sequence, such a probe will advantageously have a sequence of at least 12 nucleotides, in particular of at least 20 nucleotides, and preferably of at least 100 nucleotides.

Embodiments of the invention also comprise the nucleotide sequences utilizable as a probe or primer according to the invention, characterized in that they are labeled with a radioactive compound or with a nonradioactive compound.

The unlabeled nucleotide sequences can be used directly as probes or primers, although the sequences are generally labeled with a radioactive isotope ($^{32}P$, $^{35}S$, $^{3}H$, $^{125}I$) or with a nonradioactive molecule (biotin, acetylaminofluorene, digoxigenin, 5-bromodeoxyuridine, fluorescein) to obtain probes, which are utilizable for numerous applications.

Examples of nonradioactive labeling of nucleotide sequences are described, for example, in French Patent No. 7810975 or by Urdea et al. or by Sanchez-Pescador et al. in 1988.

In the latter case, it will also be possible to use one of the labeling methods described in patents FR-2 422 956 and FR-2 518 755.

The hybridization technique can be carried out in various manners (Matthews et al., 1988). The most general method consists in immobilizing the nucleic acid extract of cells on a support (such as nitrocellulose, nylon, polystyrene) and in incubating, under well-defined conditions, the immobilized target nucleic acid with the probe. After hybridization, the excess of probe is eliminated and the hybrid molecules formed are detected by the appropriate method (measurement of the radioactivity, of the fluorescence or of the enzymatic activity linked to the probe).

The invention, in various embodiments, likewise comprises the nucleotide sequences according to the invention, characterized in that they are immobilized on a support, covalently or noncovalently.

According to another advantageous mode of employing nucleotide sequences according to the invention, the latter can be used immobilized on a support and can thus serve to capture, by specific hybridization, the target nucleic acid obtained from the biological sample to be tested. If necessary, the solid support is separated from the sample and the hybridization complex formed between the capture probe and the target nucleic acid is then detected with the aid of a second probe, a so-called detection probe, labeled with an easily detectable element.

Another aspect of the present invention is a vector for the cloning and/or expression of a sequence, characterized in that it contains a nucleotide sequence according to the invention.

The vectors, according to the invention, characterized in that they contain the elements allowing the integration, expression and/or the secretion of the nucleotide sequences in a determined host cell, are likewise part of the invention.

The vector may then contain a promoter, signals of initiation and termination of translation, as well as appropriate regions of regulation of transcription. It may be able to be maintained stably in the host cell and can optionally have particular signals specifying the secretion of the translated protein. These different elements may be chosen as a function of the host cell used. To this end, the nucleotide sequences according to the invention may be inserted into autonomous replication vectors within the chosen host, or integrated vectors of the chosen host.

Such vectors will be prepared according to the methods currently used by a person skilled in the art, and it will be possible to introduce the clones resulting therefrom into an appropriate host by standard methods, such as, for example, lipofection, electroporation, and thermal shock.

The vectors according to the invention are, for example, vectors of plasmid or viral origin. One example of a vector for the expression of polypeptides of the invention is Baculovirus.

These vectors are useful for transforming host cells in order to clone or to express the nucleotide sequences of the invention.

The invention likewise comprises the host cells transformed by a vector according to the invention.

These cells can be obtained by the introduction into host cells of a nucleotide sequence inserted into a vector such as defined above, then the culturing of the cells under conditions allowing the replication and/or expression of the transfected nucleotide sequence.

The host cell can be selected from prokaryotic or eukaryotic systems, such as, for example, bacterial cells (Olins and Lee, 1993), but likewise yeast cells (Buckholz, 1993), as well as plants cells, such as *Arabidopsis* sp., and animal cells, in particular the cultures of mammalian cells (Edwards and Aruffo, 1993), for example, Chinese hamster ovary (CHO) cells, but likewise the cells of insects in which it is possible to use procedures employing baculoviruses, for example, Sf9 insect cells (Luckow, 1993).

Embodiments of the invention likewise relate to organisms comprising one of the transformed cells according to the invention.

The obtainment of transgenic organisms, according to the invention, of expressing one or more of the genes of *Alicyclobacillus acidocaldarius* or part of the genes may be carried out in, for example, rats, mice, or rabbits according to methods well known to a person skilled in the art, such as by viral or nonviral transfections. It will be possible to obtain the transgenic organisms expressing one or more of the genes by transfection of multiple copies of the genes under the control of a strong promoter of ubiquitous nature, or selective for one type of tissue. It will likewise be possible to obtain the transgenic organisms by homologous recombination in embryonic cell strains, transfer of these cell strains to embryos, selection of the affected chimeras at the level of the reproductive lines, and growth of the chimeras.

The transformed cells, as well as the transgenic organisms according to the invention, are utilizable in procedures for preparation of recombinant polypeptides.

It is today possible to produce recombinant polypeptides in relatively large quantity by genetic engineering using the cells transformed by expression vectors according to the invention or using transgenic organisms according to the invention.

The procedures for preparation of a polypeptide of the invention in recombinant form, characterized in that they employ a vector and/or a cell transformed by a vector according to the invention and/or a transgenic organism comprising one of the transformed cells according to the invention are themselves comprised in the present invention.

As used herein, "transformation" and "transformed" relate to the introduction of nucleic acids into a cell, whether prokaryotic or eukaryotic. Further, "transformation" and "transformed," as used herein, need not relate to growth control or growth deregulation.

Among the procedures for preparation of a polypeptide of the invention in recombinant form, the preparation procedures employing a vector, and/or a cell transformed by the vector and/or a transgenic organism comprising one of the transformed cells, containing a nucleotide sequence according to the invention coding for a polypeptide of *Alicyclobacillus acidocaldarius*.

A variant according to the invention may consist of producing a recombinant polypeptide fused to a "carrier" protein (chimeric protein). The advantage of this system is that it may allow stabilization of and/or a decrease in the proteolysis of the recombinant product, an increase in the solubility in the course of renaturation in vitro and/or a simplification of the purification when the fusion partner has an affinity for a specific ligand.

More particularly, the invention relates to a procedure for preparation of a polypeptide of the invention comprising the following steps: a) culture of transformed cells under conditions allowing the expression of a recombinant polypeptide of a nucleotide sequence according to the invention; b) if need be, recovery of the recombinant polypeptide.

When the procedure for preparation of a polypeptide of the invention employs a transgenic organism according to the invention, the recombinant polypeptide is then extracted from the organism.

The invention also relates to a polypeptide that is capable of being obtained by a procedure of the invention, such as described previously.

The invention also comprises a procedure for preparation of a synthetic polypeptide, characterized in that it uses a sequence of amino acids of polypeptides according to the invention.

The invention likewise relates to a synthetic polypeptide obtained by a procedure according to the invention.

The polypeptides according to the invention can likewise be prepared by techniques that are conventional in the field of the synthesis of peptides. This synthesis can be carried out in homogeneous solution or in solid phase.

For example, recourse can be made to the technique of synthesis in a homogeneous solution described by Houben-Weyl in 1974.

This method of synthesis consists in successively condensing, two by two, the successive amino acids in the order required, or in condensing amino acids and fragments formed previously and already containing several amino acids in the appropriate order, or alternatively several fragments previously prepared in this way, it being understood that it will be necessary to protect beforehand all the reactive functions carried by these amino acids or fragments, with the exception of amine functions of one and carboxyls of the other or vice-versa, which must normally be involved in the formation of peptide bonds, especially after activation of the carboxyl function, according to the methods well known in the synthesis of peptides.

Recourse may also be made to the technique described by Merrifield.

To make a peptide chain according to the Merrifield procedure, recourse is made to a very porous polymeric resin, on which is immobilized the first C-terminal amino acid of the chain. This amino acid is immobilized on a resin through its carboxyl group and its amine function is protected. The amino acids that are going to form the peptide chain are thus immobilized, one after the other, on the amino group, which is deprotected beforehand each time, of the portion of the peptide chain already formed, and which is attached to the resin. When the whole of the desired peptide chain has been formed, the protective groups of the different amino acids forming the peptide chain are eliminated and the peptide is detached from the resin with the aid of an acid.

The invention additionally relates to hybrid polypeptides having at least one polypeptide according to the invention, and a sequence of a polypeptide capable of inducing an immune response in man or animals.

Advantageously, the antigenic determinant is such that it is capable of inducing a humoral and/or cellular response.

It will be possible for such a determinant to comprise a polypeptide according to the invention in glycosylated, pegylated, and/or otherwise post-translationally modified form used with a view to obtaining immunogenic compositions capable of inducing the synthesis of antibodies directed against multiple epitopes.

These hybrid molecules can be formed, in part, of a polypeptide carrier molecule or of fragments thereof according to the invention, associated with a possibly immunogenic part, in particular, an epitope of the diphtheria toxin, the tetanus toxin, a surface antigen of the hepatitis B virus (Patent FR 79 21811), the VP1 antigen of the poliomyelitis virus or any other viral or bacterial toxin or antigen.

The procedures for synthesis of hybrid molecules encompass the methods used in genetic engineering for constructing hybrid nucleotide sequences coding for the polypeptide sequences sought. It will be possible, for example, to refer advantageously to the technique for obtainment of genes coding for fusion proteins described by Minton in 1984.

The hybrid nucleotide sequences coding for a hybrid polypeptide as well as the hybrid polypeptides according to the invention characterized in that they are recombinant polypeptides obtained by the expression of the hybrid nucleotide sequences are likewise part of the invention.

The invention likewise comprises the vectors characterized in that they contain one of the hybrid nucleotide sequences.

The host cells transformed by the vectors, the transgenic organisms comprising one of the transformed cells as well as the procedures for preparation of recombinant polypeptides using the vectors, the transformed cells and/or the transgenic organisms are, of course, likewise part of the invention.

The polypeptides according to the invention, the antibodies according to the invention described below and the nucleotide sequences according to the invention can advantageously be employed in procedures for the detection and/or identification of *Alicyclobacillus acidocaldarius*, in a sample capable of containing them. These procedures, according to the specificity of the polypeptides, the antibodies and the nucleotide sequences according to the invention that will be used, will in particular be able to detect and/or to identify *Alicyclobacillus acidocaldarius*.

The polypeptides according to the invention can advantageously be employed in a procedure for the detection and/or the identification of *Alicyclobacillus acidocaldarius* in a sample capable of containing them, characterized in that it comprises the following steps: a) contacting of this sample with a polypeptide or one of its fragments according to the invention (under conditions allowing an immunological reaction between the polypeptide and the antibodies possibly present in the biological sample); and b) demonstration of the antigen-antibody complexes possibly formed.

Any conventional procedure can be employed for carrying out such a detection of the antigen-antibody complexes possibly formed.

By way of example, a preferred method brings into play immunoenzymatic processes according to the ELISA technique, by immunofluorescence, or radioimmunological processes (RIA) or their equivalent.

Thus, the invention likewise relates to the polypeptides according to the invention, labeled with the aid of an adequate label, such as, of the enzymatic, fluorescent or radioactive type.

Such methods comprise, for example, the following steps: deposition of determined quantities of a polypeptide composition according to the invention in the wells of a microtiter plate, introduction into the wells of increasing dilutions of serum, or of a biological sample other than that defined previously, having to be analyzed, incubation of the wells of the microtiter plate, introduction into the wells of the microtiter plate of labeled antibodies directed against pig immunoglobulins, the labeling of these antibodies having been carried out with the aid of an enzyme selected from those which are capable of hydrolyzing a substrate by modifying the absorption of the radiation of the latter, at least at a determined wavelength, for example, at 550 nm, detection, by comparison with a control test, of the quantity of hydrolyzed substrate.

The polypeptides according to the invention allow monoclonal or polyclonal antibodies to be prepared which are characterized in that they specifically recognize the polypeptides according to the invention. It will advantageously be possible to prepare the monoclonal antibodies from hybridomas according to the technique described by Kohler and Milstein in 1975. It will be possible to prepare the polyclonal antibodies, for example, by immunization of an animal, in particular a mouse, with a polypeptide or a DNA, according to the invention, associated with an adjuvant of the immune response, and then purification of the specific antibodies contained in the serum of the immunized animals on an affinity column on which the polypeptide, which has served as an antigen, has previously been immobilized. The polyclonal antibodies according to the invention can also be prepared by purification, on an affinity column on which a polypeptide according to the invention has previously been immobilized, of the antibodies contained in the serum of an animal immunologically challenged by *Alicyclobacillus acidocaldarius*, or a polypeptide or fragment according to the invention.

The invention likewise relates to mono- or polyclonal antibodies or their fragments, or chimeric antibodies, characterized in that they are capable of specifically recognizing a polypeptide according to the invention.

It will likewise be possible for the antibodies of the invention to be labeled in the same manner as described previously for the nucleic probes of the invention, such as a labeling of enzymatic, fluorescent or radioactive type.

The invention is additionally directed at a procedure for the detection and/or identification of *Alicyclobacillus acidocaldarius* in a sample, characterized in that it comprises the following steps: a) contacting of the sample with a mono- or polyclonal antibody according to the invention (under conditions allowing an immunological reaction between the antibodies and the polypeptides of *Alicyclobacillus acidocaldarius* possibly present in the biological sample); and b) demonstration of the antigen-antibody complex possibly formed.

The present invention likewise relates to a procedure for the detection and/or the identification of *Alicyclobacillus acidocaldarius* in a sample, characterized in that it employs a nucleotide sequence according to the invention.

More particularly, the invention relates to a procedure for the detection and/or the identification of *Alicyclobacillus acidocaldarius* in a sample, characterized in that it contains the following steps: a) if need be, isolation of the DNA from the sample to be analyzed; b) specific amplification of the DNA of the sample with the aid of at least one primer, or a pair of primers, according to the invention; and c) demonstration of the amplification products.

These can be detected, for example, by the technique of molecular hybridization utilizing a nucleic probe according to the invention. This probe will advantageously be labeled with a nonradioactive (cold probe) or radioactive isotope.

For the purposes of the present invention, "DNA of the biological sample" or "DNA contained in the biological sample" will be understood as meaning either the DNA present in the biological sample considered, or possibly the cDNA obtained after the action of an enzyme of reverse transcriptase type on the RNA present in the biological sample.

A further embodiment of the invention comprises a method, characterized in that it comprises the following steps: a) contacting of a nucleotide probe according to the invention with a biological sample, the DNA contained in the biological sample having, if need be, previously been made accessible to hybridization under conditions allowing the hybridization of the nucleotide probe with the DNA of the sample; and b) demonstration of the hybrid formed between the nucleotide probe and the DNA of the biological sample.

The present invention also relates to a procedure according to the invention, characterized in that it comprises the following steps: a) contacting of a nucleotide probe immobilized on a support according to the invention with a biological sample, the DNA of the sample having, if need be, previously been made accessible to hybridization, under conditions allowing the hybridization of the nucleotide probe with the DNA of the sample; b) contacting of the hybrid formed between the nucleotide probe immobilized on a support and the DNA contained in the biological sample, if need be after elimination of the DNA of the biological sample which has not hybridized with the nucleotide probe, with a nucleotide probe labeled according to the invention; and c) demonstration of the novel hybrid formed in step b).

According to an advantageous embodiment of the procedure for detection and/or identification defined previously, this is characterized in that, prior to step a), the DNA of the biological sample is first amplified with the aid of at least one primer according to the invention.

Embodiments of methods include placing a recombinant, purified, and/or isolated polypeptide selected from the group consisting of a polypeptide having at least 90% sequence identity to SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927 in, or replacing a component, of an in-vitro transcription system such as, by way of non-limiting example, a polymerase chain reaction or a reticulocyte lysate transcription/translation system.

Further embodiments of methods include placing a cell producing or encoding a recombinant, purified, and/or isolated nucleotide sequence comprising a nucleotide sequence selected from the group consisting of a nucleotide sequence having at least 90% sequence identity to at least one of the sequences of SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2857, 2858, 2860, 2877, 2894, 2911, and 2928 and/or a recombinant, purified, and/or isolated polypeptide selected from the group consisting of a polypeptide having at least 90% sequence identity to at least one of the sequences of SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927 in an environment comprising temperatures at or above about 25, 30, 35, 40, 45, 50, 55, 60, 65, 70, 75, 80, 85, 90, and/or 95 degrees Celsius and/or a pH at, below, and/or above 8, 7, 6, 5, 4, 3, 2, 1, and/or 0.

The present invention provides cells that have been genetically manipulated to have an altered capacity to produce expressed proteins. In particular, the present invention relates to Gram-positive microorganisms, such as *Bacillus* species having enhanced expression of a protein of interest, wherein one or more chromosomal genes have been inactivated, and/or wherein one or more chromosomal genes have been deleted from the *Bacillus* chromosome. In some further embodiments, one or more indigenous chromosomal regions have been deleted from a corresponding wild-type *Bacillus* host chromosome. In further embodiments, the *Bacillus* is an *Alicyclobacillus* sp. or *Alicyclobacillus acidocaldarius*.

In additional embodiments, methods of modulating transcription or transcription or transcriptional control at temperatures at or above about 25, 30, 35, 40, 45, 50, 55, 60, 65, 70, 75, 80, 85, 90, and/or 95 degrees Celsius and/or at a pH at, below, and/or above 8, 7, 6, 5, 4, 3, 2, 1, and/or 0 via a recombinant, purified, and/or isolated nucleotide sequence comprising a nucleotide sequence selected from the group consisting of a nucleotide sequence having at least 90% sequence identity to at least one of the sequences of SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2857, 2858, 2860, 2877, 2894, 2911, and 2928 and/or a recombinant, purified, and/or isolated polypeptide selected from the group consisting of a polypeptide having at least 90% sequence identity to at least one of the sequences of SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927.

In embodiments of the invention any one of the isolated and/or purified polypeptides according to the invention may be enzymatically or functionally active at temperatures at or above about 25, 30, 35, 40, 45, 50, 55, 60, 65, 70, 75, 80, 85, 90, and/or 95 degrees Celsius and/or may be enzymatically or functionally active at a pH at, below, and/or above 8, 7, 6, 5, 4, 3, 2, 1, and/or 0. In further embodiments of the invention, glycosylation, pegylation, and/or other post-translational modification may be required for the isolated and/or purified polypeptides according to the invention to be enzymatically or functionally active at a pH at or below 8, 7, 6, 5, 4, 3, 2, 1, and/or 0 or at temperatures at or above about 25, 30, 35, 40, 45, 50, 55, 60, 65, 70, 75, 80, 85, 90, and/or 95 degrees Celsius.

The invention is described in additional detail in the following illustrative examples. Although the examples may represent only selected embodiments of the invention, it should be understood that the following examples are illustrative and not limiting.

EXAMPLES

Example 1

Transcription and Transcriptional Control Using Nucleotide and Amino Acid Sequences from *Alicyclobacillus acidocaldarius*

Provided in SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2857, 2858, 2860, 2877, 2894, 2911, and 2928 are a nucleotide sequences isolated from *Alicyclobacillus acidocaldarius* and coding for the polypeptides of SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927. The nucleotide sequences of SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2857, 2858, 2860, 2877, 2894, 2911, and 2928 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2857, 2858, 2860, 2877, 2894, 2911, and 2928 produce the polypeptides of SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927. The polypeptides of SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927 are then isolated and/or purified. The isolated and/or purified polypeptides of SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927 are then each demonstrated to have one or more of the activities provided in Table 1.

The isolated and/or purified polypeptides of SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927 are placed in an extracellular transcription system and are demonstrated to have activity in transcription or modulating transcription.

Example 2

Transcriptional Control Using Catabolite-Responsive Elements from *Alicyclobacillus acidocaldarius*

Provided in SEQ ID NOS: 2857, 2858, 2860, 2877, 2894, 2911, and 2928 are nucleotide sequences isolated from *Alicyclobacillus acidocaldarius*. The nucleotide sequences of SEQ ID NOS: 2857, 2858, 2860, 2877, 2894, 2911, and 2928 are placed into expression vectors and functionally linked to a reporter gene using techniques standard in the art. The vectors are then provided to cells such as bacteria cells or eukaryotic cells such as Sf9 cells or CHO cells. In conjunction with the normal machinery in present in the cells, the vectors comprising SEQ ID NOS: 2857, 2858, 2860, 2877, 2894, 2911, and 2928 attempt to produce the protein coded for by the reporter gene in an environment designed to assay the function of a catabolite-responsive element. The cells are then assayed for the presence or absence and/or level of the reporter gene product. SEQ ID NOS: 2857, 2858, 2860, 2877, 2894, 2911, and 2928 are then each demonstrated to have activity as a catabolite-responsive element.

All references, including publications, patents, and patent applications, cited herein are hereby incorporated by reference to the same extent as if each reference were individually and specifically indicated to be incorporated by reference and were set forth in its entirety herein.

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and that fall within the limits of the appended claims and their legal equivalents.

BIBLIOGRAPHIC REFERENCES

Barany, F., 1911, PNAS. USA, 88:189-193.
Buckholz, R. G., 1993, Yeast systems for the expression of heterologous gene products. Curr. Op. Biotechnology 4: 538-542.
Burg, J. L. et al., 1996, Mol. and Cell. Probes, 10:257-271.
Chu, B. C. F. et al., 1986, NAR, 14:5591-5603.
Duck, P. et al., 1990, Biotechniques, 9:142-147.
Edwards, C. P., and Aruffo, A., 1993, Current applications of COS cell based transient expression systems. Curr. Op. Biotechnology 4:558-563.
Guateli, J. C. et al., 1990, PNAS USA, 87:1874-1878.
Houben-Weyl, 1974, in Methoden der Organischen Chemie, E. Wunsch ed., Volume 15-I and 15-II, Thieme, Stuttgart.
Innis, M. A. et al., 1990, in PCR Protocols. A guide to Methods and Applications, San Diego, Academic Press.
Kievitis, T. et al., 1991, J. Virol. Methods, 35:273-286.
Kohler, G. et al., 1975, Nature, 256(5517):495-497.
Kwoh, D. Y. et al., 1989, PNAS. USA, 86:1173-1177.
Luckow, V. A., 1993, Baculovirus systems for the expression of human gene products. Curr. Op. Biotechnology 4:564-572.
Matthews, J. A. et al., 1988, Anal. Biochem., 169:1-25.
Merrifield, R. D., 1966, J. Am. Chem. Soc., 88(21):5051-5052.
Miele, E. A. et al., 1983, J. Mol. Biol., 171:281-295.
Olins, P. O., and Lee, S. C., 1993, Recent advances in heterologous gene expression in *E. coli*. Curr. Op. Biotechnology 4:520-525.
Rolfs, A. et al., 1991, In PCR Topics. Usage of Polymerase Chain reaction in Genetic and Infectious Disease. Berlin: Springer-Verlag.
Sambrook, J. et al., 1989, In Molecular cloning: A Laboratory Manual. Cold Spring Harbor, N.Y.: Cold Spring Harbor Laboratory Press.
Sanchez-Pescador, R., 1988, J. Clin. Microbiol., 26(10): 1934-1938.
Segev D., 1992, in "Non-radioactive Labeling and Detection of Biomolecules." Kessler C. Berlin: Springer-Verlag, New York: 197-205.
Urdea, M. S., 1988, Nucleic Acids Research, 11:4937-4957.
Walker, G. T. et al., 1992, NAR 20:1691-1696.
Walker, G. T. et al., 1992, PNAS USA, 89: 392-396.
White, B. A. et al., 1997, Methods in Molecular Biology, 67, Humana Press, Totowa, N.J.

---

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09187753B2). An electronic copy of the "Sequence Listing" will also be available from the USPTO upon request and payment of the fee set forth in 37 CFR 1.19(b)(3).

---

What is claimed is:

1. An expression vector comprising a nucleic acid encoding a polypeptide having at least 95% sequence identity to SEQ ID NO: 2126 and wherein the polypeptide is a Sigma-54-dependent transcriptional activator.

2. The expression vector of claim 1, wherein the polypeptide is a Sigma-54-dependent transcriptional activator at a temperature at or above 50 degrees Celsius.

3. The expression vector isolated of claim 1, wherein the polypeptide has 100% identity to SEQ ID NO: 2126.

4. The expression vector isolated of claim 1, wherein the nucleic acid has at least 95% identity to SEQ ID NO: 2127.

5. The expression vector isolated of claim 1, wherein the nucleic acid has 100% identity to SEQ ID NO: 2127.

6. A cell comprising the expression vector of claim 1.

7. A method of modulating transcription or transcriptional control at temperatures at or above 25 degrees Celsius, the method comprising providing to a transcriptional system the expression vector of claim 1.

8. The method according to claim 7, wherein providing to a transcriptional system expression vector of claim 1 occurs at a temperature at or above 50 degrees Celsius.

\* \* \* \* \*